US007585967B2

(12) United States Patent
Reddy et al.

(10) Patent No.: US 7,585,967 B2
(45) Date of Patent: Sep. 8, 2009

(54) NUCLEIC ACID COMPOUNDS FOR INHIBITING ANGIOGENESIS AND TUMOR GROWTH

(75) Inventors: Ramachandra Reddy, Houston, TX (US); Parkash Gill, Los Angeles, CA (US)

(73) Assignee: VasGene Therapeutics, Inc., Los Angeles, CA (US)

( * ) Notice: Subject to any disclaimer, the term of this patent is extended or adjusted under 35 U.S.C. 154(b) by 81 days.

(21) Appl. No.: 10/800,077

(22) Filed: Mar. 12, 2004

(65) Prior Publication Data

US 2005/0164965 A1 Jul. 28, 2005

Related U.S. Application Data

(60) Provisional application No. 60/454,300, filed on Mar. 12, 2003, provisional application No. 60/454,432, filed on Mar. 12, 2003.

(51) Int. Cl.
*C07H 21/04* (2006.01)

(52) U.S. Cl. ....................... 536/24.5; 536/24.31; 435/6; 435/325; 435/375; 514/44

(58) Field of Classification Search ....................... None
See application file for complete search history.

(56) References Cited

U.S. PATENT DOCUMENTS

| | | | | |
|---|---|---|---|---|
| 5,624,899 | A | 4/1997 | Bennett | |
| 5,635,177 | A | 6/1997 | Bennett | |
| 5,693,762 | A | 12/1997 | Queen et al. | |
| 5,801,154 | A * | 9/1998 | Baracchini et al. | 514/44 |
| 5,864,020 | A | 1/1999 | Bennett | |
| 6,150,162 | A * | 11/2000 | Bennett et al. | 435/375 |
| 6,271,030 | B1 * | 8/2001 | Monia et al. | 435/375 |
| 6,277,640 | B1 * | 8/2001 | Bennett et al. | 435/455 |
| 6,303,769 | B1 | 10/2001 | Cerretti | |
| 6,346,398 | B1 * | 2/2002 | Pavco et al. | 435/91.31 |
| 6,413,730 | B1 | 7/2002 | Holland | |
| 6,479,459 | B1 | 11/2002 | Cerretti | |
| 6,492,140 | B2 | 12/2002 | Cerretti | |
| 6,770,633 | B1 * | 8/2004 | Robbins et al. | 514/44 |
| 6,812,339 | B1 * | 11/2004 | Venter et al. | 536/24.31 |
| 2002/0146420 | A1 | 10/2002 | Bennett | |
| 2004/0110150 | A1 | 6/2004 | Koller et al. | |
| 2004/0234520 | A1 | 11/2004 | Aguet et al. | |
| 2004/0247592 | A1 | 12/2004 | Roifman et al. | |
| 2005/0246794 | A1 * | 11/2005 | Khvorova et al. | 800/286 |

FOREIGN PATENT DOCUMENTS

| | | |
|---|---|---|
| WO | WO-93/15201 | 8/1993 |
| WO | WO-95/27061 | 10/1995 |
| WO | WO-96/01839 | 1/1996 |
| WO | WO-96/02645 | 2/1996 |
| WO | WO-96/26958 | 9/1996 |
| WO | WO-98/01548 | 1/1998 |
| WO | WO-98/45708 | 10/1998 |
| WO | WO-99/08696 | 2/1999 |
| WO | WO-00/24413 | 5/2000 |
| WO | WO-00/30673 | 6/2000 |
| WO | WO-02/11785 | 2/2002 |
| WO | WO-02/26827 | 4/2002 |
| WO | WO-02/058538 | 8/2002 |
| WO | WO-02/061055 | 8/2002 |
| WO | WO-02/079382 | 10/2002 |
| WO | WO-02/102854 | 12/2002 |
| WO | WO-02/102972 | 12/2002 |
| WO | WO-02/102973 | 12/2002 |
| WO | WO-03/004057 | 1/2003 |
| WO | WO-2004/024773 | 3/2004 |
| WO | WO-2004/080425 | 9/2004 |

OTHER PUBLICATIONS

Miyagishi et al. Strategies for generation of an siRNA expression library directed against the human genome. Oligonucleotides 2003, vol. 13: 325-333.*

Promega siRNA Designer. SiLentGene U6 Cassette RNA Interference Version 1.1, May 2003. www.promega.com/siRNADesigner/program/default.asp.*

Bennett et al. Cloning and Characterization of HTK, a Novel Transmembrane Tyrosine Kinase of the Eph subfamily. (The Journal of Biological Chemistry, 1994, vol. 268, No. 19, pp. 14211-14218).*

Stephenson et al. Receptor protein tyrosine kinase EphB4 is up-regulated in colon cancer. BMC Molecular Biology 2001, vol. 2, No. 15, pp. 1-9.*

Tang et al. Self-stabilized antisense oligonucleotide phosphorothioates: properties and anti-HIV activity. Nucleic Acids Research 1993, vol. 21, No. 11, pp. 2729-2735.*

Taylor et al. Antisense oligonucleotides: a systematic high-throughput approach to target validation and gene function determination. (DDT 1999, vol. 4, No. 12, pp. 562-567).*

Adams, R.H., et al., "Roles of ephrinB ligands and EphB receptors in cardiovascular development: demarcation of arterial/venous domains, vascular morphogenesis, and sprouting angiogenesis," Genes Dev., 13:295-306 (1999).

Berclaz, G., et al., "Activation of the receptor protein tyrosine kinase EphB4 in endometrial hyperplasia and endometrial carcinoma," Ann Oncol., 14:220-226 (2003).

Berclaz, G., et al., "Expression of the receptor protein tyrosine kinase myk-1/htk in normal and malignant mammary epithelium," Biochem Biophys Res Commun., 24;226:869-875 (1996).

Brambilla, R., et al., "Membrane-bound LERK2 ligand can signal through three different Eph-related receptor tyrosine kinases," EMBO J., 14:3116-3126 (1995).

Bruhl, T., et al., "Homeobox A9 Transcriptionally Regulates the EphB4 Receptor to Modulate Endothelial Cell Migration and Tube Formation," Circ. Res., 743-751 (2004) [Epub ahead of print] DOI 10.1161/01res0000120861.27064.09.

(Continued)

*Primary Examiner*—Kimberly Chong
(74) *Attorney, Agent, or Firm*—Ropes & Gray LLP

(57) ABSTRACT

In certain embodiments, this present disclosure provides nucleic acid compounds, compositions, and methods for inhibiting Ephrin B2 or EphB4 expression. In certain embodiments, the present disclosure provides methods and compositions for treating cancer or for treating angiogenesis-associated diseases.

10 Claims, 105 Drawing Sheets

OTHER PUBLICATIONS

Carbone, M., et al., "The pathogenesis of mesothelioma," Semin. Oncol., 29(1):2-17 (2002).
Cheng, N., et al., "The ephrins and Eph receptors in angiogenesis," Cytokine & Growth Factor Reviews, 13:75-85 (2002).
Cowan, C.A., et al., "Ephrins in reverse, park and drive," Trends in Cell Biology, 12(7):339-346 (2002).
Davis, S., et al., "Ligands for EPH-related receptor tyrosine kinases that require membrane attachment or clustering for activity," Science, 266(5186):816-819 (1994).
Fuller, T., et al., "Forward EphB4 signaling in endothelial cells controls cellular repulsion and segregation from ephrinB2 positive cells," J. Cell Sci., 116:2461-2470 (2003).
Gerety, S.S., et al., "Symmetrical mutant phenotypes of the receptor EphB4 and its specific transmembrane ligand ephrin-B2 in cardiovascular development," Mol. Cell, 4:403-414 (1999).
Hamada, K., et al., "Distinct roles of ephrin-B2 forward and EphB4 reverse signaling in endothelial cells," Arterioscler. Thromb. Vasc. Biol., 23:190-197 (2003).
Himanen, J.P., et al., "Eph receptors and ephrins," Intl. J. Biochem. & Cell Bio., 35:130-134 (2003).
Himanen, J.P., et al., "Eph signaling: a structural view," Trends in Neurosciences, 26(1):46-51 (2003).
Hirai, H., "A novel putative tyrosine kinase receptor encoded by the eph gene," Science, 238:1717-1720 (1987).
Kiyokawa, E., et al., "Overexpression of ERK, an EPH family receptor protein tyrosine kinase, in various human tumors," Cancer Res., 54:3645-3650 (1994).
Kullander, K., et al., "Mechanisms and functions of eph and ephrin signalling," Nature Reviews, Molecular Cell Biology, 3:475-486 (2002).
Mellitzer, G., et al., "Control of cell behavior by signalling through Eph receptors and ephrins," Neurobiology, 10:400-408 (2000).
Munarini, N., et al., "Altered mammary epithelial development, pattern formation and involution in transgenic mice expressing the EphB4 receptor tyrosine kinase," J. Cell Sci., 115(Pt 1):25-37 (2002).
Nomura, A.M., et al., "Prostate cancer: a current perspective," Epidemiol Rev., 13:200-227 (1991).
Pasquale, E.B., "The Eph family of receptors," Curr. Opin. Cell Biol., 9:608-615 (1997).
Sakano, S., et al., "Characterization of a ligand for receptor protein-tyrosine kinase HTK expressed in immature hematopoietic cells," Oncogene., 13:813-822 (1996).
Schmucker, D., et al., "Signaling Downstream of Eph Receptors and Ephrin Ligands," Cell, 105:701-704 (2001).
Shin, D., et al., "Expression of ephrinB2 identifies a stable genetic difference between arterial and venous vascular smooth muscle as well as endothelial cells, and marks subsets of microvessels at sites of adult neovascularization," Dev. Biol. 230:139-150 (2001).
Sinha, U.K., et al., "Expression of EphB4 in head and neck squamous cell carcinoma," ENT J 82:721-723 (2003).
Steinle, J.J., et al., "Eph B4 receptor signaling mediates endothelial cell migration and proliferation via the phosphatidylinositol 3-kinase pathway," J. Biol. Chem., 277(46):43830-5 (Nov. 15, 2002) (Epub Sep. 13, 2002).
Stephenson, S.A., et al., "Receptor protein tyrosine kinase EphB4 is up-regulated in colon cancer," BMC Mol. Biol., 2:15 (2001).
Takai, N., et al., "Expression of receptor tyrosine kinase EphB4 and its ligand ephrin-B2 is associated with malignant potential in endometrial cancer," Oncol Rep., 8:567-573 (2001).
Tang, X.X., et al., "Coexpression of transcripts encoding EphB receptor protein tyrosine kinases and their ephrin-B ligands in human small cell lung carcinoma," Clin. Cancer Res., 5:455-460 (1999).
Wang, H.U., et al., "Molecular distinction and angiogenic interaction between embryonic arteries and veins revealed by ephrin-B2 and its receptor Eph-B4," Cell 93:741-753 (1998).
Caplen, N.J., "RNAI as a Gene Therapy Approach," Expert Opin. on Biol. Therapy, 3(4):575-586, (2003).
Cromer et al., "Identification of genes associated with tumorigenesis and metastatic protential of hypopharyngeal cancer by microarray analysis," Oncogene, Basingstoke, Hants, GB, 23(14):2484-2498, (2004).
Cruz, Santa, "EphB4 (N-19): sc-7285," Product Catalog of Santa Cruz Biotechnology, Apr. 1999.
Berclaz et al., "Loss of EphB4 receptor tyrosine kinase protein expression during carcinogenesis of the human breast," Oncology Reports, 9(5):985-989, (2002).
Yang et al., "Gene Targets of Antisense Therapies in Breast Cancer," Expert Opin. on Therapeutic Targets, 6(3):375-385, (2002).
Dermer, Gerald B., "Another Anniversary for the War on Cancer," *Bio/Technology*, 12:320 (1994).
Freshney, R. Ian, Culture of Animal Cells: A Manual of Basic Technique, pp. 3-4 (1983).
Gura, Trisha, "Systems for Identifying New Drugs Are Often Faulty," *Science*, 278:1041-1042 (1997).
Fabes et al., "Accumulation of the Inhibitory Receptor EphA4 May Prevent Regeneration of Corticospinal Tract Axons Following Lesion," *Eur. J. Neurosci.*, 23(7):1721-1730 (2006) (Abstract).
Inada et al., "Selective Expression of the Receptor Tyrosine Kinase, HTK, on Human Erythroid Progenitor Cells," Blood, 89(8):2757-2765 (1997).

* cited by examiner

Amino acid sequence of the B4ECv3 protein

MELRVLLCWASLAAALEETLLNTKLETADLKWVTFPQVDGQWEELSG
LDEEQHSVRTYEVCEVQRAPGQAHWLRTGWVPRRGAVHVYATLRFTM
LECLSLPRAGRSCKETFTVFYYESDADTATALTPAWMENPYIKVDTV
AAEHLTRKRPGAEATGKVNVKTLRLGPLSKAGFYLAFQDQGACMALL
SLHLFYKKCAQLTVNLTRFPETVPRELVVPVAGSCVVDAVPAPGPSP
SLYCREDGQWAEQPVTGCSCAPGFEAAEGNTKCRACAQGTFKPLSGE
GSCQPCPANSHSNTIGSAVCQCRVGYFRARTDPRGAPCTTPPSAPRS
VVSRLNGSSLHLEWSAPLESGGREDLTYALRCRECRPGGSCAPCGGD
LTFDPGPRDLVEPWVVVRGLRPDFTYTFEVTALNGVSSLATGPVPFE
PVNVTTDREVPPAVSDIRVTRSSPSSLSLAWAVPRAPSGAWLDYEVK
YHEKGAEGPSSVRFLKTSENRAELRGLKRGASYLVQVRARSEAGYGP
FGQEHHSQTQLDESEGWREQGSKRAILQIEGKPIPNPLLGLDSTRTG
HHHHHH

Fig. 1

Amino acid sequence of the B4ECv3NT protein

MELRVLLCWASLAAALEETLLNTKLETADLKWVTFPQVDGQWEELSGL
DEEQHSVRTYEVCEVQRAPGQAHWLRTGWVPRRGAVHVYATLRFTMLE
CLSLPRAGRSCKETFTVFYYESDADTATALTPAWMENPYIKVDTVAAE
HLTRKRPGAEATGKVNVKTLRLGPLSKAGFYLAFQDQGACMALLSLHL
FYKKCAQLTVNLTRFPETVPRELVVPVAGSCVVDAVPAPGPSPSLYCR
EDGQWAEQPVTGCSCAPGFEAAEGNTKCRACAQGTFKPLSGEGSCQPC
PANSHSNTIGSAVCQCRVGYFRARTDPRGAPCTTPPSAPRSVVSRLNG
SSLHLEWSAPLESGGREDLTYALRCRECRPGGSCAPCGGDLTFDPGPR
DLVEPWVVVRGLRPDFTYTFEVTALNGVSSLATGPVPFEPVNVTTDRE
VPPAVSDIRVTRSSPSSLSLAWAVPRAPSGAWLDYEVKYHEKGAEGPS
SVRFLKTSENRAELRGLKRGASYLVQVRARSEAGYGPFGQEHHSQTQL
DESEGWREQGSKRAILQISSTVAAARV

Fig. 2

Amino acid sequence of the B2EC protein

MAVRRDSVWKYCWGVLMVLCRTAISKSIVLEPIYWNSSNSKFLPGQGL
VLYPQIGDKLDIICPKVDSKTVGQYEYYKVYMVDKDQADRCTIKKENT
PLLNCAKPDQDIKFTIKFQEFSPNLWGLEFQKNKDYYIISTSNGSLEG
LDNQEGGVCQTRAMKILMKVGQDASSAGSTRNKDPTRRPELEAGTNGR
SSTTSPFVKPNPGSSTDGNSAGHSGNNILGSEVGSHHHHHH

Fig. 3

Amino acid sequence of the B4ECv3-FC protein

MELRVLLCWASLAAALEETLLNTKLETADLKWVTFPQVDGQWEEL
SGLDEEQHSVRTYEVCEVQRAPGQAHWLRTGWVPRRGAVHVYATL
RFTMLECLSLPRAGRSCKETFTVFYYESDADTATALTPAWMENPY
IKVDTVAAEHLTRKRPGAEATGKVNVKTLRLGPLSKAGFYLAFQD
QGACMALLSLHLFYKKCAQLTVNLTRFPETVPRELVVPVAGSCVV
DAVPAPGPSPSLYCREDGQWAEQPVTGCSCAPGFEAAEGNTKCRA
CAQGTFKPLSGEGSCQPCPANSHSNTIGSAVCQCRVGYFRARTDP
RGAPCTTPPSAPRSVVSRLNGSSLHLEWSAPLESGGREDLTYALR
CRECRPGGSCAPCGGDLTFDPGPRDLVEPWVVVRGLRPDFTYTFE
VTALNGVSSLATGPVPFEPVNVTTDREVPPAVSDIRVTRSSPSSL
SLAWAVPRAPSGAWLDYEVKYHEKGAEGPSSVRFLKTSENRAELR
GLKRGASYLVQVRARSEAGYGPFGQEHHSQTQLDESEGWREQDPE
PKSCDKTHTCPPCPAPELLGGPSVFLFPPKPKDTLMISRTPEVTC
VVVDVSHEDPEVKFNWYVDGVEVHNAKTKPREEQYNSTYRVVSVL
TVLHQDWLNGKEYKCKVSNKALPAPIEKTISKAKGQPREPQVYTL
PPSRDELTKNQVSLTCLVKGFYPSDIAVEWESNGQPENNYKTTPP
VLDSDGSFFLYSKLTVDKSRWQQGNVFSCSVMHEALHNHYTQKSL
SLSPGK

Fig. 4

Amino acid sequence of the B2EC-FC protein

MAVRRDSVWKYCWGVLMVLCRTAISKSIVLEPIYWNSSNSKFLPGQ
GLVLYPQIGDKLDIICPKVDSKTVGQYEYYKVYMVDKDQADRCTIK
KENTPLLNCAKPDQDIKFTIKFQEFSPNLWGLEFQKNKDYYIISTS
NGSLEGLDNQEGGVCQTRAMKILMKVGQDASSAGSTRNKDPTRRPE
LEAGTNGRSSTTSPFVKPNPGSSTDGNSAGHSGNNILGSEVDPEPK
SCDKTHTCPPCPAPELLGGPSVFLFPPKPKDTLMISRTPEVTCVVV
DVSHEDPEVKFNWYVDGVEVHNAKTKPREEQYNSTYRVVSVLTVLH
QDWLNGKEYKCKVSNKALPAPIEKTISKAKGQPREPQVYTLPPSRD
ELTKNQVSLTCLVKGFYPSDIAVEWESNGQPENNYKTTPPVLDSDG
SFFLYSKLTVDKSRWQQGNVFSCSVMHEALHNHYTQKSLSLSPGK

Fig. 5

B4EC-FC binding assay (Protein-A-agarose based)

B4EC-FC inhibition assay (inhibition in solution)

B2EC-FC binding assay (Protein-A-agarose based assay)

Purification and ligand binding properties of the EphB4EC proteins

Binding of Ephrin B2-AP fusion to EphB4-derived recombinant proteins immobilized on NTA-agarose beads B4v3 inhibitis neovascular response in a murine corneal hydron micropocket assay EPHB4 staining in prostate tissues array

| | negative | positive |
|---|---|---|
| Normal (n = 20) | 17 | 3 |
| Tumor (n = 32) | 8 | 24 |

$P = 3.8 \times 10^{-5}$ $\chi^2$ analysis

Migration Study of H28 with siRNA472(Boyden Chamber)

Transfection of p53 inhibit the expression of EPHB4 in 5637 cell

Growth inhibition of bladder cancer cell line(5637) upon treatment with EPHB4 siRNA 472

Cell migration study of 5637 cell upon treatment with AS10(10uM)

Invasion study of 5637 cell transfected with siRNA 472 or control siRNA

EphB4 gene

```
   1 ggggtttcat catgttggcc aggctggtct tgaactcctg acctcaaatg atccgcctgc
  61 ctctgcctcc caaaatgctg ggactacagg cgtgagccac cgcgcccgcc acacccacct
 121 tttctttacc gttgtttcct cgatttttct ctactcccta gcgcagctta gtgcgcgcct
 181 cctctggaca tttttcaggg cttggttgcg cgcacagtag gtccccaaca ctgaatgttt
 241 atggggtgac tgtgtgaacg ttcgctgcaa ggctatccaa actgggattg ctccttgagg
 301 ccccctgggc ggccgtcaat tctccaaagc ttctactccc ttttccttcc ttttccccca
 361 aaacgcagtc cctgcgccca ctagagggtg gtgggcgcat ccaagagcgg catctagagt
 421 ccgcagcaag gtcagagcgg gctttgtgtg cgcggtgaac atttacgtgc acgcctgggc
 481 ggccctccgt gttgctgctg ggtgtgtgtt ttctctgctc cctggtgcca gccgggttcg
 541 ggcctgtccc gggggtccct gggccccagc cccgacatgc tcggtcctgg acagcgcgca
 601 ccgccacggc gcacatctgg gcggtcccgg ggttcctcac ccgccgcccc tccccccttct
 661 ccaaactttc tctcaacttc ccgacctgct ccactcggtg cccctctccg cttccctcat
 721 gaattattca gtagcgtgag ctccaatcag cgcgcccggg gctcactcgc ggagcccccg
 781 cgttgggaga gctgcccccg ccccccgcgc gcccctccct cccgggcccg gcgccgcccg
 841 gcccagttcc agcgcagctc agcccctgcc cggcccggcc cgcccggctc cgcgccgcag
 901 tctccctccc tcccgctccg tccccgctcg ggctcccacc atccccgccc gcgaggagag
 961 cactcggccc ggcggcgcga gcagagccac tccagggagg gggggagacc gcgagcggcc
1021 ggctcagccc ccgccacccg gggcgggacc ccgaggcccc ggagggaccc caactccagc
1081 cacgtcttgc tgcgcgcccg cccggcgcgg ccactgccag cacgctccgg gcccgccgcc
1141 cgcgcgcgcg gcacagacgc ggggccacac ttggcgccgc cgcccggtgc cccgcacgct
1201 cgcatgggcc cgcgctgagg gccccgacga ggagtcccgc gcggagtatc ggcgtccacc
1261 cgcccaggga gagtcagacc tgggggggcg agggcccccc aaactcagtt cggatcctac
1321 ccgagtgagg cggcgccatg gagctccggg tgctgctctg ctgggcttcg ttggccgcag
1381 ctttggaagg tgagtttcct tgcggggggg ggcgcacccc gtcactcctg ggacctcccc
1441 cccaacatct gggcctcgga gtggaggggc cggcctctga ctacccctac ccgggcactg
1501 cagtcccaaa cacttcggac cgatagtgct ggaacgggag gggggcgggg aagaggcgcc
1561 cgacgggtag tggagttttc ttttgtttgg gaaagagatg gagtctggct acgacccggg
1621 acattcccct gcccgggctc cccgaactct cactgctgat tacatacgcc cctggctgcc
1681 tttcctttcc tccctacccc actattcaaa actatctgca aagtttctgt cccagtccca
1741 cctcccgccg tacatgaggg aaggtttctg gagaagcaac agcagacaag gcacaacttt
1801 tcgtgctagg ccctaaaacg acccccagcg ccaattcctt agcgatcaca ccttgatcct
1861 ccagttccac actcctgcaa caggatggcc tcctttgcat tcacacagca aacccccaaa
1921 ccgctctccc gcccactgct cctgcccctg gtatagggtg gctccttggt ttctacaggc
1981 tgcaccccat ccctttaaat gcggtctaga ccccggcccc aggtgagtcc cgggcttccc
2041 ttgagaccta ggagcgggta gaaactgacc tacacagccc ccaggtagaa actgacctac
2101 acagccccca catcgcccta actaacccag tctatctccc acctcctggt ctctccaagc
2161 atttctttgg ccatggatcg ctgtccctcc tggtccccta aagggggagc caagagccct
2221 agaaactctc ctgtgtccct aatgtccttt cagtgagctg ccaacacccc cctttctctg
2281 tctggtatga aagtggttat ggggcggtag gctatgaggg actcccaaag ggaaggattc
2341 agcggcgtta gaaaaaccct ctccccctgg ctgggcagga ctgccctggg ctggggatca
2401 aaggctaggt gtggggttgg gagtgagggg aggcttgccc agctcagaga acggagaagg
2461 gggaacaaaa accatgaacg aggggaagag gaaggccaaa ggggtggaaa aaccacgagg
2521 acgaggtgtg gtgagaagga aagacgcaaa gaggaaatgg tgattgtgac acctattacc
2581 tgagtgtttc caagcaccag gcctgtgctg agcgccttac aaatattaat ttcacccatc
```

Fig. 61A 2641 cagcaacgct aagggtggtg ctattattgc ccccattttt cagatgagga ggctggggct
2701 tagttaaggt taagtagttt atccaaggcc ctgtgccgcg aggaacagcg agaagtggag
2761 gccgaaagcg aaggagagat agtgactgtc agaaagagaa acggaggtgg acagagagtg
2821 gaggagagat aggtgagaga catgcgaact gacagatcaa agcgtggctg cagctgagct
2881 gggacgcaga aagggagcct gcgcttgctc tgggctgcgg acagcccgag gcagagacag
2941 tgtgtaaatt ggagacagga aaacactatc ccggctggaa caatggaggg tggagacggc
3001 agcctctatc cacccccttc ccagaacccg ggcatcctgt ccccagtgag cagggctgtc
3061 tcttgccacc catggggacc ttgcgcctct cacctcaggc tggctggctt cccatctgac
3121 ccctagctgg aggacatcat ttggtcccca ggaagaggct gcctcaccca ccctctttct
3181 cttctctcct gcagctccca tggggtggga gccaggtgtt ctggctcccc tctccaccct
3241 tcccagcgcc caatgccccc cacattgccg gcccccgagg ggattcctgt accctccctc
3301 ctccactctc cactgccagg ggctgtgcag tttttcctaa tcccccccct tcctccagtg
3361 cctgtcccct cccccgatga tccgagccaa gccaggtgtg ttcacccctc ccattcatac
3421 cgccccccag aatctcctcc cctctgcctt cccataacca aatccagatg tgaggcctcg
3481 gcgggagcct gggaacccta gcatcccgac ctccagtgct tcctgatcag ggcactcgtg
3541 gggagggagg tactgggatg gggccagggg ctatgcccca ggcacggagc gctcccttca
3601 aggagggaag gacggggtgt ttggtctgaa agcagagagg ggtcttggac agggaatgaa
3661 attgtggggt agagaggctg attctgggac ttaggggagg aaacgtggag gctgagacaa
3721 gaggttcccc tcccacacca gcagcctctg ctcgtggggg tcaggaccag ggcgcagctc
3781 tcattttaac cctttctgag ctgccgcccc ttctccccgt acattttgat ctccctccct
3841 cctccaggga ggcctagatc tggggtatcc caagggagcc ccatgcctac cagatgttgg
3901 gggtggggtt ggcacttagc agaagaggcc agaaatcagg cgggtgcaga gggcagggct
3961 tgctcccctc ttggcccccc aactcctcta gctcagagct aagaggatcc acctgcctcg
4021 gttcccaggg atctggtctt cctgacctcc ctccccccacc ccaggcactg actctgtctc
4081 tctgtctgtc tcagagaccc tgctgaacac aaaattggaa actgctgatc tgaagtgggt
4141 gacattccct caggtggacg ggcaggtgag agctgcaccc aggagctgga gctctggagg
4201 gaaactgagg gaggagaggg cgcctgtgcc gcctgctttc tgtgtgccac tcctctcccc
4261 tgtcccccca gatgacagca gccccagcag tgtcgtctga gcccttctca gaggcgccct
4321 cctcgcagta ccagcagccc ccctttctca gtccctctca ctttatagga ttcaccccat
4381 gcagccctct ccctggcggc tccccagccc ccttgctgac ctccttctct gcacagtggg
4441 aggaactgag cggcctggat gaggaacagc acagcgtgcg cacctacgaa gtgtgtgacg
4501 tgcagcgtgc cccgggccag gcccactggc ttcgcacagg ttgggtccca cggcggggcg
4561 ccgtccacgt gtacgccacg ctgcgcttca ccatgctcga gtgcctgtcc ctgcctcggg
4621 ctgggcgctc ctgcaaggag accttcaccg tcttctacta tgagagcgat gcggacacgg
4681 ccacggccct cacgccagcc tggatggaga acccctacat caaggtacct gggtgccccc
4741 agggctcagc cacagccaag gtgggattcc agccagcagg cccgtggcct ggagggcagc
4801 cgatgtagtt gcgaggcctc tggcccgcgc gctgggggct ggaagcagga ggcttaggtc
4861 tggggaggga agggggtgat cttctgggcg gaggagcaga atatacgggg gctgcctggc
4921 ccggcccccca gggaggccca agggtcaggc ttctcctcca gtcacctcaa ccaccctacc
4981 ccactgtgct ccagccacac tgagtttctc ccattccctg actgcacctg gctggtttcc
5041 agctcaagac tttgcagcgg tgatgtctcc acctgggggc ctctctgcct ctcacacccc
5101 tacttgtctt cggagttcca gctcccgaga tcttgcctgt gccaccttgg ctgactctct
5161 cctccctaca atcctgcata cctctgtcca cctgcctgtc tcggcactca ttttacttta
5221 tttatttttc ttttatatct atatttttaa agcggggtct tctacgttac ccaggctggt

Fig. 61B 5281 ctctaactcc tgggctcaag agatttctcc cacctcggcc tcctaaagtg ctgggattat
5341 aggcatgagg cactacgccc ggcctcatgg tactttataa cttccccagg attcattcat
5401 cgctgtctcc ttgactctga ggtcaaggcc tggcatggcg tcagtgtcag taaatgtttg
5461 tagaacgagt gaataaaaag ggggagaggt gcaggccaga ggccgggcat atcgcaggag
5521 ctttgcaagg ctgaatggac agtgtggggg cctgcagaaa gtgtgccctg ggaaggtgg
5581 agggaagatt ctggaacggg aaccaaggag gtccgggagg gtgagctggg aagaacacaa
5641 cagtccgctg ggtcctcagg gagtggggac agcagcggtg tgcctccccc ccgccggcag
5701 gtggacacgg tggccgcgga gcatctcacc cggaagcgcc ctggggccga ggccaccggg
5761 aaggtgaatg tcaagacgct gcgtctggga ccgctcagca aggctggctt ctacctggcc
5821 ttccaggacc agggtgcctg catggccctg ctatccctgc acctcttcta caaaaagtgc
5881 gcccagctga ctgtgaacct gactcgattc ccggagactg tgcctcggga gctggttgtg
5941 cccgtggccg gtagctgcgt ggtggatgcc gtccccgccc ctggccccag ccccagcctc
6001 tactgccgtg aggatggcca gtgggccgaa cagccggtca cgggctgcag ctgtgctccg
6061 gggttcgagg cagctgaggg gaacaccaag tgccgaggtg agagctggag cttcccctgc
6121 gactgctgct catccggggg agagtcctga actccactca ggacccactt cttaagtttc
6181 cattttgtat agttagatgt tgaaatggag gcttgctctg tcacccaggc tggagtgcag
6241 tggcacaatc tctgctcaac tgcaaccttt gcctcccggg tccctgttca agcagttctc
6301 ctgcctcagc ctcgtgagta gctgggacta caggcacacg ccaccacgcc cggctaattt
6361 ttgtatttta gtagagacgg ggtttcgcca tgttggccag gctggtctcg aactcctgac
6421 ctgaagtgat ttgcccgcct cggcctccca aagtgctggg attacaggcg tgcgtcacca
6481 cacccagctg gaaaaaaaaa agactttatt ttcacctgaa attcattaat ttccacttga
6541 aattccacct gcagttgtag caggacctga cacttgggcc ccatggaaat cacaggtatt
6601 gcctgacaca gtggttcatg cccatagtgc cagcactttg agatgccaag gtgggaggat
6661 cacttgagcc caggagttcg agatcagcct gggtgacaga gcaagacccc gtctctaaaa
6721 aaaatttttt tttttttttc aagacagagt cttgctctgt cgcccaggct ggagtgcagt
6781 ggtgcgatct cggctcactg caagctccgc ctcccaagtt aacaccattc tcctgcctca
6841 gcctcccgag tagctgggac tacaggcccc gccaccacgc ccggctaatt tcttgtattt
6901 ttagtagaga tggagtttca ccgtgttagc caggatggtc tcgatctcct gacctcatga
6961 tctgcccgcc ttggcctccc aaagtgctgg gattacaggt gtgagccacc acacccggat
7021 tacaaaaact ttttagataa ttatctgggc gacctgcctg accaacatgg agaaaccctg
7081 tctctactaa aaatacaaaa ttagccggac atggtggcgc atgcctgtaa tcccagctac
7141 ttgggaggct gaggcaggag aatcatttga acccaggaag cagaggttgc ggtaagccga
7201 gatcatgcca ctgcactccg gtctgggagt gcactccaac aagaaggagt ttcgctcttt
7261 ttgcccaggc tggagtgcag tggtgggatc tcagctcacc gcaacctcca cctcccgggt
7321 tcaggcgatt ctcctgcctc agcctcccaa ggagtagctg ggattatagg tatgcatcgt
7381 cacacccggc tacttttgta tttttagtag aggcaggttt ccaccatgtt ggccaggctg
7441 gtcttgaact caagtgatct gccctctttg gcctccttct caggaaaaaa aaaaaatcac
7501 aggtatttac aggccattcc aagtgccaaa agattgtttt tgctcatggt gacttcagta
7561 tcacagatgt taggagactt gctgctatat gttaagaaag aagcacaaat gttgctgtag
7621 cccaaacttt tttcctcatg tttcattgca tttcagctta attggtttcc ctggtattcc
7681 tatgtatttt gtggagtgct tttaaaatca taagttggag tagaggtctt tctgtgggct
7741 tcaccagact gccgagatca gggtcgaaac aggtgaggac cccttctctg gagagagtct
7801 cctttctcct ctaagaggaa aggttttgag atcttttgtc cattttccca ccttagcact
7861 tcatcagcct taaaagaagc tggaattttt tttttttttt ttggagatgg gatctcgata

Fig. 61C 7921 tgttgcccag gctggtcttg aacccccttgg ctcaagcgat cctccagcct cagcctccca
7981 aagtgctggg attcgaggca tgagccaccg agcccaccgt gcagatggat gtttttgtgc
8041 atgcttttga tgaatgcttt ctctctctca gcctgtgccc agggcacctt caagcccctg
8101 tcaggagaag ggtcctgcca gccatgccca gccaatagcc actctaacac cattggatca
8161 gccgtctgcc agtgccgcgt cgggtacttc cgggcacgca cagacccccg gggtgcaccc
8221 tgcaccagta agtgaccagc acccaggtgc agttcactgg ggaggggtca cagacctctg
8281 aggtggaccc tcacatggcc cccatcctcc ctgggcttct tccctttgtc cctggcatgc
8341 ttgtccctag cccggaggaa catgtggagc ccactgtctc caaggcaaga gtccagcatg
8401 gctgctggtg cctccattgc cctctcccca ccaccgcaga gcaggtcggc ctctgcctga
8461 ctccctggtc tcctgcagcc cctccttcgg ctccgcggag cgtggtttcc cgcctgaacg
8521 gctcctccct gcacctggaa tggagtgccc ccctggagtc tggtggccga gaggacctca
8581 cctacgccct ccgctgccgg gagtgccgac ccggaggctc ctgtgcgccc tgcgggggag
8641 acctgacttt tgacccccggc ccccgggacc tggtggagcc ctgggtggtg gttcgagggc
8701 tacgtcctga cttcacctat acctttgagg tcactgcatt gaacggggta tcctccttag
8761 ccacggggcc cgtcccattt gagcctgtca atgtcaccac tgaccgagag ggtgagactt
8821 gggggctggg gcggctggtg gtctggcggg agagatgtca ctgagggcct gaaggggaga
8881 ggcaggggct gtgaagttgg gtaccccgga agtgtgaggg gctaaggctt tgggggcaag
8941 aggcagaaag agggcaatgg ctgggcgcag tggctcacgc ctgtaatccc agcactttca
9001 gaggctgaga caggcggatc acttgagccc tggagttcaa gaccagcctg ggtaacatag
9061 gaagatctct ctacaaaaaa taaaaatatt agccaggcga ggtggtgcat gcctgtggtc
9121 ccagctactc aagaggctga ggcaggagga ttgcttgagc ccaggagtcg gaggctgcag
9181 tgagctatga tcgcaccgct gcatgccagc ctgggtgaca gagcagtgtg agatcctctc
9241 tcaaaataaa tgaataagaa agagagggtg aggagctcgt aaagctgggc tggagagtta
9301 agtacaggaa ggccccccagt gggactgggg ccagagagaa tcagaaggaa ttctcgaaac
9361 agccaggggg aaattgagac aagtgtagcc agcagaggaa gtgttggaaa agataaggga
9421 catggccagg ctgatcacaa ggtcaggagt tcaagactag cctggccaac gtggtgaaac
9481 cccatgtcta ctaaaaataa aaaaattagc caggcatggt ggtgggcacc tgtaatccac
9541 ttgggaagca accagaagaa ttgcttgaac ccaggaggcg gaggttgcag taagctgaga
9601 ctgcgccact gcactccagc ctgggtgata gagcacgact ccgtctcgaa aaaaaaaatt
9661 ttttttaagt taagggacag agctaccatg cacaagggtt ccctgtgtct ctgcctctca
9721 cagtacctcc tgcagtgtct gacatccggg tgacgcggtc ctcacccagc agcttgagcc
9781 tggcctgggc tgttccccgg gcacccagtg gggctgtgct ggactacgag gtcaaatacc
9841 atgagaaggt aaggccatcc cccagccctg gggtgggtgg gcaatgggtt gtgctctcct
9901 ggctgggaca cctgggttgc aggcacctgg caggcatttg aattccagct ctgccatgga
9961 ttccctgggc agccttgggt aagccccttg gcctgtctga gcctcagact cttcatctat
10021 aaaatagtta ctgtaatagt taccagcagc tggacacagt ggctgaggtt gggtgcggtg
10081 gctcacgcct gtaataccaa gcactttggg aggctgaggc gggcagaatg cttgagccta
10141 ggagtttgag accagcctgg gcaacatggt gaaacttcat ctctataaaa aacttaaaat
10201 gggccgggcg cggtagctta cgcctgtaat cccagcactt tgggaggccg aggtgggcgg
10261 atcacaaggt caggagtatc gagaccatcc tggctaacac ggtgaaaccc catctctact
10321 aaaaatacaa aaaattagcc aggcgcggtg gcaggcgcct gtagtcccag ctactcggga
10381 ggctgaggca ggagaatggc gtgaacccag gaggcggagc ttgcagtgag ccgagatagc
10441 gccactgcag tccggcctgg gcgaaagaac aagactctgt ctccaaaaaa aaaaaaaaaa
10501 aaaaaaaacg caaaaaatac ttaaaatgaa aaaaattaga ctgggcacag tggctcatgc

Fig. 61D 10561 ctgtaatccc ggcactttgg gaggccgagg tgggtagaac acctggggtg aagagttcga
10621 gaccagcctg gccaacaagg tgaaatcccc gtctctacta caaatagcaa aatcagctga
10681 gtgtgttggc gggcccctgt aatcccagct actcaggagg ctgagacagg agaatcactg
10741 gaacccaagt gattctcgac ttgaggtcga ggctgcagtg agtcgtgttt gcaccattgc
10801 attccagcct gagaaagtga gaccttgtct taaaaaaaag gaatgatatt atgaatacag
10861 cacatggctt gcatgcgtaa gttctcccaa aggcctcacc agttgcaagg caggctagtg
10921 atgggagtgg agggcgaggg aaggaggcag gaagagcaac aggaacttgg gttcccgggt
10981 gacggccacc ccactacctc tcccggacag ggcgccgagg gtcccagcag cgtgcggttc
11041 ctgaagacgt cagaaaaccg ggcagagctg cgggggctga agcggggagc cagctacctg
11101 gtgcaggtac gggcgcgctc tgaggccggc tacgggccct tcggccagga acatcacagc
11161 cagacccaac tggatggtga gcctggggaa gggggtgagg gtgggggttg gaaagacccc
11221 caaagttcct gggaagaccc caggtctcca aagtcccatc atcttttttt tttttttttt
11281 tttttgagat ggagtcttgc tctgtccctc aggctggagt gcagtggcac catctccgct
11341 cactgcaacc tccgcctccc ggattcaagc cattctcctg cctcagcctc ccgagtagct
11401 gggattacag gcgcctgcca ccgcgcctgg ccgatttttt gtatttttag tagagacggg
11461 gcttcaccgc gttggccagg ctggtctcga actcctgacc ttgtgattcg cccgcctcgg
11521 cctcccgaag tgctgggatt acaggcatga gccactgcac ccggtcaaag tcctatcttc
11581 atgtccttct tcctgtggat cacatggcat gccctagaga ggagagaacg taagatgtcg
11641 aaaccaaaac caacagctga gttttgtgaa gtctggcctg cttcactctg tacccccagg
11701 ctggagcgca gttgctcgat caaagctcac tgcacagcca ggcacagtgg ctcacccctgt
11761 aaccccagca ctttgggagg ctgaagcagg aggatcactt gaggtcagga gttcgagacc
11821 agtctgacca gcatggtgaa accgcgtctc tactaaaaat atagaagtta gctgagcgtg
11881 gtggtgcaca cctgtaatcc cagctactcg ggaggctgag gcaggagaat cgcttgaacc
11941 tgggaggtgg aggttgcagt gagctgagat tgtgccagtg cactccagcc tgggcaacag
12001 agcaagactc tgtctcaaaa aaaaaaaagc tcaccgcagg cttgactttt agcaacaacc
12061 tgacccctga gctccccatt ccccatccaa caaaatggga atatcatgaa gcttcctgca
12121 gggctttgag gattggaggt aacaggttat ttttaatatg ctaggccagt ggctttcttt
12181 tttctttcac attttttttt ttgagacgga gtctcactct gttgcccagg ctggagtgcg
12241 gtggcgcgat ctcagctcac cgcaagctcc acctcctggt ctcgatctgc tgacctcctg
12301 atccacccgc ctcggcttcc cgaaatgctg ggactgctgg cgtgagccac cacgcccggc
12361 ctaacttttt cttttttta agagacacgg tctttttat cacccaggct ggagtgcggt
12421 ggcaccatca tagctcattg cagcctacaa ctcccgagct caaccaatcc ttccacctta
12481 gcctcccaag tagctggggc tataggcatg tgctaccgtg ctcaactaaa ttttttttta
12541 tgttttgttg agacagtttc cctatgttgc ccaggctggt ctcaaattcc tgacctcgag
12601 caatcctccc gcatcggcct cccaaagtgc tgggattaca ggcatgagcc gccacaccca
12661 gcattggacc agtggctttc taaaccttgt aattttctgt aatagcttta ctgaaataca
12721 gttcccctgc catacaattt gcctgttcaa agtgtacaat cgatgacttt tgatacattc
12781 acagaattgt gcagtcacca ccacaagtaa ttttgggaca ttttcagcac cctcaaaaga
12841 gaccctatag cccttagcca tcacccccca cccagatctt tctgttgcct tagtccctgg
12901 caagcactaa cccactttct gtcttgaaat cttccagtgt ggtcttttgt gactgttcac
12961 cgagcagaat gttttcaagg tttatgtatg ttgtagtata tatccgtggg tttttttggt
13021 tgtggtttgt tttttgtttg ttttggaaac agggtctcgc tctgtcaccc aggctggagt
13081 gcagtggttc aattacagct cactgcagcc tcaacctccc aggctcaagt gatcctccca
13141 cctcagcctc ccaagcagct gggactgtag gcatgagcca ccatgcccag ctaatttttt

Fig. 61E 13201 ttggtatttt ttgtaaagac agggtttcac catgtttccc aggctggtct cgaactcctg
13261 agctcaggca atccacccac ctcagcctcc caaagtgctg tgattacagg catgagccac
13321 tggacctggc ctgtttttg tttttgtttt gaacacacga ttttgctttg tcacccaggc
13381 tggaatgtaa tggtctgatc atagtgcatt gcagcctcaa actcctgggc tcaagcgatc
13441 ctcctacctc agcctcctga gtatctggga ccacacgtgc tcaccaccat gcttggctaa
13501 ttattattat tttttgatag agacggggtc ttgctatgtt tcccaggctg gtcttgaaca
13561 cctggcctca cacaatcctc ccacctcagt atctcagagt gctgggatta caggcatgag
13621 ccactgctcc tggccaatat ttcatttctt tttatggaga cgtaataatc agttgtatgg
13681 aaatagctga ttttgttttt tattgtatct tttggtgaac atttcaattg tatcgacttt
13741 ttggataaaa acctgaaaat gtttcacctt tagaacgttt cattgaatgg agattttttt
13801 gtggactctg gtatttatac tagaaccaaa tcaaaaccac tctggcggct gggcatgcct
13861 aggctggttt gagactagcc tgtccaacct ggtgaaagcc catctctact aaaaatacac
13921 aaattagccg agcatggtgg tacacacctg taatcccagc tactcaggag gctgaggcag
13981 gagaatcgca gaacccggga ggcggagatt gcagtgagct gagattgcgc cactgcactc
14041 cagcctgggc gacagagtga gactgcgtct caaaaaaaca aacaaaaaat tactctggca
14101 gtaagaaaag atttcgaaac ttcctccctt gccctgaggt acttcagagg agcctgctgg
14161 cccctggggg agagtttgaa acccactgtt tgttccctga ccttgcctgc ttgtgtcctc
14221 tccctccacc tgtcccctgt actggggacc tgttctcagg agatcacagt tcattgctca
14281 aagccggggc tggggcctcc tacaggacca tcagtttctc ctgatcagca gcctttcctt
14341 ccgcagagag cgagggctgg cgggagcagc tggccctgat tgcgggcacg gcagtcgtgg
14401 gtgtggtcct ggtcctggtg gtcattgtgg tcgcagttct ctgcctcagg taagggctct
14461 gacacccaga ggcccctgga agccctcagt tgatggccac ctgcctgggt gctacaggac
14521 aagcctttct ggctgtcccc agcctctttt tacttgaaat cttctccaat ccctgctcct
14581 tcctttggtg tgtgtgcctc ataaagatgt gtgactcagt ttaccttttg ttcctttccc
14641 atcggctaca ggaagcagag caatgggaga gaagcagaat attcggacaa acacggacag
14701 tatctcatcg gacatggtgg gttgccctaa tttgatggga ataggggctt ggggccgggt
14761 gtggtggctc ctatctataa tcccagcact ttgggaggca gaggtgggca gatcacttga
14821 ggtcaggagt tcgagaccag cctggccaac atgttgaaac tccatctcta taaaaaatac
14881 atcagtcagc caggcatggt ggtgggcacc tgtaatccca gctactcagg aggctgaggc
14941 agaagaatca ttttaacccg ggaggcggag attgcagtga gccaagatcg cgccactgcg
15001 ctccaggcct gggtgacaga gcgagactcc atctcaggaa aaaaaaaaaa aaaaaaaaaa
15061 accacggaga caggggtttg gggctaaaag ctatgagccg agcctccgag tccagtggga
15121 gttaattccc agctgacggg gccctgcctg atttctcagg tactaaggtc tacatcgacc
15181 ccttcactta tgaagacccct aatgaggctg tgagggaatt tgcaaaagag atcgatgtct
15241 cctacgtcaa gattgaagag gtgattggtg caggtgagag ccgaaggctg cccgggcacc
15301 tgggaacgaa gcgggggtgg gcagggccac actggagcgg gagagctgat gacctctgcg
15361 tccttgtttg aaggtgagtt tggcgaggtg tgccgggggc ggctcaaggc cccagggaag
15421 aaggagagct gtgtggcaat caagaccctg aagggtggct acacggagcg gcagcggcgt
15481 gagtttctga gcgaggcctc catcatgggc cagttcgagc accccaatat catccgcctg
15541 gagggcgtgg tcaccaacag catgcccgtc atgattctca cagagttcat ggagaacggc
15601 gccctggact ccttcctgcg ggtgagcacc ctccctggct tctgcggcca cccggagttc
15661 ccacttacac ccagaggcca cttgggttaa gaagccagga cagacagtgg gtcccaggtc
15721 acctcctcca gccttttcct cttgggctaa gccctggtcc tctgcctttt cttttttta
15781 agacagagcc tcgctctgtc gcccaggctg gagtgcagtg gcgcgatctc ggctcattgc

Fig. 61F 15841 tgtctccacc tccagggttc aagcgattct cctgcctcag tctcccaagt agctggtact
15901 ataggcatgc accaccatgc tgactaattt ttgtattttt agtagacaca gggtttcacc
15961 atgtaggcca ggctggtatc aaactcctga cctcaagtga tctccccacc tcagcctccc
16021 aaagtgctgg tattacaggt gtgaggcacc acgcctggcc agccctctgc ctttaatttt
16081 ccctctggga aaggctgggc tcctgggacc ttcctttccc actgccccat acagctgaag
16141 gttgtcattc cttctttttt tttttaattt tgttttaatt gaattttttt tttttgagat
16201 ggagtttcac tcttgttgcc caggccggag tgcaatggca agatcttggc tcaccgcaac
16261 ctccgcctcc caggttcaag cgattctcct gccttagcct ccccagtagc tgggattata
16321 ggcatgtgcc accacgcttg actaattttg tatttttagt agagacgggg gtttctctgt
16381 gttggtcagg ctggtctcga actcccgacc tcaggtgatc cgcctgcctc ggcctcccaa
16441 agtgctggga ttacagacgt gagccaccgc gcccggccaa tttttttttt tttttttttaa
16501 gacagagtct cactctgtcc tctaggctgg agtgcagtgg tgcattcata gctcactgta
16561 gccttgacct cctgggctca agtgatcctc ccgcctcagc ctcctgagta gctggaacta
16621 cactcatgta ccaccatgct cagcaaattt ttaaaatttt ttgtagagac aggatctcga
16681 taggttgccc aggctggtct gaactcctgg cctcaagcga gcctccctcc tcagcctccc
16741 acagcactgg gattgcaggc atgagccact gtgcctggcc tgtcattcct tcttttgaca
16801 aatatttact gagtgctttc tacgcaccgg tcatcctccc agtccccagg aataaagcta
16861 tacacacggc aaactggatt tctcctcttg gggagcagag ggtctaatgg ggcaggggga
16921 ctgaaaatta gcaagtaaat agacaggctt tttaaaaaag taaacaaatc atttcaaatg
16981 tgaaaaaaag caaacggggt ccttcatgca gatgtggcta gagaggaaag agaactgctt
17041 aatttatttg gtcactttac cagattttac tgactttttt tttttttta actttattaa
17101 gcttttcttt tttcttgaga tggagtttcc atctgtcacc caggctggag tgcagtggtg
17161 cgttcttggc tcaccgcaac gtccacctcc tgggttcaag tgattctcct gcctcagcct
17221 cctgagtagc ttggaattgc atggcatgca ccaccatacc cagctgatgt ttgtattttt
17281 agtagagaca gggtttcatc atgttgccca ggctggtctt gaactcctgg gctcaagtga
17341 tccacccatc tcggcccctc aaagtgctgg gattacaggc atgagccacc atgcctggcc
17401 taggcatctt tttaaaaaaa tcaaaacatt tttctatgta gcaaaataac attgcattga
17461 acagagttat agcgattccc tagcgtcatt gaatacccag ttgattttca cgtttctcta
17521 gttgttctaa agatgtcctt cactgctgct ttattccaac caggatccag ttcaagaccg
17581 ggctttgtac ctggttatta tatatatttt atttatttat tttagaaaca aggtcttgcc
17641 ctttcgccca gtttagagtg cagtggtgca atcatagctc actgcagcct ccaaactcct
17701 tggctcaggt gatcctcctg cctcagcctc ctgggtagct ggaactacag gtgcacacca
17761 ccacacctgg ctaattttta aattttttac ggagatgggg gtctcgctat gttgcccagg
17821 ctggtctcaa actcctggac tcaagcgatc ctccctcctt aacctctcaa agtgctggga
17881 ttacaggcgt gagccaccac gcctgctgat tattatattt tcgagcctct ctaaatcttg
17941 agcagttcct catgatgaca ctgacacact gaagggttag gtcccttgtc cgcctgaatg
18001 tcttgatttc tggatttatg aaattcttct tatgggatca tttagcttgt ctctctgtat
18061 ttcctgtaag agaagctcta tctgatgtgg ggttttttttg gttttgtttg tttgtttttt
18121 gagatggagt cctgctgtcg cccaggctgg agtgcagtgg cacaatctcg gctcactgca
18181 acctccgcct cctgggttca agagattctt ctgcctcagc ctcctgagta gctgggacta
18241 caggcgagtg ccaccatgcc cagctaattt ttgtattttt agtagagaca gggtttcacc
18301 atattggcca ggatggtctc gaacttctga cctcgtgatc tgcccaccac ctcagcctcc
18361 cacagtgctg ggattacagg catgagccac tatgcccggc taatttttgt atttttagta

Fig. 61G

```
18421 gagacagggc ttcgccatgt tggccaggct gatctgaaac ccctggcctc aagccatcca
18481 ccctccttgg cctcccaaag tgctgggatt aaacgcgtga gccaccgtgc ctggtcgaag
18541 agacagaaag ggtcttaaag gttcagtgac acacacctgt aatcccagca ctttgggaag
18601 ctgaggctgg tggatcactc gaggccagga gttagagatc accctgggca acatggtgaa
18661 accccgtctc tacacaaaat acaaaaatgg gcagagcatg atggtgcata tctgtagtcc
18721 cagctactcg ggaggctgag gcgggaggat cacttaagcc tgggagatcg aggctgtagt
18781 gagccatcat tgcactactg cattccagcc tgggcgatcc catctcttaa aaagagagag
18841 agatgggaag accagcacag gtgaaactgg tgaacagagg agagatggta gatgctgcat
18901 tgggcagtgt gacgggaacc cgctggaggg ctttggcagg agagtagttt aagaggatcc
18961 cagctgggca cagtggctca cacttgtgat cccagcactt ggggaggccg gggcaggtgg
19021 atcacttgag gtcaggagtt cgagaccagc ctggccaaca tggtgaaacc ctgtctgtac
19081 taaaaataca aaaaccagcc aggcatggtg gtgcacccct gtaatcccag ctactcagga
19141 gactaagaca ggagaatcgc ttgaactcag gaggcagagg ttgcagtgag ccaagatcac
19201 gccactttac tccagcctgg gcagtagagc gagactccat ctcaaaaaaa taaataaata
19261 aaaagacctc tttgctgggt gctagggagc aagagcagga gctgggagag gcctgcagca
19321 gaagcctgtt gccagcatcc aggccgtggg gtgaagggaa gggtttggat ttgggacatg
19381 tcttggaagc atcaccagca gaacttgctg atggattgga agtggctggt gagggagaaa
19441 agggggtcaa aggaaactct gaggtctata ccctgaccat ctggcaagtg gtggtgttgc
19501 cacaaactga gcggggagta gggcaggtgc aggtctggag gatggattca aaattcagtt
19561 tttggagtct atgtccctgg ttctgtaggg ctgcagatgg tctgccaaat cttagcggaa
19621 cccagaatac gggatttgtt tactgtctgt gacttgttgg tttccctggt gagagcaaac
19681 tctttaaagg tcaaggttgg gcttcagacc ttggtttttg caccgatcat tggtcatact
19741 gcagttcctc actcttctct tgcaaatcca tacacagcta gtccaagaga gctgaacagc
19801 tttgtggttg gatcagcacc aatgtatctc cacctgtaga cgggttgctc aggtgactca
19861 tgcctgtaat cccagcacct tgggaggcca aggtgggaag attgcttgag gccaggagtt
19921 ggagacaagc ctgggaaaca cagtgagacc ccatatctac caaaaaaacc cctttgtttt
19981 aattagccag gtgcagtggt gtgcacctat agtcccagct actaaggagg ctgaggcaga
20041 aggatcattt gagcccagga gtttaaggct gcggtgaacc atgatcgtgc cactgcactc
20101 caacctgggg gaaagaaaga gaccttgtct ctaaaaaaac taaaaaacag aaaagcattt
20161 gttgagtatt tcctgggtat aaagcagtgt accaggttaa atggaaggaa aagttgaaat
20221 aatttttcaa ctcataatcc gattgggaga gactgaatgc ttaccattga agcaggaacc
20281 attgtaagca atgtgttgtg atactgtagc aagagctgag aaaacttggg aaaagagaaa
20341 ggaggaaggc tcacctgagg gagttggggg gcttgcccta caggtgagtt gtgaggtggg
20401 tctggaagtg acagatgcag tttaggaagt ggacgggagg ctgggtacgg tgactcaaca
20461 tctgtaatcc cagtgctttg ggagacccag gcggaaggat cgcttcaggc caggagttaa
20521 agaccagcct gggcaacata gtgggaacct atctctacta aaaattaaaa aattatccag
20581 gcataatggc acatgcctat tgttccagct actcaggagg cttgcctgag cccaggaggt
20641 tgaggctgca gtgagctatg atggcaccac tgcactccag cctgggcgac agaacaagac
20701 cctgtctcta aaaaaaaaag atgtggatgg gagggggaac ggtgggtggg ctgtcctcac
20761 caagcccccca ccctatctgc tctccagcta aacgacggac agttcacagt catccagctc
20821 gtgggcatgc tgcggggcat cgcctcgggc atgcggtacc ttgccgagat gagctacgtc
20881 caccgagacc tggctgctcg caacatccta gtcaacagca acctcgtctg caaagtgtct
20941 gactttggcc tttcccgatt cctggaggag aactcttccg atcccaccta cacgagctcc
21001 ctggtaatgc tgggggtaat actgggtgtg agcttcttag ggccaggtgg gcagggcagg
```

Fig. 61H 21061 ttggaaaggt gggaggctga gggtttggca gccctgctcc agggagagga tacaggagca
21121 ggctgtgggt ggggggacag tcagctccag gaagccgact tccagatgtc taggaaaata
21181 acagttggat aacctgggca acatagcaag accccatctc tacaaaaaaa ttaaaagatt
21241 agccaggcgc agtggcatgc acctgtagtc ccagctactt gggaggttga ggcaggagga
21301 ttgcttaagc ccaggagttg gaggctgcag tgagctatga atgtgccact gtactgcaga
21361 ctgggcgaca gagcaagacc ctgtctcaaa agaacagtgg ccaggtgtgg tggctcacgc
21421 ctgtaaatcc agcactttgg gaggctgagg caggaggatc gcctgaggtc aggagttcga
21481 gaccagcctg gccaacatgg gaaaaccctg tcgctactaa aaatacaaaa ttagctgagg
21541 gtggtggtac acgcctgtaa tccgagctac tcaggaggct gaggtaggag aaccagttga
21601 acccgggagg cggagtttca gtgagccaag atcgcaccac tgcactccaa cctgggcaaa
21661 cagagttgga gagtaggagg cttggggcct gagctagggg gaaaaagcag aggcaggtgg
21721 gggactgggg ggcagtgtgc tgggtctggt gagtccctca gtgagtcccc cagctcacct
21781 tttctccttt ttctgcaggg aggaaagatt cccatccgat ggactgcccc ggaggccatt
21841 gccttccgga agttcacttc cgccagtgat gcctggagtt acgggattgt gatgtgggag
21901 gtgatgtcat ttggggagag gccgtactgg gacatgagca atcaggacgt aagtgtcccg
21961 tggtcctacc aagctttcct cgagtgttct ctcacctggg atttggggtg aagggtgggt
22021 tcccagagag tcatcactgc tgggttcttg agaccatgga gatgacaaaa aggagaattg
22081 atctttgtat caaagagttg agatacaggg ccaggcctag tggctcaagc ctgtaatccc
22141 agcactttgg gaggccaagg tgggcagatc acctaaggtt aggagttcaa gaccagcctg
22201 gccaacatgg tgaaaccccg tctctaaaaa aatacaaaaa attagcccag catgatgggc
22261 gggtgcctgt aatcccagct actcaggagg ctgagacagg ataatcgctt gaacccagga
22321 acagaggttg cagtgagctg agatcacgcc attgctttcc agcctgggca actgagcgag
22381 actctgtctt aataaataaa taaaagagtt gggtacagca tatttgggtc gcagaaggat
22441 gcagagatgg agggcagggt tgagaggtaa catgtctgta tcatagccca agagctgctg
22501 gggccttcag ccacagagag cttcaactcc ggctaggagg attcctggat ctgttatttt
22561 ttggggggct gtggctccta tcctaccatc ttccaagtca ccatttcctg ggcctgttag
22621 catctttgct tttcctggac agcctcaccc agagcttctt cccctcttc caggtgatca
22681 atgccattga acaggactac cggctgcccc cgcccccaga ctgtcccacc tccctccacc
22741 agctcatgct ggactgttgg cagaaagacc ggaatgcccg gccccgcttc ccccaggtgg
22801 tcagcgccct ggacaagatg atccggaacc ccgccagcct caaaatcgtg gcccgggaga
22861 atggcgggtg aggactgcag agaatgggcc ctccttcccg ctctctgccc ccactccttg
22921 cccagaagtg tccgttcatt ggtgttgggt gggagggcct ctgtccgcct ctgcaaggct
22981 gggttccacc tcctcccccg gacctgggcc tggtactcag cattcctccc catccttgcc
23041 ccctagggcc tcacaccctc tcctggacca gcggcagcct cactactcag cttttggctc
23101 tgtgggcgag tggcttcggg ccatcaaaat gggaagatac gaagaaagtt tcgcagccgc
23161 tggctttggc tccttcgagc tggtcagcca gatctctgct gagtaagcag tggcaggagc
23221 tggagtgggg ctgggagagc ggggcagctg gagtcaggcc cacggggtct ccaggggctt
23281 ttggggtcag cttcgggtgc caatgctgtc ttcttgcact gcgctcatgc catgcctaga
23341 agggccccag aggagcagtc acagccccat ggagctgagg acccaaggac tctttggggc
23401 cagcctgccc gcctcacctc ctcctgccat cacagccctg ggccatcgcg cttccgcctc
23461 tcacttctag ctatctttgt gcatctatct gcattccagg cccggctctc acggtaacaa
23521 tgtgtcaact cgggttctct ttttccaacc ataaaaggag aagattgggc taggttttgg
23581 agatcctctt cagcttttat gtgaaatggt tttatgattc cttgcctccc aaaggctgcg
23641 tatccccact tggcctttgt ctgctactcc ccctttctgc cttcccgttc ctctcccaag
23701 atctcctctc accccaggtt gaataacaga aatagaagga atagaaatct gaaggccggg
23761 catggtggct catgcctgta atgccagcac tttgggaggc cgaggtgggc agatcacttg

Fig. 61I 23821 aggttaggag ttcgagacca ttgtggacaa cttggtgaaa ccttatgtct actaaaaata
23881 caaaaattag ctgggcatgg tggtgcgtgc ctgtaatacc agctactgag gaggctgagg
23941 caggagaatc gcttgaaccc gggaggtgga ggttgcagtg agccgagatc gcaccactgc
24001 actccagcct ggatgacaga gtgaaattcc atctcaaaaa aaaaaaaaaa aaaaaaaaag
24061 aaatgtgaag gccaggtggt ggctcacgcc tgtaatctca gcactttggg aggctcaggt
24121 ggaccgattg cttgagccca ggagtttgag agcagcctgg ccaaaatagc aaaacccccat
24181 ctctacaaaa caaaaacaaa aaaattagct gggcatggtg gtgcgtgcct gtggtcccag
24241 ctactcagga ggctagagcc agagggtctc aggccagtct gcccctgccc cacggggcct
24301 gggcacatcc ctccctaatt cttcccagcc tctctctgac ccagggggcc tcctctccct
24361 tttttcccct tatctcagcc tccagccatc agcaacctcc tcttcctctc cacccagctc
24421 ttcctctccc acttcggcct tttctttctc acactccatt tccctctacg gcaatctgtg
24481 cagcctcttc ccccagtctc attttgcggg cttttctctc ttttctttcc ttccctggca
24541 cccaagccaa aggccctgcc tctggcctcc agccctaccc ccttctgcgg ttgcacagaa
24601 ggatggctgc ccagctctta aaaaaactgc ccgggaactg ttgacatctg ttctccctcc
24661 cccgctggct tttctgattg gcttacaatc ctgaggctag gaccgtctca ggagccaaga
24721 gaggagagcg gccacaggga acctagggtc tcaccaagct ctcctttcct tctgcaggga
24781 cctgctccga atcggagtca ctctggcggg acaccagaag aaaatcttgg ccagtgtcca
24841 gcacatgaag tcccaggcca agccgggaac cccgggtggg acaggaggac cggccccgca
24901 gtactgacct gcaggaactc cccaccccag ggacaccgcc tccccatttt ccggggcaga
24961 gtggggactc acagaggccc ccagccctgt gccccgctgg attgcacttt gagcccgtgg
25021 ggtgaggagt tggcaatttg gagagacagg atttgggggt tctgccataa taggagggga
25081 aaatcacccc ccagccacct cggggaactc cagaccaagg gtgagggcgc ctttccctca
25141 ggactgggtg tgaccagagg aaaaggaagt gcccaacatc tcccagcctc cccaggtgcc
25201 cccctcacct tgatgggtgc gttcccgcag accaaagaga gtgtgactcc cttgccagct
25261 ccagagtggg ggggctgtcc caggggggcaa gaaggggtgt cagggcccag tgacaaaatc
25321 attggggttt gtagtcccaa cttgctgctg tcaccaccaa actcaatcat tttttccct
25381 tgtaaatgcc cctcccccag ctgctgcctt catattgaag gtttttgagt tttgtttttg
25441 gtcttaattt ttctccccgt tcccttttttg tttcttcgtt ttgtttttct accgtccttg
25501 tcataacttt gtgttggagg gaacctgttt cactatggcc tcctttgccc aagttgaaac
25561 aggggcccat catcatgtct gtttccagaa cagtgccttg gtcatcccac atccccggac
25621 cccgcctggg acccccaagc tgtgtcctat gaaggggtgt ggggtgaggt agtgaaaagg
25681 gcggtagttg gtggtggaac ccagaaacgg acgccggtgc ttggaggggt tcttaaatta
25741 tatttaaaaa agtaactttt tgtataaata aaagaaaatg ggacgtgtcc cagctccagg
25801 ggtgatgggg gtgatggact agatttctaa ggagagtggg gctgggtagg gagggctttg
25861 tggctgaccg agaggtgtca gaggtctgga ggctgcaggg ctgtaggggc tggaacttgg
25921 ttatcagccc cagggtatgt ttgaggtggt ggggtggggg ccgagcgaga tgaatcattc
25981 gcagctgctt ctaacgtctc

Fig. 61J

EphB4, mRNA

```
   1 ctcggcccgg cggcgcgagc agagccactc cagggagggg gggagaccgc gagcggccgg
  61 ctcagccccc gccacccggg gcgggacccc gaggccccgg agggacccca actccagcca
 121 cgtcttgctg cgcgcccgcc cggcgcggcc actgccagca cgctccgggc ccgccgcccg
 181 cgcgcgcggc acagacgcgg ggccacactt ggcgccgccg cccggtgccc cgcacgctcg
 241 catgggcccg cgctgagggc cccgacgagg agtcccgcgc ggagtatcgg cgtccacccg
 301 cccagggaga gtcagacctg ggggggcgag ggccccccaa actcagttcg gatcctaccc
 361 gagtgaggcg gcgccatgga gctccgggtg ctgctctgct gggcttcgtt ggccgcagct
 421 ttggaagaga ccctgctgaa cacaaaattg gaaactgctg atctgaagtg ggtgacattc
 481 cctcaggtgg acgggcagtg ggaggaactg agcggcctgg atgaggaaca gcacagcgtg
 541 cgcacctacg aagtgtgtga cgtgcagcgt gccccgggcc aggcccactg gcttcgcaca
 601 ggttgggtcc cacggcgggg cgccgtccac gtgtacgcca cgctgcgctt caccatgctc
 661 gagtgcctgt ccctgcctcg ggctgggcgc tcctgcaagg agaccttcac cgtcttctac
 721 tatgagagcg atgcggacac ggccacggcc ctcacgccag cctggatgga gaacccctac
 781 atcaaggtgg acacggtggc cgcggagcat ctcacccgga agcgccctgg ggccgaggcc
 841 accgggaagg tgaatgtcaa gacgctgcgt ctgggaccgc tcagcaaggc tggcttctac
 901 ctggccttcc aggaccaggg tgcctgcatg gccctgctat ccctgcacct cttctacaaa
 961 aagtgcgccc agctgactgt gaacctgact cgattcccgg agactgtgcc tcgggagctg
1021 gttgtgcccg tggccggtag ctgcgtggtg gatgccgtcc ccgcccctgg ccccagcccc
1081 agcctctact gccgtgagga tggccagtgg gccgaacagc cggtcacggg ctgcagctgt
1141 gctccggggt tcgaggcagc tgaggggaac accaagtgcc gagcctgtgc ccagggcacc
1201 ttcaagcccc tgtcaggaga agggtcctgc cagccatgcc cagccaatag ccactctaac
1261 accattggat cagccgtctg ccagtgccgc gtcgggtact tccgggcacg cacagacccc
1321 cggggtgcac cctgcaccac ccctccttcg gctccgcgga gcgtggtttc ccgcctgaac
1381 ggctcctccc tgcacctgga atggagtgcc cccctggagt ctggtggccg agaggacctc
1441 acctacgccc tccgctgccg ggagtgccga cccggaggct cctgtgcgcc ctgcggggga
1501 gacctgactt ttgacccccgg cccccgggac ctggtggagc cctgggtggt ggttcgaggg
1561 ctacgtcctg acttcaccta tacctttgag gtcactgcat tgaacggggt atcctcctta
1621 gccacggggc ccgtcccatt tgagcctgtc aatgtcacca ctgaccgaga ggtacctcct
1681 gcagtgtctg acatccgggt gacgcggtcc tcacccagca gcttgagcct ggcctgggct
1741 gttccccggg cacccagtgg ggctgtgctg gactacgagg tcaaatacca tgagaagggc
1801 gccgagggtc ccagcagcgt gcggttcctg aagacgtcag aaaaccgggc agagctgcgg
1861 gggctgaagc ggggagccag ctacctggtg caggtacggg cgcgctctga ggccggctac
1921 gggcccttcg gccaggaaca tcacagccag acccaactgg atgagagcga gggctggcgg
1981 gagcagctgg ccctgattgc gggcacggca gtcgtgggtg tggtcctggt cctggtggtc
2041 attgtggtcg cagttctctg cctcaggaag cagagcaatg ggagagaagc agaatattcg
2101 gacaaacacg gacagtatct catcggacat ggtactaagg tctacatcga ccccttcact
2161 tatgaagacc ctaatgaggc tgtgagggaa tttgcaaaag agatcgatgt ctcctacgtc
2221 aagattgaag aggtgattgg tgcaggtgag tttggcgagg tgtgccgggg gcggctcaag
2281 gccccaggga agaaggagag ctgtgtggca atcaagaccc tgaagggtgg ctacacggag
2341 cggcagcggc gtgagtttct gagcgaggcc tccatcatgg gccagttcga gcaccccaat
2401 atcatccgcc tggagggcgt ggtcaccaac agcatgcccg tcatgattct cacagagttc
2461 atggagaacg gcgccctgga ctccttcctg cggctaaacg acggacagtt cacagtcatc
2521 cagctcgtgg gcatgctgcg gggcatcgcc tcgggcatgc ggtaccttgc cgagatgagc
2581 tacgtccacc gagacctggc tgctcgcaac atcctagtca acagcaacct cgtctgcaaa
```

Fig. 62A

```
2641 gtgtctgact ttggcctttc ccgattcctg gaggagaact cttccgatcc cacctacacg
2701 agctccctgg gaggaaagat tcccatccga tggactgccc cggaggccat tgccttccgg
2761 aagttcactt ccgccagtga tgcctggagt tacgggattg tgatgtggga ggtgatgtca
2821 tttggggaga ggccgtactg ggacatgagc aatcaggacg tgatcaatgc cattgaacag
2881 gactaccggc tgcccccgcc cccagactgt cccacctccc tccaccagct catgctggac
2941 tgttggcaga aagaccggaa tgcccggccc cgcttccccc aggtggtcag cgccctggac
3001 aagatgatcc ggaaccccgc cagcctcaaa atcgtggccc gggagaatgg cggggcctca
3061 caccctctcc tggaccagcg gcagcctcac tactcagctt ttggctctgt gggcgagtgg
3121 cttcgggcca tcaaaatggg aagatacgaa gaaagtttcg cagccgctgg ctttggctcc
3181 ttcgagctgg tcagccagat ctctgctgag gacctgctcc gaatcggagt cactctggcg
3241 ggacaccaga agaaaatctt ggccagtgtc cagcacatga agtcccaggc caagccggga
3301 accccgggtg ggacaggagg accggccccg cagtactgac ctgcaggaac tccccacccc
3361 agggacaccg cctccccatt ttccggggca gagtggggac tcacagaggc ccccagccct
3421 gtgccccgct ggattgcact ttgagcccgt ggggtgagga gttggcaatt tggagagaca
3481 ggatttgggg gttctgccat aataggaggg gaaaatcacc ccccagccac ctcggggaac
3541 tccagaccaa gggtgagggc gcctttccct caggactggg tgtgaccaga ggaaaaggaa
3601 gtgcccaaca tctcccagcc tccccaggtg ccccccctcac cttgatgggt gcgttcccgc
3661 agaccaaaga gagtgtgact cccttgccag ctccagagtg ggggggctgt cccagggggc
3721 aagaaggggt gtcagggccc agtgacaaaa tcattggggt ttgtagtccc aacttgctgc
3781 tgtcaccacc aaactcaatc atttttttcc cttgtaaatg cccctccccc agctgctgcc
3841 ttcatattga aggtttttga gttttgtttt tggtcttaat ttttctcccc gttccctttt
3901 tgtttcttcg ttttgttttt ctaccgtcct tgtcataact ttgtgttgga gggaacctgt
3961 ttcactatgg cctcctttgc ccaagttgaa acaggggccc atcatcatgt ctgtttccag
4021 aacagtgcct tggtcatccc acatccccgg acccggcctg ggacccccaa gctgtgtcct
4081 atgaaggggt gtggggtgag gtagtgaaaa gggcggtagt tggtggtgga acccagaaac
4141 ggacgccggt gcttggaggg gttcttaaat tatatttaaa aaagtaactt tttgtataaa
4201 taaaagaaaa tgggacgtgt cccagctcca ggggt
```

Fig. 62B

EphrinB2 Gene

```
   1 gcgcctcgga gctgcctgcg ggcgcacgcc gtcttccccg ccagtctgcc ccggaggatt
  61 gggggtccca gcctgcgtcc cgtcagtccc ttcttggccc ggagtgcgcg gagctgggag
 121 tggcttcgcc atggctgtga gaagggactc cgtgtggaag tactgctggg gtgttttgat
 181 ggttttatgc agaactgcga tttccaaatc gatagtttta gagcctatct attggaattc
 241 ctcgaactcc aagtaagtgg cgtccgcgat cccccctatgt ccccgccccg gggtccgccg
 301 cgccgtccgg gcgggaggag gggtcagtcc gcggggcctc ggagcctgtt tctggaacct
 361 cggttccccg tcccccaccc ccaacccccg ccccatttca ctaggtggag actcctcgct
 421 cggctttcca acccgagccc cgctggaacg gacggtctct ccgcctttcc tccccgaac
 481 gctcccaggc gctaaaagct actatcggct cgggtgtcaa gtccgggaag gtgtccgatg
 541 gcgatacctg accctctcct gttttcgagg acgaaggaca tggccacaat ctaggctggc
 601 cggcacgcgg ggactggtgg gctctggaga gaggcggaga tgctgcattc gcggggagcg
 661 cgggcggcgt ggtccggggc ccgcgggcgg gcgaccgggg tggcaggacg ctggcagcga
 721 agcgcgttct ggagagggga gcctggagtc gctacgctgc ccgcagagcc ctggagccgg
 781 ggcgccttgg caccgcgccg ccagcccgag ggtgcgcggg gagctcgcct gcttcgcagg
 841 agaactcggg cgtcgagccc tttcctccgc gccggggaga cgggccttag gcttctccct
 901 gagggcccgc cgcacctcgg cctcccgctt cgttcataag ccggtagccc cggagtatgc
 961 ggtctcgatg gccgacctga ttgtaatgca cttcctataa aagcttaggg ccctgcccag
1021 tcgacactgc tcctgaagcc ttctccctcg ggaccctggt aggaatggga tccttaggat
1081 cagatttgct cttaccggac tctacagccg ggagcgagcc aggccttgtg gagagtaact
1141 ttcagtttgg gccaccagag tgcattcaga atttagaaaa tcccatccat ccctaaatct
1201 gtgtggtcat aactcgtagt catctgggta ttcagtactg tgtatcccct tatttcgaat
1261 cacagccaaa acatatttta cagaatcttg gaattgtagt ctcgggaaac ttggagaaga
1321 agtatgcaga cattagctgg tttctggaga aaacgtttga gatcagaagc aaaatcaatg
1381 gcctaattga agttgagcaa gttgggcctg gttttaggag aaaagaaatg ggggattgat
1441 ttagaaatca cgtcttaaag gagtgtgtcc attctcttaa aagtgtcaaa tttcaaattc
1501 actaacatgt taaccaagaa tcccttcatg aaaagggcga aaacgtcggt tacaaatcgg
1561 tttaaacaaa tgtttgtatg atgctagaag gcactttcaa caccgctcat acggagaagt
1621 tacttagctc tgcctccttc catgtagtct gctcttgcat ggattatatt tttaatgtaa
1681 attgttgtat ttgctgatga agtactggcg gcggcatctt tgcatcgatg ccggctcggg
1741 aggcgccagg tggtgccgga aggagccggg ctaggacctc gcgcagcagc gggtcccgga
1801 gtccgggaga ggcgggcggg cgggcgaggc ggtcgcgggg agcccgcggc gccgctgccc
1861 gcccggtgcc tccagaggtc actcttccat gcggaatcgc gcagcgccag gcctcgcccc
1921 tcccccaggc cgcctgctcc agccactctg cactttcact gaccggttct ctttgaggct
1981 gttttttttt ttcttatgag gatttaatat ttctgtttaa atctagttga aagcaattcc
2041 gttagcctct tcagcgttta gttcggtgtg tgtatcttta tctttgcgct atattaacta
2101 ttagtttgtg tgtatccggt aggagaatta gaaataccta gttgggagaa aaagaaaagt
2161 agaacaatag ttatttcaac ctaaggttta gacgttaata acttcttttt gtaatgtgtc
2221 gagatggggg gtcctggggg gaggtgacag gtactcacca ctcccccccc ccattctgat
2281 gatgaagatg agtctgtctt tccagctatg tccagacctg cgagggccct gcgtttctgg
2341 aagcctgccg tttgcgcggt tgaggttgct gctgctgtct tgtcctccac agcagcattt
2401 cttttaaaat tctcctgata acggcctgcc tggatgactg gataatgtgt gcctggaaaa
2461 ggtctccctt gcagctgaat gctagctcca gagatcagaa agatttcttc ctgtaggagc
2521 cataggaaag agtcctctct aagtttttga gaatgcatac aacccctga tgacaggggg
2581 tcgctttcct tggggaagtt ttatatttat ttccagagga aagtttgaat cggtaaatat
```

Fig. 63A 2641 gatgtggcag gaaggtaatc aaatgcattg aagtttcaca tcagttccta tgaactgtgg
2701 aacaattcat ttgtaatgaa gccgccatca gtaattagat ttgtttcatt cagaggtcag
2761 ctttttttagc aggtggtcga cacagggagc atgcagcagc tgtttggata cagggtccag
2821 aaaacccttt gtaaattcag cgtctccgta actactttaa tcacattgtc ggctctcccg
2881 tccctgactg tatgtaataa tggaaagatg tcctgcgtgc tgaaacagta gctgccctgt
2941 taggttattc acattgcttt gatacgttct ggtagagttg ggtccgttgt agccattttg
3001 gttgtttaaa gttttggttt tttttttgtt tttttttaa ttcagcagag aacagtaatg
3061 cctagcttcc gtttttaact taacacttca gtagaacatt ttcttccaag agggagattt
3121 tggcctaagt aaagtagtgg gctcttttttt aaaaaaaaat taattttact ttaatgtgag
3181 caaatctgta ttggtatggt gttctgcaat gcattacact gactttgaaa atttcgagta
3241 ctaatgcctt atgtctgggg ttaccattcc ctgtgcatca catactagtt agttaacata
3301 gcattttgct tttcccatgt aattttttcc ctatataata ctggattcct gatactaatt
3361 gacttgatac aaaagaatgg ctggatgata tccagataac gtataataca tgggcttcac
3421 cacaatcagg ctctgaataa atacagacct gtcagagatt gataaaataa actacaatgg
3481 atagtgctgt ttaaacagtc cattcaataa catatataag ccagcctgcc ttccattgtg
3541 tctgaaattc ttatttttgt aggtaaacaa atgcacattc agcactgatt gaatagcccc
3601 ttgaactatg ctccacagtt tgcgtttggg ttaatcttgt cggttttaat atagagagaa
3661 aaaagctcaa agcaccaggg gtggaattgt tagtgctttc acatccacat tcctcacatt
3721 ttgtcaggat gataaactgt aggtaatgga ctgtcgttgt tctgcaggac aactgagcca
3781 ggcagagcac aaagactaag ctaaagcgat acctcacaac atgcttggta gccttctttt
3841 cagatgagaa tttatttgag aatcatgtgt ctagggactg cacatcttaa cctcaacagt
3901 tacagcttca agccccagaa acaggagctg gaggttaaga tgatttgcta agcacctggt
3961 tctaaatctt ttacaaagca taagctgttg acgctggttc tgccgacgca aagacatgca
4021 gatgactcca acatttccag aggcttctga cttaagctaa agtgtgtgga caggtgaatt
4081 cgccatgggc ctggagacca gcttgctaaa aactatgtgt ttgaatggtt cctccagaca
4141 gagtcagctg aagaacaatt ggtggattta tattaaaacc tcttgtctgt aaacttactg
4201 aggtgcatcc ttcggttggt ggatcagtga gataattgcc ttcagatgga cattgcaact
4261 ggagcaacta aatccttgct gtctttcctt cctctgaaat cttccaggta gctcccgaga
4321 gcttcagtat gacaccaaac ttcgggcgac gttttagagt gcgttcacct aatgggaaac
4381 tattcgagat cccagcgtga ctgcagtaat gcgtcatagg aatgggagtg gcaggggaaa
4441 aggaaataca gattgtagac cctaataaaa aaatttttag gaaagatatt tctttaacgt
4501 tttatgagaa cttcattctt aaaatactta attgcaaatt agacaaatag aagtgctctt
4561 ctaaggaagg tgattaaact ggtcctccta tcagcctaat ctctgcctgc ctttgctgct
4621 gacataaaga acctgttttt caggtcactt aatatacatc tacatagatt tgcttatgag
4681 ctcacccttt gtgtagcgga gtagagcctt aaagaggagt gctcaactgt ttaaaatatt
4741 ttgattaaaa tatgcagaac ccatagaact ataagcttct agtcaggaat tagctctttc
4801 agggaacagc tcccccttc tttttaaggg gggaattaga aggaggctgg gggaggaata
4861 taagaacagc aaagaaggaa ggatagcaaa tgggacatgt tccgaacagc ttggaaaaac
4921 tcctgtggct tcattgtctc tataaagcca aagaatacaa agacataagc aattcagccc
4981 ttctcccatg atggaagatg taaaccgttg acatgcctcc cctgtttaac ttgtttaatt
5041 ctcattttaa attcagcacg atactagccg tgtgaactct gaagatttct ttagtaatcc
5101 attttgtagt tccgaatcaa aaacaaagtg aaagggtctg acacaatttg cttttatttt
5161 taggcaaatc aaccctggtc atagttaata aggggattac aactcagact aggtctttac
5221 agatgtgatg taaatcaagg gcagagtata aagaaactga tccctttttga ttgaagtata

Fig. 63B 5281 gtaaaaaggc atagagaaac tagcagcagt aatctgattg tatggcaata aaaccaccat
5341 tttctgtctt tcagataaaa ataatgtggt aaatccatgc agttcataag atgtaaaggc
5401 agataaaggg tgaagccatg gcaacatata gattagcttg atgttagaaa tgacacgtct
5461 ctgaaaaggg cgcgggacga aggccccttgc ctccaggctg ttgggcatta tgtgagaacc
5521 acacagactt ggaaactggg attaggaagt atgaaagctc tacttgtggt ctgggatggc
5581 tgaggcagta aagaaaagct gctcagttct tgctcattgg tggtggataa tatggcaaag
5641 gtagatttca ttgactgcct tttttataga ttgagattgg ggctgattaa aacttcagat
5701 cactgcagtt gttagggcct gggagatttt cctttttaac tcctggccta acagcagcag
5761 ccgttctgta ggattaactg cacttcgcgg tcgttgcctt aatctatttg ggcttcaggc
5821 agggacatgc tgggaaggaa cagagaccag aggggatagg tagggctggg gttatctgaa
5881 aagaaaacag agacctttg atttcagcca tcttttcaga cccagctccc tctcccgctg
5941 catgggagaa gcaaaggtaa acaggacaca ttgtccctct ccctcagcca cagagctctt
6001 ctgtgagttt tgtctttccc accctggaaa aaaagataaa atacaatttt taaaagggga
6061 gggaggaatt tagttttaat tcaaatgagt agtaatccaa tatgccaaaa gcagtgggct
6121 ctacctagat gtaattttac tcgtaaatgt gagtcttaaa ctttgagttg aatggggcag
6181 gctgttagag gtggtgtaaa ttacaggatt ataaaaatgt tagtgctgcc cagccttaaa
6241 gtcaaaaaca gaaaaatctc tgtgctgttg agtcttcccg ccctctctcc tgaacaacct
6301 tgtaagtaag ctagactttt gtttttgcct tccatacttt ccatttcagc cattaaacaa
6361 aataagccat tgaaaccacg attgggttcc atgcagagtg acatccgcaa tcgggtcaag
6421 ccagaaggaa atacttgctc gattgccccc tatttggcat tacaggaaag tctccacact
6481 ttggaagagt ctgaactctc aagacattga aaatgccaaa ggctgcaaac accctgtgtc
6541 tttcttgatg gagtgcatct tggtgtgttt tacaaagggg aattcagtgc tgttttttg
6601 ttgttgttgt tgttttttt ttttaaagag cagcataggg cccttctaga ctcttggatt
6661 ctgtgtctga caaaaatggt cattaaatga gcaatattat aatttagacc catttcactg
6721 attttgttcc aaattctcaa ctgacttgag catctgtttg gggctgtaga tacattgccc
6781 ttgttgactg tttttctcgt ttctatggga attactgtag ccattactat gtagctttca
6841 tagactcaaa acatttttaa agtattgcat ataggctggc catatccagt gcctgttact
6901 ttaccttctt tttctaactt aatgcagcag tctgtattaa cagatccatt tcatttgtct
6961 agcttcatca gagagaggct accccctgat ttacaggctg ctcacatcca agcaccttgc
7021 attctacact tgacagtgat tgctaatggc ccattcaact aaagtatttg cttgttaaca
7081 gggaacagaa catgataaat gtccagcaag cttgctgcct ccttcagctt ttcaaacgca
7141 gactggtgca tatttatggc aggcaaatga caaaagaaaa agctgaattg ccctggcctc
7201 cagctttcta tcagaaacag ggttaaagtg attaaagcaa tcattcaaga aagccctgcc
7261 gtttgtttac taaccttcat ccaacattta gctttgtagt ctacctgtga gaagatattt
7321 cagaagtatt agagataagg aaggaggatc tagcaaacca gtgaaaagag taggtgacca
7381 gttataaaat gctttccatg cacattgaat gccaggcgaa cctatttctg ttattccagc
7441 agacaatcag cagtggctct agattattaa catattttcc tttcatgtat aaattcaaat
7501 atgtaattct agtccaaagc attctgtggc tggtaagcac atacttgctg atttcaaata
7561 agaaaacata gcaagggaaa gctccattaa acaagttgtt tctgccctta gtaattctct
7621 aaacaagata ggaagaaaaa gtggacagta gtggagtatt aatagtgtgc tcttttcatt
7681 ctctaaagca cgagtaagta agcgttcaaa ctactctgtg gtgggcatac atttagagcg
7741 ctgtgaatga accactgctg ttctgccata cttaatttat ttatattatt atttttattt
7801 tattgttgtt tttatgtatt attataatta tttatttata ttactaattt attttctcaa
7861 tttaaatcct gttgcatcca attttaatta cagtttttgt atctgccttc ccatacttgc

Fig. 63C 7921 tacccacgtc cccattgcca ctgcggcctt atccatgttt tctgtgtaca ccactctcgt
7981 atcaccccag aataattatg agtgctaccc agacttttga aaccactaga gtcaacatgt
8041 ttgtctttga ggaaagccaa tgatgcttta gcatttttgg caggggtgga tgtgtgttta
8101 agtggggtgg gtgcagctcc ttattgtctg cctattctac tgttgttccc aatccacatt
8161 ccctgcgggg cacctaacct gtgtgcatag caaagaattt ccgaccttca gagccagaag
8221 tgtttctcaa ttgatctctt ccagcctagg gttatagctg atgaattata atccttgctc
8281 tttccacacc tttacctggg cttaccatgg ccctaaaaca tttgcccaga atcagaattg
8341 tctcatgagt gagtggggca aggcaaatcc tgttccagac cagctgagaa tgtacctagc
8401 tgcagaagaa gttagaaagt gtcatctttt acttatctac cagaactata ttcgaggtac
8461 atttagatt taaaaaaaaa gcaagttctc gtaggccttg aatccccccc ttgctatggg
8521 aaaatggatc attattataa tggactgtcc agtaaagttc atgatttctc ctagacatgt
8581 tctctctctt tatgacctag atcaagagtg atctctttaa gtcttttctt cataatccca
8641 cagcactttg tacttagatg tacttagaaa gaaccatata cacggtacgt catgattgat
8701 atgcaagcct tcaccactct acctgtccta aaagtcaggg acacaccttc ttcatttcat
8761 cagtccctac ttctatccag cattggcatc cagtaagtat tagtggaatg gacagacaac
8821 ccgaatttgt gctgatggca gtttaccctg ttttaactgt catccttctg ctactagaca
8881 tggatgagac ctgagacgat gggactgctc agaggtccct ggctcttgaa ctttagggca
8941 ccagaatccc ctgcagggct tgagaaaaca ggggtttctg ggccccaccc ccagagttcc
9001 tgattcctga ggtctggggt ggggcttgaa gatggacatg tttaacaagc tcccaggtga
9061 cgctggcaac tgctgcctca gggccatgct gagaaccctc gccctacaca aacctttctg
9121 ggaaaacaac tcaacattaa agctgtttgg ggatctctga agaaatctgt agtccttgcc
9181 ttgttggggg agcatcaggg atctaaccat tgatggtgga gtatttgttg ttaattcagc
9241 aagcaactat taagtgttag gcctgttact cggctctaac aatacaaggc agagtgacct
9301 gtaccctcga gatttaaagt ctaagtcctg tagagagaag cccaggtggg agcaagcaca
9361 tttagagtta ggtgcttggt gcaaggtggg gacacagaag aagggaatgg catttgcctc
9421 tggaggggtc cggaaacagc ctagggagga ggagcttgag tcttgaaata ctgtgggcat
9481 ctctaagcaa agtcacagta gacagctgaa ataaagaaaa tagtaagcaa gccaaagaaa
9541 cagtatttca gccaagggca gcgtgtgtct atcacgtcca cctgtgaaca cgtcccagga
9601 ttctctgcat ccggccattg ctcaagacag atccctcaca ggaacagcta agccactgat
9661 ttcagctacc tgttcacgtg agaattatca gtacctactg cttttcaaaa tgagtatgat
9721 catggatagg tgaggcaatt cagtttcgca gagacagtag ggcaagtgcc actgtagttt
9781 agttaagggc acatgcttta gagtttggct atgtgagtcc aatcccagtt tagccattta
9841 ttagctgggt agctttagga gcagtagcct tagtgtctct cagttgtccc atctctataa
9901 tagggacaat aacataatag tgctgaataa aagagtaaca aaattttggt caacatttaa
9961 tgtatttaaa gagctaagct ccgtgattgg cacaatgaac caatcaatca aacaccagtt
10021 gttattaata aaagtcagtt gaatatgtac tgtgtgcctg gccgtggttc aatttgcctt
10081 tgcatacaag gaaaaaatta aaatactctg ttaataaaga ctatagcata atactttcac
10141 cttaaacttc ttgatgttaa tttattttgt ttacctgcca aacttctact cattccttat
10201 gactttctgc tacatgaaac accctttgta attcttttgt cctattaaat taagttctct
10261 ctcctctgct ttcctgcttt tggtgctttc taataacact tttaaccctg gactttctca
10321 ttcagctgtg caactgtgga ctgagaggag gctctttgaa ttcattttgt atattctagt
10381 agagagtact gtgagcagtt gggttgttga atgaatacat taattcaacc tggagggatg
10441 ggcagtattg catttttttac attgatatta catgatattt agaaaactgc ttaactggtg
10501 gacgttgttt tattaacagc atttgtgtat tagcactcac tatgtgccag ctgctattct

Fig. 63D 10561 aactgcctga caaatactcc tgaaaccttc atggtaacca tatgagggaa gcacttttaa
10621 tatatccata ataccaacgg ggagactgtg gccaaattgg ttaattaact tagccaaagt
10681 catattgaac taataagtgg atttaaaccc agctagtctg ggccagggt ccctctttta
10741 atcttctgcc tcctgcttat gctgttgcat ggagtagtct ttatcatata actaaattaa
10801 gcatgcattt gcttaaagca gtgcatacat gatggatcaa aaagtttgtg gtataattgg
10861 tttaattctg tcattatcca ttttgattta tagtcacttt cttatgatgg tcgtgtagtt
10921 ttaaatggaa cctttgaatc tttgatataa taaggttatg tcaaatcttg ggtataataa
10981 ggttataccc aatggaaaca gaataatgat cagcccattt aaaggatgac tggagagtta
11041 ttacaataca taatagtcat gcatatattg agtagtattc ctttggtaac attttccttt
11101 taaaaattgt aacatttgat tgttccttgt tgggagaaaa ggaggtcaga tttttgaggg
11161 gagatccatt tggtgagatg ctgagtgtgt gtcaagctaa ggagatagta tgacatcttt
11221 tttagagtct agtcacaatt aaatgccatt ttattttgga ttttgggatc cgtgccagct
11281 tccagcttgt cagagctgag aagactcaaa tcaagtccag gcttatttct acagcaaact
11341 gggattctgg cttcttgccg gtggattcat tcagtacagc ccatctggct tttgatgttc
11401 tgcaagtttg gagccatttg ttgaaggaag ccaggcggtg aatattggtg gtcctggggt
11461 tctcttgact ccaagtggtg cccccttggtt tgcattttca ccatgcttag catctgctta
11521 cctggagacc atgcagccgc cggccagagg tctccaacaa ccaaatcttc atgcctttta
11581 gaactcagag tccccagcac atcctccttc ctcctccttg tccaattact ttcatgcagt
11641 tctcagtagc tgcttgtttg aatcacttat agtatttaac ttctagggtg tttttgggtt
11701 ttggtcaagg taattccagg ctgaatgtgg tgactaagca ggaaataaat gggtcgtcct
11761 caaagttaca gtggagcgct gtttctattt tcctaaggta cacagttgtg ggggcgatcc
11821 gtatggaagt caggaaccca gtctgatttt gcttcctttt gatggtagca gtacagacct
11881 ggctgttttg tagcctgctt tgtttttctt ccttttcttc cctaacttca cgggctgtgg
11941 caaagccctg agacgtgcag gaaaatgtct cctgtcatac gcccacagca gacctagccc
12001 tgaccctcct ctgaagccca ggaaggaggt atctgtgaag cagcctgctt gtaaagcaat
12061 tgcacacagc cttgtaaact gtgttactgg gctgattata cttgattggc aaggtgaatc
12121 tcttatagca aaagagaact tggagagttt tatctcatct tatgccttat taatttgttc
12181 attctttaat tacacagcca cctattgagc accctattta tgcaaggtac ctggtcgggg
12241 gtcagaggga gggtcccatg gtaaacgaga cagactcaat cctggaggag caggaatggc
12301 agcccctcgc tgggctgttg gccccaccaa aagggaaagg tttcatttta ataatacatg
12361 ggtgaatcat ttttgtcaat aggcaaaatt ctttgtagtt aaaaaaaaat atgatggtag
12421 gaaggaaagg gatgggcaga gggttaaaac aaaagatatg ctctccctaa ctctagattg
12481 tagtattgtt atgcttgtca ctgtagctga attccatttc tttgagtttt ttcaatgcca
12541 aggcattccc tgtatgactt acgtgagcct ttcatctccg cgatttttcc cattcaggta
12601 aatgagcaaa tggatttgaa cactcatatc taaaacaaga gagaaccagc tggaaatgcc
12661 ctttgaattt ctttctctat gtaaaccatt tttctttctg gtgcctcacc tataaataac
12721 aggagttcca ccttccttta tagactcttg ctgaaagcat ggtttggaac aagaccgtac
12781 aggtgcacac aaattacagt tgggaaagaa gcctgcagtg catcttgtct ctgaaggtta
12841 tgaaatcctc cttttagtaa tggagctggc gtgatcaagc cagcaggatg aaatttggca
12901 tttgtgagat caccccccctt ctcacttgcc cactgtacat agcatcccag ccttactctt
12961 caaatctcca catttttttct tatctagcta caaaattcat aggctgattt ttttggggtg
13021 cgtgtgtggt ttttttttg ttttttggt aaataaagac ctgcattttt attttgatat
13081 aggtggttga gttttgtctt taatttcatg acagagattt aactagtctc aacttttgaa
13141 aagacaacaa tgatatttgg ggatcacaca cttaaagtta gatttctaga tgattaatac

Fig. 63E 13201 caaagtagat gatttttag cctcagccat ttataggtat gcccttctgt gaatttttta
13261 tgacagtgaa aatcatggca cagataaaaa ttaaataaat acttctgtta ttttcctgaa
13321 gaaaaaaaaa aaaagcttaa actatgagaa tactgtcttt gagcacttta aaataaaatt
13381 gacttcagcc agcaggattt tgagcattac atcacaaata aaaaacaaga ttaacatcaa
13441 aaggagtcag ttttcattca attgtgcagc actgtgggct gtgaaattta atattatttt
13501 gactcatatg ctaattgtag actgacagag gaaaatggat tgtgtttaaa taaaaggata
13561 cacagcatca cacgcagctg tatcaaatac aagttgaggt ctttgggcca ggaactgggg
13621 gccctctagc tctgttattg cagattcaag tttgacaaat aaaactttcc tttagactgt
13681 agtttaatta cttttttca aaggtatgcg tgatgaagag gcacaaatac acctcacctt
13741 gaagagttgc taaactggtt tgtgtgccga tcagttcacc gtgtgtttga atttctgtgc
13801 ttctcatctt tcctttctt gaaaagattt tgcttgtcat tggtgtgaat tgtacccccc
13861 acccccaccc atctagtctt tgctctcaga tttataacac tttaatggtt ccaaattgta
13921 tagcctgctc ttagacccct tttcttttcc ttgaataaat caggttcatg ttgcagacga
13981 tatttgtttt aggaaagtgt gaaagaaggg gcacctgtga aaacacgcaa ttgttccaac
14041 acacatatac atccaaatta aagcagaaaa tgtcaaagcc tccaatcact accttatttc
14101 ttggaggttt aaagccgctg agaagatagt ggtgccctcg ctggaagttt taaggtaatt
14161 actttttact ctaagcagta gtatctggta acctaattcc gtataaacct gacaccctat
14221 cgctacaccc cagtatttct ctgatttcag aataagtctg cgtagaaact tgttctgatg
14281 ttaaagtgca aaagggggca gtaaagtgct atccacaaaa aaggaaaaac attttccaag
14341 tatttcttat tactgcctgt gtctttcgta ggccctgcct ttatttattc attttataac
14401 aaaactctta tgtttggggc attcagagaa taccttatta agctgttgca gcaatctagc
14461 attaaatgga agacatgcaa gactgaagat cctgcctgtt tatgaagtgt gccatcaaat
14521 tcacatgctc atgatgcaga gtccttcttt gggagtattc gtattcccaa gtgcacagag
14581 cacttcggaa aggagccttg gtctttggtg ttaatgctct cctagctccg tatagatgtg
14641 gcaggcccaa agtacatggt ggggtgaagg gtcaagggtt tgggcttatc cagagcagcg
14701 tgcatccttt gtcaggaggt gactggaaac accagccaat tacagcagaa ctgcagactg
14761 ctcatctgca ttcggaattg cagatgaacc agtttgtact cgacttctct tcttcactgt
14821 aggctttgac atttaattaa aaattaaagc cttttatgga aaaagtacat gttttccaaa
14881 atggggtaaa ttcgaagtat acttgataca gaacactggc ttgggaataa acctgtgata
14941 ttacatgact tttggtttgc aactgctagg ctgagcctct ttgtaaagct gggatttaga
15001 atctttgaaa tgtttgtaca gttcaatgat taagcataaa ttgtatatat tcccttttt
15061 tcacttattt gagtaaacaa gtttgttact acagcttctg tggactcaga gatttatgta
15121 ttaaataggc cacaacttca actaggataa ttttatttat ctgcttgtta gggaattgca
15181 tcaaaagttt aagtctgtag gcattaaata ttttaaatgc ttatttttaa agtcaattat
15241 gaaagatagc acaaagtttt tctgaaacta cattaaaaaa ataatgtttt aatcttatca
15301 caaaagcatt gactatttat tgcaaagaaa acacagaaag ctaaaaatca ttctaagtcc
15361 accattcagt agcccaaagt ggtctcaggt aaaggcggtg tgtgtgacca tttgtttatg
15421 gttgtctccg tgcagtcagc aaaataaaca gaacaacatg ccatatatta ttgatgtgta
15481 tattttcaac tgaaattagc catctgctta caatgatcat atacactaat ggtataattt
15541 tgaaatgaaa agaaaaataa aataattctt tgtggagagt aatgcgaatt gacttatgaa
15601 tctcgccctg cttggcagtt tgctctagag gtagaagagc tttatgtgtg ggcctcctcc
15661 ccccccacac atttattctg ctcacacttg caccagcatc catgtcagga ctcaccttgt
15721 cctgttacat gagtaacatg gccctgattc tcaagtgcat gataactgcc ataattacac
15781 ataaatatta aatatttaaa tagatcttta cgtgtgtaat attaggtaga agtggctctg

Fig. 63F 15841 gatcgaatct gatgcttttt aaatagaagc tttcccacaa catttccaag cactgtcatc
15901 gtgtctgtct cgatttgggg tttacctggc ctagttatct gtctgggtgt agaaactggt
15961 agttcctgtt tgtatctttt ttgttctgat ctctttattc tgtgtcagct aaatattctt
16021 gcagtcagtt actaacatat taactcatcc ttgtttggaa actttggcat atccttccat
16081 ggtttccttc cgtggacctg tcgcgtctct caggagagcc accaggtata ttgtcacaca
16141 tttcgcatgt attttcagag actacagcag catcaagtgg ccccccagcg atttgggttt
16201 tcttctcggt taatctacac tctttggcca accgtgagaa aacttgtaag aaggcatcag
16261 atgtttgtgc taaggtgcgt gtagtatggt cagaggaaga aagaagcagg gaaaatggag
16321 tggccgtggg tgggagggga agcagggagt gcaatttcgg gttcactaca cagctctcca
16381 taaacttctc cactgctggc ttcccacgga tcctcctatt acactgggca aagtgcagaa
16441 atagatcagg cgaccactgc ctccgtccat ttcccaggca ccctgtgaga cccgataatg
16501 caatacaggt cagcagaaaa gtccagactt gacatcccaa cgtgccatgg tctggtctgt
16561 gaatgaaaat cacatgaggt gacctctgaa ctctaagtgg ctggtttatg ttttcagtgt
16621 attaggcccg tgttttaaac aagcatgtgc tcgtagtgta ggttaaaact ttctgttgtc
16681 ttcattaatt atgctgtgtt ctagtctatt aatattaaag aatattgtgt tgcataatga
16741 ctaatttttt tatttttttgg agacggagtc ttgctctgtc acccaggctg gagtgcagta
16801 gtgcgatctc ggctcactgc aacctccgcc tctcggattc aagcaattct ctgtctcagc
16861 ctccgagtaa ctaggactac aggcgcccgc caccatgccc agctaagtgt tgtattttta
16921 atagagacgg ggttttacca tcttggccag gctggtcttg aactcctgac ctcgtgatcc
16981 acccgcctca gcctcccaaa gtgctgggat tataggcgtg agccaccacg cctggcaaca
17041 taaggactat tttttaaagt ttttacaatt atgactgtga agttgaaatg tctaaattat
17101 tagagatcca gtttagatta ctaaatattt atgtctaatt gagatgatta gacttagcca
17161 aagtatccat gtagaagtat tagagtctag attggtgaaa aacttgaaaa agcttggctt
17221 aagttcaata ggtaatccaa gagtaaaaac agattccaat atcagatctt ttcaccatag
17281 tcatgttaag tttggaagcc ctacttgagt gtttccagtt ttttccacat tatattgtgt
17341 ctatatttga ttcaaaggca gggcatctat tgtcttgctt aggactgatt cactgggaaa
17401 agccactgga gttgcctatt tccactcagt atgcctcact cttagagtag cttcccatgg
17461 ttcccaggca ggccctccag tgagaatgca ccaagccaca cgccatggcc tgggaagcag
17521 tcctgaacct ggagattgtc ttgatggaaa ggaagaggca gccttcccct cccaggaaga
17581 tagtagagag cctgctctga cttcgctcag ggatggaact ggtctggctc agttctctct
17641 cctgtgtggg acatgaatca ctcttggtgg tctttgcttt ttatttgggc ttaaaatcag
17701 cagactttat taaatgacac ctctctctaa ccactctctg tctgggcgaa gtttaacaag
17761 aacagcctcc ccccatgtgg tatgggttgt aactgtggcg gtttccctct gctgtttttg
17821 gttacaagat gaacattatc tgaacacaca gaaagaaatc tgtatttggc atccataatg
17881 gaaagtcagt ttagtaattt aaacttagcc agttatcatc atcataattc tttttaacac
17941 tttcaaagtc agcataggag aagtgtattg ttgaatatta caaaatattt agggcataga
18001 tagatgtgct gtgtagtttg atttgttaat gtgtctaagc aatcaaagca acagaattca
18061 aatataaacc ccatcacttc caaaatagga actctgttta ctgacttgat tataacatat
18121 ggaactcaat tgttttccat taaaaaatga tactattagg aaactcaccc cattttcttt
18181 tcatatatat tctgctattt gcataattgt ctggagtcca tatgtaatat taaatgtaaa
18241 acacaaatgc catgtagctg gtctgtttct tcctcacctt ttggttcctg gcctcctggg
18301 gaagggttgc acatctgagc cgtggtctca gatgactgcc tcggaagaag cctcttccct
18361 tcaggcacca ctgatgtgtg cttggtgtgg agctagactt tccctggctc tccatgtgac
18421 gctcacatgt gcgtgtcttg atttccctta acttcatggc ttatctatga acagcttgat

Fig. 63G

```
18481 ttgggggaaa aaaatgtgtt tcccaatgct ggagttataa ttgaatgtgc tgcagtcaaa
18541 actgaaatgt gtgcagagaa agggggcttt tcctgtcatg ctcattgggc accagtgtgt
18601 cttcacctgt tttgtgtgtt aggtccatgc gtcatgctga aatgaagaac atgggatgta
18661 tggggctttg gacagtgctg agccaaaagc aagtgctcaa aagcagctgt gtttgtatta
18721 ttagtggttc tggaggtggc tgattgcctt gcattttaag tagagaggga ttgtagaaga
18781 ctgccaatac ttagaacttt ttccagagag gaagggtcag aaactgcatc tgcagggctc
18841 cttgctctcc agaaatgcca gtgtgcctgg gagggcatct tcagaaatcc agtctctcct
18901 cctcagtgtg tcctgtaccg actcagtggt tctgtcttca gaattcctat catgtctgtg
18961 atctgcaaat agtggtattt aatttgactt caatttgtat aaatgttagc ttctatttgt
19021 tcattcctat tttttgttca attaatacat tatttattga gcatctactc tgtgtcagcc
19081 ccttgggtgt ttaatactga attagtcaca tgtgggactt gcctgccctc agggagctag
19141 actataaatt cctaatgatc agtggtctcc acttttctgt cactcataat gtctggcaca
19201 acataggtta cttgagttgt tacactcaca gtactgttgt ttgctgccat ggtgctttag
19261 gaagtgtgag agttcccggg aggcagagtc aataatgcag actacacgta gtgaaaacat
19321 ggccaggaga gctgtagttc aggctctcag ctcaactgca ctctgtccac tgagaagcca
19381 taatttcttc acttaaagtg actgtgcgct atggctgttt atatatacgc ttaaaaagta
19441 aaagctgcta aaccactcaa ggattggggc cttttgtatt gatttaatta aaggaacaat
19501 cattgtttta atgagctcta gaaacaatta cttttgaaga gccgaggatc aaattcttgc
19561 ctcacgtttt gccacagtgt gttctgaaag gtgaattaat gcttttggaa tcatcaggaa
19621 tagtgagctt tgtcacgatt tactttttac aagcgtatct aatatgcata ttgaaatgtg
19681 agcctcccca ccacacttcc gctttgataa gcatcccccg gattgccgtc actgaccatt
19741 atagattttt aacaaagttg gacagtacac actgaatgaa aactttacat caaggaaggc
19801 ctggcgtgtt tgtaaaatga attaaaaggc tcattaaatg atttatatga cttacgcctt
19861 ctgaaaatat ggcctcaaac acagagatcc ccaaagccac accgacccct gcgtcccatg
19921 ttctcgacct caccgcatca gcaccagcaa gacctgtcgc tgagacggtg agtgatgaga
19981 gtcaagagga gtgacttgca tggcctggga ggaaacctcc tgtgaatctt tagttaagca
20041 ggaaaaaaaa aatcctcatg aaggaaacag gatcttggga gcattttgaa tgaagaagga
20101 gcttagtgag ccaaacttga gacatagggt gtaatgtggg agagttttaa gatttgcaga
20161 gatgtacagc ttgggagggg gtgtaatgca ttttcttaaa agagctgaat gaatggttga
20221 ggaaatgggt acatctggtt tggttaagga tcctaatctc tgaagcctgg gatgcccccca
20281 gggcttgtaa tttaggaata cttcccctaa tagtagctaa cccttatata gtgctgtctg
20341 tgcaggctac aaaaggagca gattaaggat agaaaaggtt tggagtgtat gagaaaccct
20401 aggcaggaat tgactcctgg tgtttgtaaa ccttaaagat gtcctaaaaa ggtcaaggaa
20461 taagacagga gaaaaaggaa atgtcaggaa gatgatcaat ttaatgttta tggaatttag
20521 tttgtactta ctgccccggca tcttgcctga ggtttttaac ctcagcagca catcagaatt
20581 actgtgtgtg tgttggaggg gctgggggag ataaagaaat tagcctcatc ccaaacattc
20641 tgattcagtc tgttacttga gaaactgaat tgtgttttgt ccataaagaa gatgaaattg
20701 tctacagaga acacattgcc attcacaagg ttgaggggat accacagaga ggctcccact
20761 gtgatttgca tttgtcaaaa gttctagaga attcttcaac agtacacaca tggttgtttt
20821 aaatatatca ttgttataaa aattcgtttt gagttctgtt tcacagaaag tttttttgaa
20881 tgaatgaatg tcatatatcc ttgctaaagg agctcagtta aaaaaaaagg gaccatcctt
20941 ctcttttggg ggttgtacag taacacattc ccaagaaaga ggtaacagcc acatacattt
21001 ttcttcccaa taaagagtgt gggtttttaa tatgaatcca tagtatgatt tctgttatgt
21061 tttgtgctgc ttcataacca cactcatgca cttttcagaa aattaatacc attcattagc
```

Fig. 63H

```
21121 ataaatcata aactattccc ttggtatggg tttgaaattg ggggtgccct atcatccttg
21181 ctttatctct tagtgaatta tgaccctgta gtcatcatgg ctggtggcg tctctggtta
21241 aagaaagggt tggattggaa ggattcagag gcgattcttt gttcttaggc tttaatattt
21301 taatgagcct gcaggcttgg ctgcttacga acgagctgag atttctaagt gtgttgttag
21361 tgttagcact tgtagaagga tgttcattag gaagttcttg tttcagtttt tcagagaaac
21421 tccccattaa gaaagatcat tcaggaacat ggctaccaag aaagaggaaa gggaggaggg
21481 aggctttcag ctataagcat taaggggata ttgtatcagt agtcttagtt ctaaagattt
21541 gcttctgaga attaattgga gcaaatacat ctcaagggaa gaaaaaaaaa gatttatagg
21601 gcagggacag tagttgtcct tgcaagtaga ggacacttca ttttgcagct gaatcaatac
21661 cacaactaat tatttctggt tatcttttac gcatttgtaa gacattgctt ttgttcagtg
21721 taataaaaaa cccattgttt gatcagtgac tgactaatta tgataagtaa tttgaaacat
21781 tcttgatgaa acttgtctgt taattaacat caacagcaca gggaaactaa caggacaaca
21841 aagtattagt ggatccactg ttccctccaa ttgacgagct ttctctgtgg catgcccaat
21901 aaactaaagc tgccaatggt taaaaaataa caaacatgtg ggagatctga ctcaccacgg
21961 aggaagagtt atggtaaagt tacacaaagg agtactgaaa tattacaagc gagggggtgg
22021 taaagaaatg tcagcaggta gcctgatcct acagcttaga gtaaggaaag tggtttcttt
22081 ctgtctttcc tttttctttt aaagcttaat tccaaaatac attcatccca tattgatctg
22141 aagtaagaga cttttgataa attaaagtgt gaatctgaaa atgtgtagtt tgggattatg
22201 ggcattgcct ggctatcttg taactgtcat taatactgtt aatttttatc aactcaatgg
22261 cttttttttc ttatgctttt agatttctac ctggacaagg actggtacta tacccacaga
22321 taggagacaa attggatatt atttgcccca aagtggactc taaaactgtt ggccagtatg
22381 aatattataa agtttatatg gttgataaag accaagcaga cagatgcact attaagaagg
22441 aaaatacccc tctcctcaac tgtgccaaac cagaccaaga tatcaaattc accatcaagt
22501 ttcaagaatt cagccctaac ctctggggtc tagaatttca gaagaacaaa gattattaca
22561 ttatatgtaa gtataatttt attcatttat tttatagaaa ttaagataag ctatataggt
22621 ttgtatcaat tttttgtttc cttaaaatta ttgtgacaaa taatttgatg aaaatctatg
22681 tggaaaaatt gtcccccccc ccttttttttt tttcaaagaa aacttcattg aatttgggac
22741 cctgtgctac cagtattcat taagtataca tacccaaaga gaaaaaaaaa cactagaatt
22801 cttaatagta ttgaaataaa tgtattatat gaatatattc agcatctcta ctgacaaaac
22861 catttttaag gaccattggt ggattttgat aggtaaatct tgtgcattgc cttttctctt
22921 cacccatcca tccattcatt cactcattca tttcgtattt attctgtgcc agagactgtg
22981 cttaagggct agggattcag cagtgaaagg tggtaaaata gcatgttttc ctcaagaagt
23041 taacagtcta gagaagatgg agctcataaa ttcgaaagat ggggatgaca ggtcacatta
23101 aaaccagatt cagaagaaaa agacgaaact tggtttgctt agtacattac tctttttttgc
23161 atacatatat ataatttgac acgctgtttc aagaagagat ggtacgtatc ccttgggtca
23221 tatctgaggc tgacttgtga ggatgtgaag tcagctgatg agcacatttg gagcccacgc
23281 ctactatgtg cagatctctc gtcagcgtca ttcccagggc cccaggtggt gttaaagtct
23341 aggtgactca gacagctgtt cgcgtcattc aagcaatgaa gtctttttttc ttaatttctt
23401 tggtttaaaa ttatactcat aattaattgg gttgaatttt ccagtggctt ggttaccata
23461 gacttcagtt tattagggaa ctgctatctg ccactggttt attatttgcc ccaaggtgga
23521 ctctaaaact ttaggtagga gactcttggt gatcaaactg aaactcttgc atctcaacct
23581 atgagccgca ctttattgtt attttatttt tttagagaca gggtctagct ttgttgccga
23641 ggctggcgtg cagtggcatg atcacagctc actgtagcct tgaactccag ggctcaagtg
23701 atcctcccac ctcagcctcc aagtagctcg gactacaggc atgtgccact gcacccagct
23761 caagagctac acttcaaagc acagaatgaa aacctatttt taaagccaac ttgatacata
```

Fig. 63I 23821 gagtagctta ccaagaatta gtaacaacaa caacaagaaa aaaaagagag aatgtggtag
23881 agtatatact tagtaaggag taattattat aaaataaaag cattctgaaa tgaaacaggt
23941 agatggggtg gccaagtatg cagcatagta gggaaatctt tgaaaatgta aaatagttac
24001 caggtaaaat aaatggaaac tttaagcttt tggaagccta acaatgtatt tatattagta
24061 aagactttat tttttattt tattttattt tatttttgag acggagtctc tctctttcgt
24121 caggctggag tgcagtggcg tgatctcggc tcactgcaac ctccacctcc tgggttcaag
24181 tgattctcct gcctcagcct cccaagtagc tgggactaca ggtgtgcgct aatttttgta
24241 tttttagtca agacggggtt tcaccatgtt ggccaggatc atctggatct cttgaccttg
24301 tgatccttcc gccttggcct cccaaagtac tgggattcca ggcgtgagcc accgcgcctg
24361 gccttagtaa agacttttaa agtaagactt tttcagtgaa agctactgtt aggcatgaca
24421 tttacaggca actgaaactg atcagatgca tttattaaga aggttaatgc ccctaggtgg
24481 ggtgggagaa agaaggtcgt ggtacgggaa gaggggacac actagagatg agatgcccta
24541 gggcagtgaa cgcatgtccc taatgcgtgg atgcagccca cgtccaccga taatgccgac
24601 acacccagag tctctcttct tactttagct tatgacttca cgaagaatgc tttgcaaatt
24661 ctaagttcgc actgggcgca agtggaattt tagtaaacat taagagttta acctttagtg
24721 tgaaataata tgcaagatat gcaaataatt gtttaccaac atctctttgc ttaatgtggt
24781 gagcatttaa taattgcttt ttattaatac atgagagatt tgtatttaga agcagtttaa
24841 tttataatta taatattaat ctacacaata acgacatcta ttattttctt tttttggaaa
24901 ctcttcatac cacactaaca ggttcattgc agttactgaa ctactctggc catcagagct
24961 ctccttagag ttacgattta ccatgcaaaa gcatatggta gcctgggata aatgaatctt
25021 tcttaataca gaattgaggg tctcaagttt gaaactacga gaggctattt gaatgttgct
25081 ttgggggact gtcataaggg ctgggtggag gactcagggc taagaagttt gccaggaagt
25141 ccagttgaga ctttcagcag agttgaaaga cttccacgat ggcgtaggca gaggaaggcg
25201 tttcagatac ttgggaaaat atagaagcca atttctcacc caccctacag caaagctcat
25261 tgatctacaa gtttccctag aaaggaaatg ggaaatgcag agaacaaatg ttaaaatagt
25321 tttagaaatt aatattgact ttgtattgct tctgcataag ttccaagaca ccaaaacaat
25381 gaatggattt taaaaagtca ctactttgca tatcagacaa atgcacacac acacacacac
25441 acacacacac acacacacac acacacagtc aagctctgta ctggcttttt tgagaaggaa
25501 agtgtttgaa gttagtaatt tttatatcag tacatttata aatagtgcta ggtagcatga
25561 cggaaagtat taaaatttac atgtatattt ttaacacttc aaatcgttgg ttcactttga
25621 gacagtaaat aatattagca tttgagttca gctttaataa attctacatg ggtttaaccc
25681 caaatctgag tgtctagttg gtaagcgcct tcagaacgag cagtgttata ataaatatgt
25741 tattgtgtgc tggtttcttt ccatggagag gaaaaagaga cctgatgctt tggaggagtg
25801 cttgactttt ccccagtgag gagtagtcca gagggactga cttgcattgg ggagtaccct
25861 acatgaacag catttcagaa gaattaaacc aggaacctag agtcctactt gctagtcctg
25921 cttcctaagc ttaatgagaa agtcaatttt atttctttga actttaattt atttccctaa
25981 aaaacgcttt tagtattgtc attgttctgg ctaatgatgg cggtctcctc cagtttcaag
26041 ccaccttagg gctgggcata caaatgcaat ataggatcac ttgttagtgt ggtttcaaat
26101 ggacatgatc ctctgtaaat tctttaaaaa catttaattt gatttgtggt gttacctgct
26161 ttaaaatata gtcatcacac ttgtgagttt cagacgtgaa tatgaatttt taatttgaac
26221 tgtattttta aacacactaa gtattaacta agtcccctta ggagatatgt ggcaaactga
26281 tatgcatcct cattcattct tctcatagat ggttatttgt tttttaactt gtggcaaaat
26341 tatatatgaa tggtcaccga cttaaaatag ttccacttaa atttttcaac tttctgatgg

Fig. 63J

```
26401 gtttattgga gtattaaatg tattttcaat ttaatgatat tttcagctta ccttgtgctt
26461 atcaagtatc aagacatagc cccacctaag tcatggagca tctgtatatg ggtttttatt
26521 cttgtttaga attgactttt tcaagtgacc tatttcagta attagccctg ggcctgattt
26581 gcataatgag atctcctaat cttcaagtaa tgcaaagatg gagatattat ggccatgtgg
26641 tctgaagaga ccttttcttt attatgttca gatctttaat tgccttaaaa atagagtagc
26701 taatttacct aacctctagt tattttatta ttgtctttaa agtttttttt aatgttcatg
26761 aaataactgt tctgaaattg cctattttca agggaagctg tgtcttagac ttactaaatg
26821 ctccagttga tactgggaaa gccttcttgt gttcgtagcc tttatccgta gagttttctt
26881 tgcagcattt tctgtgcctg gtttagtttc ttttcagagg cgacacccag agctgaatga
26941 gtcagcaggt ttggtgtgtc gaccctttgc aacagctgtc cttacgaagg ttctgtgggc
27001 tggttattct accttcgcat aaaaccttgc aaaataaccc acaaagaggt tttcgtcaca
27061 ctaccaaaat catgtgagtc agagatggat gaaaaatgaa tgccattgtg ttcatacttt
27121 tccagtgaac agtagctaca gcagagctgt tagacaaaga aaaccgtatt aatgaagcgc
27181 ctcccaattt agcttcatat ggcttttgca ttattttgct gcaaatccat agctaagaca
27241 catcttgtgg catagtccgt aagtcatctt tccgaaggac tgtttgatta aaggttgttc
27301 tgtgagatcc accctgtgtt gttcatggca tcctcttgga ggcctccctc actctccatg
27361 ccttggcaaa gtcttcctta aggaacactg aacaagtctg gagaagctgc catttcttag
27421 ggccctcatt ggttcagttg tctatagctt tttatttttt attttttttt taataaagag
27481 tatgtaaaat tggaaagctt cacaaacagc tttgctattt tttagacatg tactccactt
27541 ctaagcaaaa tcacaaaata aagtaaaatg cttccacaaa tataatgaaa caatattctt
27601 aaagaatcaa agcagaagaa cttcagagtc tgttgcttat gttaagcata tatttgtttt
27661 cttctctgct tttgatttac ttatttctgg ggtgtaggtt tggcaagtag tactgaaacg
27721 tactgaatgc actgttcttt agcaagatag ttacaggagc tttcaaatgt cctcttaaca
27781 tatagatttc ttttagaata tagaataatg tgtgggctgt ataaagcgat tatgtgcttt
27841 atttgatgaa ttatttatgt acgataaatg tagcaaaagc cacatttcca tcattaaatg
27901 taatcccatt tggtgataca gcaacatcag cctgtcattt gggtcctctg attgaggggt
27961 gaggatttct gtttgatacc ttgtgcataa tggctgcgtt caagcattta aactcatttt
28021 tatttctaac ctacagctgt catctttgta ataggatatt catcagaatc ttgccagaga
28081 ctgtgcattt gggatcttgg gggatacagc accaccacca ccctccccct gtccaagaga
28141 aacagatcaa catcttaggt tgagagtctg gggtctggaa gacccgagtt cctgagtgcc
28201 ctttgacaag taacttaacc cctgtctgcc tcagtctctt catctgtaaa gtggggataa
28261 tgacagcacc tgcttcacag ggttgatggg aatccagatg tggtgggata tagaaaatgc
28321 ttattacttc cacctttgac accaaataca tataactaag agttaacttt ggagcagggg
28381 aggaagtgtg aggctccagg ctggaggcag acctgtgttc ggctgcaagc tggagaggat
28441 ggaccccaaa agcttggctg atttgaagtc catccataaa atggaactcc agagagttta
28501 cacgtttcag taatgctgca taacttaatt ataagatctt ctctctttgt cttctttcag
28561 tgttataaaa gctcttttgt ccttgagctt cctttaccaa gaaacatgca tttatgtatc
28621 tttttgttca tggaattgcc caagcttgtt agcagatcct ttgtaagacc caaaagagac
28681 agacagggga ggagtcttca gatacatata atcatttttc ccaatttcca tgttaccagc
28741 cttgccagga ctttttctca gttccctgtt acacaatgaa aatagtgtct ctttattgat
28801 aattttagta gcatcctaat gtggtataaa tcgtcttcca gagaagaaaa tgtgtcaggg
28861 ttgcgttatc actgaggcta gctgggaaag tagatcagcc cattagtctg ataattcgaa
28921 gcgttgtttc tgttatttct gaacatcatg tgaactcctt ttctgggtgt attaaaggtt
28981 ttcccagtgt gtgtcagtga gactcctgat tgaatttaat atgaataaag ataaattctt
29041 tacatttaag gattaaagtc tcagcttctg cttaacttga gattgcactg agaaactcct
```

Fig. 63K 29101 ggctctcggg tatagcggag tcacgacctg ggatgtctg tcccatatgg ctctgtgtgt
29161 aagaagaaaa agctgctgtg gacggagact ctgttcacat taaatgacat cacctaagcc
29221 atcatgacag caagaattat ttaggaattg ctcagaataa aactgccttc attatttcat
29281 aaaatgtatc ttggtatctt tagcacctta tttatggctt tttaaaggtt cactgggatt
29341 tataaataat tggacaatgc tagagaccta gtacaagaat gaaagaggac aggcttcttt
29401 cttaataacc tttaaacatt catcaggaag ataaaacttt aaagcaaaat aaaacacatg
29461 aaaatagcca agatgcacag accagacaag caaatactac tttaacttat ttgtatagtt
29521 cttaagagtc acatttgttc ctgaagtttc aaaatctcgg gctgagtgtt tgatcactta
29581 gggaagtgtt gtggccttca catactcttg tctcactttg aagtctagaa acacaggtct
29641 tagagcaatt tttatcactg tgagaaagct gaaacttagt gtgagtagct tagtacaatt
29701 cagttggcca tcaaatgtca gaaacaaaac tcagtccagg gccgctggac ccttaggccg
29761 gcgttgttag tttacaacag tgcctcctgg gtccaaacat ctaagtgcac atgtagcaat
29821 agtaaagata gtatgtatgc atacataaca catatgtaga gacagcagag tatacgtaca
29881 cacatgttgc atacatagca acagcagaga agctcatgaa ctataaagga tggactgtat
29941 gcttgtatca gacattttgg tactgacgct ttgtcatata ttgtgtaaca tataaccagc
30001 ttgcaatcat ctgcccccaa agttgaacta agaaaatcct acagggtact aggaaaggaa
30061 ggccattggg aaaaggtggt tatagtggca atttgttagc tcttatgaat tttctttttc
30121 tttttagaca tactcttaat tccatttttt caataaatct atactatttt gtgtttttat
30181 gttagcaagt actttaagcc cctcaataga aagttgctac atcatatagt gattaaaaat
30241 aaaaatctct caaacataca agtagaggtg gtatgagact tcaaattccc ttagccaagt
30301 acaagtgcag cagttttgtt ggctggctgg ctgcatagaa ggactgatgg attggcagac
30361 cctcaagctg gagtgtaatt gatctcatta cagaggagcc aggctgggtg acagttgtgc
30421 tttgcaagtg gttttttgca ttggtgaagt agcccatttt gttgttcctg atgttaaaca
30481 ggggatgaag gtattctttt attggcacaa acgcgggaaa ttgctctgga ttcttagagg
30541 atagaacatg tcccctggac ggaataaggt tcatgtgtag ggcaaattta gataggggca
30601 ccttattggg gttactactg gtctctagat ggtcaaagca aacaacatgt ccatctaagc
30661 tgtgatgtcc atctaagctg tgtgtgtcca tgagagtgac gcattttctc ctctgcagtg
30721 ttgttatatt ctaaactgtc agcagacatt aattcggtcg ctggtgaagt cccaccgcct
30781 agagatgaac tctgcctccg atggatgttt tccacttcag tgccactcgt ctcgcaatta
30841 ctgggtcatt aatatcattg catgcaatta gtgacagtag aaagagctag agggttgtgg
30901 gatgtgcacc ctccccacca tgaacttttt actctgaccc tttcccagct agaccttttc
30961 gtatcttggc aaggatattt taatgattga gactgtcaga atcttcagag caggcactgg
31021 attatgtgct ggaaataatt cactcaaaca cctgcttctc catggttcag aatattttca
31081 ttagatatta tcactatccc ttccctggga agtttcattt ttaaaaatct gatgcttaag
31141 tacagctaat atagacaata gggaattatg ttttatcttt agaactctta cattattctt
31201 ttctttaaaa atgtgagctg agtcattgct attgcagtgg tcatctggcc gcctattttt
31261 aaaacacaat tcctctatct tagtagattt tggcccatat taagcatatc aagaatgact
31321 tttttttttt caagacatgg ggttttattg ggggcttata tacaaggaaa gagagagtcc
31381 agtggcagtg ggctggacaa gatatccaca tggccctgtg gcagtgagct gggcaggaaa
31441 actgcaactg cttgcaaaca gcatgtagtt catctatagc attttcactt aacaccaccc
31501 agctaatgac ttccacctgg caaccttcat ttaatccaga acttaggacc tcgagtccct
31561 gtacggccca tgttccacag gatgggccga gggctcagct gttcctcata gacaaggaat
31621 gactctccac attggccact ccccggattcc ctagctcagg acacatattc aggtgtgtct
31681 aaggctggct cttctatgtg aagttactta ttcttttacc attgactctc atgttcccac
31741 tatattaagt ttttctgaat tactgtggca ataagaaacg gtcccttaaa ttatactaga

Fig. 63L 31801 agaaaagctt ttttttgtt ttgtttttta ttttgaaatt atgttaaatt tttttctta
31861 actgagagat tccacctgca taaatcgtca taacttttaa cagtaagatc ttagacttag
31921 aaagtgatgt ttttcctcaa cagaatttat taaaaatcaa gacaccaagc tgttccaaac
31981 aatagtttga ggggaaataa aataaacaac tccataaata atcttatgtt gttaaacatg
32041 tctctagcaa aacaaacaaa caaaaaagtc gggggttggg ggaggtgcag tttattgcca
32101 gtactgtctg gtctttctca gaaaagcgtc agtgtacatc actgagcctg gacggtatgt
32161 tttcttgatc tatacccccct atgtgtacat gtgcttgcac gcacacacat gtagacacgc
32221 acacatgtgc acctgccatc actttctgct cttccgtctt ttcactcttg agtgtctgta
32281 gccagtagct ttccaggtct gtatagtcaa agatacctat ggccctgaat gtcttcactg
32341 attgctattt gacattcata cggtttttaa tggttaaaag gctttatgcg aaagctgtga
32401 tagaatttct cctgttctag atgtggtgtt tattgcttta ttttgtgact tttctctcag
32461 tagattgacc ttctccctca gtgtccaagc ctcgcatagc atgatggcac ctgtaaactc
32521 agttctgtat cctggtatcc tttctcttcc caagtagaag caattaagta atatatgtca
32581 tcaaaacctt ttaagtgcac atacaaacaa aatcaactta ccaaactgct tcaaagttgt
32641 tccatgttta acactcttct ttctgagctc tgggtagaat gtcctattat tgttcatcat
32701 gaatatttga aattaaagaa ataaaactgt accattttct ttaagagcat ccatttgtac
32761 ttgataacat cttcagtcat atttcaatgc tggcaaagag gaggggagtt ctaaactgtg
32821 actcaatttt agaatctact ttttccaaat tattctgttt agtgcagaaa actaattaat
32881 agtgttgcat agaaaagtca ctgaagctaa gccagttatt acttcttaat gcatgattta
32941 ctgctttaag ttttcaaaac acaaccatag caatgtggta ttaattcaag tgattcttcc
33001 tatcatattg aacgatattt tcacgggtga aaaactcaca catcctacat cactgatagt
33061 ttatacagtg ttttagctgt ggctccctgc atgcaaaata agagttaatc aaatgtcagt
33121 gagaaccatc tcatcaagta gagggcttgt tttgtttaaa ttaactttgc taagtataaa
33181 tttcttcttg aaaataaatt ctgggccggg cgcggtggct cacgcctgta atcctagcac
33241 tttgggaggc cgaggcgggc ggatcacgag gtcaggagat cgagaccaaa ctggctaaca
33301 ctgtgaaacc ccgtctctac taaaaataca aaaaatgagc cgggtgtggt ggcgggctcc
33361 tgtagtccca gctactcggg aggctgaggc aggagaatgg cgtgaacctg ggaggcagag
33421 cttgtggtga gccaagatca caccactgca ctccagcctg ggtgacagag cgagactccg
33481 tctcaaaaaa aaaaaaaagg aaaataaatt cttctgtatt tttctttctt caagtgaggc
33541 catttagggg aaagtatacc ataaaacttg ctctaagata aggcaaattt ggtattatag
33601 gatgaagtgc tatgtgattt gaagtaatgc tgaatttttt aaatatatta aactaaacaa
33661 gaataatgag gcccctcggaa agtcatgatt atatttctca tttttctcat tttaaagcca
33721 cagtgaaaaa cacataaaag gaagaagtta gaaaaaaaaa tgaatgaaat tcttttttttc
33781 cttttggcaa attaaataga tgtttctgtt tcagaagatt ttattaatta actttaaaga
33841 aacagtcatt tatttttggc attcagtgaa cactatcatt tccatgttta gaacttttct
33901 tctaagttag catcttaaaa gataactgtg aaactcaagg cattcaacta cattaatttg
33961 agtttcagaa attgaattct tgtttctaga gtacatagtt tgaattgatg tcagggtgtt
34021 aaatagataa atcttagctt cctaggttgt atattcacac taattatttt tttatcagcc
34081 ttcttatttt tcaacttacc ttattctttt tgtttttttg acactcagat ttgatagccc
34141 tgtggtagaa gaaaacagta atacagtttg gtttgttgtt gtgtttgtgt ttattttaaa
34201 gtcacggctt tgctttccat gttgttactg gattatgctt tttttaattc ttcagtttgc
34261 caagataaca gtcttccgat cttcagaagt ctgtatcaag cttaaggaaa ctgatgtgta
34321 ggaagactcg cctaagaagt ccaaattagc aaggctagca tgtgaggaca tgctggaaaa
34381 gaatagttcc catagatatt gacagagaat gttcataaaa tgctacttgt tttgtggtta
34441 catgagagta acttgtgtcc agtgcagctg tatgtaaggg caacgttttt attctgacga

Fig. 63M 34501 ctctgtggtt ttcatgaccc tggatgctta tcatgtctct ctgttggact tcttcaacgg
34561 agttgataca aatacttgct tccaagtgtc catctgccct ctcctccatc ctggccccat
34621 acaaatacgc tacattttta aataatttga aataccctca atagtattta tatttcctgg
34681 tgcttcattc tttccataag aactgtgata ccattattct gtaggatttt tttgtgcttc
34741 cccgtttcac atctctgtgc cagtgagacc catatatcgg tgcaaatcca gaagtttgat
34801 tgtccatctg attagcacac tgttagcaat gtggtggact aaacacagcc aagatgtggg
34861 gctggagctt agcctcctgg gagcagagcg gtgaacatca gatgaagaca tgtgaaaatg
34921 gagtactact tcctcttcct ggggatgggc taaaaagcac agccagaaat attcttgccc
34981 ttccagtctg ctttacagtt actcactggt tctctttttt ttcctactca gataaccagt
35041 atactcttcc cagtgactaa gaactgcaga taagtatagg tgcaaataga tggcaaaccg
35101 cagatggcag ctgtgtggtt tcagatgtgc tgcagaactt ttagacgatg tgaacgcaag
35161 gaactttttt gctgagcagt aatctctacc cactggaaat taggccctgg ggggaacaat
35221 gtagtgactt ctatatactt actacatgca gttagacccc tgaagcaaaa gcttttaaaa
35281 acaggctgta aaatgcccat gtatctttat taagcctatt ttccaactgg atagagaaat
35341 tttctggtaa tttttaaatt tgtaaagtct attttttttcc tgagccaagg gaaaaaaaat
35401 atctgggccc taaaagctta gttataacaa tgttattttt tctatctctg aatgattaaa
35461 tgtgatttca tttatgtagc aatactatga ttgtggctgc attagatcac gctgatagaa
35521 agatacaaag aaaaactaag tataatgaac taacaattta ttttcactct ttctctaagt
35581 taaaaattcc cagtacattc aaatgaacaa tgaaaataat tgcagaattg tctcctgaaa
35641 tggaaataga tttttttcc caagcattag caatttcttg ttatttttca aaatcagcca
35701 ctaagccttt cagagcttct tggtgactat tgcaggagaa atcagaatat taatcttgtg
35761 gttttatttc agagttcgct gccaggaagg aggtataatt gggataggag actttttttt
35821 tttagctgtg tcactgttca aggaggggggg tttggaacct cagcataaga attacactct
35881 gtgatgagga tgtagcaggg gagaagaaag gtgattttca ctatgggaag ctatacttac
35941 atcaagtata aaatagactg aagtcatttt gaattacgtt atacttgtaa agtttacctc
36001 ctggagtttc agttagtacc agtgtactaa ctgggttaaa acagttcatg gcaccttaga
36061 tcatttctaa ctcatggcaa aaatctttcc tggtggaacg tgtaactgta ttttaaatgc
36121 ccctttataa gcaaccaagt atttgggatg ttattttgat attagtagtg aatttttcag
36181 tatcttccag taccctttgc aagtcacagg ttgacttaaa aggaaaagaa gcaaaatgct
36241 gaatatagca gaaaaactgt ctgcattcag actgttcagc ccactttgc tcccccacgtg
36301 gcaagcacac tccccaaac aagcaatagc ctgtggcttc agaggaacct acaaaggcag
36361 catctgtaga tttttccttc ttcaactcta agacttgaat gtttccctct tccccacaca
36421 cttttttttt aaaccaagaa ataaaaaagt tttcactctt aaaggtgcaa agcagtttca
36481 ttcttatgca acacagcctt cctcctactg tcttatagtc tgtggatgtt aaattataga
36541 ttccaattga attttaatac tctagagatt ttacatttgt ggttgtcaag accccgtttt
36601 ggtaaaccta gggagctccg cacaaaagca ttgatattca gaaaaggcac tgacctacaa
36661 attaaaagaa aaaaaaatca aataatgtgc acctcttgtg cttccagttt gacaaagcag
36721 aagtcatcag cagtttctcc ctctgcagac gcagttctca attctattta caagtaactg
36781 ctctactgtg cctgtttttc tcttgctgat actcatttaa ttgtttttct tttggatctg
36841 aatctttgac tgtcttttcc ccctcaagat taaaataaat acatctgtat tcctcccctt
36901 tctttctgtg cactgccctt cagatctcat tttgtcattt ttcagcttag tgttgaaact
36961 tttagcaaca aaaagtcagt tacttacttt gagtaagtaa ctcaaagtaa gttaactttg
37021 agtttgagtg cacttttgcg tgtaggttca tttatgtgct tgtgaattta aaaacattgg
37081 gattccacct gaatgaagta aaccaaacat tttaaactat cagccagata gagacatcag
37141 cctttcactt ctttctatat gcagacatat cctaattttt tagaaaaatc aaataggaaa

Fig. 63N 37201 attctcaaca attaattgaa gattatagct ctgctctgaa atggtccaga aataggatct
37261 gctcatagaa actcatagtt tgaagcctct gggaggaaag gatactttaa aatttagtca
37321 catatttgga ggagggaaaa gggaaagagc agaatgaaga actgaaaaaa atcacacacc
37381 ggggcctgtc gtgaggtggg ggactggggg agggatagca ttaggagata tacctaatgt
37441 aaatgacgag ttaacaggcg cagcccacca acatggcaca cgtatacata tgtaacaaac
37501 ctgcacgttg tgcacatgta ccctagaact taaagtataa taaaaaaaaa ttttaatagc
37561 cccattaaat aattaaaaag atttttttta gattcacaga agtgtacaaa atttttaggt
37621 tttttttttt ttaagctgtc tgctgaatag tttcttaatg gtctacaatg tttgtatcta
37681 caaacagata ctgtctgctt cttactaccc ttccaagaca agtattatta tggcaattat
37741 tgcccagttt cccgggaaaa atttatccac agttacagaa gaatgagatg caattgtgag
37801 actgtaaagt ttaagcaagc actcagagaa gcacagtgat atgtatgcac agaagaggca
37861 gtctttgttt tgaggaaaac agtgaaagta aagttaattc aagaccacaa agacaagtaa
37921 ataagtgcct tatttttgta gttaatataa tttcagtgga atgcatattt ctaccataaa
37981 tgcatataga acttgtttgc tgacctactg tttggaaaac aaacaatccc attagaagaa
38041 tgtctttggg atttattttt accagaaaat caatcctttt ttcagtccct tgcaaagtac
38101 agtgttacaa gccaagactt tgataatcag gtagaaaatg gatttaaatt gcagaaatgt
38161 atatgaaaca cttttgttcc ttgccccttg aactttaggg gaatgaaaat gtctagcact
38221 ctccaccttc ttttctctcc tggaacttga actgtaattc aaagcctgtt tctcattaaa
38281 gtacctggca gcctatctct ttacagcttg agttacaaag ctattcagag acctcgctgg
38341 tctaaagaga cagaacaagg atgtgtttaa atagagcata ggctgttgaa aaaaaaaatg
38401 ctgaaaatgg taaaatgatt ctgtccttcc ttccactcct cactgctgag gtggagaggg
38461 aattcagttg gtgaacacca gcaagtggct ggtaaaagtc cccactttct ctccagggct
38521 gccacaggac ccagaatgag tggtgggcat gtgtgtgaac cctctattca gccagagttt
38581 tcccgcaaca ggtagtttgg ttgaagaggt tgactaaggt tgacattggc agtaataaca
38641 cgtatgttct tctgatttac aaaacgatgg aggaaaaagg ggagattttg aagacctgat
38701 ttctggtata cttcttaagc atgcataagg ctgaaaaaag aagacaaggg ttgtgggagg
38761 ctcctggtct agtgtttaca gaacttggat gcttgacaaa cagagcgtca agctaattgt
38821 tcttgaagca ggaaatctgc agtggaggaa gcaggtgtgg ggggatgatt accacgtttg
38881 gaaatggctg cattaactat tttgctcttc tgagtttggc cccaaaagag tccatagact
38941 ttttgaagga tgccatccct tttatttata gactaacatt aaatcagtca tttgtgaagg
39001 aaggagaaag tgcctaaata aatttggagt cagatagcat acgtgcggca gtgtttccga
39061 tatccatttc tctttatttc tttttctttt tctttttggc tttcagcatc cccatacttt
39121 cagaaaactt gtgactaaga gtgaattctt atttttcaaa ttgttttcag acatttcatg
39181 ttcatgtaaa cttggcttat tgatttcctg atttttcttt atttttttgt tttgtccatt
39241 ttatttttaa tcagctacat caaatgggtc tttggagggc ctggataacc aggagggagg
39301 ggtgtgccag acaagagcca tgaagatcct catgaaagtt ggacaaggta aagaccatct
39361 gctgcttcat gacgccactg tgacctggtg tagcccccag ctagtatggt gctaatgttg
39421 ccgatgccca ccttcattcg ctcttctttt tagttttcaa agcaaaccct tctgcacttt
39481 gagccactga cagatttcct caagtcaatg tactaagctt ttattggaga tctaagagtt
39541 aagatcagca aggtagaatg tctattgcca tagatagata gatagataga tagataatag
39601 atagatagat agatagatag atatttcttt ttaaaaagca aaacactttg gttcaaaatc
39661 aaaatatcca gaatgaaaac taaaagcttg tgcagttttg ctcatttctg aatcttgact
39721 acagaagagt tttgttcatt gtgacttttc caatatagat aacctattgt gcagaaagaa
39781 ataattattc ttctaattaa aaattggtat agtagtcaat caacttgctc agttaaattg
39841 aaatgtcatc tgcaatgctt tgcctgccaa atgcaagaat ccctatagtt tccacagatg

Fig. 63O 39901 gcctcacgtt ctaaacctct gaaataacta gtataaccat tttgttttaa aagaaaaatt
39961 atattcttgt atttcacagt actttgcata aagactctta tgttcattgc tattcatgcc
40021 tgttgaaata tatatgcagc tcctaaagct agatattgtc agatgtctgt gccgtaatta
40081 atcatttgtt tttcatatag atgcaagttc tgctggatca accaggaata aagatccaac
40141 aagacgtcca gaactagaag ctggtacaaa tggaagaagt tcgacaacaa gtccctttgt
40201 aaaaccaaat ccaggtataa cagcatgatc tgtgtgtatg gaggtctgtg ggtaccacat
40261 tcttagtagt atcttaaaag gtagggcaga gtctaaagac ttctaaccag ttaggattag
40321 ctggaagtta cagtgatcag gaatctttgc tgtcagtgag tcattattaa ttacactcaa
40381 taagaacaaa ataactcatt ccaatgaaag tcatatattc aaaggagtag agttcatgag
40441 ctgtaagtgc cagttattag aactactctg tcaggccaaa ggtttcattg gctgacattt
40501 tatcaagctg gttgtcaact ccagcttaaa gctgatgtta atgtatatgt aattaatgtg
40561 ctaatccctc atctaattat atctaagcca cagagggttt aattgatcct cttctaaatt
40621 ttaaatggta acatttttaa atattgcata atagtatttt ttcaggtggt tatcgttatt
40681 ttgtttcaca ttttccatgt aaaagaaaat attaaacagg tccctgacaa aagtgtagaa
40741 taccagataa aattgtccgt cgttgacctt cgttttctta acagtcttgg aacaaatagt
40801 tctgtatttg ttaccatgct aatgaaggtt ttatagagta gctgttgagc agacatcagc
40861 agttttgtat taggattgtt gtgtgcttgc ttggtcgttg tgcaaattta tcgtctgcag
40921 caatattcca tccctttcca agagtcaagg agggaagttg ttatttctaa ctttcaatga
40981 caagatgtgt caaattcttg tgacaaactg ataaatggat aatataatga tgccaggcag
41041 tttttagtg cttaacattt gggctggcag tctgttcggt gtgagagttt ctgctgcctt
41101 ccaaatatat tttaagtgta aatcaaataa tacagacgag ttacgagctg aacattttcc
41161 caggcccccct cactccttcc gcgttcccga gctgttctgt tctgccagga ggcagggctc
41221 ttctttagaa ggcaggccct ttgaaggttt gcatgaaact ccctttctca aaggaggcgg
41281 aagagcaata ccacataaac gctcaccgct gacctggaga attggccact tcccttttc
41341 ttccctgccg ctgccccagg ctggctgaca cgggttagaa gatgaagcaa gatcaagggc
41401 tggctgtcac cgacagtctg tgctcttgct ggataatgat acaaaggaaa ccctgtggct
41461 tgggagggta gggaagtccc tcctagagat acctctcatt tcctttgcg ttgagctctt
41521 agacgaggta ttggcgaggc aaagtccagc ttctagttag taataagcct ggcttatttt
41581 tcacattttt aagggtcata aaagcagtcc gtctgcactg ggacagcagt aactatctct
41641 gaccttttct gtctccgcgt ctgcaggttc tagcacagac ggcaacagcg ccggacattc
41701 ggggaacaac atcctcggtt ccgaagtggc cttatttgca gggattgctt caggatgcat
41761 catcttcatc gtcatcatca tcacgctggt ggtcctcttg ctgaagtacc ggaggagaca
41821 caggaagcac tcgccgcagc acacgaccac gctgtcgctc agcacactgg ccacacccaa
41881 gcgcagcggc aacaacaacg gctcagagcc cagtgacatt atcatcccgc taaggactgc
41941 ggacagcgtc ttctgccctc actacgagaa ggtcagcggc gactacgggc acccggtgta
42001 catcgtccag gagatgcccc cgcagagccc ggcgaacatt tactacaagg tctgagaggg
42061 accctggtgg tacctgtgct ttcccagagg acacctaatg tcccgatgcc tcccttgagg
42121 gtttgagagc ccgcgtgctg gagaattgac tgaagcacag caccgggga gagggacact
42181 cctcctcgga agagcccgtc gcgctggaca gcttacctag tcttgtagca ttcggccttg
42241 gtgaacacac acgctccctg gaagctggaa gactgtgcag aagacgccca ttcggactgc
42301 tgtgccgcgt cccacgtctc ctcctcgaag ccatgtgctg cggtcactca ggcctctgca
42361 gaagccaagg gaagacagtg gtttgtggac gagagggctg tgagcatcct ggcaggtgcc
42421 ccaggatgcc acgcctggaa gggccggctt ctgcctgggg tgcatttccc ccgcagtgca
42481 taccggactt gtcacacgga cctcgggcta gttaaggtgt gcaaagatct ctagagttta
42541 gtccttactg tctcactcgt tctgttaccc agggctctgc agcacctcac ctgagacctc

Fig. 63P

```
42601 cactccacat ctgcatcact catggaacac tcatgtctgg agtcccctcc tccagccgct
42661 ggcaacaaca gcttcagtcc atgggtaatc cgttcataga aattgtgttt gctaacaagg
42721 tgccctttag ccagatgcta ggctgtctgc gaagaaggct aggagttcat agaagggagt
42781 ggggctgggg aaagggctgg ctgcaattgc agctcactgc tgctgcctct gaaacagaaa
42841 gttggaaagg aaaaaagaaa aaagcaatta ggtagcacag cactttggtt ttgctgagat
42901 cgaagaggcc agtaggagac acgacagcac acacagtgga ttccagtgca tggggaggca
42961 ctcgctgtta tcaaatagcg atgtgcagga agaaaagccc ctcttcattc cggggaacaa
43021 agacgggtat tgttgggaaa ggaacaggct tggagggaag ggagaaagta ggccgctgat
43081 gatatattcg ggcaggactg ttgtggtact ggcaataaga tacacagctc cgagctgtag
43141 gagagtcggt ctgctttgga tgatttttta agcagactca gctgctatac ttatcacatt
43201 ttattaaaca cagggaaagc atttaggaga atagcagaga gccaaatctg acctaaaagt
43261 tgaaaagcca aaggtcaaac aggctgtaat tccatcatca tcgttgttat taaagaatcc
43321 ttatctataa aaggtaggtc agatccccct cccccaggt tcctccttcc cctcccgatt
43381 gagccttacg acactttggt ttatgcggtg ctgtccgggt gccagggctg cagggtcggt
43441 actgatggag gctgcagcgc ccggtgctct gtgtcaaggt gaagcacata cggcagacct
43501 cttagagtcc ttaagacgga agtaaattat gatgtccagg gggagaagga agataggacg
43561 tatttataat aggtatatag aacacaaggg atataaaatg aaagattttt actaatatat
43621 attttaaggt tgcacacagt acacaccaga agatgtgaaa ttcatttgtg gcaattaagt
43681 ggtcccaatg ctcagcgctt aaaaaaacaa attggacagc tacttctggg aaaaacaaca
43741 tcattccaaa aagaacaata atgagagcaa atgcaaaaat aaccaagtcc tccgaaggca
43801 tctcacggaa ccgtagacta ggaagtacga gccccacaga gcaggaagcc gatgtgactg
43861 catcatatat ttaacaatga caagatgttc cggcgtttat ttctgcgttg ggttttccct
43921 tgccttatgg gctgaagtgt tctctaga
```

Fig. 63Q

EphrinB2, mRNA

```
   1 gcgcggagct gggagtggct tcgccatggc tgtgagaagg gactccgtgt ggaagtactg
  61 ctggggtgtt ttgatggttt tatgcagaac tgcgatttcc aaatcgatag ttttagagcc
 121 tatctattgg aattcctcga actccaaatt tctacctgga caaggactgg tactataccc
 181 acagatagga gacaaattgg atattatttg ccccaaagtg gactctaaaa ctgttggcca
 241 gtatgaatat tataaagttt atatggttga taaagaccaa gcagacagat gcactattaa
 301 gaaggaaaat acccctctcc tcaactgtgc caaaccagac caagatatca aattcaccat
 361 caagtttcaa gaattcagcc ctaacctctg ggtctagaa tttcagaaga acaaagatta
 421 ttacattata tctacatcaa atgggtcttt ggagggcctg gataaccagg agggaggggt
 481 gtgccagaca agagccatga agatcctcat gaaagttgga caagatgcaa gttctgctgg
 541 atcaaccagg aataaagatc caacaagacg tccagaacta gaagctggta caaatggaag
 601 aagttcgaca acaagtccct ttgtaaaacc aaatccaggt tctagcacag acggcaacag
 661 cgccggacat tcggggaaca acatcctcgg ttccgaagtg gccttatttg cagggattgc
 721 ttcaggatgc atcatcttca tcgtcatcat catcacgctg gtggtcctct tgctgaagta
 781 ccggaggaga cacaggaagc actcgccgca gcacacgacc acgctgtcgc tcagcacact
 841 ggccacaccc aagcgcagcg gcaacaacaa cggctcagag cccagtgaca ttatcatccc
 901 gctaaggact gcggacagcg tcttctgccc tcactacgag aaggtcagcg gggactacgg
 961 gcacccggtg tacatcgtcc aggagatgcc cccgcagagc ccggcgaaca tttactacaa
1021 ggtctgagag ggaccctggt ggtacctgtg ctttcccaga ggacacctaa tgtcccgatg
1081 cctcccttga gggtttgaga gcccgcgtgc tggagaattg actgaagcac agcaccgggg
1141 gagagggaca ctcctcctcg gaagagcccg tcgcgctgga cagcttacct agtcttgtag
1201 cattcggcct tggtgaacac acacgctccc tggaagctgg aagactgtgc agaagacgcc
1261 cattcggact gctgtgccgc gtcccacgtc tcctcctcga agccatgtgc tgcggtcact
1321 caggcctctg cagaagccaa gggaagacag tggtttgtgg acgagagggc tgtgagcatc
1381 ctggcaggtg ccccaggatg ccacgcctgg aagggccggc ttctgcctgg ggtgcatttc
1441 ccccgcagtg cataccggac ttgtcacacg gacctcgggc tagttaaggt gtgcaaagat
1501 ctctagagtt tagtccttac tgtctcactc gttctgttac ccagggctct gcagcacctc
1561 acctgagacc tccactccac atctgcatca ctcatggaac actcatgtct ggagtcccct
1621 cctccagccg ctggcaacaa cagcttcagt ccatgggtaa tccgttcata gaaattgtgt
1681 ttgctaacaa ggtgcccttt agccagatgc taggctgtct gcgaagaagg ctaggagttc
1741 atagaaggga gtggggctgg ggaaagggct ggctgcaatt gcagctcact gctgctgcct
1801 ctgaaacaga aagttggaaa ggaaaaaaga aaaaagcaat taggtagcac agcactttgg
1861 ttttgctgag atcgaagagg ccagtaggag acacgacagc acacacagtg gattccagtg
1921 catggggagg cactcgctgt tatcaaatag cgatgtgcag gaagaaaagc ccctcttcat
1981 tccggggaac aaagacgggt attgttggga aaggaacagg cttggaggga agggagaaag
2041 taggccgctg atgatatatt cgggcaggac tgttgtggta ctggcaataa gatacacagc
2101 tccgagctgt aggagagtcg gtctgctttg gatgattttt taagcagact cagctgctat
2161 acttatcaca ttttattaaa cacagggaaa gcatttagga gaatagcaga gagccaaatc
2221 tgacctaaaa gttgaaaagc caaaggtcaa acaggctgta attccatcat catcgttgtt
2281 attaaagaat ccttatctat aaaaggtagg tcagatcccc ctccccccag gttcctcctt
2341 cccctcccga ttgagcctta cgacactttg gtttatgcgg tgctgtccgg gtgccagggc
2401 tgcagggtcg gtactgatgg aggctgcagc gcccggtgct ctgtgtcaag gtgaagcaca
2461 tacggcagac ctcttagagt ccttaagacg gaagtaaatt atgatgtcca gggggagaag
2521 gaagatagga cgtatttata ataggtatat agaacacaag ggatataaaa tgaaagattt
2581 ttactaatat atattttaag gttgcacaca gtacacacca gaagatgtga aattcatttg
```

Fig. 64A 2641 tggcaattaa gtggtcccaa tgctcagcgc ttaaaaaaac aaattggaca gctacttctg
2701 ggaaaaacaa catcattcca aaaagaacaa taatgagagc aaatgcaaaa ataaccaagt
2761 cctccgaagg catctcacgg aaccgtagac taggaagtac gagccccaca gagcaggaag
2821 ccgatgtgac tgcatcatat atttaacaat gacaagatgt tccggcgttt atttctgcgt
2881 tgggttttcc cttgccttat gggctgaagt gttctctaga atccagcagg tcacactggg
2941 ggcttcaggt gacgatttag ctgtggctcc ctcctcctgt cctcccccgc accccctccc
3001 ttctgggaaa caagaagagt aaacaggaaa cctacttttt atgtgctatg caaaatagac
3061 atctttaaca tagtcctgtt actatggtaa cactttgctt tctgaattgg aagggaaaaa
3121 aaatgtagcg acagcatttt aaggttctca gacctccagt gagtacctgc aaaaatgagt
3181 tgtcacagaa attatgatcc tctatttcct gaacctggaa atgatgttgg tccaaagtgc
3241 gtgtgtgtat gtgtgagtgg gtgcgtggta tacatgtgta catatatgta taatatatat
3301 ctacaatata tattatatat atctatatca tatttctgtg gagggttgcc atggtaacca
3361 gccacagtac atatgtaatt ctttccatca ccccaacctc tcctttctgt gcattcatgc
3421 aagagtttct tgtaagccat cagaagttac ttttaggatg ggggagaggg gcgagaaggg
3481 gaaaaatggg aaatagtctg attttaatga aatcaaatgt atgtatcatc agttggctac
3541 gttttggttc tatgctaaac tgtgaaaaat cagatgaatt gataaaagag ttccctgcaa
3601 ccaattgaaa agtgttctgt gcgtctgttt tgtgtctggt gcagaatatg acaatctacc
3661 aactgtccct ttgtttgaag ttggtttagc tttggaaagt tactgtaaat gccttgcttg
3721 tatgatcgtc cctggtcacc cgactttgga atttgcacca tcatgtttca gtgaagatgc
3781 tgtaaatagg ttcagatttt actgtctatg gatttggggt gttacagtag ccttattcac
3841 ctttttaata aaaatacaca tgaaaacaag aaagaaatgg cttttcttac ccagattgtg
3901 tacatagagc aatgttggtt ttttataaag tctaagcaag atgttttgta taaaatctga
3961 attttgcaat gtatttagct acagcttgtt taacggcagt gtcattcccc tttgcactgt
4021 aatgaggaaa aaatggtata aaaggttgcc aaattgctgc atatttgtgc cgtaattatg
4081 taccatgaat atttatttaa aatttcgttg tccaatttgt aagtaacaca gtattatgcc
4141 tgagttataa atattttttt ctttctttgt tttattttaa tagcctgtca taggttttaa
4201 atctgcttta gtttcacatt gcagttagcc ccagaaaatg aaatccgtga agtcacattc
4261 cacatctgtt tcaaactgaa tttgttctta aaaaaataaa atattttttt cctatggaaa
4321 aaaaaaaaaa aaaaa

Fig. 64B

EphB4 Precursor Protein

```
  1 melrvllcwa slaaaleetl lntkletadl kwvtfpqvdg qweelsglde eqhsvrtyev
 61 cdvqrapgqa hwlrtgwvpr rgavhvyatl rftmleclsl pragrscket ftvfyyesda
121 dtataltpaw menpyikvdt vaaehltrkr pgaeatgkvn vktlrlgpls kagfylafqd
181 qgacmallsl hlfykkcaql tvnltrfpet vprelvvpva gscvvdavpa pgpspslycr
241 edgqwaeqpv tgcscapgfe aaegntkcra caqgtfkpls gegscqpcpa nshsntigsa
301 vcqcrvgyfr artdprgapc ttppsaprsv vsrlngsslh lewsaplesg gredltyalr
361 crecrpggsc apcggdltfd pgprdlvepw vvvrglrpdf tytfevtaln gvsslatgpv
421 pfepvnvttd revppavsdi rvtrsspssl slawavprap sgavldyevk yhekgaegps
481 svrflktsen raelrglkrg asylvqvrar seagygpfgq ehhsqtqlde segwreqlal
541 iagtavvgvv lvlvvivvav lclrkqsngr eaeysdkhgq ylighgtkvy idpftyedpn
601 eavrefakei dvsyvkieev igagefgevc rgrlkapgkk escvaiktlk ggyterqrre
661 flseasimgq fehpniirle gvvtnsmpvm iltefmenga ldsflrlndg qftviqlvgm
721 lrgiasgmry laemsyvhrd laarnilvns nlvckvsdfg lsrfleenss dptytsslgg
781 kipirwtape aiafrkftsa sdawsygivm wevmsfgerp ywdmsnqdvi naieqdyrlp
841 pppdcptslh qlmldcwqkd rnarprfpqv vsaldkmirn paslkivare nggashplld
901 qrqphysafg svgewlraik mgryeesfaa agfgsfelvs qisaedllri gvtlaghqkk
961 ilasvqhmks qakpgtpggt ggpapqy
```

Fig. 65

EphrinB2

```
  1 mavrrdsvwk ycwgvlmvlc rtaisksivl epiywnssns kflpgqglvl ypqigdkldi
 61 icpkvdsktv gqyeyykvym vdkdqadrct ikkentplln cakpdqdikf tikfqefspn
121 lwglefqknk dyyiistsng slegldnqeg gvcqtramki lmkvgqdass agstrnkdpt
181 rrpeleagtn grssttspfv kpnpgsstdg nsaghsgnni lgsevalfag iasgciifiv
241 iiitlvvlll kyrrrhrkhs pqhtttlsls tlatpkrsgn nngsepsdii iplrtadsvf
301 cphyekvsgd yghpvyivqe mppqspaniy ykv
```

Fig. 66

NUCLEIC ACID COMPOUNDS FOR INHIBITING ANGIOGENESIS AND TUMOR GROWTH

RELATED APPLICATIONS

This application claims the benefit of priority of U.S. Provisional Application No. 60/454,300 filed Mar. 12, 2003 and U.S. Provisional Application No. 60/454,432 filed Mar. 12, 2003. The entire teachings of the referenced Provisional Applications are incorporated herein by reference in their entirety.

BACKGROUND OF THE INVENTION

Angiogenesis, the development of new blood vessels from the endothelium of a preexisting vasculature, is a critical process in the growth, progression, and metastasis ofsolid tumors within the host. During physiologically normal angiogenesis, the autocrine, paracrine, and amphicrine interactions of the vascular endothelium with its surrounding stromal components are tightly regulated both spatially and temporally. Additionally, the levels and activities of proangiogenic and angiostatic cytokines and growth factors are maintained in balance. In contrast, the pathological angiogenesis necessary for active tumor growth is sustained and persistent, representing a dysregulation of the normal angiogenic system. Solid and hematopoietic tumor types are particularly associated with a high level of abnormal angiogenesis.

It is generally thought that the development of tumor consists of sequential, and interrelated steps that lead to the generation of an autonomous clone with aggressive growth potential. These steps include sustained growth and unlimited self-renewal. Cell populations in a tumor are generally characterized by growth signal self-sufficiency, decreased sensitivity to growth suppressive signals, and resistance to apoptosis. Genetic or cytogenetic events that initiate aberrant growth sustain cells in a prolonged "ready" state by preventing apoptosis.

It is a goal of the present disclosure to provide agents and therapeutic treatments for inhibiting angiogenesis and tumor growth.

SUMMARY OF THE INVENTION

In certain aspects, the disclosure provides nucleic acid compounds that decrease the expression of EphB4 or EphrinB2. As demonstrated herein, EphB4 and EphrinB2 participate in various disease states, including cancers and diseases related to unwanted or excessive angiogenesis. Accordingly, certain nucleic acid compounds disclosed herein may be used to treat such diseases. In further aspects, the disclosure relates to the discovery that EphB4 and/or EphrinB2 are expressed, often at high levels, in a variety of tumors. Therefore, reagents that donwregulate EphB4 or EphrinB2 may affect tumors by a direct effect on the tumor cells as well as an indirect effect on the angiogenic processes recruited by the tumor. In certain embodiments, the disclosure provides the identity of tumor types particularly suited to treatment with an agent that downregulates EphB4 or EphrinB2, including agents that inhibit expression of EphB4 or EphrinB2.

In certain aspects, the disclosure provides isolated nucleic acid compounds comprising at least a portion that hybridizes to an EphB4 transcript under physiological conditions and decreases the expression of EphB4 in a cell. The EphB4 transcript may be any pre-splicing transcript (i.e., including introns), post-splicing transcript, as well as any splice variant.

In certain embodiments, the EphB4 transcript has a sequence set forth in FIG. 62. In certain aspects, the disclosure provides isolated nucleic acid compounds comprising at least a portion that hybridizes to an EphrinB2 transcript under physiological conditions and decreases the expression of EphrinB2 in a cell. The EphrinB2 transcript may be any pre-splicing transcript (i.e., including introns), post-splicing transcript, as well as any splice variant. In certain embodiments, the EphrinB2 transcript has a sequence set forth in FIG. 64. Examples of categories of nucleic acid compounds include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50 nucleotides of the EphB4 or EphrinB2 nucleic acid sequence as designated by FIG. 62 and FIG. 64, respectively. The region of complementarity will preferably be at least 8 nucleotides, and optionally at least 10 or at least 15 nucleotides. A region of complementarity may fall within an intron, a coding sequence or a noncoding sequence of an EphB4 or EphrinB2 transcript, such as the coding sequence portion of the sequences set forth in FIGS. 62 and 64, respectively. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. Examples of various EphB4 and EphrinB2 antisense and RNAi constructs having differing levels of efficacy are presented in Tables 6-9. In the case of a RNAi construct, the strand complementary to the target transcript will generally be RNA or modifications thereof. The other strand may be RNA, DNA or any other variation. The duplex portion of double stranded or single stranded "hairpin" RNAi construct will preferably have a length of 18 to 25 nucleotides in length and optionally about 21 to 23 nucleotides in length. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on cellular phenotypes. In the case of certain cancer cell lines, cell death or decreased rate of expansion may be measured upon administration of EphB4 or EphrinB2-targeted nucleic acid compounds. Preferably, cell expansion will be inhibited by greater than 50% at an experimentally meaningful concentration of the nucleic acid.

In certain aspects, the disclosure provides pharmaceutical compostions comprising any of the various EphB4 or EphrinB2-targeted nucleic acid compounds. A pharmaceutical composition will generally include a pharmaceutically acceptable carrier. A pharmaceutical composition may comprise a nucleic acid compound that hybridizes to an EphB4 transcript under physiological conditions and decreases the expression of EphB4 in a cell. A pharmaceutical composition may also comprise a nucleic acid compound that hybridizes to an EphrinB2 transcript under physiological conditions and decreases the expression of EphrinB2 in a cell.

In certain aspects the disclosure provides methods for inhibiting EphB4 expression in a cell, comprising contacting the cell with an effective amount of a nucleic acid compound that hybridizes to an EphB4 transcript under physiological conditions and decreases the expression of EphB4 in a cell. Any of the EphB4 targeted nucleic acid compounds disclosed may be used in such a method. In certain aspects the disclosure provides methods for inhibiting EphrinB2 expression in a cell, comprising contacting the cell with an effective amount of a nucleic acid compound that hybridizes to an EphrinB2 transcript under physiological conditions and decreases the expression of EphrinB2 in a cell. Any of the EphrinB2 targeted nucleic acid compounds disclosed may be used in such a method.

In certain aspects, the disclosure provides methods for reducing the growth rate of a tumor in a subject, comprising administering an amount of a nucleic acid compound sufficient to reduce the growth rate of the tumor. In certain aspects, the disclosure provides methods for treating a patient suffering from a cancer, comprising administering to the patient a nucleic acid moclecule. The nucleic acid molecule may be, for example, selected from the group consisting of: (a) a nucleic acid compound that hybridizes to an EphB4 transcript under physiological conditions and decreases the expression of EphB4 in a cell; and (b) a nucleic acid compound that hybridizes to an EphrinB2 transcript under physiological conditions and decreases the expression of EphrinB2 in a cell. The nucleic acid compound may, for example, be an antisense or an RNAi nucleic acid compound, and may be formulated with a pharmaceutically acceptable carrier. Optionally, the tumor will comprise one or more cancer cells expressing EphB4 and/or EphrinB2. The EphB4 and/or EphrinB2 may be overexpressed relative to a cell from a comparable tissue. The tumor may also be a metastatic tumor, and angiogenesis-dependent tumor or an angiogenesis independent tumor. Optionally, the tumor is seleted from the group consisting of colon carcinoma, breast tumor, mesothelioma, prostate tumor, squamous cell carcinoma, Kaposi sarcoma, and leukemia. Such treatment may be combined with at least one additional anti-cancer chemotherapeutic agent that inhibits cancer cells in an additive or synergistic manner with the nucleic acid compound. The nucleic acid compound and the additional anticancer agent(s) may be formulated in advance as a combination formulation, or may be formulated independently and administered in such a manner (e.g., timing, dosage) so as to achieve the combined effect.

In certain aspects, the disclosure provides methods for treating a patient suffering from an unwanted angiogenesis-associated disease or process, comprising administering to the patient an amount of a nucleic acid compound sufficient to inhibit angiogenesis. The nucleic acid molecule may be, for example, selected from the group consisting of: (a) a nucleic acid compound that hybridizes to an EphB4 transcript under physiological conditions and decreases the expression of EphB4 in a cell; and (b) a nucleic acid compound that hybridizes to an EphrinB2 transcript under physiological conditions and decreases the expression of EphrinB2 in a cell. The nucleic acid compound may, for example, be an antisense or an RNAi nucleic acid compound, and may be formulated with a pharmaceutically acceptable carrier. Examples of angiogenesis-associated diseases or processes are angiogenesis-dependent cancer, benign tumors, inflammatory disorders, chronic articular rheumatism and psoriasis, ocular angiogenic diseases, Osler-Webber Syndrome, myocardial angiogenesis, plaque neovascularization, telangiectasia, hemophiliac joints, angiofibroma, wound granulation, wound healing, telangiectasia psoriasis scleroderma, pyogenic granuloma, cororany collaterals, ischemic limb angiogenesis, rubeosis, arthritis and diabetic neovascularization. Such treatment may be combined with an additional anti-angiogenesis agent that inhibits angiogenesis in an additive or synergistic manner with the nucleic acid compound. The nucleic acid compound and the additional agent(s) may be formulated in advance as a combination formulation, or may be formulated independently and administered in such a manner (e.g., timing, dosage) so as to achieve the combined effect.

In certain aspects, the disclosure provides for the use of a nucleic acid compound in the manufacture of a medicament. For example, the disclosure provides for the use of an EphB4 or EphrinB2-targeted nucleic acid compound of in the manufacture of medicament for the treatment of cancer or the treatment of angiogenesis-associated diseases or processes.

In certain aspects, the disclosure provides methods for treating a patient suffering from a cancer, comprising: (a) identifying in the patient a tumor having a plurality of cancer cells that express EphB4 and/or EphrinB2; and (b) administering to the patient, as appropriate, an EphB4 or EphrinB2-targeted nucleic acid compound. For example, a nucleic acid compound may be selected from the group consisting of: (i) a nucleic acid compound that hybridizes to an EphB4 transcript under physiological conditions and decreases the expression of EphB4 in a cell; and (ii) a nucleic acid compound that hybridizes to an EphrinB2 transcript under physiological conditions and decreases the expression of EphrinB2 in a cell. A method may include, as a diagnostic part, identifying in the patient a tumor having a plurality of cancer cells having a gene amplification of the EphB4 and/or EphrinB2 gene. Gene amplifications may be detected in a variety of ways, including, for example, fluorescent in situ hybridization (FISH).

In certain aspects, the disclosure provides methods for identifying a tumor that is suitable for treatment with an inhibitor of EphrinB2 or EphB4 expression. A method may include detecting in the tumor a cell having one or more of the following characteristics: (a) expression of EphB4 protein and/or mRNA; (b) expression of EphrinB2 protein and/or mRNA; (c) gene amplification of the EphB4 gene; and (d) gene amplification of the EphrinB2 gene. A tumor comprising cells having one or more of characteristics (a)-(d) is likely to be sensitive to treatment with an inhibitor of EphrinB2 or EphB4 expression. It should be noted that tumors that do not directly express EphrinB2 or EphB4 may also be sensitive to treatments targeted at these proteins, as these proteins are known to be expressed in the vascular endothelium and to participate in the formation of new capillaries that service growing tumors. An inhibitor of EphrinB2 or EphB4 expression may be, for example, (i) a nucleic acid compound that hybridizes to an EphB4 transcript under physiological conditions and decreases the expression of EphB4 in a cell; or (ii) a nucleic acid compound that hybridizes to an EphrinB2 transcript under physiological conditions and decreases the expression of EphrinB2 in a cell.

One aspect of the present disclosure provides a method for reducing the growth rate of a tumor expressing Ephrin B2 and/or EphB4. Such method comprises administering an amount of an ephrin therapeutic agent that blocks signaling through the Ephrin B2/EphB4 pathway, sufficient to reduce the growth rate of the tumor. For example, the ephrin therapeutic agent may exert its inhibitory effect by inhibiting the interaction between Ephrin B2 and EphB4, inhibiting gene expression of Ephrin B2 or EphB4, inhibiting activity of Ephrin B2 or EphB4, inhibiting clustering of Ephrin B2 or EphB4, inhibiting phosphorylation of Ephrin B2 or EphB4, or inhibiting any downstream signaling event upon binding of Ephrin B2 to EphB4. Exemplary tumors include, but are not limited to, colon carcinoma, breast cancer, mesothelioma, prostate cancer (hormone refractory), squamous cell carcinoma, Kaposi sarcoma, and leukemia.

Another aspect of the present disclosure provides a packaged pharmaceutical. Such packaged pharmaceutical comprises: (i) a therapeutically effective amount of a nucleic acid compound disclosed herein; and (ii) instructions and/or a label for administration of compound for the treatment of patients having tumors that express Ephrin B2 and/or EphB4.

Another aspect of the present disclosure provides a method for treating a patient suffering from a cancer. Such method comprises: (i) assessing the Ephrin B2 and/or ephB4 status of a sample of tumor cells from said patient; and (ii) treating the patient with an therapeutic agent targeted to EphrinB2 or EphB4 if said tumor cells express Ephrin B2 and/or ephB4. Exemplary cancers include, but are not limited to, colon carcinoma, breast cancer, mesothelioma, prostate cancer (hormone refractory), squamous cell carcinoma, Kaposi sarcoma, and leukemia.

BRIEF DESCRIPTION OF THE DRAWINGS

FIG. 1 shows amino acid sequence of the B4ECv3 protein (predicted sequence of the precursor including uncleaved Eph B4 leader peptide is shown), SEQ ID NO: 386.

FIG. 2 shows amino acid sequence of the B4ECv3NT protein (predicted sequence of the precursor including uncleaved Eph B4 leader peptide is shown), SEQ ID NO: 387.

FIG. 3 shows amino acid sequence of the B2EC protein (predicted sequence of the precursor including uncleaved Ephrin B2 leader peptide is shown), SEQ ID NO: 388.

FIG. 4 shows amino acid sequence of the B4ECv3-FC protein (predicted sequence of the precursor including uncleaved Eph B4 leader peptide is shown), SEQ ID NO: 389.

FIG. 5 shows amino acid sequence of the B2EC-FG protein (predicted sequence of the precursor including uncleaved Ephrin B2 leader peptide is shown), SEQ ID NO: 390.

Shown is the mean±s.e.m. of triplicate samples at the indicated concentrations of siRNA 472 and GFP siRNA (control).

FIG. 33 shows that EphB4 and EphrinB2 are expressed in mesothelioma cell lines as shown by RT-PCR (A) and Western Blot (B).

Figure 34:
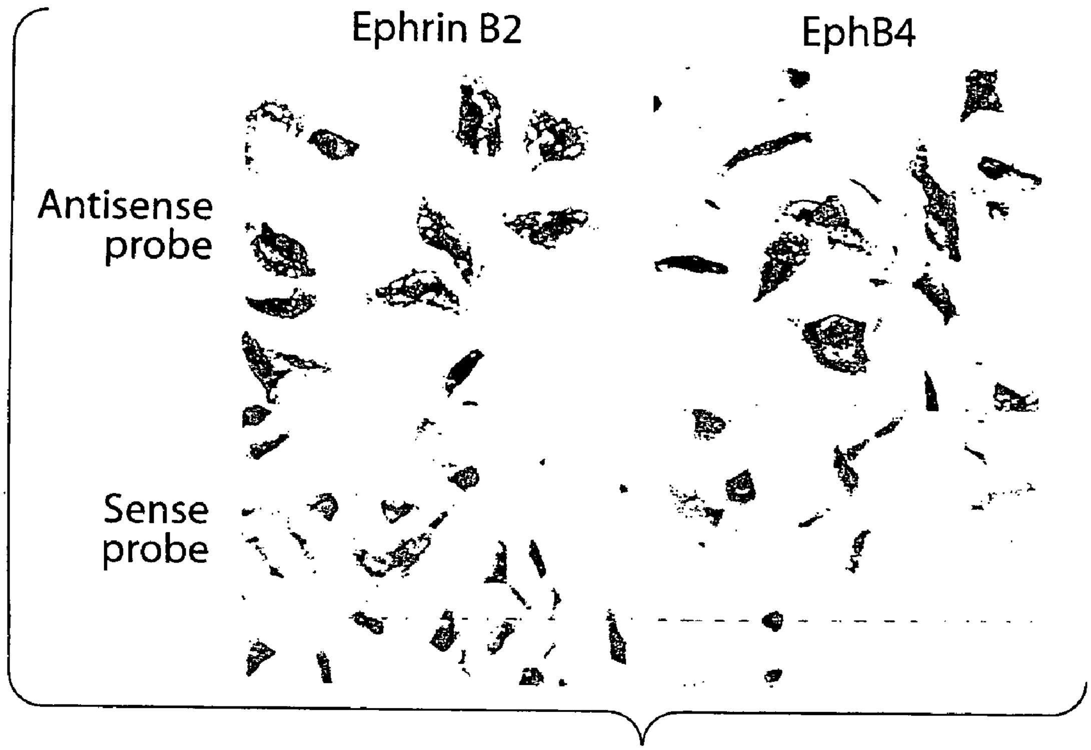

FIG. 34 shows expression of ephrin B2 and EphB4 by in situ hybridization in mesothelioma cells. NCI H28 mesothelioma cell lines cultured in chamber slides hybridized with antisense probe to ephrin B2 or EphB4 (top row). Control for each hybridization was sense (bottom row). Positive reaction is dark blue cytoplasmic stain.

Figure 35:
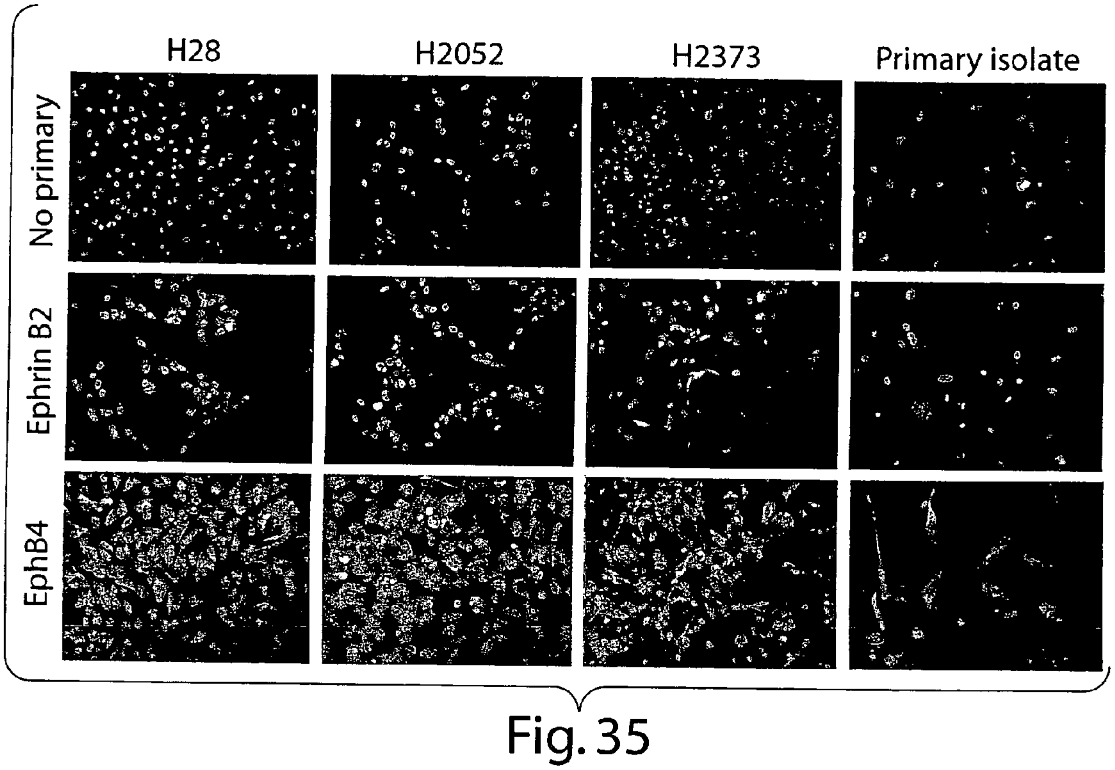

FIG. 35 shows cellular expression of EphB4 and ephrin B2 in mesothelioma cultures. Immunofluorescence staining of primary cell isolate derived from pleural effusion of a patient with malignant mesothelioma and cell lines NCI H28, NCI H2373, and NCI H2052 for ephrin B2 and EphB4. Green color is positive signal for FITC labeled secondary antibody. Specificity of immunofluorescence staining was demonstrated by lack of signal with no primary antibody (first row). Cell nuclei were counterstained with DAPI (blue color) to reveal location of all cells.

Shown are merged images of DAPI and FITC fluorescence. Original magnification 200×.

Figure 36:
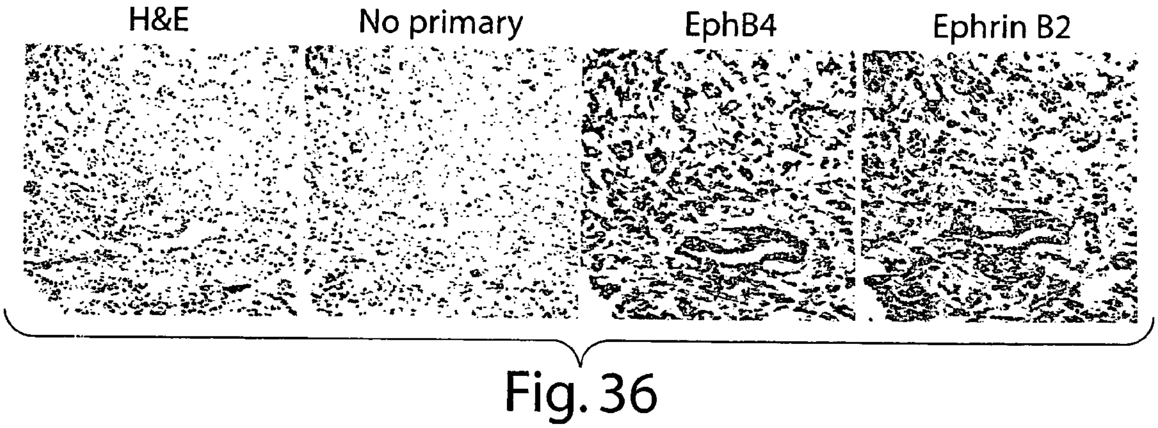

FIG. 36 shows expression of ephrin B2 and EphB4 in mesothelioma tumor. Immunohistochemistry of malignant mesothelioma biopsy. H&E stained section to reveals tumor architecture; bottom left panel is background control with no primary antibody. EphB4 and ephrin B2 specific staining is brown color. Original magnification 200×.

FIG. 37 shows effects of EPHB4 antisense probes (A) and EPHB4 siRNAs (B) on the growth of H28 cells.

FIG. 38 shows effects of EPHB4 antisense probes (A) and EPHB4 siRNAs (B) on cell migration.

FIG. 39 shows that EphB4 is expressed in HNSCC primary tissues and metastases. A) Top: Immunohistochemistry of a representative archival section stained with EphB4 monoclonal antibody as described in the methods and visualized with DAB (brown color) localized to tumor cells. Bottom: Hematoxylin and Eosin (H&E) stain of an adjacent section. Dense purple staining indicates the presence of tumor cells.

The right hand column are frozen sections of lymph node metastasis stained with EphB4 polyclonal antibody (top right) and visualized with DAB. Control (middle) was incubation with goat serum and H&E (bottom) reveals the location of the metastatic foci surrounded by stroma which does not stain. B) In situ hybridization of serial frozen sections of a HNSCC case probed with EphB4 (left column) and ephrin B2 (right column) DIG labeled antisense or sense probes generated by run-off transcription. Hybridization signal (dark blue) was detected using alkaline-phosphatase-conjugated anti-DIG antibodies and sections were counterstained with Nuclear Fast Red. A serial section stained with H&E is shown (bottom left) to illustrate tumor architecture. C) Western blot of protein extract of patient samples consisting of tumor (T), uninvolved normal tissue (N) and lymph node biopsies (LN). Samples were fractionated by polyacrylamide gel electrophoresis in 4-20% Tris-glycine gels and subsequently electroblotted onto nylon membranes. Membranes were sequentially probed with EphB4 monoclonal antibody and β-actin MoAb. Chemiluminescent signal was detected on autoradiography film. Shown is the EphB4 specific band which migrated at 120 kD and β-actin which migrated at 40 kD. The β-actin signal was used to control for loading and transfer of each sample.

FIG. 40 shows that EphB4 is expressed in HNSCC cell lines and is regulated by EGF: A) Survey of EphB4 expression in SCC cell lines. Western blot of total cell lysates sequentially probed with EphB4 monoclonal antibody, stripped and reprobed with β-actin monoclonal antibody as described for FIG. 39C. B) Effect of the specific EGFR inhibitor AG1478 on EphB4 expression: Western blot of crude cell lysates of SCC15 treated with 0-1000 nM AG 1478 for 24 h in media supplemented with 10% FCS (left) or with 1 mM AG 1478 for 4, 8, 12 or 24 h (right). Shown are membranes sequentially probed for EphB4 and β-actin. C) Effect of inhibition of EGFR signaling on EphB4 expression in SCC cell lines: Cells maintained in growth media containing 10% FCS were treated for 24 hr with 1 μM AG 1478, after which crude cell lysates were analyzed by Western blots of cell lysates sequentially probed with for EGFR, EphB4, ephrin B2 and β-actin antibodies. Specific signal for EGFR was detected at 170 kD and ephrin B2 at 37 kD in addition to EphB4 and β-actin as described in FIG. 1C. β-actin serves as loading and transfer control.

Figure 41A:
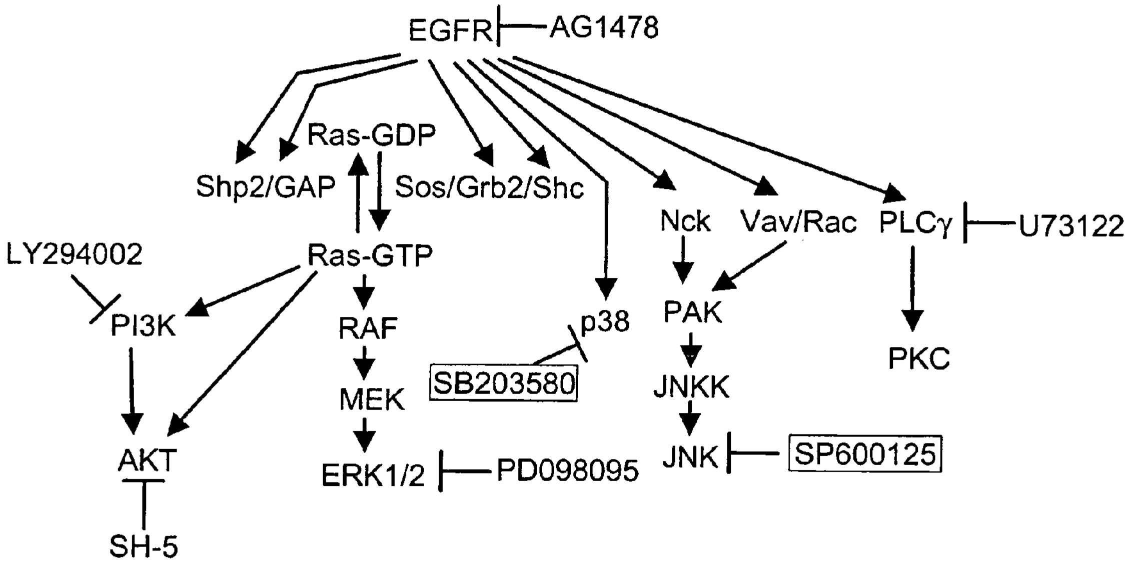

FIG. 41 shows mechanism of regulation of EphB4 by EGF: A) Schematic of the EGFR signaling pathways, showing in red the sites of action and names of specific kinase inhibitors used. B) SCC15 cells were serum-starved for 24 h prior to an additional 24 incubation as indicated with or without EGF (10 ng/ml), 3 μM U73122, or 5 μM SH-5, 5 μM SP600125, 25 nM LY294002,—μM PD098095 or 5 μM SB203580. N/A indicates cultures that received equal volume of diluent (DMSO) only. Cell lysates were subjected to Western Blot with EphB4 monoclonal antibody. β-actin signal serves as control of protein loading and transfer.

FIG. 42 shows that specific EphB4 siRNAs inhibit EphB4 expression, cell viability and cause cell cycle arrest. A) 293 cells stably expressing full length EphB4 were transfected with 50 nM RNAi using Lipofectamine™2000. 40 h post-transfection cells were harvested, lysed and processed for Western blot. Membranes were probed with EphB4 monoclonal antibody, stripped and reprobed with β-actin monoclonal antibody as control for protein loading and transfer. Negative reagent control was RNAi to scrambled green fluorescence protein (GFP) sequence and control is transfection with Lipofectamine™2000 alone. B) MTT cell viability assays of SCC cell lines treated with siRNAs for 48 h as described in the Methods section. Shown is mean+s.e.m. of triplicate samples. C) SCC15 cells transfected with siRNAs as indicated were analyzed 24 h post transfection for cell cycle status by flow cytometry as described in the Methods. Shown are the plots of cell number vs. propidium iodide fluorescence intensity. Top and middle row show plots for cells 16 h after siRNA transfection, bottom row shows plots for cells 36 h post transfection. Specific siRNA and concentration are indicated for each plot. Lipo=Lipofectamine™200 mock transfection.

FIG. 43 shows in vitro effects of specific EphB4 AS-ODNs on SCC cells. A) 293 cells transiently transfected with EphB4 full-length expression plasmid were treated 6 h post transfection with antisense ODNs as indicated. Cell lysates were collected 24 h after AS-ODN treatment and subjected to Western Blot. B) SCC25 cells were seeded on 48 well plates at equal densities and treated with EphB4 AS-ODNs at 1, 5, and 10 μM on days 2 and 4. Cell viability was measured by MTT assay on day 5. Shown is the mean±s.e.m. of triplicate samples. Note that AS-ODNs that were active in inhibiting EphB4 protein levels were also effective inhibitors of SCC15 cell viability. C) Cell cycle analysis of SCC15 cells treated for 36 h with AS-10 (bottom) compared to cells that were not treated (top). D) Confluent cultures of SCC15 cells scraped with a plastic Pasteur pipette to produce 3 mm wide breaks in the monolayer. The ability of the cells to migrate and close the wound in the presence of inhibiting EphB4 AS-ODN (AS-10) and non-inhibiting AS-ODN (AS-1) was assessed after 48 h. Scrambled ODN is included as a negative control ODN. Culture labeled no treatment was not exposed to ODN. At initiation of the experiment, all cultures showed scrapes of equal width and similar to that seen in 1 μM EphB4 AS-10 after 48 h. The red brackets indicate the width of the original scrape. E) Migration of SCC15 cells in response to 20 mg/ml EGF in two-chamber assay as described in the Methods. Shown are representative photomicrographs of non-treated (NT), AS-6 and AS-10 treated cells and 10 ng/ml Taxol as positive control of migration inhibition. F) Cell numbers were counted in 5 individual high-powered fields and the average+s.e.m. is shown in the graph.

Figure 44:
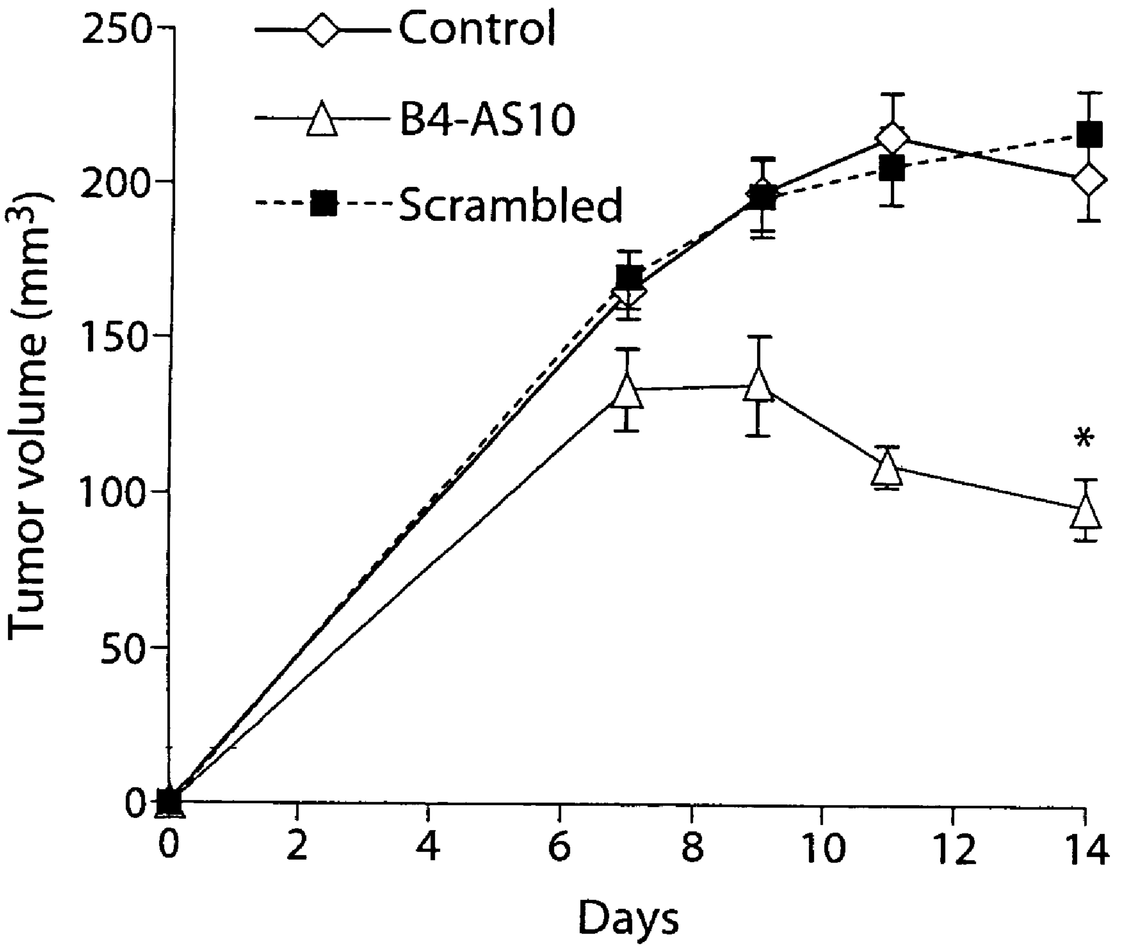

FIG. 44 shows that EphB4 AS-ODN inhibits tumor growth in vivo. Growth curves for SCC15 subcutaneous tumor xenografts in Balb/C nude mice treated with EphB4 AS-10 or scrambled ODN at 20 mg/kg/day starting the day following implantation of 5×106 cells. Control mice received and equal volume of diluent (PBS). Shown are the mean+s.e.m. of 6 mice/group. * P=0.0001 by Student's t-test compared to scrambled ODN treated group.

FIG. 45 shows that Ephrin B2, but not EphB4 is expressed in KS biopsy tissue. (A) In situ hybridization with antisense probes for ephrin B2 and EphB4 with corresponding H&E stained section to show tumor architecture. Dark blue color in the ISH indicates positive reaction for ephrin B2. No signal for EphB4 was detected in the Kaposi's sarcoma biopsy. For contrast, ISH signal for EphB4 is strong in squamous cell carcinoma tumor cells. Ephrin B2 was also detected in KS using EphB4-AP fusion protein (bottom left). (B) Detection of ephrin B2 with EphB4/Fc fusion protein. Adjacent sections were stained with H&E (left) to show tumor architecture, black rectangle indicates the area shown in the EphB4/Fc treated section (middle) detected with FITC-labeled anti-human Fc antibody as described in the methods section. As a control an adjacent section was treated with human Fc fragment (right). Specific signal arising from EphB4/Fc binding to the section is seen only in areas of tumor cells. (C) Co-expression of ephrin B2 and the HHV8 latency protein LANA1. Double-label confocal immunofluorescence microscopy with antibodies to ephrin B2 (red) LANA1 (green), or EphB4 (red) of frozen KS biopsy material directly demonstrates co-expression of LANA1 and ephrin B2 in KS biopsy. Coexpression is seen as yellow color. Double label confocal image of biopsy with antibodies to PECAM-1 (green) in cells with nuclear propidium iodide stain (red), demonstrating the vascular nature of the tumor.

Figure 46A:
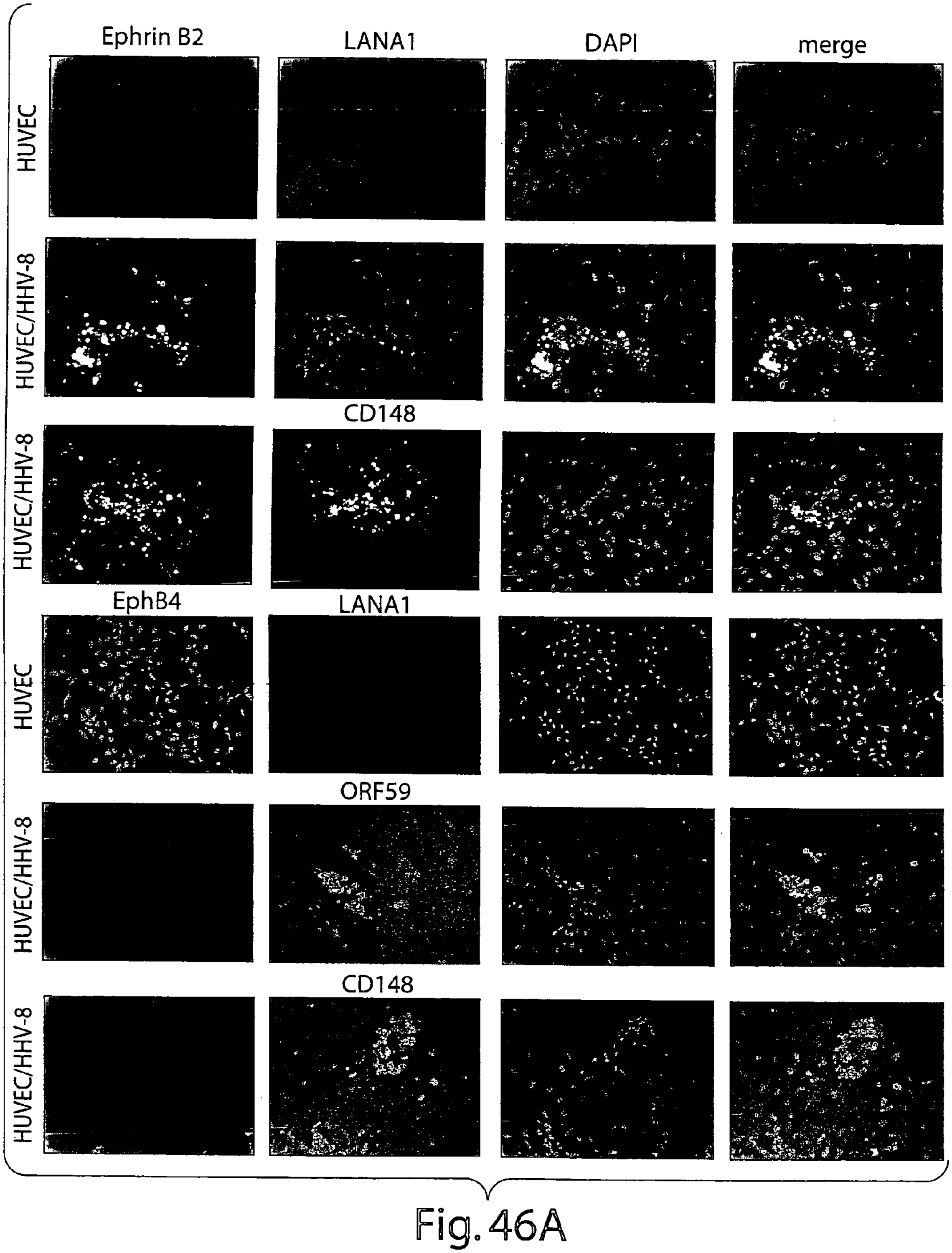

FIG. 46 shows that HHV-8 induces arterial marker expression in venous endothelial cells. (A) Immunofluorescence of cultures of HUVEC and HUVEC/BC-1 for artery/vein markers and viral proteins. Cultures were grown on chamber slides and processed for immunofluorescence detection of ephrin B2 (a, e, i), EphB4 (m, q, u), CD148 (j, v), and the HHV-8 proteins LANA1 (b, f, m) or ORF59 (r) as described in the Materials and Methods. Yellow color in the merged images of the same field demonstrate co-expression of ephrin B2 and LANA or ephrin B2 and CD148. The positions of viable cells were revealed by nuclear staining with DAPI (blue) in the third column (c, g, k, o, s, w). Photomicrographs are of representative fields. (B) RT-PCR of HUVEC and two HHV-8 infected cultures (HUVEC/BC-1 and HUVEC/BC-3) for ephrin B2 and EphB4. Ephrin B2 product (200 bp) is seen in HUVEC/BC-1, HUVEC/BC-3 and EphB4 product (400 bp) is seen in HUVEC. Shown also is β-actin RT-PCR as a control for amount and integrity of input RNA.

FIG. 47 shows that HHV-8 induces arterial marker expression in Kaposi's sarcoma cells. (A) Western blot for ephrin B2 on various cell lysates. SLK-vGPCR is a stable clone of SLK expressing the HHV-8 vGPCR, and SLK-pCEFL is control stable clone transfected with empty expression vector. SLK cells transfected with LANA or LANAΔ440 are SLK-LANA and SLK-Δ440 respectively. Quantity of protein loading and transfer was determined by reprobing the membranes with β-actin monoclonal antibody. (B) Transient transfection of KS-SLK cells with expression vector pvGPCR-CEFL resulted in the expression of ephrin B2 as shown by immunofluorescence staining with FITC (green), whereas the control vector pCEFL had no effect. KS-SLK cells (0.8×105/well) were transfected with 0.8 μg DNA using Lipofectamine 2000. 24 hr later cells were fixed and stained with ephrin B2 polyclonal antibody and FITC conjugated secondary antibody as described in the methods. (C) Transient transfection of HUVEC with vGPCR induces transcription from ephrin B2 luciferase constructs. 8×103 HUVEC in 24 well plates were transfected using Superfect with 0.8 μg/well ephrin B2 promoter constructs containing sequences from −2941 to −11 with respect to the translation start site, or two 5'-deletions as indicated, together with 80 ng/well pCEFL or pvGPCR-CEFL. Luciferase was determined 48 h post transfection and induction ratios are shown to the right of the graph. pGL3Basic is promoterless luciferase control vector. Luciferase was normalized to protein since GPCR induced expression of the cotransfected β-galactosidase. Graphed is mean+SEM of 6 replicates. Shown is one of three similar experiments.

FIG. 48 shows that VEGF and VEGF-C regulate ephrin B2 expression. A) Inhibition of ephrin B2 by neutralizing antibodies. Cells were cultured in full growth medium and exposed to antibody (100 ng/ml) for 36 hr before collection and lysis for Western blot. B) For induction of ephrin B2 expression cells were cultured in EBM growth medium containing 5% serum lacking growth factors. Individual growth factors were added as indicated and the cells harvested after 36 h. Quantity of protein loading and transfer was determined by reprobing the membranes β-actin monoclonal antibody.

FIG. 49 shows that Ephrin B2 knock-down with specific siRNA inhibits viability in KS cells and HUVEC grown in the presence of VEGF but not IGF, EGF or bFGF. A) KS-SLK cells were transfected with various siRNA to ephrin B2 and controls. After 48 hr the cells were harvested and crude cell lysates fractionated on 4-20% SDS-PAGE. Western blot was performed with monoclonal antibody to ephrin B2 generated in-house. The membrane was stripped and reprobed with β-actin monoclonal antibody (Sigma) to illustrate equivalent loading and transfer. B) 3 day cell viability assay of KS-SLK cultures in the presence of ephrin B2 and EphB4 siRNAs. $1\times10^5$ cells/well in 24-well plates were treated with 0, 10 and 100 ng/ml siRNAs as indicated on the graph. Viability of cultures was determined by MTT assay as described in the methods section. Shown are the mean±standard deviation of duplicate samples. C) HUVE cells were seeded on eight wells chamber slides coated with fibronectin. The HUVE cells were grown overnight in EGM-2 media, which contains all growth supplements. On the following day, the media was replaced with media containing VEGF (10 ng/ml) or EGF, FGF and IGF as indicated. After 2 hrs of incubation at 37° C., the cells were transfected using Lipofectamine 2000 (Invitrogen) in Opti-MEM medium containing 10 nM of siRNA to ephrin B2, Eph B4 or green fluorescence protein (GFP) as control. The cells were incubated for 2 hr and then the fresh media containing growth factors or VEGF alone was added to their respective wells. After 48 hrs, the cells were stained with crystal violet and the pictures were taken immediately by digital camera at 10× magnification.

Figure 50:
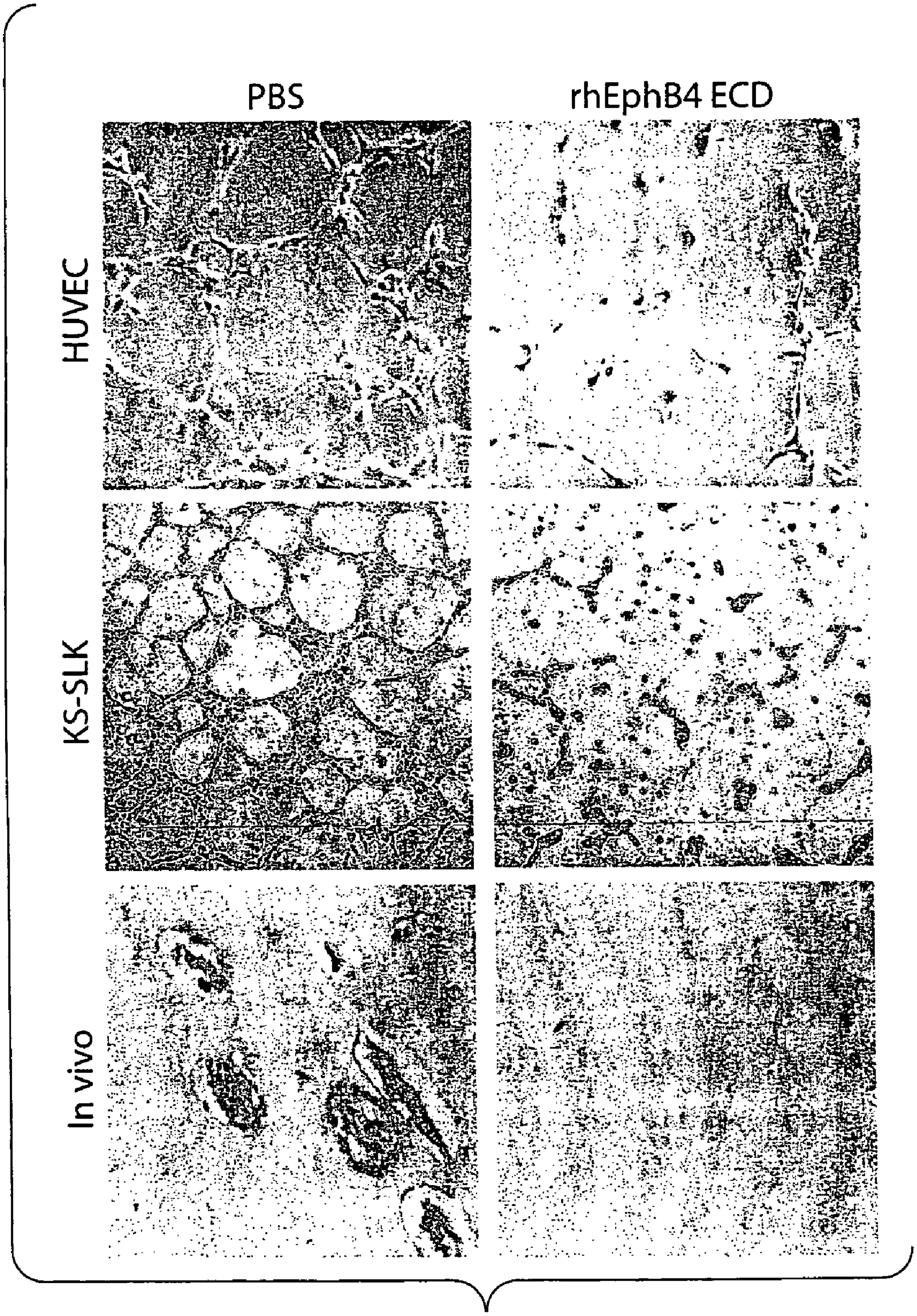

FIG. 50 shows that soluble EphB4 inhibits KS and EC cord formation and in vivo angiogenesis. Cord formation assay of HUVEC in Matrigel™ (upper row). Cells in exponential growth phase were treated overnight with the indicated concentrations of EphB4 extracellular domain (ECD) prior to plating on Matrigel™. Cells were trypsinized and plated ($1\times10^5$ cells/well) in a 24-well plate containing 0.5 ml Matrigel™. Shown are representative 20× phase contrast fields of cord formation after 8 hr plating on Matrigel™ in the continued presence of the test compounds as shown. Original magnification 200×. KS-SLK cells treated in a similar manner (middle row) in a cord formation assay on Matrigel™. Bottom row shows in vivo Matrigel™ assay: Matrigel™ plugs containing growth factors and EphB4 ECD or PBS were implanted subcutaneously in the mid-ventral region of mice. After 7 days the plugs were removed, sectioned and stained with H&E to visualize cells migrating into the matrix. Intact vessels with large lumens are observed in the control, whereas EphB4 ECD almost completely inhibited migration of cells into the Matrigel.

Figure 51:
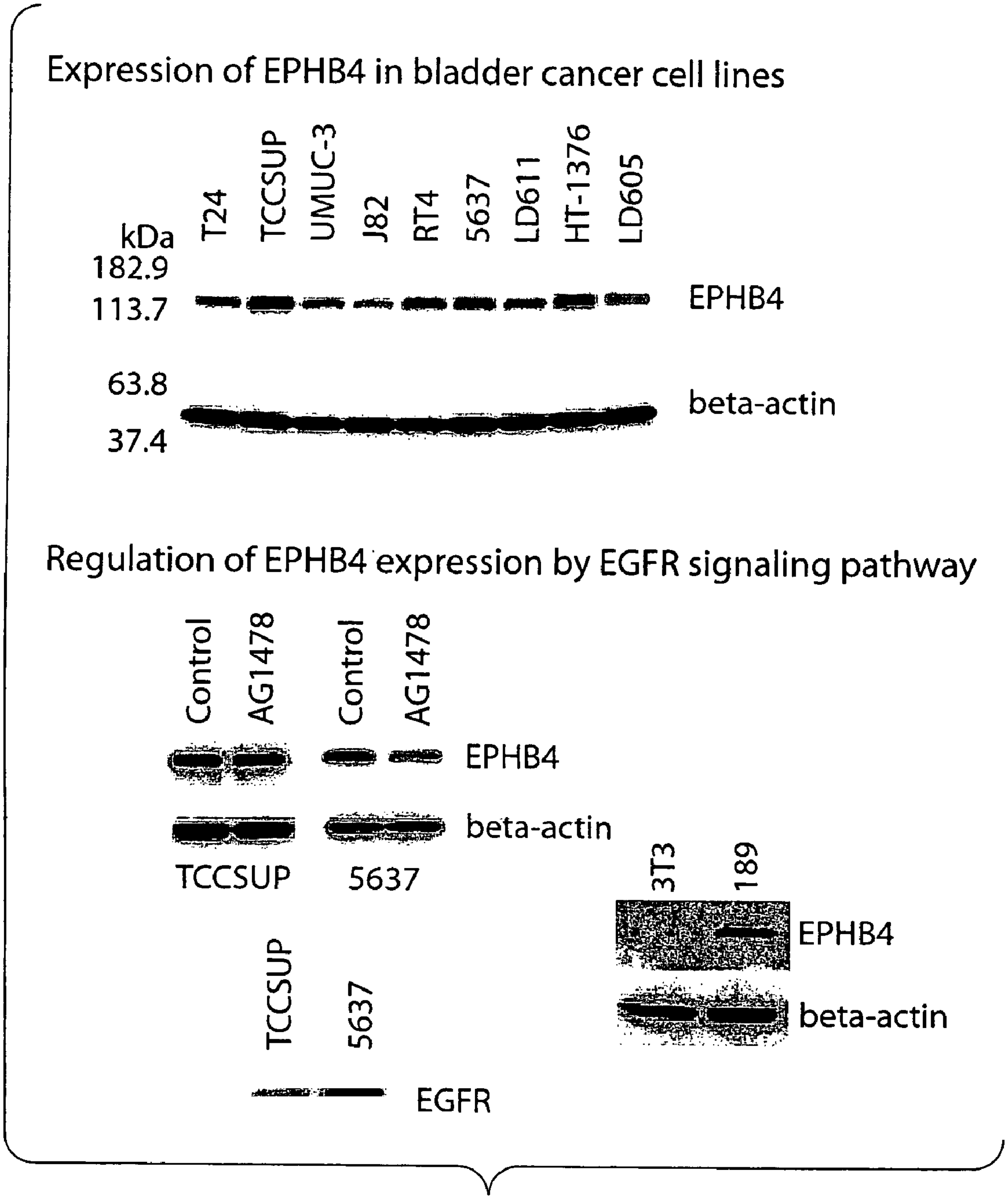

FIG. 51 shows expression of EPHB4 in bladder cancer cell lines (A), and regulation of EPHB4 expression by EGFR signaling pathway (B).

Figure 52:
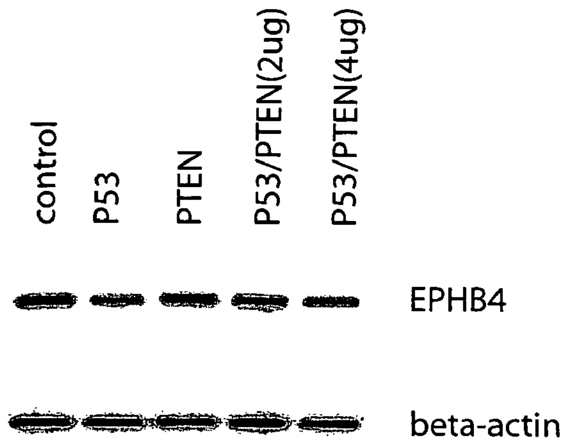

FIG. 52 shows that transfection of p53 inhibit the expression of EPHB4 in 5637 cell.

Figure 53:
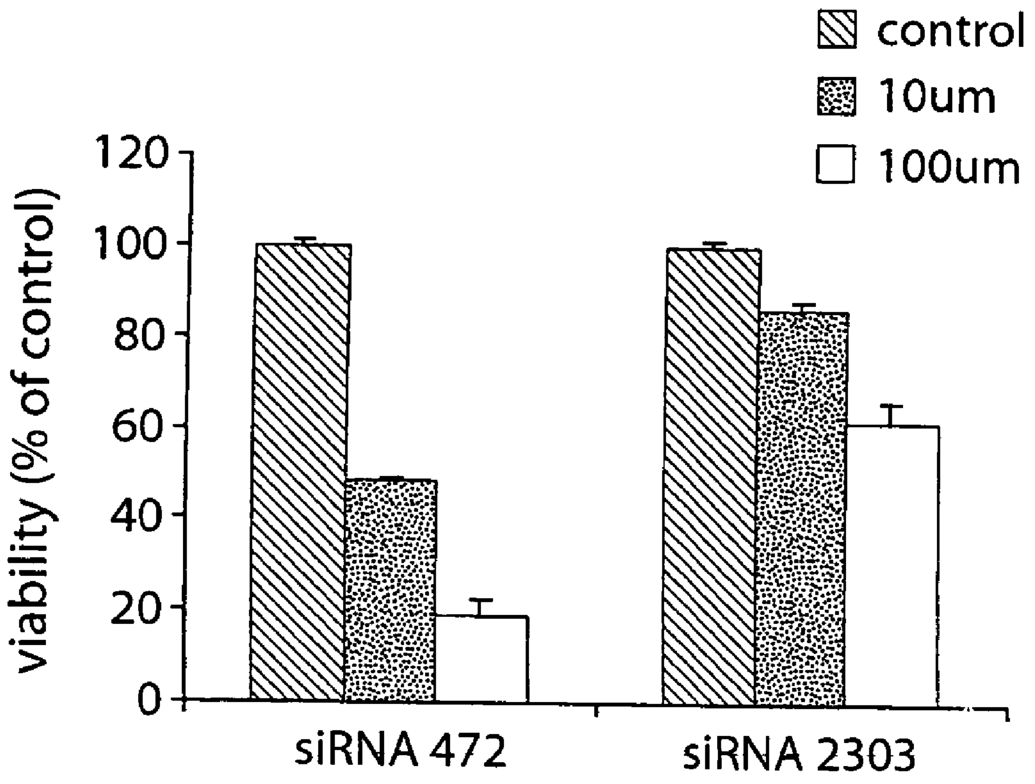

FIG. 53 shows growth inhibition of bladder cancer cell line (5637) upon treatment with EPHB4 siRNA 472.

Figure 54:
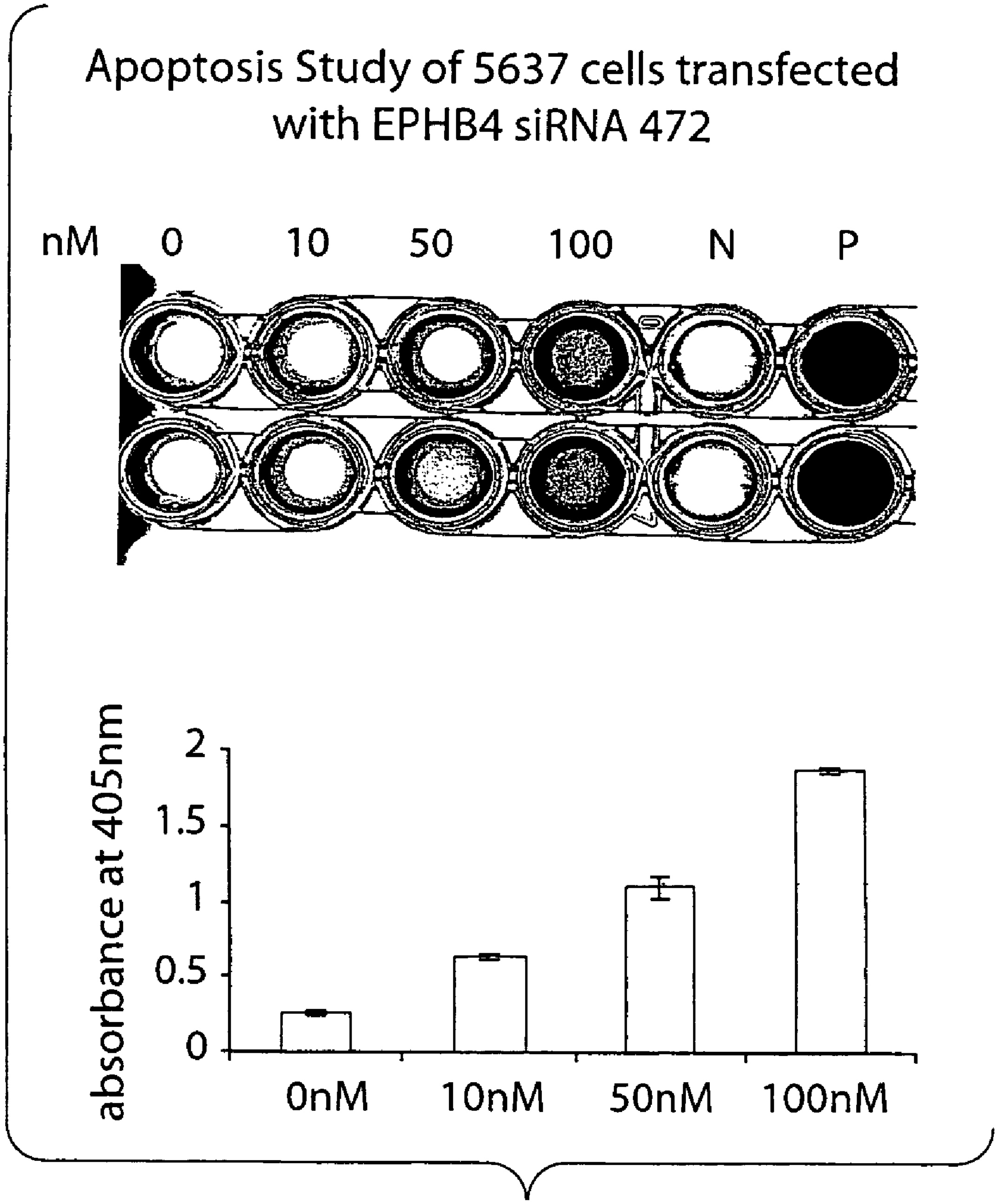

FIG. 54 shows results on apoptosis study of 5637 cells transfected with EPHB4 siRNA 472.

Figure 55:
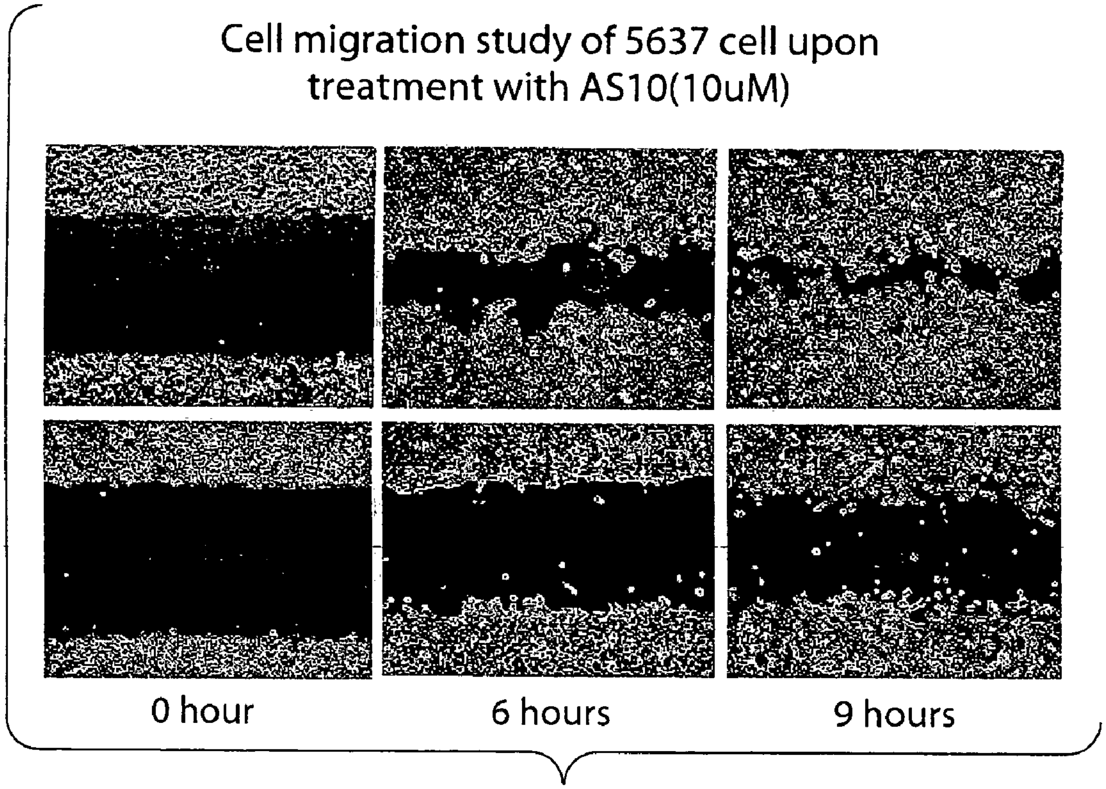

FIG. 55 shows effects of EPHB4 antisense probes on cell migration. 5637 cells were treated with EPHB4AS10 (10 μM).

Figure 56:
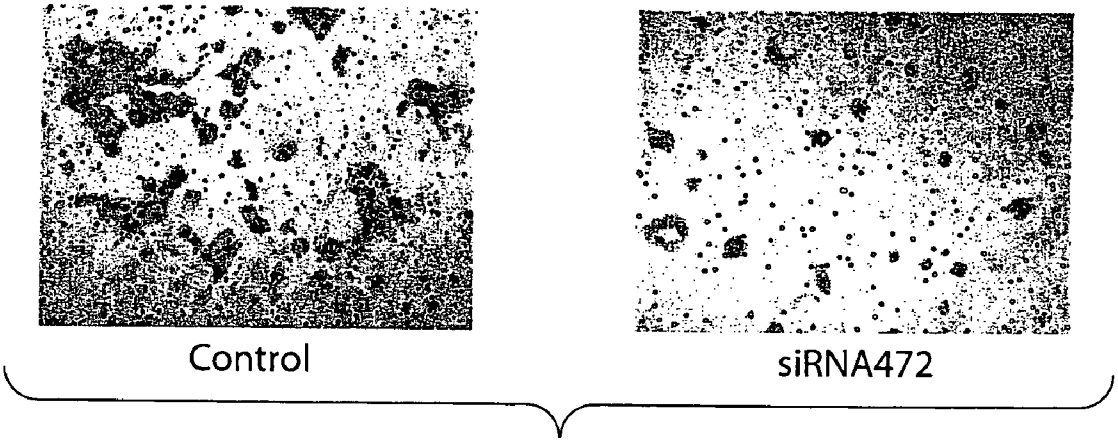

FIG. 56 shows effects of EPHB4 siRNA on cell invasion. 5637 cells were transfected with siRNA 472 or control siRNA.

Figure 57:
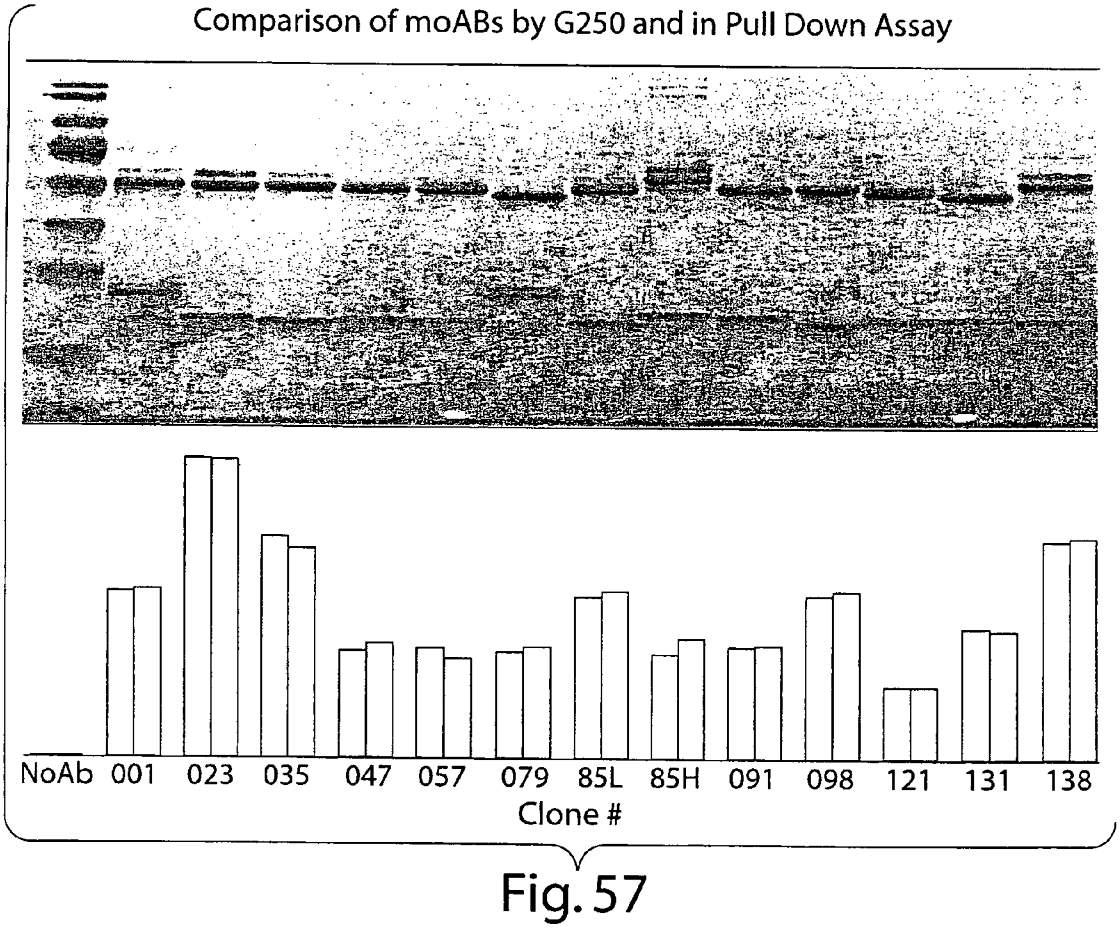

FIG. 57 shows comparison of EphB4 monoclonal antibodies by G250 and in pull-down assay.

Figure 58:
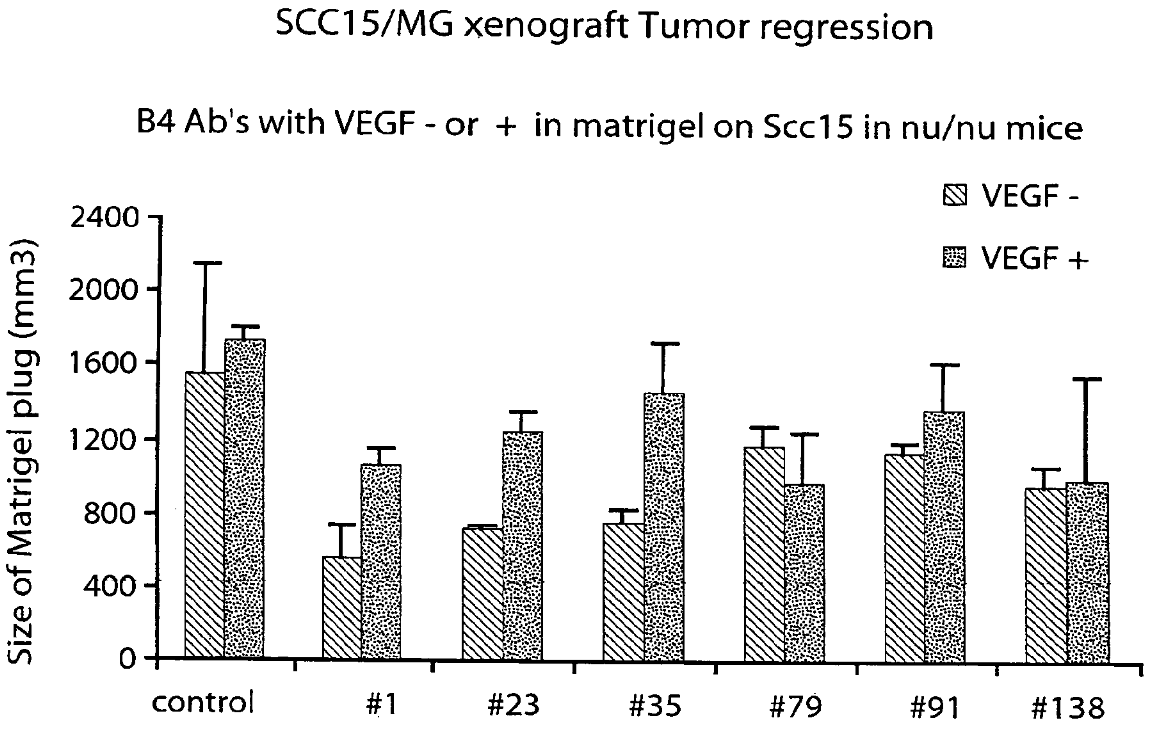

FIG. 58 shows that EphB4 antibodies inhibit the growth of SCC15 xenograft tumors.

Figure 59:
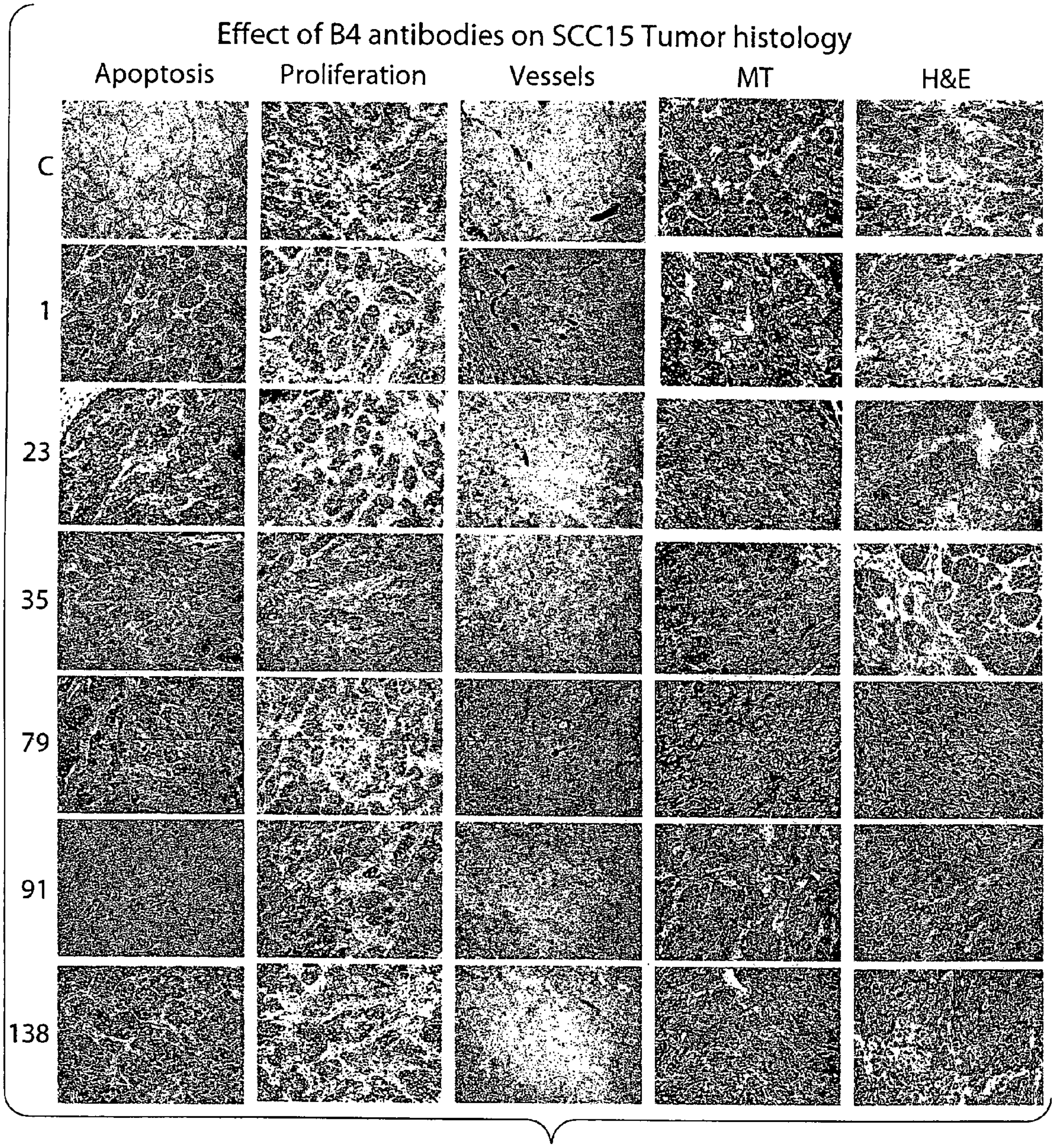

FIG. 59 shows that EphB4 antibodies cause apoptosis, necrosis and decreased angiogenesis in SCC15, head and neck carcinoma tumor type.

Figure 60:
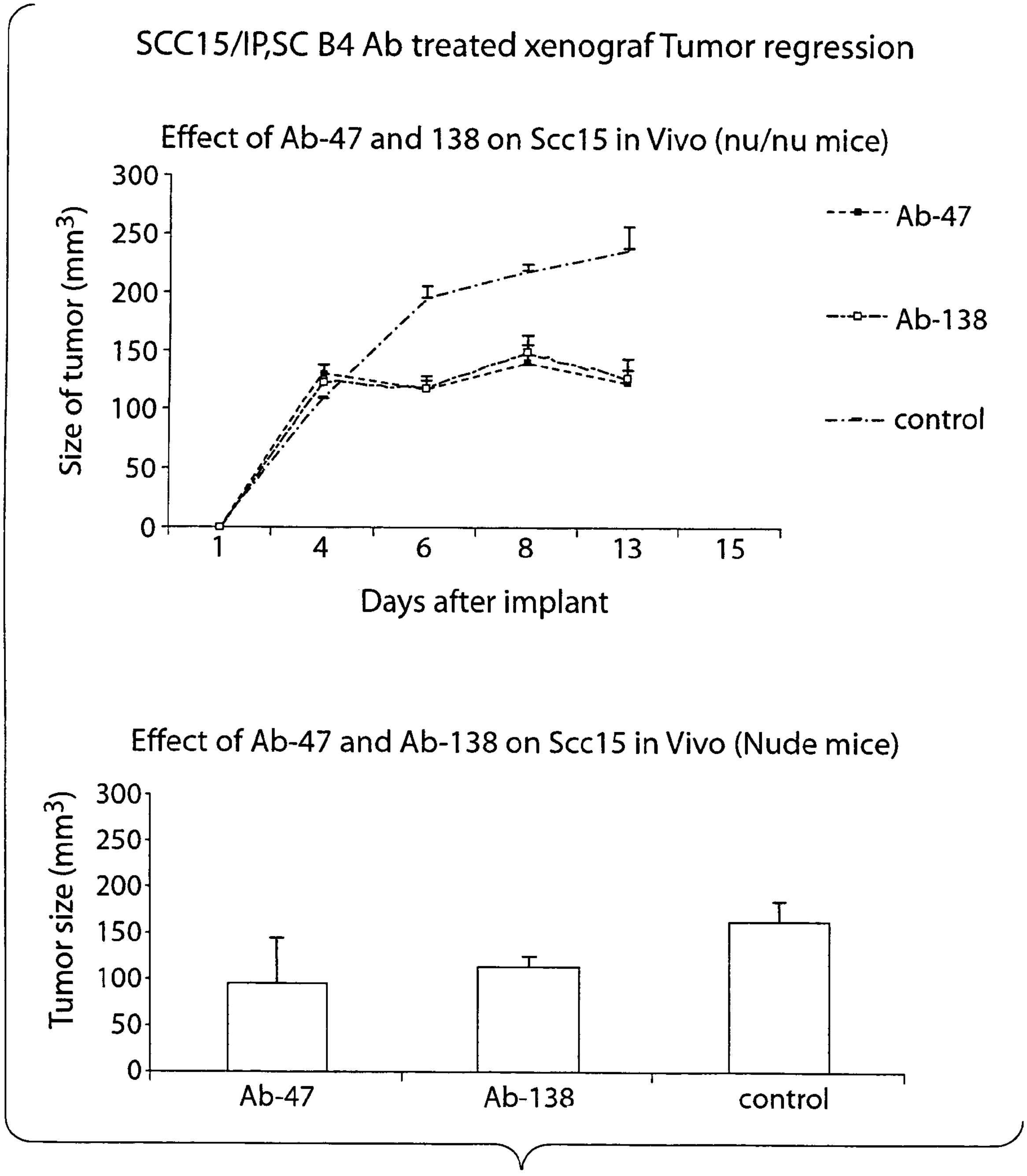

FIG. 60 shows that systemic administration of EphB4 antibodies leads to tumor regression.

FIG. 61 shows a genomic nucleotide sequence of human EphB4, SEQ ID NO: 391.

FIG. 62 shows a cDNA nucleotide sequence of human EphB4, SEQ ID NO: 392.

FIG. 63 shows a genomic nucleotide sequence of human Ephrin B2, SEQ ID NO: 393.

FIG. 64 shows a cDNA nucleotide sequence of human Ephrin B2, SEQ ID NO: 394.

FIG. 65 shows an amino acid sequence of human EphB4, SEQ ID NO: 395.

FIG. 66 shows an amino acid sequence of human Ephrin B2, SEQ ID NO: 396.

DETAILED DESCRIPTION OF THE INVENTION

I. Overview

The current disclosure is based in part on the discovery that signaling through the ephrin/ephrin receptor pathway contributes to tumorigenesis. Applicants detected expression of ephrin B2 and EphB4 in tumor tissues and developed anti-tumor therapeutic agents for blocking signaling through the ephrin/ephrin receptor. In addition, the disclosure provides nucleic acids and methods for antisense or RNAi-based inhibition of the expression of EphB4 and EphrinB2. Accordingly, in certain aspects, the disclosure provides a large number of nucleic acid compounds that may be used to treat cancer as well as angiogenesis related disorders and unwanted angiogenesis related processes.

As used herein, the terms Ephrin and Eph are used to refer, respectively, to ligands and receptors. They can be from any of a variety of animals (e.g., mammals/non-mammals, vertebrates/non-vertebrates, including humans). The nomenclature in this area has changed rapidly and the terminology used herein is that proposed as a result of work by the Eph Nomenclature Committee, which can be accessed, along with previously-used names at web site http://www.eph-nomenclature.com.

The work described herein, particularly in the examples, refers to Ephrin B2 and EphB4. However, the present invention contemplates any ephrin ligand and/or Eph receptor within their respective family, which is expressed in a tumor. The ephrins (ligands) are of two structural types, which can be further subdivided on the basis of sequence relationships and, functionally, on the basis of the preferential binding they exhibit for two corresponding receptor subgroups. Structurally, there are two types of ephrins: those which are membrane-anchored by a glycerophosphatidylinositol (GPI) linkage and those anchored through a transmembrane domain. Conventionally, the ligands are divided into the Ephrin-A subclass, which are GPI-linked proteins which bind preferentially to EphA receptors, and the Ephrin-B subclass, which are transmembrane proteins which generally bind preferentially to EphB receptors.

The Eph family receptors are a family of receptor protein-tyrosine kinases which are related to Eph, a receptor named for its expression in an erythropoietin-producing human hepatocellular carcinoma cell line. They are divided into two subgroups on the basis of the relatedness of their extracellular domain sequences and their ability to bind preferentially to Ephrin-A proteins or Ephrin-B proteins. Receptors which interact preferentially with Ephrin-A proteins are EphA receptors and those which interact preferentially with Ephrin-B proteins are EphB receptors.

Figure 16:
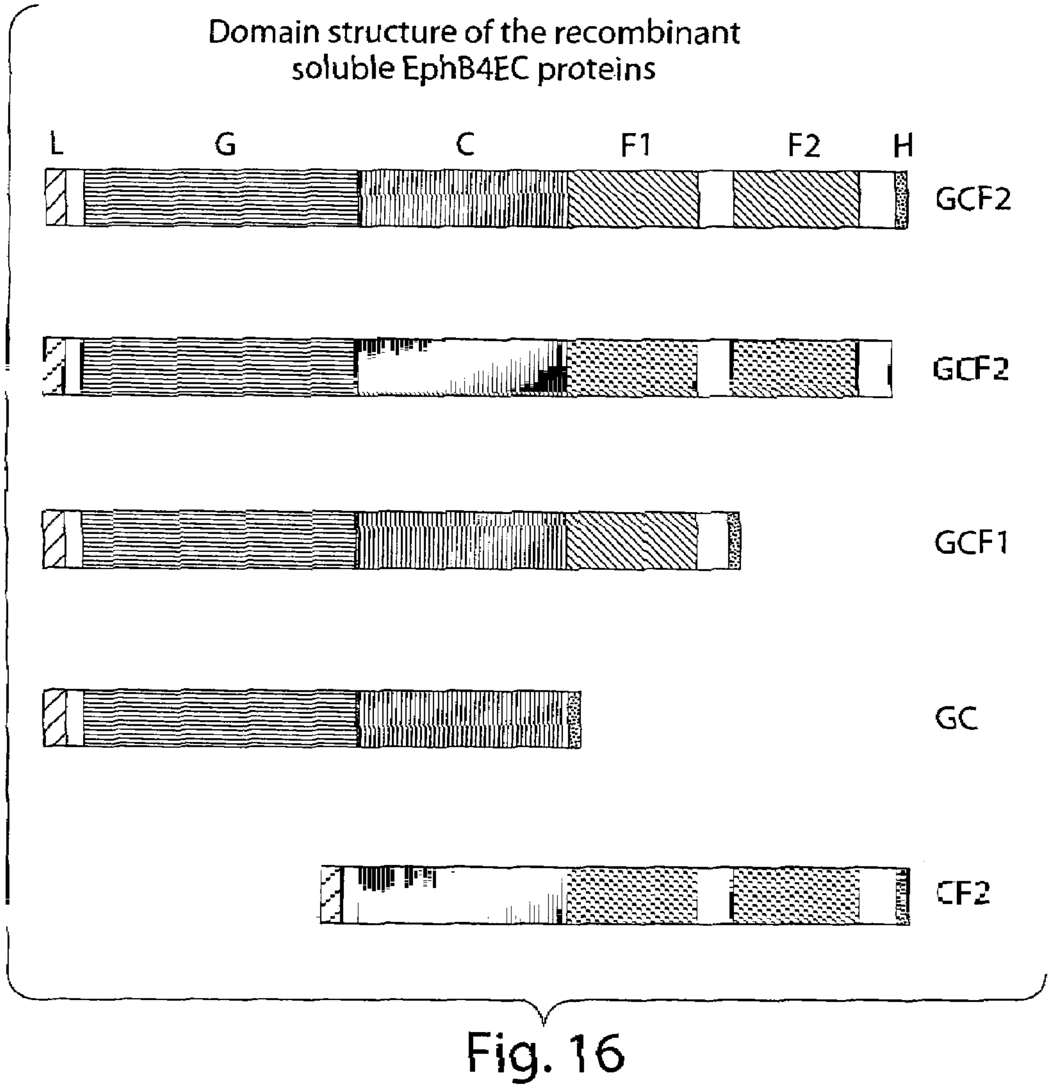
FIG. 16 shows the domain structure of the recombinant soluble EphB4EC proteins. Designation of the domains are as follows: L—leader peptide, G—globular (ligand-binding domain), C—Cys-rich domain, F1, F2—fibronectin type III repeats, H—6xHis-tag.

Eph receptors have an extracellular domain composed of the ligand-binding globular domain, a cysteine rich region followed by a pair of fibronectin type III repeats (e.g., see FIG. 16). The cytoplasmic domain consists of a juxtamembrane region containing two conserved tyrosine residues; a protein tyrosine kinase domain; a sterile α-motif (SAM) and a PDZ-domain binding motif. EphB4 is specific for the membrane-bound ligand Ephrin B2 (Sakano, S. et al 1996; Brambilla R. et al 1995). Ephrin B2 belongs to the class of Eph ligands that have a transmembrane domain and cytoplasmic region with five conserved tyrosine residues and PDZ domain. Eph receptors are activated by binding of clustered, membrane attached ephrins (Davis S et al, 1994), indicating that contact between cells expressing the receptors and cells expressing the ligands is required for Eph activation.

Upon ligand binding, an Eph receptor dimerizes and autophosphorylate the juxtamembrane tyrosine residues to acquire full activation (Kalo M S et al, 1999, Binns K S, 2000). In addition to forward signaling through the Eph receptor, reverse signaling can occur through the ephrin Bs. Eph engagement of ephrins results in rapid phosphorylation of the conserved intracellular tyrosines (Bruckner K, 1997) and somewhat slower recruitment of PDZ binding proteins (Palmer A 2002). Recently, several studies have shown that high expression of Eph/ephrins may be associated with increased potentials for tumor growth, tumorigenicity, and metastasis (Easty D J, 1999; Kiyokawa E, 1994; Tang X X, 1999; Vogt T, 1998; Liu W, 2002; Stephenson S A, 2001; Steube K G 1999; Berclaz G, 1996).

One aspect of the present disclosure provides a method for reducing the growth rate of a tumor expressing Ephrin B2 and/or EphB4. Such method comprises administering an amount of a nucleic acid therapeutic agent that inhibits gene expression of Ephrin B2, EphB4, or both.

II. Nucleic Acid Therapeutic Agents

This disclosure relates to nucleic acid therapeutic agents and methods for inhibiting or reducing gene expression of ephrin and/or ephrin receptor (Eph). By “inhibit” or “reduce,” it is meant that the expression of the gene, or level of nucleic acids or equivalent nucleic acids encoding one or more proteins or protein subunits, such as Ephrin B2 and/or EphB4, is reduced below that observed in the absence of the nucleic acid therapeutic agents of the disclosure. By “gene,” it is meant a nucleic acid that encodes a RNA, for example, nucleic acid sequences including but not limited to structural genes encoding a polypeptide.

As used herein, the term “nucleic acid therapeutic agent” or “nucleic acid agent” or “nucleic acid compound” refers to any nucleic acid-based compound that contains nucleotides and has a desired effect on a target gene. The nucleic acid therapeutic agents can be single-, double-, or multiple-stranded, and can comprise modified or unmodified nucleotides or non-nucleotides or various mixtures, and combinations thereof. Examples of nucleic acid therapeutic agents of the disclosure include, but are not limited to, antisense nucleic acids, dsRNA, siRNA, and enzymatic nucleic acid compounds.

In one embodiment, the disclosure features one or more nucleic acid therapeutic agents that independently or in combination modulate expression of the Ephrin B2 gene encoding an Ephrin B2 protein (e.g., Genbank Accession No.: NP_004084) or the EphB4 receptor gene which encodes an EphB4 protein (e.g., Genbank Accession No.: NP_004435).

A. Antisense Nucleic Acids

In certain embodiments, the disclosure relates to antisense nucleic acids. By "antisense nucleic acid," it is meant a non-enzymatic nucleic acid compound that binds to a target nucleic acid by means of RNA-RNA, RNA-DNA or RNA-PNA (protein nucleic acid) interactions and alters the activity of the target nucleic acid (for a review, see Stein and Cheng, 1993 Science 261, 1004 and Woolf et al., U.S. Pat. No. 5,849, 902). Typically, antisense molecules are complementary to a target sequence along a single contiguous sequence of the antisense molecule. However, in certain embodiments, an antisense molecule can form a loop and binds to a substrate nucleic acid which forms a loop. Thus, an antisense molecule can be complementary to two (or more) non-contiguous substrate sequences, or two (or more) non-contiguous sequence portions of an antisense molecule can be complementary to a target sequence, or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49.

In addition, antisense DNA can be used to target nucleic acid by means of DNA-RNA interactions, thereby activating RNase H, which digests the target nucleic acid in the duplex. The antisense oligonucleotides can comprise one or more RNAse H activating region, which is capable of activating RNAse H to cleave a target nucleic acid. Antisense DNA can be synthesized chemically or expressed via the use of a single stranded DNA expression vector or equivalent thereof. By "RNase H activating region" is meant a region (generally greater than or equal to 4-25 nucleotides in length, preferably from 5-11 nucleotides in length) of a nucleic acid compound capable of binding to a target nucleic acid to form a non-covalent complex that is recognized by cellular RNase H enzyme (see for example Arrow et al., U.S. Pat. No. 5,849, 902; Arrow et al., U.S. Pat. No. 5,989,912). The RNase H enzyme binds to a nucleic acid compound-target nucleic acid complex and cleaves the target nucleic acid sequence.

The RNase H activating region comprises, for example, phosphodiester, phosphorothioate, phosphorodithioate, 5'-thiophosphate, phosphoramidate or methylphosphonate backbone chemistry, or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of the RNase H activating region and the instant disclosure.

Thus, the antisense nucleic acids of the disclosure include natural-type oligonucleotides and modified oligonucleotides including phosphorothioate-type oligodeoxyribonucleotides, phosphorodithioate-type oligodeoxyribonucleotides, methylphosphonate-type oligodeoxyribonucleotides, phosphoramidate-type oligodeoxyribonucleotides, H-phosphonate-type oligodeoxyribonucleotides, triester-type oligodeoxyribonucleotides, alpha-anomer-type oligodeoxyribonucleotides, peptide nucleic acids, other artificial nucleic acids, and nucleic acid-modified compounds.

Other modifications include those which are internal or at the end(s) of the oligonucleotide molecule and include additions to the molecule of the internucleoside phosphate linkages, such as cholesterol, cholesteryl, or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position).

Other examples of modifications to sugars include modifications to the 2' position of the ribose moiety which include but are not limited to 2'-O-substituted with an —O— lower alkyl group containing 1-6 saturated or unsaturated carbon atoms, or with an —O-aryl, or allyl group having 2-6 carbon atoms wherein such —O-alkyl, aryl or allyl group may be unsubstituted or may be substituted, (e.g., with halo, hydroxy, trifluoromethyl cyano, nitro acyl acyloxy, alkoxy, carboxy, carbalkoxyl, or amino groups), or with an amino, or halo group. Nonlimiting examples of particularly useful oligonucleotides of the disclosure have 2'-O-alkylated ribonucleotides at their 3', 5', or 31 and 5' termini, with at least four or five contiguous nucleotides being so modified. Examples of 2'-O-alkylated groups include, but are not limited to, 2'-O-methyl, 2'-O-ethyl, 2'-O-propyl, and 2'-O-butyls.

In certain cases, the synthesis of the natural-type and modified antisense nucleic acids can be carried out with, for example, a 381A DNA synthesizer or 394 DNA/RNA synthesizer manufactured by ABI (Applied Biosystems Inc.) in accordance with the phosphoramidite method (see instructions available from ABI, or F. Eckstein, Oligonucleotides and Analogues: A Practical Approach, IRL Press (1991)). In the phosphoramidite method, a nucleic acid-related molecule is synthesized by condensation between the 3'-terminus of a modified deoxyribonucleoside or modified ribonucleoside and the 5'-terminus of another modified deoxyribonucleoside, modified ribonucleoside, oligo-modified deoxyribonucleotide or oligo-modified-ribonucleotide by use of a reagent containing phosphoramidite protected with a group such as cyanoethyl group. The final cycle of this synthesis is finished to give a product with a protective group (e.g., dimethoxytrityl group) bound to a hydroxyl group at the 5'-terminus of the sugar moiety. The oligomer thus synthesized at room temperature is cleaved off from the support, and its nucleotide and phosphate moieties are deprotected. In this manner, the natural-type oligonucleic acid compound is obtained in a crude form. The phosphorothioate-type nucleic acids can also be synthesized in a similar manner to the above natural type by the phosphoramidite method with the synthesizer from ABI. The procedure after the final cycle of the synthesis is also the same as with the natural type.

The crude nucleic acids (natural type or modified) thus obtained can be purified in a usual manner e.g., ethanol precipitation, or reverse phase chromatography, ion-exchange chromatography and gel filtration chromatography in high performance liquid chromatography (HPLC), supercritical fluid chromatography, and it may be further purified by electrophoresis. A cartridge for reverse phase chromatography, such as tC18-packed SepPak Plus (long body/ENV) (Waters), can also be used. The purity of the natural-type and modified (e.g., phosphorothioate-type) nucleic acids can be analyzed by HPLC.

In certain embodiments, the antisense nucleic acids of the disclosure can be delivered, for example, as an expression plasmid which, when transcribed in the cell, produces RNA which is complementary to at least a unique portion of the cellular mRNA which encodes an ephrin B2 or EphB4 polypeptide. Alternatively, the construct is an oligonucleotide which is generated ex vivo and which, when introduced into the cell causes inhibition of expression by hybridizing with the mRNA and/or genomic sequences encoding an ephrin B2 or EphB4 polypeptide. Such oligonucleotide probes are optionally modified oligonucleotide which are resistant to endogenous nucleases, e.g., exonucleases and/or endonucleases, and are therefore stable in vivo. Exemplary nucleic acid compounds for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in nucleic acid therapy have been reviewed, for example, by van der Krol et al., (1988) Biotechniques 6:958-976; and Stein et al., (1988) Cancer Res 48:2659-2668.

B. dsRNA and RNAi Constructss

In certain embodiments, the disclosure relates to double stranded RNA (dsRNA) and RNAi constructs. The term "dsRNA" as used herein refers to a double stranded RNA molecule capable of RNA interference (RNAi), including siRNA (see for example, Bass, 2001, Nature, 411, 428-429; Elbashir et al., 2001, Nature, 411, 494-498; and Kreutzer et al., PCT Publication No. WO 00/44895; Zernicka-Goetz et al., PCT Publication No. WO 01/36646; Fire, PCT Publication No. WO 99/32619; Plaetinck et al., PCT Publication No. WO 00/01846; Mello and Fire, PCT Publication No. WO 01/29058; Deschamps-Depaillette, PCT Publication No. WO 99/07409; and Li et al., PCT Publication No. WO 00/44914). In addition, RNAi is a term initially applied to a phenomenon observed in plants and worms where double-stranded RNA (dsRNA) blocks gene expression in a specific and post-transcriptional manner. RNAi provides a useful method of inhibiting gene expression in vitro or in vivo.

The term "short interfering RNA," "siRNA," or "short interfering nucleic acid," as used herein, refers to any nucleic acid compound capable of mediating RNAi or gene silencing when processed appropriately be a cell. For example, the siRNA can be a double-stranded polynucleotide molecule comprising self-complementary sense and antisense regions, wherein the antisense region comprises complementarity to a target nucleic acid compound (e.g., Ephrin B2 or EphB4). The siRNA can be a single-stranded hairpin polynucleotide having self-complementary sense and antisense regions, wherein the antisense region comprises complementarity to a target nucleic acid compound. The siRNA can be a circular single-stranded polynucleotide having two or more loop structures and a stem comprising self-complementary sense and antisense regions, wherein the antisense region comprises complementarity to a target nucleic acid compound, and wherein the circular polynucleotide can be processed either in vivo or in vitro to generate an active siRNA capable of mediating RNAi. The siRNA can also comprise a single stranded polynucleotide having complementarity to a target nucleic acid compound, wherein the single stranded polynucleotide can further comprise a terminal phosphate group, such as a 5'-phosphate (see for example Martinez et al., 2002, Cell., 110, 563-574), or 5',3'-diphosphate.

Optionally, the siRNAs of the disclosure contain a nucleotide sequence that hybridizes under physiologic conditions of the cell to the nucleotide sequence of at least a portion of the mRNA transcript for the gene to be inhibited (the "target" gene). The double-stranded RNA need only be sufficiently similar to natural RNA that it has the ability to mediate RNAi. Thus, the disclosure has the advantage of being able to tolerate sequence variations that might be expected due to genetic mutation, strain polymorphism or evolutionary divergence. The number of tolerated nucleotide mismatches between the target sequence and the siRNA sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the siRNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

The double-stranded structure of dsRNA may be formed by a single self-complementary RNA strand, two complementary RNA strands, or a DNA strand and a complementary RNA strand. Optionally, RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

As described herein, the subject siRNAs are around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the subject dsRNAs (e.g., siRNAs) can be carried out by chemical synthetic methods or by recombinant nucleic acid techniques. Endogenous RNA polymerase of the treated cell may mediate transcription in vivo, or cloned RNA polymerase can be used for transcription in vitro. As used herein, dsRNA or siRNA molecules of the disclosure need not be limited to those molecules containing only RNA, but further encompasses chemically-modified nucleotides and non-nucleotides. For example, the dsRNAs may include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The dsRNAs may be produced enzymatically or by partial/total organic synthesis, any modified ribonucleotide can be introduced by in vitro enzymatic or organic synthesis. Methods of chemically modifying RNA molecules can be adapted for modifying dsRNAs (see, e.g., Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an dsRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the disclosure lack 2'-hydroxy(2'-OH) containing nucleotides.

In a specific embodiment, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In another specific embodiment, the subject dsRNA can also be in the form of a long double-stranded RNA. For example, the dsRNA is at least 25, 50, 100, 200, 300 or 400 bases. In some cases, the dsRNA is 400-800 bases in length. Optionally, the dsRNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In a further specific embodiment, the dsRNA is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

PCT application WO 01/77350 describes an exemplary vector for bi-directional transcription of a transgene to yield both sense and antisense RNA transcripts of the same transgene in a eukaryotic cell. Accordingly, in certain embodiments, the present disclosure provides a recombinant vector having the following unique characteristics: it comprises a viral replicon having two overlapping transcription units arranged in an opposing orientation and flanking a transgene for a dsRNA of interest, wherein the two overlapping transcription units yield both sense and antisense RNA transcripts from the same transgene fragment in a host cell.

C. Enzymatic Nucleic Acid Compounds

In certain embodiments, the disclosure relates to enzymatic nucleic acid compounds. By "enzymatic nucleic acid compound," it is meant a nucleic acid compound which has complementarity in a substrate binding region to a specified target gene, and also has an enzymatic activity which is active to specifically cleave a target nucleic acid. It is understood that the enzymatic nucleic acid compound is able to intermolecularly cleave a nucleic acid and thereby inactivate a target nucleic acid compound. These complementary regions allow sufficient hybridization of the enzymatic nucleic acid compound to the target nucleic acid and thus permit cleavage. One hundred percent complementarity (identity) is preferred, but complementarity as low as 50-75% can also be useful in this disclosure (see for example Werner and Uhlenbeck, 1995, Nucleic Acids Research, 23, 2092-2096; Hammann et al., 1999, Antisense and Nucleic Acid Drug Dev., 9, 25-31). The enzymatic nucleic acids can be modified at the base, sugar, and/or phosphate groups. As described herein, the term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid compounds with enzymatic activity. The specific enzymatic nucleic acid compounds described in the instant application are not limiting in the disclosure and those skilled in the art will recognize that all that is important in an enzymatic nucleic acid compound of this disclosure is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

Several varieties of naturally-occurring enzymatic nucleic acids are currently known. Each can catalyze the hydrolysis of nucleic acid phosphodiester bonds in trans (and thus can cleave other nucleic acid compounds) under physiological conditions. In general, enzymatic nucleic acids act by first binding to a target nucleic acid. Such binding occurs through the target binding portion of a enzymatic nucleic acid which is held in close proximity to an enzymatic portion of the molecule that acts to cleave the target nucleic acid. Thus, the enzymatic nucleic acid first recognizes and then binds a target nucleic acid through complementary base-pairing, and once bound to the correct site, acts enzymatically to cut the target nucleic acid. Strategic cleavage of such a target nucleic acid will destroy its ability to direct synthesis of an encoded protein. After an enzymatic nucleic acid has bound and cleaved its nucleic acid target, it is released from that nucleic acid to search for another target and can repeatedly bind and cleave new targets.

In a specific embodiment, the subject enzymatic nucleic acid is a ribozyme designed to catalytically cleave an mRNA transcripts to prevent translation of mRNA (see, e.g., PCT International Publication WO90/11364, published Oct. 4, 1990; Sarver et al., 1990, Science 247:1222-1225; and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNAs have the following sequence of two bases: 5'-UG-3'. The construction and production of hammerhead ribozymes is well known in the art and is described more fully in Haseloff and Gerlach, 1988, Nature, 334:585-591. The ribozymes of the present disclosure also include RNA endoribonucleases (hereinafter "Cech-type ribozymes") such as the one which occurs naturally in *Tetrahymena thermophila* (known as the IVS or L-19 IVS RNA) and which has been extensively described (see, e.g., Zaug, et al., 1984, Science, 224: 574-578; Zaug and Cech, 1986, Science, 231: 470-475; Zaug, et al., 1986, Nature, 324:429-433; published International patent application No. WO88/04300 by University Patents Inc.; Been and Cech, 1986, Cell, 47:207-216).

In another specific embodiment, the subject enzymatic nucleic acid is a DNA enzyme. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid. Briefly, to design an ideal DNA enzyme that specifically recognizes and cleaves a target nucleic acid, one of skill in the art must first identify the unique target sequence. Preferably, the unique or substantially sequence is a G/C rich of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462.

In certain embodiments, the nucleic acid therapeutic agents of the disclosure can be between 12 and 200 nucleotides in length. In one embodiment, exemplary enzymatic nucleic acid compounds of the disclosure are between 15 and 50 nucleotides in length, including, for example, between 25 and 40 nucleotides in length (for example see Jarvis et al., 1996, J. Biol. Chem., 271, 29107-29112). In another embodiment, exemplary antisense molecules of the disclosure are between 15 and 75 nucleotides in length, including, for example, between 20 and 35 nucleotides in length (see for example Woolf et al., 1992, PNAS., 89, 7305-7309; Milner et al., 1997, Nature Biotechnology, 15, 537-541). In another embodiment, exemplary siRNAs of the disclosure are between 20 and 27 nucleotides in length, including, for example, between 21 and 23 nucleotides in length. Those skilled in the art will recognize that all that is required is that the subject nucleic acid therapeutic agent be of length and conformation sufficient and suitable for catalyzing a reaction contemplated herein. The length of the nucleic acid therapeutic agents of the instant disclosure is not limiting within the general limits stated.

III. Target Sites

Targets for useful nucleic acid compounds of the disclosure (e.g., antisense nucleic acids, dsRNA, and enzymatic nucleic acid compounds) can be determined as disclosed in Draper et al., 30 WO 93/23569; Sullivan et al., WO 93/23057; Thompson et al., WO 94/02595; Draper et al., WO 95/04818; McSwiggen et al., U.S. Pat. No. 5,525,468. Other examples include the following PCT applications inactivation of expression of disease-related genes: WO 95/23225, WO 95/13380, WO 94/02595. Rather than repeat the guidance provided in those documents here, below are provided specific examples of such methods, not limiting to those in the art.

Enzymatic nucleic acid compounds, siRNA and antisense to such targets are designed as described in those applications and synthesized to be tested in vitro and in vivo, as also described. For examples, the sequences of human Ephrin B2 and/or EphB4 RNAs are screened for optimal nucleic acid target sites using a computer-folding algorithm. Potential nucleic acid binding/cleavage sites are identified. For example, for enzymatic nucleic acid compounds of the disclosure, the nucleic acid compounds are individually analyzed by computer folding (Jaeger et al., 1989 Proc. Natl. Acad. Sci. USA, 86, 7706) to assess whether the sequences fold into the appropriate secondary structure. Those nucleic acid compounds with unfavorable intramolecular interactions such as between the binding arms and the catalytic core can be eliminated from consideration.

The subject nucleic acid (e.g., antisense, RNAi, and/or enzymatic nucleic acid compound) binding/cleavage sites are identified and are designed to anneal to various sites in the nucleic acid target (e.g., Ephrin B2 and/or EphB4). The binding arms of enzymatic nucleic acid compounds of the disclosure are complementary to the target site sequences described above. Antisense and RNAi sequences are designed to have partial or complete complementarity to the nucleic acid target. The nucleic acid compounds can be chemically synthesized. The method of synthesis used follows the procedure for normal DNA/RNA synthesis as described below and in Usman et al., 1987 J Am. Chem. Soc., 109, 7845; Scaringe et al., 1990 Nucleic Acids Res., 18, 5433; and Wincott et al., 1995 Nucleic Acids Res. 23, 2677-2684; Caruthers et al., 1992, Methods in Enzymology 211, 3-19.

Additionally, it is expected that nucleic acid therapeutic agents having a CpG motif are at an increased likelihood of causing a non-specific immune response. Generally, CpG motifs include a CG (Cytosine-Guanosine) sequence adjacent to one or more purines in the 5' direction and one or more pyrimidines in the 3' direction. Lists of known CpG motifs are available in the art. Preferred nucleic acid therapeutics will be selected so as to have a selective effect on the target gene (possibly affecting other closely related genes) without triggering a generalized immune response. By avoiding nucleic acid therapeutics having a CpG motif, it is possible to decrease the likelihood that a particular nucleic acid will trigger an immune response.

IV. Synthesis of Nucleic Acid Therapeutic Agents

Synthesis of nucleic acids greater than 100 nucleotides in length is difficult using automated methods, and the therapeutic cost of such molecules is prohibitive. In this disclosure, small nucleic acid motifs (small refers to nucleic acid motifs less than about 100 nucleotides in length, preferably less than about 80 nucleotides in length, and more preferably less than about 50 nucleotides in length (e.g., antisense oligonucleotides, enzymatic nucleic acids, and RNAi constructs) are preferably used for exogenous delivery. The simple structure of these molecules increases the ability of the nucleic acid to invade targeted regions of RNA structure.

Exemplary molecules of the instant disclosure are chemically synthesized, and others can similarly be synthesized. To illustrate, oligonucleotides (e.g., DNA) are synthesized using protocols known in the art as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001, 311. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer with a 2.5 min coupling step for 2'-O-methylated nucleotides and a 45 sec coupling step for 2'-deoxy nucleotides. Alternatively, syntheses can be performed on a 96-well plate synthesizer, such as the instrument produced by Protogene (Palo Alto, Calif.) with minimal modification to the cycle.

Optionally, the nucleic acid compounds of the present disclosure can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

Preferably, the nucleic acid compounds of the present disclosure are modified extensively to enhance stability by modification with nuclease resistant groups, for example, 2'-amino, 2'-C-allyl, 2'-flouro, 2'-O-methyl, 2'-H (for a review see Usman and Cedergren, 1992, TIBS 17, 34; Usman et al., 1994, Nucleic Acids Symp. Ser. 31, 163). Ribozymes are purified by gel electrophoresis using general methods or are purified by high pressure liquid chromatography (HPLC; See Wincott et al., Supra, the totality of which is hereby incorporated herein by reference) and are re-suspended in water.

V. Optimizing Activity of the Nucleic Acid Compounds

Nucleic acid compounds with modifications (e.g., base, sugar and/or phosphate) can prevent their degradation by serum ribonucleases and thereby increase their potency. There are several examples in the art describing sugar, base and phosphate modifications that can be introduced into nucleic acid compounds with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid compounds have been extensively described in the art (see Eckstein et al., PCT Publication No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. PCT Publication No. WO 93/15187; Sproat, U.S. Pat. No. 5,334,711 and Beigelman et al., 1995, J. Biol. Chem., 270, 25702; Beigelman et al., PCT publication No. WO 97/26270; Beigelman et al., U.S. Pat. No. 5,716,824; Usman et al., U.S. Pat. No. 5,627,053; Woolf et al., PCT Publication No. WO 98/13526; Thompson et al., U.S. S No. 60/082,404 which was filed on Apr. 20, 1998; Karpeisky et al., 1998, Tetrahedron Lett., 39, 1131; Earnshaw and Gait, 1998, Biopolymers (Nucleic acid Sciences), 48, 39-55; Verma and Eckstein, 1998, Annu. Rev. Biochem., 67, 99-134; and Burlina et al., 1997, Bioorg. Med. Chem., 5, 1999-2010). Similar modifications can be used to modify the nucleic acid compounds of the instant disclosure.

While chemical modification of oligonucleotide internucleotide linkages with phosphorothioate, phosphorothioate, and/or 5'-methylphosphonate linkages improves stability, an over-abundance of these modifications can cause toxicity. Therefore, the amount of these internucleotide linkages should be evaluated and appropriately minimized when designing the nucleic acid compounds. The reduction in the concentration of these linkages should lower toxicity resulting in increased efficacy and higher specificity of these molecules.

In one embodiment, nucleic acid compounds of the disclosure include one or more G-clamp nucleotides. A G-clamp nucleotide is a modified cytosine analog wherein the modifications confer the ability to hydrogen bond both Watson-Crick and Hoogsteen faces of a complementary guanine within a duplex, see for example, Lin and Matteucci, 1998, J. Am. Chem. Soc., 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acid compounds of the disclosure results in both enhanced affinity and specificity to nucleic acid targets. In another embodiment, nucleic acid compounds of the disclosure include one or more LNA (locked nucleic acid) nucleotides such as a 2',4'-C mythylene bicyclo nucleotide (see for example Wengel et al., PCT Publication Nos. WO 00/66604 and WO 99/14226).

In another embodiment, the disclosure features conjugates and/or complexes of nucleic acid compounds targeting Ephrin B2 and/or EphB4. Such conjugates and/or complexes can be used to facilitate delivery of nucleic acid compounds into a biological system, such as cells. The conjugates and complexes provided by the instant disclosure can impart therapeutic activity by transferring therapeutic compounds across cellular membranes, altering the pharmacokinetics, and/or modulating the localization of nucleic acid compounds of the disclosure.

The present disclosure encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid compounds of the disclosure into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

The term "biodegradable nucleic acid linker molecule" as used herein, refers to a nucleic acid compound that is designed as a biodegradable linker to connect one molecule to another molecule, for example, a biologically active molecule. The stability of the biodegradable nucleic acid linker molecule can be modulated by using various combinations of ribonucleotides, deoxyribonucleotides, and chemically modified nucleotides, for example, 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid compound, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus based linkage, for example, a phosphoramidate or phosphodiester linkage. The biodegradable nucleic acid linker molecule can also comprise nucleic acid backbone, nucleic acid sugar, or nucleic acid base modifications. The term "biodegradable" as used herein, refers to degradation in a biological system, for example enzymatic degradation or chemical degradation.

Therapeutic nucleic acid compounds, such as the molecules described herein, delivered exogenously are optimally stable within cells until translation of the target RNA has been inhibited long enough to reduce the levels of the undesirable protein. This period of time varies between hours to days depending upon the disease state. These nucleic acid compounds should be resistant to nucleases in order to function as effective intracellular therapeutic agents. Improvements in the chemical synthesis of nucleic acid compounds described in the instant disclosure and in the art have expanded the ability to modify nucleic acid compounds by introducing nucleotide modifications to enhance their nuclease stability as described above.

In another aspect the nucleic acid compounds comprise a 5' and/or a 3'-cap structure. By "cap structure," it is meant chemical modifications, which have been incorporated at either terminus of the oligonucleotide (see for example Wincott et al., WO 97/26270). These terminal modifications protect the nucleic acid compound from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofliranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al, PCT publication No. WO 97/26270). In other non-limiting examples, the 3'-cap includes, for example, 4',5'-methylene nucleotide; 1-(bela-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threopentofuranosy nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, Tetrahedron 49, 1925).

VI. Methods of Treatment

In certain embodiments, the present disclosure provides methods of inhibiting angiogenesis and methods of treating angiogenesis-associated diseases. In other embodiments, the present disclosure provides methods of inhibiting or reducing tumor growth and methods of treating an individual suffering from cancer. These methods involve administering to the individual a therapeutically effective amount of one or more nucleic acid therapeutic agent as described above. These methods are particularly aimed at therapeutic and prophylactic treatments of animals, and more particularly, humans.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis.

It is understood that methods and compositions of the disclosure are also useful for treating any angiogenesis-independent cancers (tumors). As used herein, the term "angiogenesis-independent cancer" refers to a cancer (tumor) where there is no or little neovascularization in the tumor tissue.

As described herein, the tumor includes a tumor inside an individual, a tumor xenograft, or a tumor cultured in vitro. In particular, nucleic acid therapeutic agents of the present disclosure are useful for treating or preventing a cancer (tumor), including, but not limited to, colon carcinoma, breast cancer, mesothelioma, prostate cancer, bladder cancer, squamous cell carcinoma of the head and neck (HNSCC), Kaposi sarcoma, and leukemia.

In certain embodiments of such methods, one or more nucleic acid therapeutic agents can be administered, together (simultaneously) or at different times (sequentially). In addition, nucleic acid therapeutic agents can be administered with another type of compounds for treating cancer or for inhibiting angiogenesis.

In certain embodiments, the subject methods of the disclosure can be used alone. Alternatively, the subject methods may be used in combination with other conventional anticancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject nucleic acid therapeutic agent.

A wide array of conventional compounds have been shown to have anti-neoplastic activities. These compounds have been used as pharmaceuticalal agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a nucleic acid therapeutic agent of the present disclosure is administered in combination with another conventional anti-neoplastic agent, either concomitantly or sequentially, such therapeutic agent is shown to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceuticalal compounds that may be used for combinatory anti-angiogenesis therapy include: (1) inhibitors of release of “angiogenic molecules,” such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6573256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha_v\beta_3$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the nucleic acid therapeutic agents of the disclosure may be continued while the other therapy is being administered and/or thereafter. Administration of the nucleic acid therapeutic agents may be made in a single dose, or in multiple doses. In some instances, administration of the nucleic acid therapeutic agents is commenced at least several days prior to the conventional therapy, while in other instances, administration is begun either immediately before or at the time of the administration of the conventional therapy.

VII. Methods of Administration and Pharmaceutical Compositions

Methods for delivering the subject nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

In certain embodiments, the subject nucleic acids (e.g., antisense nucleic acids, RNAi constructs, and enzymatic nucleic acids) of the present disclosure are formulated with a pharmaceutically acceptable carrier. Such therapeutic agents can be administered alone or as a component of a pharmaceuticalal formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject nucleic acids include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-tumor or anti-angiogenesis therapeutic agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject nucleic acid therapeutic agent as an active ingredient.

In solid dosage forms for oral administration (capsules, tablets, pills, dragees, powders, granules, and the like), one or more nucleic acid therapeutic agents of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceuticalal compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In particular, methods of the disclosure can be administered topically, either to skin or to mucosal membranes such as those on the cervix and vagina. This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject nucleic acids may be mixed under sterile conditions with a pharmaceutically acceptable carrier, and with any preservatives, buffers, or propellants which may be required. The ointments, pastes, creams and gels may contain, in addition to a subject nucleic acid molecule, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject nucleic acid therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more nucleic acid therapeutic agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceuticalal compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceuticalal form may be brought about by the inclusion of agents which delay absorption, such as aluminum monostearate and gelatin.

Injectable depot forms are made by forming microencapsule matrices of one or more nucleic acid therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations for intravaginal or rectally administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In certain embodiments, the nucleic acids of the instant disclosure are formulated with a pharmaceutically acceptable agent that allows for the effective distribution of the nucleic acid compounds of the instant disclosure in the physical location most suitable for their desired activity. Non-limiting examples of such pharmaceutically acceptable agents include: PEG, phospholipids, phosphorothioates, P-glycoprotein inhibitors (such as Pluronic P85) which can enhance entry of drugs into various tissues, biodegradable polymers, such as poly(DL-lactide-coglycolide) microspheres for sustained release delivery after implantation (Emerich, D F et al, 1999, Cell Transplant, 8, 47-58), and loaded nanoparticles such as those made of polybutylcyanoacrylate, which can deliver drugs across the blood brain barrier and can alter neuronal uptake mechanisms (Prog Neuropsychopharmacol Biol Psychiatry, 23, 941-949, 1999).

In other embodiments, certain of the nucleic acid compounds of the instant disclosure can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, Proc. Natl. Acad. Sci. USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45). Those skilled in the art realize that any nucleic acid can be expressed in eukaryotic cells from the appropriate DNA/RNA vector. The activity of such nucleic acids can be augmented by their release from the primary transcript by an enzymatic nucleic acid (Draper et al, PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856; all of these references are hereby incorporated in their totalities by reference herein). Gene therapy approaches specific to the CNS are described by Blesch et al., 2000, Drug News Perspect., 13, 269-280; Peterson et al., 2000, Cent. Nerv. Syst. Dis., 485-508; Peel and Klein, 2000, J. Neurosci. Methods, 98, 95-104; Hagihara et al., 2000, Gene Ther., 7, 759-763; and Herrlinger et al., 2000, Methods Mol. Med., 35, 287-312. AAV-mediated delivery of nucleic acid to cells of the nervous system is further described by Kaplitt et al., U.S. Pat. No. 6,180,613.

In another aspect of the disclosure, RNA molecules of the present disclosure are preferably expressed from transcription units (see for example Couture et al., 1996, TIG., 12, 510) inserted into DNA or RNA vectors. The recombinant vectors are preferably DNA plasmids or viral vectors. Ribozyme expressing viral vectors can be constructed based on, but not limited to, adeno-associated virus, retrovirus, adenovirus, or alphavirus. Preferably, the recombinant vectors capable of expressing the nucleic acid compounds are delivered as described above, and persist in target cells. Alternatively, viral vectors can be used that provide for transient expression of nucleic acid compounds. Such vectors can be repeatedly administered as necessary. Once expressed, the nucleic acid compound binds to the target mRNA. Delivery of nucleic acid compound expressing vectors can be systemic, such as by intravenous or intramuscular administration, by administration to target cells ex-planted from the patient followed by reintroduction into the patient, or by any other means that would allow for introduction into the desired target cell (for a review see Couture et al., 1996, TIG., 12, 510).

In one aspect, the disclosure contemplates an expression vector comprising a nucleic acid sequence encoding at least one of the nucleic acid compounds of the instant disclosure. The nucleic acid sequence is operably linked in a manner which allows expression of the nucleic acid compound of the disclosure. For example, the disclosure features an expression vector comprising: a) a transcription initiation region (e.g., eukaryotic pol I, II or III initiation region); b) a transcription termination region (e.g., eukaryotic pol I, II or III termination region); c) a nucleic acid sequence encoding at least one of the nucleic acid catalyst of the instant disclosure; and wherein said sequence is operably linked to said initiation region and said termination region, in a manner which allows expression and/or delivery of said nucleic acid compound. The vector can optionally include an open reading frame (ORF) for a protein operably linked on the 5' side or the 3'-side of the sequence encoding the nucleic acid catalyst of the disclosure; and/or an intron (intervening sequences).

EXEMPLIFICATION

The disclosure now being generally described, it will be more readily understood by reference to the following examples, which are included merely for purposes of illustration of certain aspects and embodiments of the present disclosure, and are not intended to limit the disclosure.

Example 1

Figure 14:
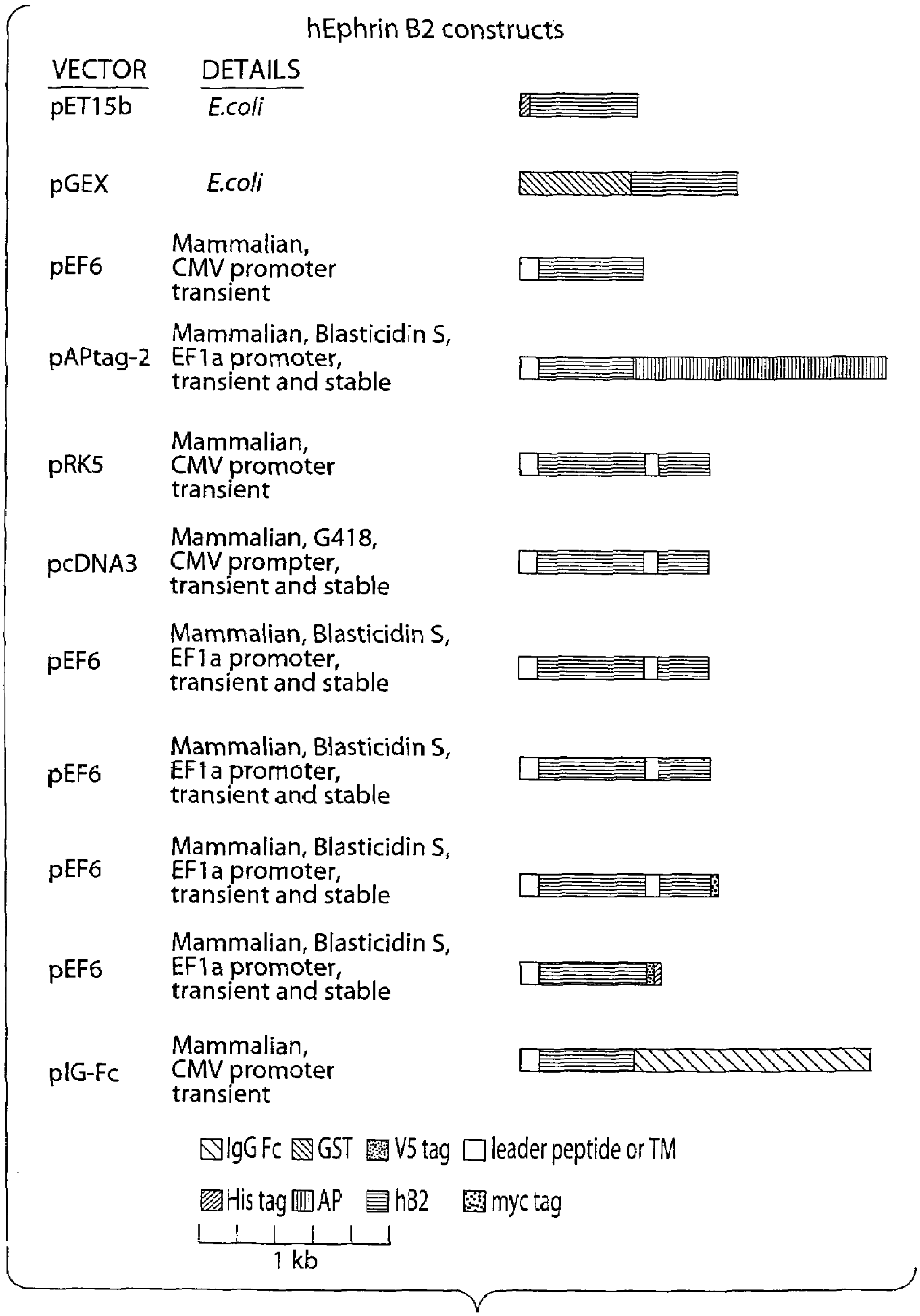
FIG. 14 is a schematic representation of human Ephrin B2 constructs.
Figure 15:
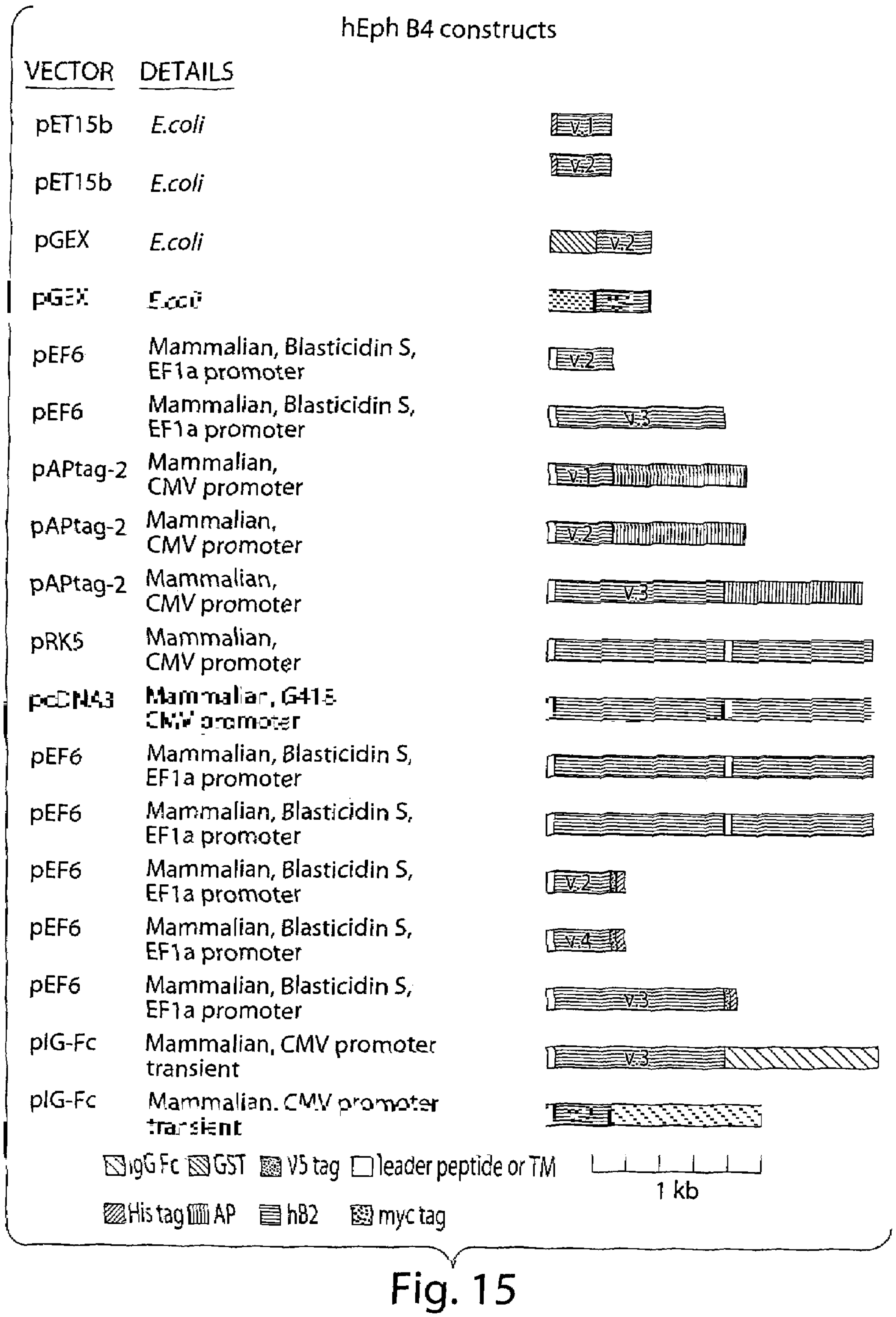
FIG. 15 is a schematic representation of human EphB4 constructs.

Soluble Derivatives of the Extracellular Domains of Human Ephrin B2 and EphB4 Proteins Soluble derivatives of the extracellular domains of human Ephrin B2 and EphB4 proteins represent either truncated full-length predicted extracellular domains of Ephrin B2 (B4ECv3, B2EC) or translational fusions of the domains with constant region of human immunoglobulins (IgG1 Fc fragment), such as B2EC-FC, B4ECv2-FC and B4ECv3-FC. Representative human Ephrin B2 constructs and human EphB4 constructs are shown FIGS. 14 and 15.

Figure 7:
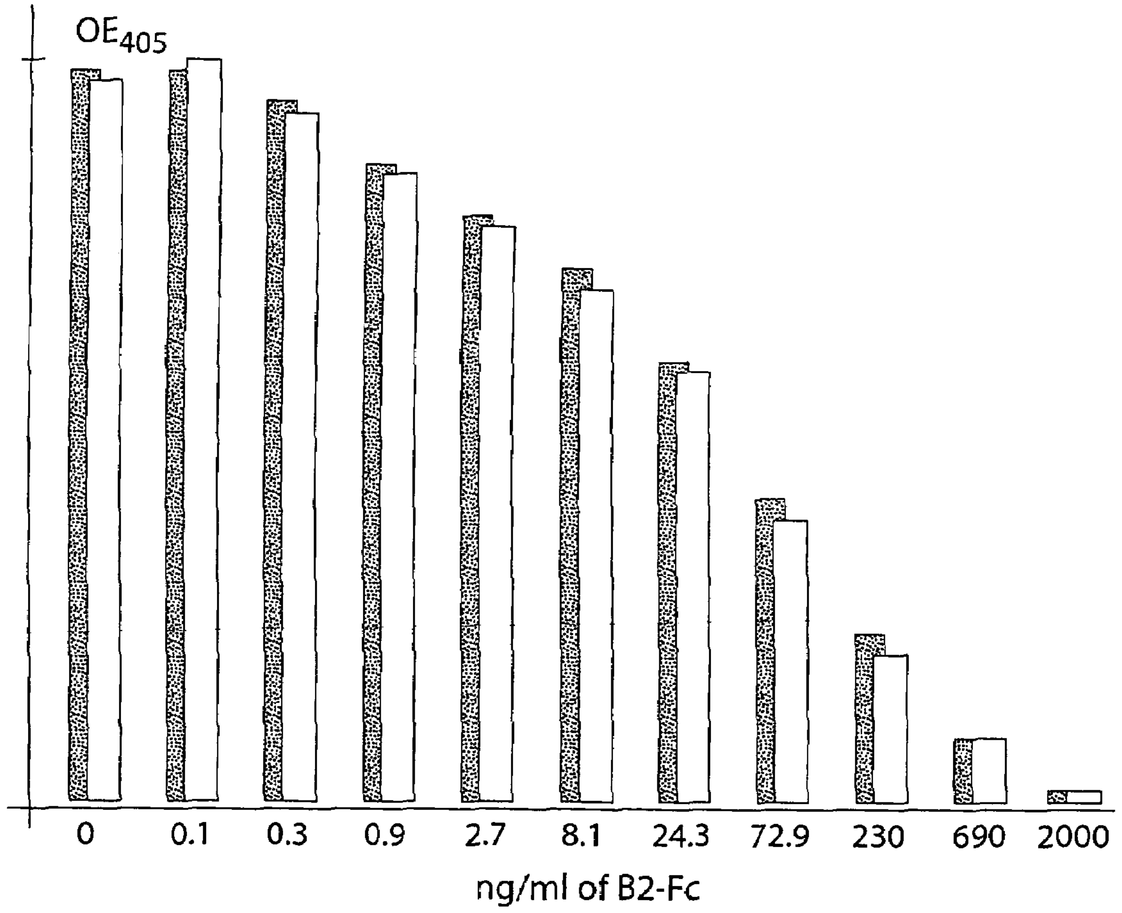
FIG. 7 shows B4EC-FC inhibition assay (Inhibition in solution).
Figure 8:
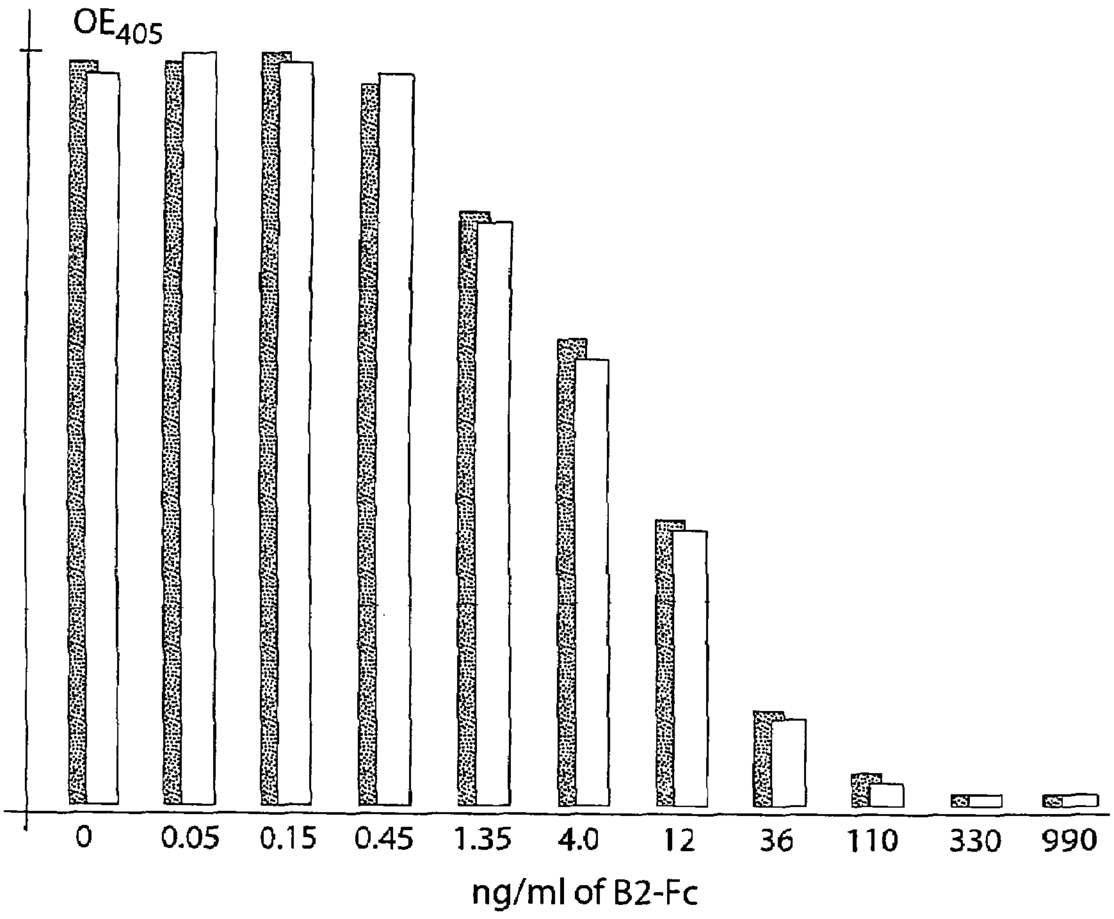
FIG. 8 shows B2EC-FC binding assay (Protein-A-agarose based assay).

The cDNA fragments encoding these recombinant proteins were subcloned into mammalian expression vectors, expressed in transiently or stably transfected mammalian cell lines and purified to homogeneity as described in detail in Materials and Methods section (see below). Predicted amino acid sequences of the proteins are shown in FIGS. 1-5. High purity of the isolated proteins and their recognition by the corresponding anti-Ephrin B2 and anti-EphB4 monoclonal or polyclonal antibodies were confirmed. The recombinant proteins exhibit the expected high-affinity binding, binding competition and specificity properties with their corresponding binding partners as corroborated by the biochemical assays (see e.g., FIGS. 6-8).

Figure 9:
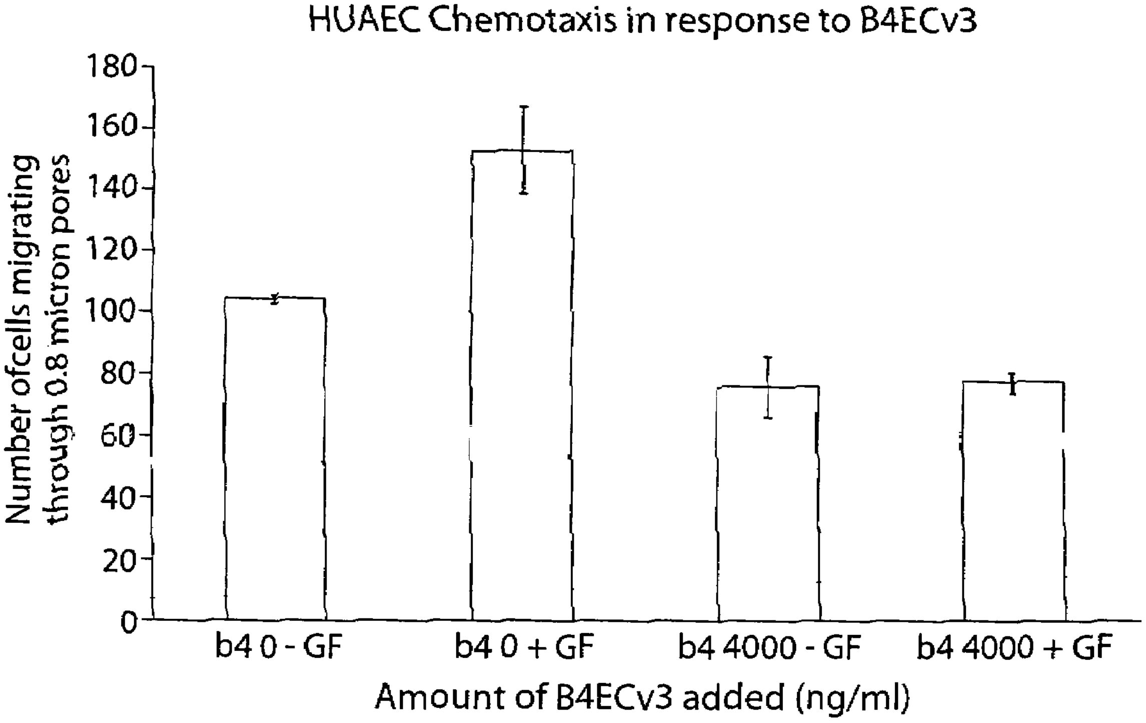
FIG. 9 shows chemotaxis of HUAEC in response to B4Ecv3.
Figure 10:
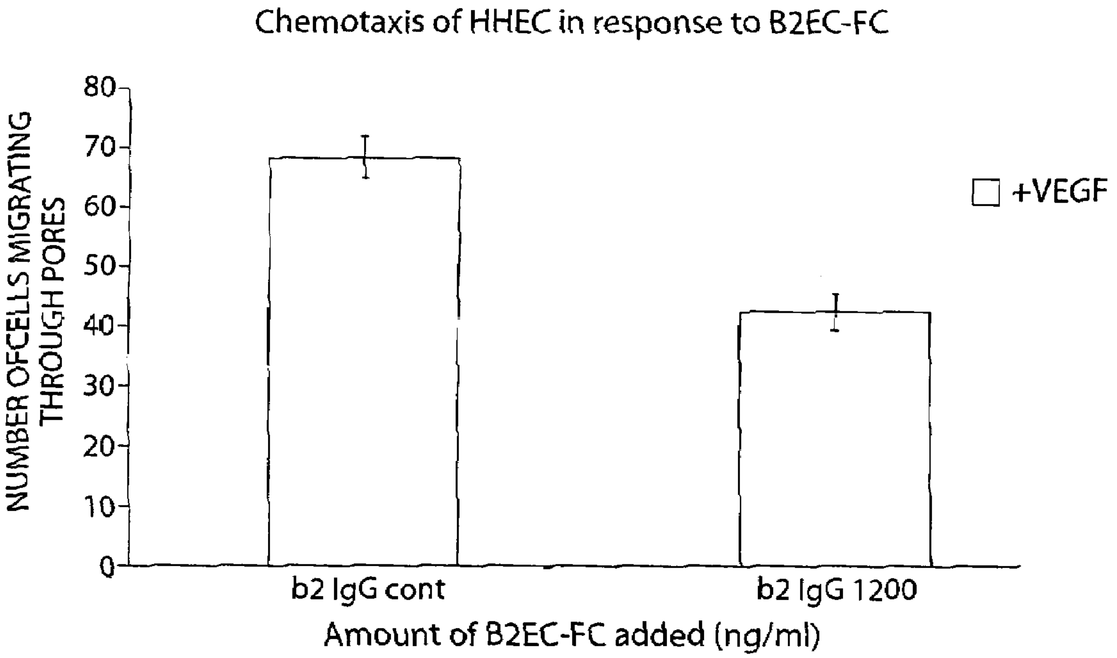
FIG. 10 shows chemotaxis of HHEC in response to B2EC-FC.
Figure 11:
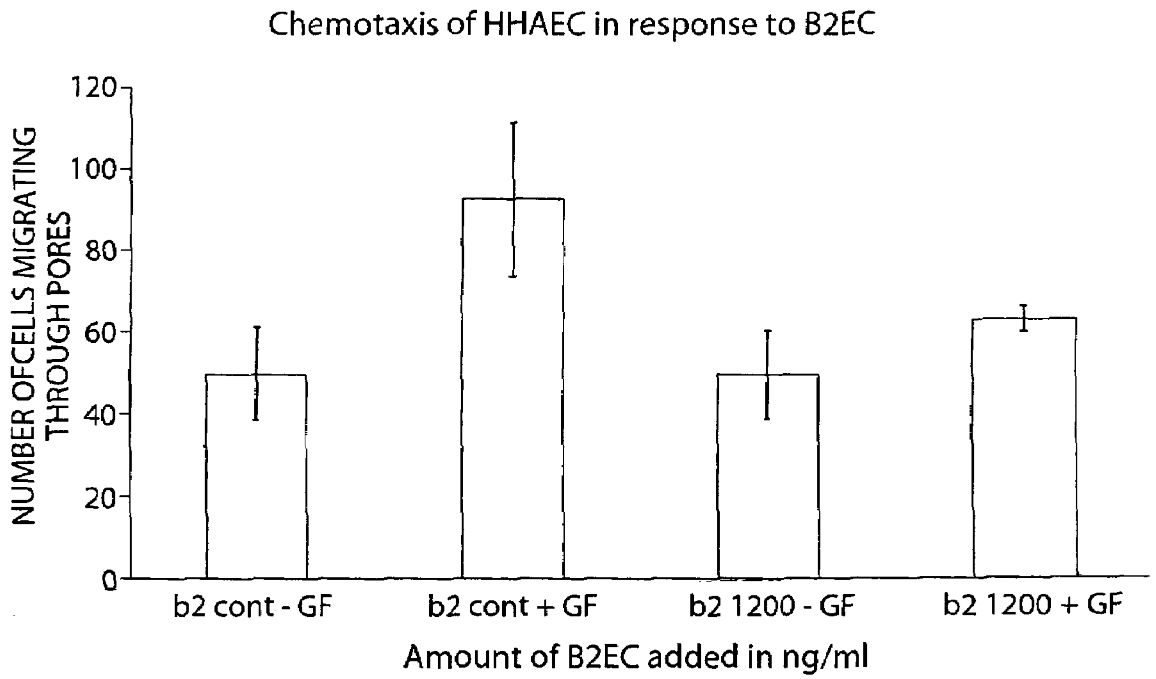
FIG. 11 shows chemotaxis of HHAEC in response to B2EC.
Figure 12:
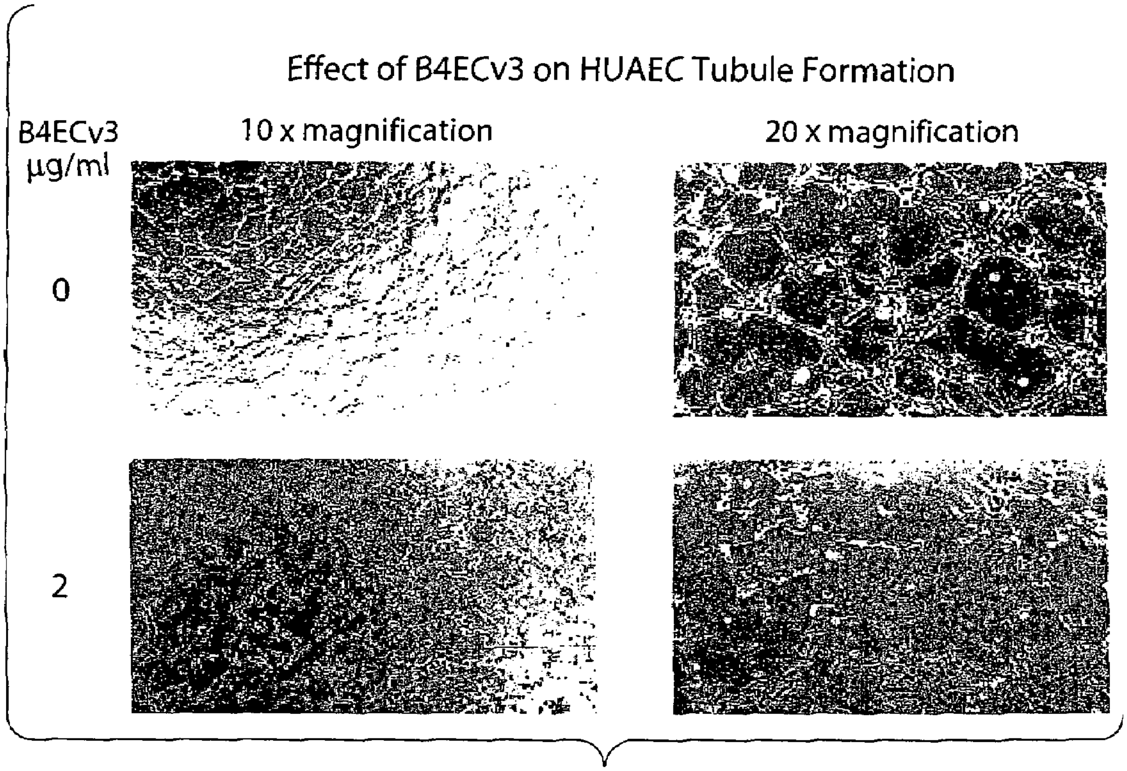
FIG. 12 shows effect of B4Ecv3 on HUAEC tubule formation.
Figure 13:
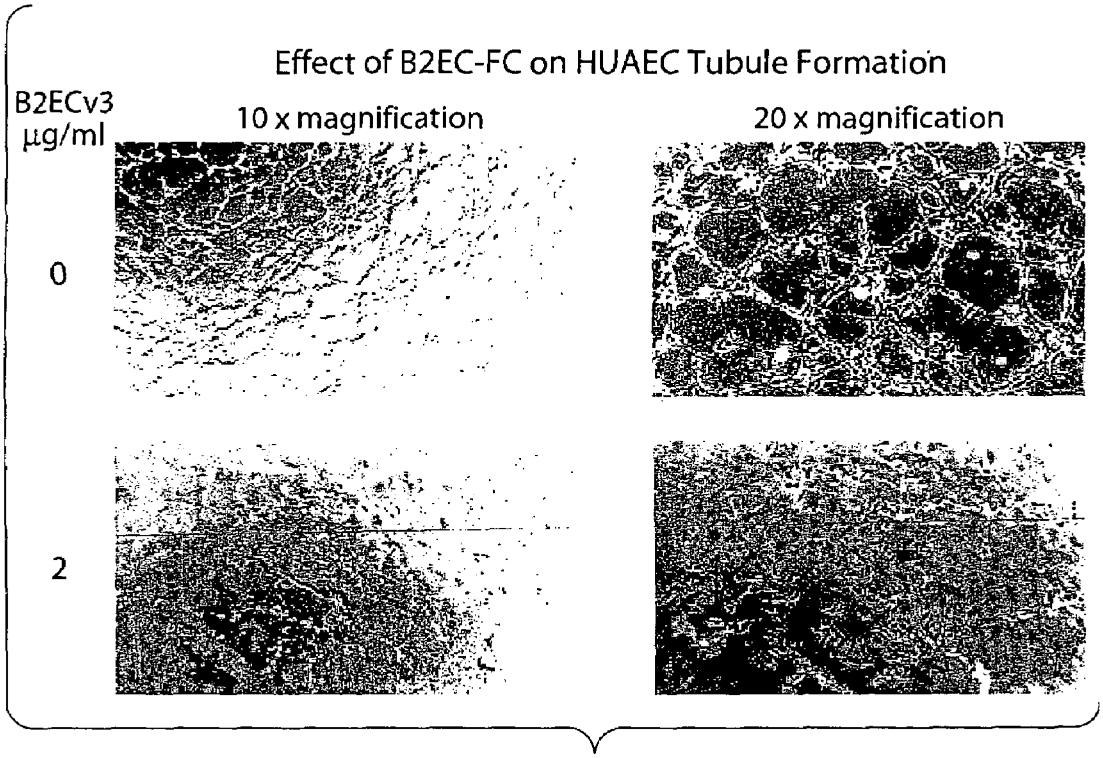
FIG. 13 shows effect of B2EC-FC on HUAEC tubule formation.

Such soluble derivative proteins human Ephrin B2 and EphB4 exhibit potent biological activity in several cell-based assays and in vivo assays which measure angiogenesis or anti-cancer activities, and are therefore perspective drug candidates for anti-angiogenic and anti-cancer therapy. B4ECv3 as well as B2EC and B2EC-FC proteins blocked chemotaxis of human endothelial cells (as tested with umbilical cord and hepatic AECs or VECs), with a decrease in degradation of the extracellular matrix, Matrigel, and a decrease in migration in response to growth factor stimuli (FIGS. 9-11). B4ECv3 and B2EC-FC proteins have potent anti-angiogenic effect as demonstrated by their inhibition of endothelial cell tube formation (FIGS. 12-13).

Materials and Methods

1) Mammalian Expression Vectors for Producing Recombinant Soluble Derivatives of Ephrin B2 and Eph B4

Plasmids vectors for expressing recombinant soluble derivatives of Ephrin B2 and EphB4 were based on pEF6/V5-His-TOPO vector (Invitrogen), pIG (Novagen) or pRK5. pEF6/V5-His-TOPO contains human elongation factor 1a enhancer/promoter and blasticidin resistance marker. pIG vector is designed for high-level expression of protein fusions with Fc portion of human IgG1under CMV promoter control and pRK5 is a general purpose CMV promoter-containing mammalian expression vector. To generate plasmid construct pEF6-B4EC-NT, cDNA fragment of human EphB4 was amplified by PCR using oligo primers 5'-GGATCCGCC ATGGAGCTC CGGGTGCTGCT-3' (SEQ ID NO: 1) and 5'-TGGATCCCT GCTCCCGC CAGCCCTCG CTCT-CATCCA-3' (SEQ ID NO: 2), and TOPO-cloned into pEF6/V5-His-TOPO vector. pEF6-hB4ECv3 was derived from pEF6-B4ECNT by digesting the plasmid DNA with EcoRV and BstBI, filling-in the ends with Klenow enzyme and religating the vector. Recombinant EphB4 derivative encoded by pEF6-B4EC-NT does not contain epitope- or purification tags, while the similar B4ECv3 protein encoded by pEF6-hB4ECv3 contains V5 epitope tag and 6xHis tag on its C-terminus to facilitate purification from conditioned media. Plasmid construct pEF6-hB2EC was created by PCR amplification of Ephrin B2 cDNA using oligo primers 5'-TGGATCCAC CATGGCTGT GAGAAGGGAC-3' (SEQ ID NO: 3) plus 5'-ATTAATGGTGATGGT GAT GATGACTAC CCACTTCGG AACCGAGGATGTTGTTC-3'(SEQ ID NO: 4) and TOPO-cloning into pEF6/V5-His-TOPO vector. Plasmid construct pIG-hB2EC-FC was created by PCR amplification of Ephrin B2 cDNA with oligo primers 5'-TAAAGCT-TCCGCCATGG CTGTGAGAAGGGAC-3' (SEQ ID NO: 5) and 5'-TAGGATCCACTTCGGA ACCGAGGATGTTGTT CCC-3'(SEQ ID NO: 6), followed by TOPO-cloning and sequencing the resulting PCR fragment with consecutive subcloning in pIG hIgG1Fc fusion expression vector cut with Bam HI and Hind III, Similarly, pIG-hB2EC and pIG-hB4ECv3 were generated by PCR amplifying portions of EphB4 ECD cDNA using oligo primers 5'-ATAAGCTTCC GCCATGGAGC TCCGGGTGCTG-3' (SEQ ID NO: 7) plus 5'-TTGGATCCTGCTCCCG CCAGCCCTCGC TCT-CATC-3' (SEQ ID NO: 8) with consecutive subcloning into pIG hIgG1 Fc fusion expression vector cut with Bam HI and Hind III, Predicted sequences of the proteins encoded by the vectors described above are shown in FIGS. 1-5.

2) Mammalian Cell Culture and Transfections

HEK293T (human embryonic kidney line) cells were maintained in DMEM with 10% dialyzed fetal calf serum and 1% penicillin/streptomycin/neomycin antibiotics. Cells were maintained at 37° C. in a humidified atmosphere of 5% $CO_2$/95% air. Transfections were performed using Lipofectamine 2000 reagent (Invitrogen) according to the manufacturer's protocol. One day before transfections, 293T cells were seeded at a high density to reach 80% confluence at the time of transfection. Plasmid DNA and Lipofectamine reagent at 1:3 ratio were diluted in Opti-MEM I reduced serum medium (Invitrogen) for 5 min and mixed together to form DNA: Lipofectamine complex. For each 10 cm culture dish, 10 μg of plasmid DNA was used. After 20 min, above complex was added directly to cells in culture medium. After 16 hours of transfection, medium was aspirated, washed once with serum free DMEM and replaced with serum free DMEM. Secreted proteins were harvested after 48 hours by collecting conditional medium. Conditional medium was clarified by centrifugation at 10,000 g for 20 min, filtered through 0.2 μm filter and used for purification.

3) Generating Stable Cell Lines

To create stable cell lines producing EphB4ECv3 and EphB4ECnt HEK293 or HEK293T cells were transfected with either pEF6-B4ECv3 or pEF6-B4EC-NT plasmid constructs as described above and selected using antibiotic Blasticidin. After 24 hours of transfection, cells were seeded at low density. Next day, cells were treated with 10 μg/ml of Blasticidin. After two weeks of drug selection, surviving cells were pooled and selected further for single cell clone expansion. After establishing stable cells, they were maintained at 4 μg/ml Blasticidin. Conditioned media were tested to confirm expression and secretion of the respective recombinant proteins. Specificity of expression was confirmed by Western blot with anti-B4 mono- or polyclonal ABs and B2EC-AP reagent binding and competition assays.

4) Protein Purification

HEK293 cells were transiently transfected with a plasmid encoding secreted form of EphB4ectodomain (B4ECv3). Conditional media was harvested and supplemented with 10 mM imidazole, 0.3 M NaCl and centrifuged at 20,000g for 30 min to remove cell debris and insoluble particles. 80 ml of obtained supernatant were applied onto the pre-equilibrated column with 1 ml of Ni-NTA-agarose (Qiagen) at the flow rate of 10 ml/h. After washing the column with 10 ml of 50 mM Tris-HCl, 0.3 M NaCl and 10 mM imidazole, pH 8, remaining proteins were eluted with 3 ml of 0.25 M imidazole. Eluted proteins were dialyzed against 20 mM Tris-HCl, 0.15 M NaCl, pH 8 overnight. Purity and identity of B4ECv3 was verified by PAGE/Coomassie G-250 and Western blot with anti-Eph.B4 antibody. Finally, the concentration of B4ECv3 was measured, and the protein was aliquoted and stored at −70° C.

B4EC-FC protein and B2EC-FC protein were similarly purified.

5) Biochemical Assays

A. Binding Assay

10 μl of Ni-NTA-Agarose were incubated in microcentrifuge tubes with 50 μl of indicated amount of B4ECv3 diluted in binding buffer BB (20 mM Tris-HCl, 0.15 M NaCl, 0.1% bovine serum albumin pH 8) After incubation for 30 min on shaking platform, Ni-NTA beads were washed twice with 1.4 ml of BB, followed by application of 50 μl of B2-AP in the final concentration of 50 nM. Binding was performed for 30 min on shaking platform, and then tubes were centrifuged and washed one time with 1.4 ml of BB. Amount of precipitated AP was measured calorimetrically after application of PNPP.

B. Inhibition Assay

Inhibition in solution. Different amounts of B4ECv3 diluted in 50 μl of BB were pre-incubated with 50 μl of 5 nM B2EC-AP reagent (protein fusion of Ephrin B2 ectodomain with placental alkaline phosphatase). After incubation for 1 h, unbound B2EC-AP was precipitated with 5,000 HEK293 cells expressing membrane-associated full-length EphB4 for 20 min. Binding reaction was stopped by dilution with 1.2 ml of BB, followed by centrifugation for 10 min. Supernatants were discarded and alkaline phosphatase activities associated with collected cells were measured by adding para-nitrophenyl phosphate (PNPP) substrate.

Cell based inhibition. B4ECv3 was serially diluted in 20 mM Tris-HCl, 0.15 M NaCl, 0.1% BSA, pH 8 and mixed with 5,000 HEK293 cells expressing membrane-associated full-length Ephrin B2. After incubation for 1 h, 50 μl of 5 nM B4EC-AP reagent (protein fusion of EphB4 ectodomain with placental alkaline phosphatase were added into each tube for 30 min to detect unoccupied Ephrin B2 binding sites. Binding reactions were stopped by dilution with 1.2 ml of BB and centrifugation. Colorimetric reaction of cell-precipitated AP was developed With PNPP substrate.

C. B4EC-FC Binding Assay

Figure 6:
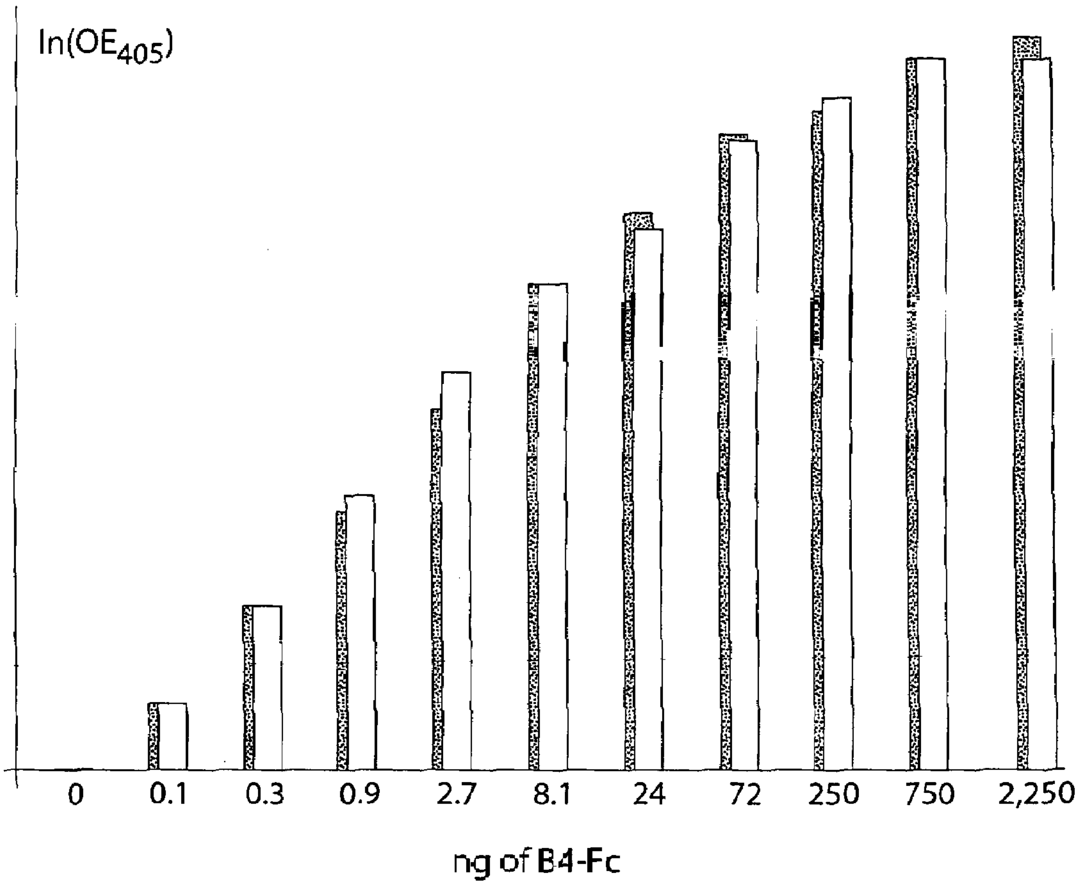
FIG. 6 shows B4EC-FC binding assay (Protein A-agarose based).

Protein A-agarose based assay. 10 μl of Protein A-agarose were incubated in Eppendorf tubes with 50 μl of indicated amount of B4EC-FC diluted in binding buffer BB (20 mM Tris-HCl, 0.15 M NaCl, 0.1% BSA pH 8). After incubation for 30 min on shaking platform, Protein AAagarose beads were washed twice with 1.4 ml of BB, followed by application of 50 μl of B2ECAP reagent at the final concentration of 50 nM. Binding was performed for 30 min on shaking platform, and then tubes were centrifuged and washed once with 1.4 ml of BB. Colorimetric reaction of precipitated AP was measured after application of PNPP (FIG. 6).

Nitrocellulose based assay. B4EC-FC was serially diluted in 20 mM Tris-HCl, 0.15 M NaCl, 50 μg/ml BSA, pH 8.2 μl of each fraction were applied onto nitrocellulose strip and spots were dried out for 3 min. Nitrocellulose strip was blocked with 5% non-fat milk for 30 min, followed by incubation with 5 nM B2EC-AP reagent. After 45 min incubation for binding, nitrocellulose was washed twice with 20 mM Tris-HCl, 0.15 M NaCl, 50 μg/ml BSA, pH 8 and color was developed by application of alkaline phosphatase substrate Sigma Fast (Sigma).

D. B4EC-FC Inhibition Assay

Inhibition in solution. See above, for B4ECv3. The results were shown in FIG. 7.

Cell based inhibition. See above, for B4ECv3.

E. B2EC-FC Binding Assay

Protein-A-agarose based assay. See above, for B4EC-FC. The results were shown in FIG. 8.

Nitrocellulose based assay. See above, for B4EC-FC.

6) Cell-Based Assays

A. Growth Inhibition Assay

Human umbilical cord vein endothelial cells (HUVEC) ($1.5 \times 10^3$) are plated in a 96-well plate in 100 μl of EBM-2 (Clonetic # CC3162). After 24 hours (day 0), the test recombinant protein (100 μl) is added to each well at 2× the desired concentration (5-7 concentration levels) in EBM-2 medium. On day 0, one plate is stained with 0.5% crystal violet in 20% methanol for 10 minutes, rinsed with water, and air-dried. The remaining plates are incubated for 72 h at 37° C. After 72 h, plates are stained with 0.5% crystal violet in 20% methanol, rinsed with water and airdried. The stain is eluted with 1:1 solution of ethanol: 0.1 M sodium citrate (including day 0 plate), and absorbance is measured at 540 nm with an ELISA reader (Dynatech Laboratories). Day 0 absorbance is subtracted from the 72 h plates and data is plotted as percentage of control proliferation (vehicle treated cells). IC50 (drug concentration causing 50% inhibition) is calculated from the plotted data.

B. Cord Formation Assay (Endothelial Cell Tube Formation Assay)

Matrigel (60 μl of 10 mg/ml; Collaborative Lab # 35423) is placed in each well of an ice-cold 96-well plate. The plate is allowed to sit at room temperature for 15 minutes then incubated at 37° C. for 30 minutes to permit the matrigel to polymerize. In the mean time, HUVECs are prepared in EGM-2 (Clonetic # CC3162) at a concentration of $2\times10^5$ cells/ml. The test compound is prepared at 2× the desired concentration (5 concentration levels) in the same medium. Cells (500 μl) and 2× drug (500 μl) is mixed and 200 μl of this suspension are placed in duplicate on the polymerized matrigel. After 24 h incubation, triplicate pictures are taken for each concentration using a Bioquant Image Analysis system. Drug effect (IC50) is assessed compared to untreated controls by measuring the length of cords formed and number of junctions.

C. Cell Migration Assay

Migration is assessed using the 48-well Boyden chamber and 8 μm pore size collagen-coated (10 μg/ml rat tail collagen; Collaborative Laboratories) polycarbonate filters (Osmonics, Inc.). The bottom chamber wells receive 27-29 μl of DMEM medium alone (baseline) or medium containing chemo-attractant (bFGF, VEGF or Swiss 3T3 cell conditioned medium). The top chambers receive 45 μl of HUVEC cell suspension ($1\times10^6$ cells/ml) prepared in DMEM+1% BSA with or without test compound. After 5 h incubation at 37° C., the membrane is rinsed in PBS, fixed and stained in Diff-Quick solutions. The filter is placed on a glass slide with the migrated cells facing down and cells on top are removed using a Kimwipe. The testing is performed in 4-6 replicates and five fields are counted from each well. Negative unstimulated control values are subtracted from stimulated control and drug treated values and data is plotted as mean migrated cell±S.D. IC50 is calculated from the plotted data.

Example 2

Extracellular Domain Fragments of EphB4 Receptor Inhibit Angiogenesis and Tumor Growth A. Globular Domain of EphB4 is Required for EphrinB2 Binding and for the Activity of EphB4-Derived Soluble Proteins in Endothelial Tube Formation Assay.

To identify subdomain(s) of the ectopic part of EphB4 necessary and sufficient for the anti-angiogenic activity of the soluble recombinant derivatives of the receptor, four recombinant deletion variants of EphB4EC were produced and tested (FIG. 16). Extracellular part of EphB4, similarly to the other members of EphB and EphA receptor family, contains N-terminal ligand-binding globular domain followed by cysteine-rich domain and two fibronectin type III repeats (FNIII). In addition to the recombinant B4-GCF2 protein containing the complete ectopic part of EphB4, we constructed three deletion variants of EphB4EC containing globular domain and Cys-rich domain (B4-GC); globular, Cys-rich and the first FNIII domain (GCF1) as well as the ECD version with deleted globular domain (CF2). Our attempts to produce several versions of truncated EphB4EC protein containing the globular domain alone were not successful due to the lack of secretion of proteins expressed from all these constructs and absence of ligand binding by the intracellularly expressed recombinant proteins. In addition, a non-tagged version of B4-GCF2, called GCF2-F, containing complete extracellular domain of EphB4 with no additional fused amino acids was expressed, purified and used in some of the experiments described here.

Figure 17A:
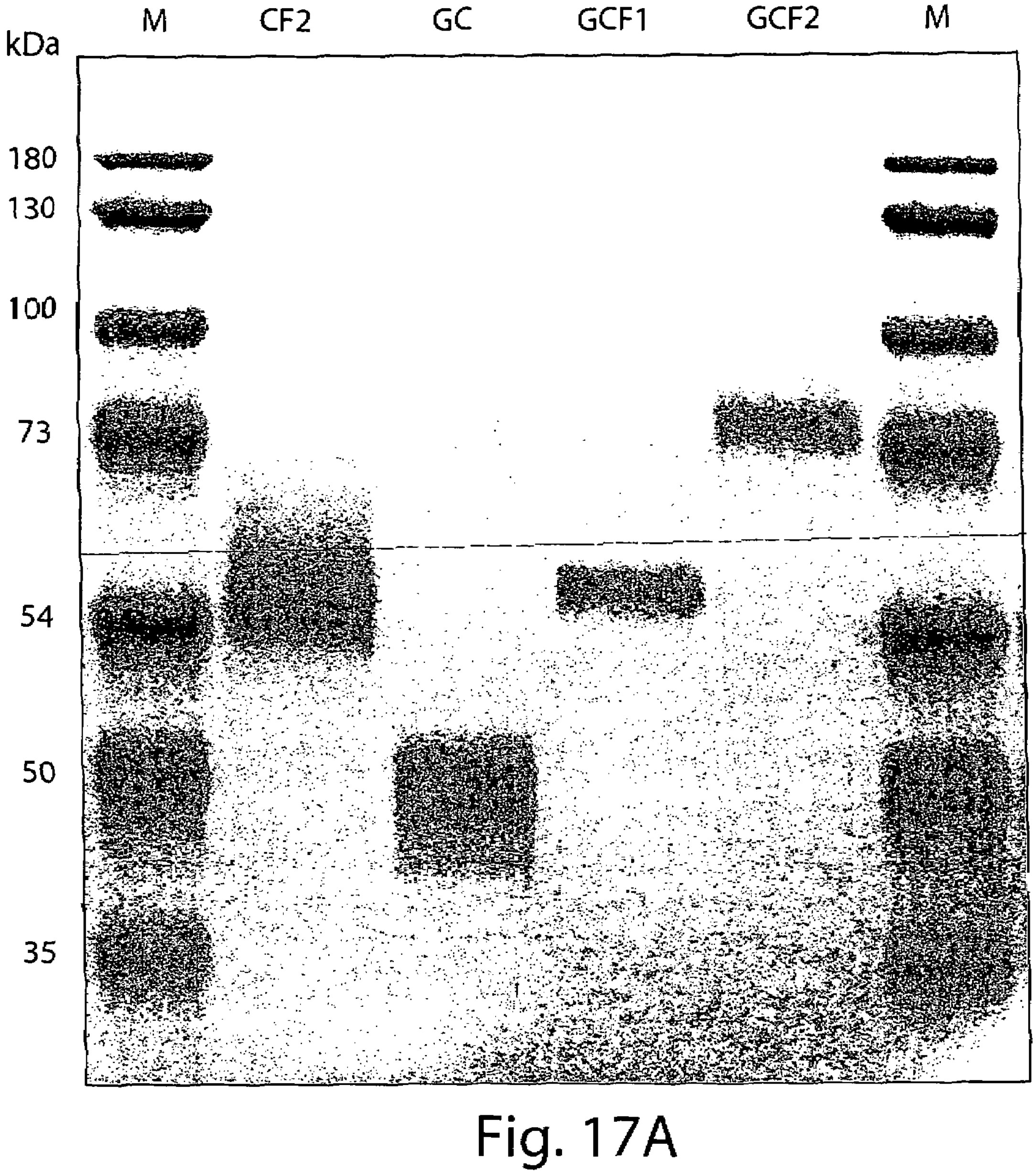
FIG. 17 shows purification and ligand binding properties of the EphB4EC proteins. A. SDS-PAAG gel electrophoresis of purified EphB4-derived recombinant soluble proteins (Coomassie-stained). B. Binding of Ephrin B2-AP fusion to EphB4-derived recombinant proteins immobilized on Ni-NTA-agarose beads. Results of three independent experiments are shown for each protein. Vertical axis—optical density at 420 nm.
Figure 17B:
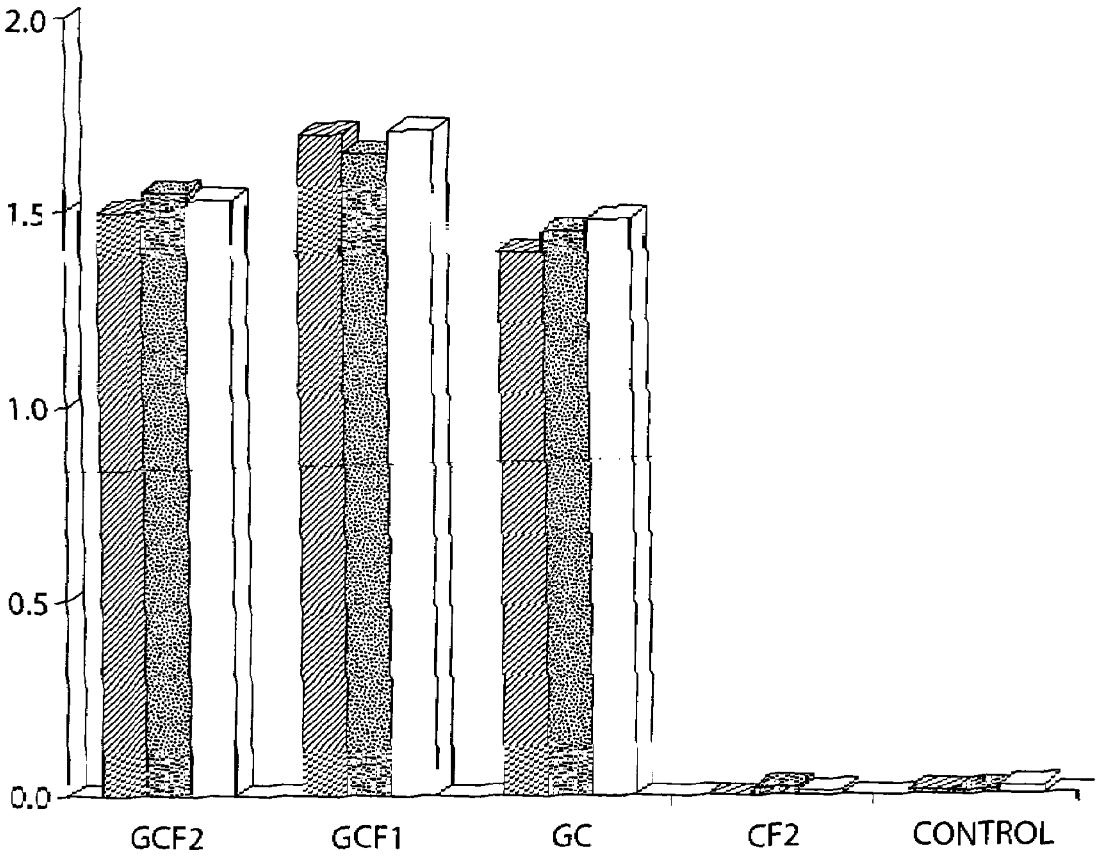

All four C-terminally 6xHis tagged recombinant proteins were preparatively expressed in transiently transfected cultured mammalian cells and affinity purified to homogeneity from the conditioned growth media using chromatography on $Ni^{2+}$-chelate resin (FIG. 17). Apparently due to their glycosylation, the proteins migrate on SDS-PAAG somewhat higher than suggested by their predicted molecular weights of 34.7 kDa (GC), 41.5 (CF2), 45.6 kDa (GCF1) and 57.8 kDa (GCF2). Sequence of the extracellular domain of human EphB4 contains three predicted N-glycosylation sites (NXS/T) which are located in the Cys-rich domain, within the first fibronectin type III repeat and between the first and the second fibronectin repeats.

To confirm ability of the purified recombinant proteins to bind Ephrin B2, they were tested in an in vitro binding assay. As expected, GC, GCF1 and GCF2, but not CF2 are binding the cognate ligand Ephrin B2 as confirmed by interaction between Ephrin B2-alkaline phosphatase (Ephrin B2-AP) fusion protein with the B4 proteins immobilized on $Ni^{2+}$-resin or on nitrocellulose membrane (FIG. 17).

All four proteins were also tested for their ability to block ligand-dependent dimerization and activation of Eph B4 receptor kinase in PC3 cells. The PC3 human prostate cancer cell line is known to express elevated levels of human Eph B4. Stimulation of PC3 cells with Ephrin B2 IgG Fc fusion protein leads to a rapid induction of tyrosine phosphorylation of the receptor. However, preincubation of the ligand with GCF2, GCF1 or GC, but not CF2 proteins suppresses subsequent EphB4 autophosphorylation. Addition of the proteins alone to the PC3 cells or preincubation of the cells with the proteins followed by changing media and adding the ligand does not affect EphB4 phosphorylation status.

Further, we found that globular domain of EphB4 is required for the activity of EphB4-derived soluble proteins in endothelial tube formation assay.

B. Effects of Soluble EphB4 on HUV/AEC In Vitro.

Figure 18:
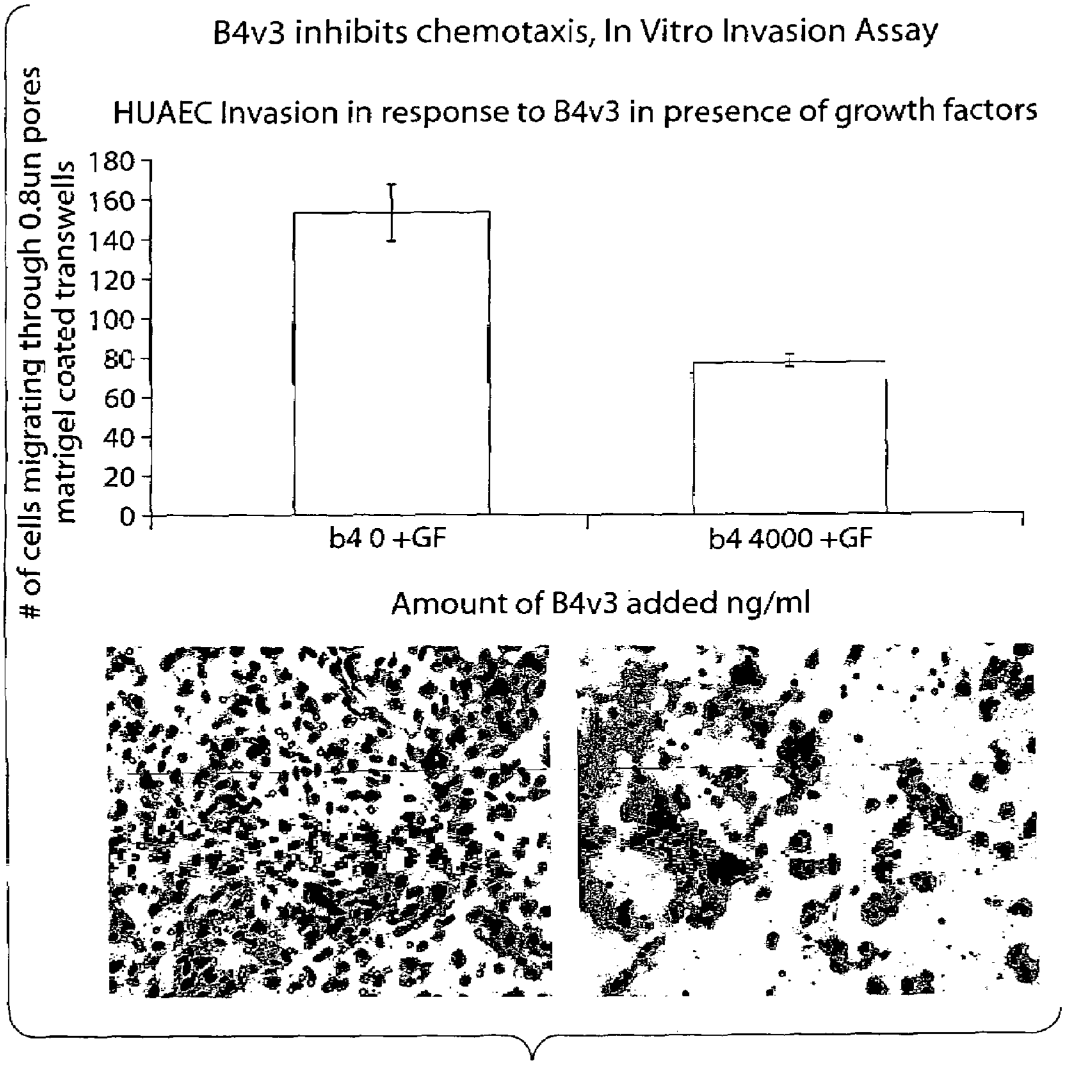
FIG. 18 shows that EphB4v3 inhibits chemotaxis.
Figure 19A:
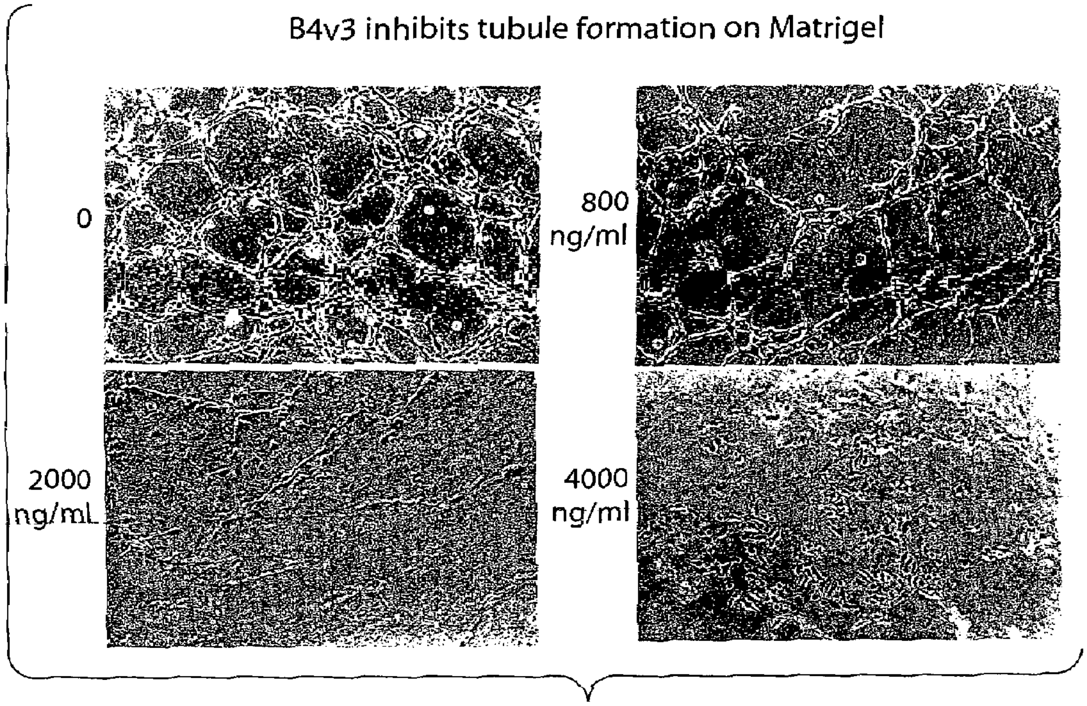
FIG. 19 shows that EphB4v3 inhibits tubule formation on Matrigel. A displays the strong inhibition of tubule formation by B4v3 in a representative experiment. B shows a quantitation of the reduction of tube-length obtained with B4v3 at increasing concentrations as well as a reduction in the number of junctions, in comparison to cells with no protein. Results are displayed as mean values_S.D. obtained from three independent experiments performed with duplicate wells.
Figure 19B:
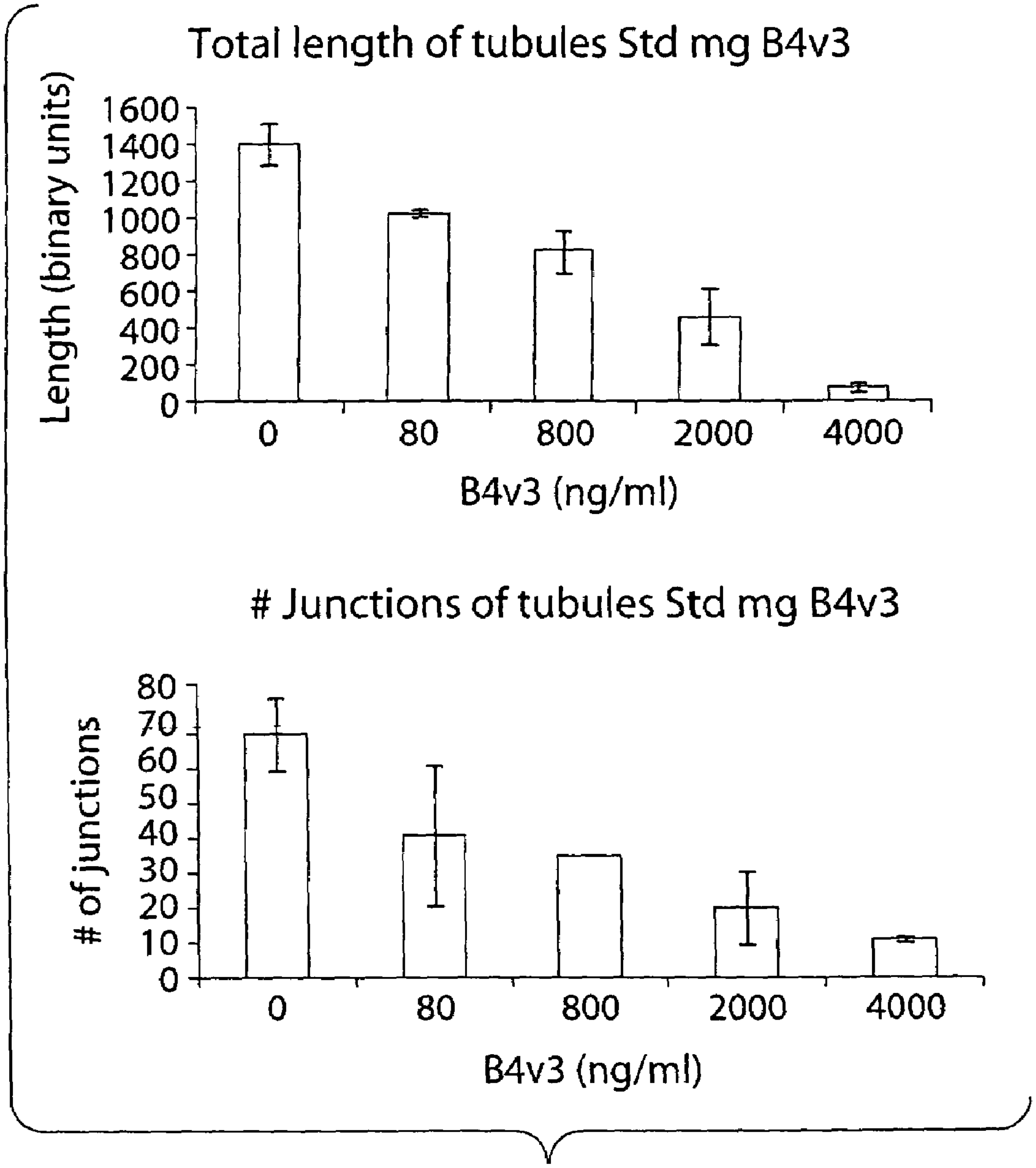
Figure 20:
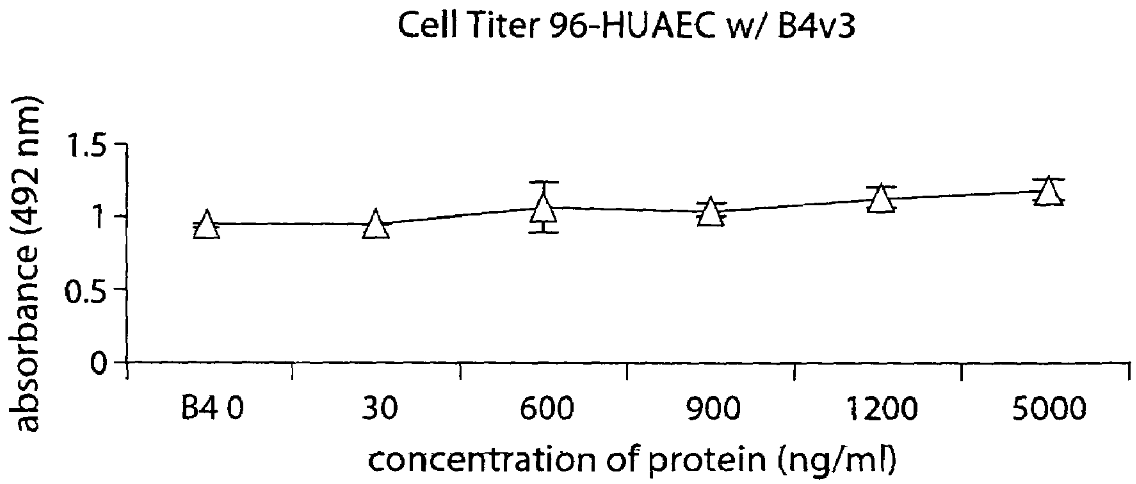
FIG. 20 shows that soluble EphB4 has no detectable cytotoxic effect as assessed by MTS assay.

Initial experiments were performed to determine whether soluble EphB4 affected the three main stages in the angiogenesis pathway. These were carried out by establishing the effects of soluble EphB4 on migration/invasion, proliferation and tubule formation by HUV/AEC in vitro. Exposure to soluble EphB4 significantly inhibited both bFGF and VEGF-induced migration in the Boyden chamber assay in a dose-dependent manner, achieving significance at nM (FIG. 18). Tubule formation by HUV/AECS on wells coated with Matrigel was significantly inhibited by soluble EphB4 in a dose-dependent manner in both the absence and presence of bFGF and VEGF (FIG. 19). We also assessed in vitro, whether nM of soluble EphB4 was cytotoxic for HUVECS. Soluble EphB4 was found to have no detectable cytotoxic effect at these doses, as assessed by MTS assay (FIG. 20).

C. Soluble EphB4 Receptor Inhibits Vascularization of Matrigel Plugs, In Vivo

Figure 21:
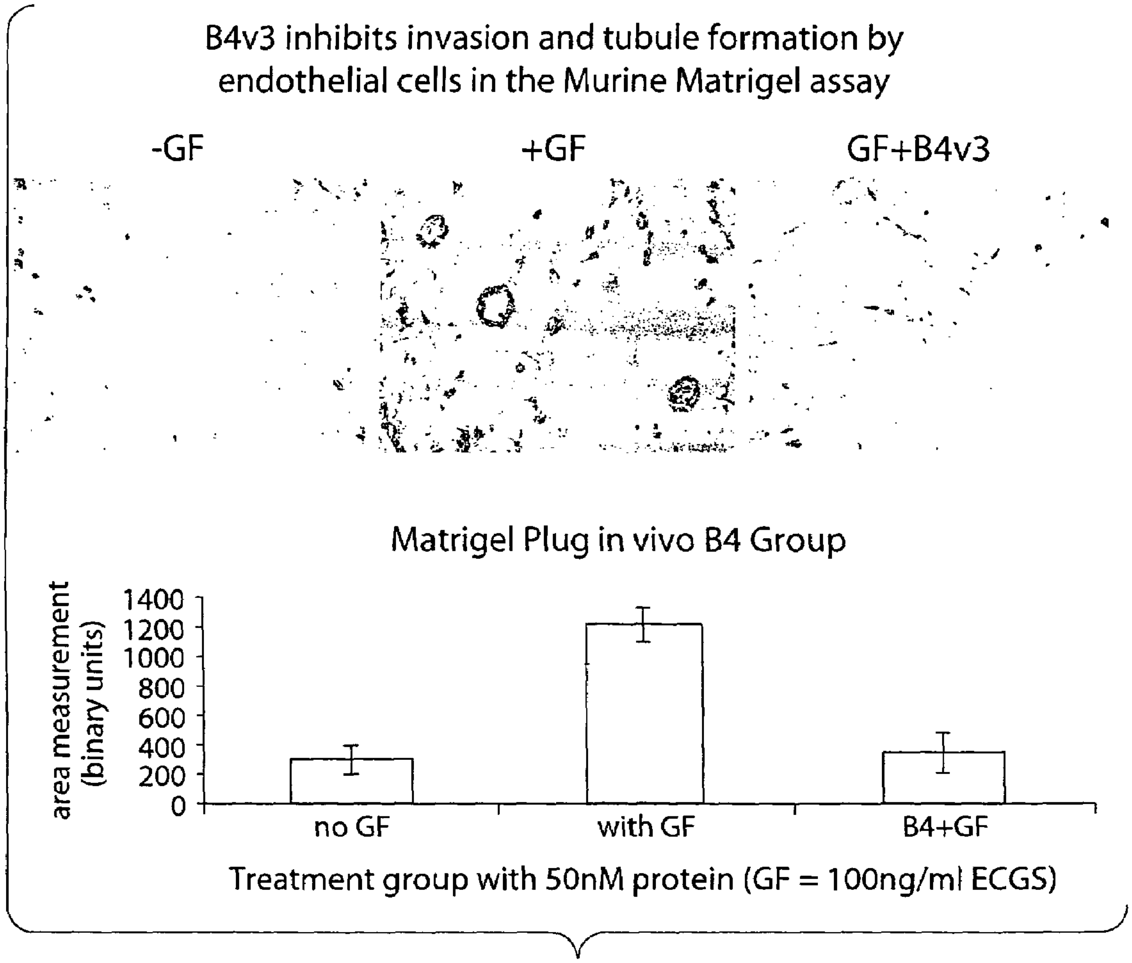
FIG. 21 shows that B4v3 inhibits invasion and tubule formation by endothelial cells in the Matrigel assay. (A) to detect total invading cells, photographed at 20× magnification or with Masson's Trichrome Top left of A B displays section of a Matrigel plug with no GF, top right of A displays section with B4IgG containing GF and lower left section contains GF, and lower right shows GF in the presence of B4v3. Significant invasion of endothelial cells is only seen in GF containing Matrigel. Top right displays an area with a high number of invaded cells induced by B4IgG, which signifies the dimeric form of B4v3. The left upper parts of the pictures correspond to the cell layers formed around the Matrigel plug from which cells invade toward the center of the plug located in the direction of the right lower corner. Total cells in sections of the Matrigel plugs were quantitated with Scion Image software. Results obtained from two experiments with duplicate plugs are displayed as mean values_S.D.

To demonstrate that soluble EphB4 can directly inhibit angiogenesis in vivo, we performed a murine matrigel plug experiment. Matrigel supplemented with bFGF and VEGF with and without soluble EphB4 was injected s.c. into Balb/C nu/nu mice, forming semi-solid plugs, for six days. Plugs without growth factors had virtually no vascularization or vessel structures after 6 days (FIG. 21). In contrast, plugs supplemented with bFGF and VEGF had extensive vascularization and vessels throughout the plug. Plugs taken from mice treated with μg of soluble EphB4 had markedly reduced vascularization of plugs, comparable to plugs without growth factor (FIG. 21). Furthermore, histological examination of plugs showed decreased vessel staining (FIG. 21). Treatment at 0 μg/dose significantly inhibited the amount of infiltration in Matrigel plugs compared to control (FIG. 21).

Figure 22:
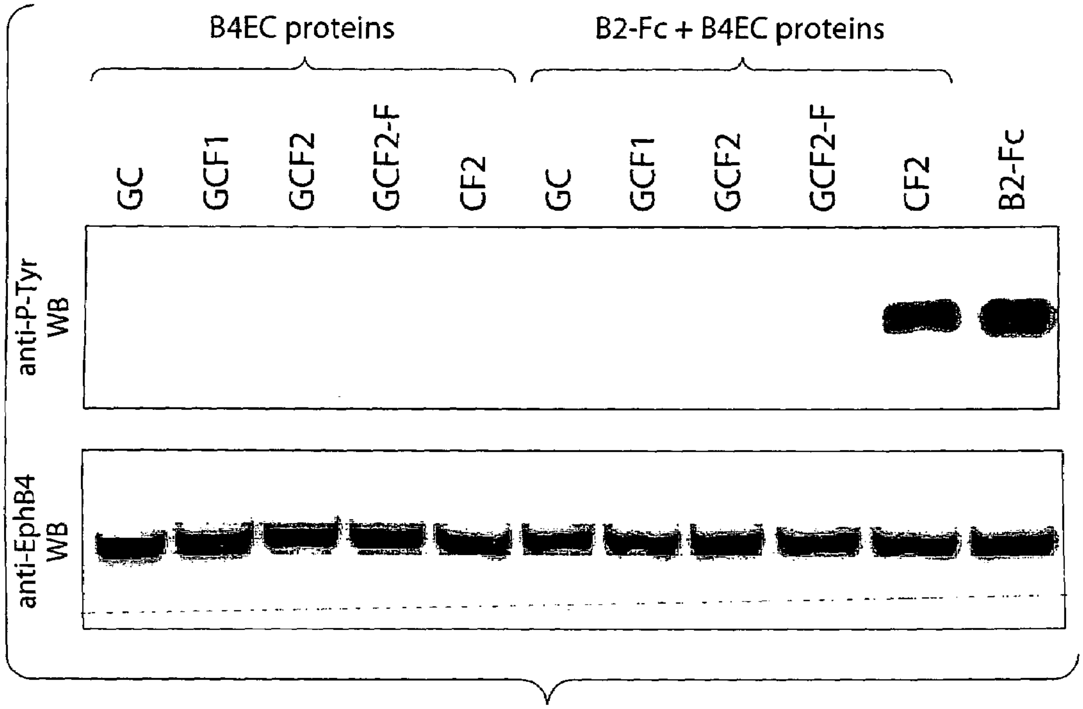
FIG. 22 shows tyrosine phosphorylation of EphB4 receptor in PC3 cells in response to stimulation with EphrinB2-Fc fusion in presence or absence of EphB4-derived recombinant soluble proteins.

We examined EphB4 receptor phosphorylation in HUVECs by performing Western blot analyses with lysates from soluble EphB4-treated cells and antibodies against phosphor-tyrosine. We found that soluble EphB4 treatment of serum-starved HUVECs stimulated a rapid and transient decrease in the level of phosphorylated EphB4, in the presence of EphrinB2Fc, EphB4 ligand dimer. Ephrin B2Fc without the soluble EphB4 protein induced phosphorylation of EphB4 receptor (FIG. 22).

D. Effects of Soluble EphB4 on Tumor Growth, In Vitro.

Figure 23A:
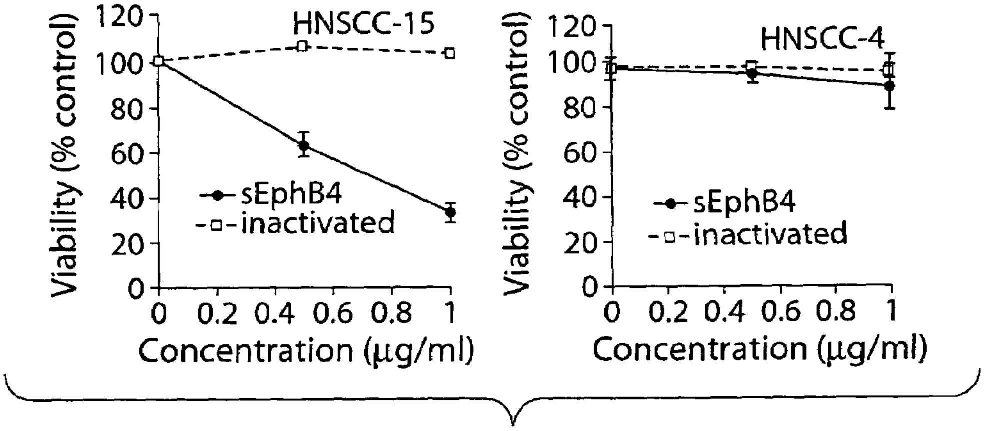
FIG. 23 shows effects of soluble EphB4ECD on viability and cell cycle. A) 3-day cell viability assay of two HNSCC cell lines. B) FACS analysis of cell cycle in HNSCC-15 cells treated as in A. Treatment of these cells resulted in accumulation in subG0/G1 and S/G2 phases as indicated by the arrows.
Figure 23B:
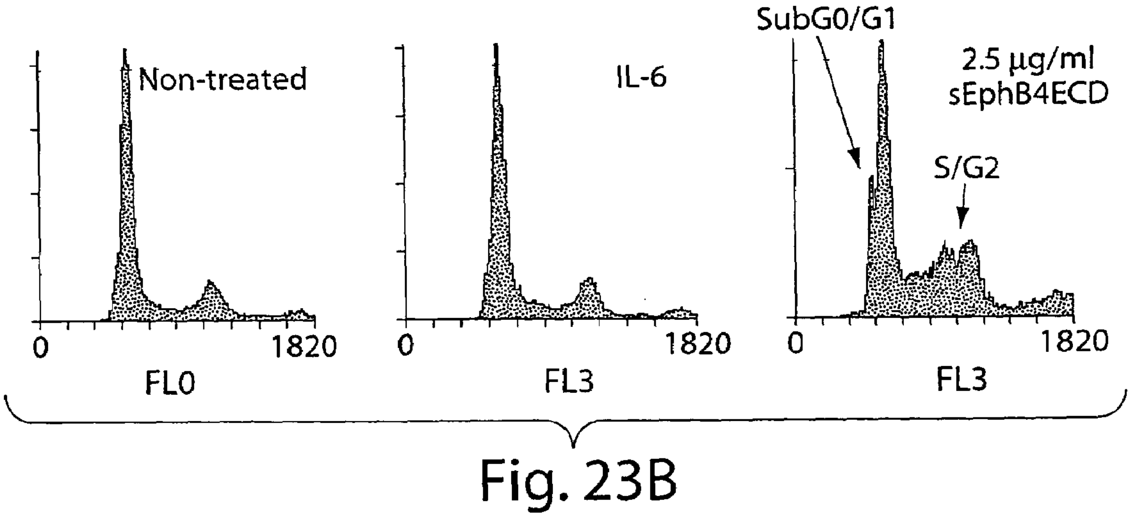

We found that soluble EphB4 inhibits the growth of SCC15 tumors grown in Balb/C Nu/Nu mice (FIG. 23).

E. Soluble EphB4 Inhibited Corneal Neovascularization

Figure 24:
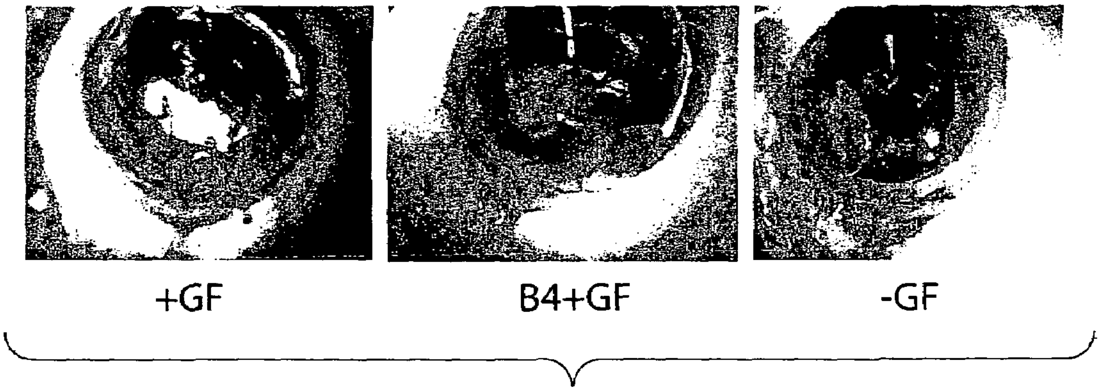
FIG. 24 shows that B4v3 inhibitis neovascular response in a murine corneal hydron micropocket assay.

To further investigate the antiangiogenic activity of soluble EphB4 in vivo, we studied the inhibitory effect of administration of soluble EphB4 on neovascularization in the mouse cornea induced by bFGF. Hydron Pellets implanted into corneal micropocket could induce angiogenesis, in the presence of growth factors, in a typically avascular area. The angiogenesis response in mice cornea was moderate, the appearance of vascular buds was delayed and the new capillaries were sparse and grew slowly. Compared with the control group, on day 7 of implantation, the neovascularization induced by bFGF in mice cornea was markedly inhibited in soluble EphB4-treated group (FIG. 24).

F. Effects of Soluble EphB4 on Tumor Growth, In Vivo.

The same model was used to determine the effects of soluble EphB4 in vivo. SCC15 tumors implanted subcutaneously, pre-incubated with matrigel and with or w/o growth factors, as well as implanted sc alone, and mice treated sc or ip daily with 1-5 ug of soluble EphB4 were carried out.

Figure 25:
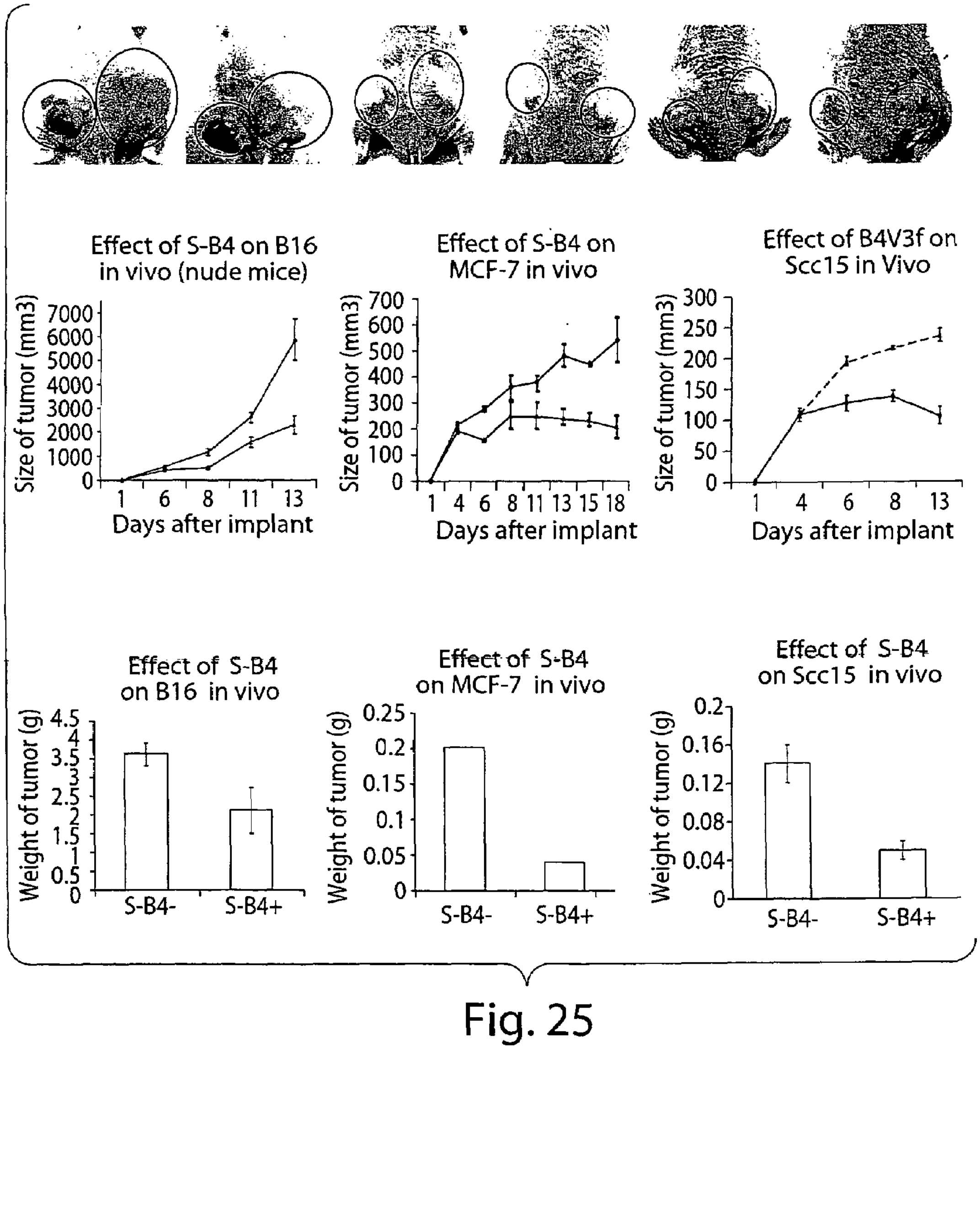
FIG. 25 shows that that SCC15, B16, and MCF-7 co-injected with sB4v3 in the presence of matrigel and growth factors, inhibits the in vivo tumor growth of these cells.

Tumors in the control group continued to grow steadily over the treatment period, reaching a final tumor volume of mm3. However, animals injected with soluble EphB4 exhibited a significantly (p<0.0/) reduced growth rate, reaching a final tumor volume of only mm3 (FIG. 25). Similar results were obtained in two further cohorts of such tumor-bearing mice. Soluble EphB4 administration appeared to be well tolerated in vivo, with no significant effect on body weight or the general well-being of the animals (as determined by the absence of lethargy, intermittent hunching, tremors or disturbed breathing patterns).

G. Effects of Soluble EphB4 on Tumor Histology.

Figure 26:
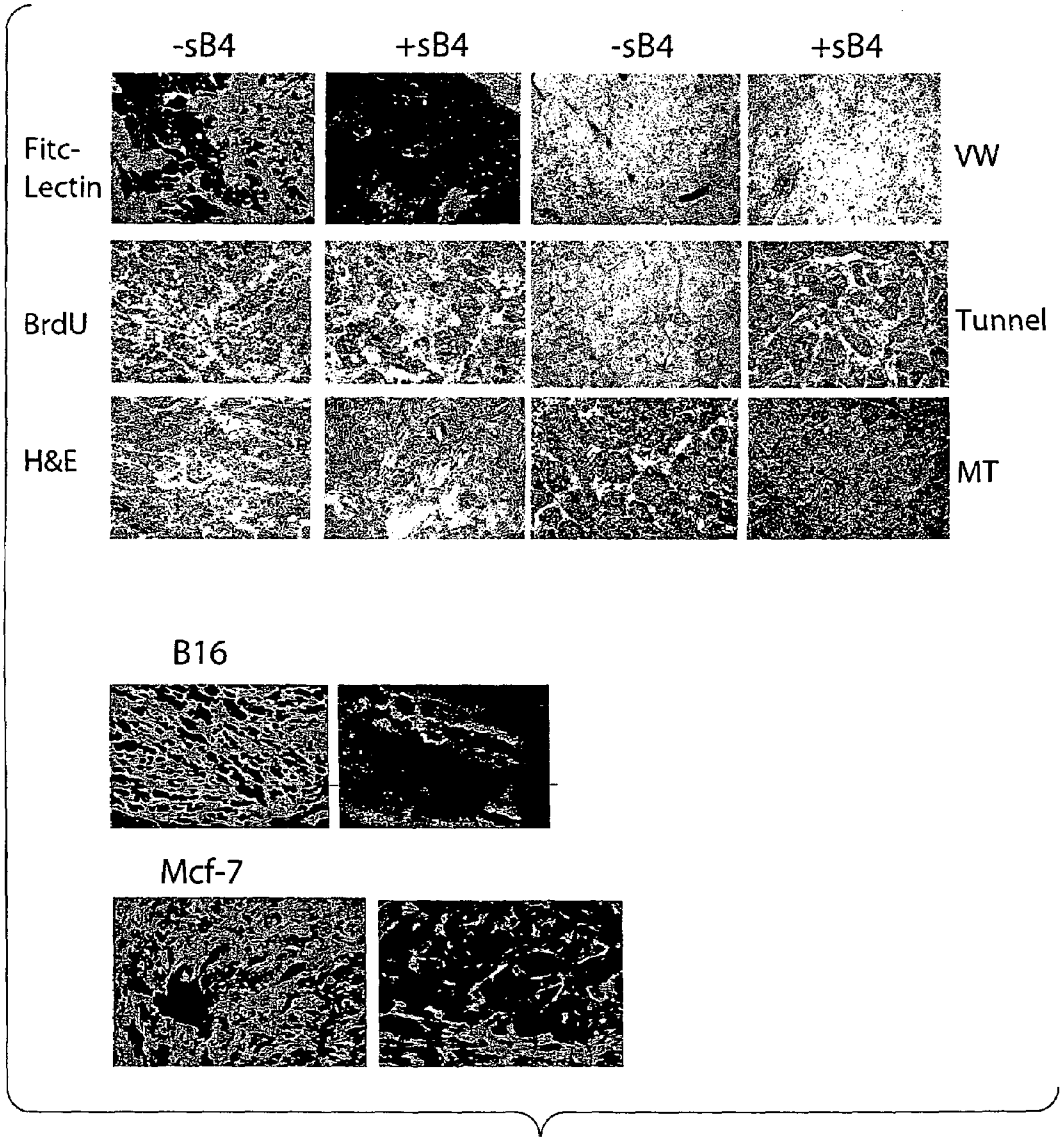
FIG. 26 shows that soluble EphB4 causes apoptosis, necrosis and decreased angiogenesis in three tumor types, B16 melanoma, SCC15, head and neck carcinoma, and MCF-7 Breast carcinoma. Tumors were injected premixed with Matrigel plus growth factors and soluble EphB4 subcutaneously. After 10 to 14 days, the mice were injected intravenously with fitc-lectin (green) to assess blood vessel perfusion. Tumors treated with control PBS displayed abundant tumor density and a robust angiogenic response Tumors treated with sEphB4 displayed a decrease in tumor cell density and a marked inhibition of tumor angiogenesis in regions with viable tumor cells, as well as tumor necrosis and apoptosis.

Histological analysis revealed the presence of a central area of necrosis in all SCC15 tumors, which was usually surrounded by a viable rim of tumor cells um in width. The central necrotic areas were frequently large and confluent and showed loss of cellular detail. Necrosis, assessed as a percentage of tumor section area, was significantly (p<0.02) more extensive in the soluble EphB4-treated group (% necrosis in treated vs. control). To determine whether the reduced volume of soluble EphB4 treated tumors was due to an effect of this protein on the tumor vascular supply, endothelial cells in blood vessels were identified in tumor sections using immunostaining with an anti-platelet cell adhesion molecule (PECAM-1; CD31) antibody (FIG. 26) and the density of microvessels was assessed. Microvessel density was similar in the outer viable rim of tumor cells (the uniform layer of cells adjacent to the tumor periphery with well defined nuclei) in control and soluble EphB4-treated tumors. Microvessel density was significantly in the inner, less viable region of tumor cells abutting the necrotic central areas in soluble EphB4-treated than control tumors. Fibrin deposition, as identified by Masson's Trichrome staining, was increased in and around blood vessels in the inner viable rim and the central necrotic core of soluble EphB4 treated than control tumors. In the outer viable rim of soluble EphB4 treated tumors, although the vessel lumen remained patent and contained red blood cells, fibrin deposition was evident around many vessels. Soluble EphB4 was found to have no such effects on the endothelium in the normal tissues examined (lungs, liver and kidneys).

H. Materials and Methods

1) Expression Constructs

To construct expression vectors for producing soluble, 6xHis-tagged EphB4-ECD variants, cloned full-length human EphB4 cDNA was amplified by PCR using the following oligo primers: TACTAGTCCGCCATGGAGCTCCGGGTGCTGCT (SEQ ID NO: 9) (common EphB4 N-terminal primer) and GCGGCCGCTTAATGGTGATGGTGATGATGAGCCGA AGGAGGGGTGGTGCA (SEQ ID NO: 10) (B4-GC), AGCGGCCGCTTAATGGTGATGG TGATGATGGACATTGA CAGGCTCAAATGGGA (SEQ ID NO: 11) (B4-GCF1) or TGCGGCCGCTTAATG GTGATGGTGATGAT GCTGCTCCCGCCAGCCCTCGCTCTCAT (SEQ ID NO: 12) (B4-GCF2). The resulting PCR fragments were TA-cloned into mammalian expression vector pEF6/V5-His-TOPO (Invitrogen) under EF-1α promoter control. The expressed recombinant proteins encode the following fragments of the mature extracellular part of human EphB4: amino acid positions 1-522 (GCF2), 1-412 (GCF1) and 1-312 (GC). To generate the B4-CF2 deletion (δ amino acids 13-183) PCR fragment for pEF6 cloning, EphB4 cDNA was amplified by two-step overlap PCR using oligo primers TACTAGTCCGCCATGGA

```
TACTAGTCCGCCATGGAGCTCCGGGTGCTGCT,
(SEQ ID NO: 13)

CAGCTGAGTTTCCAATTTTGTGTTC,
(SEQ ID NO: 14)

GAACACAAAATTGGAAACTCAGCTGACTGTGAACCTGAC
(SEQ ID NO: 15)
and

GCGGCCGCCCTG CTCCCGCCAGCCCTCGCT.
(SEQ ID NO: 16)
```

Vector for producing secreted human EphrinB2-alkaline phosphatase (B2-AP) reagent was constructed by PCR amplification of human Ephrin B2 cDNA using primers TAAAGCTTCCGCCATGGCTGTGAGAAGGGAC (SEQ ID NO: 17) and TAGGATCCTTCG GAACCGAGGATGTTGTTCCC (SEQ ID NO: 18) and cloning the resulting fragment, digested with Hind III and Bam HI, into Hind III-Bgl II digested pAPTag2 vector (GenHunter, Inc.). In each case, inserts in expression vectors were verified by complete sequencing.

2) Antibodies and Other Reagents

Anti-Eph B4 monoclonal antibodies mAB79 and mAB23 were raised in mice against the GCF2 protein containing amino acids 1-522 of mature human EphB4 and purified from hybridoma supernatants by Protein A chromatography. The anti-phosphotyrosine antibody 4G10 was from UBI (Lake Placid, N.Y.). Protein G-HRP conjugate was purchased from Bio-Rad.

3) Expression and Purification of EphB4-Derived Recombinant Proteins

To produce the EphB4-ECD soluble proteins, cultured human embryonic kidney cells HEK293T were transfected with the corresponding plasmid constructs using standard calcium phosphate or Lipofectamin 2000 reagent (Invitrogen) protocols. Twelve to sixteen hours post-transfection, the growth medium (DMEM+10% fetal bovine serum) was aspirated, cells washed once with serum free DMEM and replaced with serum free DMEM. Conditioned media containing the secreted proteins were harvested 72-96 hours later, clarified by centrifugation and used for purification of His-tagged proteins using Ni-NTA Agarose (Qiagen). The purity and quantity of the recombinant proteins was tested by SDS-PAAG electrophoresis with Coomassie Blue or silver staining, Western blotting and UV spectroscopy. Purified proteins were dialyzed against 20 mM Tris-HCl, 0.15 M NaCl, pH 8 and stored at −70° C.

To test ligand binding properties of the proteins, 10 μl of Ni-NTA-Agarose (Qiagen) were incubated in microcentrifuge tubes with 10-500 ng sample of a B4-ECD protein diluted in 0.5 ml of binding buffer BB (20 mM Tris-HCl, 0.15 M NaCl, 0.1% bovine serum albumin, pH 8). After incubation for 30 min on shaking platform, Ni-NTA beads were washed twice with 1.4 ml of BB, followed by addition of B2-AP fusion protein at concentration of 50 nM. Binding was performed for 30 min on a shaking platform. Tubes were centrifuged and washed once with 1.4 ml of BB. Amount of precipitated AP was measured colorimetrically at 420 nm after application of p-nitrophenyl phosphate (PNPP) and incubation for 5-30 min.

4) Immunoprecipitation

All lysates were processed at 4° C. Cells were lysed in 1 ml of buffer containing 20 mM Hepes at pH 7.4, 100 mM sodium chloride, 50 mM sodium fluoride, 2 mM EDTA, 2 mM EGTA, 1 mM sodium orthovanadate, 1%(v/v) NP-40, 0.5% (w/v) sodium deoxycholate, 1 mM phenyl methylsulphonyl fluoride (added freshly) and 100 U Trasylol. Lysates were scraped into Eppendorf tubes and 50 μl of boiled, formalin-fixed *Staphylococcus aureus* was added (Calbiochem, San Diego). After 30 min of mixing, the lysates were centrifuged for 5 min at 25,000 g in a minifuge and the supernatants transferred to new tubes containing the appropriate antibody. Lysates were mixed with antibodies for 1 h, after which time 50 μl of protein A-Sepharose beads were added and the contents of the tubes mixed for 1 h to collect the immunoprecipitates. Protein A beads were collected by centrifugation at 25,000 g for 30 s. The supernatants were discarded and the beads washed three times with 1 ml lysis buffer minus deoxycholate.

5) Cell-Based EphB4 Tyrosine Kinase Assay

The human prostate carcinoma cell line PC3 cells were maintained in RPMI medium with 10% dialyzed fetal calf serum and 1% penicillin/streptomycin/neomycin antibiotics mix. Cells were maintained at 37° C. in a humidified atmosphere of 5% $CO_2$/95% air. Typically, cells were grown in 60 mm dishes until confluency and were either treated with mouse Ephrin B2-Fc fusion at 1 μg/ml in RPMI for 10 min to activate EphB4 receptor or plain medium as a control. To study the effect of different derivatives of soluble EphB4 ECD proteins on EphB4 receptor activation, three sets of cells were used. In the first set, cells were treated with various proteins (5 proteins; GC, GCF1, GCF2, GCF2-F, CF2) at 5 μg/ml for 20 min. In the second set of cells, prior to application, proteins were premixed with ephrinB2-Fc at 1:5 (EphB4 protein: B2-Fc) molar ratio, incubated for 20 min and applied on cells for 10 min. In the third set of cells, cells were first treated with the proteins for 20 min at 5 μg/ml, media was replaced with fresh media containing 1 μg/ml of EphrinB2-Fc and incubated for another 10 min.

After the stimulation, cells were immediately harvested with protein extraction buffer containing 20 mM Tris-HCl, pH 7.4, 150 mM NaCl, 1% (v/v) Triton X100, 1 mM EDTA, 1 mM PMSF, 1 mM Sodium vanadate. Protein extracts were clarified by centrifugation at 14,000 rpm for 20 min at 4° C. Clarified protein samples were incubated overnight with protein A/G coupled agarose beads pre-coated with anti-EphB4 monoclonal antibodies. The IP complexes were washed twice with the same extraction buffer containing 0.1% Triton X100. The immunoprecipitated proteins were solubilized in 1×SDS-PAGE sample loading buffer and separated on 10% SDS-PAGE. For EphB4 receptor activation studies, electroblotted membrane was probed with anti-pTyr specific antibody 4G10 at 1:1000 dilution followed by Protein G-HRP conjugate at 1:5000 dilutions.

6) Cell Culture

Normal HUVECs were obtained from Cambrex (BioWhittaker) and maintained in EBM2 medium supplemented with 0.1 mg/ml endothelial growth supplement (crude extract from bovine brain), penicillin (50 U/ml), streptomycin (50 U/ml), 2 mmol/l glutamine and 0.1 mg/ml sodium heparin. Aliquots of cells were preserved frozen between passages 1 and 3. For all experiments, HUVECs were used at passages 4 or below and collected from a confluent dish.

7) Endothelial Cell Tube Formation Assay

Matrigel (60 μl of 10 mg/ml; Collaborative Lab, Cat. No. 35423) was placed in each well of an ice-cold 96-well plate. The plate was allowed to sit at room temperature for 15 minutes then incubated at 37° C. for 30 minutes to permit Matrigel to polymerize. In the mean time, human umbilical vein endothelial cells were prepared in EGM-2 (Clonetic, Cat. No. CC3162) at a concentration of $2\times10^5$ cells/ml. The test protein was prepared at 2× the desired concentration (5 concentration levels) in the same medium. Cells (500 μl) and 2× protein (500 μl) were mixed and 200 μl of this suspension were placed in duplicate on the polymerized Matrigel. After 24 h incubation, triplicate pictures were taken for each concentration using a Bioquant Image Analysis system. Protein addition effect ($IC_{50}$) was assessed compared to untreated controls by measuring the length of cords formed and number of junctions.

8) Cell Migration Assay

Chemotaxis of HUVECs to VEGF was assessed using a modified Boyden chamber, transwell membrane filter inserts in 24 well plates, 6.5 mm diam, 8 μm pore size, 10 μm thick matrigel coated, polycarbonate membranes (BD Biosciences). The cell suspensions of HUVECs ($2\times10^5$ cells/ml) in 200 μl of EBM were seeded in the upper chamber and the soluble EphB4 protein were added simultaneously with stimulant (VEGF or bFGF) to the lower compartment of the chamber and their migration across a polycarbonate filter in response to 10-20 ng/ml of VEGF with or without 100 nM-1 μM test compound was investigated. After incubation for 4-24 h at 37° C., the upper surface of the filter was scraped with swab and filters were fixed and stained with Diff Quick. Ten random fields at 200× mag were counted and the results expressed as mean # per field. Negative unstimulated control values were subtracted from stimulated control and protein treated sample values and the data was plotted as mean migrated cell±S.D. $IC_{50}$ was calculated from the plotted data.

9) Growth Inhibition Assay

HUVEC ($1.5\times10^3$ cells) were plated in a 96-well plate in 100 μl of EBM-2 (Clonetic, Cat. No. CC3162). After 24 hours (day 0), the test recombinant protein (100 μl) is added to each well at 2× the desired concentration (5-7 concentration levels) in EBM-2 medium. On day 0, one plate was stained with 0.5% crystal violet in 20% methanol for 10 minutes, rinsed with water, and air-dried. The remaining plates were incubated for 72 h at 37° C. After 72 h, plates were stained with 0.5% crystal violet in 20% methanol, rinsed with water and air-dried. The stain was eluted with 1:1 solution of ethanol: 0.1 M sodium citrate (including day 0 plate), and absorbance measured at 540 nm with an ELISA reader (Dynatech Laboratories). Day 0 absorbance was subtracted from the 72 h plates and data is plotted as percentage of control proliferation (vehicle treated cells). $IC_{50}$ value was calculated from the plotted data.

10) Murine Matrigel Plug Angiogenesis Assay

In vivo angiogenesis was assayed in mice as growth of blood vessels from subcutaneous tissue into a Matrigel plug containing the test sample. Matrigel rapidly forms a solid gel at body temperature, trapping the factors to allow slow release and prolonged exposure to surrounding tissues. Matrigel (8.13 mg/ml, 0.5 ml) in liquid form at 4° C. was mixed with Endothelial Cell Growth Supplement (ECGS), test proteins plus ECGS or Matrigel plus vehicle alone (PBS containing 0.25% BSA). Matrigel (0.5 ml) was injected into the abdominal subcutaneous tissue of female nu/nu mice (6 wks old) along the peritoneal mid line. There were 3 mice in each group. The animals were cared for in accordance with institutional and NIH guidelines. At day 6, mice were sacrificed and plugs were recovered and processed for histology. Typically the overlying skin was removed, and gels were cut out by retaining the peritoneal lining for support, fixed in 10% buffered formalin in PBS and embedded in paraffin. Sections of 3 μM were cut and stained with H&E or Masson's trichrome stain and examined under light microscope.

11) Mouse Corneal Micropocket Assay

Mouse corneal micropocket assay was performed according to that detailed by Kenyon et al., 1996. Briefly, hydron pellets (polyhydroxyethylmethacrylate [polyHEMA], Interferon Sciences, New Brunswick, N.J., U.S.A.) containing either 90 ng of bFGF (R&D) or 180 ng of VEGF (R&D Systems, Minneapolis, Minn., U.S.A.) and 40 μg of sucrose aluminium sulfate (Sigma) were prepared. Using an operating microscope, a stromal linear keratotomy was made with a surgical blade (Bard-Parker no. 15) parallel to the insertion of the lateral rectus muscle in an anesthetized animal. An intrastromal micropocket was dissected using a modified von Graefe knife (2"30 mm). A single pellet was implanted and advanced toward the temporal corneal limbus (within 0±7±1±0 mm for bFGF pellets and 0±5 mm for VEGF pellets). The difference in pellet location for each growth factor was determined to be necessary given the relatively weaker angiogenic stimulation of VEGF in this model. Antibiotic ointment (erythromycin.) was then applied to the operated eye to prevent infection and to decrease surface irregularities. The subsequent vascular response was measured extending from the limbal vasculature toward the pellet and the contiguous circumferential zone of neovascularization Data and clinical photos presented here were obtained on day 6 after pellet implantation, which was found to be the day of maximal angiogenic response.

12) In Vitro Invasion Assay

"Matrigel" matrix-coated 9-mm cell culture inserts (pore size, 8 μm; Becton Dickinson, Franklin Lakes, N.J.) were set in a 24-well plate. The HUVEC cells were seeded at a density of $5\times10^3$ cells per well into the upper layer of the culture insert and cultured with serum-free EBM in the presence of EphB4 ECD for 24 h. The control group was cultured in the same media without EphB4. Then 0.5 ml of the human SCC15 cell line, conditioned medium was filled into the lower layer of the culture insert as a chemo-attractant. The cells were incubated for 24 h, then the remaining cells in the upper layer were swabbed with cotton and penetrating cells in the lower layer were fixed with 5% glutaraldehyde and stained with Diff Quick. The total number of cells passing through the Matrigel matrix and each 8 μm pore of the culture insert was counted using optical microscopy and designated as an invasion index (cell number/area).

13) SCC15 Tumor Growth in Mice

Subcutaneously inject logarithmically growing SCC15, head and neck squamous cell carcinoma cell line, at $5\times10^6$ cell density; with or without EphB4 ECD in the presence or absence of human bFGF, into athymic Balb/c nude mice, along with Matrigel (BD Bioscience) synthetic basement membrane (1:1 v/v), and examine tumors within 2 weeks. Tumor volumes in the EphB4 ECD group, in the presence and absence of growth factor after implantation were three-fold smaller than those in the vehicle groups. There was no difference in body weight between the groups. Immunohistochemical examination of cross-sections of resected tumors and TUNEL-positive apoptosis or necrosis, CD34 immunostaining, and BrdU proliferation rate will be performed, after deparaffinized, rehydrated, and quenched for endogenous peroxidase activity, and after 10 min permeabilization with proteinase K. Quantitative assessment of vascular densities will also be performed. Local intratumoral delivery or IV delivery of EphB4 ECD will also be performed twice a week.

30 athymic nude mice, BALB/c (nu/nu), were each injected with $1\times10^6$ B16 melanoma cells with 0.1 ml PBS mixed with 0.1 ml matrigel or $1.5\times10^6$ SCC15 cells resuspended in 200 μl of DMEM serum-free medium and injected subcutaneously on day 0 on the right shoulder region of mice. Proteins were injected intravenously or subcutaneously, around the tumor beginning on day 1 at a loading dose of 4 μg/mg, with weekly injections of 2 ug/mg. (10 μg/g, 50 μg/kg/day), and at 2 weeks post-inoculation. Mice are sacrificed on Day 14. Control mice received PBS 50 μl each day.

14) Tumor Formation in Nude Mice

All animals were treated under protocols approved by the institutional animal care committees. Cancer cells ($5\times10^6$) were subcutaneously inoculated into the dorsal skin of nude mice. When the tumor had grown to a size of about 100 $mm^3$ (usually it took 12 days), sEphB4 was either intraperitoneally or subcutaneously injected once/day, and tumorigenesis was monitored for 2 weeks. Tumor volume was calculated according to the formula $a^2\times b$, where a and b are the smallest and largest diameters, respectively. A Student's t test was used to compare tumor volumes, with $P<0.05$ being considered significant.

15) Quantification of Microvessel Density

Tumors were fixed in 4% formaldehyde, embedded in paraffin, sectioned by 5 μm, and stained with hematoxylineosin. Vessel density was semi-quantitated using a computer-based image analyzer (five fields per section from three mice in each group).

Example 3

EphB4 is Upregulated and Imparts Growth Advantage in Prostate Cancer

A. Expression of EphB4 in Prostate Cancer Cell Lines

Figure 27A:
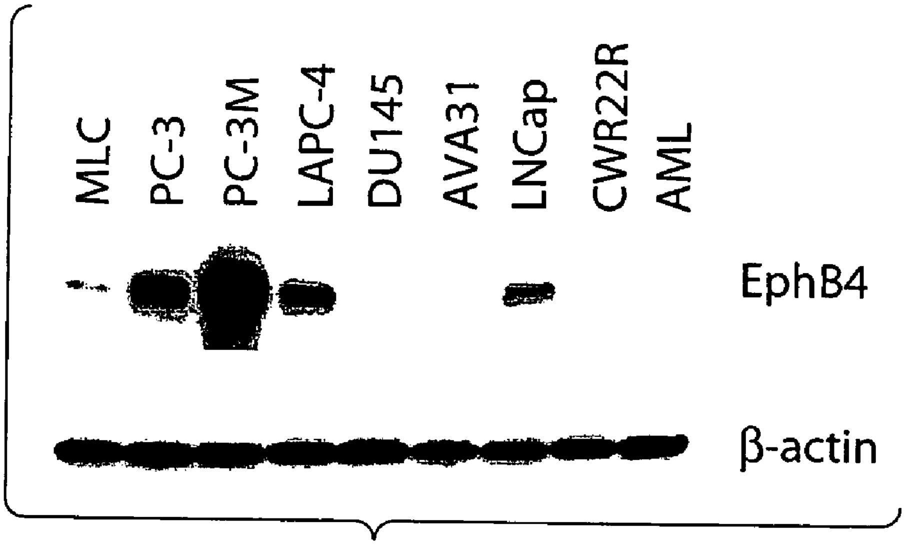
FIG. 27 shows expression of EphB4 in prostate cell lines. A) Western blot of total cell lysates of various prostate cancer cell lines, normal prostate gland derived cell line (MLC) and acute myeloblastic lymphoma cells (AML) probed with EphB4 monoclonal antibody. B) Phosphorylation of EphB4 in PC-3 cells determined by Western blot.
Figure 27B:
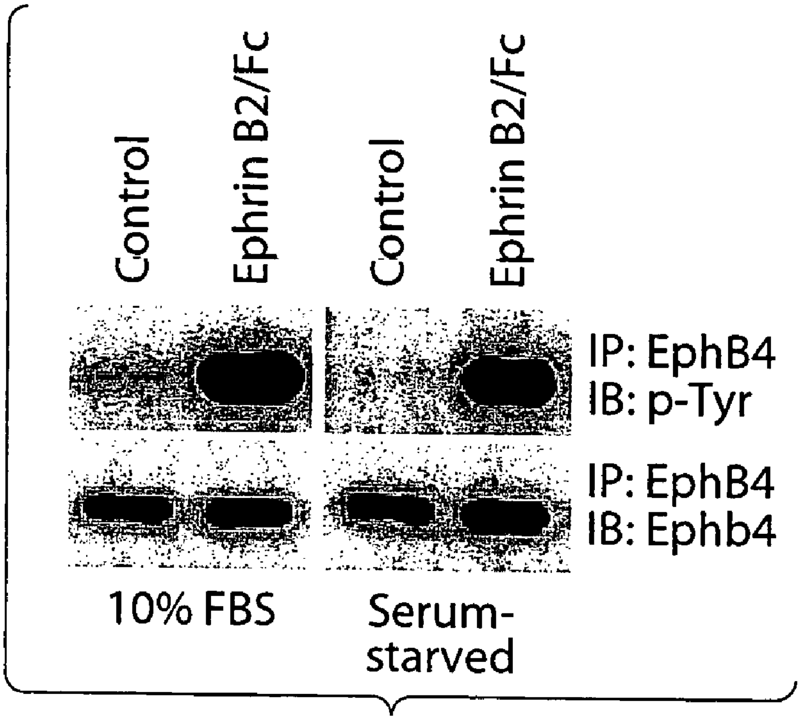

We first examined the expression of EphB4 protein in a variety of prostate cancer cell lines by Western blot. We found that prostate cancer cell lines show marked variation in the abundance of the 120 kD EphB4. The levels were relatively high in PC3 and even higher in PC3M, a metastatic clone of PC3, while normal prostate gland derived cell lines (MLC) showed low or no expression of EphB4 (FIG. 27A). We next checked the activation status of EphB4 in PC3 cells by phosphorylation study. We found that even under normal culture conditions, EphB4 is phosphorylated though it can be further induced by its ligand, ephrin B2 (FIG. 27B).

B. Expression of EphB4 in Clinical Prostate Cancer Samples

Figure 28:
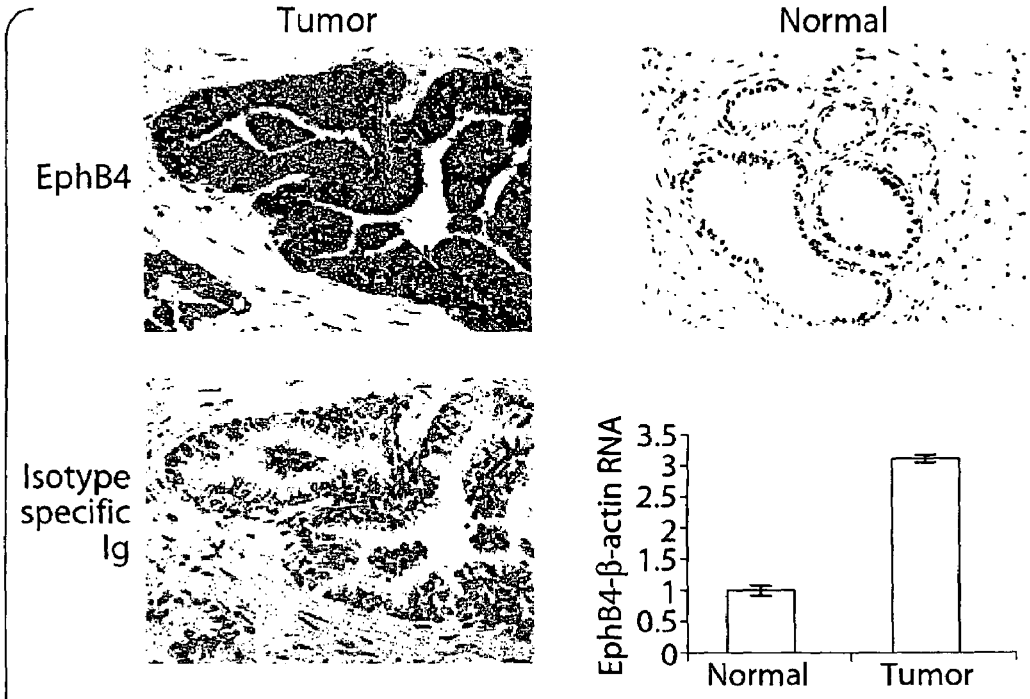
FIG. 28 shows expression of EphB4 in prostate cancer tissue. Representative prostate cancer frozen section stained with EphB4 monoclonal antibody (top left) or isotype specific control (bottom left). Adjacent BPH tissue stained with EphB4 monoclonal antibody (top right). Positive signal is brown color in the tumor cells. Stroma and the normal epithelia are negative. Note membrane localization of stain in the tumor tissue, consistent with trans-membrane localization of EphB4. Representative QRT-PCR of RNA extracted from cancer specimens and adjacent BPH tissues (lower right).

To determine whether EphB4 is expressed in clinical prostate samples, tumor tissues and adjacent normal tissue from prostate cancer surgical specimens were examined. The histological distribution of EphB4 in the prostate specimens was determined by immunohistochemistry. Clearly, EphB4 expression is confined to the neoplastic epithelium (FIG. 28, top left), and is absent in stromal and normal prostate epithelium (FIG. 28, top right). In prostate tissue array, 24 of the 32 prostate cancers examined were positive. We found EphB4 mRNA is expressed both in the normal and tumor tissues of clinical samples by quantitative RT-PCR. However, tumor EphB4 mRNA levels were at least 3 times higher than in the normal in this case (FIG. 28, lower right).

C. p53 and PTEN Inhibited the Expression of EphB4 in PC3 Cells

Figure 29A:
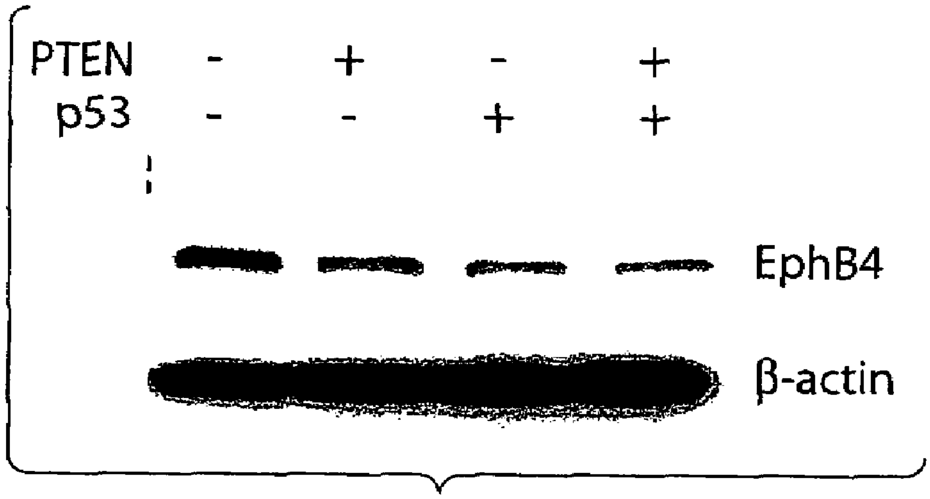
FIG. 29 shows downregulation of EphB4 in prostate cancer cells by tumor suppressors and RXR expression. A) PC3 cells were co-transfected with truncated CD4 and p53 or PTEN or vector only. 24 h later CD4-sorted cells were collected, lysed and analyzed sequentially by Western blot for the expression of EphB4 and β-actin, as a normalizer protein. B) Western blot as in (A) of various stable cell lines. LNCaP-FGF is a stable transfection clone of FGF-8, while CWR22R-RXR stably expresses the RXR receptor. BPH-1 was established from benign hypertrophic prostatic epithelium.

PC3 cells are known to lack PTEN expression (Davis, et al., 1994, Science. 266:816-819) and wild-type p53 function (Gale, et al., 1997, Cell Tissue Res. 290:227-241). We investigated whether the relatively high expression of EphB4 is related to p53 and/or PTEN by re-introducing wild-type p53 and/or PTEN into PC3 cells. To compensate for the transfection efficiency and the dilution effect, transfected cells were sorted for the cotransfected truncated CD4 marker. We found that the expression of EphB4 in PC3 cells was reduced by the re-introduction of either wild-type p53 or PTEN. The co-transfection of p53 and PTEN did not further inhibit the expression of EphB4 (FIG. 29A).

D. Retinoid X Receptor (RXR α) Regulates the Expression of EphB4

Figure 29B:
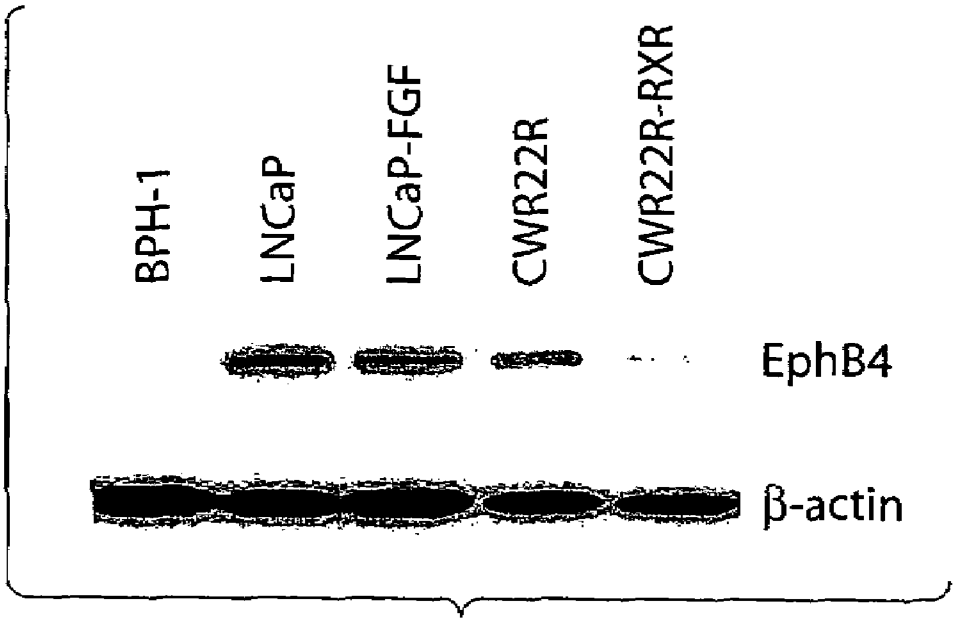

We previously found that RXRα was down-regulated in prostate cancer cell lines (Zhong, et al., 2003, Cancer Biol Ther. 2:179-184) and here we found EphB4 expression has the reverse expression pattern when we looked at "normal" prostate (MLC), prostate cancer (PC3), and metastatic prostate cancer (PC3M) (FIG. 27A), we considered whether RXRα regulates the expression of EphB4. To confirm the relationship, the expression of EphB4 was compared between CWR22R and CWR22R-RXRα, which constitutively expresses RXRα. We found a modest decrease in EphB4 expression in the RXRα overexpressing cell line, while FGF8 has no effect on EphB4 expression. Consistent with initial results, EphB4 was not found in "normal" benign prostate hypertrophic cell line BPH-1 (FIG. 29B).

Figure 30A:
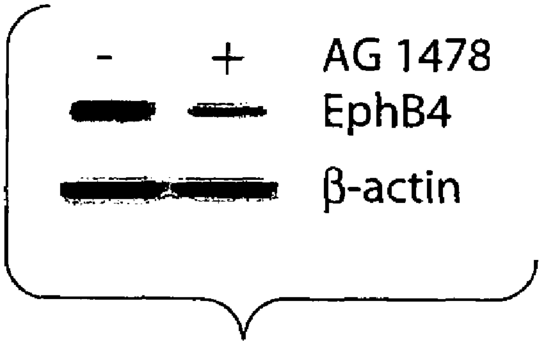
FIG. 30 shows downregulation of EphB4 in prostate cancer cells by EGFR and IGFR-1. A) Western blot of PC3 cells treated with or without EGFR specific inhibitor AG1478 (1 nM) for 36 hours. Decreased EphB4 signal is observed after AG 1478 treatment. The membrane was stripped and reprobed with β-actin, which was unaffected. B) Western Blot of triplicate samples of PC3 cells treated with or without IGFR-1 specific neutralizing antibody MAB391 (2 μg/ml; overnight). The membrane was sequentially probed with EphB4, IGFR-1 and β-actin antibodies. IGFR-1 signal shows the expected repression of signal with MAB391 treatment.
Figure 30B:
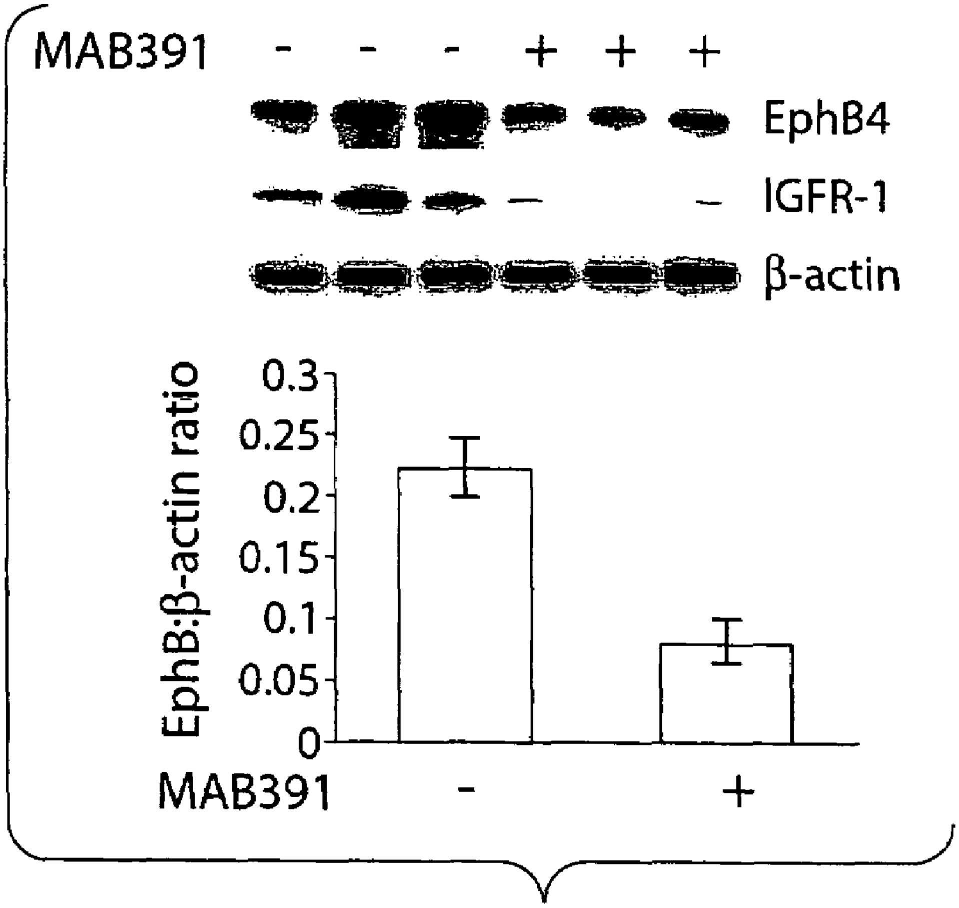

E. Growth Factor Signaling Pathway of EGFR and IGF-1R Regulates EphB4 Expression EGFR and IGF-1R have both been shown to have autocrine and paracrine action on PC3 cell growth. Because we found that EphB4 expression is higher in the more aggressive cell lines, we postulated that EphB4 expression might correlate with these pro-survival growth factors. We tested the relationship by independently blocking EGFR and IGF-1R signaling. EphB4 was down-regulated after blocking the EGFR signaling using EGFR kinase inhibitor AG 1478 (FIG. 30A) or upon blockade of the IGF-R signaling pathway using IGF-1R neutralizing antibody (FIG. 30B).

F. EphB4 siRNA and Antisense ODNs Inhibit PC3 Cell Viability

Figure 31A:
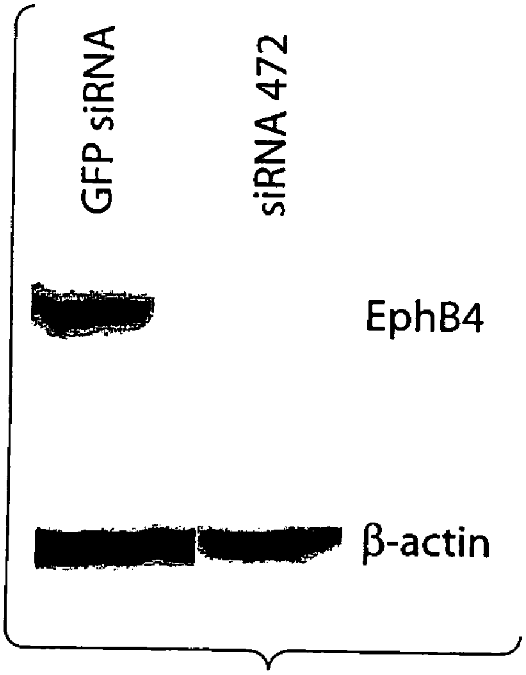
FIG. 31 shows effect of specific EphB4 AS-ODNs and siRNA on expression and prostate cell functions. A) 293 cells stably expressing full-length construct of EphB4 was used to evaluate the ability of siRNA 472 to inhibit EphB4 expression. Cells were transfected with 50 nM RNAi using Lipofectamine 2000. Western blot of cell lysates 40 h post transfection with control siRNA (green fluorescence protein; GFP siRNA) or EphB4 siRNA 472, probed with EphB4 monoclonal antibody, stripped and reprobed with β-actin monoclonal antibody. B) Effect of EphB4 AS-10 on expression in 293 transiently expressing full-length EphB4. Cells were exposed to AS-10 or sense ODN for 6 hours and analyzed by Western blot as in (A). C) 48 h viability assay of PC3 cells treated with siRNA as described in the Methods section. Shown is mean±s.e.m. of triplicate samples. D) 5-day viability assay of PC3 cells treated with ODNs as described in the Methods. Shown is mean±s.e.m. of triplicate samples. E) Scrape assay of migration of PC3 cells in the presence of 50 nM siRNAs transfected as in (A). Shown are photomicrographs of representative 20× fields taken immediately after the scrape was made in the monolayer (0 h) and after 20 h continued culture. A large number of cells have filled in the scrape after 20 h with control siRNA, but not with EphB4 siRNA 472. F) Shown is a similar assay for cells treated with AS-10 or sense ODN (both 10 μM). G) Matrigel invasion assay of PC3 cells transfected with siRNA or control siRNA as described in the methods. Cells migrating to the underside of the Matrigel coated insert in response to 5 mg/ml fibronectin in the lower chamber were fixed and stained with Giemsa. Shown are representative photomicrographs of control siRNA and siRNA 472 treated cells. Cell numbers were counted in 5 individual high-powered fields and the average±s.e.m. is shown in the graph (bottom right).
Figure 31B:
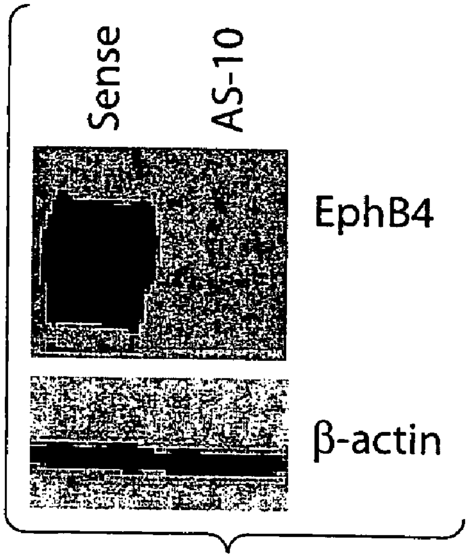
Figure 31C:
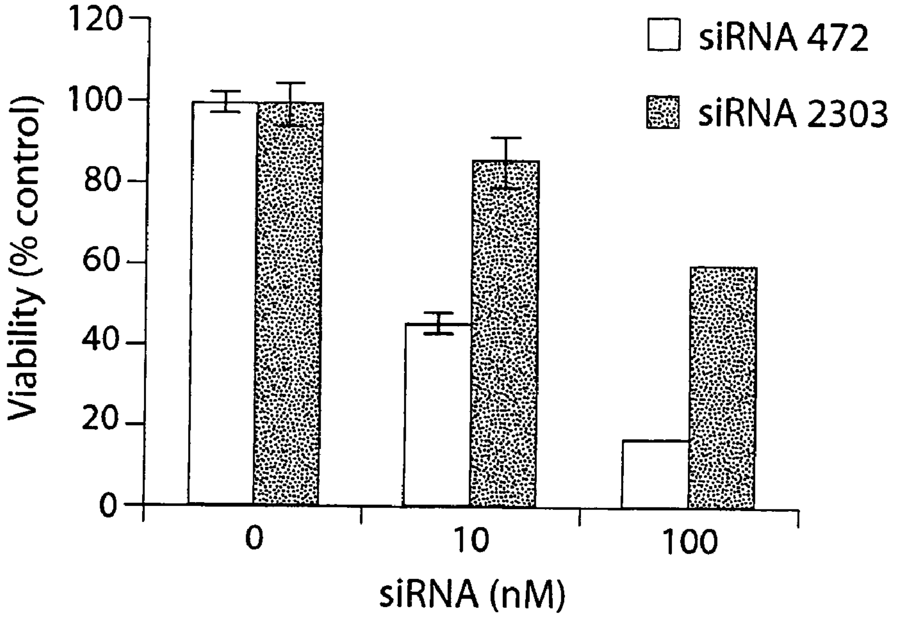
Figure 31D:
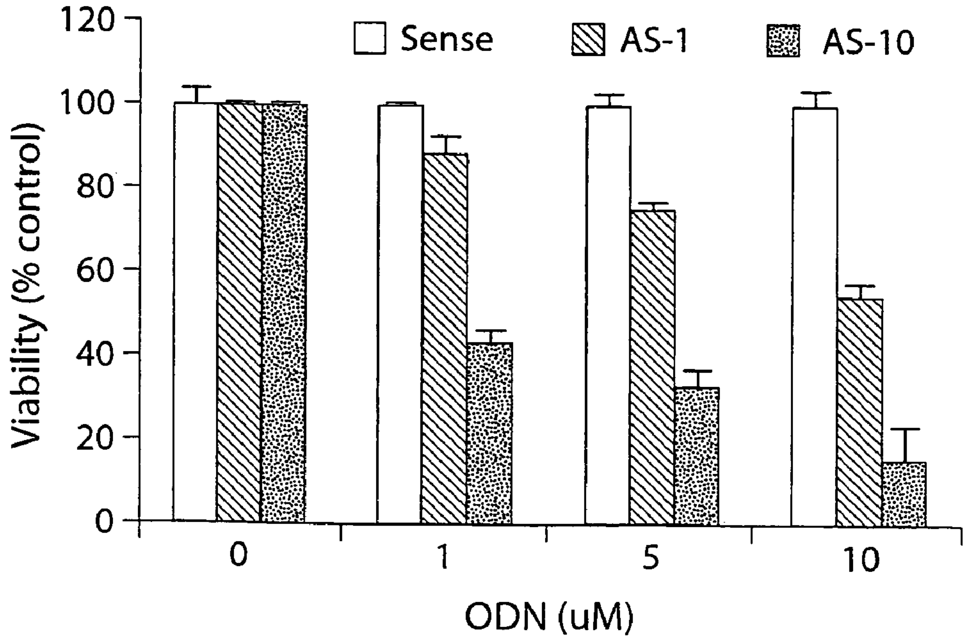

To define the significance of this EphB4 overexpression in our prostate cancer model, we concentrated our study on PC3 cells, which have a relatively high expression of EphB4. The two approaches to decreasing EphB4 expression were siRNA and AS-ODNs. A number of different phosphorothioate-modified AS-ODNs complementary to different segments of the EphB4 coding region were tested for specificity and efficacy of EphB4 inhibition. Using 293 cells transiently transfected with full-length EphB4 expression vector AS-10 was found to be the most effective (FIG. 31B). A Similar approach was applied to the selection of specific siRNA. EphB4 siRNA 472 effectively knocks down EphB4 protein expression (FIG. 31A). Both siRNA 472 and antisense AS-10 ODN reduced the viability of PC3 cells in a dose dependent manner (FIGS. 31C, D). Unrelated siRNA or sense oligonucleotide had no effect on viability.

G. EphB4 siRNA and Antisense ODNs Inhibit the Mobility of PC3 Cells

Figure 31E:
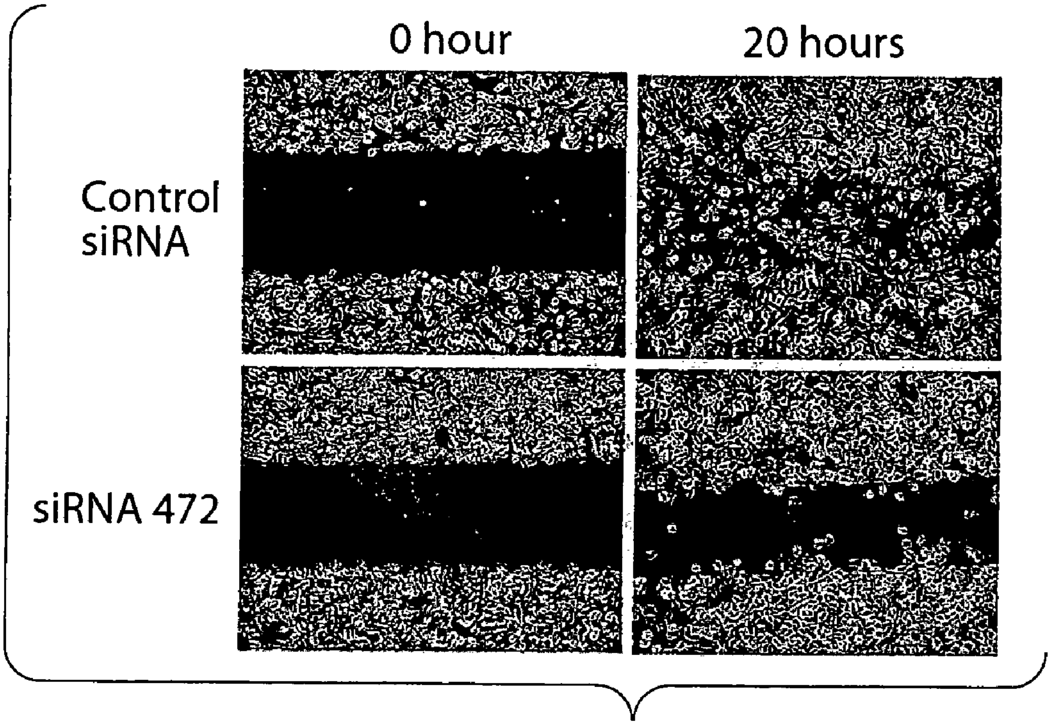
Figure 31F:
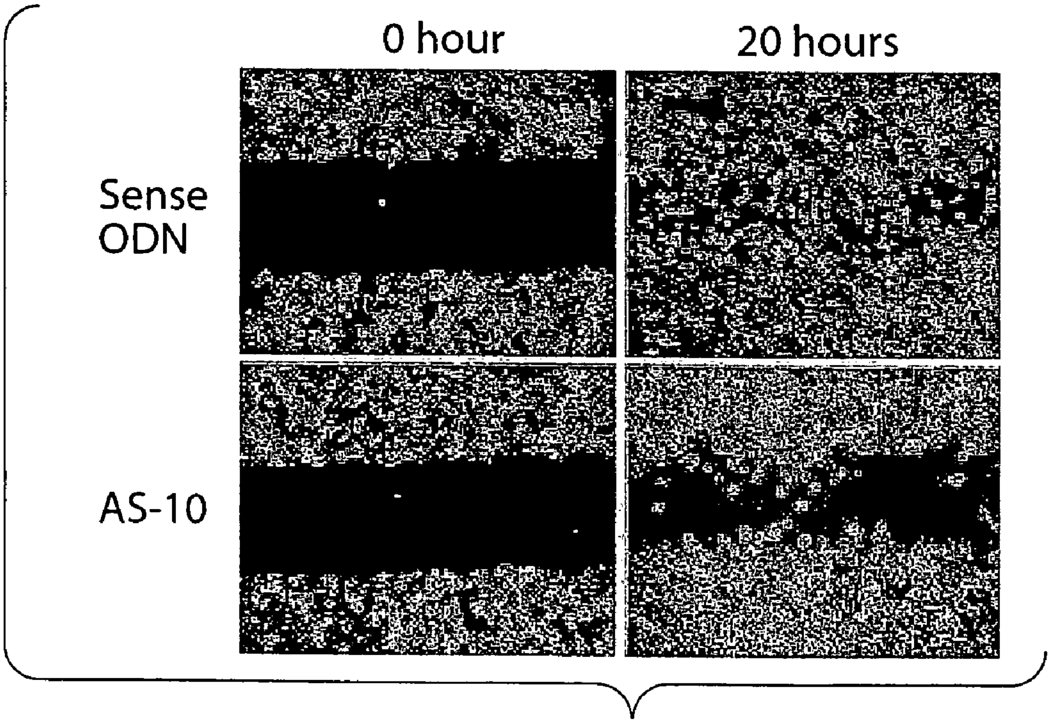
Figure 31G:
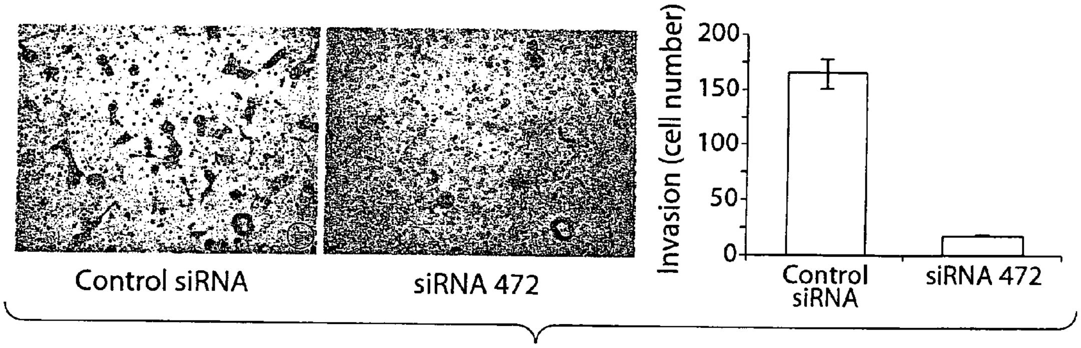

PC3 cells can grow aggressively locally and can form lymph node metastases when injected orthotopically into mice. In an effort to study the role of EphB4 on migration of PC3 cells in vitro, we performed a wound-healing assay. When a wound was introduced into a monolayer of PC3 cells, over the course of the next 20 hours cells progressively migrated into the cleared area. However, when cells were transfected with siRNA 472 and the wound was introduced, this migration was significantly inhibited (FIG. 31E). Pretreatment of PC3 cells with 10 μM EphB4 AS-10 for 12 hours generated the same effect (FIG. 31F). In addition, knock-down of EphB4 expression in PC3 cells with siRNA 472 severely reduced the ability of these cells to invade Matrigel as assessed by a double-chamber invasion assay (FIG. 31G), compared to the control siRNA.

H. EphB4 siRNA Induces Cell Cycle Arrest and Apoptosis in PC3 Cells

Figure 32A:
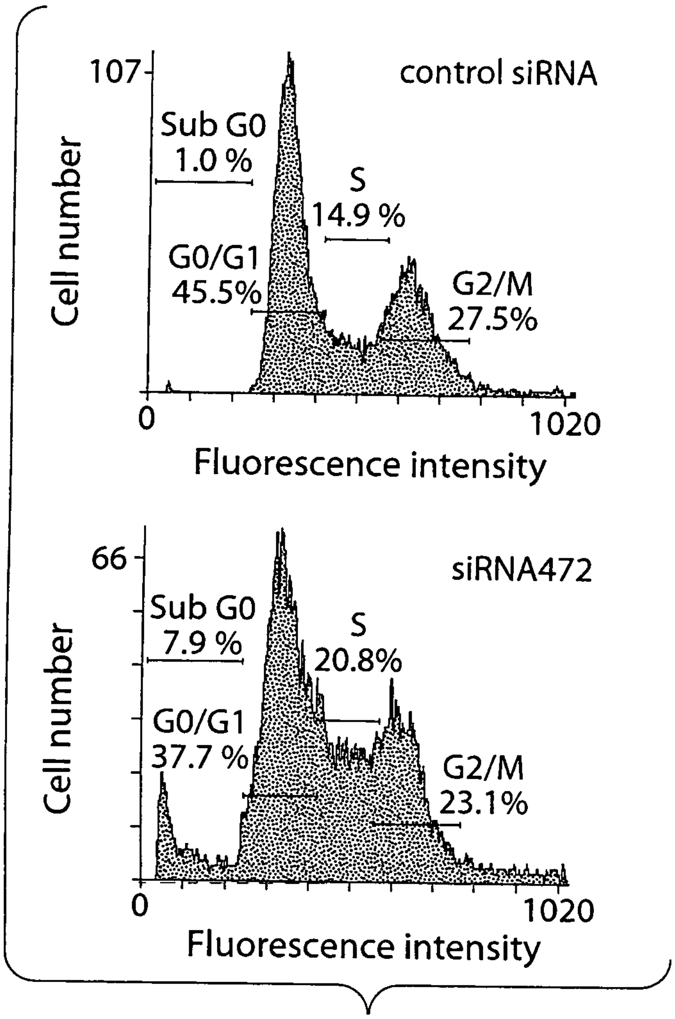
FIG. 32 shows effect of EphB4 siRNA 472 on cell cycle and apoptosis. A) PC3 cells transfected with siRNAs as indicated were analyzed 24 h post transfection for cell cycle status by flow cytometry as described in the Methods. Shown are the plots of cell number vs. propidium iodide fluorescence intensity. 7.9% of the cell population is apoptotic (in the Sub G0 peak) when treated with siRNA 472 compared to 1% with control siRNA. B) Apoptosis of PC3 cells detected by Cell Death Detection ELISA$^{plus}$ kit as described in the Methods. Absorbance at 405 nm increases in proportion to the amount of histone and DNA-POD in the nuclei-free cell fraction.
Figure 32B:
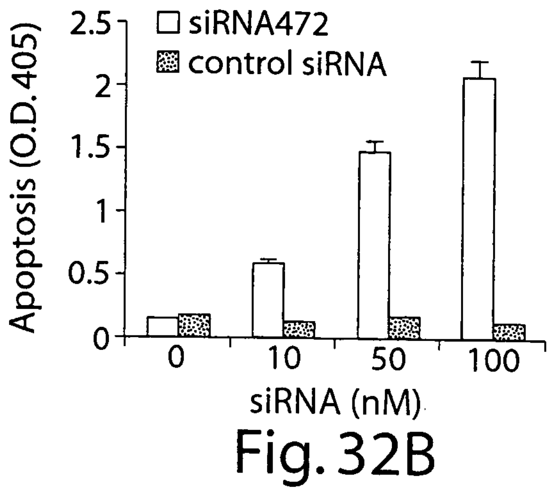

Since knock-down of EphB4 resulted in decreased cell viability (FIG. 31C) we sought to determine whether this was due to effects on the cell cycle. In comparison to control siRNA transfected cells, siRNA 472 resulted in an accumulation of cells in the sub G0 and S phase fractions compared to cells treated with control siRNA. The sub G0 fraction increased from 1% to 7.9%, and the S phase fraction from 14.9% to 20.8% in siRNA 472 treated cells compared to control siRNA treated cells (FIG. 32A). Cell cycle arrest at sub G0 and G2 is indicative of apoptosis. Apoptosis as a result of EphB4 knock-down was confirmed by ELISA assay. A dose-dependent increase in apoptosis was observed when PC3 cells were transfected with siRNA 472, but not with control siRNA (FIG. 32B). At 100 nM there was 15 times more apoptosis in siRNA 472 transfected than control siRNA transfected PC3 cells.

I. Materials and Methods

1) Reagents

Neutralizing IGF-1R antibody was from R&D Systems (Minneapolis Minn.). Anti-IGF-IR(β), -EGFR, -EphB4(C-16) were from Santa Cruz Biotech (Santa Cruz, Calif.). β-actin monoclonal antibody was purchased from Sigma Chemical Co. (St Louis, Mo.). Media and fetal bovine serum (FBS) were from Invitrogen (Carlsbad, Calif.). AG 1478(4-(3'-Chloroanilino)-6,7-dimethoxy-quinazoline) was from Calbiochem (San Diego, Calif.).

2) Antisense Oligodeoxynucleotides and EphB4 siRNAs

EphB4 specific antisense phosphorothioate-modified oligodeoxynucleotide (ODN) and sense ODN were synthesized and purified by Qiagen (Alameda Calif.). The sequences are: Sense, 5'-TCC-TGC-AAG-GAG-ACC-TTC-AC-3' (SEQ ID NO: 19); AS1: 5'-GTG-CAG-GGA-TAG-CAG-GGC-CAT-3' (SEQ ID NO: 20); AS10: 5'-ATG-GAG-GCC-TCG-CTC- AGA-AA-3'(SEQ ID NO: 21). siRNAs were synthesized at the USC/Norris Comprehensive Cancer Center Microchemical Core laboratory. Sequences of EphB4 siRNAs are siRNA 472 5'-GGU-GAA-UGU-CAA-GAC-GCU-GUU-3' (SEQ ID NO: 22) and siRNA 2303 5'-cuc-uuc-cga-ucc-cac-cua-cuu-3' (SEQ ID NO: 23). Negative control siRNA to scrambled GAPDH was from Ambion (Austin, Tex.).

3) Cell Lines and Culture

The prostate cancer cell lines, PC3, PC3M, DU145, ALVA31, LAPC-4, LNCaP, CWR22R and adult human normal prostate epithelial cell line MLC SV40, and BPH-1 were obtained and cultured as described previously (7). Stable cell line CWR22R-RXR, LNCaP-FGF8 were established and cultured as described before (7, 33).

4) Generation of EphB4 Monoclonal Antibody

The extracellular domain (ECD) of EphB4 was cloned into pGEX-4T-1 to generate GST-fused ECD (GST-ECD). EphB4ECD expressed as a GST fusion protein in BL21 *E. coli* was purified by affinity chromatography and the GST domain was cleaved by thrombin. Monoclonal antibody was generated and the sensitivity and specificity of the antibody was reconfirmed by Western blot with whole cell lysate of 293 cells stably transfected with EphB4.

5) One-Step RT-PCR and Quantitative RT-PCR

Total RNA was extracted using RNA STAT-60 (Tel-Test, Inc. Friendswood Tex.) from prostate cancer specimens and adjacent normal specimens. For quantitative RT-PCR first strand cDNA was synthesized from 5 μg of total RNA using SuperScript III (Invitrogen, Carlsbad Calif.). Quantitative RT-PCR was performed on the Stratagene MX3000P system (Stratagene, La Jolla Calif.) using SYBR Green I Brilliant Mastermix (Stragene) according to the manufacture's instructions. Optimized reactions for EphB4 and β-actin (used as the normalizer gene) were 150 nM each of the forward primer (β-actin, 5'-GGA-CCT-GAC-TGA-CTA-CCT-A-3' (SEQ ID NO: 24); EphB4, 5'-AAG-GAG-ACC-TTC-ACC-GTC-TT-3'(SEQ ID NO: 25)) and reverse primer (β-actin 5'-TTG-AAG-GTA-GTT-TCG-TGG-AT-3'(SEQ ID NO: 26); EphB4, 5'-TCG-AGT-CAG-GTT-CAC-AGT-CA-3' (SEQ ID NO: 27')) with DNA denaturation/activation of polymerase at 95° C. for 10 mm followed by 40 cycles of 95° C. for 30s, 60° C. for 1 mm, 72° C. for 1 min. The specificity of the gene-specific amplification was confirmed by the presence of a single dissociation peak. All reactions were performed in triplicate with RT and no template negative controls.

6) Immunohistochemistry

OCT-embedded tissues were sectioned at 5 μm and fixed in phosphate-buffered 4% paraformaldehyde. Sections were washed for 3×5 min in PBS and endogenous peroxidase was blocked by incubation in 0.3% $H_2O_2$ in PBS for 10 min at room temperature. Sections were incubated with Eph4 (C-16) antibody (1:50) for 1 h at room temperature followed by three washes in PBS and incubation with donkey anti-goat secondary antibody (Santa Cruz Biotech.) for 1 h at room temperature. After three washes in PBS, peroxidase activity was localized by incubation in DAB substrate solution (Vector Laboratories, Inc. Burlingame Calif.) for 10 min at room temperature. Sections were counterstained with Hematoxylin for 20 s, dehydrated and mounted. Negative control for staining was substitution of normal goat serum for primary antibody. Immunohistochemical staining on prostate array (BioMeda, Foster City, Calif.) was done using goat ABC Staining System (Santa Cruz Biotech.) according to the manufacturer's instructions.

7) Western Blot

Whole cell lysates were prepared using Cell Lysis Buffer (GeneHunter, Basgvukke Tenn.) supplemented with protease inhibitor cocktail (Pierce, Rockford Ill.), unless otherwise noted. Total protein was determined using the DC reagent system (Bio-Rad, Hercules Calif.). Typically, 20 μg whole cell lysate was run on 4-20% Tris-Glycine gradient gel. The samples were electro-transferred to PVDF membrane and the non-specific binding was blocked in TBST buffer (0.5 mM Tris-HCl, 45 mM NaCl, 0.05% Tween-20, pH 7.4) containing 5% non-fat milk. Membranes were first probed with primary antibody overnight, stripped with Restore™ Western Blot stripping buffer (Pierce, Rockford Ill.) and reprobed with β-actin to confirm equivalent loading and transfer of protein. Signal was detected using SuperSignal West Femto Maximum Sensitivity Substrate (Pierce).

8) Phosphorylation Analysis

Cells growing in 60 mm dishes were either serum starved (1% FBS supplemented RPMI 1640, 24 hours) or cultured in normal conditions (10% FBS) and then treated with or without 1 μg/ml mouse ephrin B2/$F_c$ for 10 min to activate EphB4 receptor Cleared cell lysates were incubated with EphB4 monoclonal antibody overnight at 4° C. Antigen-antibody complex was immunoprecipitated by the addition of 100 μl of Protein G-Sepharose in 20 mM sodium phosphate, pH 7.0 with incubation overnight at 4° C. Immunoprecipitates were analyzed by Western blot with pTyr specific antibody (Upstate, clone 4G 10) at 1:1000 dilution followed by incubation with protein G-HRP (Bio-Rad) at 1:5000 dilution. To monitor immunoprecipitation efficiency, a duplicate membrane was probed with EphB4 specific monoclonal antibody.

9) Transient Transfection and Sorting of Transfected Cells

PC3 cells were cotransfected with pMACS 4.1 coding for CD4 and wild type p53 (pC53-SN3) or PTEN vector or both using Lipofectamine 2000 (Invitrogen) according to the manufacturer's instructions. The molar ratio of CD4 to p53 or PTEN or vector was 1:3 and total plasmid was 24 μg for a 10 $cm^2$ dish of 90% confluent cells using 60 μl of Lipofectamine 2000. 24 hours after transfection, a single cell suspension was made and sorted using truncated CD4 as a surface marker according to the manufacturer's protocol (Miltenyi Biotec, Germany). Sorted cells were lysed in 1×SDS sampling buffer and analyzed by Western blot.

10) Study of IGF and EGF Signaling Pathway on the Expression of EphB4

PC3 cells were seeded into 6-well plates and cultured until 80% confluent and treated with 2 μg/ml neutralizing IGF-1R monoclonal antibody, MAB391 (Hailey, et al., 2002, Mol Cancer Ther. 1:1349-1353), or with 1 nM AG 1478, a strong EGFR inhibitor (Liu, et al., 1999, J Cell Sci. 112 (Pt 14): 2409-2417) for 24 h. Crude cell lysates were analyzed by Western blot. Band density was quantified with the Bio-Rad QuantityOne System software.

11) Cell Viability Assay

PC3 cells were seeded on 48-well plates at a density of approximately $1\times10^4$ cells/well in a total volume of 200 ml. Media was changed after the cells were attached and the cells were treated with various concentrations (1-10 μM) of EphB4 antisense ODN or sense ODN as control. After three days media was changed and fresh ODNs added. Following a further 48 h incubation, cell viability was assessed by MTT as described previously (36). EphB4 siRNAs (10-100 nM) were introduced into $2\times10^4$ PC3 cells/well of a 48-well plate using 2 μl of Lipofectamine™ 2000 according to the manufacturer's instructions. 4 h post-transfection the cells were returned to growth media (RPMI 1640 supplemented with 10% FBS). Viability was assayed by MTT 48 h following transfection.

12) Wound Healing Migration Assay

PC3 cells were seeded into 6-well plates and cultured until confluent. 10 μM AS-10 or sense ODN as control were introduced to the wells as described for the viability assay 12 hours before wounding the monolayer by scraping it with a sterile pipette tip. Medium was changed to RPMI 1640 supplemented with 5% FBS and fresh ODNs. Confluent cultures transfected with 50 nM siRNA 472 or GAPDH negative control siRNA 12 hours prior to wounding were also examined. The healing process was examined dynamically and recorded with a Nikon Coolpix 5000 digital camera with microscope adapter.

13) Invasion Assay

PC3 cells were transfected with siRNA 472 or control siRNA using Lipofectamine™ 2000 and 6 hours later 0.5×105 cells were transferred into 8 μm Matrigel-precoated inserts (BD Bioscience, Palo Alto, Calif.). The inserts were placed in companion wells containing RPMI supplemented with 5% FBS and 5 μg/ml fibronectin as a chemoattractant. Following 22 h incubation the inserts were removed and the noninvading cells on the upper surface were removed by with a cotton swab. The cells on the lower surface of the membrane were fixed in 100% methanol for 15 min, air dried and stained with Giemsa stain for 2 min. The cells were counted in five individual high-powered fields for each membrane under a light microscope. Assays were performed in triplicate for each treatment group.

14) Cell Cycle Analysis

80% confluent cultures of PC3 cells in 6-well plates were transfected with siRNA472 (100 nM) using Lipofectamine™ 2000. 24 hours after transfection, cells were trypsinized, washed in PBS and incubated for 1 h at 4° C. in 1 ml of hypotonic solution containing 50 μg/ml propidium iodide, 0.1% sodium citrate, 0.1 Triton X-100 and 20 μg/ml Dnase-free RnaseA. Cells were analyzed in linear mode at the USC Flow cytometry facility. Results were expressed as percentages of elements detected in the different phases of the cell cycle, namely Sub G0 peak (apoptosis), G0/G1 (no DNA synthesis), S (active DNA systhesis), G2 (premitosis) and M (mitosis).

15) Apoptosis ELISA

Apoptosis was studied using the Cell Death Detection ELISAplus Kit (Roche, Piscataway, N.J.) according to the manufacturer's instructions. Briefly, PC3 80% confluent cultures in 24-well plates were transfected using Lipofectamine™ 2000 with various concentrations (0-100 nM) of siRNA 472 or 100 nM control siRNA. 16 hours later, cells were detached and $1\times10^4$ cells were incubated in 200 μl lysis buffer. Nuclei were pelleted by centrifugation and 20 μl of supernatant containing the mono- or oligonucleosomes was taken for ELISA analysis. Briefly, the supernatant was incubated with anti-histone-biotin and anti-DNA-POD in streptavidin-coated 96-well plate for 2 hours at room temperature. The color was developed with ABST and absorbance at 405 nm was read in a microplate reader (Molecular Devices, Sunnyvale, Calif.).

Example 4

Expression of EPHB4 in Mesothelioma: a Candidate Target for Therapy

Malignant mesothelioma (MM) is a rare neoplasm that most often arises from the pleural and peritoneal cavity serous surface. The pleural cavity is by far the most frequent site affected (>90%), followed by the peritoneum (6-10%) (Carbone et al., 2002, Semin Oncol. 29:2-17). There is a strong association with asbestos exposure, about 80% of malignant mesothelioma cases occur in individuals who have ingested or inhaled asbestos. This tumor is particularly resistant to the current therapies and, up to now, the prognosis of these patients is dramatically poor (Lee et al., 2000, Curr Opin Pulm Med. 6:267-74).

Several clinical problems regarding the diagnosis and treatment of malignant mesothelioma remain unsolved. Making a diagnosis of mesothelioma from pleural or abdominal fluid is notoriously difficult and often requires a thoracoscopic or laproscopic or open biopsy and Immunohistochemical staining for certain markers such as meosthelin expressed preferentially in this tumor. Until now, no intervention has proven to be curative, despite aggressive chemotherapeutic regimens and prolonged radiotherapy. The median survival in most cases is only 12-18 months after diagnosis.

In order to identify new diagnostic markers and targets to be used for novel diagnostic and therapeutic approaches, we assessed the expression of EPHB4 and its ligand EphrinB2 in mesothelioma cell lines and clinical samples.

A. EPHB4 and EphrinB2 is Expressed in Mesothelioma Cell Lines

Figure 33A:
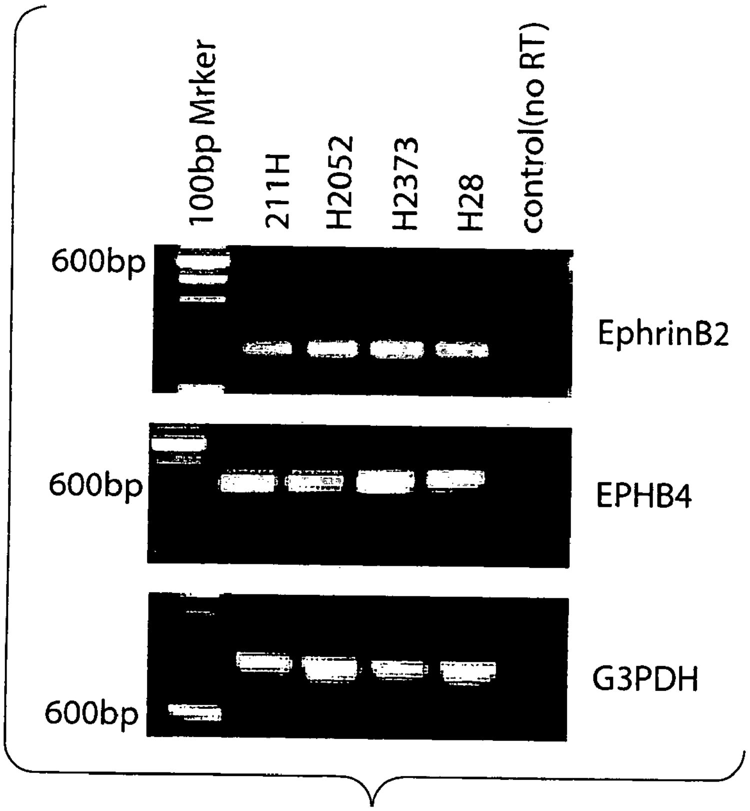
Figure 33B:
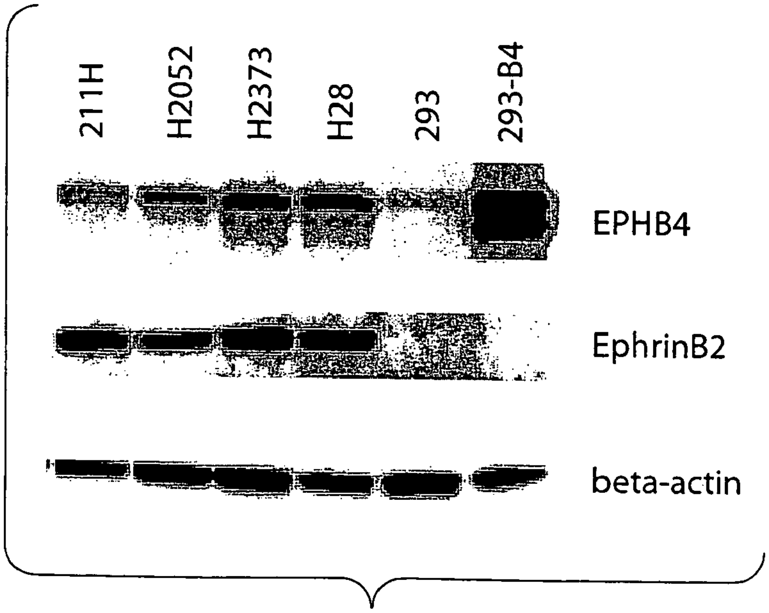

The expression of Ephrin B2 and EphB4 in malignant mesothelioma cell lines was determined at the RNA and protein level by a variety of methods. RT-PCR showed that all of the four cell lines express EphrinB2 and EPHB4 (FIG. 33A). Protein expression was determined by Western blot in these cell lines. Specific bands for EphB4 were seen at 120 kD. In addition, Ephrin B2 was detected in all cell lines tested as a 37 kD band on Western blot (FIG. 33B). No specific band for Ephrin B2 was observed in 293 human embryonic kidney cells, which were included as a negative control.

To confirm the presence of EphB4 transcription in mesothelioma cells, in situ hybridization was carried out on NCI H28 cell lines cultured on chamber slides. Specific signal for EphB4 was detected using antisense probe Ephrin B2 transcripts were also detected in the same cell line. Sense probes for both EphB4 and Ephrin B2 served as negative controls and did not hybridize to the cells (FIG. 34). Expression of EphB4 and Ephrin B2 proteins was confirmed in the cell lines by immunofluorescence analysis (FIG. 35). Three cell lines showed strong expression of EphB4, whereas expression of Ephrin B2 was present in H28 and H2052, and weakly detectable in H2373.

B. Evidence of Expression of EPHB4 and EphrinB2 in Clinical Samples

Tumor cells cultured from the pleural effusion of a patient diagnosed with pleural malignant mesothelioma were isolated and showed positive staining for both EphB4 and Ephrin B2 at passage 1 (FIG. 35, bottom row). These results confirm co-expression of EphB4 and Ephrin B2 in mesothelioma cell lines. To determine whether these results seen in tumor cell lines were a real reflection of expression in the disease state, tumor biopsy samples were subjected to immunohistochemical staining for EphB4 and Ephrin B2. Antibodies to both proteins revealed positive stain in the tumor cells. Representative data is shown in FIG. 36.

C. EPHB4 is Involved in the Cell Growth and Migration of Mesothelioma

Figure 37A:
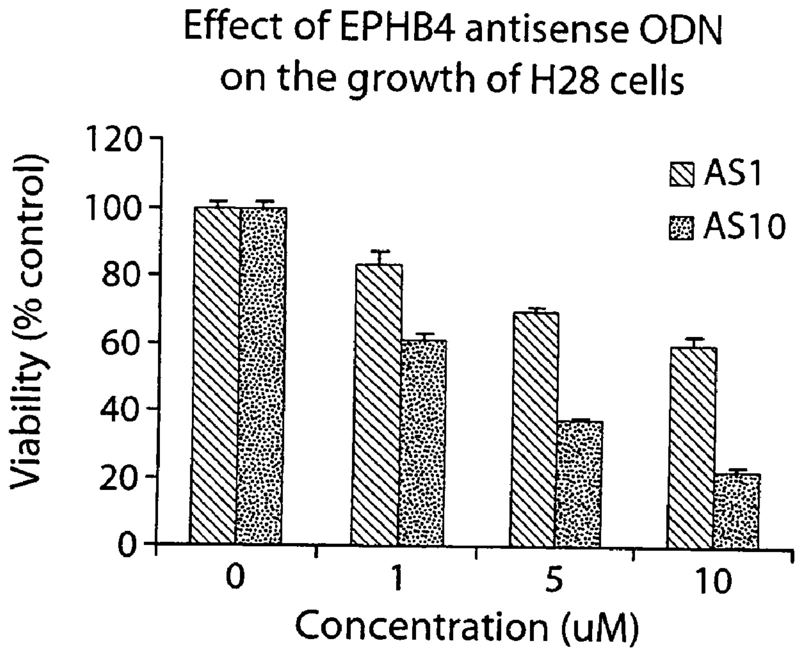
Figure 37B:
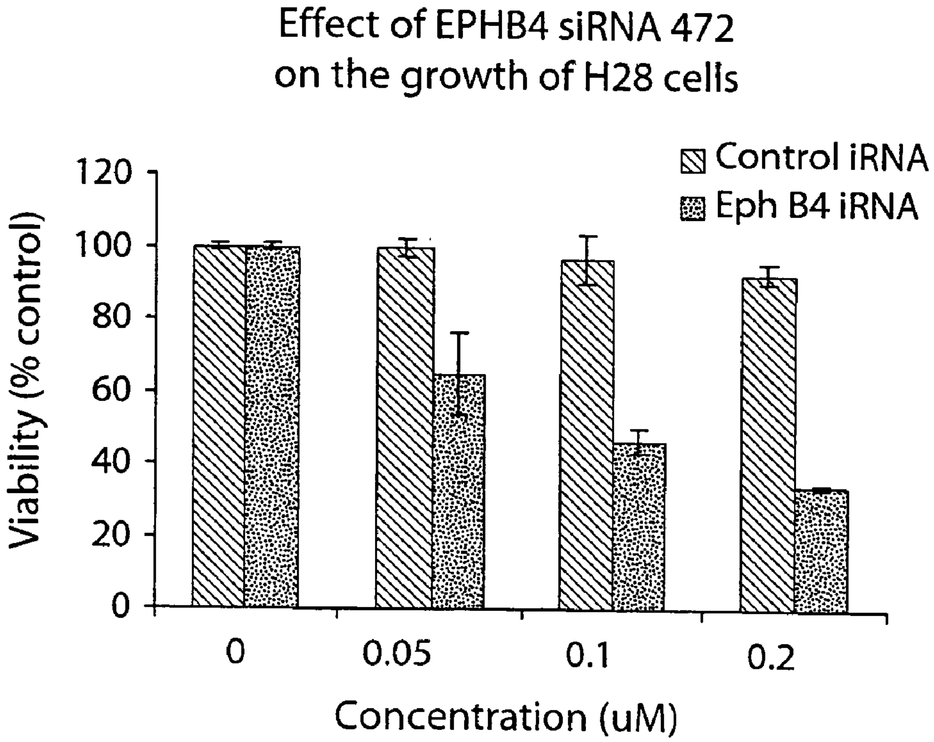

The role of EphB4 in cell proliferation was tested using EPHB4 specific antisepses oligonucleotides and siRNA. The treatment of cultured H28 with EPHB4 antisense reduced cell viability. One of the most active inhibitor of EphB4 expression is EPHB4AS-10 (FIG. 37A). Transfection of EPHB4 siRNA 472 generated the same effect (FIG. 37B).

Figure 38A:
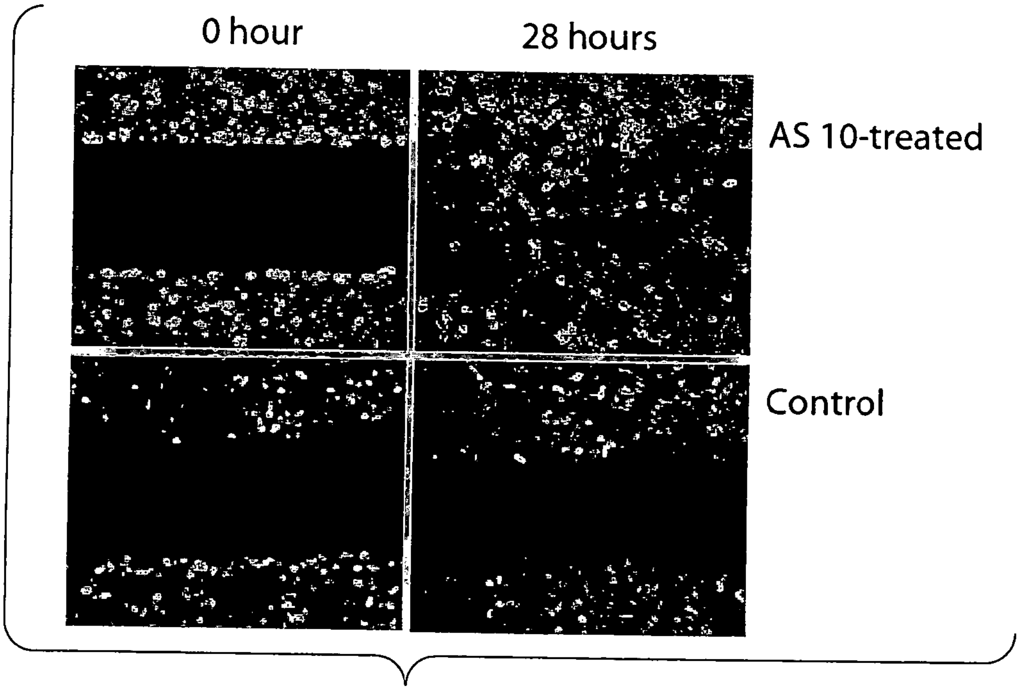
Figure 38B:
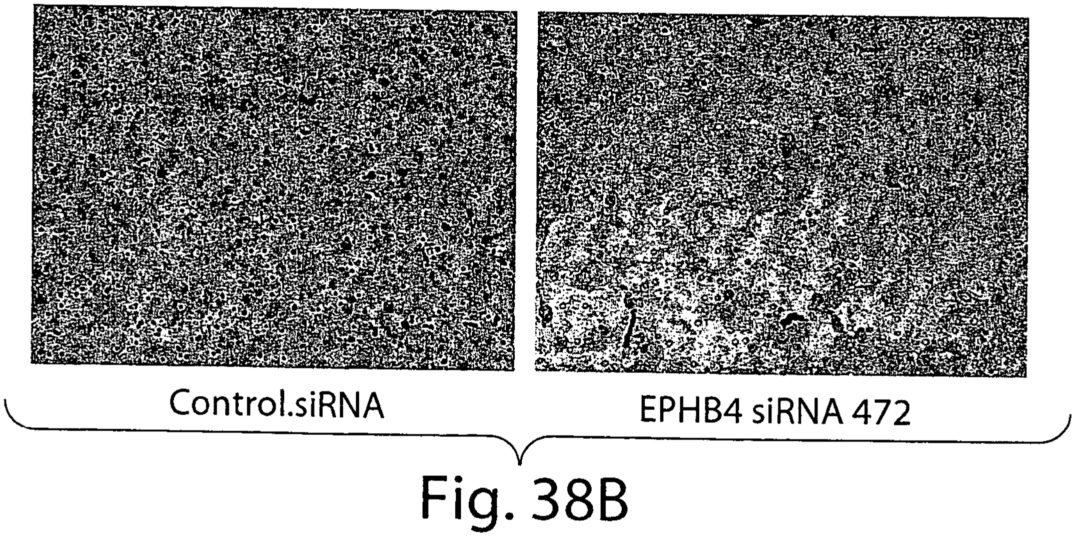

MM is a locally advancing disease with frequent extension and growth into adjacent vital structures such as the chest wall, heart, and esophagus. In an effort to study this process in vitro, we perform wound healing assay using previously described techniques (3:36). When a wound was introduced into sub confluent H28 cells, over the course of the next 28 hours cells would progressively migrate into the area of the wound. However, when cells were pretreated with EPHB4AS-10 for 24 hours, and the wound was introduced, this migration was virtually completely prevented (FIG. 38A). The migration study with Boyden Chamber assay with EPHB4 siRNA showed that cell migration was greatly inhibited with the inhibition of EPHB4 expression (FIG. 38B).

D. Materials and Methods

1) Cell Lines and Reagents

NCI H28, NCI H2052, NCI H2373, MSTO 211H mesothelioma cell lines and 293 human embryonic kidney cells were obtained from the ATCC (Manassas, Va.). Cells were maintained in RPMI 1640 media supplemented with 10% heat-inactivated fetal bovine serum (FBS; Life Technologies, Gaithersburg, Md.) and antibiotics. Primary cells were obtained from pleural effusion of patients with mesothelioma. A large number of EPHB4 phosphorothioate modified antisense oligonucleotides were synthesized. Similarly a number of EphB4 specific siRNAs were generated. Monoclonal antibody produced against EPHB4 was used for western blot. Polyclonal antibody against EphrinB2 and EPHB4 (C-16) (for immunohistochemical staining) was from Santa Cruz.

2) RT-PCR

Total RNA was reversed transcribed by use of random hexamers (Invitrogen). Primers for EphB4 and EphrinB2 were designed with Primer 3 software. The sequences for all primers are as follows: EPHB4 forward primer and EPHB4 reverse primer (see, e.g., in Example 2); EphrinB2 forward primer and EphrinB2 reverse primer (see, e.g., in Example 6); G3PDH forward primer, 5'-GGAGCCAAAAGGGTCATCAT-3'(SEQ ID NO: 28'); G3PDH reverse primer, 5'-GGCATTGCTGCAAAGAAAGAG-3' (SEQ ID NO: 29'); Clonetics kit was used for PCR. PCRs were performed with the ABI PCR System 2700 (Applied Biosystem). The PCR conditions were 95° C. for 5 min, followed by 35 cycles of 95° C. for 30 seconds, 60° C. for 30 seconds and 72° C. for 1 min.

3) Preparation of Digoxigenin-Labeled RNA Probes

Ephrin-B2 and EphB4 PCR products were cloned using the pGEM-T Easy System (Promega, Madison Wis.) according to the manufacturer's description. The primers and PCR products were 5'-tccgtgtggaagtactgctg-3' (SEQ ID NO: 30) (forward), 5'-tctggtttggcacagttgag-3' (SEQ ID NO: 31) (reverse), for ephrin-B2 that yielded a 296-bp product and 5'-ctttggaagagaccctgctg-3' (SEQ ID NO: 32) (forward), 5'-agacggtgaaggtctccttg-3' (SEQ ID NO: 33), for EphB4 that yielded a 297-bp product. The authenticity and insert orientation were confirmed by DNA sequencing.

The pGEM-T Easy plasmids containing the PCR product of the human ephrin-B2 or EphB4 gene were linearized with Spe I or Nco I. Antisense or sense digoxigenin (DIG)-labeled RNA probes were transcribed from T7 or SP6 promoters by run-off transcription using a DIG RNA labeling kit (Roche, Indianapolis Ind.). RNA probes were quantitated by spot assay as described in the DIG RNA labeling kit instructions.

4) In Situ Hybridization

Cells were cultured in Labtech II 4-well chamber slides (Nalge Nunc International, Naperville, Ill.). Cells were washed in PBS (37° C.), then fixed for 30 min at 25° C. in a solution of 4% (w/v) formaldehyde, 5% (v/v) acetic acid, and 0.9% (w/v) NaCl. After fixation, slides were rinsed with PBS and stored in 70% ethanol at 4° C. until further use. Before in situ hybridization, cells were dehydrated, washed in 100% xylene to remove residual lipid and then rehydrated, finally in PBS. Cells were permeabilized by incubating at 37° C. with 0.1% (w/v) pepsin in 0.1 N HCl for 20 min and post-fixed in 1% formaldehyde for 10 min. Prehybridization was performed for 30 min at 37° C. in a solution of 4×SSC containing 50%(v/v) deionized formamide. Slides were hybridized overnight at 42° C. with 25 ng antisense or sense RNA probes in 40% deionized formamide, 10% dextran sulfate, 1× Denhardt's solution, 4×SSC, 10 mM DTT, 1 mg/ml yeast t-RNA and 1 mg/ml denatured and sheared salmon sperm DNA in a total volume of 40 μl. Slides were then washed at 37° C. as follows: 2×15 min with 2×SSC, 2×15 min with 1×SSC, 2×15 min with 0.5×SSC and 2×30 min with 0.2×SSC. Hybridization signal was detected using alkaline-phosphatase-conjugated anti-DIG antibodies (Roche) according to the manufacturer's instructions. Color development was stopped by two washes in 0.1 M Tris-HCl, 1 mM EDTA, pH 8.0 for 10 min. Cells were visualized by counterstaining of nucleic acids with Nuclear Fast Red (Vector Laboratories, Burlingame, Calif.) and the slides were mounted with IMMU-MOUNT (Shandon, Astmoor UK).

5) Western Blot

Crude cell lysates were prepared by incubation in cell lysis buffer (10 mM Tris, pH 7.5, 1 mM EDTA, 150 mM NaCl, 1% Triton X-100, 1 mM DTT, 10% glycerol). Lysates were cleared by centrifugation at 10,000×g for 10 min. Total protein was determined by Bradford assay (Bio-Rad). Samples (20 μg protein) were fractionated on a 4-20% Tris-glycine polyacrylamide gel and transferred to polyvinylidene difluoride (PVDT) membrane (Bio-Rad) by electroblotting. Membranes were blocked with 5% non-fat milk prior to incubation with antibody to EphB4 (1:5000 dilution) at 4° C., for 16 h. Secondary antibody (1:100,000 dilution) conjugated with horseradish peroxidase was applied for 1 h at 25° C. The membranes were developed using the SuperSignal West Femto Maximum sensitivity chemiluminescent substrate (Pierce, Rockford, Ill.) according to the manufacturer's instructions.

6) Immunohistochemistry

Formalin-fixed tissue sections were deparaffinized and incubated with 10% goat serum at −70° C. for 10 minutes and incubated with the primary rabbit antibodies against either Ephrin B2 or EphB4 (Santa Cruz Biotechnologies; 1:100) at 4° C. overnight. Isotype-specific rabbit IgG was used as control. The immunoreactivity for these receptors was revealed using an avidin-biotin kit from Vector Laboratories. Peroxidase activity was revealed by the diaminobenzidine (Sigma) cytochemical reaction. The slides were then counterstained with H&E.

7) Immunofluorescence Studies

Cells were cultured on Labtech II 4-well chamber slides and fixed in 4% paraformaldehyde in Dulbecco's phosphate buffered saline pH 7.4 (PBS) for 30 min. The slides were rinsed twice in PBS and preincubated with blocking buffer (0.2% Triton-X100, 1% BSA in PBS) for 20 min. The slides were then incubated with antibodies to EphB4 or ephrin B2 (1:100 dilution in PBS) in blocking buffer at 4° C. for 16 hr. After washing three times, the slides were incubated with the appropriate fluorescein-conjugated secondary antibodies (Sigma-Aldrich, St. Louis, Mo.). Nuclei were counterstained with 4',6-diamidino-2-phenylindole dihydrochloride hydrate (DAPI), washed extensively with PBS and mounted with Vectasheild antifade mounting solution (Vector Laboratories). Images were obtained using an Olympus AX70 fluorescence microscope and Spot v2.2.2 (Diagnostic Instruments Inc., Sterling Heights, Mich.) digital imaging system.

8) Cell Viability Assay

Cells were seeded at a density of $5\times10^3$ per well in 48-well plates on day 0 in appropriate growth media containing 2% fetal calf serum (FCS). On the following day, the media was changed and cells were treated with various concentrations (1-10 μM) of EphB4 Antisense. On day 4, viability was assessed using 3-(4,5-dimethylthiazol-2-yl)-2,5-diphenyltetrazolium bromide (MTT) at a final concentration of 0.5 mg/ml. Cells were incubated for 2 hr, medium was aspirated, and the cells were dissolved in acidic isopropanol (90% isopropanol, 0.5% SDS and 40 mM HCl). Optical density was read in an ELISA reader at 490 nm using isopropanol as blank (Molecular Devices, Calif.).

9) Cell Migration

In vitro wound healing assay was adopted. Briefly, cells were seeded onto 6-cm plates in full culture media for 24 hours, and then switched to medium containing 5% FBS. EPHB4 antisense 10 (10 μM) was also added to treated well. 24 hours later, wounds were made using the tip of a p-200 pipette man; a line was drawn through the middle of the plates. The plate was photographed at 0, 12, 24 hours. The experiment was repeated three times.

Example 5

EphB4 is Expressed in Squamous Cell Carcinoma of the Head and Neck: Regulation by Epidermal Growth Factor Signaling Pathway and Growth Advantage Squamous cell carcinoma of the head and neck (HNSCC) is the sixth most frequent cancer worldwide, with estimated 900,000 cases diagnosed each year. It comprises almost 50% of all malignancies in some developing nations. In the United States, 50,000 new cases and 8,000 deaths are reported each year. Tobacco carcinogens are believed to be the primary etiologic agents of the disease, with alcohol consumption, age, gender, and ethnic background as contributing factors.

The differences between normal epithelium of the upper aerodigestive tract and cancer cells arising from that tissue are the result of mutations in specific genes and alteration of their expression. These genes control DNA repair, proliferation, immortalization, apoptosis, invasion, and angiogenesis. For head and neck cancer, alterations of three signaling pathways occur with sufficient frequency and produce such dramatic phenotypic changes as to be considered the critical transforming events of the disease. These changes include mutation of the p53 tumor suppressor, overexpression of epidermal growth factor receptor (EGFR), and inactivation of the cyclin dependent kinase inhibitor p16. Other changes such as Rb mutation, ras activation, cyclin D amplification, and myc overexpression are less frequent in HNSCC.

Although high expression of EphB4 has been reported in hematologic malignancies, breast carcinoma, endometrial carcinoma, and colon carcinoma, there is limited data on the protein levels of EphB4, and complete lack of data on the biological significance of this protein in tumor biology such as HNSCC.

A. HNSCC Tumors Express EphB4

Figure 39A:
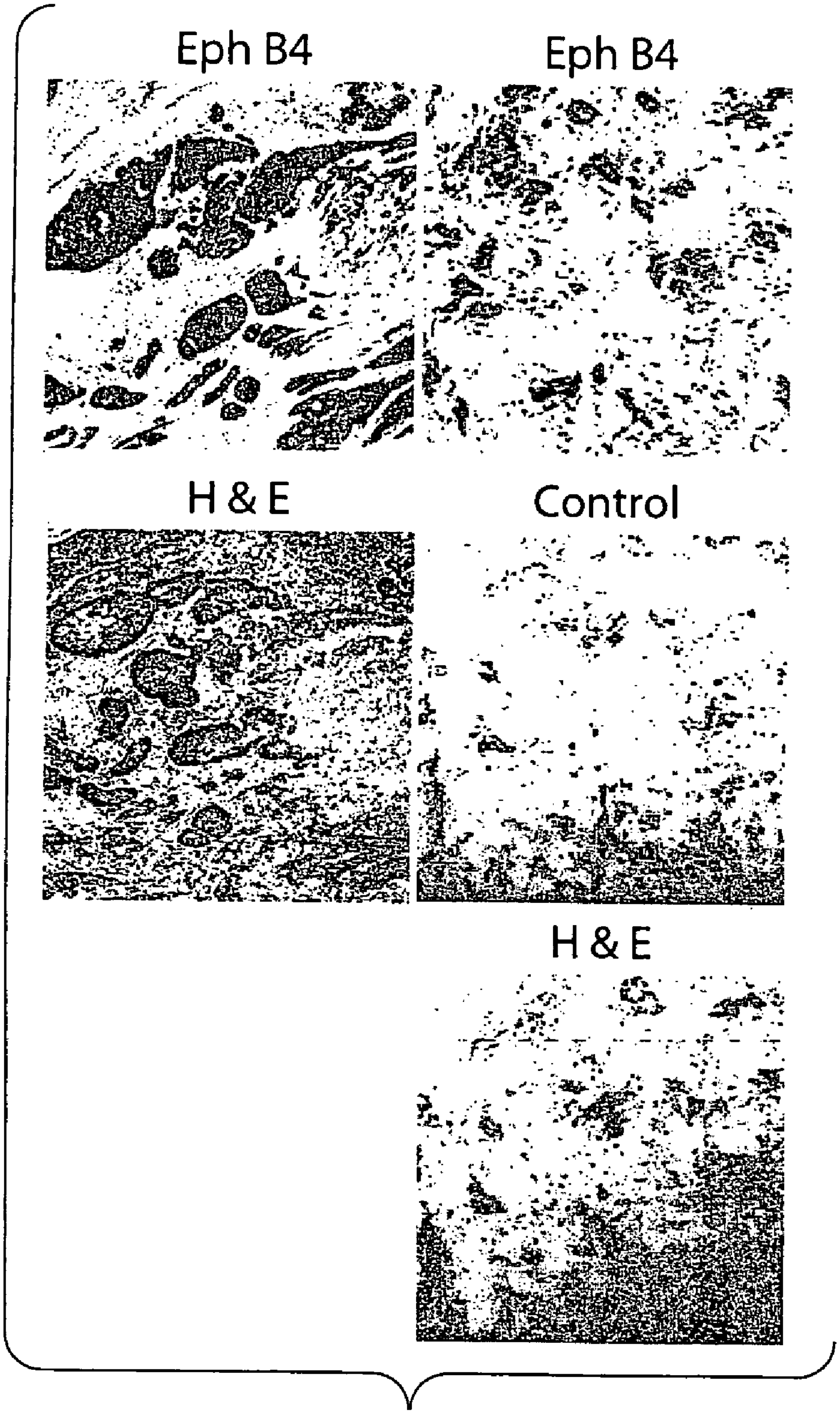

We studied the expression of EphB4 in human tumor tissues by immunohistochemistry, in situ hybridization, and Western blot. Twenty prospectively collected tumor tissues following IRB approval have been evaluated with specific EphB4 monoclonal antibody that does not react with other members of the EphB and EphA family. EphB4 expression is observed in all cases, with varying intensity of staining. FIG. 39A (top left) illustrates a representative case, showing that EphB4 is expressed in the tumor regions only, as revealed by the H&E tumor architecture (FIG. 39A bottom left). Note the absence of staining for EphB4 in the stroma. Secondly, a metastatic tumor site in the lymph node shows positive staining while the remainder of the lymph node is negative (FIG. 39A, top right).

Figure 39B:
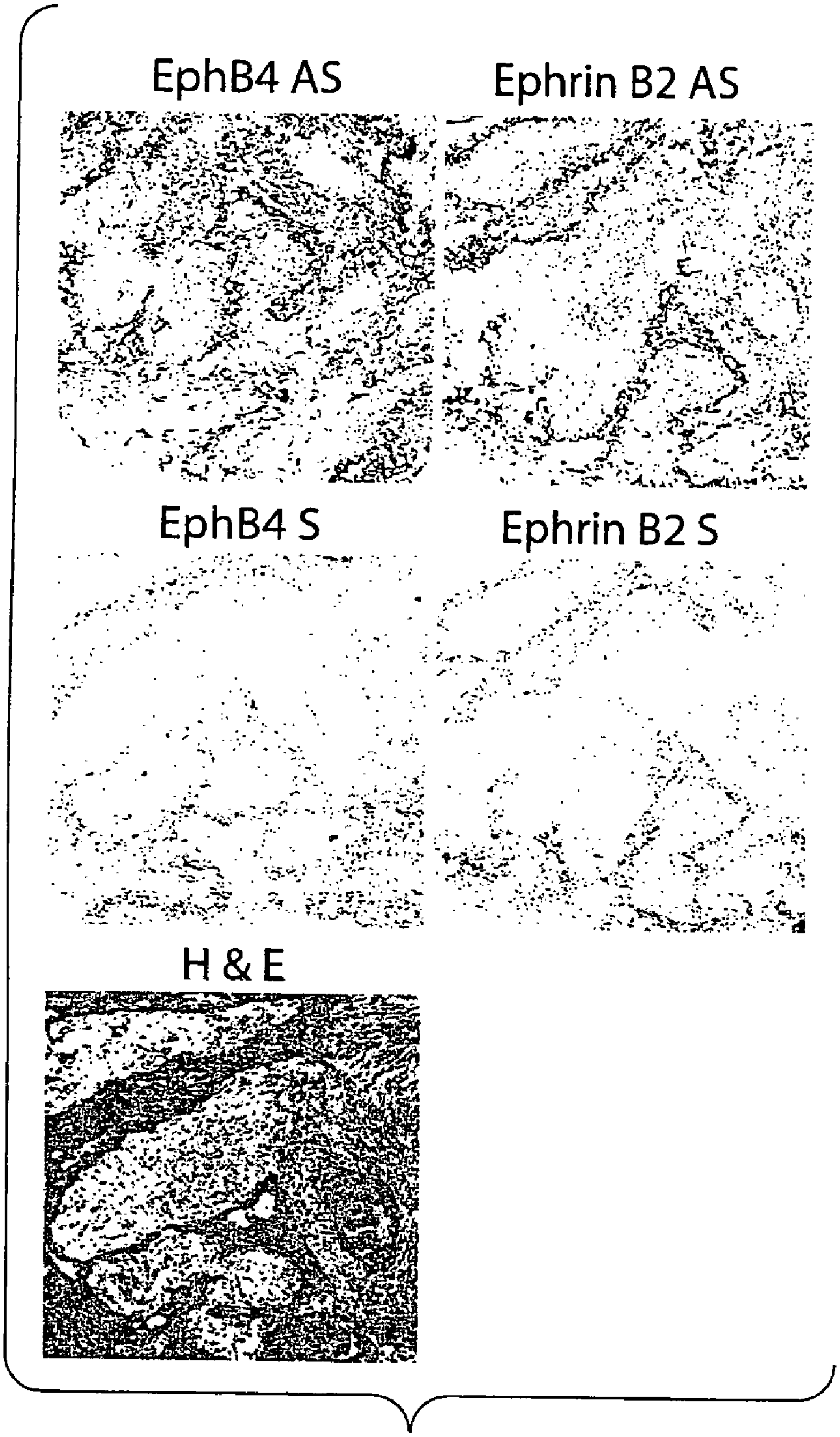

In situ hybridization was carried out to determine the presence and location of EphB4 transcripts in the tumor tissue. Strong signal for EphB4 specific antisense probe was detected indicating the presence of transcripts (FIG. 39B, top left). Comparison with the H&E stain (FIG. 39B, bottom left) to illustrate tumor architecture reveals that the signal was localized to the tumor cells, and was absent from the stromal areas. Ephrin B2 transcripts were also detected in tumor sample, and as with EphB4, the signal was localized to the tumor cells (FIG. 39B, top right). Neither EphB4 nor ephrin B2 sense probes hybridized to the sections, proving specificity of the signals.

B. High expression of EphB4 in Primary and Metastatic Sites of HNSCC

Figure 39C:
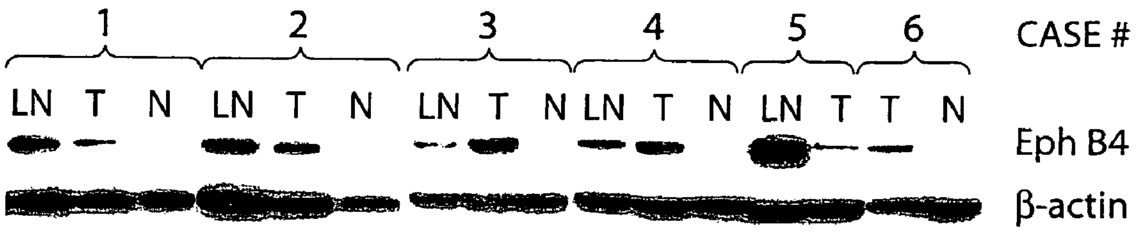

Western blots of tissue from primary tumor, lymph node metastases and uninvolved tissue were carried out to determine the relative levels of EphB4 expression in these sites. Tumor and normal adjacent tissues were collected on 20 cases, while lymph nodes positive for tumor were harvested in 9 of these 20 cases. Representative cases are shown in FIG. 39C. EphB4 expression is observed in each of the tumor samples. Similarly, all tumor positive lymph nodes show EphB4 expression that was equal to or greater than the primary tumor. No or minimal expression is observed in the normal adjacent tissue.

C. EphB4 Expression and Regulation by EGFR Activity in HNSCC Cell Lines

Figure 40A:
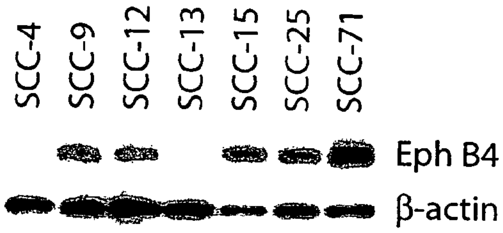
Figure 40B:
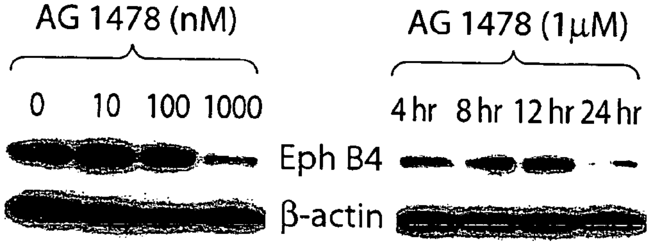
Figure 40C:
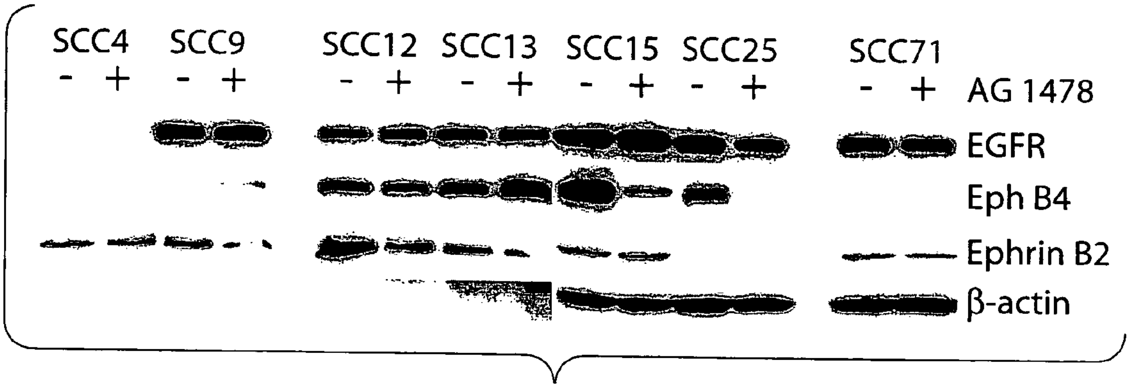

Having demonstrated the expression of EphB4 limited to tumor cells, we next sought to determine whether there was an in vitro model of EphB4 expression in HNSCC. Six HN SCC cell lines were surveyed for EphB4 protein expression by Western Blot (FIG. 40A). A majority of these showed strong EphB4 expression and thus established the basis for subsequent studies. Since EGFR is strongly implicated in HNSCC we asked whether EphB4 expression is associated with the activation of EGFR. Pilot experiments in SCC-15, which is an EGFR positive cell line, established an optimal time of 24 h and concentration of 1 mM of the specific EGFR kinase inhibitor AG 1478 (FIG. 40B) to inhibit expression of EphB4. When all the cell lines were studied, we noted robust EGFR expression in all but SCC-4, where it is detectable but not strong (FIG. 40C, top row). In response to EGFR inhibitor AG1478 marked loss in the total amount of EphB4 was observed in certain cell lines (SCC-15, and SCC-25) while no effect was observed in others (SCC-9, -12, -13 and -71). Thus SCC-15 and -25 serve as models for EphB4 being regulated by EGFR activity, while SCC-9, -12, -13 and -71 are models for regulation of EphB4 in HNSCC independent of EGFR activity, where there may be input from other factors such as p53, PTEN, IL-6 etc. We also noted expression of the ligand of EphB4, namely ephrin B2, in all of the cell lines tested. As with EphB4 in some lines ephrin B2 expression appears regulated by EGFR activity, while it is independent in other cell lines.

Figure 41B:
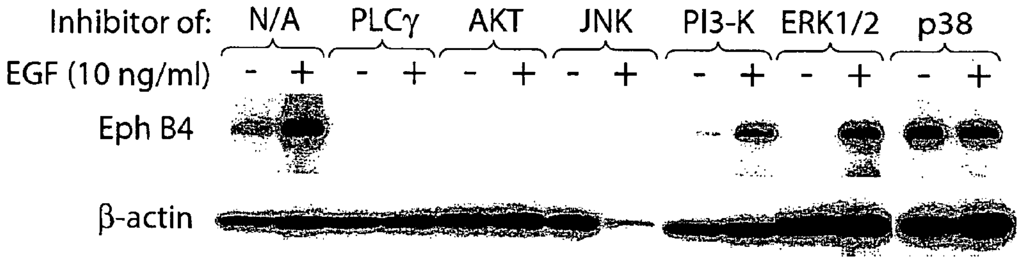

Clearly, inhibition of constitutive EGFR signaling repressed EphB4 levels in SCC15 cells. We next studied whether EGF could induce EphB4. We found that EphB4 levels were induced in SCC15 cells that had been serum starved for 24 h prior to 24 h treatment with 10 ng/ml EGF as shown in FIG. 41B (lanes 1 and 2). The downstream signaling pathways known for EGFR activation shown in FIG. 41A, (for review see Yarden & Slikowski 2001) were then investigated for their input into EGF mediated induction of EphB4. Blocking PLCg, AKT and JNK phosphorylation with the specific kinase inhibitors U73122, SH-5 and SP600125 respectively reduced basal levels and blocked EGF stimulated induction of EphB4 (FIG. 41B, lanes 3-8). In contrast, inhibition of ERK1/2 with PD098095 and P13-K with LY294002 or Wortmannin had no discernible effect on EGF induction of EphB4 levels. However, basal levels of EphB4 were reduced when ERK1/2 phosphorylation was inhibited. Interestingly, inhibition of p38 MAPK activation with SB203580 increased basal, but not EGF induced EphB4 levels. Similar results were seen in the SCC25 cell line (data not shown).

Figure 42A:
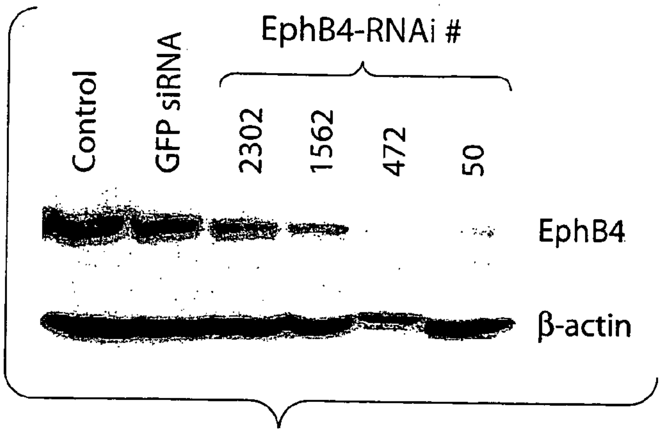
Figure 42B:
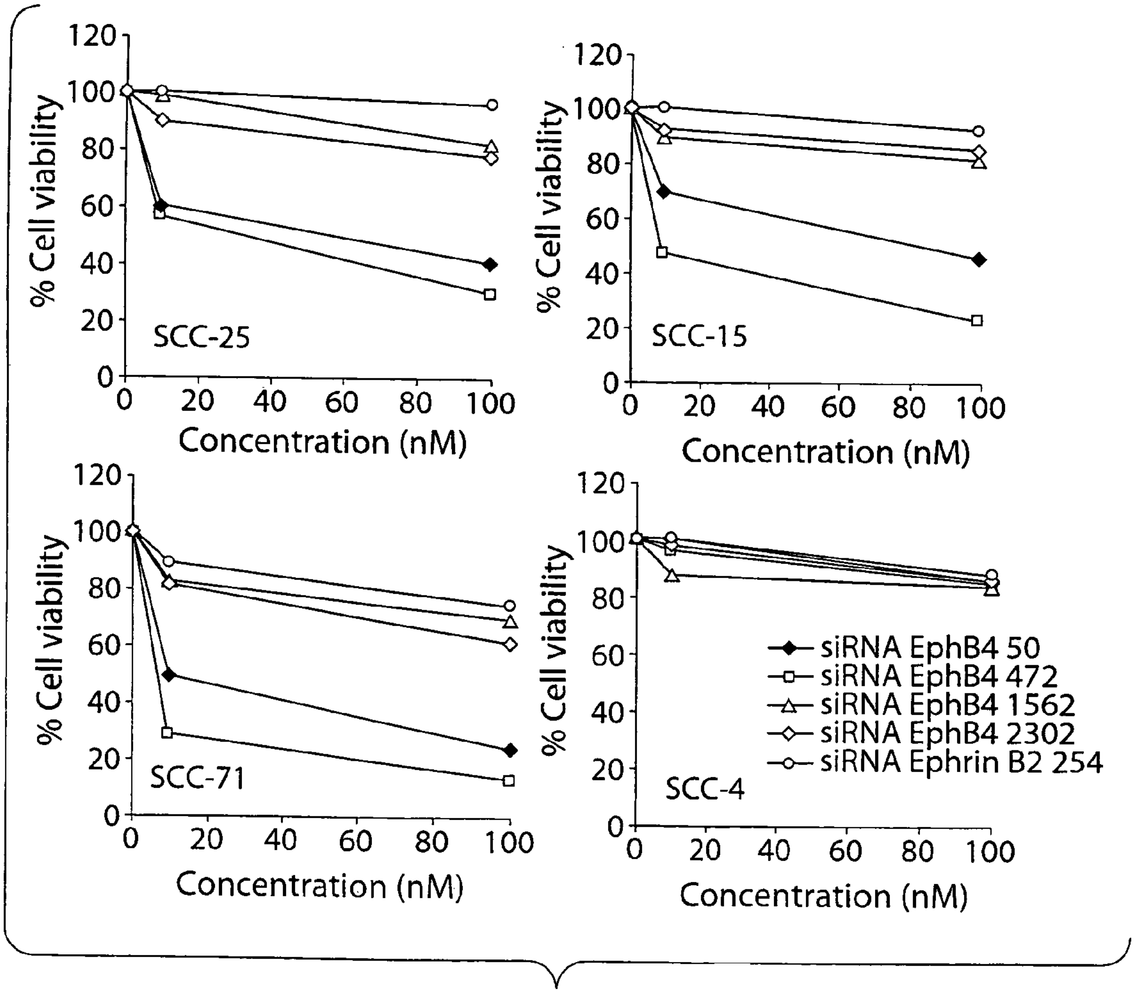
Figure 42C:
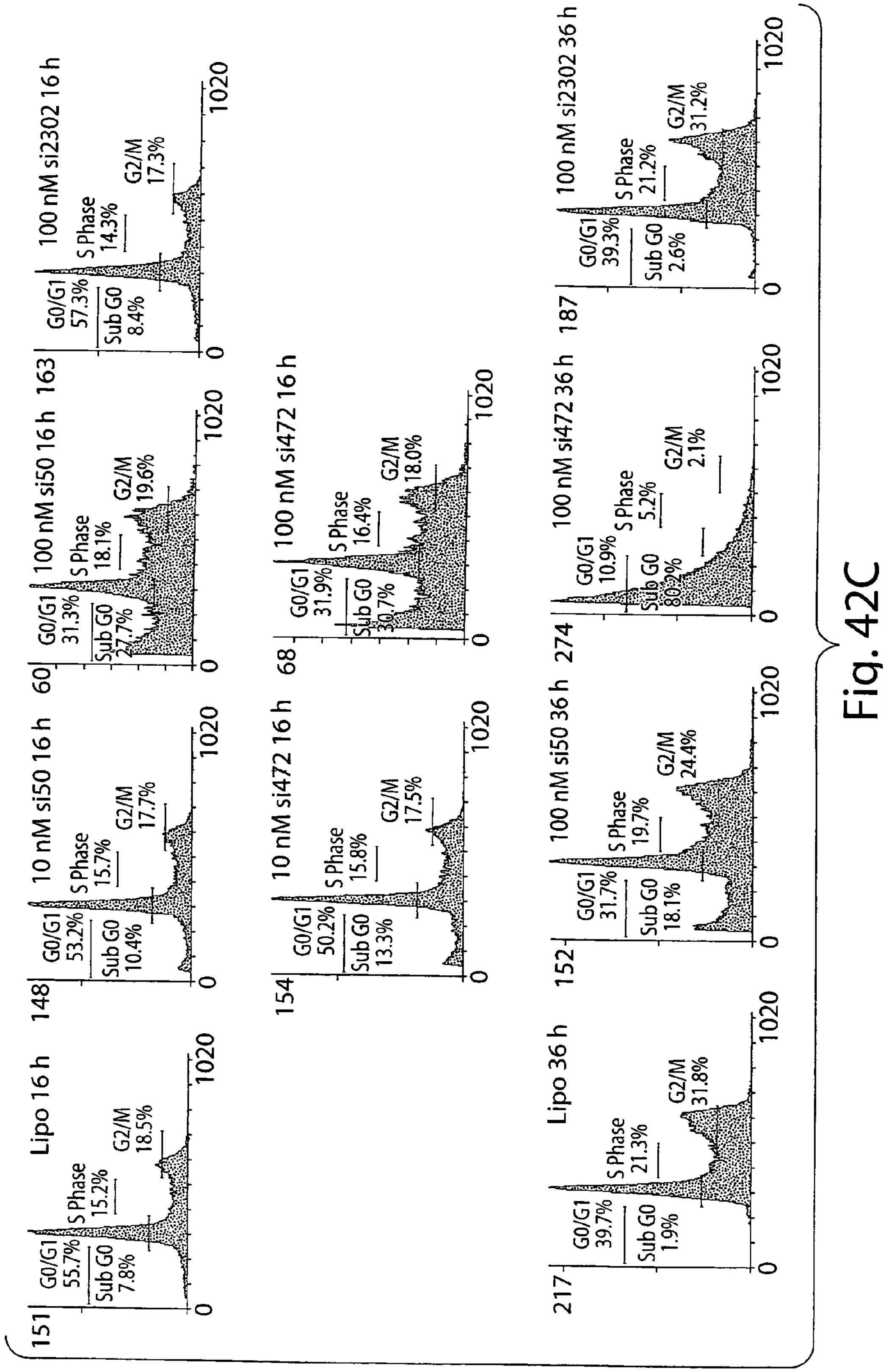

D. Inhibition of EphB4 in High Expressing Cell Lines Results in Reduced Viability and Causes Cell-Cycle Arrest We next turned to the role of EphB4 expression in HNSCC by investigating the effect of ablating expression using siRNA or AS-ODN methods. Several siRNAs to EphB4 sequence were developed (Table 1) which knocked-down EphB4 expression to varying degrees as seen in FIG. 42A. Viability was reduced in SCC-15, -25 and -71 cell lines transfected with siRNAs 50 and 472, which were most effective in blocking EphB4 expression (FIG. 42B). Little effect on viability was seen with EphB4 siRNA 1562 and 2302 or ephrin B2 siRNA 254. Note that in SCC-4, which does not express EphB4 (see FIG. 40A) there was no reduction in cell viability. The decreased cell viability seen with siRNA 50 and 472 treatment was attributable to accumulation of cells in sub G0, indicative of apoptosis. This effect was both time and dose-dependant (FIG. 42C and Table 2). In contrast, siRNA2302 that was not effective in reducing EphB4 levels and had only minor effects on viability did not produce any changes in the cell cycle when compared with the mock Lipofectamine™2000 transfection.

TABLE 1

EphB4 siRNAs

| Name | siRNA sequence | SEQ. ID NO: |
|---|---|---|
| Eph B4 50: | 5'-GAGACCCUGCUGAACACAAUU-3' | 34 |
| | 3'-UUCUCUGGGACGACUUGUGUU-5' | 35 |
| Eph B4 472: | 5'-GGUGAAUGUCAAGACGCUGUU-3' | 36 |
| | 3'-UUCCACUUACAGUUCUGCGAC-5' | 37 |
| Eph B4 1562: | 5'-CAUCACAGCCAGACCCAACUU-3' | 38 |
| | 3'-UUGUAGUGUCGGUCUGGGUUG-5' | 39 |
| Eph B4 2302: | 5'-CUCUUCCGAUCCCACCUACUU-3' | 40 |
| | 3'-UUGAGAAGGCUAGGGUGGAUG-5' | 41 |

TABLE 2

Effect of different EphB4 siRNA on Cell Cycle

| Treatment | Sub G0 | G1 | S | G2 |
|---|---|---|---|---|
| 36 hr | | | | |
| Lipo alone | 1.9 | 39.7 | 21.3 | 31.8 |
| 100 nM 2302 | 2.0 | 39.3 | 21.2 | 31.2 |
| 100 nM 50 | 18.1 | 31.7 | 19.7 | 24.4 |
| 100 nM 472 | 80.2 | 10.9 | 5.2 | 2.1 |
| 16 hr | | | | |
| Lipo alone | 7.8 | 55.7 | 15.2 | 18.5 |
| 100 nM 2302 | 8.4 | 57.3 | 14.3 | 17.3 |
| 10 nM 50 | 10.4 | 53.2 | 15.7 | 17.7 |
| 100 nM 50 | 27.7 | 31.3 | 18.1 | 19.6 |
| 10 nM 472 | 13.3 | 50.2 | 15.8 | 17.5 |
| 100 nM 472 | 30.7 | 31.9 | 16.4 | 18.0 |

Figure 43A:
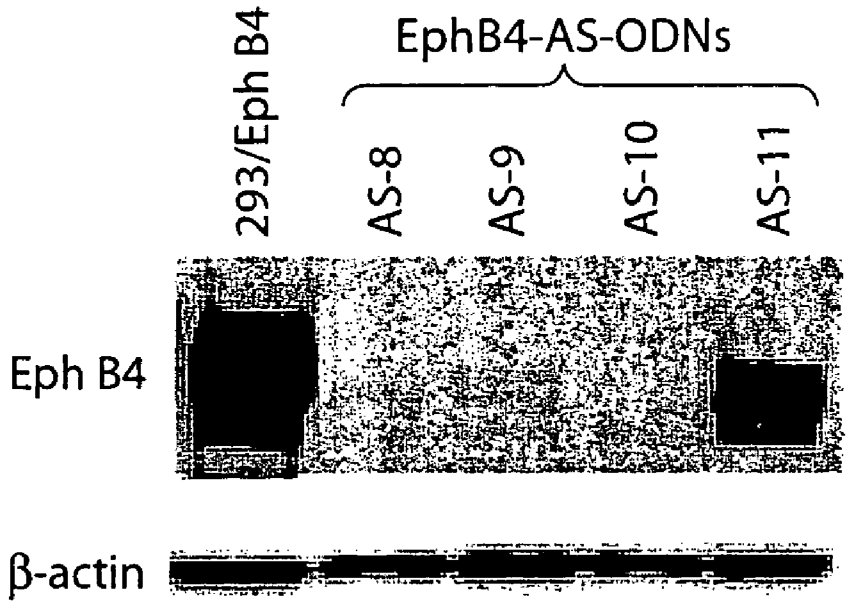
Figure 43B:
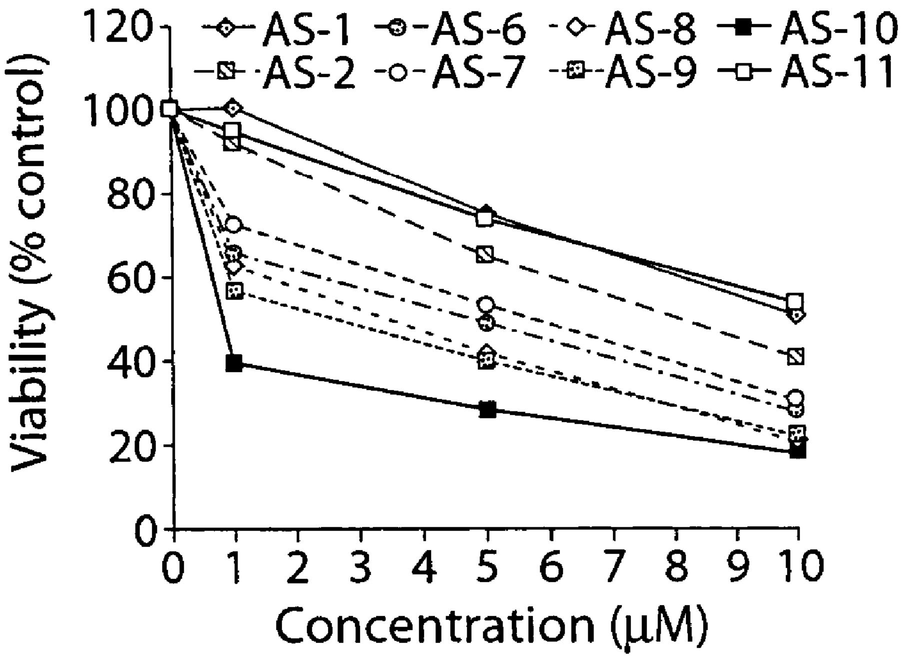
Figure 43C:
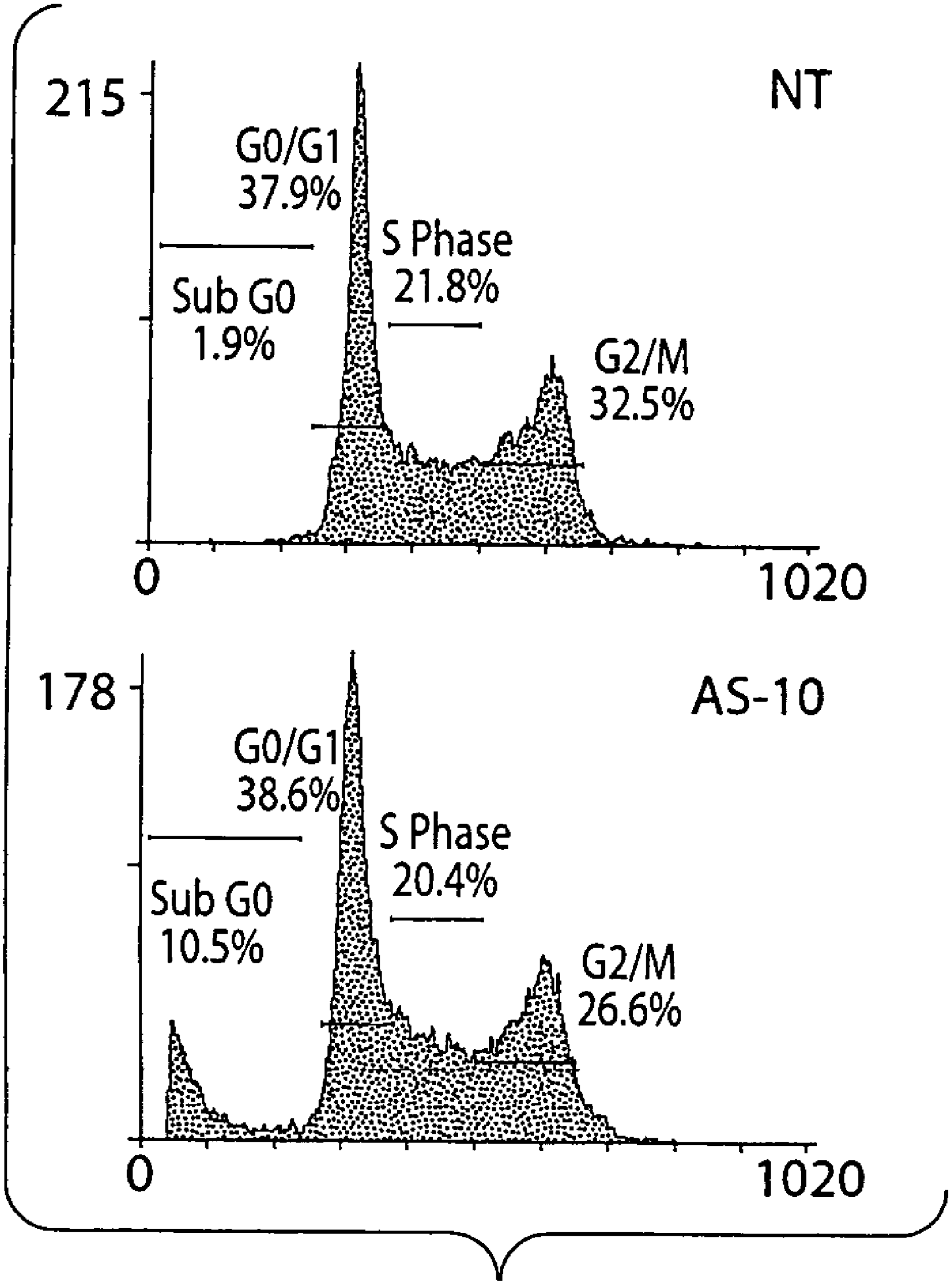

In addition, over 50 phosphorothioate AS-ODNs complementary to the human EphB4 coding sequences were synthesized and tested for their ability to inhibit EphB4 expression in 293 cells transiently transfected with full length EphB4 expression plasmid. FIG. 43A shows a representative sample of the effect of some of these AS-ODNs on EphB4 expression. Note that expression is totally abrogated with AS-10, while AS-11 has only a minor effect. The effect on cell viability in SCC15 cells was most marked with AS-ODNs that are most effective in inhibiting EphB4 expression as shown in FIG. 43B. The $IC_{50}$ for AS-10 was approximately 1 μM, while even 10 μM AS-11 was not sufficient to attain 50% reduction of viability. When the effect that AS-10 had on the cell cycle was investigated, it was found that the sub G0 fraction increased from 1.9% to 10.5% compared to non-treated cells, indicative of apoptosis (FIG. 43C).

E. EphB4 Regulates Cell Migration

Figure 43D:
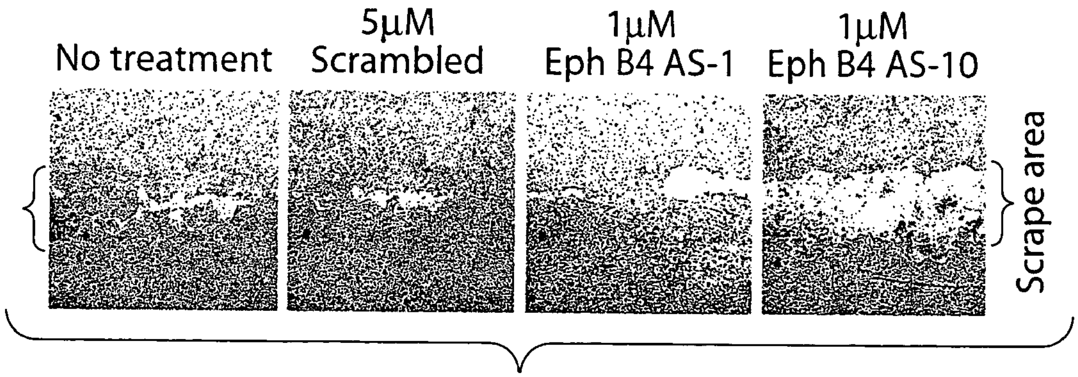
Figure 43E:
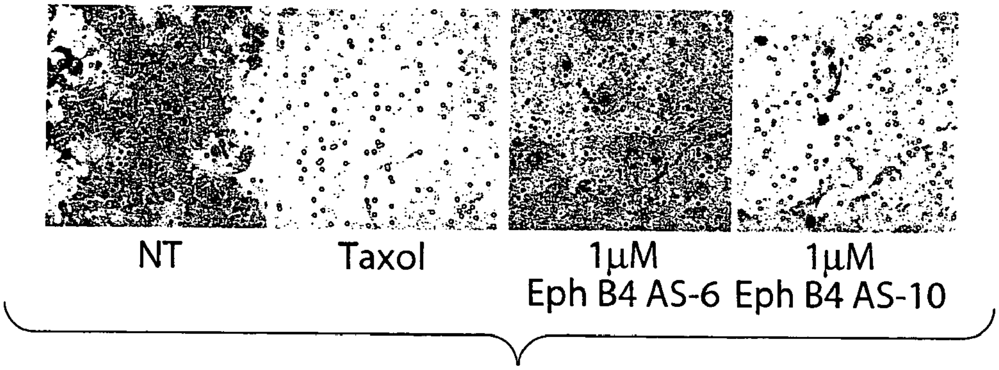
Figure 43F:
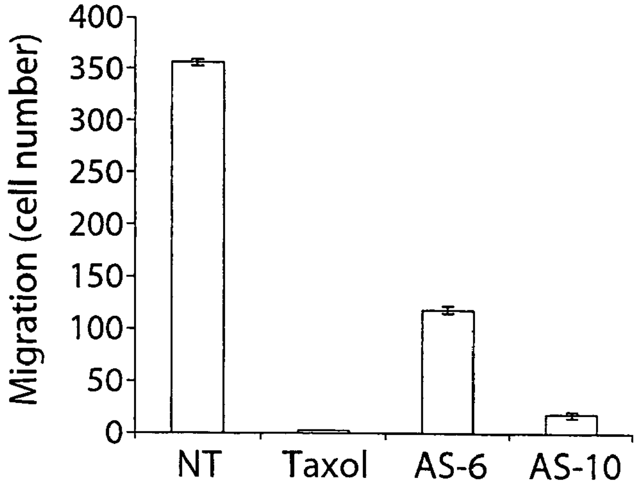

We next wished to determine if EphB4 participates in the migration of HNSCC. Involvement in migration may have implications for growth and metastasis. Migration was assessed using the wound-healing/scrape assay. Confluent SCC15 and SCC25 cultures were wounded by a single scrape with a sterile plastic Pasteur pipette, which left a 3 mm band with clearly defined borders. Migration of cells into the cleared area in the presence of test compounds was evaluated and quantitated after 24, 48 and 72 hr. Cell migration was markedly diminished in response to AS-10 that block EphB4 expression while the inactive compounds, AS-1 and scrambled ODN had little to no effect as shown in FIG. 43D. Inhibition of migration with AS-10 was also shown using the Boyden double chamber assay (FIG. 43E).

F. EphB4 AS-10 In Vivo Anti-Tumor Activity

The effect of EphB4 AS-10, which reduces cell viability and motility, was determined in SCC15 tumor xenografts in Balb/C nude mice. Daily treatment of mice with 20 mg/kg AS-10, sense ODN or equal volume of PBS by I.P. injection was started the day following tumor cell implantation. Growth of tumors in mice receiving AS-10 was significantly retarded compared to mice receiving either sense ODN or PBS diluent alone (FIG. 44). Non-specific effects attributable to ODN were not observed, as there was no difference between the sense ODN treated and PBS treated groups.

G. Materials and Methods

1) Cell Lines and Reagents

HNSCC-4, -9, 12, -13, -15, -25, and -71 were obtained from and 293 human embryonic kidney cells were obtained from the ATCC (Manassas, Va.). Cells were maintained in RPMI 1640 media supplemented with 10% heat-inactivated fetal bovine serum (FBS; Invitrogen, Carlsbad, Calif.) and antibiotics. EGFR, EphB4(C-16) polyclonal antibodies were from Santa Cruz Biotech (Santa Cruz, Calif.). β-actin monoclonal antibody was purchased from Sigma Chemical Co. (St Louis, Mo.). Ephrin B2 and EphB4 polyclonal antibodies and their corresponding blocking peptides were obtained from Santa Cruz Biotechnology (Santa Cruz, Calif.). AG 1478 (4-(3'-Chloroanilino)-6,7-dimethoxy-quinazoline) was from Calbiochem (San Diego, Calif.). Kinase inhibitors SH-5 and SP 600125 were from A.G. Scientific (San Diego, Calif.), PD98095, U73122, SB203580, LY294002, and Wortmannin were obtained from Sigma.

2) Preparation of Digoxigenin-Labeled RNA Probes

See above, e.g., Example 3.

3) In Situ Hybridization

See above, e.g., Example 3.

4) Immunohistochemistry

Formalin-fixed tissue sections were deparaffinized and incubated with 10% goat serum at −70° C. for 10 minutes and incubated with the EphB4 monoclonal antibody 4° C. overnight. Isotype specific rabbit IgG was used as control. The immunoreactivity for these receptors was revealed using an avidin-biotin kit from Vector Laboratories. Peroxidase activity was revealed by the diaminobenzidine (Sigma) cytochemical reaction. The slides were then counterstained with 0.12% methylene blue or H&E. For frozen sections, OCT-embedded tissues were sectioned at 5 μm and fixed in phosphate-buffered 4% paraformaldehyde. Sections were washed for 3×5 min in PBS and endogenous peroxidase was blocked by incubation in 0.3% $H_2O_2$ in PBS for 10 min at room temperature. Sections were incubated with Eph4 (C-16) antibody (1:50) for 1 h at room temperature followed by three washes in PBS and incubation with donkey anti-goat secondary antibody (Santa Cruz Biotech.) for 1 h at room temperature. After three washes in PBS, peroxidase activity was localized by incubation in DAB substrate solution (Vector Laboratories, Inc. Burlingame Calif.) for 10 min at room temperature. Sections were counterstained with Hematoxylin for 20 s, dehydrated and mounted. Negative control for staining was substitution of normal goat serum for primary antibody. Immunohistochemical staining on prostate array (BioMeda, Foster City, Calif.) was done using goat ABC Staining System (Santa Cruz Biotech.) according to the manufacturer's instructions.

5) Western Blot

See above, e.g., Example 3.

6) Synthesis of EphB4 siRNA by In Vitro Transcription

The Silencer™ siRNA construction kit (Ambion, Austin Tex.) was used to synthesize siRNA to EphB4. Briefly, 21 bp target sequences containing 19 bp downstream of 5'-AA dinucleotides were identified that showed no significant homology to other sequences in the GenBank database. Sense and antisense siRNA 29-mer DNA oligonucleotide templates were synthesized at the USC Norris Microchemical Core Facility. Antisense template corresponded to the target sequence followed by 8 bp addition (5'-CCTGTCTC-3') at the 3' end complementary to the T7 promoter primer provided by the Silencer™ siRNA construction kit. Sense template comprised 5'-AA followed by the complement of the target 19 bp, then the T7 8 bp sequence as above.

In separate reactions, the two siRNA oligonucleotide templates were hybridized to a T7 promoter primer. The 3' ends of the hybridized oligonucleotides were extended by the Klenow fragment of DNA polymerase to create double-stranded siRNA transcription templates. The sense and antisense siRNA templates were transcribed by T7 RNA polymerase and the resulting RNA transcripts were hybridized to create dsRNA. The leader sequences were removed by digesting the dsRNA with a single-stranded specific ribonuclease leaving the overhanging UU dinucleotides. The DNA template was removed at the same time by treatment with RNase free deoxyribonuclease. The resulting siRNA was purified by glass fiber filter binding to remove excess nucleotides, short oligomers, proteins, and salts in the reaction. The end products (shown in Table 3) were double-stranded 21-mer siRNAs with 3' terminal uridine that can effectively reduce the expression of target mRNA when transfected into cells.

A number of phosphorothioate AS-ODNs were also synthesized (Operon, Valencia Calif.) to test for inhibition of EphB4 expression (Table 3).

TABLE 3

EphB4 Antisense ODNs

| Name | Position | Sequence (5' → 3') | SEQ. ID NO: |
|---|---|---|---|
| Eph B4 AS-1 | (552-572) | GTG CAG GGA TAG CAG GGC CAT | 42 |
| Eph B4 AS-2 | (952-972) | AAG GAG GGG TGG TGC ACG GTG | 43 |
| Eph B4 AS-3 | (1007-1027) | TTC CAG GTG CAG GGA GGA GCC | 44 |
| Eph B4 AS-4 | (1263-1285) | GTG GTG ACA TTG ACA GGC TCA | 45 |
| Eph B4 AS-5 | (1555-1575) | TCT GGC TGT GAT GTT CCT GGC | 46 |
| Eph B4 AS-6 | (123-140) | GCC GCT CAG TTC CTC CCA | 47 |
| Eph B4 AS-7 | (316-333) | TGA AGG TCT CCT TGC AGG | 48 |
| Eph B4 AS-8 | (408-428) | CGC GGC CAC CGT GTC CAC CTT | 49 |
| Eph B4 AS-9 | (1929-1949) | CTT CAG GGT CTT GAT TGC CAC | 50 |
| Eph B4 AS-10 | (1980-1999) | ATG GAG GCC TCG CTC AGA AA | 51 |
| Eph b4 AS-11 | (2138-2158) | CAT GCC CAC GAG CTG GAT GAC | 52 |

7) Cell Viability Assay

Cells were seeded at a density of $5\times10^3$ per well in 48-well plates on day 0 in appropriate growth media containing 2% fetal calf serum (FCS). Cells were treated with various concentrations (1-10 μg/ml) of ODNs on days 2 and 4. On day 5, viability was assessed using 3-(4,5-dimethylthiazol-2-yl)-2,5-diphenyltetrazolium bromide (MTT) as previously described (Masood et al '03). For viability with siRNA, $2\times10^4$ cells/well of SCC-4, -15, -25 or -71 in a 48-well plate were transfected with siRNAs (10-100 nM) using 2 μl of Lipofectamine™ 2000 according to the manufacturer's instructions. 4 h post-transfection the cells were returned to growth media (RPMI 1640 supplemented with 10% FBS). Viability was assayed by MTT 48 h following transfection.

8) Cell Cycle Analysis

80% confluent cultures of SCC15 cells in 6-well plates were transfected with siRNA472 (100 nM) using Lipofectamine™ 2000. Either 16 or 36 hours after transfection, cells were trypsinized, washed in PBS and incubated for 1 h at 4° C. in 1 ml of hypotonic solution containing 50 μg/ml propidium iodide, 0.1% sodium citrate, 0.1 Triton X-100 and 20 μg/ml DNase-free RNaseA. Cells were analyzed in linear mode at the USC Flow cytometry facility. Results were expressed as percentages of elements detected in the different phases of the cell cycle, namely Sub G0 peak (apoptosis), G0/G1 (no DNA synthesis), S (active DNA systhesis), G2 (premitosis) and M (mitosis). For AS-ODN experiment the cells were exposed to 5 μM ODN for 36 h prior to processing.

9) Wound Healing Migration Assay

SCC15 cells were seeded into 6-well plates and cultured until confluent. 10 μM AS-1, AS-10, or sense ODN as control were introduced to the wells as described for the viability assay 12 hours before wounding the monolayer by scraping it with a sterile pipette tip. Medium was changed to RPMI 1640 supplemented with 5% FBS and fresh ODNs. The healing process was examined dynamically and recorded with a Nikon Coolpix 5000 digital camera with microscope adapter.

10) Boyden Chamber Assay of Migration

Cell migration assays were performed as previously described (Masood ANUP paper '99) except that 1 μM AS-10 or AS-6 were added to the upper chamber. EGF (20 ng/ml) was used as chemoattractant in the lower chamber. Taxol at 10 ng/ml was used as a negative control.

11) In Vivo Studies

SCC15 ($5\times10^6$ cells) were injected subcutaneously in the lower back of 5-week old male Balb/C $Nu^+/nu^+$ athymic mice. Treatment consisted of daily intraperitoneal injection of ODN (20 mg/kg in a total volume of 100 μl) or diluent (PBS) begun the day following tumor cell implantation and continued for two weeks. Tumor growth in mice was measured as previously described (Masood CCR '01). Mice were sacrificed at the conclusion of the study. All mice were maintained in accord with the University of Southern California Animal Care and Use Committee guidelines governing the care of laboratory mice.

Example 6

Ephrin B2 Expression in Kaposi's Sarcoma is Induced by Human Herpesvirus Type 8: Phenotype Switch from Venous to Arterial Endothelium Kaposi's Sarcoma (KS) manifests as a multifocal angioproliferative disease, most commonly of the skin and mucus membranes, with subsequent spread to visceral organs (1) Hallmarks of the disease are angiogenesis, edema, infiltration of lymphomononuclear cells and growth of spindle-shaped tumor cells. Pathologically, established lesions exhibit an extensive vascular network of slit-like spaces. The KS vascular network is distinct from normal vessels in the lack of basement membranes and the abnormal spindle shaped endothelial cell (tumor cell) lining these vessels. Defective vasculature results in an accumulation of the blood components including albumin, red and mononuclear cells in the lesions (1). The KS tumor is endothelial in origin; the tumor cells express many endothelial markers, including lectin binding sites for *Ulex europeaus* agglutinin-1 (UEA-1), CD34, EN-4, PAL-E (2) and the endothelial cell specific tyrosine kinase receptors, VEGFR-1 (Flt-1), VEGFR-2 (Flk-1/KDR), VEGFR-3 (Flt-4), Tie-1 and Tie-2 (3, RM & PSG unpublished data). KS cells co-express lymphatic endothelial cell related proteins including LYVE and podoplanin (4).

The herpesvirus HHV-8 is considered the etiologic agent for the disease. In 1994 sequences of this new herpes virus were identified in KS tumor tissue (5), and subsequent molecular-epidemiology studies have shown that nearly all KS tumors contain viral genome. Sero-epidemiology studies show that HIV infected patients with KS have the highest prevalence of HHV-8 and secondly that those with HIV infection but no KS have increased risk of developement of KS over the ensuing years if they are also seropositive for HHV-8 (6). Direct evidence for the role of HHV-8 in KS is the transformation of bone marrow endothelial cells after infection with HHV-8 (7). A number of HHV-8 encoded genes could contribute to cellular transformation (reviewed in 8). However, the most evidence has accumulated for the G-protein coupled receptor (vGPCR) in this role (9).

We investigated whether KS tumor cells are derived from arterial or venous endothelium. In addition, we investigated whether HHV-8 has an effect on expression of arterial or venous markers in a model of KS. KS tumor cells were found to express the ephrin B2 arterial marker. Further, ephrin B2 expression was induced by HHV-8 vGPCR in KS and endothelial cell lines. Ephrin B2 is a potential target for treatment of KS because inhibition of ephrin B2 expression or signaling was detrimental to KS cell viability and function.

A. KS Tumors Express Ephrin B2, but Not EphB4

Figure 45A:
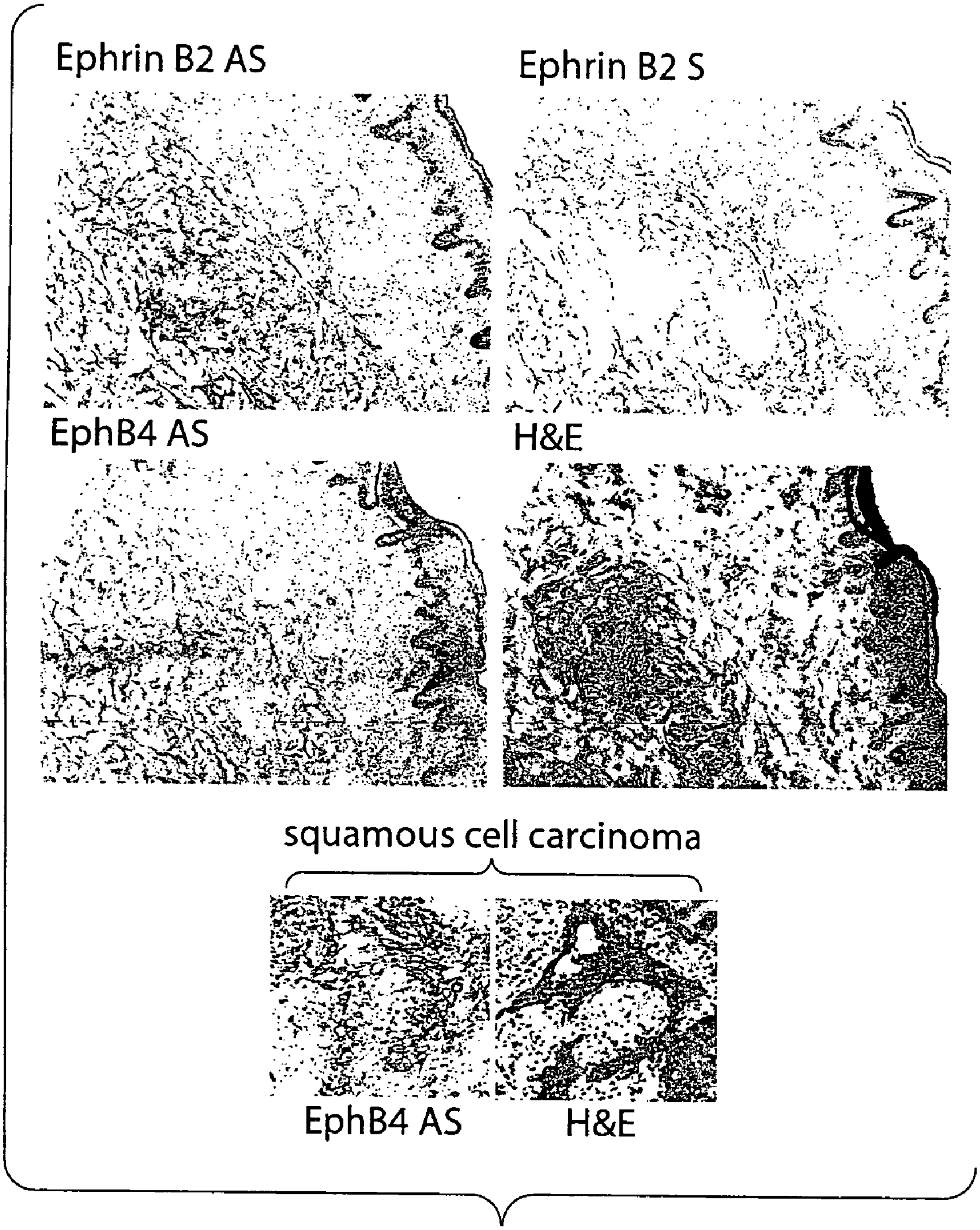
Figure 45B:
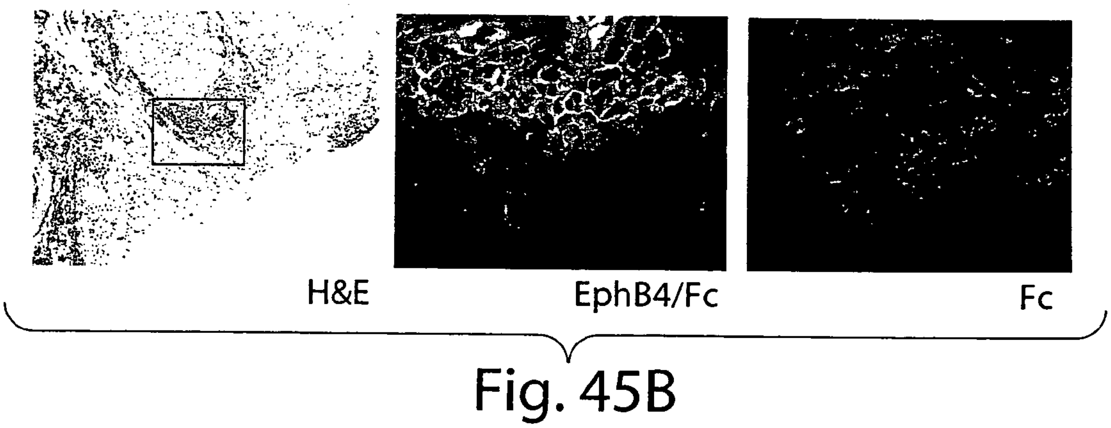
Figure 45C:
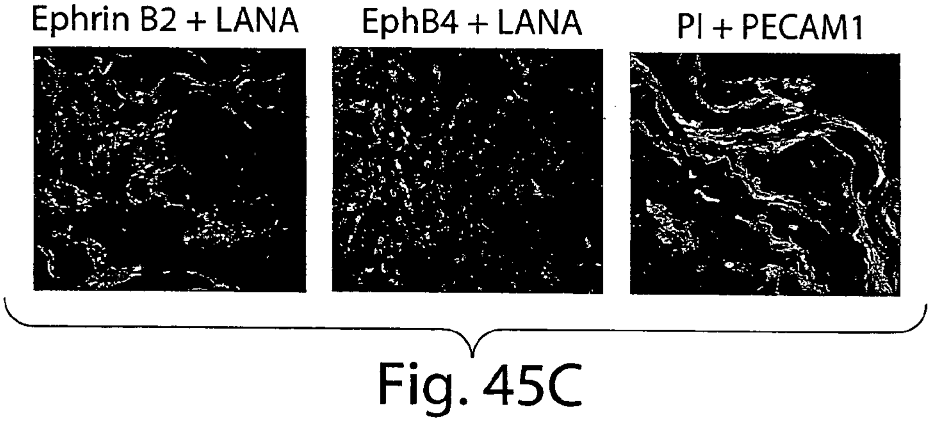

The highly vascular nature of KS lesions and the probable endothelial cell origin of the tumor cells prompted investigation of expression of EphB4 and ephrin B2 which are markers for venous and arterial endothelial cells, respectively. Ephrin B2, but not EphB4 transcripts were detected in tumor cells of KS biopsies by in situ hybridization (FIG. 45A). Comparison of the positive signal with ephrin B2 antisense probe and tumor cells as shown by H&E staining shows that ephrin B2 expression is limited to the areas of the biopsy that contain tumor cells. The lack of signal in KS with EphB4 antisense probe is not due to a defect in the probe, as it detected transcripts in squamous cell carcinoma, which we have shown expresses this protein (18). Additional evidence for the expression of ephrin B2 in KS tumor tissue is afforded by the localization of EphB4/Fc signal to tumor cells, detected by FITC conjugated anti human Fc antibody. Because ephrin B2 is the only ligand for EphB4 this reagent is specific for the expression of ephrin B2 (FIG. 45B, left). An adjacent section treated only with the secondary reagent shows no specific signal. Two-color confocal microscopy demonstrated the presence of the HHV-8 latency protein, LANA1 in the ephrin B2 positive cells (FIG. 45C, left), indicating that it is the tumor cells, not tumor vessels, which are expressing this arterial marker. Staining of tumor biopsy with PECAM-1 antibody revealed the highly vascular nature of this tumor (FIG. 45C, right). A pilot study of the prevalence of this pattern of ephrin B2 and EphB4 expression on KS biopsies was conducted by RT-PCR analysis. All six samples were positive for ephrin B2, while only 2 were weakly positive for EphB4 (data not shown).

Figure 46B:
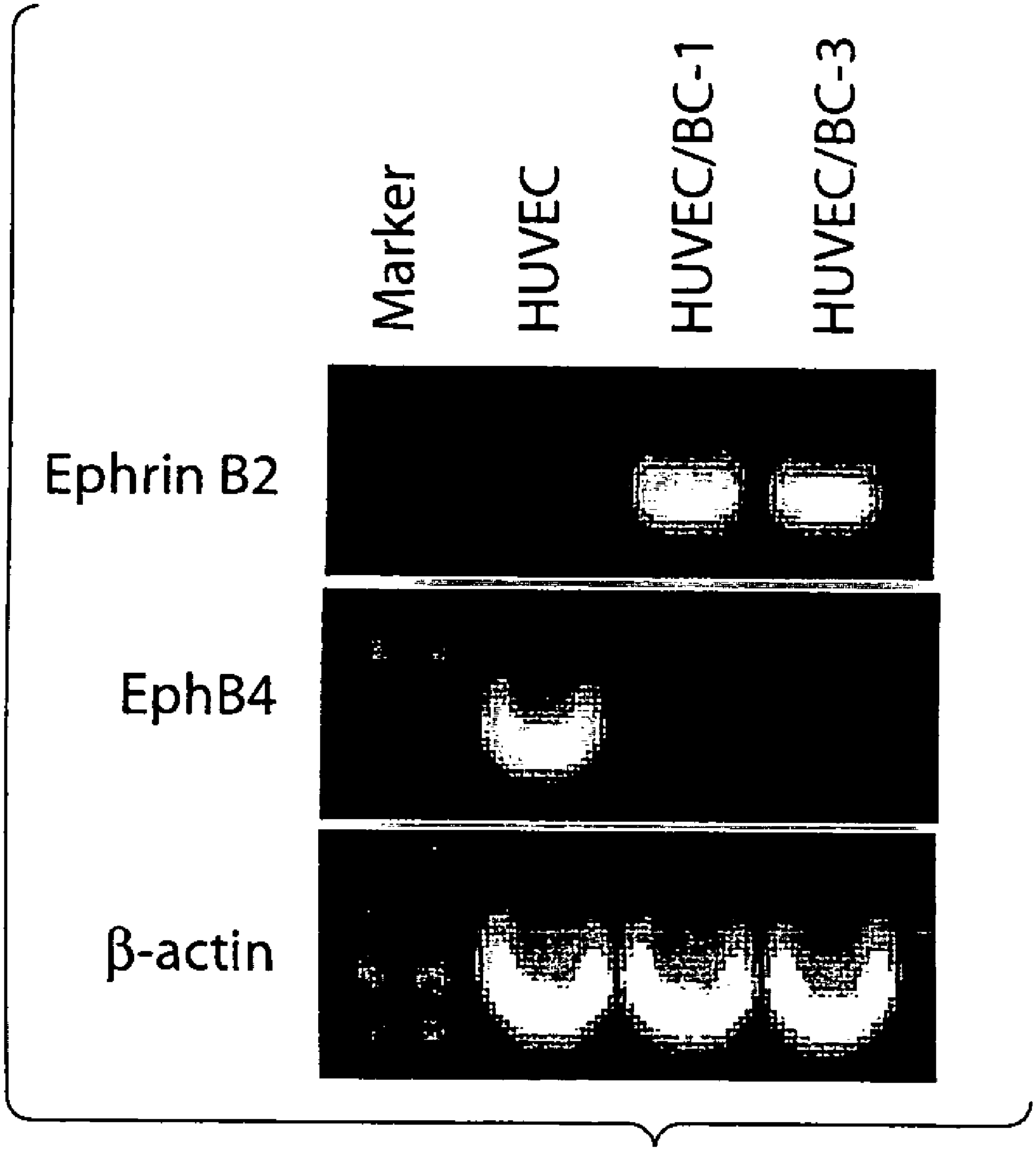

B. Infection of Venous Endothelial Cells with HHV-8 Causes a Phenotype Switch to Arterial Markers We next asked whether HHV-8, the presumed etiologic agent for KS, could itself induce expression of ephrin B2 and repress EphB4 expression in endothelial cells. Co-culture of HUVEC and BC-1 lymphoma cells, which are productively infected with HHV-8, results in effective infection of the endothelial cells (16). The attached monolayers of endothelial cells remaining after extensive washing were examined for ephrin B2 and EphB4 by RT-PCR and immunofluorescence. HUVEC express EphB4 venous marker strongly at the RNA level, but not ephrin B2 (FIG. 46B). In contrast, HHV-8 infected cultures (HUVEC/BC-1 and HUVEC/BC-3) express ephrin B2, while EphB4 transcripts are almost absent.

Immunofluorescence analysis of cultures of HUVEC and HUVEC/HHV-8 for artery/vein markers and viral proteins was undertaken to determine whether changes in protein expression mirrored that seen in the RNA. In addition, cellular localization of the proteins could be determined. Consistent with the RT-PCR data HUVEC are ephrin B2 negative and EphB4 positive (FIG. 46A(a & m)). As expected they do not express any HHV-8 latency associated nuclear antigen (LANA1) (FIG. 46A(b, n)). Co-culture of BC-1 cells, which are productively infected with HHV-8, resulted in infection of HUVEC as shown by presence of viral proteins LANA1 and ORF59 (FIG. 46A(f, r)). HHV-8 infected HUVEC now express ephrin B2 but not EphB4 (FIG. 46A(e, q, u), respectively). Expression of ephrin B2 and LANA1 co-cluster as shown by yellow signal in the merged image (FIG. 46A (h)). HHV-8 infected HUVEC positive for ephrin B2 and negative for Eph B4 also express the arterial marker CD148 (19) (FIG. 46A (j, v)). Expression of ephrin B2 and CD148 co-cluster as shown by yellow signal in the merged image (FIG. 46A(l)). Uninfected HUVEC expressing Eph B4 were negative for CD148 (not shown).

C. HHV-8 vGPCR Induces Ephrin B2 Expression

Figure 47A:
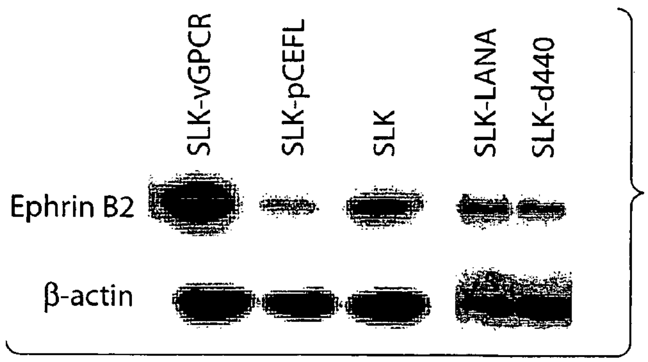
Figure 47B:
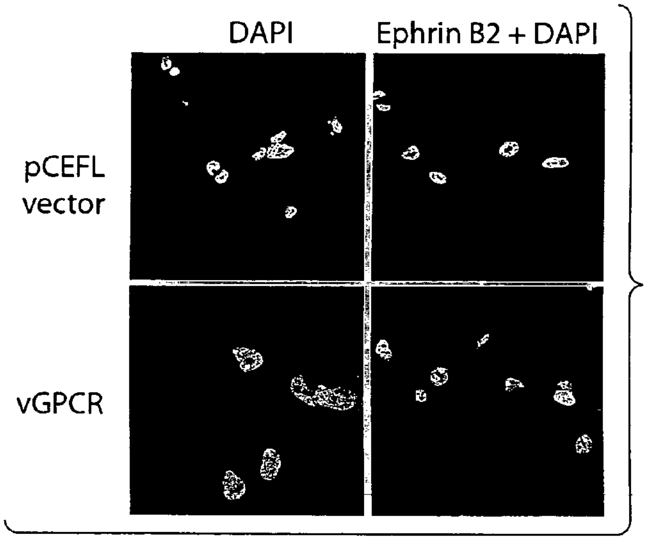
Figure 47C:
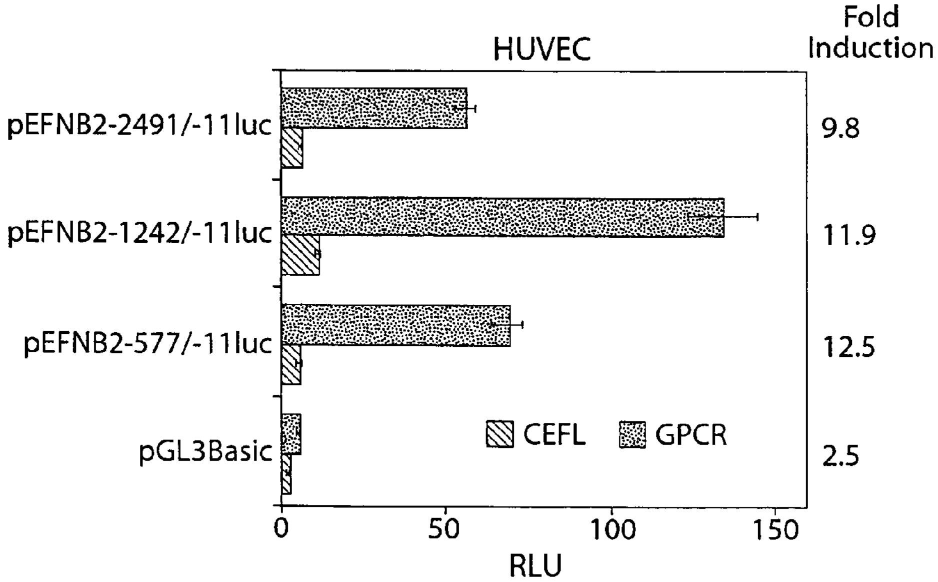

To test whether individual viral proteins could induce the expression of ephrin B2 seen with the whole virus KS-SLK cells were stably transfected with HHV-8 LANA, or LANAΔ440 or vGPCR. Western Blot of stable clones revealed a five-fold induction of ephrin B2 in KS-SLK transfected with vGPCR compared to SLK-LANA or SLK-LANAΔ440 (FIG. 47A). SLK Transfected with vector alone (pCEFL) was used as a control. SLK-vGPCR and SLK-pCEFL cells were also examined for ephrin B2 and Eph B4 expression by immunofluorescence in transiently transfected KS-SLK cells. FIG. 47B shows higher expression of ephrin B2 in the SLK-vGPCR cells compared to SLK-pCEFL. No changes in Eph B4 were observed in SLK-vGPCR compared to SLK-pCEFL. This clearly demonstrates that SLK-vGPCR cells expressed high levels of ephrin B2 compared to SLK-pCEFL cells. This suggests that vGPCR of HHV-8 is directly involved in the induction of Ephrin B2 and the arterial phenotype switch in KS. Since we had shown that HHV-8 induced expression of ephrin B2 in HUVEC, we next asked if this could be mediated by a transcriptional effect. Ephrin B2 5'-flanking DNA-luciferase reporter plasmids were constructed as described in the Materials and Methods and transiently transfected into HUVECs. Ephrin B2 5'-flanking DNA sequences −2491/−11 have minimal activity in HUVEC cells (FIG. 47C). This is consistent with ephrin B2 being an arterial, not venous marker. However, we have noted that HUVEC in culture do express some ephrin B2 at the RNA level. Cotransfection of HHV-8 vGPCR induces ephrin B2 transcription approximately 10-fold compared to the control expression vector pCEFL. Roughly equal induction was seen with ephrin B2 sequences −2491/−11, −1242/−11, or −577/−11, which indicates that elements between −577 and −11 are sufficient to mediate the response to vGPCR, although maximal activity is seen with the −1242/−11 luciferase construct.

D. Expression of Ephrin B2 is Regulated by VEGF and VEGF-C

Figure 48A:
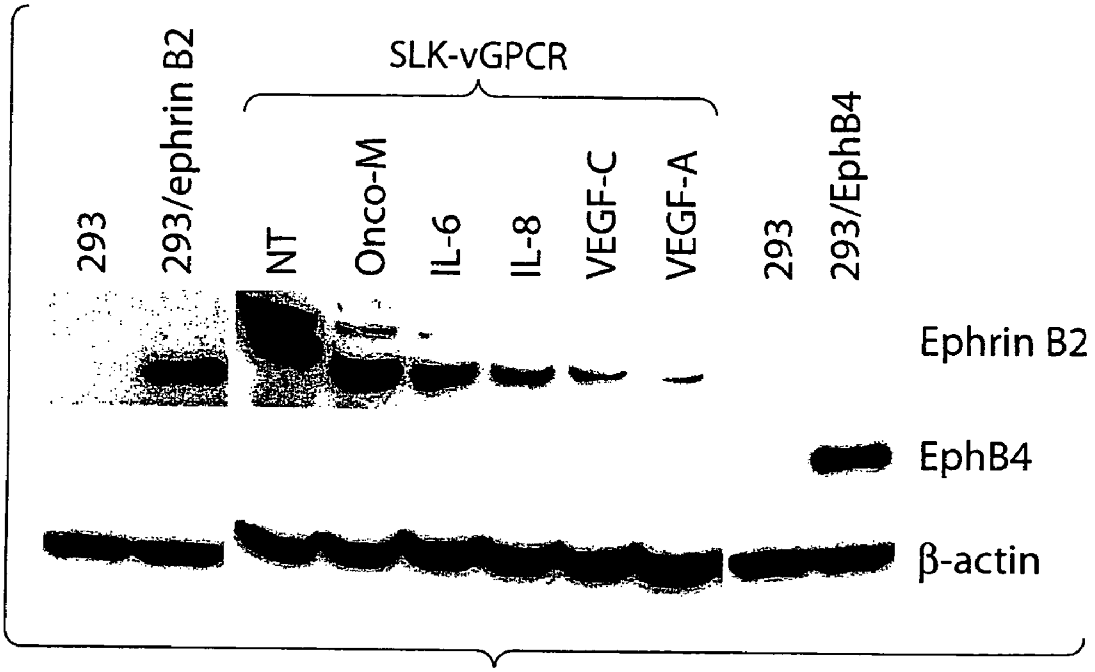
Figure 48B:
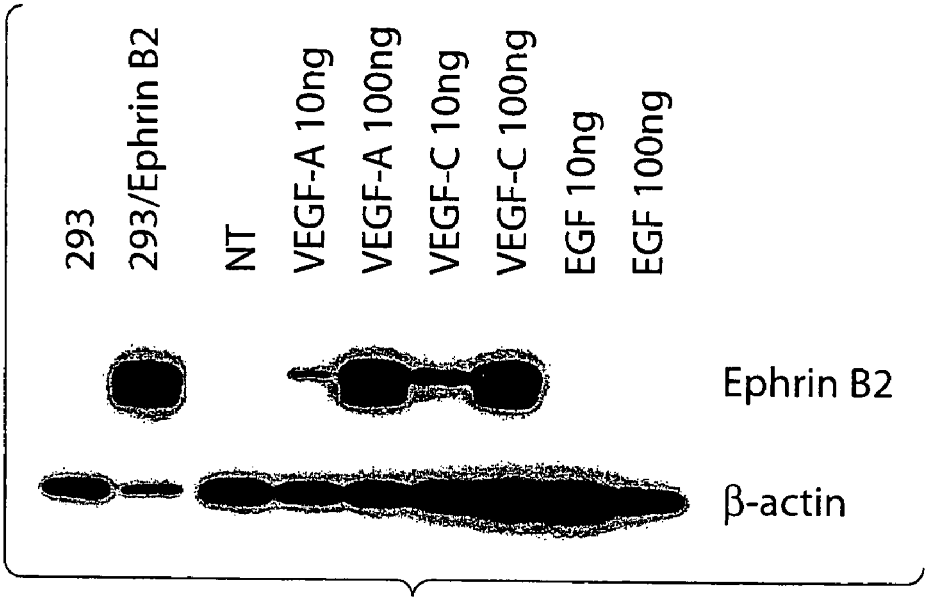

We next asked whether known KS growth factors could be involved in the vGPCR-mediated induction of ephrin B2 expression. SLK-vGPCR cells were treated with neutralizing antibodies to oncostatin-M, IL-6, IL-8, VEGF or VEGF-C for 36 hr. FIG. 48A shows that neutralization of VEGF completely blocked expression of ephrin B2 in SLK-vGPCR cells. A lesser, but significant decrease in ephrin B2 was seen neutralization of VEGF-C and IL-8. No appreciable effect was seen with neutralization of oncostatin-M or IL-6. To verify that VEGF and VEGF-C are integral to the induction of ephrin B2 expression we treated HUVEC with VEGF, VEGF-C or EGF. HUVECs were grown in EBM-2 media containing 5% FBS with two different concentration of individual growth factor (10 ng, 100 ng/ml) for 48 h. Only VEGF-A or VEGF-C induced ephrin B2 expression in a dose dependent manner (FIG. 48B). In contrast, EGF had no effect on expression of ephrin B2.

E. Ephrin B2 siRNA Inhibits the Expression of Ephrin B2 in KS

Figure 49A:
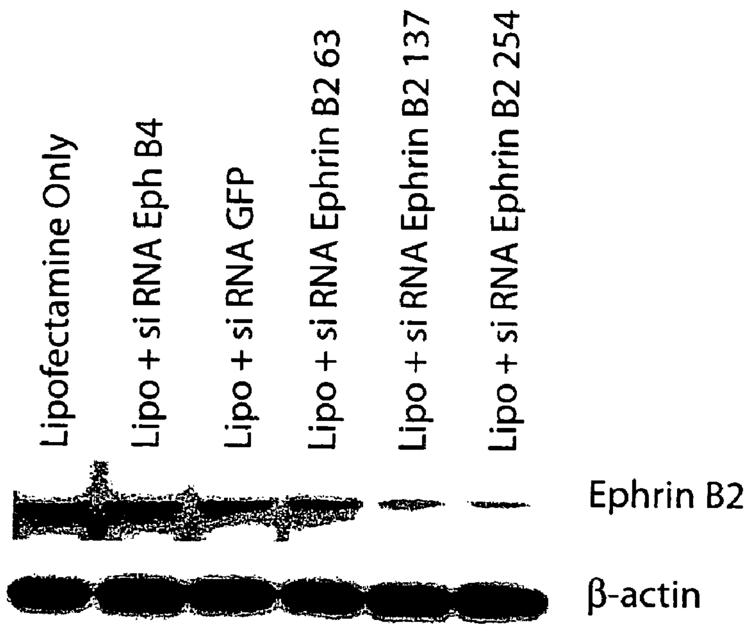

Three ephrin B2 siRNA were synthesized as described in the methods section. KS-SLK cells were transfected with siRNA and 48 h later ephrin B2 expression was determined by Western Blot. Ephrin B2 siRNAs 137 or 254 inhibited about 70% of ephrin B2 expression compared to control siRNA such as siRNA Eph B4 50 or siRNA GFP. Ephrin B2 63 siRNA was less effective than the above two siRNA Ephrin B2 (FIG. 49A).

Figure 49B:
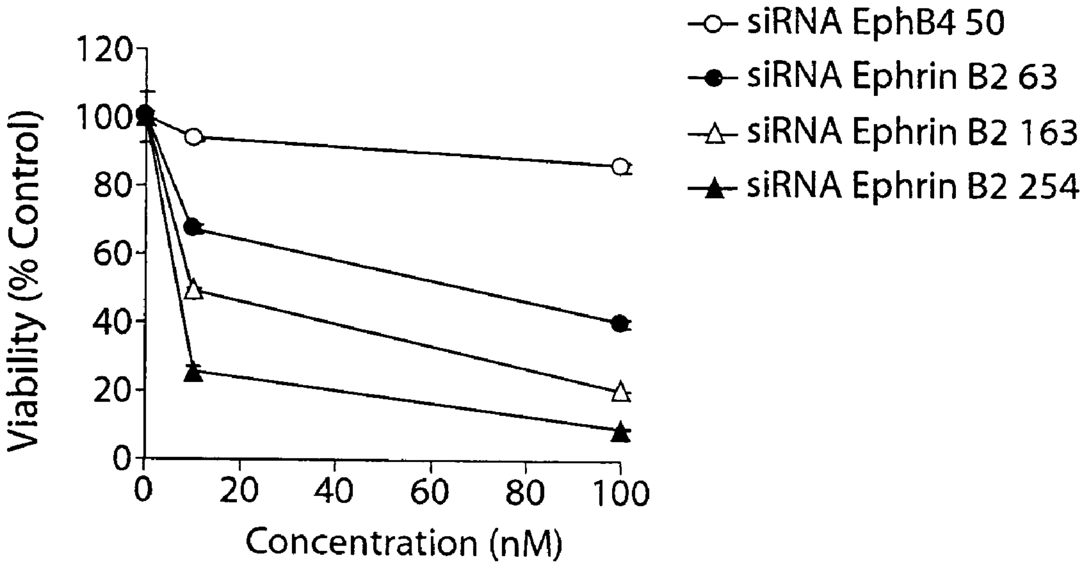
Figure 49C:
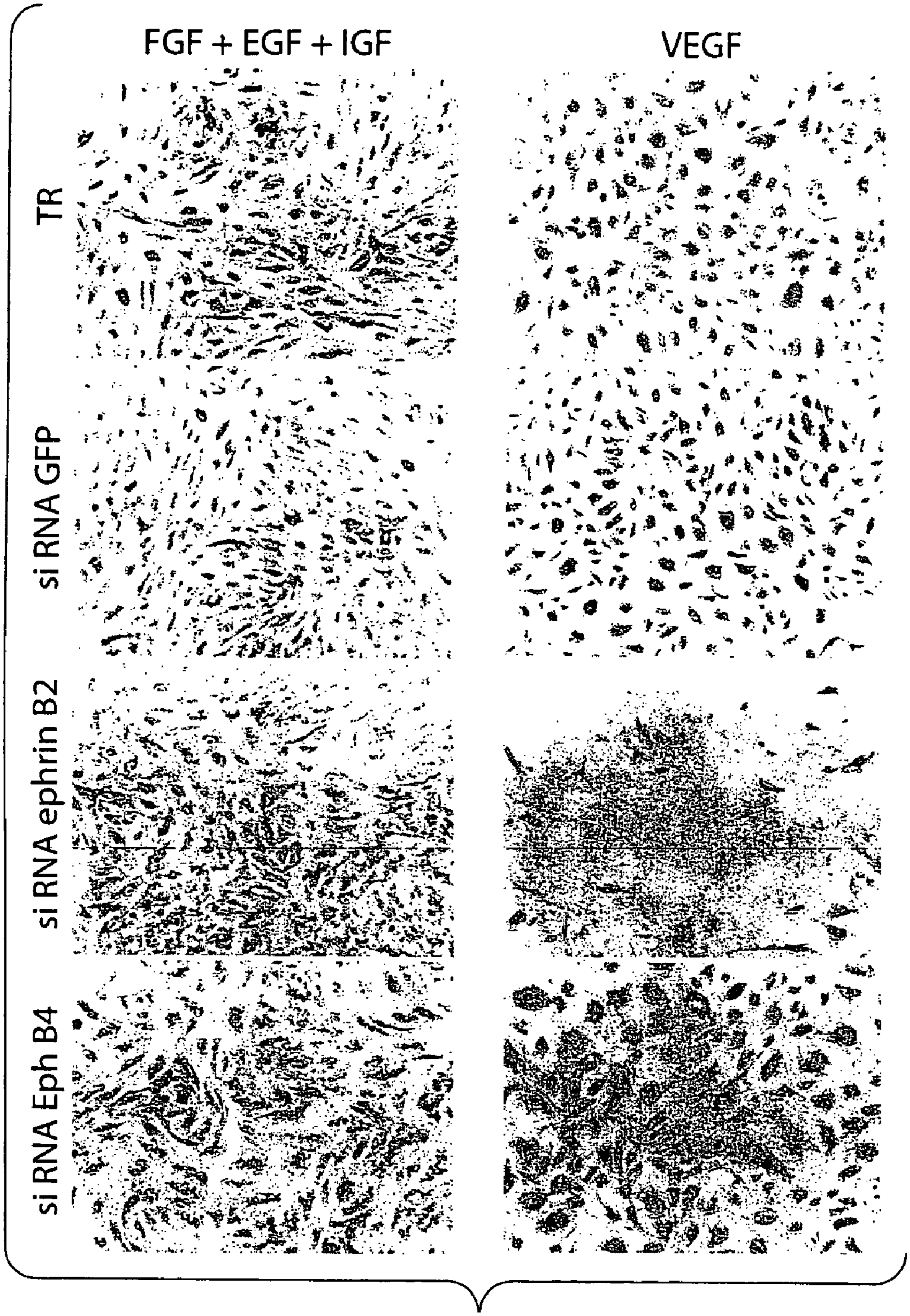

F. Ephrin B2 is Necessary for Full KS and EC Viability, Cord Formation and In Vivo Angiogenesis Activities The most effective ephrin B2 siRNA (254) was then used to determine whether inhibiting expression of ephrin B2 has any effect on the growth of KS-SLK or HUVEC cells. The viability of KS-SLK cells was decreased by the same siRNAs that inhibited ephrin B2 protein levels (FIG. 49B). KS-SLK express high levels of ephrin B2 and this result shows maintenance of ephrin B2 expression is integral to cell viability in this setting. HUVECs do not express ephrin B2, except when stimulated by VEGF as shown in FIG. 48B. Ephrin B2 siRNA 264 dramatically reduced growth of HUVECs cultured with VEGF as the sole growth factor. In contrast, no significant effect was seen when HUVECs were cultured with IGF, EGF and bFGF. As a control, EphB4 siRNA 50 had no detrimental effect on HUVECs in either culture condition (FIG. 49C). In addition to inhibition of viability of KS and primary endothelial cells, EphB4-ECD inhibits cord formation in HUVEC and KS-SLK and in vivo angiogenesis in the Matrigel™ plug assay (FIG. 50).

G. Methods and Materials

1) Cell Lines and Reagents

Human vascular endothelial cells (HUVEC) were from Clonetics (San Diego, Calif.) and were maintained in EGM-2 and EGM-2MV media respectively (Clonetics). T1 human fibroblast line was from Dr. Peter Jones, USC. BC-1 and BC-3 human pleural effusion lymphoma cell lines and monoclonal antibodies to LANA1 and ORF59 were the kind gift of Dr. Dharam Ablashi (Advanced Biotechnologies Inc., Columbia, Md.). KS-SLK was isolated from a Classic Kaposi's sarcoma patient (15). Polyclonal antibodies to EphB4, ephrin B2, CD148, PECAM-1 were obtained from Santa Cruz Biotechnology (Santa Cruz, Calif.). Mouse EphB4/$F_c$' and monoclonal antibodies to human vascular endothelial growth factor (VEGF), VEGF-C, interleukin-(IL)6, IL-8 and oncostatin-M were purchased from R & D Systems (Minneapolis, Minn.). Expression vectors pKSvGPCR-CEFL and pCEFL were the kind gift of Dr. Enrique Mesri (Cornell University, New York, N.Y.). Expression vectors for HHV-8 latency associated nuclear antigen (LANA) were kindly provided by Dr Matthew Rettig, Veteran's Administration Greater Los Angeles Healthcare System.

2) Collection and Preparation of Human Tissue

Human cutaneous Kaposi's sarcoma biopsy material was obtained under local anesthesia with informed consent from patients at the LAC/USC Medical Center, using an IRB approved consent form. Biopsies were processed for either total RNA, paraffin blocks or frozen tissue blocks in OCT. Total RNA was extracted by homogenization in guanidine isothiocyanate, (RNAzol: Tel-Test, Inc., Friendswoods, Tex.). cDNAs were synthesized by reverse transcriptase using a random hexamer primer (Superscript II; Invitrogen, Carlsbad, Calif.).

3) Preparation of Digoxigenin-Labeled RNA Probes

Ephrin B2 and EphB4 PCR products from the primers shown in Table 4 for in situ hybridization were cloned using the pGEM-T Easy system (Promega, Madison Wis.) according to the manufacturer's description using. The authenticity and insert orientation were confirmed by DNA sequencing. The pGEM-T Easy plasmids containing the PCR product of the human ephrin-B2 or EphB4 gene were linearized with Spe I or Nco I. Antisense or sense digoxigenin (DIG)-labeled RNA probes were transcribed from T7 or SP6 promoters by run-off transcription using a DIG RNA labeling kit (Roche, Indianapolis Ind.). RNA probes were quantitated by spot assay as described in the DIG RNA labeling kit instructions.

6) Preparation of cDNA and RT-PCR

The TITANIUM™ One-Step RT-PCR kit (Clontech, Palo Alto, Calif.) was used for RT-PCR from $1\times10^5$ cells. Primer pairs for amplification of EphB4, ephrin B2 and β-actin are shown in Table 4. Each PCR cycle consisted of denaturation at 94° C. for 30 s, primer annealing at 60° C. for 30 s and extension at 72° C. for 30 s. The samples were amplified for 30 cycles. PCR products were separated on 1.5% agarose gels and stained with ethidium bromide.

7) Cell Viability Assay

KS-SLK cells were seeded at a density of $1\times10^4$ per well in 48-well plates on day 0 in appropriate growth media containing 2% fetal calf serum (FCS). On the following day, the media was changed and cells were treated with 0, 10 or 100 nM siRNA. On day 3, viability was assessed using 3-(4,5-dimethylthiazol-2-yl)-2,5-diphenyltetrazolium bromide (MTT) as previously described (17).

8) Immunofluorescence Studies

Cells cultured on Labtech II 4-well chamber slides or frozen sections of KS biopsy material were fixed in 4% paraformaldehyde in Dulbecco's phosphate buffered saline pH 7.4 (PBS) for 30 min. The slides were rinsed twice in PBS and preincubated with blocking buffer (0.2% Triton-X100, 1% BSA in PBS) for 20 min, followed by incubation with antibodies to EphB4, ephrin B2, CD148, LANA1 or ORF59 (1:100 dilution in PBS) in blocking buffer at 4° C. for 16 hr.

TABLE 4

Primers for Ephrin B2 and EphB4.

| Gene | Primer sequence | Product Size (bp) | SEQ. ID NO: |
|---|---|---|---|
| ISH Probe Primers | | | |
| ephrin B2 | 5'-TCC GTG TGG AGT ACT GCT G-3' | 296 | 53 |
| | 5'-TCT GGT TTG GCA CAG TTG AG-3' | | 54 |
| EphB4 | 5'-CTT TGG AAG AGA CCC TGC TG-3' | 297 | 55 |
| | 5'-AGA CGG TGA AGG TCT CCT TG-3' | | 56 |
| RT-PCR Primers | | | |
| ephrin B2 | 5'-AGA CAA GAG CCA TGA AGA TC-3' | 200 | 57 |
| | 5'-GGA TCC CAC TTC GGA CCC GAG-3' | | 58 |
| EphB4 | 5'-TCA GGT CAC TGC ATT GAA CGG G-3' | 400 | 59 |
| | 5'-AAC TCG CTC TCA TCC AGT T-3' | | 60 |
| β-actin | 5'-GTG GGG CGC CCC AGG CAC CA-3' | 546 | 61 |
| | 5'-CTC CTT AAT GTC ACG CAC GAT TTC-3' | | 62 |

4) In Situ Hybridization

See above, e.g., Example 3.

5) Co-Culture of HUVEC and BC-1

HUVEC cells were grown to 50-70% confluence in EGM-2 on gelatin-coated Labtech II 4-well chamber slides (Nalge Nunc International, Naperville, Ill.). Co-culture with BC-1 or BC-3 was essentially as described by Sakurada and coworkers (16). Briefly, BC-1 or BC-3 cells were pretreated with TPA (20 ng/ml) to induce virus for 48 hrs and then added to the HUVEC culture at a ratio of 10:1 for cocultivation for two days. The HUVECs were washed extensively with PBS to remove the attached BC-1 or BC-3 cells.

After washing three times, the slides were incubated with the appropriate fluorescein or rhodamine-conjugated secondary antibodies (Sigma-Aldrich, St. Louis, Mo.). Nuclei were counterstained with 4',6-diamidino-2-phenylindole dihydrochloride hydrate (DAPI), washed extensively with PBS and mounted with Vectasheild antifade mounting solution (Vector Laboratories, Burlingame, Calif.). Images were obtained using a Olympus AX70 fluorescence microscope and Spot v2.2.2 (Diagnostic Instruments Inc., Sterling Heights, Mich.) digital imaging system.

Immunofluorescence detection of EphrinB2 with EPHB4-Fc was done as follows. Frozen sections fixed in 4% paraformaldehyde and blocked with 20% FBS were incubated with 5 μg/ml EphB4/Fc (R&D Systems) for 1 h at RT. Sections were then incubated with 10 μg/ml rabbit anti-human IgG-FITC in PBS (Jackson ImmunoResearch Laboratories West Grove, Pa.) at RT for 1 hour. Nuclei were counterstained with DAPI and sections mounted as above. Human Fc (Jackson ImmunoResearch) was used as the negative control.

9) Western Blot

Crude cell lysates were prepared, quantitated, fractionated and transferred to membranes as described previously (17). Membranes were blocked with 5% non-fat milk prior to incubation with antibody to ephrin B2 (1:5000 dilution) at 4° C., for 16 h. Secondary antibody (1:100,000 dilution) conjugated with horseradish peroxidase was applied for 1 h at 25° C. The membranes were developed using the SuperSignal West Femto Maximum sensitivity chemiluminescent substrate (Pierce, Rockford, Ill.) according to the manufacturer's instructions. Membranes were stripped using Restore™ Western Blot Stripping Buffer (Pierce) and reprobed with EphB4 or actin.

10) Cord Formation Assay

Matrigel™ Basement Membrane Matrix (BD Biosciences Discovery Labware, Bedford, Mass.) was mixed with growth medium (3:1) on ice and 0.5 ml liquid placed in 24-well plates. Incubation of plates at 37° C. for 15 min caused Matrigel™ polymerization. HUVEC or KS-SLK in exponential phase growth were treated with 2 or 8 μg/ml EphB4-ECD or PBS as control for 16 h prior to trypsinizing and plating on the Matrigel™. Culture on Matrigel™ was continued in the presence of recombinant fusion proteins for 6 h. Cultures were fixed in 4% paraformaldehyde for 30 min and evaluated by inverted phase-contrast photomicroscopy.

11) Synthesis of Ephrin B2 and EphB4 siRNA by In Vitro Transcription

The Silencer™ siRNA construction kit (Ambion, Austin Tex.) was used to synthesize siRNA to ephrin B2 and EphB4. Briefly, three 21 bp target sequences comprising 19 bp downstream of a 5'-AA dinucleotide were identified in the ephrin B2 cDNA (Accession number NM_004093) that showed no significant homology to other sequences in the GenBank database. Sense and antisense siRNA 29-mer DNA oligonucleotide templates were synthesized at the USC Norris Microchemical Core Facility. Antisense template corresponded to the target sequence followed by 8 bp addition (5'-CCTGTCTC-3') at the 3' end complementary to the T7 promoter primer provided with the Silencer SiRNA Construction Kit. Sense template comprised 5'-AA followed by the complement of the target 19 bp, then the T7 8 bp sequence as above. In separate reactions, the two siRNA oligonucleotide templates were hybridized to a T7 promoter primer. The 3' ends of the hybridized oligonucleotides were extended-by the Klenow fragment of DNA polymerase to create double-stranded siRNA transcription templates. The sense and antisense siRNA templates were transcribed by T7 RNA polymerase and the resulting RNA transcripts were hybridized to create dsRNA. The dsRNA consisted of 5' terminal single-stranded leader sequences, a 19 nt target specific dsRNA, and 3' terminal UUs. The leader sequences were removed by digesting the dsRNA with a single-stranded specific ribonuclease. The DNA template was removed at the same time by treatment with RNAse free deoxyribonuclease.

The resulting siRNAs were purified by glass fiber filter binding to remove excess nucleotides, short oligomers, proteins, and salts in the reaction. End product double-stranded 21mer siRNAs are shown in Table 5. Similarly, an EphB4 and green fluorescence protein (GFP) siRNAs were synthesized.

TABLE 5

| siRNAs of ephrin B2 and EphB4. | |
|---|---|
| ephrin B2 264 | 5'-GCAGACAGAUGCACUAUUAUU-3'<br>SEQ ID NO: 63 |
| | 3'-UUCGUCUGUCUACGUGAUAAU-5'<br>SEQ ID NO: 64 |
| ephrin B2 63: | 5'-CUGCGAUUUCCAAAUCGAUUU-3'<br>SEQ ID NO: 65 |
| | 3'-UUGACGCUAAAGGUUUAGCUA-5'<br>SEQ ID NO: 66 |
| ephrin B2 137: | 5'-GGACUGGUACUAUACCCACUU-3'<br>SEQ ID NO: 67 |
| | 3'-UUCCUGACCAUGAUAUGGGUG-5'<br>SEQ ID NO: 68 |
| Eph B4 50: | 5'-GAGACCCUGCUGAACACAAUU-3'<br>SEQ ID NO: 69 |
| | 3'-UUCUCUGGGACGACUUGUGUU-5'<br>SEQ ID NO: 70 |
| GFP | 5'-CGCUGACCCUGAAGUUCAUUU-3'<br>SEQ ID NO: 71 |
| | 3'-UUGCGACUGGGACUUCAAGUA-5'<br>SEQ ID NO: 72 |

12) Transfection of Ephrin B2 or EphB4 siRNA

HUVEC were seeded on eight-well chamber slides coated with fibronectin and grown overnight in EGM-2 (Cambrex, Walkersville, Md.). 16 h later media was replaced either with EBM-2 supplemented with 5% fetal calf serum (FCS) and EGM-2 BulletKit supplements bFGF, hEGF and $R^3$-IGF-I at the concentrations provided by the manufacturer, or EBM-2 supplemented with 5% FCS and 10 ng/ml rhVEGF (R&D Systems). After 2 h incubation at 37° C., the cells were transfected using Lipofectamine 2000 (1 μg/ml; Invitrogen) and 10 nM specific siRNAs in Opti-MEM-1 serum-free medium (Invitrogen). Following transfection for 2 hr in Opti-MEM-1, media supplemented as above was replaced in the appropriate wells. After 48 hrs, the cells were stained with crystal violet and immediately photographed at 10× magnification.

13) Construction of Ephrin B2 Reporter Plasmids

Human ephrin B2 5'-flanking DNA from −2491 to −11 with respect to the translation start site was amplified from BACPAC clone RP11-297I6 (BacPac Resources, Children's Hospital, Oakland, Calif.) using the Advantage GC Genomic PCR kit (Clontech Palo Alto, Calif.) to overcome the large tracts of CG-rich sequence in the target area. Primers were designed to contain MluI sites for cloning. Amplified product was digested with MluI, gel purified and ligated into the MluI site in the multiple cloning site of pGL3Basic (Promega, Madison, Wis.). Orientation of the resulting clones was confirmed by restriction digest analysis. The correct clone was designated pEFNB2$_{-2491/-11}$luc. Digestion of this clone with either KpnI or SacI followed by recircularization yielded pEFNB2$_{-1242/-11}$luc and pEFNB2$_{-577/-11}$luc, respectively. Plasmid DNAs used for transient transfections were purified using a Mega Prep kit (QIAGEN, Valencia, Calif.).

14) Transient Transfection

HUVEC cells (0.8×$10^4$ cells/well in 24 well plates) maintained in EGM-2 media were transiently co-transfected with 0.5 μg/well ephrin B2 promoter-luciferase constructs together with 50 ng/well either pCEFL or pKSvGPCR-CEFL, using Superfect reagent (QIAGEN) according to the manufacturer's instructions. Cells were harvested 48 h post-transfection and lysed with Luciferase cell lysis buffer (Promega). Luciferase activity was assayed using the Luciferase Assay System (Promega) according to the manufacturer's instructions. Luciferase was normalized to protein, because pCEFL-vGPCR induced the expression of β-galactosidase from pCMV-Sport-βgal (Invitrogen).

15) Construction and Purification of EphB4 Extra Cellular Domain (ECD) Protein

See above, e.g., Example 1.

Example 7

Expression of EphB4 in Bladder Cancer: a Candidate Target for Therapy

FIG. 51 shows expression of EPHB4 in bladder cancer cell lines (A), and regulation of EPHB4 expression by EGFR signaling pathway (B).

FIG. 52 shows that transfection of p53 inhibit the expression of EPHB4 in 5637 cell.

FIG. 53 shows growth inhibition of bladder cancer cell line (5637) upon treatment with EPHB4 siRNA 472.

FIG. 54 shows results on apoptosis study of 5637 cells transfected with EPHB4 siRNA 472.

FIG. 55 shows effects of EPHB4 antisense probes on cell migration. 5637 cells were treated with EPHB4AS10 (10 μM).

FIG. 56 shows effects of EPHB4 siRNA on cell invasion. 5637 cells were transfected with siRNA 472 or control siRNA.

Example 8

Inhibition of EphB4 Gene Expression by EphB4 Antisense Probes and RNAi Probes

Cell lines expressing EphB4 were treated with the synthetic phosphorothioate modified oligonucleotides and harvested after 24 hr. Cell lysates were prepared and probed by western blot analysis for relative amounts of EphB4 compared to untreated control cells.

Studies on inhibition of cell proliferation were done in HNSCC cell lines characterized to express EphB4. Loss of cell viability was shown upon knock-down of EphB4 expression. Cells were treated in vitro and cultured in 48-well plates, seeded with 10 thousand cells per well. Test compounds were added and the cell viability was tested on day 3. The results on EphB4 antisense probes were summarized below in Table 6. The results on EphB4 RNAi probes were summarized below in Table 7.

TABLE 6

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 169 | TCA GTA CTG CGG GGC CGG TCC | (2944-2963) | ++ | 36 | 73 |
| Eph B4 168 | TCC TGT CCC ACC CGG GGT TC | (2924-2943) | ++ | 51 | 74 |
| Eph B4 167 | CCG GCT TGG CCT GGG ACT TC | (2904-2923) | +++ | 66 | 75 |
| Eph B4 166 | ATG TGC TGG ACA CTG GCC AA | (2884-2903) | ++++ | 70 | 76 |
| Eph B4 165 | GAT TTT CTT CTG GTG TCC CG | (2864-2883) | ++++ | 75 | 77 |
| Eph B4 164 | CCA GAG TGA CTC CGA TTC GG | (2844-2863) | ++ | 40 | 78 |
| Eph B4 163 | AGC AGG TCC TCA GCA GAG AT | (2824-2843) | ++++ | 66 | 79 |
| Eph B4 162 | CTG GCT GAC CAG CTC GAA GG | (2804-2823) | | 25 | 80 |
| Eph B4 161 | AGC CAA AGC CAG CGG CTG CG | (2784-2803) | + | 33 | 81 |
| Eph B4 160 | AAA CTT TCT TCG TAT CTT CC | (2763-2783) | + | 25 | 82 |
| Eph B4 159 | CAT TTT GAT GGC CCG AAG CC | (2743-2762) | ++ | 40 | 83 |
| Eph B4 158 | ACT CGC CCA CAG AGC CAA AA | (2723-2742) | | 30 | 84 |
| Eph B4 157 | GCT GAG TAG TGA GGC TGC CG | (2703-2722) | + | 25 | 85 |
| Eph B4 156 | CTG GTC CAG GAG AGG GTG TG | (2683-2702) | ++ | 30 | 86 |
| Eph B4 155 | AGG CCC CGC CAT TCT CCC GG | (2663-2682) | | 25 | 87 |
| Eph B4 154 | GCC ACG ATT TTG AGG CTG GC | (2643-2662) | ++ | 40 | 88 |
| Eph B4 153 | GGG GTT CCG GAT CAT CTT GT | (2623-2642) | ++ | 35 | 89 |
| Eph B4 152 | CCA GGG CGC TGA CCA CCT GG | (2603-2622) | + | 30 | 90 |
| Eph B4 151 | GGG AAG CGG GGC CGG GCA TT | (2583-2602) | + | 25 | 91 |
| Eph B4 150 | CCG GTC TTT CTG CCA ACA GT | (2563-2582) | ++ | 25 | 92 |

TABLE 6-continued

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 149 | CCA GCA TGA GCT GGT GGA GG | (2543-2562) | ++ | 20 | 93 |
| Eph B4 148 | GAG GTG GGA CAG TCT GGG GG | (2523-2542) | + | 30 | 94 |
| Eph B4 147 | CGG GGG CAG CCG GTA GTC CT | (2503-2522) | ++ | 40 | 95 |
| Eph B4 146 | GTT CAA TGG CAT TGA TCA CG | (2483-2502) | ++++ | 70 | 96 |
| Eph B4 145 | TCC TGA TTG CTC ATG TCC CA | (2463-2482) | ++++ | 80 | 97 |
| Eph B4 144 | GTA CGG CCT CTC CCC AAA TG | (2443-2462) | +++ | 60 | 98 |
| Eph B4 143 | ACA TCA CCT CCC ACA TCA CA | (2423-2442) | ++++ | 80 | 99 |
| Eph B4 142 | ATC CCG TAA CTC CAG GCA TC | (2403-2422) | ++ | 40 | 100 |
| Eph B4 141 | ACT GGC GGA AGT GAA CTT CC | (2383-2402) | +++ | 50 | 101 |
| Eph B4 140 | GGA AGG CAA TGG CCT CCG GG | (2363-2382) | ++ | 45 | 102 |
| Eph B4 139 | GCA GTC CAT CGG ATG GGA AT | (2343-2362) | ++++ | 70 | 103 |
| Eph B4 138 | CTT TCC TCC CAG GGA GCT CG | (2323-2342) | ++++ | 70 | 104 |
| Eph B4 137 | TGT AGG TGG GAT CGG AAG AG | (2303-2322) | ++ | 40 | 105 |
| Eph B4 136 | TTC TCC TCC AGG AAT CGG GA | (2283-2302) | ++ | 35 | 106 |
| Eph B4 135 | AAG GCC AAA GTC AGA CAC TT | (2263-2282) | ++++ | 60 | 107 |
| Eph B4 134 | GCA GAC GAG GTT GCT GTT GA | (2243-2262) | ++ | 50 | 108 |
| Eph B4 133 | CTA GGA TGT TGC GAG CAG CC | (2223-2242) | ++ | 40 | 109 |
| Eph B4 132 | AGG TCT CGG TGG ACG TAG CT | (2203-2222) | ++ | 40 | 110 |
| Eph B4 131 | CAT CTC GGC AAG GTA CCG CA | (2183-2202) | +++ | 50 | 111 |
| Eph B4 130 | TGC CCG AGG CGA TGC CCC GC | (2163-2182) | ++ | 50 | 112 |
| Eph B4 129 | AGC ATG CCC ACG AGC TGG AT | (2143-2162) | ++ | 50 | 113 |
| Eph B4 128 | GAC TGT GAA CTG TCC GTC GT | (2123-2142) | ++ | 50 | 114 |
| Eph B4 127 | TTA GCC GCA GGA AGG AGT CC | (2103-2122) | +++ | 60 | 115 |
| Eph B4 126 | AGG GCG CCG TTC TCC ATG AA | (2083-2102) | ++ | 50 | 116 |
| Eph B4 125 | CTC TGT GAG AAT CAT GAC GG | (2063-2082) | ++++ | 80 | 117 |
| Eph B4 124 | GCA TGC TGT TGG TGA CCA CG | (2043-2062) | ++++ | 70 | 118 |
| Eph B4 123 | CCC TCC AGG CGG ATG ATA TT | (2023-2042) | ++ | 50 | 119 |
| Eph B4 122 | GGG GTG CTC GAA CTG GCC CA | (2003-2022) | ++++ | 80 | 120 |
| Eph B4 121 | TGA TGG AGG CCT CGC TCA GA | (1983-2002) | ++ | 50 | 121 |
| Eph B4 120 | AAC TCA CGC CGC TGC CGC TC | (1963-1982) | ++ | 40 | 122 |
| Eph B4 119 | CGT GTA GCC ACC CTT CAG GG | (1943-1962) | ++++ | 75 | 123 |
| Eph B4 118 | TCT TGA TTG CCA CAC AGC TC | (1923-1942) | ++++ | 80 | 124 |
| Eph B4 117 | TCC TTC TTC CCT GGG GCC TT | (1903-1922) | ++++ | 70 | 125 |
| Eph B4 116 | GAG CCG CCC CCG GCA CAC CT | (1883-1902) | ++ | 50 | 126 |
| Eph B4 115 | CGC CAA ACT CAC CTG CAC CA | (1863-1882) | ++++ | 60 | 127 |
| Eph B4 114 | ATC ACC TCT TCA ATC TTG AC | (1843-1862) | ++++ | 65 | 128 |

TABLE 6-continued

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 113 | GTA GGA GAC ATC GAT CTC TT | (1823-1842) | ++++ | 90 | 129 |
| Eph B4 112 | TTG CAA ATT CCC TCA CAG CC | (1803-1822) | ++++ | 70 | 130 |
| Eph B4 111 | TCA TTA GGG TCT TCA TAA GT | (1783-1802) | ++++ | 70 | 131 |
| Eph B4 110 | GAA GGG GTC GAT GTA GAC CT | (1763-1782) | ++++ | 80 | 132 |
| Eph B4 109 | TAG TAC CAT GTC CGA TGA GA | (1743-1762) | ++ | 50 | 133 |
| Eph B4 108 | TAC TGT CCG TGT TTG TCC GA | (1723-1742) | ++ | 45 | 134 |
| Eph B4 107 | ATA TTC TGC TTC TCT CCC AT | (1703-1722) | ++++ | 70 | 135 |
| Eph B4 106 | TGC TCT GCT TCC TGA GGC AG | (1683-1702) | ++++ | 70 | 136 |
| Eph B4 105 | AGA ACT GCG ACC ACA ATG AC | (1663-1682) | ++ | 40 | 137 |
| Eph B4 104 | CAC CAG GAC CAG GAC CAC AC | (1643-1662) | ++++ | 70 | 138 |
| Eph B4 103 | CCA CGA CTG CCG TGC CCG CA | (1623-1642) | ++ | 40 | 139 |
| Eph B4 102 | ATC AGG GCC AGC TGC TCC CG | (1603-1622) | +++ | 50 | 140 |
| Eph B4 101 | CCA GCC CTC GCT CTC ATC CA | (1583-1602) | ++++ | 80 | 141 |
| Eph B4 100 | GTT GGG TCT GGC TGT GAT GT | (1563-1582) | ++++ | 80 | 142 |
| Eph B4 99 | TCC TGG CCG AAG GGC CCG TA | (1543-1562) | ++ | 35 | 143 |
| Eph B4 98 | GCC GGC CTC AGA GCG CGC CC | (1523-1542) | ++ | 50 | 144 |
| Eph B4 97 | GTA CCT GCA CCA GGT AGC TG | (1503-1522) | ++++ | 80 | 145 |
| Eph B4 96 | GCT CCC CGC TTC AGC CCC CG | (1483-1502) | ++ | 50 | 146 |
| Eph B4 95 | CAG CTC TGC CCG GTT TTC TG | (1463-1482) | ++ | 50 | 147 |
| Eph B4 94 | ACG TCT TCA GGA ACC GCA CG | (1443-1462) | ++++ | 80 | 148 |
| Eph B4 93 | CTG CTG GGA CCC TCG GCG CC | (1423-1442) | ++ | 40 | 149 |
| Eph B4 92 | CTT CTC ATG GTA TTT GAC CT | (1403-1422) | ++++ | 80 | 150 |
| Eph B4 91 | CGT AGT CCA GCA CAG CCC CA | (1383-1402) | ++++ | 85 | 151 |
| Eph B4 90 | CTG GGT GCC CGG GGA ACA GC | (1363-1382) | +++ | 50 | 152 |
| Eph B4 89 | CCA GGC CAG GCT CAA GCT GC | (1343-1462) | ++++ | 70 | 153 |
| Eph B4 88 | TGG GTG AGG ACC GCG TCA CC | (1323-1342) | ++ | 40 | 154 |
| Eph B4 87 | CGG ATG TCA GAC ACT GCA GG | (1303-1322) | ++++ | 60 | 155 |
| Eph B4 86 | AGG TAC CTC TCG GTC AGT GG | (1283-1302) | ++ | 50 | 156 |
| Eph B4 85 | TGA CAT TGA CAG GCT CAA AT | (1263-1282) | ++++ | 80 | 157 |
| Eph B4 84 | GGG ACG GGC CCC GTG GCT AA | (1243-1262) | ++ | 50 | 158 |
| Eph B4 83 | GGA GGA TAC CCC GTT CAA TG | (1223-1242) | +++ | 60 | 159 |
| Eph B4 82 | CAG TGA CCT CAA AGG TAT AG | (1203-1222) | ++++ | 70 | 160 |
| Eph B4 81 | GTG AAG TCA GGA CGT AGC CC | (1183-1202) | +++ | 60 | 161 |
| Eph B4 80 | TCG AAC CAC CAC CCA GGG CT | (1163-1182) | +++ | 50 | 162 |
| Eph B4 79 | CCA CCA GGT CCC GGG GGC CG | (1143-1162) | ++ | 40 | 163 |
| Eph B4 78 | GGG TCA AAA GTC AGG TCT CC | (1123-1142) | ++++ | 70 | 164 |

TABLE 6-continued

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 77 | CCC GCA GGG CGC ACA GGA GC | (1103-1122) | +++ | 60 | 165 |
| Eph B4 76 | CTC CGG GTC GGC ACT CCC GG | (1083-1102) | +++ | 60 | 166 |
| Eph B4 75 | CAG CGG AGG GCG TAG GTG AG | (1063-1082) | ++ | 40 | 167 |
| Eph B4 74 | GTC CTC TCG GCC ACC AGA CT | (1043-1062) | ++ | 50 | 168 |
| Eph B4 73 | CCA GGG GGG CAC TCC ATT CC | (1023-1042) | ++ | 50 | 169 |
| Eph B4 72 | AGG TGC AGG GAG GAG CCG TT | (1003-1022) | ++++ | 70 | 170 |
| Eph B4 71 | CAG GCG GGA AAC CAC GCT CC | (983-1002) | ++ | 40 | 171 |
| Eph B4 70 | GCG GAG CCG AAG GAG GGG TG | (963-982) | +++ | 50 | 172 |
| Eph B4 69 | GTG CAG GGT GCA CCC CGG GG | (943-962) | +++ | 50 | 173 |
| Eph B4 68 | GTC TGT GCG TGC CCG GAA GT | (923-942) | ++ | 40 | 174 |
| Eph B4 67 | ACC CGA CGC GGC ACT GGC AG | (903-922) | ++ | 40 | 175 |
| Eph B4 66 | ACG GCT GAT CCA ATG GTG TT | (883-902) | ++ | 50 | 176 |
| Eph B4 65 | AGA GTG GCT ATT GGC TGG GC | (863-882( | ++++ | 60 | 177 |
| Eph B4 64 | ATG GCT GGC AGG ACC CTT CT | (843-862) | ++++ | 80 | 178 |
| Eph B4 63 | CCT GAC AGG GGC TTG AAG GT | (823-842) | ++++ | 80 | 179 |
| Eph B4 62 | GCC CTG GGC ACA GGC TCG GC | (803-822) | +++ | 70 | 180 |
| Eph B4 61 | ACT TGG TGT TCC CCT CAG CT | (783-802) | ++++ | 80 | 181 |
| Eph B4 60 | GCC TCG AAC CCC GGA GCA CA | (763-782) | +++ | 50 | 182 |
| Eph B4 59 | GCT GCA GCC CGT GAC CGG CT | (743-762) | +++ | 50 | 183 |
| Eph B4 58 | GTT CGG CCC ACT GGC CAT CC | (723-742) | ++ | 45 | 184 |
| Eph B4 57 | TCA CGG CAG TAG AGG CTG GG | (703-722) | +++ | 70 | 185 |
| Eph B4 56 | GCT GGG GCC AGG GGC GGG GA | (683-702) | ++ | 50 | 186 |
| Eph B4 55 | CGG CAT CCA CCA CGC AGC TA | (663-682) | ++ | 50 | 187 |
| Eph B4 54 | CCG GCC ACG GGC ACA ACC AG | (643-662) | ++ | 50 | 188 |
| Eph B4 53 | CTC CCG AGC CAC AGT CTC CG | (623-642) | +++ | 50 | 189 |
| Eph B4 52 | GGA ATC GAG TCA GGT TCA CA | (603-622) | ++++ | 90 | 190 |
| Eph B4 51 | GTC AGC TGC GCG CAC TTT TT | (583-602) | +++ | 70 | 191 |
| Eph B4 50 | GTA GAA GAG GTG CAG CGA TA | (563-582) | ++++ | 80 | 192 |
| Eph B4 49 | GCA GGG CCA TGC AGC CAC CC | (543-562) | ++++ | 80 | 193 |
| Eph B4 48 | TGG TCC TGG AAG GCC AGG TA | (523-542) | ++++ | 90 | 194 |
| Eph B4 47 | GAA GCC AGC CTT GCT GAG CG | (503-522) | ++++ | 80 | 195 |
| Eph B4 46 | GTC CCA GAC GCA GCG TCT TG | (483-502) | ++ | 40 | 196 |
| Eph B4 45 | ACA TTC ACC TTC CCG GTG GC | (463-482) | +++ | 50 | 197 |
| Eph B4 44 | CTC GGC CCC AGC GCG CTT CC | (443-462) | ++ | 50 | 198 |
| Eph B4 43 | GGG TGA GAT GCT CCG CGG CC | (423-442) | +++ | 60 | 199 |
| Eph B4 42 | ACC GTG TCC ACC TTG ATG TA | (403-422) | ++++ | 80 | 200 |

TABLE 6-continued

Inhibition of EphB4 Gene Expression by EphB4 antisense probes

| Name | Sequence 5' → 3' | position | Inhibition of EphB4 Expression | Percent reduction in viability | SEQ ID NO: |
|---|---|---|---|---|---|
| Eph B4 41 | GGG GTT CTC CAT CCA GGC TG | (383-402) | ++++ | 80 | 201 |
| Eph B4 40 | GCG TGA GGG CCG TGG CCG TG | (363-382) | ++ | 50 | 202 |
| Eph B4 39 | TCC GCA TCG CTC TCA TAG TA | (343-362) | +++ | 60 | 203 |
| Eph B4 38 | GAA GAC GCT GAA GGT CTC CT | (323-342) | ++++ | 80 | 204 |
| Eph B4 37 | TGC AGG AGC GCC CAG CCC GA | (303-322) | +++ | 50 | 205 |
| Eph B4 36 | GGC AGG GAC AGG CAC TCG AG | (283-302) | +++ | 45 | 206 |
| Eph B4 35 | CAT GGT GAA GCG CAG CGT GG | (263-282) | ++ | 50 | 207 |
| Eph B4 34 | CGT ACA CGT GGA CGG CGC CC | (243-262) | ++ | 40 | 208 |
| Eph B4 33 | CGC CGT GGG ACC CAA CCT GT | (223-242) | +++ | 60 | 209 |
| Eph B4 32 | GCG AAG CCA GTG GGC CTG GC | (203-222) | ++++ | 70 | 210 |
| Eph B4 31 | CCG GGG CAC GCT GCA CGT CA | (183-202) | +++ | 60 | 211 |
| Eph B4 30 | CAC ACT TCG TAG GTG CGC AC | (163-182) | +++ | 70 | 212 |
| Eph B4 29 | GCT GTG CTG TTC CTC ATC CA | (143-162) | ++++ | 80 | 213 |
| Eph B4 28 | GGC CGC TCA GTT CCT CCC AC | (123-142) | ++ | 40 | 214 |
| Eph B4 27 | TGC CCG TCC ACC TGA GGG AA | (103-122) | ++ | 50 | 215 |
| Eph B4 26 | TGT CAC CCA CTT CAG ATC AG | (83-102) | ++++ | 70 | 216 |
| Eph B4 25 | CAG TTT CCA ATT TTG TGT TC | (63-82) | ++++ | 70 | 217 |
| Eph B4 24 | AGC AGC GTC TCT TCC AAA GC | (43-62) | ++++ | 80 | 218 |
| Eph B4 23 | TGC GGC CAA CGA AGC CCA GC | (23-42) | ++ | 50 | 219 |
| Eph B4 22 | AGA GCA GCA CCC GGA GCT CC | (3-22) | +++ | 50 | 220 |
| Eph B4 21 | AGC AGC ACC CGC AGC TCC AT | (1-20) | +++ | 50 | 221 |
| | Additional antisense probes described in the specification | | | | |
| EphB4 AS-1 | GTG CAG GGA TAG CAG GCC CAT | (552-572) | | | 222 |
| EphB4 AS-2 | AAG GAG GCG TGG TGC ACG GTG | (952-972) | | | 223 |
| EphB4 AS-3 | TTC CAG GTG CAG GGA GGA GCC | (1007-1027) | | | 224 |
| EphB4 AS-4 | GTG GTG ACA TTG ACA GCC TCA | (1263-1285) | | | 225 |
| EphB4 AS-5 | TCT GGC TGT GAT GTT CCT GGC | (1555-1575) | | | 226 |
| EphB4 AS-6 | GCC GCT CAG TTC CTC CCA | (123-140) | | | 227 |
| EphB4 AS-7 | TGA AGC TCT CCT TGC AGG | (316-333) | | | 228 |
| EphB4 AS-8 | CGC GGC CAC CGT GTC CAC CTT | (408-428) | | | 229 |
| EphB4 AS-9 | CTT CAG GCT CTT GAT TGC CAC | (1929-1949) | | | 230 |
| EphB4 AS-10 | ATG GAG GCC TCG CTC AGA AA | (1980-1999) | | | 231 |
| Ephb4 AS-11 | CAT GCC CAC GAG CTG GAT GAC | (2138-2158) | | | 232 |

TABLE 7

Inhibition of EphB4 Gene Expression by EphB4 RNAi probes

| RNAi | | EphB4 RNAi sequence | | Inhibition of EphB4 Expression | Percent reduction in viability | SEQ ID NO: |
|---|---|---|---|---|---|---|
| 1 | 446 | aaattggaaactgctgatctg | 466 | | | 233 |
| 2 | 447 | aattggaaactgctgatctga | 467 | +++ | 70 | 234 |
| 3 | 453 | aaactgctgatctgaagtggg | 473 | ++++ | 70 | 235 |
| 4 | 454 | aactgctgatctgaagtgggt | 474 | +++ | 80 | 236 |
| 5 | 854 | aatgtcaagacgctgcgtctg | 874 | +++ | 65 | 237 |
| 6 | 467 | aagtgggtgacattccctcag | 487 | + | 35 | 238 |
| 7 | 848 | aaggtgaatgtcaagacgctg | 868 | ++ | 50 | 239 |
| 8 | 698 | aaggagaccttcaccgtcttc | 718 | +++ | 75 | 240 |
| 9 | 959 | aaaaagtgcgcccagctgact | 979 | + | 40 | 241 |
| 10 | 1247 | aatagccactctaacaccatt | 1267 | ++ | 50 | 242 |
| 11 | 1259 | aacaccattggatcagccgtc | 1279 | ++ | 50 | 243 |
| 12 | 1652 | aatgtcaccactgaccgagag | 1672 | + | 35 | 244 |
| 13 | 1784 | aaataccatgagaagggcgcc | 1804 | +++ | 65 | 245 |
| 14 | 1832 | aagacgtcagaaaaccgggca | 1852 | + | 30 | 246 |
| 15 | 1938 | aacatcacagccagacccaac | 19 | ++ | 50 | 247 |
| 16 | 2069 | aagcagagcaatgggagagaa | 2089 | ++++ | 75 | 248 |
| 17 | 2078 | aatgggagagaagcagaatat | 2098 | +++ | 65 | 249 |
| 18 | 2088 | aagcagaatattcggacaaac | 2108 | +++ | 70 | 250 |
| 19 | 2094 | aatattcggacaaacacggac | 2114 | ++ | 40 | 251 |
| 20 | 2105 | aaacacggacagtatctcatc | 2125 | ++ | 50 | 252 |
| 21 | 2106 | aacacggacagtatctcatcg | 2126 | + | 35 | 253 |
| 22 | 2197 | aaaagagatcgatgtctccta | 2217 | +++ | 65 | 254 |
| 23 | 2174 | aatgaggctgtgagggaattt | 2194 | ++ | 50 | 255 |
| 24 | 2166 | aagaccctaatgaggctgtga | 2186 | ++ | 50 | 256 |
| 25 | 2198 | aaagagatcgatgtctcctac | 2218 | +++ | 55 | 257 |
| 26 | 2199 | aagagatcgatgtctcctacg | 2219 | +++ | 70 | 258 |
| 27 | 2229 | aagaggtgattggtgcaggtg | 2249 | + | 33 | 259 |
| 28 | 2222 | aagattgaagaggtgattggt | 2242 | + | 30 | 260 |
| 29 | 2429 | aacagcatgcccgtcatgatt | 2449 | ++ | 40 | 261 |
| 30 | 2291 | aagaaggagagctgtgtggca | 2311 | +++ | 50 | 262 |
| 31 | 2294 | aaggagagctgtgtggcaatc | 2314 | +++ | 60 | 263 |
| 32 | 2311 | aatcaagaccctgaagggtgg | 2331 | +++ | 70 | 264 |
| 33 | 2497 | aaacgacggacagttcacagt | 2517 | + | 35 | 265 |

TABLE 7-continued

Inhibition of EphB4 Gene Expression by EphB4 RNAi probes

| RNAi | EphB4 RNAi sequence | | | Inhibition of EphB4 Expression | Percent reduction in viability | SEQ ID NO: |
|---|---|---|---|---|---|---|
| 34 | 2498 | aacgacggacagttcacagtc | 2518 | + | 40 | 266 |
| 35 | 2609 | aacatcctagtcaacagcaac | 2629 | ++ | 50 | 267 |
| 36 | 2621 | aacagcaacctcgtctgcaaa | 2641 | + | 35 | 268 |
| 37 | 2678 | aactcttccgatcccacctac | 2698 | ++ | 50 | 269 |
| 38 | 2640 | aagtgtctgactttggccttt | 2660 | +++ | 70 | 270 |
| 39 | 2627 | aacctcgtctgcaaagtgtct | 2647 | ++ | 50 | 271 |
| 40 | 2639 | aaagtgtctgactttggcctt | 2659 | + | 25 | 272 |
| 41 | 2852 | aatcaggacgtgatcaatgcc | 2872 | +++ | 75 | 273 |
| 42 | 2716 | aaagattcccatccgatggac | 2736 | ++ | 50 | 274 |
| 43 | 2717 | aagattcccatccgatggact | 2737 | ++ | 60 | 275 |
| 44 | 2762 | aagttcacttccgccagtgat | 2782 | +++ | 70 | 276 |
| 45 | 3142 | aagatacgaagaaagtttcgc | 3162 | ++ | 50 | 277 |
| 46 | 3136 | aatgggaagatacgaagaaag | 3156 | +++ | 66 | 278 |
| 47 | 2867 | aatgccattgaacaggactac | 2887 | | | 279 |
| 48 | 3029 | aaaatcgtggcccgggagaat | 3049 | + | 33 | 280 |
| 49 | 3254 | aaaatcttggccagtgtccag | 3274 | ++ | 50 | 281 |
| 50 | 3255 | aaatcttggccagtgtccagc | 3275 | +++ | 75 | 282 |
| 51 | 3150 | aagaaagtttcgcagccgctg | 3170 | +++ | 80 | 283 |
| 52 | 3251 | aagaaaatcttggccagtgtc | 3271 | ++ | 50 | 284 |
| 53 | 3256 | aatcttggccagtgtccagca | 3276 | ++ | 50 | 285 |

Additional RNAi probes described in the specification

| | | |
|---|---|---|
| Eph B4 50 | gagacccugcugaacacaauu | 286 |
| Eph B4 472 | ggugaaugucaagacgcuguu | 287 |
| Eph B4 1562 | caucacagccagacccaacuu | 288 |
| siRNA 2303 | cucuuccgaucccaccuacuu | 289 |
| Eph B4 2302 | cucuuccgaucccaccuacuu | 290 |

Example 9

Inhibition of Ephrin B2 Gene Expression by Ephrin B2 Antisense Probes and RNAi Probes KS SLK, a cell line expressing endogenous high level of ephrin B2. Cell viability was tested using fixed dose of each oligonuceotide (5UM). Gene expression downregulation was done using cell line 293 engineered to stably express full-length ephrin B2. KS SLK expressing EphrinB2 were also used to test the viability in response to RNAi probes tested at the fixed dose of 50 nM. Protein expression levels were measured using 293 cells stably expressing full-length EphrinB2, in cell lysates after 24 hr treatment with fixed 50 nM of RNAi probes.

The results on Ephrin B2 antisense probes were summarized below in Table 8. The results on Ephrin B2 RNAi probes were summarized below in Table 9.

TABLE 8

Ephrin B2 antisense ODNs.

| | sequence | Coding region | Percent reduction in viability | Inhibition of Ephrin B2 Expression | SEQ ID NO: |
|---|---|---|---|---|---|
| Ephrin AS-51 | TCA GAC CTT GTA GTA AAT GT | (983-1002) | 35 | ++ | 291 |
| Ephrin AS-50 | TCG CCG GGC TCT GCG GGG GC | (963-982) | 50 | +++ | 292 |
| Ephrin AS-49 | ATC TCC TGG ACG ATG TAC AC | (943-962) | 45 | ++ | 293 |
| Ephrin AS-48 | CGG GTG CCC GTA GTC CCC GC | (923-942) | 35 | ++ | 294 |
| Ephrin AS-47 | TGA CCT TCT CGT AGT GAG GG | (903-922) | 40 | +++ | 295 |
| Ephrin AS-46 | CAG AAG ACG CTG TCC GCA GT | (883-902) | 40 | ++ | 296 |
| Ephrin AS-45 | CCT TAG CGG GAT GAT AAT GT | (863-882) | 35 | ++ | 297 |
| Ephrin AS-44 | CAC TGG GCT CTG AGC CGT TG | (843-862) | 60 | +++ | 298 |
| Ephrin AS-43 | TTG TTG CCG CTG CGC TTG GG | (823-842) | 40 | ++ | 299 |
| Ephrin AS-42 | TGT GGC CAG TGT GCT GAG CG | (803-822) | 40 | ++ | 300 |
| Ephrin AS-41 | ACA GCG TGG TCG TGT GCT GC | (783-802) | 70 | +++ | 301 |
| Ephrin AS-40 | GGC GAG TGC TTC CTG TGT CT | (763-782) | 80 | ++++ | 302 |
| Ephrin AS-39 | CCT CCG GTA CTT CAG CAA GA | (743-762) | 50 | +++ | 303 |
| Ephrin AS-38 | GGA CCA CCA GCG TGA TGA TG | (723-742) | 60 | +++ | 304 |
| Ephrin AS-37 | ATG ACG ATG AAG ATG ATG CA | (703-722) | 70 | +++ | 305 |
| Ephrin AS-36 | TCC TGA AGC AAT CCC TGC AA | (683-702) | 60 | +++ | 306 |
| Ephrin AS-35 | ATA AGG CCA CTT CGG AAC CG | (663-682) | 45 | ++ | 307 |
| Ephrin AS-34 | AGG ATG TTG TTC CCC GAA TG | (643-662) | 50 | +++ | 308 |
| Ephrin AS-33 | TCC GGC GCT GTT GCC GTC TG | (623-642) | 75 | +++ | 309 |
| Ephrin AS-32 | TGC TAG AAC CTG GAT TTG GT | (603-622) | 60 | +++ | 310 |
| Ephrin AS-31 | TTT ACA AAG GGA CTT GTT GT | (583-602) | 66 | +++ | 311 |
| Ephrin AS-30 | CGA ACT TCT TCC ATT TGT AC | (563-582) | 50 | ++ | 312 |
| Ephrin AS-29 | CAG CTT CTA GTT CTG GAC GT | (543-562) | 50 | +++ | 313 |
| Ephrin AS-28 | CTT GTT GGA TCT TTA TTC CT | (523-542) | 70 | +++ | 314 |
| Ephrin AS-27 | GGT TGA TCC AGC AGA ACT TG | (503-522) | 65 | +++ | 315 |
| Ephrin AS-26 | CAT CTT GTC CAA CTT TCA TG | (483-502) | 75 | +++ | 316 |
| Ephrin AS-25 | AGG ATC TTC ATG GCT CTT GT | (463-482) | 60 | +++ | 317 |
| Ephrin AS-24 | CTG GCA CAC CCC TCC CTC CT | (443-462) | 45 | ++ | 318 |
| Ephrin AS-23 | GGT TAT CCA GGC CCT CCA AA | (423-442) | 50 | +++ | 319 |
| Ephrin AS-22 | GAC CCA TTT GAT GTA GAT AT | (403-422) | 50 | +++ | 320 |
| Ephrin AS-21 | AAT GTA ATA ATC TTT GTT CT | (383-402) | 60 | +++ | 321 |
| Ephrin AS-20 | TCT GAA ATT CTA GAC CCC AG | (363-382) | 60 | +++ | 322 |
| Ephrin AS-19 | AGG TTA GGG CTG AAT TCT TG | (343-362) | 75 | +++ | 323 |
| Ephrin AS-18 | AAA CTT GAT GGT GAA TTT GA | (323-342) | 60 | +++ | 324 |
| Ephrin AS-17 | TAT CTT GGT CTG GTT TGG CA | (303-322) | 50 | ++ | 325 |
| Ephrin AS-16 | CAG TTG AGG AGA GGG GTA TT | (283-302) | 40 | ++ | 326 |

TABLE 8-continued

Ephrin B2 antisense ODNs.

| | sequence | Coding region | Percent reduction in viability | Inhibition of Ephrin B2 Expression | SEQ ID NO: |
|---|---|---|---|---|---|
| Ephrin AS-15 | TTC CTT CTT AAT AGT GCA TC | (263-282) | 66 | +++ | 327 |
| Ephrin AS-14 | TGT CTG CTT GGT CTT TAT CA | (243-262) | 70 | ++++ | 328 |
| Ephrin AS-13 | ACC ATA TAA ACT TTA TAA TA | (223-242) | 50 | +++ | 329 |
| Ephrin AS-12 | TTC ATA CTG GCC AAC AGT TT | (203-222) | 50 | +++ | 330 |
| Ephrin AS-11 | TAG AGT CCA CTT TGG GGC AA | (183-202) | 70 | ++++ | 331 |
| Ephrin AS-10 | ATA ATA TCC AAT TTG TCT CC | (163-182) | 70 | ++++ | 332 |
| Ephrin AS-9 | TAT CTG TGG GTA TAG TAC CA | (143-162) | 80 | ++++ | 333 |
| Ephrin AS-8 | GTC CTT GTC CAG GTA GAA AT | (123-142) | 60 | +++ | 334 |
| Ephrin AS-7 | TTG GAG TTC GAG GAA TTC CA | (103-122) | 80 | ++++ | 335 |
| Ephrin AS-6 | ATA GAT AGG CTC TAA AAC TA | (83-102) | 70 | +++ | 336 |
| Ephrin AS-5 | TCG ATT TGG AAA TCG CAG TT | (63-82) | 50 | +++ | 337 |
| Ephrin AS-4 | CTG CAT AAA ACC ATC AAA AC | (43-62) | 80 | ++++ | 338 |
| Ephrin AS-3 | ACC CCA GCA GTA CTT CCA CA | (23-42) | 85 | ++++ | 339 |
| Ephrin AS-2 | CGG AGT CCC TTC TCA CAG CC | (3-22) | 70 | +++ | 340 |
| Ephrin AS-1 | GAG TCC CTT CTC ACA GCC AT | (1-20) | 80 | ++++ | 341 |

TABLE 9

Ephrin B2 RNAi probes.

| | RNAi Sequence and homology with other human genes. | | Percent reduction in viability | Inhibition of Ephrin B2 Expression | RNAi no. | SEQ ID NO: |
|---|---|---|---|---|---|---|
| 89 | aactgcgatttccaaatc-gat | 109 | 80 | ++++ | 1 | 342 |
| 141 | aactccaaatttctac-ctgga | 161 | 70 | ++++ | 2 | 343 |
| 148 | aatttctacctggacaag-gac | 168 | 75 | +++ | 3 | 344 |
| 147 | aaatttctacctgga-caagga | 167 | 60 | +++ | 4 | 345 |
| 163 | aaggactggtactatac-ccac | 183 | 40 | ++ | 5 | 346 |
| 217 | aagtggactctaaaact-gttg | 237 | 80 | ++++ | 6 | 347 |
| 229 | aaactgttggccagtat-gaat | 249 | 50 | +++ | 7 | 348 |
| 228 | aaaactgttggccagtat-gaa | 248 | 80 | ++++ | 8 | 349 |
| 274 | aagaccaagcagacagat-gca | 294 | 80 | ++++ | 11 | 350 |
| 273 | aaagaccaagcagaca-gatgc | 293 | 60 | +++ | 12 | 351 |
| 363 | aagtttcaagaattcagc-cct | 383 | 66 | +++ | 13 | 352 |

TABLE 9-continued

Ephrin B2 RNAi probes.

| | RNAi Sequence and homology with other human genes. | | Percent reduction in viability | Inhibition of Ephrin B2 Expression | RNAi no. | SEQ ID NO: |
|---|---|---|---|---|---|---|
| 370 | aagaattcagccctaac-ctct | 390 | 50 | +++ | 14 | 353 |
| 373 | aattcagccctaac-ctctggg | 393 | 50 | +++ | 15 | 354 |
| 324 | aactgtgccaaaccagac-caa | 344 | 90 | ++++ | 16 | 355 |
| 440 | aaatgggtctttg-gagggcct | 460 | 80 | ++++ | 17 | 356 |
| 501 | aagatcctcatgaaagt-tgga | 521 | 50 | +++ | 18 | 357 |
| 513 | aaagttggacaagatg-caagt | 533 | 50 | +++ | 19 | 358 |
| 491 | aagagccatgaagatcct-cat | 511 | 50 | +++ | 20 | 359 |
| 514 | aagttggacaagatg-caagtt | 534 | 66 | +++ | 21 | 360 |
| 523 | aagatgcaagttctgctg-gat | 543 | 66 | +++ | 22 | 361 |
| 530 | aagttctgctggatcaac-cag | 550 | 50 | +++ | 23 | 362 |
| 545 | aaccaggaataaagatc-caac | 565 | 35 | ++ | 24 | 363 |
| 555 | aaagatccaacaa-gacgtcca | 575 | 40 | ++ | 25 | 364 |
| 556 | aagatccaacaagacgtc-cag | 576 | 60 | +++ | 26 | 365 |
| 563 | aacaagacgtccagaac-taga | 583 | 60 | +++ | 27 | 366 |
| 566 | aagacgtccagaacta-gaagc | 586 | 70 | +++ | 28 | 367 |
| 593 | aaatggaagaagttcga-caac | 613 | 75 | ++++ | 29 | 368 |
| 577 | aactagaagctggta-caaatg | 597 | 66 | +++ | 30 | 369 |
| 594 | aatggaagaagttcga-caaca | 614 | 35 | ++ | 31 | 370 |
| 583 | aagctggtacaaatggaa-gaa | 603 | 50 | +++ | 32 | 371 |
| 611 | aacaagtccctttg-taaaacc | 631 | 70 | ++++ | 33 | 372 |
| 599 | aagaagttcgacaa-caagtcc | 619 | 70 | ++++ | 34 | 373 |
| 602 | aagttcgacaacaagtc-cctt | 622 | 80 | ++++ | 35 | 374 |
| 626 | aaaaccaaatccaggt-tctag | 646 | 50 | +++ | 36 | 375 |
| 627 | aaaccaaatccaggt-tctagc | 647 | 25 | + | 37 | 376 |
| 628 | aaccaaatccaggt-tctagca | 648 | 30 | ++ | 38 | 377 |
| 632 | aaatccaggttctagca-caga | 652 | 60 | +++ | 39 | 378 |

TABLE 9-continued

Ephrin B2 RNAi probes.

| RNAi Sequence and homology with other human genes. | | Percent reduction in viability | Inhibition of Ephrin B2 Expression | RNAi no. | SEQ ID NO: |
|---|---|---|---|---|---|
| 633 aatccaggttctagcaca-gac | 653 | 40 | ++ | 40 | 379 |
| 678 aacaacatcctcggttc-cgaa | 698 | 30 | ++ | 41 | 380 |
| 681 aacatcctcggttc-cgaagtg | 701 | 20 | + | 42 | 381 |
| 697 aagtggccttatttg-caggga | 717 | 30 | ++ | 43 | 382 |
| Additional Ephrin B2 RNAi probes described in the specification | | | | | |
| GCAGACAGAUGCACUAUUAUU | | | | ephrin B2 264 | 383 |
| CUGCGAUUUCCAAAUCGAUUU | | | | ephrin B2 63 | 384 |
| GGACUGGUACUAUACCCACUU | | | | ephrin B2 137 | 385 |

Example 10

EphB4 Antibodies Inhibit Tumor Growth

FIG. 57 shows results on comparison of EphB4 monoclonal antibodies by G250 and in Pull-down assay.

FIG. 58 shows that EphB4 antibodies, in the presence of matrigel and growth factors, inhibit the in vivo tumor growth of SCC15 cells.

BalbC nude mice were injected subcutaneously with 2.5×$10^6$ viable tumor cells SCC15 is a head and neck squamous cell carcinoma line. Tumors were initiated in nu/nu mice by injecting 2.5-5×$10^6$ cells premixed with matrigel and Growth factors, and Ab's subcutaneously to initiate tumor xenografts. Mice were opened 14 days after injections. SCC15 is a head and neck squamous cell carcinoma line, B16 is a melanoma cell line, and MCF-7 is a breast carcinoma line. The responses of tumors to these treatments were compared to control treated mice, which receive PBS injections. Animals were observed daily for tumor growth and subcutaneous tumors were measured using a caliper every 2 days. Antibodies #1 and #23 showed significant regression of SCC15 tumor size compared to control, especially with no additional growth factor added.

FIG. 59 shows that EphB4 antibodies cause apoptosis, necrosis and decreased angiogenesis in SCC15, head and neck carcinoma tumor type.

Angiogenesis was assessed by CD-31 immunohistochemistry. Tumor tissue sections from treated and untreated mice were stained for CD31. Apoptosis was assessed by immunohistochemical TUNNEL, and proliferation by BrdU assay. Following surgical removal, tumors were immediately sliced into 2 mm serial sections and embedded in paraffin using standard procedures. Paraffin embedded tissue were sectioned at 5 μm, the wax removed and the tissue rehydrated. The rehydrated tissues were microwave irradiated in antigen retreival solution. Slides were rinsed in PBS, and TUNNEL reaction mixture (Terminal deoxynucleotidyl transferase and flourescein labeled nucleotide solution), and BrdU were added in a humidity chamber completely shielded from light. The TUNNEL and BrdU reaction mixture were then removed, slides were rinsed and anti-flourescein antibody comjugated with horseradish peroxidase was added. After incubation and rinsing, 3,3'diaminobenzidine was added. Masson's Trichrome and Hematoxylin and Eosin were also used to stain the slides to visualize morphology. Masson's Trichrome allows to visualize necrosis and fibrosis. The tumor gets blood support from tumor/skin, muscle boundary. As tumor grows, inner regions get depleted of nutrients. This leads to necrosis (cell death), preferably at the tumor center. After cells die, (tumor) tissue gets replaced with fibroblastic tissue. Slides were visualized under 20-fold magnification with digital images acquired. A different morphology was obtained on SCC tumors with each antibody administered. Ab #1 showed an increase in necrosis and fibrosis but not apoptosis. Ab #23 showed an increase in apoptosis, necrosis and fibrosis and a decrease in vessel infiltration. Ab #35 showed an increase in necrosis and fibrosis, and a small increase in apoptosis and a decrease in vessel infiltration. Ab #79 showed a large increase in apoptosis, and necrosis and fibrosis. Ab #91 showed no change in apoptosis but an increase in proliferation. And Ab #138 showed an increase in apoptosis, necrosis, fibrosis and a decrease in proliferation and vessel infiltration. Tumors treated with control PBS displayed abundant tumor density and a robust angiogenic response. Tumors treated with EphB4 antibodies displayed a decrease in tumor cell density and a marked inhibition of tumor angiogenesis in regions with viable tumor cells, as well as tumor necrosis and apoptosis.

FIG. 60 shows that systemic administration os antibodies on xenografts leads to tumor regression in SCC15 tumor xenografts.

Alternate day treatment with EphB4 monoclonal antibody or an equal volume of PBS as control were initiated on day 4, after the tumors have established, and continued for 14 days. Systemic administration was administered either IP or SC with no significant difference. All the experiments were carried out in a double-blind manner to eliminate investigator bias. Mice were sacrificed at the conclusion of the two week treatment period. Tumors were harvested immediately postmortem and fixed and processed for immunohistochemistry. EphB4 antibodies 40 mg per kg body weight were administered. Treatment with EphB4 antibody significantly inhibited human SCC tumor growth compared with control-treated mice ($p<0.05$). Treatment with EphB4 antibody significantly inhibited tumor weight compared with control-treated mice ($p<0.05$).

INCORPORATED BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. An isolated nucleic acid compound between 20 and 35 nucleotides in length, which is 100% complementary to a region of an EphB4 transcript sequence set forth in SEQ ID NO: 392, wherein the nucleic acid compound decreases expression of EphB4 in a cell, and wherein the nucleic acid compound is an antisense nucleic acid compound comprising the sequence of SEQ ID NO: 231 and one or more modified backbone or base moieties.

2. The nucleic acid compound of claim 1, wherein the nucleic acid compound is single-stranded.

3. The nucleic acid compound of claim 1, wherein the nucleic acid compound is double-stranded.

4. The nucleic acid compound of claim 1, wherein the nucleic acid compound is a DNA molecule.

5. The nucleic acid compound of claim 1, wherein the nucleic acid compound is a RNA molecule.

6. The nucleic acid compound of claim 1, wherein the nucleic acid compound comprises a DNA strand and a RNA strand.

7. The nucleic acid compound of claim 1, wherein the antisense nucleic acid compound has at least one internucleotide linkage selected from the group consisting of alicyiphosphonates, phosphorothioaies, phosphorodithioates, alkylphosphonothioates, phosphoramidates, phosphate esters, carbamates, acetamidate, carboxylmethyl esters, carbonates, and phosphate triesters.

8. A pharmaceutical composition comprising a nucleic acid compound and a pharmaceutically acceptable carrier, wherein the nucleic acid compound is between 20 and 35 nucleotides in length and is 100% complementary to a region of an EphB4 transcript sequence set forth in SEQ ID NO: 392, wherein the nucleic acid compound decreases expression of EphB4 in a cell, and wherein the nucleic acid compound is an antisense nucleic acid compound comprising the sequence of SEQ ID NO: 231 and one or more modified backbone or base moieties.

9. The nucleic acid compound of claim 1, wherein the antisense nucleic acid comprises at least one 2'-O-alkylated ribonucleotide.

10. The pharmaceutical composition of claim 8, wherein the antisense nucleic acid comprises at least one 2'-O-alkylated ribonucleotide.

* * * * *

UNITED STATES PATENT AND TRADEMARK OFFICE

CERTIFICATE OF CORRECTION

PATENT NO. : 7,585,967 B2
APPLICATION NO. : 10/800077
DATED : September 8, 2009
INVENTOR(S) : Reddy et al.

It is certified that error appears in the above-identified patent and that said Letters Patent is hereby corrected as shown below:

In the Claims:

In claim 7, column 296, line 1-2, please replace "alicyiphosphonates" with --alkylphosphonates--;

In claim 7, column 296, line 2, please replace "phosphorothioaies" with --phosphorothioates--.

Signed and Sealed this

Nineteenth Day of January, 2010

David J. Kappos
*Director of the United States Patent and Trademark Office*

SEQUENCE LISTING

```
<160> NUMBER OF SEQ ID NOS: 396

<210> SEQ ID NO 1
<211> LENGTH: 29
<212> TYPE: DNA
<213> ORGANISM: Unknown
<220> FEATURE:
<223> OTHER INFORMATION: Oligonucleotide

<400> SEQUENCE: 1

ggatccgcca tggagctccg ggtgctgct                                       29


<210> SEQ ID NO 2
<211> LENGTH: 36
<212> TYPE: DNA
<213> ORGANISM: Unknown
<220> FEATURE:
<223> OTHER INFORMATION: Oligonucleotide

<400> SEQUENCE: 2

tggatccctg ctcccgccag ccctcgctct catcca                                36


<210> SEQ ID NO 3
<211> LENGTH: 28
<212> TYPE: DNA
<213> ORGANISM: Unknown
<220> FEATURE:
<223> OTHER INFORMATION: Oligonucleotide

<400> SEQUENCE: 3

tggatccacc atggctgtga gaagggac                                         28


<210> SEQ ID NO 4
<211> LENGTH: 53
<212> TYPE: DNA
<213> ORGANISM: Unknown
<220> FEATURE:
<223> OTHER INFORMATION: Oligonucleotide

<400> SEQUENCE: 4

attaatggtg atggtgatga tgactaccca cttcggaacc gaggatgttg ttc             53


<210> SEQ ID NO 5
<211> LENGTH: 31
<212> TYPE: DNA
<213> ORGANISM: Unknown
<220> FEATURE:
<223> OTHER INFORMATION: Oligonucleotide
```

-continued

<400> SEQUENCE: 5
taaagcttcc gccatggctg tgagaaggga c 31

<210> SEQ ID NO 6
<211> LENGTH: 34
<212> TYPE: DNA
<213> ORGANISM: Unknown
<220> FEATURE:
<223> OTHER INFORMATION: Oligonucleotide

<400> SEQUENCE: 6
taggatccac ttcggaaccg aggatgttgt tccc 34

<210> SEQ ID NO 7
<211> LENGTH: 31
<212> TYPE: DNA
<213> ORGANISM: Unknown
<220> FEATURE:
<223> OTHER INFORMATION: Oligonucleotide

<400> SEQUENCE: 7
ataagcttcc gccatggagc tccgggtgct g 31

<210> SEQ ID NO 8
<211> LENGTH: 34
<212> TYPE: DNA
<213> ORGANISM: Unknown
<220> FEATURE:
<223> OTHER INFORMATION: Oligonucleotide

<400> SEQUENCE: 8
ttggatcctg ctcccgccag ccctcgctct catc 34

<210> SEQ ID NO 9
<211> LENGTH: 32
<212> TYPE: DNA
<213> ORGANISM: Unknown
<220> FEATURE:
<223> OTHER INFORMATION: Oligonucleotide

<400> SEQUENCE: 9
tactagtccg ccatggagct ccgggtgctg ct 32

<210> SEQ ID NO 10
<211> LENGTH: 50
<212> TYPE: DNA
<213> ORGANISM: Unknown
<220> FEATURE:
<223> OTHER INFORMATION: Oligonucleotide

<400> SEQUENCE: 10
gcggccgctt aatggtgatg gtgatgatga gccgaaggag gggtggtgca 50

<210> SEQ ID NO 11
<211> LENGTH: 53
<212> TYPE: DNA
<213> ORGANISM: Unknown
<220> FEATURE:
<223> OTHER INFORMATION: Oligonucleotide

<400> SEQUENCE: 11
agcggccgct taatggtgat ggtgatgatg gacattgaca ggctcaaatg gga 53

-continued

<210> SEQ ID NO 12
<211> LENGTH: 56
<212> TYPE: DNA
<213> ORGANISM: Unknown
<220> FEATURE:
<223> OTHER INFORMATION: Oligonucleotide

<400> SEQUENCE: 12
tgcggccgct taatggtgat ggtgatgatg ctgctcccgc cagccctcgc tctcat 56

<210> SEQ ID NO 13
<211> LENGTH: 32
<212> TYPE: DNA
<213> ORGANISM: Unknown
<220> FEATURE:
<223> OTHER INFORMATION: Oligonucleotide

<400> SEQUENCE: 13
tactagtccg ccatggagct ccgggtgctg ct 32

<210> SEQ ID NO 14
<211> LENGTH: 25
<212> TYPE: DNA
<213> ORGANISM: Unknown
<220> FEATURE:
<223> OTHER INFORMATION: Oligonucleotide

<400> SEQUENCE: 14
cagctgagtt tccaattttg tgttc 25

<210> SEQ ID NO 15
<211> LENGTH: 39
<212> TYPE: DNA
<213> ORGANISM: Unknown
<220> FEATURE:
<223> OTHER INFORMATION: Oligonucleotide

<400> SEQUENCE: 15
gaacacaaaa ttggaaactc agctgactgt gaacctgac 39

<210> SEQ ID NO 16
<211> LENGTH: 30
<212> TYPE: DNA
<213> ORGANISM: Unknown
<220> FEATURE:
<223> OTHER INFORMATION: Oligonucleotide

<400> SEQUENCE: 16
gcggccgccc tgctcccgcc agccctcgct 30

<210> SEQ ID NO 17
<211> LENGTH: 31
<212> TYPE: DNA
<213> ORGANISM: Unknown
<220> FEATURE:
<223> OTHER INFORMATION: Oligonucleotide

<400> SEQUENCE: 17
taaagcttcc gccatggctg tgagaaggga c 31

<210> SEQ ID NO 18
<211> LENGTH: 32
<212> TYPE: DNA
<213> ORGANISM: Unknown
<220> FEATURE:
<223> OTHER INFORMATION: Oligonucleotide -continued

<400> SEQUENCE: 18
taggatcctt cggaaccgag gatgttgttc cc 32

<210> SEQ ID NO 19
<211> LENGTH: 20
<212> TYPE: DNA
<213> ORGANISM: Unknown
<220> FEATURE:
<223> OTHER INFORMATION: Oligonucleotide

<400> SEQUENCE: 19
tcctgcaagg agaccttcac 20

<210> SEQ ID NO 20
<211> LENGTH: 21
<212> TYPE: DNA
<213> ORGANISM: Unknown
<220> FEATURE:
<223> OTHER INFORMATION: Oligonucleotide

<400> SEQUENCE: 20
gtgcagggat agcagggcca t 21

<210> SEQ ID NO 21
<211> LENGTH: 20
<212> TYPE: DNA
<213> ORGANISM: Unknown
<220> FEATURE:
<223> OTHER INFORMATION: Oligonucleotide

<400> SEQUENCE: 21
atggaggcct cgctcagaaa 20

<210> SEQ ID NO 22
<211> LENGTH: 21
<212> TYPE: RNA
<213> ORGANISM: Unknown
<220> FEATURE:
<223> OTHER INFORMATION: Oligonucleotide

<400> SEQUENCE: 22
ggugaauguc aagacgcugu u 21

<210> SEQ ID NO 23
<211> LENGTH: 21
<212> TYPE: RNA
<213> ORGANISM: Unknown
<220> FEATURE:
<223> OTHER INFORMATION: Oligonucleotide

<400> SEQUENCE: 23
cucuuccgau cccaccuacu u 21

<210> SEQ ID NO 24
<211> LENGTH: 19
<212> TYPE: DNA
<213> ORGANISM: Unknown
<220> FEATURE:
<223> OTHER INFORMATION: Oligonucleotide

<400> SEQUENCE: 24
ggacctgact gactaccta 19

-continued

<210> SEQ ID NO 25
<211> LENGTH: 20
<212> TYPE: DNA
<213> ORGANISM: Unknown
<220> FEATURE:
<223> OTHER INFORMATION: Oligonucleotide

<400> SEQUENCE: 25
aaggagacct tcaccgtctt 20

<210> SEQ ID NO 26
<211> LENGTH: 20
<212> TYPE: DNA
<213> ORGANISM: Unknown
<220> FEATURE:
<223> OTHER INFORMATION: Oligonucleotide

<400> SEQUENCE: 26
ttgaaggtag tttcgtggat 20

<210> SEQ ID NO 27
<211> LENGTH: 20
<212> TYPE: DNA
<213> ORGANISM: Unknown
<220> FEATURE:
<223> OTHER INFORMATION: Oligonucleotide

<400> SEQUENCE: 27
tcgagtcagg ttcacagtca 20

<210> SEQ ID NO 28
<211> LENGTH: 20
<212> TYPE: DNA
<213> ORGANISM: Unknown
<220> FEATURE:
<223> OTHER INFORMATION: Oligonucleotide

<400> SEQUENCE: 28
ggagccaaaa gggtcatcat 20

<210> SEQ ID NO 29
<211> LENGTH: 21
<212> TYPE: DNA
<213> ORGANISM: Unknown
<220> FEATURE:
<223> OTHER INFORMATION: Oligonucleotide

<400> SEQUENCE: 29
ggcattgctg caaagaaaga g 21

<210> SEQ ID NO 30
<211> LENGTH: 20
<212> TYPE: DNA
<213> ORGANISM: Unknown
<220> FEATURE:
<223> OTHER INFORMATION: Oligonucleotide

<400> SEQUENCE: 30
tccgtgtgga agtactgctg 20

<210> SEQ ID NO 31
<211> LENGTH: 20
<212> TYPE: DNA
<213> ORGANISM: Unknown
<220> FEATURE:
<223> OTHER INFORMATION: Oligonucleotide -continued

<400> SEQUENCE: 31
tctggtttgg cacagttgag 20

<210> SEQ ID NO 32
<211> LENGTH: 20
<212> TYPE: DNA
<213> ORGANISM: Unknown
<220> FEATURE:
<223> OTHER INFORMATION: Oligonucleotide

<400> SEQUENCE: 32
ctttggaaga gaccctgctg 20

<210> SEQ ID NO 33
<211> LENGTH: 20
<212> TYPE: DNA
<213> ORGANISM: Unknown
<220> FEATURE:
<223> OTHER INFORMATION: Oligonucleotide

<400> SEQUENCE: 33
agacggtgaa ggtctccttg 20

<210> SEQ ID NO 34
<211> LENGTH: 21
<212> TYPE: RNA
<213> ORGANISM: Unknown
<220> FEATURE:
<223> OTHER INFORMATION: Oligonucleotide

<400> SEQUENCE: 34
gagacccugc ugaacacaau u 21

<210> SEQ ID NO 35
<211> LENGTH: 21
<212> TYPE: RNA
<213> ORGANISM: Unknown
<220> FEATURE:
<223> OTHER INFORMATION: Oligonucleotide

<400> SEQUENCE: 35
uuguguucag cagggucucu u 21

<210> SEQ ID NO 36
<211> LENGTH: 21
<212> TYPE: RNA
<213> ORGANISM: Unknown
<220> FEATURE:
<223> OTHER INFORMATION: Oligonucleotide

<400> SEQUENCE: 36
ggugaauguc aagacgcugu u 21

<210> SEQ ID NO 37
<211> LENGTH: 21
<212> TYPE: RNA
<213> ORGANISM: Unknown
<220> FEATURE:
<223> OTHER INFORMATION: Oligonucleotide

<400> SEQUENCE: 37
cagcgucuug acauucaccu u 21

-continued

<210> SEQ ID NO 38
<211> LENGTH: 21
<212> TYPE: RNA
<213> ORGANISM: Unknown
<220> FEATURE:
<223> OTHER INFORMATION: Oligonucleotide

<400> SEQUENCE: 38
caucacagcc agacccaacu u 21

<210> SEQ ID NO 39
<211> LENGTH: 21
<212> TYPE: RNA
<213> ORGANISM: Unknown
<220> FEATURE:
<223> OTHER INFORMATION: Oligonucleotide

<400> SEQUENCE: 39
guugggucug gcugugaugu u 21

<210> SEQ ID NO 40
<211> LENGTH: 21
<212> TYPE: RNA
<213> ORGANISM: Unknown
<220> FEATURE:
<223> OTHER INFORMATION: Oligonucleotide

<400> SEQUENCE: 40
cucuuccgau cccaccuacu u 21

<210> SEQ ID NO 41
<211> LENGTH: 21
<212> TYPE: RNA
<213> ORGANISM: Unknown
<220> FEATURE:
<223> OTHER INFORMATION: Oligonucleotide

<400> SEQUENCE: 41
guagguggga ucggaagagu u 21

<210> SEQ ID NO 42
<211> LENGTH: 21
<212> TYPE: DNA
<213> ORGANISM: Unknown
<220> FEATURE:
<223> OTHER INFORMATION: Oligonucleotide

<400> SEQUENCE: 42
gtgcagggat agcagggcca t 21

<210> SEQ ID NO 43
<211> LENGTH: 21
<212> TYPE: DNA
<213> ORGANISM: Unknown
<220> FEATURE:
<223> OTHER INFORMATION: Oligonucleotide

<400> SEQUENCE: 43
aaggaggggt ggtgcacggt g 21

<210> SEQ ID NO 44
<211> LENGTH: 21
<212> TYPE: DNA
<213> ORGANISM: Unknown
<220> FEATURE:
<223> OTHER INFORMATION: Oligonucleotide -continued

<400> SEQUENCE: 44
ttccaggtgc agggaggagc c 21

<210> SEQ ID NO 45
<211> LENGTH: 21
<212> TYPE: DNA
<213> ORGANISM: Unknown
<220> FEATURE:
<223> OTHER INFORMATION: Oligonucleotide

<400> SEQUENCE: 45
gtggtgacat tgacaggctc a 21

<210> SEQ ID NO 46
<211> LENGTH: 21
<212> TYPE: DNA
<213> ORGANISM: Unknown
<220> FEATURE:
<223> OTHER INFORMATION: Oligonucleotide

<400> SEQUENCE: 46
tctggctgtg atgttcctgg c 21

<210> SEQ ID NO 47
<211> LENGTH: 18
<212> TYPE: DNA
<213> ORGANISM: Unknown
<220> FEATURE:
<223> OTHER INFORMATION: Oligonucleotide

<400> SEQUENCE: 47
gccgctcagt tcctccca 18

<210> SEQ ID NO 48
<211> LENGTH: 18
<212> TYPE: DNA
<213> ORGANISM: Unknown
<220> FEATURE:
<223> OTHER INFORMATION: Oligonucleotide

<400> SEQUENCE: 48
tgaaggtctc cttgcagg 18

<210> SEQ ID NO 49
<211> LENGTH: 21
<212> TYPE: DNA
<213> ORGANISM: Unknown
<220> FEATURE:
<223> OTHER INFORMATION: Oligonucleotide

<400> SEQUENCE: 49
cgcggccacc gtgtccacct t 21

<210> SEQ ID NO 50
<211> LENGTH: 21
<212> TYPE: DNA
<213> ORGANISM: Unknown
<220> FEATURE:
<223> OTHER INFORMATION: Oligonucleotide

<400> SEQUENCE: 50
cttcagggtc ttgattgcca c 21

-continued

<210> SEQ ID NO 51
<211> LENGTH: 20
<212> TYPE: DNA
<213> ORGANISM: Unknown
<220> FEATURE:
<223> OTHER INFORMATION: Oligonucleotide

<400> SEQUENCE: 51
atggaggcct cgctcagaaa 20

<210> SEQ ID NO 52
<211> LENGTH: 21
<212> TYPE: DNA
<213> ORGANISM: Unknown
<220> FEATURE:
<223> OTHER INFORMATION: Oligonucleotide

<400> SEQUENCE: 52
catgcccacg agctggatga c 21

<210> SEQ ID NO 53
<211> LENGTH: 19
<212> TYPE: DNA
<213> ORGANISM: Unknown
<220> FEATURE:
<223> OTHER INFORMATION: Oligonucleotide

<400> SEQUENCE: 53
tccgtgtgga gtactgctg 19

<210> SEQ ID NO 54
<211> LENGTH: 20
<212> TYPE: DNA
<213> ORGANISM: Unknown
<220> FEATURE:
<223> OTHER INFORMATION: Oligonucleotide

<400> SEQUENCE: 54
tctggtttgg cacagttgag 20

<210> SEQ ID NO 55
<211> LENGTH: 20
<212> TYPE: DNA
<213> ORGANISM: Unknown
<220> FEATURE:
<223> OTHER INFORMATION: Oligonucleotide

<400> SEQUENCE: 55
ctttggaaga gaccctgctg 20

<210> SEQ ID NO 56
<211> LENGTH: 20
<212> TYPE: DNA
<213> ORGANISM: Unknown
<220> FEATURE:
<223> OTHER INFORMATION: Oligonucleotide

<400> SEQUENCE: 56
agacggtgaa ggtctccttg 20

<210> SEQ ID NO 57
<211> LENGTH: 20
<212> TYPE: DNA
<213> ORGANISM: Unknown
<220> FEATURE:
<223> OTHER INFORMATION: Oligonucleotide -continued

<400> SEQUENCE: 57
agacaagagc catgaagatc 20

<210> SEQ ID NO 58
<211> LENGTH: 21
<212> TYPE: DNA
<213> ORGANISM: Unknown
<220> FEATURE:
<223> OTHER INFORMATION: Oligonucleotide

<400> SEQUENCE: 58
ggatcccact tcggacccga g 21

<210> SEQ ID NO 59
<211> LENGTH: 22
<212> TYPE: DNA
<213> ORGANISM: Unknown
<220> FEATURE:
<223> OTHER INFORMATION: Oligonucleotide

<400> SEQUENCE: 59
tcaggtcact gcattgaacg gg 22

<210> SEQ ID NO 60
<211> LENGTH: 19
<212> TYPE: DNA
<213> ORGANISM: Unknown
<220> FEATURE:
<223> OTHER INFORMATION: Oligonucleotide

<400> SEQUENCE: 60
aactcgctct catccagtt 19

<210> SEQ ID NO 61
<211> LENGTH: 20
<212> TYPE: DNA
<213> ORGANISM: Unknown
<220> FEATURE:
<223> OTHER INFORMATION: Oligonucleotide

<400> SEQUENCE: 61
gtggggcgcc ccaggcacca 20

<210> SEQ ID NO 62
<211> LENGTH: 24
<212> TYPE: DNA
<213> ORGANISM: Unknown
<220> FEATURE:
<223> OTHER INFORMATION: Oligonucleotide

<400> SEQUENCE: 62
ctccttaatg tcacgcacga tttc 24

<210> SEQ ID NO 63
<211> LENGTH: 21
<212> TYPE: RNA
<213> ORGANISM: Unknown
<220> FEATURE:
<223> OTHER INFORMATION: Oligonucleotide

<400> SEQUENCE: 63
gcagacagau gcacuauuau u 21

-continued

<210> SEQ ID NO 64
<211> LENGTH: 21
<212> TYPE: RNA
<213> ORGANISM: Unknown
<220> FEATURE:
<223> OTHER INFORMATION: Oligonucleotide

<400> SEQUENCE: 64
uaauagugca ucugucugcu u 21

<210> SEQ ID NO 65
<211> LENGTH: 21
<212> TYPE: RNA
<213> ORGANISM: Unknown
<220> FEATURE:
<223> OTHER INFORMATION: Oligonucleotide

<400> SEQUENCE: 65
cugcgauuuc caaaucgauu u 21

<210> SEQ ID NO 66
<211> LENGTH: 21
<212> TYPE: RNA
<213> ORGANISM: Unknown
<220> FEATURE:
<223> OTHER INFORMATION: Oligonucleotide

<400> SEQUENCE: 66
aucgauuugg aaaucgcagu u 21

<210> SEQ ID NO 67
<211> LENGTH: 21
<212> TYPE: RNA
<213> ORGANISM: Unknown
<220> FEATURE:
<223> OTHER INFORMATION: Oligonucleotide

<400> SEQUENCE: 67
ggacugguac uauacccacu u 21

<210> SEQ ID NO 68
<211> LENGTH: 21
<212> TYPE: RNA
<213> ORGANISM: Unknown
<220> FEATURE:
<223> OTHER INFORMATION: Oligonucleotide

<400> SEQUENCE: 68
guggguauag uaccaguccu u 21

<210> SEQ ID NO 69
<211> LENGTH: 21
<212> TYPE: RNA
<213> ORGANISM: Unknown
<220> FEATURE:
<223> OTHER INFORMATION: Oligonucleotide

<400> SEQUENCE: 69
gagacccugc ugaacacaau u 21

<210> SEQ ID NO 70
<211> LENGTH: 21
<212> TYPE: RNA
<213> ORGANISM: Unknown
<220> FEATURE:
<223> OTHER INFORMATION: Oligonucleotide -continued

<400> SEQUENCE: 70
uuguguucag cagggucucu u 21

<210> SEQ ID NO 71
<211> LENGTH: 21
<212> TYPE: RNA
<213> ORGANISM: Unknown
<220> FEATURE:
<223> OTHER INFORMATION: Oligonucleotide

<400> SEQUENCE: 71
cgcugacccu gaaguucauu u 21

<210> SEQ ID NO 72
<211> LENGTH: 21
<212> TYPE: RNA
<213> ORGANISM: Unknown
<220> FEATURE:
<223> OTHER INFORMATION: Oligonucleotide

<400> SEQUENCE: 72
augaacuuca gggucagcgu u 21

<210> SEQ ID NO 73
<211> LENGTH: 21
<212> TYPE: DNA
<213> ORGANISM: Unknown
<220> FEATURE:
<223> OTHER INFORMATION: Oligonucleotide

<400> SEQUENCE: 73
tcagtactgc ggggccggtc c 21

<210> SEQ ID NO 74
<211> LENGTH: 20
<212> TYPE: DNA
<213> ORGANISM: Unknown
<220> FEATURE:
<223> OTHER INFORMATION: Oligonucleotide

<400> SEQUENCE: 74
tcctgtccca cccggggttc 20

<210> SEQ ID NO 75
<211> LENGTH: 20
<212> TYPE: DNA
<213> ORGANISM: Unknown
<220> FEATURE:
<223> OTHER INFORMATION: Oligonucleotide

<400> SEQUENCE: 75
ccggcttggc ctgggacttc 20

<210> SEQ ID NO 76
<211> LENGTH: 20
<212> TYPE: DNA
<213> ORGANISM: Unknown
<220> FEATURE:
<223> OTHER INFORMATION: Oligonucleotide

<400> SEQUENCE: 76
atgtgctgga cactggccaa 20

-continued

<210> SEQ ID NO 77
<211> LENGTH: 20
<212> TYPE: DNA
<213> ORGANISM: Unknown
<220> FEATURE:
<223> OTHER INFORMATION: Oligonucleotide

<400> SEQUENCE: 77
gattttcttc tggtgtcccg 20

<210> SEQ ID NO 78
<211> LENGTH: 20
<212> TYPE: DNA
<213> ORGANISM: Unknown
<220> FEATURE:
<223> OTHER INFORMATION: Oligonucleotide

<400> SEQUENCE: 78
ccagagtgac tccgattcgg 20

<210> SEQ ID NO 79
<211> LENGTH: 20
<212> TYPE: DNA
<213> ORGANISM: Unknown
<220> FEATURE:
<223> OTHER INFORMATION: Oligonucleotide

<400> SEQUENCE: 79
agcaggtcct cagcagagat 20

<210> SEQ ID NO 80
<211> LENGTH: 20
<212> TYPE: DNA
<213> ORGANISM: Unknown
<220> FEATURE:
<223> OTHER INFORMATION: Oligonucleotide

<400> SEQUENCE: 80
ctggctgacc agctcgaagg 20

<210> SEQ ID NO 81
<211> LENGTH: 20
<212> TYPE: DNA
<213> ORGANISM: Unknown
<220> FEATURE:
<223> OTHER INFORMATION: Oligonucleotide

<400> SEQUENCE: 81
agccaaagcc agcggctgcg 20

<210> SEQ ID NO 82
<211> LENGTH: 20
<212> TYPE: DNA
<213> ORGANISM: Unknown
<220> FEATURE:
<223> OTHER INFORMATION: Oligonucleotide

<400> SEQUENCE: 82
aaactttctt cgtatcttcc 20

<210> SEQ ID NO 83
<211> LENGTH: 20
<212> TYPE: DNA
<213> ORGANISM: Unknown
<220> FEATURE:
<223> OTHER INFORMATION: Oligonucleotide -continued

<400> SEQUENCE: 83
cattttgatg gcccgaagcc 20

<210> SEQ ID NO 84
<211> LENGTH: 20
<212> TYPE: DNA
<213> ORGANISM: Unknown
<220> FEATURE:
<223> OTHER INFORMATION: Oligonucleotide

<400> SEQUENCE: 84
actcgcccac agagccaaaa 20

<210> SEQ ID NO 85
<211> LENGTH: 20
<212> TYPE: DNA
<213> ORGANISM: Unknown
<220> FEATURE:
<223> OTHER INFORMATION: Oligonucleotide

<400> SEQUENCE: 85
gctgagtagt gaggctgccg 20

<210> SEQ ID NO 86
<211> LENGTH: 20
<212> TYPE: DNA
<213> ORGANISM: Unknown
<220> FEATURE:
<223> OTHER INFORMATION: Oligonucleotide

<400> SEQUENCE: 86
ctggtccagg agagggtgtg 20

<210> SEQ ID NO 87
<211> LENGTH: 20
<212> TYPE: DNA
<213> ORGANISM: Unknown
<220> FEATURE:
<223> OTHER INFORMATION: Oligonucleotide

<400> SEQUENCE: 87
aggccccgcc attctcccgg 20

<210> SEQ ID NO 88
<211> LENGTH: 20
<212> TYPE: DNA
<213> ORGANISM: Unknown
<220> FEATURE:
<223> OTHER INFORMATION: Oligonucleotide

<400> SEQUENCE: 88
gccacgattt tgaggctggc 20

<210> SEQ ID NO 89
<211> LENGTH: 20
<212> TYPE: DNA
<213> ORGANISM: Unknown
<220> FEATURE:
<223> OTHER INFORMATION: Oligonucleotide

<400> SEQUENCE: 89
ggggttccgg atcatcttgt 20

-continued

<210> SEQ ID NO 90
<211> LENGTH: 20
<212> TYPE: DNA
<213> ORGANISM: Unknown
<220> FEATURE:
<223> OTHER INFORMATION: Oligonucleotide

<400> SEQUENCE: 90
ccagggcgct gaccacctgg 20

<210> SEQ ID NO 91
<211> LENGTH: 20
<212> TYPE: DNA
<213> ORGANISM: Unknown
<220> FEATURE:
<223> OTHER INFORMATION: Oligonucleotide

<400> SEQUENCE: 91
gggaagcggg gccgggcatt 20

<210> SEQ ID NO 92
<211> LENGTH: 20
<212> TYPE: DNA
<213> ORGANISM: Unknown
<220> FEATURE:
<223> OTHER INFORMATION: Oligonucleotide

<400> SEQUENCE: 92
ccggtctttc tgccaacagt 20

<210> SEQ ID NO 93
<211> LENGTH: 20
<212> TYPE: DNA
<213> ORGANISM: Unknown
<220> FEATURE:
<223> OTHER INFORMATION: Oligonucleotide

<400> SEQUENCE: 93
ccagcatgag ctggtggagg 20

<210> SEQ ID NO 94
<211> LENGTH: 20
<212> TYPE: DNA
<213> ORGANISM: Unknown
<220> FEATURE:
<223> OTHER INFORMATION: Oligonucleotide

<400> SEQUENCE: 94
gaggtgggac agtctggggg 20

<210> SEQ ID NO 95
<211> LENGTH: 20
<212> TYPE: DNA
<213> ORGANISM: Unknown
<220> FEATURE:
<223> OTHER INFORMATION: Oligonucleotide

<400> SEQUENCE: 95
cgggggcagc cggtagtcct 20

<210> SEQ ID NO 96
<211> LENGTH: 20
<212> TYPE: DNA
<213> ORGANISM: Unknown
<220> FEATURE:
<223> OTHER INFORMATION: Oligonucleotide -continued

<400> SEQUENCE: 96
gttcaatggc attgatcacg 20

<210> SEQ ID NO 97
<211> LENGTH: 20
<212> TYPE: DNA
<213> ORGANISM: Unknown
<220> FEATURE:
<223> OTHER INFORMATION: Oligonucleotide

<400> SEQUENCE: 97
tcctgattgc tcatgtccca 20

<210> SEQ ID NO 98
<211> LENGTH: 20
<212> TYPE: DNA
<213> ORGANISM: Unknown
<220> FEATURE:
<223> OTHER INFORMATION: Oligonucleotide

<400> SEQUENCE: 98
gtacggcctc tccccaaatg 20

<210> SEQ ID NO 99
<211> LENGTH: 20
<212> TYPE: DNA
<213> ORGANISM: Unknown
<220> FEATURE:
<223> OTHER INFORMATION: Oligonucleotide

<400> SEQUENCE: 99
acatcacctc ccacatcaca 20

<210> SEQ ID NO 100
<211> LENGTH: 20
<212> TYPE: DNA
<213> ORGANISM: Unknown
<220> FEATURE:
<223> OTHER INFORMATION: Oligonucleotide

<400> SEQUENCE: 100
atcccgtaac tccaggcatc 20

<210> SEQ ID NO 101
<211> LENGTH: 20
<212> TYPE: DNA
<213> ORGANISM: Unknown
<220> FEATURE:
<223> OTHER INFORMATION: Oligonucleotide

<400> SEQUENCE: 101
actggcggaa gtgaacttcc 20

<210> SEQ ID NO 102
<211> LENGTH: 20
<212> TYPE: DNA
<213> ORGANISM: Unknown
<220> FEATURE:
<223> OTHER INFORMATION: Oligonucleotide

<400> SEQUENCE: 102
ggaaggcaat ggcctccggg 20

-continued

<210> SEQ ID NO 103
<211> LENGTH: 20
<212> TYPE: DNA
<213> ORGANISM: Unknown
<220> FEATURE:
<223> OTHER INFORMATION: Oligonucleotide

<400> SEQUENCE: 103
gcagtccatc ggatgggaat 20

<210> SEQ ID NO 104
<211> LENGTH: 20
<212> TYPE: DNA
<213> ORGANISM: Unknown
<220> FEATURE:
<223> OTHER INFORMATION: Oligonucleotide

<400> SEQUENCE: 104
ctttcctccc agggagctcg 20

<210> SEQ ID NO 105
<211> LENGTH: 20
<212> TYPE: DNA
<213> ORGANISM: Unknown
<220> FEATURE:
<223> OTHER INFORMATION: Oligonucleotide

<400> SEQUENCE: 105
tgtaggtggg atcggaagag 20

<210> SEQ ID NO 106
<211> LENGTH: 20
<212> TYPE: DNA
<213> ORGANISM: Unknown
<220> FEATURE:
<223> OTHER INFORMATION: Oligonucleotide

<400> SEQUENCE: 106
ttctcctcca ggaatcggga 20

<210> SEQ ID NO 107
<211> LENGTH: 20
<212> TYPE: DNA
<213> ORGANISM: Unknown
<220> FEATURE:
<223> OTHER INFORMATION: Oligonucleotide

<400> SEQUENCE: 107
aaggccaaag tcagacactt 20

<210> SEQ ID NO 108
<211> LENGTH: 20
<212> TYPE: DNA
<213> ORGANISM: Unknown
<220> FEATURE:
<223> OTHER INFORMATION: Oligonucleotide

<400> SEQUENCE: 108
gcagacgagg ttgctgttga 20

<210> SEQ ID NO 109
<211> LENGTH: 20
<212> TYPE: DNA
<213> ORGANISM: Unknown
<220> FEATURE:
<223> OTHER INFORMATION: Oligonucleotide -continued

```
<400> SEQUENCE: 109

ctaggatgtt gcgagcagcc                                                20


<210> SEQ ID NO 110
<211> LENGTH: 20
<212> TYPE: DNA
<213> ORGANISM: Unknown
<220> FEATURE:
<223> OTHER INFORMATION: Oligonucleotide

<400> SEQUENCE: 110

aggtctcggt ggacgtagct                                                20


<210> SEQ ID NO 111
<211> LENGTH: 20
<212> TYPE: DNA
<213> ORGANISM: Unknown
<220> FEATURE:
<223> OTHER INFORMATION: Oligonucleotide

<400> SEQUENCE: 111

catctcggca aggtaccgca                                                20


<210> SEQ ID NO 112
<211> LENGTH: 20
<212> TYPE: DNA
<213> ORGANISM: Unknown
<220> FEATURE:
<223> OTHER INFORMATION: Oligonucleotide

<400> SEQUENCE: 112

tgcccgaggc gatgccccgc                                                20


<210> SEQ ID NO 113
<211> LENGTH: 20
<212> TYPE: DNA
<213> ORGANISM: Unknown
<220> FEATURE:
<223> OTHER INFORMATION: Oligonucleotide

<400> SEQUENCE: 113

agcatgccca cgagctggat                                                20


<210> SEQ ID NO 114
<211> LENGTH: 20
<212> TYPE: DNA
<213> ORGANISM: Unknown
<220> FEATURE:
<223> OTHER INFORMATION: Oligonucleotide

<400> SEQUENCE: 114

gactgtgaac tgtccgtcgt                                                20


<210> SEQ ID NO 115
<211> LENGTH: 20
<212> TYPE: DNA
<213> ORGANISM: Unknown
<220> FEATURE:
<223> OTHER INFORMATION: Oligonucleotide

<400> SEQUENCE: 115

ttagccgcag gaaggagtcc                                                20
```

-continued

<210> SEQ ID NO 116
<211> LENGTH: 20
<212> TYPE: DNA
<213> ORGANISM: Unknown
<220> FEATURE:
<223> OTHER INFORMATION: Oligonucleotide

<400> SEQUENCE: 116
agggcgccgt tctccatgaa 20

<210> SEQ ID NO 117
<211> LENGTH: 20
<212> TYPE: DNA
<213> ORGANISM: Unknown
<220> FEATURE:
<223> OTHER INFORMATION: Oligonucleotide

<400> SEQUENCE: 117
ctctgtgaga atcatgacgg 20

<210> SEQ ID NO 118
<211> LENGTH: 20
<212> TYPE: DNA
<213> ORGANISM: Unknown
<220> FEATURE:
<223> OTHER INFORMATION: Oligonucleotide

<400> SEQUENCE: 118
gcatgctgtt ggtgaccacg 20

<210> SEQ ID NO 119
<211> LENGTH: 20
<212> TYPE: DNA
<213> ORGANISM: Unknown
<220> FEATURE:
<223> OTHER INFORMATION: Oligonucleotide

<400> SEQUENCE: 119
ccctccaggc ggatgatatt 20

<210> SEQ ID NO 120
<211> LENGTH: 20
<212> TYPE: DNA
<213> ORGANISM: Unknown
<220> FEATURE:
<223> OTHER INFORMATION: Oligonucleotide

<400> SEQUENCE: 120
ggggtgctcg aactggccca 20

<210> SEQ ID NO 121
<211> LENGTH: 20
<212> TYPE: DNA
<213> ORGANISM: Unknown
<220> FEATURE:
<223> OTHER INFORMATION: Oligonucleotide

<400> SEQUENCE: 121
tgatggaggc ctcgctcaga 20

<210> SEQ ID NO 122
<211> LENGTH: 20
<212> TYPE: DNA
<213> ORGANISM: Unknown
<220> FEATURE:
<223> OTHER INFORMATION: Oligonucleotide -continued

<400> SEQUENCE: 122
aactcacgcc gctgccgctc 20

<210> SEQ ID NO 123
<211> LENGTH: 20
<212> TYPE: DNA
<213> ORGANISM: Unknown
<220> FEATURE:
<223> OTHER INFORMATION: Oligonucleotide

<400> SEQUENCE: 123
cgtgtagcca cccttcaggg 20

<210> SEQ ID NO 124
<211> LENGTH: 20
<212> TYPE: DNA
<213> ORGANISM: Unknown
<220> FEATURE:
<223> OTHER INFORMATION: Oligonucleotide

<400> SEQUENCE: 124
tcttgattgc cacacagctc 20

<210> SEQ ID NO 125
<211> LENGTH: 20
<212> TYPE: DNA
<213> ORGANISM: Unknown
<220> FEATURE:
<223> OTHER INFORMATION: Oligonucleotide

<400> SEQUENCE: 125
tccttcttcc ctggggcctt 20

<210> SEQ ID NO 126
<211> LENGTH: 20
<212> TYPE: DNA
<213> ORGANISM: Unknown
<220> FEATURE:
<223> OTHER INFORMATION: Oligonucleotide

<400> SEQUENCE: 126
gagccgcccc cggcacacct 20

<210> SEQ ID NO 127
<211> LENGTH: 20
<212> TYPE: DNA
<213> ORGANISM: Unknown
<220> FEATURE:
<223> OTHER INFORMATION: Oligonucleotide

<400> SEQUENCE: 127
cgccaaactc acctgcacca 20

<210> SEQ ID NO 128
<211> LENGTH: 20
<212> TYPE: DNA
<213> ORGANISM: Unknown
<220> FEATURE:
<223> OTHER INFORMATION: Oligonucleotide

<400> SEQUENCE: 128
atcacctctt caatcttgac 20

-continued

<210> SEQ ID NO 129
<211> LENGTH: 20
<212> TYPE: DNA
<213> ORGANISM: Unknown
<220> FEATURE:
<223> OTHER INFORMATION: Oligonucleotide

<400> SEQUENCE: 129
gtaggagaca tcgatctctt 20

<210> SEQ ID NO 130
<211> LENGTH: 20
<212> TYPE: DNA
<213> ORGANISM: Unknown
<220> FEATURE:
<223> OTHER INFORMATION: Oligonucleotide

<400> SEQUENCE: 130
ttgcaaattc cctcacagcc 20

<210> SEQ ID NO 131
<211> LENGTH: 20
<212> TYPE: DNA
<213> ORGANISM: Unknown
<220> FEATURE:
<223> OTHER INFORMATION: Oligonucleotide

<400> SEQUENCE: 131
tcattagggt cttcataagt 20

<210> SEQ ID NO 132
<211> LENGTH: 20
<212> TYPE: DNA
<213> ORGANISM: Unknown
<220> FEATURE:
<223> OTHER INFORMATION: Oligonucleotide

<400> SEQUENCE: 132
gaaggggtcg atgtagacct 20

<210> SEQ ID NO 133
<211> LENGTH: 20
<212> TYPE: DNA
<213> ORGANISM: Unknown
<220> FEATURE:
<223> OTHER INFORMATION: Oligonucleotide

<400> SEQUENCE: 133
tagtaccatg tccgatgaga 20

<210> SEQ ID NO 134
<211> LENGTH: 20
<212> TYPE: DNA
<213> ORGANISM: Unknown
<220> FEATURE:
<223> OTHER INFORMATION: Oligonucleotide

<400> SEQUENCE: 134
tactgtccgt gtttgtccga 20

<210> SEQ ID NO 135
<211> LENGTH: 20
<212> TYPE: DNA
<213> ORGANISM: Unknown
<220> FEATURE:
<223> OTHER INFORMATION: Oligonucleotide -continued

<400> SEQUENCE: 135
atattctgct tctctcccat 20

<210> SEQ ID NO 136
<211> LENGTH: 20
<212> TYPE: DNA
<213> ORGANISM: Unknown
<220> FEATURE:
<223> OTHER INFORMATION: Oligonucleotide

<400> SEQUENCE: 136
tgctctgctt cctgaggcag 20

<210> SEQ ID NO 137
<211> LENGTH: 20
<212> TYPE: DNA
<213> ORGANISM: Unknown
<220> FEATURE:
<223> OTHER INFORMATION: Oligonucleotide

<400> SEQUENCE: 137
agaactgcga ccacaatgac 20

<210> SEQ ID NO 138
<211> LENGTH: 20
<212> TYPE: DNA
<213> ORGANISM: Unknown
<220> FEATURE:
<223> OTHER INFORMATION: Oligonucleotide

<400> SEQUENCE: 138
caccaggacc aggaccacac 20

<210> SEQ ID NO 139
<211> LENGTH: 20
<212> TYPE: DNA
<213> ORGANISM: Unknown
<220> FEATURE:
<223> OTHER INFORMATION: Oligonucleotide

<400> SEQUENCE: 139
ccacgactgc cgtgcccgca 20

<210> SEQ ID NO 140
<211> LENGTH: 20
<212> TYPE: DNA
<213> ORGANISM: Unknown
<220> FEATURE:
<223> OTHER INFORMATION: Oligonucleotide

<400> SEQUENCE: 140
atcagggcca gctgctcccg 20

<210> SEQ ID NO 141
<211> LENGTH: 20
<212> TYPE: DNA
<213> ORGANISM: Unknown
<220> FEATURE:
<223> OTHER INFORMATION: Oligonucleotide

<400> SEQUENCE: 141
ccagccctcg ctctcatcca 20

-continued

<210> SEQ ID NO 142
<211> LENGTH: 20
<212> TYPE: DNA
<213> ORGANISM: Unknown
<220> FEATURE:
<223> OTHER INFORMATION: Oligonucleotide

<400> SEQUENCE: 142
gttgggtctg gctgtgatgt 20

<210> SEQ ID NO 143
<211> LENGTH: 20
<212> TYPE: DNA
<213> ORGANISM: Unknown
<220> FEATURE:
<223> OTHER INFORMATION: Oligonucleotide

<400> SEQUENCE: 143
tcctggccga agggcccgta 20

<210> SEQ ID NO 144
<211> LENGTH: 20
<212> TYPE: DNA
<213> ORGANISM: Unknown
<220> FEATURE:
<223> OTHER INFORMATION: Oligonucleotide

<400> SEQUENCE: 144
gccggcctca gagcgcgccc 20

<210> SEQ ID NO 145
<211> LENGTH: 20
<212> TYPE: DNA
<213> ORGANISM: Unknown
<220> FEATURE:
<223> OTHER INFORMATION: Oligonucleotide

<400> SEQUENCE: 145
gtacctgcac caggtagctg 20

<210> SEQ ID NO 146
<211> LENGTH: 20
<212> TYPE: DNA
<213> ORGANISM: Unknown
<220> FEATURE:
<223> OTHER INFORMATION: Oligonucleotide

<400> SEQUENCE: 146
gctccccgct tcagcccccg 20

<210> SEQ ID NO 147
<211> LENGTH: 20
<212> TYPE: DNA
<213> ORGANISM: Unknown
<220> FEATURE:
<223> OTHER INFORMATION: Oligonucleotide

<400> SEQUENCE: 147
cagctctgcc cggttttctg 20

<210> SEQ ID NO 148
<211> LENGTH: 20
<212> TYPE: DNA
<213> ORGANISM: Unknown
<220> FEATURE:
<223> OTHER INFORMATION: Oligonucleotide -continued

<400> SEQUENCE: 148
acgtcttcag gaaccgcacg 20

<210> SEQ ID NO 149
<211> LENGTH: 20
<212> TYPE: DNA
<213> ORGANISM: Unknown
<220> FEATURE:
<223> OTHER INFORMATION: Oligonucleotide

<400> SEQUENCE: 149
ctgctgggac cctcggcgcc 20

<210> SEQ ID NO 150
<211> LENGTH: 20
<212> TYPE: DNA
<213> ORGANISM: Unknown
<220> FEATURE:
<223> OTHER INFORMATION: Oligonucleotide

<400> SEQUENCE: 150
cttctcatgg tatttgacct 20

<210> SEQ ID NO 151
<211> LENGTH: 20
<212> TYPE: DNA
<213> ORGANISM: Unknown
<220> FEATURE:
<223> OTHER INFORMATION: Oligonucleotide

<400> SEQUENCE: 151
cgtagtccag cacagcccca 20

<210> SEQ ID NO 152
<211> LENGTH: 20
<212> TYPE: DNA
<213> ORGANISM: Unknown
<220> FEATURE:
<223> OTHER INFORMATION: Oligonucleotide

<400> SEQUENCE: 152
ctgggtgccc ggggaacagc 20

<210> SEQ ID NO 153
<211> LENGTH: 20
<212> TYPE: DNA
<213> ORGANISM: Unknown
<220> FEATURE:
<223> OTHER INFORMATION: Oligonucleotide

<400> SEQUENCE: 153
ccaggccagg ctcaagctgc 20

<210> SEQ ID NO 154
<211> LENGTH: 20
<212> TYPE: DNA
<213> ORGANISM: Unknown
<220> FEATURE:
<223> OTHER INFORMATION: Oligonucleotide

<400> SEQUENCE: 154
tgggtgagga ccgcgtcacc 20

-continued

<210> SEQ ID NO 155
<211> LENGTH: 20
<212> TYPE: DNA
<213> ORGANISM: Unknown
<220> FEATURE:
<223> OTHER INFORMATION: Oligonucleotide

<400> SEQUENCE: 155
cggatgtcag acactgcagg 20

<210> SEQ ID NO 156
<211> LENGTH: 20
<212> TYPE: DNA
<213> ORGANISM: Unknown
<220> FEATURE:
<223> OTHER INFORMATION: Oligonucleotide

<400> SEQUENCE: 156
aggtacctct cggtcagtgg 20

<210> SEQ ID NO 157
<211> LENGTH: 20
<212> TYPE: DNA
<213> ORGANISM: Unknown
<220> FEATURE:
<223> OTHER INFORMATION: Oligonucleotide

<400> SEQUENCE: 157
tgacattgac aggctcaaat 20

<210> SEQ ID NO 158
<211> LENGTH: 20
<212> TYPE: DNA
<213> ORGANISM: Unknown
<220> FEATURE:
<223> OTHER INFORMATION: Oligonucleotide

<400> SEQUENCE: 158
gggacgggcc ccgtggctaa 20

<210> SEQ ID NO 159
<211> LENGTH: 20
<212> TYPE: DNA
<213> ORGANISM: Unknown
<220> FEATURE:
<223> OTHER INFORMATION: Oligonucleotide

<400> SEQUENCE: 159
ggaggatacc ccgttcaatg 20

<210> SEQ ID NO 160
<211> LENGTH: 20
<212> TYPE: DNA
<213> ORGANISM: Unknown
<220> FEATURE:
<223> OTHER INFORMATION: Oligonucleotide

<400> SEQUENCE: 160
cagtgacctc aaaggtatag 20

<210> SEQ ID NO 161
<211> LENGTH: 20
<212> TYPE: DNA
<213> ORGANISM: Unknown
<220> FEATURE:
<223> OTHER INFORMATION: Oligonucleotide -continued

<400> SEQUENCE: 161
gtgaagtcag gacgtagccc 20

<210> SEQ ID NO 162
<211> LENGTH: 20
<212> TYPE: DNA
<213> ORGANISM: Unknown
<220> FEATURE:
<223> OTHER INFORMATION: Oligonucleotide

<400> SEQUENCE: 162
tcgaaccacc acccagggct 20

<210> SEQ ID NO 163
<211> LENGTH: 20
<212> TYPE: DNA
<213> ORGANISM: Unknown
<220> FEATURE:
<223> OTHER INFORMATION: Oligonucleotide

<400> SEQUENCE: 163
ccaccaggtc ccgggggccg 20

<210> SEQ ID NO 164
<211> LENGTH: 20
<212> TYPE: DNA
<213> ORGANISM: Unknown
<220> FEATURE:
<223> OTHER INFORMATION: Oligonucleotide

<400> SEQUENCE: 164
gggtcaaaag tcaggtctcc 20

<210> SEQ ID NO 165
<211> LENGTH: 20
<212> TYPE: DNA
<213> ORGANISM: Unknown
<220> FEATURE:
<223> OTHER INFORMATION: Oligonucleotide

<400> SEQUENCE: 165
cccgcagggc gcacaggagc 20

<210> SEQ ID NO 166
<211> LENGTH: 20
<212> TYPE: DNA
<213> ORGANISM: Unknown
<220> FEATURE:
<223> OTHER INFORMATION: Oligonucleotide

<400> SEQUENCE: 166
ctccgggtcg gcactcccgg 20

<210> SEQ ID NO 167
<211> LENGTH: 20
<212> TYPE: DNA
<213> ORGANISM: Unknown
<220> FEATURE:
<223> OTHER INFORMATION: Oligonucleotide

<400> SEQUENCE: 167
cagcggaggg cgtaggtgag 20

-continued

<210> SEQ ID NO 168
<211> LENGTH: 20
<212> TYPE: DNA
<213> ORGANISM: Unknown
<220> FEATURE:
<223> OTHER INFORMATION: Oligonucleotide

<400> SEQUENCE: 168
gtcctctcgg ccaccagact 20

<210> SEQ ID NO 169
<211> LENGTH: 20
<212> TYPE: DNA
<213> ORGANISM: Unknown
<220> FEATURE:
<223> OTHER INFORMATION: Oligonucleotide

<400> SEQUENCE: 169 ccagggggc actccattcc 20

<210> SEQ ID NO 170
<211> LENGTH: 20
<212> TYPE: DNA
<213> ORGANISM: Unknown
<220> FEATURE:
<223> OTHER INFORMATION: Oligonucleotide

<400> SEQUENCE: 170
aggtgcaggg aggagccgtt 20

<210> SEQ ID NO 171
<211> LENGTH: 20
<212> TYPE: DNA
<213> ORGANISM: Unknown
<220> FEATURE:
<223> OTHER INFORMATION: Oligonucleotide

<400> SEQUENCE: 171
caggcgggaa accacgctcc 20

<210> SEQ ID NO 172
<211> LENGTH: 20
<212> TYPE: DNA
<213> ORGANISM: Unknown
<220> FEATURE:
<223> OTHER INFORMATION: Oligonucleotide

<400> SEQUENCE: 172
gcggagccga aggaggggtg 20

<210> SEQ ID NO 173
<211> LENGTH: 20
<212> TYPE: DNA
<213> ORGANISM: Unknown
<220> FEATURE:
<223> OTHER INFORMATION: Oligonucleotide

<400> SEQUENCE: 173
gtgcagggtg caccccgggg 20

<210> SEQ ID NO 174
<211> LENGTH: 20
<212> TYPE: DNA
<213> ORGANISM: Unknown
<220> FEATURE:
<223> OTHER INFORMATION: Oligonucleotide -continued

<400> SEQUENCE: 174
gtctgtgcgt gcccggaagt 20

<210> SEQ ID NO 175
<211> LENGTH: 20
<212> TYPE: DNA
<213> ORGANISM: Unknown
<220> FEATURE:
<223> OTHER INFORMATION: Oligonucleotide

<400> SEQUENCE: 175
acccgacgcg gcactggcag 20

<210> SEQ ID NO 176
<211> LENGTH: 20
<212> TYPE: DNA
<213> ORGANISM: Unknown
<220> FEATURE:
<223> OTHER INFORMATION: Oligonucleotide

<400> SEQUENCE: 176
acggctgatc caatggtgtt 20

<210> SEQ ID NO 177
<211> LENGTH: 20
<212> TYPE: DNA
<213> ORGANISM: Unknown
<220> FEATURE:
<223> OTHER INFORMATION: Oligonucleotide

<400> SEQUENCE: 177
agagtggcta ttggctgggc 20

<210> SEQ ID NO 178
<211> LENGTH: 20
<212> TYPE: DNA
<213> ORGANISM: Unknown
<220> FEATURE:
<223> OTHER INFORMATION: Oligonucleotide

<400> SEQUENCE: 178
atggctggca ggacccttct 20

<210> SEQ ID NO 179
<211> LENGTH: 20
<212> TYPE: DNA
<213> ORGANISM: Unknown
<220> FEATURE:
<223> OTHER INFORMATION: Oligonucleotide

<400> SEQUENCE: 179
cctgacaggg gcttgaaggt 20

<210> SEQ ID NO 180
<211> LENGTH: 20
<212> TYPE: DNA
<213> ORGANISM: Unknown
<220> FEATURE:
<223> OTHER INFORMATION: Oligonucleotide

<400> SEQUENCE: 180
gccctgggca caggctcggc 20

-continued

<210> SEQ ID NO 181
<211> LENGTH: 20
<212> TYPE: DNA
<213> ORGANISM: Unknown
<220> FEATURE:
<223> OTHER INFORMATION: Oligonucleotide

<400> SEQUENCE: 181
acttggtgtt cccctcagct 20

<210> SEQ ID NO 182
<211> LENGTH: 20
<212> TYPE: DNA
<213> ORGANISM: Unknown
<220> FEATURE:
<223> OTHER INFORMATION: Oligonucleotide

<400> SEQUENCE: 182
gcctcgaacc ccggagcaca 20

<210> SEQ ID NO 183
<211> LENGTH: 20
<212> TYPE: DNA
<213> ORGANISM: Unknown
<220> FEATURE:
<223> OTHER INFORMATION: Oligonucleotide

<400> SEQUENCE: 183
gctgcagccc gtgaccggct 20

<210> SEQ ID NO 184
<211> LENGTH: 20
<212> TYPE: DNA
<213> ORGANISM: Unknown
<220> FEATURE:
<223> OTHER INFORMATION: Oligonucleotide

<400> SEQUENCE: 184
gttcggccca ctggccatcc 20

<210> SEQ ID NO 185
<211> LENGTH: 20
<212> TYPE: DNA
<213> ORGANISM: Unknown
<220> FEATURE:
<223> OTHER INFORMATION: Oligonucleotide

<400> SEQUENCE: 185
tcacggcagt agaggctggg 20

<210> SEQ ID NO 186
<211> LENGTH: 20
<212> TYPE: DNA
<213> ORGANISM: Unknown
<220> FEATURE:
<223> OTHER INFORMATION: Oligonucleotide

<400> SEQUENCE: 186
gctggggcca ggggcgggga 20

<210> SEQ ID NO 187
<211> LENGTH: 20
<212> TYPE: DNA
<213> ORGANISM: Unknown
<220> FEATURE:
<223> OTHER INFORMATION: Oligonucleotide

<400> SEQUENCE: 187
cggcatccac cacgcagcta 20

<210> SEQ ID NO 188
<211> LENGTH: 20
<212> TYPE: DNA
<213> ORGANISM: Unknown
<220> FEATURE:
<223> OTHER INFORMATION: Oligonucleotide

<400> SEQUENCE: 188
ccggccacgg gcacaaccag 20

<210> SEQ ID NO 189
<211> LENGTH: 20
<212> TYPE: DNA
<213> ORGANISM: Unknown
<220> FEATURE:
<223> OTHER INFORMATION: Oligonucleotide

<400> SEQUENCE: 189
ctcccgaggc acagtctccg 20

<210> SEQ ID NO 190
<211> LENGTH: 20
<212> TYPE: DNA
<213> ORGANISM: Unknown
<220> FEATURE:
<223> OTHER INFORMATION: Oligonucleotide

<400> SEQUENCE: 190
ggaatcgagt caggttcaca 20

<210> SEQ ID NO 191
<211> LENGTH: 20
<212> TYPE: DNA
<213> ORGANISM: Unknown
<220> FEATURE:
<223> OTHER INFORMATION: Oligonucleotide

<400> SEQUENCE: 191
gtcagctggg cgcacttttt 20

<210> SEQ ID NO 192
<211> LENGTH: 20
<212> TYPE: DNA
<213> ORGANISM: Unknown
<220> FEATURE:
<223> OTHER INFORMATION: Oligonucleotide

<400> SEQUENCE: 192
gtagaagagg tgcagggata 20

<210> SEQ ID NO 193
<211> LENGTH: 20
<212> TYPE: DNA
<213> ORGANISM: Unknown
<220> FEATURE:
<223> OTHER INFORMATION: Oligonucleotide

<400> SEQUENCE: 193
gcagggccat gcaggcaccc 20

-continued

<210> SEQ ID NO 194
<211> LENGTH: 20
<212> TYPE: DNA
<213> ORGANISM: Unknown
<220> FEATURE:
<223> OTHER INFORMATION: Oligonucleotide

<400> SEQUENCE: 194
tggtcctgga aggccaggta 20

<210> SEQ ID NO 195
<211> LENGTH: 20
<212> TYPE: DNA
<213> ORGANISM: Unknown
<220> FEATURE:
<223> OTHER INFORMATION: Oligonucleotide

<400> SEQUENCE: 195
gaagccagcc ttgctgagcg 20

<210> SEQ ID NO 196
<211> LENGTH: 20
<212> TYPE: DNA
<213> ORGANISM: Unknown
<220> FEATURE:
<223> OTHER INFORMATION: Oligonucleotide

<400> SEQUENCE: 196
gtcccagacg cagcgtcttg 20

<210> SEQ ID NO 197
<211> LENGTH: 20
<212> TYPE: DNA
<213> ORGANISM: Unknown
<220> FEATURE:
<223> OTHER INFORMATION: Oligonucleotide

<400> SEQUENCE: 197
acattcacct tcccggtggc 20

<210> SEQ ID NO 198
<211> LENGTH: 20
<212> TYPE: DNA
<213> ORGANISM: Unknown
<220> FEATURE:
<223> OTHER INFORMATION: Oligonucleotide

<400> SEQUENCE: 198
ctcggcccca gggcgcttcc 20

<210> SEQ ID NO 199
<211> LENGTH: 20
<212> TYPE: DNA
<213> ORGANISM: Unknown
<220> FEATURE:
<223> OTHER INFORMATION: Oligonucleotide

<400> SEQUENCE: 199
gggtgagatg ctccgcggcc 20

<210> SEQ ID NO 200
<211> LENGTH: 20
<212> TYPE: DNA
<213> ORGANISM: Unknown
<220> FEATURE:
<223> OTHER INFORMATION: Oligonucleotide -continued

<400> SEQUENCE: 200
accgtgtcca ccttgatgta 20

<210> SEQ ID NO 201
<211> LENGTH: 20
<212> TYPE: DNA
<213> ORGANISM: Unknown
<220> FEATURE:
<223> OTHER INFORMATION: Oligonucleotide

<400> SEQUENCE: 201
ggggttctcc atccaggctg 20

<210> SEQ ID NO 202
<211> LENGTH: 20
<212> TYPE: DNA
<213> ORGANISM: Unknown
<220> FEATURE:
<223> OTHER INFORMATION: Oligonucleotide

<400> SEQUENCE: 202
gcgtgagggc cgtggccgtg 20

<210> SEQ ID NO 203
<211> LENGTH: 20
<212> TYPE: DNA
<213> ORGANISM: Unknown
<220> FEATURE:
<223> OTHER INFORMATION: Oligonucleotide

<400> SEQUENCE: 203
tccgcatcgc tctcatagta 20

<210> SEQ ID NO 204
<211> LENGTH: 20
<212> TYPE: DNA
<213> ORGANISM: Unknown
<220> FEATURE:
<223> OTHER INFORMATION: Oligonucleotide

<400> SEQUENCE: 204
gaagacggtg aaggtctcct 20

<210> SEQ ID NO 205
<211> LENGTH: 20
<212> TYPE: DNA
<213> ORGANISM: Unknown
<220> FEATURE:
<223> OTHER INFORMATION: Oligonucleotide

<400> SEQUENCE: 205
tgcaggagcg cccagcccga 20

<210> SEQ ID NO 206
<211> LENGTH: 20
<212> TYPE: DNA
<213> ORGANISM: Unknown
<220> FEATURE:
<223> OTHER INFORMATION: Oligonucleotide

<400> SEQUENCE: 206
ggcagggaca ggcactcgag 20

-continued

<210> SEQ ID NO 207
<211> LENGTH: 20
<212> TYPE: DNA
<213> ORGANISM: Unknown
<220> FEATURE:
<223> OTHER INFORMATION: Oligonucleotide

<400> SEQUENCE: 207
catggtgaag cgcagcgtgg 20

<210> SEQ ID NO 208
<211> LENGTH: 20
<212> TYPE: DNA
<213> ORGANISM: Unknown
<220> FEATURE:
<223> OTHER INFORMATION: Oligonucleotide

<400> SEQUENCE: 208
cgtacacgtg gacggcgccc 20

<210> SEQ ID NO 209
<211> LENGTH: 20
<212> TYPE: DNA
<213> ORGANISM: Unknown
<220> FEATURE:
<223> OTHER INFORMATION: Oligonucleotide

<400> SEQUENCE: 209
cgccgtggga cccaacctgt 20

<210> SEQ ID NO 210
<211> LENGTH: 20
<212> TYPE: DNA
<213> ORGANISM: Unknown
<220> FEATURE:
<223> OTHER INFORMATION: Oligonucleotide

<400> SEQUENCE: 210
gcgaagccag tgggcctggc 20

<210> SEQ ID NO 211
<211> LENGTH: 20
<212> TYPE: DNA
<213> ORGANISM: Unknown
<220> FEATURE:
<223> OTHER INFORMATION: Oligonucleotide

<400> SEQUENCE: 211
ccggggcacg ctgcacgtca 20

<210> SEQ ID NO 212
<211> LENGTH: 20
<212> TYPE: DNA
<213> ORGANISM: Unknown
<220> FEATURE:
<223> OTHER INFORMATION: Oligonucleotide

<400> SEQUENCE: 212
cacacttcgt aggtgcgcac 20

<210> SEQ ID NO 213
<211> LENGTH: 20
<212> TYPE: DNA
<213> ORGANISM: Unknown
<220> FEATURE:
<223> OTHER INFORMATION: Oligonucleotide

<400> SEQUENCE: 213
gctgtgctgt tcctcatcca 20

<210> SEQ ID NO 214
<211> LENGTH: 20
<212> TYPE: DNA
<213> ORGANISM: Unknown
<220> FEATURE:
<223> OTHER INFORMATION: Oligonucleotide

<400> SEQUENCE: 214
ggccgctcag ttcctcccac 20

<210> SEQ ID NO 215
<211> LENGTH: 20
<212> TYPE: DNA
<213> ORGANISM: Unknown
<220> FEATURE:
<223> OTHER INFORMATION: Oligonucleotide

<400> SEQUENCE: 215
tgcccgtcca cctgagggaa 20

<210> SEQ ID NO 216
<211> LENGTH: 20
<212> TYPE: DNA
<213> ORGANISM: Unknown
<220> FEATURE:
<223> OTHER INFORMATION: Oligonucleotide

<400> SEQUENCE: 216
tgtcacccac ttcagatcag 20

<210> SEQ ID NO 217
<211> LENGTH: 20
<212> TYPE: DNA
<213> ORGANISM: Unknown
<220> FEATURE:
<223> OTHER INFORMATION: Oligonucleotide

<400> SEQUENCE: 217
cagtttccaa ttttgtgttc 20

<210> SEQ ID NO 218
<211> LENGTH: 20
<212> TYPE: DNA
<213> ORGANISM: Unknown
<220> FEATURE:
<223> OTHER INFORMATION: Oligonucleotide

<400> SEQUENCE: 218
agcagggtct cttccaaagc 20

<210> SEQ ID NO 219
<211> LENGTH: 20
<212> TYPE: DNA
<213> ORGANISM: Unknown
<220> FEATURE:
<223> OTHER INFORMATION: Oligonucleotide

<400> SEQUENCE: 219
tgcggccaac gaagcccagc 20

-continued

<210> SEQ ID NO 220
<211> LENGTH: 20
<212> TYPE: DNA
<213> ORGANISM: Unknown
<220> FEATURE:
<223> OTHER INFORMATION: Oligonucleotide

<400> SEQUENCE: 220
agagcagcac ccggagctcc 20

<210> SEQ ID NO 221
<211> LENGTH: 20
<212> TYPE: DNA
<213> ORGANISM: Unknown
<220> FEATURE:
<223> OTHER INFORMATION: Oligonucleotide

<400> SEQUENCE: 221
agcagcaccc ggagctccat 20

<210> SEQ ID NO 222
<211> LENGTH: 21
<212> TYPE: DNA
<213> ORGANISM: Unknown
<220> FEATURE:
<223> OTHER INFORMATION: Oligonucleotide

<400> SEQUENCE: 222
gtgcagggat agcagggcca t 21

<210> SEQ ID NO 223
<211> LENGTH: 21
<212> TYPE: DNA
<213> ORGANISM: Unknown
<220> FEATURE:
<223> OTHER INFORMATION: Oligonucleotide

<400> SEQUENCE: 223
aaggaggggt ggtgcacggt g 21

<210> SEQ ID NO 224
<211> LENGTH: 21
<212> TYPE: DNA
<213> ORGANISM: Unknown
<220> FEATURE:
<223> OTHER INFORMATION: Oligonucleotide

<400> SEQUENCE: 224
ttccaggtgc agggaggagc c 21

<210> SEQ ID NO 225
<211> LENGTH: 21
<212> TYPE: DNA
<213> ORGANISM: Unknown
<220> FEATURE:
<223> OTHER INFORMATION: Oligonucleotide

<400> SEQUENCE: 225
gtggtgacat tgacaggctc a 21

<210> SEQ ID NO 226
<211> LENGTH: 21
<212> TYPE: DNA
<213> ORGANISM: Unknown
<220> FEATURE:
<223> OTHER INFORMATION: Oligonucleotide -continued

<400> SEQUENCE: 226
tctggctgtg atgttcctgg c 21

<210> SEQ ID NO 227
<211> LENGTH: 18
<212> TYPE: DNA
<213> ORGANISM: Unknown
<220> FEATURE:
<223> OTHER INFORMATION: Oligonucleotide

<400> SEQUENCE: 227
gccgctcagt tcctccca 18

<210> SEQ ID NO 228
<211> LENGTH: 18
<212> TYPE: DNA
<213> ORGANISM: Unknown
<220> FEATURE:
<223> OTHER INFORMATION: Oligonucleotide

<400> SEQUENCE: 228
tgaaggtctc cttgcagg 18

<210> SEQ ID NO 229
<211> LENGTH: 21
<212> TYPE: DNA
<213> ORGANISM: Unknown
<220> FEATURE:
<223> OTHER INFORMATION: Oligonucleotide

<400> SEQUENCE: 229
cgcggccacc gtgtccacct t 21

<210> SEQ ID NO 230
<211> LENGTH: 21
<212> TYPE: DNA
<213> ORGANISM: Unknown
<220> FEATURE:
<223> OTHER INFORMATION: Oligonucleotide

<400> SEQUENCE: 230
cttcagggtc ttgattgcca c 21

<210> SEQ ID NO 231
<211> LENGTH: 20
<212> TYPE: DNA
<213> ORGANISM: Unknown
<220> FEATURE:
<223> OTHER INFORMATION: Oligonucleotide

<400> SEQUENCE: 231
atggaggcct cgctcagaaa 20

<210> SEQ ID NO 232
<211> LENGTH: 21
<212> TYPE: DNA
<213> ORGANISM: Unknown
<220> FEATURE:
<223> OTHER INFORMATION: Oligonucleotide

<400> SEQUENCE: 232
catgcccacg agctggatga c 21

-continued

<210> SEQ ID NO 233
<211> LENGTH: 21
<212> TYPE: DNA
<213> ORGANISM: Unknown
<220> FEATURE:
<223> OTHER INFORMATION: Oligonucleotide

<400> SEQUENCE: 233
aaattggaaa ctgctgatct g 21

<210> SEQ ID NO 234
<211> LENGTH: 21
<212> TYPE: DNA
<213> ORGANISM: Unknown
<220> FEATURE:
<223> OTHER INFORMATION: Oligonucleotide

<400> SEQUENCE: 234
aattggaaac tgctgatctg a 21

<210> SEQ ID NO 235
<211> LENGTH: 21
<212> TYPE: DNA
<213> ORGANISM: Unknown
<220> FEATURE:
<223> OTHER INFORMATION: Oligonucleotide

<400> SEQUENCE: 235
aaactgctga tctgaagtgg g 21

<210> SEQ ID NO 236
<211> LENGTH: 21
<212> TYPE: DNA
<213> ORGANISM: Unknown
<220> FEATURE:
<223> OTHER INFORMATION: Oligonucleotide

<400> SEQUENCE: 236
aactgctgat ctgaagtggg t 21

<210> SEQ ID NO 237
<211> LENGTH: 21
<212> TYPE: DNA
<213> ORGANISM: Unknown
<220> FEATURE:
<223> OTHER INFORMATION: Oligonucleotide

<400> SEQUENCE: 237
aatgtcaaga cgctgcgtct g 21

<210> SEQ ID NO 238
<211> LENGTH: 21
<212> TYPE: DNA
<213> ORGANISM: Unknown
<220> FEATURE:
<223> OTHER INFORMATION: Oligonucleotide

<400> SEQUENCE: 238
aagtgggtga cattccctca g 21

<210> SEQ ID NO 239
<211> LENGTH: 21
<212> TYPE: DNA
<213> ORGANISM: Unknown
<220> FEATURE:
<223> OTHER INFORMATION: Oligonucleotide -continued

<400> SEQUENCE: 239
aaggtgaatg tcaagacgct g 21

<210> SEQ ID NO 240
<211> LENGTH: 21
<212> TYPE: DNA
<213> ORGANISM: Unknown
<220> FEATURE:
<223> OTHER INFORMATION: Oligonucleotide

<400> SEQUENCE: 240
aaggagacct tcaccgtctt c 21

<210> SEQ ID NO 241
<211> LENGTH: 21
<212> TYPE: DNA
<213> ORGANISM: Unknown
<220> FEATURE:
<223> OTHER INFORMATION: Oligonucleotide

<400> SEQUENCE: 241
aaaaagtgcg cccagctgac t 21

<210> SEQ ID NO 242
<211> LENGTH: 21
<212> TYPE: DNA
<213> ORGANISM: Unknown
<220> FEATURE:
<223> OTHER INFORMATION: Oligonucleotide

<400> SEQUENCE: 242
aatagccact ctaacaccat t 21

<210> SEQ ID NO 243
<211> LENGTH: 21
<212> TYPE: DNA
<213> ORGANISM: Unknown
<220> FEATURE:
<223> OTHER INFORMATION: Oligonucleotide

<400> SEQUENCE: 243
aacaccattg gatcagccgt c 21

<210> SEQ ID NO 244
<211> LENGTH: 21
<212> TYPE: DNA
<213> ORGANISM: Unknown
<220> FEATURE:
<223> OTHER INFORMATION: Oligonucleotide

<400> SEQUENCE: 244
aatgtcacca ctgaccgaga g 21

<210> SEQ ID NO 245
<211> LENGTH: 21
<212> TYPE: DNA
<213> ORGANISM: Unknown
<220> FEATURE:
<223> OTHER INFORMATION: Oligonucleotide

<400> SEQUENCE: 245
aaataccatg agaagggcgc c 21

-continued

<210> SEQ ID NO 246
<211> LENGTH: 21
<212> TYPE: DNA
<213> ORGANISM: Unknown
<220> FEATURE:
<223> OTHER INFORMATION: Oligonucleotide

<400> SEQUENCE: 246
aagacgtcag aaaaccgggc a 21

<210> SEQ ID NO 247
<211> LENGTH: 21
<212> TYPE: DNA
<213> ORGANISM: Unknown
<220> FEATURE:
<223> OTHER INFORMATION: Oligonucleotide

<400> SEQUENCE: 247
aacatcacag ccagacccaa c 21

<210> SEQ ID NO 248
<211> LENGTH: 21
<212> TYPE: DNA
<213> ORGANISM: Unknown
<220> FEATURE:
<223> OTHER INFORMATION: Oligonucleotide

<400> SEQUENCE: 248
aagcagagca atgggagaga a 21

<210> SEQ ID NO 249
<211> LENGTH: 21
<212> TYPE: DNA
<213> ORGANISM: Unknown
<220> FEATURE:
<223> OTHER INFORMATION: Oligonucleotide

<400> SEQUENCE: 249
aatgggagag aagcagaata t 21

<210> SEQ ID NO 250
<211> LENGTH: 21
<212> TYPE: DNA
<213> ORGANISM: Unknown
<220> FEATURE:
<223> OTHER INFORMATION: Oligonucleotide

<400> SEQUENCE: 250
aagcagaata ttcggacaaa c 21

<210> SEQ ID NO 251
<211> LENGTH: 21
<212> TYPE: DNA
<213> ORGANISM: Unknown
<220> FEATURE:
<223> OTHER INFORMATION: Oligonucleotide

<400> SEQUENCE: 251
aatattcgga caaacacgga c 21

<210> SEQ ID NO 252
<211> LENGTH: 21
<212> TYPE: DNA
<213> ORGANISM: Unknown
<220> FEATURE:
<223> OTHER INFORMATION: Oligonucleotide -continued

<400> SEQUENCE: 252
aaacacggac agtatctcat c 21

<210> SEQ ID NO 253
<211> LENGTH: 21
<212> TYPE: DNA
<213> ORGANISM: Unknown
<220> FEATURE:
<223> OTHER INFORMATION: Oligonucleotide

<400> SEQUENCE: 253
aacacggaca gtatctcatc g 21

<210> SEQ ID NO 254
<211> LENGTH: 21
<212> TYPE: DNA
<213> ORGANISM: Unknown
<220> FEATURE:
<223> OTHER INFORMATION: Oligonucleotide

<400> SEQUENCE: 254
aaaagagatc gatgtctcct a 21

<210> SEQ ID NO 255
<211> LENGTH: 21
<212> TYPE: DNA
<213> ORGANISM: Unknown
<220> FEATURE:
<223> OTHER INFORMATION: Oligonucleotide

<400> SEQUENCE: 255
aatgaggctg tgagggaatt t 21

<210> SEQ ID NO 256
<211> LENGTH: 21
<212> TYPE: DNA
<213> ORGANISM: Unknown
<220> FEATURE:
<223> OTHER INFORMATION: Oligonucleotide

<400> SEQUENCE: 256
aagaccctaa tgaggctgtg a 21

<210> SEQ ID NO 257
<211> LENGTH: 21
<212> TYPE: DNA
<213> ORGANISM: Unknown
<220> FEATURE:
<223> OTHER INFORMATION: Oligonucleotide

<400> SEQUENCE: 257
aaagagatcg atgtctccta c 21

<210> SEQ ID NO 258
<211> LENGTH: 21
<212> TYPE: DNA
<213> ORGANISM: Unknown
<220> FEATURE:
<223> OTHER INFORMATION: Oligonucleotide

<400> SEQUENCE: 258
aagagatcga tgtctcctac g 21

-continued

<210> SEQ ID NO 259
<211> LENGTH: 21
<212> TYPE: DNA
<213> ORGANISM: Unknown
<220> FEATURE:
<223> OTHER INFORMATION: Oligonucleotide

<400> SEQUENCE: 259
aagaggtgat tggtgcaggt g 21

<210> SEQ ID NO 260
<211> LENGTH: 21
<212> TYPE: DNA
<213> ORGANISM: Unknown
<220> FEATURE:
<223> OTHER INFORMATION: Oligonucleotide

<400> SEQUENCE: 260
aagattgaag aggtgattgg t 21

<210> SEQ ID NO 261
<211> LENGTH: 21
<212> TYPE: DNA
<213> ORGANISM: Unknown
<220> FEATURE:
<223> OTHER INFORMATION: Oligonucleotide

<400> SEQUENCE: 261
aacagcatgc ccgtcatgat t 21

<210> SEQ ID NO 262
<211> LENGTH: 21
<212> TYPE: DNA
<213> ORGANISM: Unknown
<220> FEATURE:
<223> OTHER INFORMATION: Oligonucleotide

<400> SEQUENCE: 262
aagaaggaga gctgtgtggc a 21

<210> SEQ ID NO 263
<211> LENGTH: 21
<212> TYPE: DNA
<213> ORGANISM: Unknown
<220> FEATURE:
<223> OTHER INFORMATION: Oligonucleotide

<400> SEQUENCE: 263
aaggagagct gtgtggcaat c 21

<210> SEQ ID NO 264
<211> LENGTH: 21
<212> TYPE: DNA
<213> ORGANISM: Unknown
<220> FEATURE:
<223> OTHER INFORMATION: Oligonucleotide

<400> SEQUENCE: 264
aatcaagacc ctgaagggtg g 21

<210> SEQ ID NO 265
<211> LENGTH: 21
<212> TYPE: DNA
<213> ORGANISM: Unknown
<220> FEATURE:
<223> OTHER INFORMATION: Oligonucleotide -continued

<400> SEQUENCE: 265
aaacgacgga cagttcacag t 21

<210> SEQ ID NO 266
<211> LENGTH: 21
<212> TYPE: DNA
<213> ORGANISM: Unknown
<220> FEATURE:
<223> OTHER INFORMATION: Oligonucleotide

<400> SEQUENCE: 266
aacgacggac agttcacagt c 21

<210> SEQ ID NO 267
<211> LENGTH: 21
<212> TYPE: DNA
<213> ORGANISM: Unknown
<220> FEATURE:
<223> OTHER INFORMATION: Oligonucleotide

<400> SEQUENCE: 267
aacatcctag tcaacagcaa c 21

<210> SEQ ID NO 268
<211> LENGTH: 21
<212> TYPE: DNA
<213> ORGANISM: Unknown
<220> FEATURE:
<223> OTHER INFORMATION: Oligonucleotide

<400> SEQUENCE: 268
aacagcaacc tcgtctgcaa a 21

<210> SEQ ID NO 269
<211> LENGTH: 21
<212> TYPE: DNA
<213> ORGANISM: Unknown
<220> FEATURE:
<223> OTHER INFORMATION: Oligonucleotide

<400> SEQUENCE: 269
aactcttccg atcccaccta c 21

<210> SEQ ID NO 270
<211> LENGTH: 21
<212> TYPE: DNA
<213> ORGANISM: Unknown
<220> FEATURE:
<223> OTHER INFORMATION: Oligonucleotide

<400> SEQUENCE: 270
aagtgtctga ctttggcctt t 21

<210> SEQ ID NO 271
<211> LENGTH: 21
<212> TYPE: DNA
<213> ORGANISM: Unknown
<220> FEATURE:
<223> OTHER INFORMATION: Oligonucleotide

<400> SEQUENCE: 271
aacctcgtct gcaaagtgtc t 21

-continued

<210> SEQ ID NO 272
<211> LENGTH: 21
<212> TYPE: DNA
<213> ORGANISM: Unknown
<220> FEATURE:
<223> OTHER INFORMATION: Oligonucleotide

<400> SEQUENCE: 272
aaagtgtctg actttggcct t 21

<210> SEQ ID NO 273
<211> LENGTH: 21
<212> TYPE: DNA
<213> ORGANISM: Unknown
<220> FEATURE:
<223> OTHER INFORMATION: Oligonucleotide

<400> SEQUENCE: 273
aatcaggacg tgatcaatgc c 21

<210> SEQ ID NO 274
<211> LENGTH: 21
<212> TYPE: DNA
<213> ORGANISM: Unknown
<220> FEATURE:
<223> OTHER INFORMATION: Oligonucleotide

<400> SEQUENCE: 274
aaagattccc atccgatgga c 21

<210> SEQ ID NO 275
<211> LENGTH: 21
<212> TYPE: DNA
<213> ORGANISM: Unknown
<220> FEATURE:
<223> OTHER INFORMATION: Oligonucleotide

<400> SEQUENCE: 275
aagattccca tccgatggac t 21

<210> SEQ ID NO 276
<211> LENGTH: 21
<212> TYPE: DNA
<213> ORGANISM: Unknown
<220> FEATURE:
<223> OTHER INFORMATION: Oligonucleotide

<400> SEQUENCE: 276
aagttcactt ccgccagtga t 21

<210> SEQ ID NO 277
<211> LENGTH: 21
<212> TYPE: DNA
<213> ORGANISM: Unknown
<220> FEATURE:
<223> OTHER INFORMATION: Oligonucleotide

<400> SEQUENCE: 277
aagatacgaa gaaagtttcg c 21

<210> SEQ ID NO 278
<211> LENGTH: 21
<212> TYPE: DNA
<213> ORGANISM: Unknown
<220> FEATURE:
<223> OTHER INFORMATION: Oligonucleotide -continued

<400> SEQUENCE: 278
aatgggaaga tacgaagaaa g 21

<210> SEQ ID NO 279
<211> LENGTH: 21
<212> TYPE: DNA
<213> ORGANISM: Unknown
<220> FEATURE:
<223> OTHER INFORMATION: Oligonucleotide

<400> SEQUENCE: 279
aatgccattg aacaggacta c 21

<210> SEQ ID NO 280
<211> LENGTH: 21
<212> TYPE: DNA
<213> ORGANISM: Unknown
<220> FEATURE:
<223> OTHER INFORMATION: Oligonucleotide

<400> SEQUENCE: 280
aaaatcgtgg cccgggagaa t 21

<210> SEQ ID NO 281
<211> LENGTH: 21
<212> TYPE: DNA
<213> ORGANISM: Unknown
<220> FEATURE:
<223> OTHER INFORMATION: Oligonucleotide

<400> SEQUENCE: 281
aaaatcttgg ccagtgtcca g 21

<210> SEQ ID NO 282
<211> LENGTH: 21
<212> TYPE: DNA
<213> ORGANISM: Unknown
<220> FEATURE:
<223> OTHER INFORMATION: Oligonucleotide

<400> SEQUENCE: 282
aaatcttggc cagtgtccag c 21

<210> SEQ ID NO 283
<211> LENGTH: 21
<212> TYPE: DNA
<213> ORGANISM: Unknown
<220> FEATURE:
<223> OTHER INFORMATION: Oligonucleotide

<400> SEQUENCE: 283
aagaaagttt cgcagccgct g 21

<210> SEQ ID NO 284
<211> LENGTH: 21
<212> TYPE: DNA
<213> ORGANISM: Unknown
<220> FEATURE:
<223> OTHER INFORMATION: Oligonucleotide

<400> SEQUENCE: 284
aagaaaatct tggccagtgt c 21

-continued

<210> SEQ ID NO 285
<211> LENGTH: 21
<212> TYPE: DNA
<213> ORGANISM: Unknown
<220> FEATURE:
<223> OTHER INFORMATION: Oligonucleotide

<400> SEQUENCE: 285
aatcttggcc agtgtccagc a 21

<210> SEQ ID NO 286
<211> LENGTH: 21
<212> TYPE: RNA
<213> ORGANISM: Unknown
<220> FEATURE:
<223> OTHER INFORMATION: Oligonucleotide

<400> SEQUENCE: 286
gagacccugc ugaacacaau u 21

<210> SEQ ID NO 287
<211> LENGTH: 21
<212> TYPE: RNA
<213> ORGANISM: Unknown
<220> FEATURE:
<223> OTHER INFORMATION: Oligonucleotide

<400> SEQUENCE: 287
ggugaauguc aagacgcugu u 21

<210> SEQ ID NO 288
<211> LENGTH: 21
<212> TYPE: RNA
<213> ORGANISM: Unknown
<220> FEATURE:
<223> OTHER INFORMATION: Oligonucleotide

<400> SEQUENCE: 288
caucacagcc agacccaacu u 21

<210> SEQ ID NO 289
<211> LENGTH: 21
<212> TYPE: RNA
<213> ORGANISM: Unknown
<220> FEATURE:
<223> OTHER INFORMATION: Oligonucleotide

<400> SEQUENCE: 289
cucuuccgau cccaccuacu u 21

<210> SEQ ID NO 290
<211> LENGTH: 21
<212> TYPE: RNA
<213> ORGANISM: Unknown
<220> FEATURE:
<223> OTHER INFORMATION: Oligonucleotide

<400> SEQUENCE: 290
cucuuccgau cccaccuacu u 21

<210> SEQ ID NO 291
<211> LENGTH: 20
<212> TYPE: DNA
<213> ORGANISM: Unknown
<220> FEATURE:
<223> OTHER INFORMATION: Oligonucleotide -continued

<400> SEQUENCE: 291
tcagaccttg tagtaaatgt 20

<210> SEQ ID NO 292
<211> LENGTH: 20
<212> TYPE: DNA
<213> ORGANISM: Unknown
<220> FEATURE:
<223> OTHER INFORMATION: Oligonucleotide

<400> SEQUENCE: 292
tcgccgggct ctgcgggggc 20

<210> SEQ ID NO 293
<211> LENGTH: 20
<212> TYPE: DNA
<213> ORGANISM: Unknown
<220> FEATURE:
<223> OTHER INFORMATION: Oligonucleotide

<400> SEQUENCE: 293
atctcctgga cgatgtacac 20

<210> SEQ ID NO 294
<211> LENGTH: 20
<212> TYPE: DNA
<213> ORGANISM: Unknown
<220> FEATURE:
<223> OTHER INFORMATION: Oligonucleotide

<400> SEQUENCE: 294
cgggtgcccg tagtccccgc 20

<210> SEQ ID NO 295
<211> LENGTH: 20
<212> TYPE: DNA
<213> ORGANISM: Unknown
<220> FEATURE:
<223> OTHER INFORMATION: Oligonucleotide

<400> SEQUENCE: 295
tgaccttctc gtagtgaggg 20

<210> SEQ ID NO 296
<211> LENGTH: 20
<212> TYPE: DNA
<213> ORGANISM: Unknown
<220> FEATURE:
<223> OTHER INFORMATION: Oligonucleotide

<400> SEQUENCE: 296
cagaagacgc tgtccgcagt 20

<210> SEQ ID NO 297
<211> LENGTH: 20
<212> TYPE: DNA
<213> ORGANISM: Unknown
<220> FEATURE:
<223> OTHER INFORMATION: Oligonucleotide

<400> SEQUENCE: 297
ccttagcggg atgataatgt 20

-continued

<210> SEQ ID NO 298
<211> LENGTH: 20
<212> TYPE: DNA
<213> ORGANISM: Unknown
<220> FEATURE:
<223> OTHER INFORMATION: Oligonucleotide

<400> SEQUENCE: 298
cactgggctc tgagccgttg 20

<210> SEQ ID NO 299
<211> LENGTH: 20
<212> TYPE: DNA
<213> ORGANISM: Unknown
<220> FEATURE:
<223> OTHER INFORMATION: Oligonucleotide

<400> SEQUENCE: 299
ttgttgccgc tgcgcttggg 20

<210> SEQ ID NO 300
<211> LENGTH: 20
<212> TYPE: DNA
<213> ORGANISM: Unknown
<220> FEATURE:
<223> OTHER INFORMATION: Oligonucleotide

<400> SEQUENCE: 300
tgtggccagt gtgctgagcg 20

<210> SEQ ID NO 301
<211> LENGTH: 20
<212> TYPE: DNA
<213> ORGANISM: Unknown
<220> FEATURE:
<223> OTHER INFORMATION: Oligonucleotide

<400> SEQUENCE: 301
acagcgtggt cgtgtgctgc 20

<210> SEQ ID NO 302
<211> LENGTH: 20
<212> TYPE: DNA
<213> ORGANISM: Unknown
<220> FEATURE:
<223> OTHER INFORMATION: Oligonucleotide

<400> SEQUENCE: 302
ggcgagtgct tcctgtgtct 20

<210> SEQ ID NO 303
<211> LENGTH: 20
<212> TYPE: DNA
<213> ORGANISM: Unknown
<220> FEATURE:
<223> OTHER INFORMATION: Oligonucleotide

<400> SEQUENCE: 303
cctccggtac ttcagcaaga 20

<210> SEQ ID NO 304
<211> LENGTH: 20
<212> TYPE: DNA
<213> ORGANISM: Unknown
<220> FEATURE:
<223> OTHER INFORMATION: Oligonucleotide -continued

<400> SEQUENCE: 304
ggaccaccag cgtgatgatg 20

<210> SEQ ID NO 305
<211> LENGTH: 20
<212> TYPE: DNA
<213> ORGANISM: Unknown
<220> FEATURE:
<223> OTHER INFORMATION: Oligonucleotide

<400> SEQUENCE: 305
atgacgatga agatgatgca 20

<210> SEQ ID NO 306
<211> LENGTH: 20
<212> TYPE: DNA
<213> ORGANISM: Unknown
<220> FEATURE:
<223> OTHER INFORMATION: Oligonucleotide

<400> SEQUENCE: 306
tcctgaagca atccctgcaa 20

<210> SEQ ID NO 307
<211> LENGTH: 20
<212> TYPE: DNA
<213> ORGANISM: Unknown
<220> FEATURE:
<223> OTHER INFORMATION: Oligonucleotide

<400> SEQUENCE: 307
ataaggccac ttcggaaccg 20

<210> SEQ ID NO 308
<211> LENGTH: 20
<212> TYPE: DNA
<213> ORGANISM: Unknown
<220> FEATURE:
<223> OTHER INFORMATION: Oligonucleotide

<400> SEQUENCE: 308
aggatgttgt tccccgaatg 20

<210> SEQ ID NO 309
<211> LENGTH: 20
<212> TYPE: DNA
<213> ORGANISM: Unknown
<220> FEATURE:
<223> OTHER INFORMATION: Oligonucleotide

<400> SEQUENCE: 309
tccggcgctg ttgccgtctg 20

<210> SEQ ID NO 310
<211> LENGTH: 20
<212> TYPE: DNA
<213> ORGANISM: Unknown
<220> FEATURE:
<223> OTHER INFORMATION: Oligonucleotide

<400> SEQUENCE: 310
tgctagaacc tggatttggt 20

-continued

<210> SEQ ID NO 311
<211> LENGTH: 20
<212> TYPE: DNA
<213> ORGANISM: Unknown
<220> FEATURE:
<223> OTHER INFORMATION: Oligonucleotide

<400> SEQUENCE: 311
tttacaaagg gacttgttgt 20

<210> SEQ ID NO 312
<211> LENGTH: 20
<212> TYPE: DNA
<213> ORGANISM: Unknown
<220> FEATURE:
<223> OTHER INFORMATION: Oligonucleotide

<400> SEQUENCE: 312
cgaacttctt ccatttgtac 20

<210> SEQ ID NO 313
<211> LENGTH: 20
<212> TYPE: DNA
<213> ORGANISM: Unknown
<220> FEATURE:
<223> OTHER INFORMATION: Oligonucleotide

<400> SEQUENCE: 313
cagcttctag ttctggacgt 20

<210> SEQ ID NO 314
<211> LENGTH: 20
<212> TYPE: DNA
<213> ORGANISM: Unknown
<220> FEATURE:
<223> OTHER INFORMATION: Oligonucleotide

<400> SEQUENCE: 314
cttgttggat ctttattcct 20

<210> SEQ ID NO 315
<211> LENGTH: 20
<212> TYPE: DNA
<213> ORGANISM: Unknown
<220> FEATURE:
<223> OTHER INFORMATION: Oligonucleotide

<400> SEQUENCE: 315
ggttgatcca gcagaacttg 20

<210> SEQ ID NO 316
<211> LENGTH: 20
<212> TYPE: DNA
<213> ORGANISM: Unknown
<220> FEATURE:
<223> OTHER INFORMATION: Oligonucleotide

<400> SEQUENCE: 316
catcttgtcc aactttcatg 20

<210> SEQ ID NO 317
<211> LENGTH: 20
<212> TYPE: DNA
<213> ORGANISM: Unknown
<220> FEATURE:
<223> OTHER INFORMATION: Oligonucleotide -continued

<400> SEQUENCE: 317
aggatcttca tggctcttgt 20

<210> SEQ ID NO 318
<211> LENGTH: 20
<212> TYPE: DNA
<213> ORGANISM: Unknown
<220> FEATURE:
<223> OTHER INFORMATION: Oligonucleotide

<400> SEQUENCE: 318
ctggcacacc cctccctcct 20

<210> SEQ ID NO 319
<211> LENGTH: 20
<212> TYPE: DNA
<213> ORGANISM: Unknown
<220> FEATURE:
<223> OTHER INFORMATION: Oligonucleotide

<400> SEQUENCE: 319
ggttatccag gccctccaaa 20

<210> SEQ ID NO 320
<211> LENGTH: 20
<212> TYPE: DNA
<213> ORGANISM: Unknown
<220> FEATURE:
<223> OTHER INFORMATION: Oligonucleotide

<400> SEQUENCE: 320
gacccatttg atgtagatat 20

<210> SEQ ID NO 321
<211> LENGTH: 20
<212> TYPE: DNA
<213> ORGANISM: Unknown
<220> FEATURE:
<223> OTHER INFORMATION: Oligonucleotide

<400> SEQUENCE: 321
aatgtaataa tctttgttct 20

<210> SEQ ID NO 322
<211> LENGTH: 20
<212> TYPE: DNA
<213> ORGANISM: Unknown
<220> FEATURE:
<223> OTHER INFORMATION: Oligonucleotide

<400> SEQUENCE: 322
tctgaaattc tagaccccag 20

<210> SEQ ID NO 323
<211> LENGTH: 20
<212> TYPE: DNA
<213> ORGANISM: Unknown
<220> FEATURE:
<223> OTHER INFORMATION: Oligonucleotide

<400> SEQUENCE: 323
aggttagggc tgaattcttg 20

-continued

<210> SEQ ID NO 324
<211> LENGTH: 20
<212> TYPE: DNA
<213> ORGANISM: Unknown
<220> FEATURE:
<223> OTHER INFORMATION: Oligonucleotide

<400> SEQUENCE: 324
aaacttgatg gtgaatttga 20

<210> SEQ ID NO 325
<211> LENGTH: 20
<212> TYPE: DNA
<213> ORGANISM: Unknown
<220> FEATURE:
<223> OTHER INFORMATION: Oligonucleotide

<400> SEQUENCE: 325
tatcttggtc tggtttggca 20

<210> SEQ ID NO 326
<211> LENGTH: 20
<212> TYPE: DNA
<213> ORGANISM: Unknown
<220> FEATURE:
<223> OTHER INFORMATION: Oligonucleotide

<400> SEQUENCE: 326
cagttgagga gaggggtatt 20

<210> SEQ ID NO 327
<211> LENGTH: 20
<212> TYPE: DNA
<213> ORGANISM: Unknown
<220> FEATURE:
<223> OTHER INFORMATION: Oligonucleotide

<400> SEQUENCE: 327
ttccttctta atagtgcatc 20

<210> SEQ ID NO 328
<211> LENGTH: 20
<212> TYPE: DNA
<213> ORGANISM: Unknown
<220> FEATURE:
<223> OTHER INFORMATION: Oligonucleotide

<400> SEQUENCE: 328
tgtctgcttg gtctttatca 20

<210> SEQ ID NO 329
<211> LENGTH: 20
<212> TYPE: DNA
<213> ORGANISM: Unknown
<220> FEATURE:
<223> OTHER INFORMATION: Oligonucleotide

<400> SEQUENCE: 329
accatataaa ctttataata 20

<210> SEQ ID NO 330
<211> LENGTH: 20
<212> TYPE: DNA
<213> ORGANISM: Unknown
<220> FEATURE:
<223> OTHER INFORMATION: Oligonucleotide -continued

<400> SEQUENCE: 330
ttcatactgg ccaacagttt 20

<210> SEQ ID NO 331
<211> LENGTH: 20
<212> TYPE: DNA
<213> ORGANISM: Unknown
<220> FEATURE:
<223> OTHER INFORMATION: Oligonucleotide

<400> SEQUENCE: 331
tagagtccac tttggggcaa 20

<210> SEQ ID NO 332
<211> LENGTH: 20
<212> TYPE: DNA
<213> ORGANISM: Unknown
<220> FEATURE:
<223> OTHER INFORMATION: Oligonucleotide

<400> SEQUENCE: 332
ataatatcca atttgtctcc 20

<210> SEQ ID NO 333
<211> LENGTH: 20
<212> TYPE: DNA
<213> ORGANISM: Unknown
<220> FEATURE:
<223> OTHER INFORMATION: Oligonucleotide

<400> SEQUENCE: 333
tatctgtggg tatagtacca 20

<210> SEQ ID NO 334
<211> LENGTH: 20
<212> TYPE: DNA
<213> ORGANISM: Unknown
<220> FEATURE:
<223> OTHER INFORMATION: Oligonucleotide

<400> SEQUENCE: 334
gtccttgtcc aggtagaaat 20

<210> SEQ ID NO 335
<211> LENGTH: 20
<212> TYPE: DNA
<213> ORGANISM: Unknown
<220> FEATURE:
<223> OTHER INFORMATION: Oligonucleotide

<400> SEQUENCE: 335
ttggagttcg aggaattcca 20

<210> SEQ ID NO 336
<211> LENGTH: 20
<212> TYPE: DNA
<213> ORGANISM: Unknown
<220> FEATURE:
<223> OTHER INFORMATION: Oligonucleotide

<400> SEQUENCE: 336
atagataggc tctaaaacta 20

-continued

<210> SEQ ID NO 337
<211> LENGTH: 20
<212> TYPE: DNA
<213> ORGANISM: Unknown
<220> FEATURE:
<223> OTHER INFORMATION: Oligonucleotide

<400> SEQUENCE: 337
tcgatttgga aatcgcagtt 20

<210> SEQ ID NO 338
<211> LENGTH: 20
<212> TYPE: DNA
<213> ORGANISM: Unknown
<220> FEATURE:
<223> OTHER INFORMATION: Oligonucleotide

<400> SEQUENCE: 338
ctgcataaaa ccatcaaaac 20

<210> SEQ ID NO 339
<211> LENGTH: 20
<212> TYPE: DNA
<213> ORGANISM: Unknown
<220> FEATURE:
<223> OTHER INFORMATION: Oligonucleotide

<400> SEQUENCE: 339
accccagcag tacttccaca 20

<210> SEQ ID NO 340
<211> LENGTH: 20
<212> TYPE: DNA
<213> ORGANISM: Unknown
<220> FEATURE:
<223> OTHER INFORMATION: Oligonucleotide

<400> SEQUENCE: 340
cggagtccct tctcacagcc 20

<210> SEQ ID NO 341
<211> LENGTH: 20
<212> TYPE: DNA
<213> ORGANISM: Unknown
<220> FEATURE:
<223> OTHER INFORMATION: Oligonucleotide

<400> SEQUENCE: 341
gagtcccttc tcacagccat 20

<210> SEQ ID NO 342
<211> LENGTH: 21
<212> TYPE: DNA
<213> ORGANISM: Unknown
<220> FEATURE:
<223> OTHER INFORMATION: Oligonucleotide

<400> SEQUENCE: 342
aactgcgatt tccaaatcga t 21

<210> SEQ ID NO 343
<211> LENGTH: 21
<212> TYPE: DNA
<213> ORGANISM: Unknown
<220> FEATURE:
<223> OTHER INFORMATION: Oligonucleotide -continued

<400> SEQUENCE: 343
aactccaaat ttctacctgg a 21

<210> SEQ ID NO 344
<211> LENGTH: 21
<212> TYPE: DNA
<213> ORGANISM: Unknown
<220> FEATURE:
<223> OTHER INFORMATION: Oligonucleotide

<400> SEQUENCE: 344
aatttctacc tggacaagga c 21

<210> SEQ ID NO 345
<211> LENGTH: 21
<212> TYPE: DNA
<213> ORGANISM: Unknown
<220> FEATURE:
<223> OTHER INFORMATION: Oligonucleotide

<400> SEQUENCE: 345
aaatttctac ctggacaagg a 21

<210> SEQ ID NO 346
<211> LENGTH: 21
<212> TYPE: DNA
<213> ORGANISM: Unknown
<220> FEATURE:
<223> OTHER INFORMATION: Oligonucleotide

<400> SEQUENCE: 346
aaggactggt actataccca c 21

<210> SEQ ID NO 347
<211> LENGTH: 21
<212> TYPE: DNA
<213> ORGANISM: Unknown
<220> FEATURE:
<223> OTHER INFORMATION: Oligonucleotide

<400> SEQUENCE: 347
aagtggactc taaaactgtt g 21

<210> SEQ ID NO 348
<211> LENGTH: 21
<212> TYPE: DNA
<213> ORGANISM: Unknown
<220> FEATURE:
<223> OTHER INFORMATION: Oligonucleotide

<400> SEQUENCE: 348
aaactgttgg ccagtatgaa t 21

<210> SEQ ID NO 349
<211> LENGTH: 21
<212> TYPE: DNA
<213> ORGANISM: Unknown
<220> FEATURE:
<223> OTHER INFORMATION: Oligonucleotide

<400> SEQUENCE: 349
aaaactgttg gccagtatga a 21

-continued

<210> SEQ ID NO 350
<211> LENGTH: 21
<212> TYPE: DNA
<213> ORGANISM: Unknown
<220> FEATURE:
<223> OTHER INFORMATION: Oligonucleotide

<400> SEQUENCE: 350
aagaccaagc agacagatgc a 21

<210> SEQ ID NO 351
<211> LENGTH: 21
<212> TYPE: DNA
<213> ORGANISM: Unknown
<220> FEATURE:
<223> OTHER INFORMATION: Oligonucleotide

<400> SEQUENCE: 351
aaagaccaag cagacagatg c 21

<210> SEQ ID NO 352
<211> LENGTH: 21
<212> TYPE: DNA
<213> ORGANISM: Unknown
<220> FEATURE:
<223> OTHER INFORMATION: Oligonucleotide

<400> SEQUENCE: 352
aagtttcaag aattcagccc t 21

<210> SEQ ID NO 353
<211> LENGTH: 21
<212> TYPE: DNA
<213> ORGANISM: Unknown
<220> FEATURE:
<223> OTHER INFORMATION: Oligonucleotide

<400> SEQUENCE: 353
aagaattcag ccctaacctc t 21

<210> SEQ ID NO 354
<211> LENGTH: 21
<212> TYPE: DNA
<213> ORGANISM: Unknown
<220> FEATURE:
<223> OTHER INFORMATION: Oligonucleotide

<400> SEQUENCE: 354
aattcagccc taacctctgg g 21

<210> SEQ ID NO 355
<211> LENGTH: 21
<212> TYPE: DNA
<213> ORGANISM: Unknown
<220> FEATURE:
<223> OTHER INFORMATION: Oligonucleotide

<400> SEQUENCE: 355
aactgtgcca aaccagacca a 21

<210> SEQ ID NO 356
<211> LENGTH: 21
<212> TYPE: DNA
<213> ORGANISM: Unknown
<220> FEATURE:
<223> OTHER INFORMATION: Oligonucleotide -continued

<400> SEQUENCE: 356
aaatgggtct ttggagggcc t 21

<210> SEQ ID NO 357
<211> LENGTH: 21
<212> TYPE: DNA
<213> ORGANISM: Unknown
<220> FEATURE:
<223> OTHER INFORMATION: Oligonucleotide

<400> SEQUENCE: 357
aagatcctca tgaaagttgg a 21

<210> SEQ ID NO 358
<211> LENGTH: 21
<212> TYPE: DNA
<213> ORGANISM: Unknown
<220> FEATURE:
<223> OTHER INFORMATION: Oligonucleotide

<400> SEQUENCE: 358
aaagttggac aagatgcaag t 21

<210> SEQ ID NO 359
<211> LENGTH: 21
<212> TYPE: DNA
<213> ORGANISM: Unknown
<220> FEATURE:
<223> OTHER INFORMATION: Oligonucleotide

<400> SEQUENCE: 359
aagagccatg aagatcctca t 21

<210> SEQ ID NO 360
<211> LENGTH: 21
<212> TYPE: DNA
<213> ORGANISM: Unknown
<220> FEATURE:
<223> OTHER INFORMATION: Oligonucleotide

<400> SEQUENCE: 360
aagttggaca agatgcaagt t 21

<210> SEQ ID NO 361
<211> LENGTH: 21
<212> TYPE: DNA
<213> ORGANISM: Unknown
<220> FEATURE:
<223> OTHER INFORMATION: Oligonucleotide

<400> SEQUENCE: 361
aagatgcaag ttctgctgga t 21

<210> SEQ ID NO 362
<211> LENGTH: 21
<212> TYPE: DNA
<213> ORGANISM: Unknown
<220> FEATURE:
<223> OTHER INFORMATION: Oligonucleotide

<400> SEQUENCE: 362
aagttctgct ggatcaacca g 21

-continued

<210> SEQ ID NO 363
<211> LENGTH: 21
<212> TYPE: DNA
<213> ORGANISM: Unknown
<220> FEATURE:
<223> OTHER INFORMATION: Oligonucleotide

<400> SEQUENCE: 363
aaccaggaat aaagatccaa c 21

<210> SEQ ID NO 364
<211> LENGTH: 21
<212> TYPE: DNA
<213> ORGANISM: Unknown
<220> FEATURE:
<223> OTHER INFORMATION: Oligonucleotide

<400> SEQUENCE: 364
aaagatccaa caagacgtcc a 21

<210> SEQ ID NO 365
<211> LENGTH: 21
<212> TYPE: DNA
<213> ORGANISM: Unknown
<220> FEATURE:
<223> OTHER INFORMATION: Oligonucleotide

<400> SEQUENCE: 365
aagatccaac aagacgtcca g 21

<210> SEQ ID NO 366
<211> LENGTH: 21
<212> TYPE: DNA
<213> ORGANISM: Unknown
<220> FEATURE:
<223> OTHER INFORMATION: Oligonucleotide

<400> SEQUENCE: 366
aacaagacgt ccagaactag a 21

<210> SEQ ID NO 367
<211> LENGTH: 21
<212> TYPE: DNA
<213> ORGANISM: Unknown
<220> FEATURE:
<223> OTHER INFORMATION: Oligonucleotide

<400> SEQUENCE: 367
aagacgtcca gaactagaag c 21

<210> SEQ ID NO 368
<211> LENGTH: 21
<212> TYPE: DNA
<213> ORGANISM: Unknown
<220> FEATURE:
<223> OTHER INFORMATION: Oligonucleotide

<400> SEQUENCE: 368
aaatggaaga agttcgacaa c 21

<210> SEQ ID NO 369
<211> LENGTH: 21
<212> TYPE: DNA
<213> ORGANISM: Unknown
<220> FEATURE:
<223> OTHER INFORMATION: Oligonucleotide

<400> SEQUENCE: 369
aactagaagc tggtacaaat g 21

<210> SEQ ID NO 370
<211> LENGTH: 21
<212> TYPE: DNA
<213> ORGANISM: Unknown
<220> FEATURE:
<223> OTHER INFORMATION: Oligonucleotide

<400> SEQUENCE: 370
aatggaagaa gttcgacaac a 21

<210> SEQ ID NO 371
<211> LENGTH: 21
<212> TYPE: DNA
<213> ORGANISM: Unknown
<220> FEATURE:
<223> OTHER INFORMATION: Oligonucleotide

<400> SEQUENCE: 371
aagctggtac aaatggaaga a 21

<210> SEQ ID NO 372
<211> LENGTH: 21
<212> TYPE: DNA
<213> ORGANISM: Unknown
<220> FEATURE:
<223> OTHER INFORMATION: Oligonucleotide

<400> SEQUENCE: 372
aacaagtccc tttgtaaaac c 21

<210> SEQ ID NO 373
<211> LENGTH: 21
<212> TYPE: DNA
<213> ORGANISM: Unknown
<220> FEATURE:
<223> OTHER INFORMATION: Oligonucleotide

<400> SEQUENCE: 373
aagaagttcg acaacaagtc c 21

<210> SEQ ID NO 374
<211> LENGTH: 21
<212> TYPE: DNA
<213> ORGANISM: Unknown
<220> FEATURE:
<223> OTHER INFORMATION: Oligonucleotide

<400> SEQUENCE: 374
aagttcgaca acaagtccct t 21

<210> SEQ ID NO 375
<211> LENGTH: 21
<212> TYPE: DNA
<213> ORGANISM: Unknown
<220> FEATURE:
<223> OTHER INFORMATION: Oligonucleotide

<400> SEQUENCE: 375
aaaaccaaat ccaggttcta g 21

-continued

<210> SEQ ID NO 376
<211> LENGTH: 21
<212> TYPE: DNA
<213> ORGANISM: Unknown
<220> FEATURE:
<223> OTHER INFORMATION: Oligonucleotide

<400> SEQUENCE: 376
aaaccaaatc caggttctag c 21

<210> SEQ ID NO 377
<211> LENGTH: 21
<212> TYPE: DNA
<213> ORGANISM: Unknown
<220> FEATURE:
<223> OTHER INFORMATION: Oligonucleotide

<400> SEQUENCE: 377
aaccaaatcc aggttctagc a 21

<210> SEQ ID NO 378
<211> LENGTH: 21
<212> TYPE: DNA
<213> ORGANISM: Unknown
<220> FEATURE:
<223> OTHER INFORMATION: Oligonucleotide

<400> SEQUENCE: 378
aaatccaggt tctagcacag a 21

<210> SEQ ID NO 379
<211> LENGTH: 21
<212> TYPE: DNA
<213> ORGANISM: Unknown
<220> FEATURE:
<223> OTHER INFORMATION: Oligonucleotide

<400> SEQUENCE: 379
aatccaggtt ctagcacaga c 21

<210> SEQ ID NO 380
<211> LENGTH: 21
<212> TYPE: DNA
<213> ORGANISM: Unknown
<220> FEATURE:
<223> OTHER INFORMATION: Oligonucleotide

<400> SEQUENCE: 380
aacaacatcc tcggttccga a 21

<210> SEQ ID NO 381
<211> LENGTH: 21
<212> TYPE: DNA
<213> ORGANISM: Unknown
<220> FEATURE:
<223> OTHER INFORMATION: Oligonucleotide

<400> SEQUENCE: 381
aacatcctcg gttccgaagt g 21

<210> SEQ ID NO 382
<211> LENGTH: 21
<212> TYPE: DNA
<213> ORGANISM: Unknown
<220> FEATURE:
<223> OTHER INFORMATION: Oligonucleotide -continued

<400> SEQUENCE: 382
aagtggcctt atttgcaggg a 21

<210> SEQ ID NO 383
<211> LENGTH: 21
<212> TYPE: RNA
<213> ORGANISM: Unknown
<220> FEATURE:
<223> OTHER INFORMATION: Oligonucleotide

<400> SEQUENCE: 383
gcagacagau gcacuauuau u 21

<210> SEQ ID NO 384
<211> LENGTH: 21
<212> TYPE: RNA
<213> ORGANISM: Unknown
<220> FEATURE:
<223> OTHER INFORMATION: Oligonucleotide

<400> SEQUENCE: 384
cugcgauuuc caaaucgauu u 21

<210> SEQ ID NO 385
<211> LENGTH: 21
<212> TYPE: RNA
<213> ORGANISM: Unknown
<220> FEATURE:
<223> OTHER INFORMATION: Oligonucleotide

<400> SEQUENCE: 385
ggacugguac uauacccacu u 21

<210> SEQ ID NO 386
<211> LENGTH: 570
<212> TYPE: PRT
<213> ORGANISM: Unknown
<220> FEATURE:
<223> OTHER INFORMATION: Recombinant B4ECv3 protein

<400> SEQUENCE: 386

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160
```

-continued

```
Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Gly Ser Lys Arg Ala Ile Leu
    530                 535                 540

Gln Ile Glu Gly Lys Pro Ile Pro Asn Pro Leu Leu Gly Leu Asp Ser
545                 550                 555                 560

Thr Arg Thr Gly His His His His His His
                565                 570
```

-continued

<210> SEQ ID NO 387
<211> LENGTH: 555
<212> TYPE: PRT
<213> ORGANISM: Unknown
<220> FEATURE:
<223> OTHER INFORMATION: Recombinant B4ECv3NT protein

<400> SEQUENCE: 387

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365
```

-continued

```
Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Gly Ser Lys Arg Ala Ile Leu
    530                 535                 540

Gln Ile Ser Ser Thr Val Ala Ala Ala Arg Val
545                 550                 555


<210> SEQ ID NO 388
<211> LENGTH: 233
<212> TYPE: PRT
<213> ORGANISM: Unknown
<220> FEATURE:
<223> OTHER INFORMATION: Recombinant B2EC protein

<400> SEQUENCE: 388

Met Ala Val Arg Arg Asp Ser Val Trp Lys Tyr Cys Trp Gly Val Leu
 1               5                  10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
        35                  40                  45

Val Leu Tyr Pro Gln Ile Gly Asp Lys Leu Asp Ile Ile Cys Pro Lys
    50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175
```

-continued

```
Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Gly Ser His His His His His His
225                 230
```

<210> SEQ ID NO 389
<211> LENGTH: 771
<212> TYPE: PRT
<213> ORGANISM: Unknown
<220> FEATURE:
<223> OTHER INFORMATION: Recombinant B4ECv3-FC protein

<400> SEQUENCE: 389

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300
```

-continued

```
Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Asp Pro Glu Pro Lys Ser Cys
    530                 535                 540

Asp Lys Thr His Thr Cys Pro Pro Cys Pro Ala Pro Glu Leu Leu Gly
545                 550                 555                 560

Gly Pro Ser Val Phe Leu Phe Pro Pro Lys Pro Lys Asp Thr Leu Met
                565                 570                 575

Ile Ser Arg Thr Pro Glu Val Thr Cys Val Val Val Asp Val Ser His
            580                 585                 590

Glu Asp Pro Glu Val Lys Phe Asn Trp Tyr Val Asp Gly Val Glu Val
        595                 600                 605

His Asn Ala Lys Thr Lys Pro Arg Glu Glu Gln Tyr Asn Ser Thr Tyr
    610                 615                 620

Arg Val Val Ser Val Leu Thr Val Leu His Gln Asp Trp Leu Asn Gly
625                 630                 635                 640

Lys Glu Tyr Lys Cys Lys Val Ser Asn Lys Ala Leu Pro Ala Pro Ile
                645                 650                 655

Glu Lys Thr Ile Ser Lys Ala Lys Gly Gln Pro Arg Glu Pro Gln Val
            660                 665                 670

Tyr Thr Leu Pro Pro Ser Arg Asp Glu Leu Thr Lys Asn Gln Val Ser
        675                 680                 685

Leu Thr Cys Leu Val Lys Gly Phe Tyr Pro Ser Asp Ile Ala Val Glu
    690                 695                 700

Trp Glu Ser Asn Gly Gln Pro Glu Asn Asn Tyr Lys Thr Thr Pro Pro
705                 710                 715                 720
```

-continued

Val Leu Asp Ser Asp Gly Ser Phe Phe Leu Tyr Ser Lys Leu Thr Val
725 730 735

Asp Lys Ser Arg Trp Gln Gln Gly Asn Val Phe Ser Cys Ser Val Met
740 745 750

His Glu Ala Leu His Asn His Tyr Thr Gln Lys Ser Leu Ser Leu Ser
755 760 765

Pro Gly Lys
770

<210> SEQ ID NO 390
<211> LENGTH: 459
<212> TYPE: PRT
<213> ORGANISM: Unknown
<220> FEATURE:
<223> OTHER INFORMATION: Recombinant B2EC-FC protein

<400> SEQUENCE: 390

Met Ala Val Arg Arg Asp Ser Val Trp Lys Tyr Cys Trp Gly Val Leu
1 5 10 15

Met Val Leu Cys Arg Thr Ala Ile Ser Lys Ser Ile Val Leu Glu Pro
20 25 30

Ile Tyr Trp Asn Ser Ser Asn Ser Lys Phe Leu Pro Gly Gln Gly Leu
35 40 45

Val Leu Tyr Pro Gln Ile Gly Asp Lys Leu Asp Ile Ile Cys Pro Lys
50 55 60

Val Asp Ser Lys Thr Val Gly Gln Tyr Glu Tyr Tyr Lys Val Tyr Met
65 70 75 80

Val Asp Lys Asp Gln Ala Asp Arg Cys Thr Ile Lys Lys Glu Asn Thr
85 90 95

Pro Leu Leu Asn Cys Ala Lys Pro Asp Gln Asp Ile Lys Phe Thr Ile
100 105 110

Lys Phe Gln Glu Phe Ser Pro Asn Leu Trp Gly Leu Glu Phe Gln Lys
115 120 125

Asn Lys Asp Tyr Tyr Ile Ile Ser Thr Ser Asn Gly Ser Leu Glu Gly
130 135 140

Leu Asp Asn Gln Glu Gly Gly Val Cys Gln Thr Arg Ala Met Lys Ile
145 150 155 160

Leu Met Lys Val Gly Gln Asp Ala Ser Ser Ala Gly Ser Thr Arg Asn
165 170 175

Lys Asp Pro Thr Arg Arg Pro Glu Leu Glu Ala Gly Thr Asn Gly Arg
180 185 190

Ser Ser Thr Thr Ser Pro Phe Val Lys Pro Asn Pro Gly Ser Ser Thr
195 200 205

Asp Gly Asn Ser Ala Gly His Ser Gly Asn Asn Ile Leu Gly Ser Glu
210 215 220

Val Asp Pro Glu Pro Lys Ser Cys Asp Lys Thr His Thr Cys Pro Pro
225 230 235 240

Cys Pro Ala Pro Glu Leu Leu Gly Gly Pro Ser Val Phe Leu Phe Pro
245 250 255

Pro Lys Pro Lys Asp Thr Leu Met Ile Ser Arg Thr Pro Glu Val Thr
260 265 270

Cys Val Val Val Asp Val Ser His Glu Asp Pro Glu Val Lys Phe Asn
275 280 285

Trp Tyr Val Asp Gly Val Glu Val His Asn Ala Lys Thr Lys Pro Arg
290 295 300

-continued

```
Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455


<210> SEQ ID NO 391
<211> LENGTH: 26000
<212> TYPE: DNA
<213> ORGANISM: Homo sapiens

<400> SEQUENCE: 391

ggggtttcat catgttggcc aggctggtct tgaactcctg acctcaaatg atccgcctgc     60

ctctgcctcc caaaatgctg ggactacagg cgtgagccac cgcgcccgcc acacccacct    120

tttctttacc gttgtttcct cgatttttct ctactcccta gcgcagctta gtgcgcgcct    180

cctctggaca tttttcaggg cttggttgcg cgcacagtag gtccccaaca ctgaatgttt    240

atggggtgac tgtgtgaacg ttcgctgcaa ggctatccaa actgggattg ctccttgagg    300

ccccctgggc ggccgtcaat tctccaaagc ttctactccc ttttccttcc ttttccccca    360

aaacgcagtc cctgcgccca ctagagggtg gtgggcgcat ccaagagcgg catctagagt    420

ccgcagcaag gtcagagcgg gctttgtgtg cgcggtgaac atttacgtgc acgcctgggc    480

ggccctccgt gttgctgctg ggtgtgtgtt ttctctgctc cctggtgcca gccgggttcg    540

ggcctgtccc gggggtccct gggccccagc cccgacatgc tcggtcctgg acagcgcgca    600

ccgccacggc gcacatctgg gcggtcccgg ggttcctcac ccgccgcccc tccccccttct    660

ccaaactttc tctcaacttc ccgacctgct ccactcggtg cccctctccg cttccctcat    720

gaattattca gtagcgtgag ctccaatcag cgcgcccggg gctcactcgc ggagcccccg    780

cgttgggaga gctgccccccg ccccccgcgc gcccctccct cccgggcccg gcgccgcccg    840

gcccagttcc agcgcagctc agcccctgcc cggcccggcc cgcccggctc cgcgccgcag    900

tctccctccc tcccgctccg tccccgctcg ggctcccacc atccccgccc gcgaggagag    960

cactcggccc ggcggcgcga gcagagccac tccagggagg gggggagacc gcgagcggcc   1020

ggctcagccc ccgccacccg gggcgggacc ccgaggcccc ggagggaccc caactccagc   1080

cacgtcttgc tgcgcgcccg cccggcgcgg ccactgccag cacgctccgg gcccgccgcc   1140

cgcgcgcgcg gcacagacgc ggggccacac ttggcgccgc cgcccggtgc cccgcacgct   1200

cgcatgggcc cgcgctgagg gccccgacga ggagtcccgc gcggagtatc ggcgtccacc   1260
```

-continued

```
cgcccaggga gagtcagacc tgggggggcg agggcccccc aaactcagtt cggatcctac   1320
ccgagtgagg cggcgccatg gagctccggg tgctgctctg ctgggcttcg ttggccgcag   1380
ctttggaagg tgagtttcct tgcggggggg ggcgcacccc gtcactcctg ggacctcccc   1440
cccaacatct gggcctcgga gtggaggggc cggcctctga ctacccctac ccgggcactg   1500
cagtcccaaa cacttcggac cgatagtgct ggaacgggag gggggcgggg aagaggcgcc   1560
cgacgggtag tggagttttc ttttgtttgg gaaagagatg gagtctggct acgacccggg   1620
acattcccct gcccgggctc cccgaactct cactgctgat tacatacgcc cctggctgcc   1680
tttcctttcc tccctacccc actattcaaa actatctgca aagtttctgt cccagtccca   1740
cctcccgccg tacatgaggg aaggtttctg gagaagcaac agcagacaag gcacaacttt   1800
tcgtgctagg ccctaaaacg acccccagcg ccaattcctt agcgatcaca ccttgatcct   1860
ccagttccac actcctgcaa caggatggcc tcctttgcat tcacacagca aacccccaaa   1920
ccgctctccc gcccactgct cctgccccctg gtatagggtg gctccttggt ttctacaggc   1980
tgcaccccat ccctttaaat gcggtctaga ccccggcccc aggtgagtcc cgggcttccc   2040
ttgagaccta ggagcgggta gaaactgacc tacacagccc ccaggtagaa actgacctac   2100
acagccccca catcgcccta actaacccag tctatctccc acctcctggt ctctccaagc   2160
atttctttgg ccatggatcg ctgtccctcc tggtccccta aagggggagc caagagccct   2220
agaaactctc ctgtgtccct aatgtccttt cagtgagctg ccaacacccc cctttctctg   2280
tctggtatga aagtggttat ggggcggtag gctatgaggg actcccaaag ggaaggattc   2340
agcggcgtta gaaaaaccct ctccccctgg ctgggcagga ctgccctggg ctggggatca   2400
aaggctaggt gtggggttgg gagtgagggg aggcttgccc agctcagaga acggagaagg   2460
gggaacaaaa accatgaacg aggggaagag gaaggccaaa ggggtggaaa aaccacgagg   2520
acgaggtgtg gtgagaagga aagacgcaaa gaggaaatgg tgattgtgac acctattacc   2580
tgagtgtttc caagcaccag gcctgtgctg agcgccttac aaatattaat ttcacccatc   2640
cagcaacgct aagggtggtg ctattattgc cccccatttt cagatgagga ggctggggct   2700
tagttaaggt taagtagttt atccaaggcc ctgtgccgcg aggaacagcg agaagtggag   2760
gccgaaagcg aaggagagat agtgactgtc agaaagagaa acggaggtgg acagagagtg   2820
gaggagagat aggtgagaga catgcgaact gacagatcaa agcgtggctg cagctgagct   2880
gggacgcaga aagggagcct gcgcttgctc tgggctgcgg acagcccgag gcagagacag   2940
tgtgtaaatt ggagacagga aaacactatc ccggctggaa caatggaggg tggagacggc   3000
agcctctatc caccccccttc ccagaacccg ggcatcctgt ccccagtgag cagggctgtc   3060
tcttgccacc catggggacc ttgcgcctct cacctcaggc tggctggctt cccatctgac   3120
ccctagctgg aggacatcat ttggtcccca ggaagaggct gcctcaccca ccctctttct   3180
cttctctcct gcagctccca tggggtggga gccaggtgtt ctggctcccc tctccaccct   3240
tcccagcgcc caatgccccc cacattgccg gcccccgagg ggattcctgt accctccctc   3300
ctccactctc cactgccagg ggctgtgcag tttttcctaa tcccccccct tcctccagtg   3360
cctgtcccct cccccgatga tccgagccaa gccaggtgtg ttcacccctc ccattcatac   3420
cgccccccag aatctcctcc cctctgcctt cccataacca aatccagatg tgaggcctcg   3480
gcgggagcct gggaacccta gcatcccgac ctccagtgct tcctgatcag ggcactcgtg   3540
gggagggagg tactgggatg ggggccaggg ctatgcccca ggcacggagc gctcccttca   3600
aggagggaag gacggggtgt ttggtctgaa agcagagagg ggtcttggac agggaatgaa   3660
```

-continued

```
attgtggggt agagaggctg attctgggac ttaggggagg aaacgtggag gctgagacaa   3720
gaggttcccc tcccacacca gcagcctctg ctcgtggggg tcaggaccag ggcgcagctc   3780
tcattttaac cctttctgag ctgccgcccc ttctccccgt acattttgat ctccctccct   3840
cctccaggga ggcctagatc tggggtatcc caagggagcc ccatgcctac cagatgttgg   3900
gggtggggtt ggcacttagc agaagaggcc agaaatcagg cgggtgcaga gggcagggct   3960
tgctcccctc ttggcccccc aactcctcta gctcagagct aagaggatcc acctgcctcg   4020
gttcccaggg atctggtctt cctgacctcc ctcccccacc ccaggcactg actctgtctc   4080
tctgtctgtc tcagagaccc tgctgaacac aaaattggaa actgctgatc tgaagtgggt   4140
gacattccct caggtggacg ggcaggtgag agctgcaccc aggagctgga gctctggagg   4200
gaaactgagg gaggagaggg cgcctgtgcc gcctgctttc tgtgtgccac tcctctcccc   4260
tgtcccccca gatgacagca gccccagcag tgtcgtctga gcccttctca gaggcgccct   4320
cctcgcagta ccagcagccc ccctttctca gtccctctca ctttatagga ttcaccccat   4380
gcagccctct ccctggcggc tccccagccc ccttgctgac ctccttctct gcacagtggg   4440
aggaactgag cggcctggat gaggaacagc acagcgtgcg cacctacgaa gtgtgtgacg   4500
tgcagcgtgc cccgggccag gcccactggc ttcgcacagg ttgggtccca cggcggggcg   4560
ccgtccacgt gtacgccacg ctgcgcttca ccatgctcga gtgcctgtcc ctgcctcggg   4620
ctgggcgctc ctgcaaggag accttcaccg tcttctacta tgagagcgat gcggacacgg   4680
ccacggccct cacgccagcc tggatggaga accccctacat caaggtacct gggtgccccc   4740
agggctcagc cacagccaag gtgggattcc agccagcagg cccgtggcct ggagggcagc   4800
cgatgtagtt gcgaggcctc tggcccgcgc gctgggggct ggaagcagga ggcttaggtc   4860
tggggaggga agggggtgat cttctgggcg gaggagcaga atatacgggg gctgcctggc   4920
ccggccccca gggaggccca agggtcaggc ttctcctcca gtcacctcaa ccaccctacc   4980
ccactgtgct ccagccacac tgagtttctc ccattccctg actgcacctg gctggtttcc   5040
agctcaagac tttgcagcgg tgatgtctcc acctgggggc ctctctgcct ctcacacccc   5100
tacttgtctt cggagttcca gctcccgaga tcttgcctgt gccaccttgg ctgactctct   5160
cctccctaca atcctgcata cctctgtcca cctgcctgtc tcggcactca ttttacttta   5220
tttatttttc ttttatatct atatttttaa agcggggtct tctacgttac ccaggctggt   5280
ctctaactcc tgggctcaag agatttctcc cacctcggcc tcctaaagtg ctgggattat   5340
aggcatgagg cactacgccc ggcctcatgg tactttataa cttccccagg attcattcat   5400
cgctgtctcc ttgactctga ggtcaaggcc tggcatggcg tcagtgtcag taaatgtttg   5460
tagaacgagt gaataaaaag ggggagaggt gcaggccaga ggccgggcat atcgcaggag   5520
ctttgcaagg ctgaatggac agtgtggggg cctgcagaaa gtgtgccctg gggaaggtgg   5580
agggaagatt ctggaacggg aaccaaggag gtccgggagg gtgagctggg aagaacacaa   5640
cagtccgctg ggtcctcagg gagtggggac agcagcggtg tgcctccccc ccgccggcag   5700
gtggacacgg tggccgcgga gcatctcacc cggaagcgcc ctggggccga ggccaccggg   5760
aaggtgaatg tcaagacgct gcgtctggga ccgctcagca aggctggctt ctacctggcc   5820
ttccaggacc agggtgcctg catggccctg ctatccctgc acctcttcta caaaaagtgc   5880
gcccagctga ctgtgaacct gactcgattc ccggagactg tgcctcggga gctggttgtg   5940
cccgtggccg gtagctgcgt ggtggatgcc gtccccgccc ctggccccag ccccagcctc   6000
tactgccgtg aggatggcca gtgggccgaa cagccggtca cgggctgcag ctgtgctccg   6060
```

-continued

```
gggttcgagg cagctgaggg gaacaccaag tgccgaggtg agagctggag cttcccctgc   6120
gactgctgct catccggggg agagtcctga actccactca ggacccactt cttaagtttc   6180
cattttgtat agttagatgt tgaaatggag gcttgctctg tcacccaggc tggagtgcag   6240
tggcacaatc tctgctcaac tgcaaccttt gcctcccggg tccctgttca agcagttctc   6300
ctgcctcagc ctcgtgagta gctgggacta caggcacacg ccaccacgcc cggctaattt   6360
ttgtatttta gtagagacgg ggtttcgcca tgttggccag gctggtctcg aactcctgac   6420
ctgaagtgat ttgcccgcct cggcctccca aagtgctggg attacaggcg tgcgtcacca   6480
cacccagctg gaaaaaaaaa agactttatt ttcacctgaa attcattaat ttccacttga   6540
aattccacct gcagttgtag caggacctga cacttgggcc ccatggaaat cacaggtatt   6600
gcctgacaca gtggttcatg cccatagtgc cagcactttg agatgccaag gtgggaggat   6660
cacttgagcc caggagttcg agatcagcct gggtgacaga gcaagacccc gtctctaaaa   6720
aaaatttttt ttttttttc aagacagagt cttgctctgt cgcccaggct ggagtgcagt   6780
ggtgcgatct cggctcactg caagctccgc ctcccaagtt aacaccattc tcctgcctca   6840
gcctcccgag tagctgggac tacaggcccc gccaccacgc ccggctaatt tcttgtattt   6900
ttagtagaga tggagtttca ccgtgttagc caggatggtc tcgatctcct gacctcatga   6960
tctgcccgcc ttggcctccc aaagtgctgg gattacaggt gtgagccacc acacccggat   7020
tacaaaaact ttttagataa ttatctgggc gacctgcctg accaacatgg agaaaccctg   7080
tctctactaa aaatacaaaa ttagccggac atggtggcgc atgcctgtaa tcccagctac   7140
ttgggaggct gaggcaggag aatcatttga acccaggaag cagaggttgc ggtaagccga   7200
gatcatgcca ctgcactccg gtctgggagt gcactccaac aagaaggagt ttcgctcttt   7260
ttgcccaggc tggagtgcag tggtgggatc tcagctcacc gcaacctcca cctcccgggt   7320
tcaggcgatt ctcctgcctc agcctcccaa ggagtagctg ggattatagg tatgcatcgt   7380
cacacccggc tacttttgta tttttagtag aggcaggttt ccaccatgtt ggccaggctg   7440
gtcttgaact caagtgatct gccctctttg gcctccttct caggaaaaaa aaaaaatcac   7500
aggtatttac aggccattcc aagtgccaaa agattgtttt tgctcatggt gacttcagta   7560
tcacagatgt taggagactt gctgctatat gttaagaaag aagcacaaat gttgctgtag   7620
cccaaacttt tttcctcatg tttcattgca tttcagctta attggtttcc ctggtattcc   7680
tatgtatttt gtggagtgct tttaaaatca taagttggag tagaggtctt tctgtgggct   7740
tcaccagact gccgagatca gggtcgaaac aggtgaggac cccttctctg gagagagtct   7800
cctttctcct ctaagaggaa aggttttgag atcttttgtc cattttccca ccttagcact   7860
tcatcagcct taaaagaagc tggaattttt tttttttttt ttggagatgg gatctcgata   7920
tgttgcccag gctggtcttg aaccccttgg ctcaagcgat cctccagcct cagcctccca   7980
aagtgctggg attcgaggca tgagccaccg agcccaccgt gcagatggat gtttttgtgc   8040
atgcttttga tgaatgcttt ctctctctca gcctgtgccc agggcacctt caagcccctg   8100
tcaggagaag ggtcctgcca gccatgccca gccaatagcc actctaacac cattggatca   8160
gccgtctgcc agtgccgcgt cgggtacttc cgggcacgca cagacccccg gggtgcaccc   8220
tgcaccagta agtgaccagc acccaggtgc agttcactgg ggaggggtca cagacctctg   8280
aggtggaccc tcacatggcc cccatcctcc ctgggcttct tcccctttgtc cctggcatgc   8340
ttgtccctag cccggaggaa catgtggagc ccactgtctc caaggcaaga gtccagcatg   8400
gctgctggtg cctccattgc cctctcccca ccaccgcaga gcaggtcggc ctctgcctga   8460
```

-continued

```
ctccctggtc tcctgcagcc cctccttcgg ctccgcggag cgtggtttcc cgcctgaacg   8520
gctcctccct gcacctggaa tggagtgccc ccctggagtc tggtggccga gaggacctca   8580
cctacgccct ccgctgccgg gagtgccgac ccggaggctc ctgtgcgccc tgcgggggag   8640
acctgacttt tgaccccggc ccccgggacc tggtggagcc ctgggtggtg gttcgagggc   8700
tacgtcctga cttcacctat acctttgagg tcactgcatt gaacggggta tcctccttag   8760
ccacggggcc cgtcccattt gagcctgtca atgtcaccac tgaccgagag ggtgagactt   8820
gggggctggg gcggctggtg gtctggcggg agagatgtca ctgagggcct gaaggggaga   8880
ggcaggggct gtgaagttgg gtaccccgga agtgtgaggg gctaaggctt tgggggcaag   8940
aggcagaaag agggcaatgg ctgggcgcag tggctcacgc ctgtaatccc agcactttca   9000
gaggctgaga caggcggatc acttgagccc tggagttcaa gaccagcctg ggtaacatag   9060
gaagatctct ctacaaaaaa taaaaatatt agccaggcga ggtggtgcat gcctgtggtc   9120
ccagctactc aagaggctga ggcaggagga ttgcttgagc ccaggagtcg gaggctgcag   9180
tgagctatga tcgcaccgct gcatgccagc ctgggtgaca gagcagtgtg agatcctctc   9240
tcaaaataaa tgaataagaa agagagggtg aggagctcgt aaagctgggc tggagagtta   9300
agtacaggaa ggcccccagt gggactgggg ccagagagaa tcagaaggaa ttctcgaaac   9360
agccaggggg aaattgagac aagtgtagcc agcagaggaa gtgttggaaa agataaggga   9420
catggccagg ctgatcacaa ggtcaggagt tcaagactag cctggccaac gtggtgaaac   9480
cccatgtcta ctaaaaataa aaaaattagc caggcatggt ggtgggcacc tgtaatccac   9540
ttgggaagca accagaagaa ttgcttgaac ccaggaggcg gaggttgcag taagctgaga   9600
ctgcgccact gcactccagc ctgggtgata gagcacgact ccgtctcgaa aaaaaaaatt   9660
ttttttaagt taagggacag agctaccatg cacaagggtt ccctgtgtct ctgcctctca   9720
cagtacctcc tgcagtgtct gacatccggg tgacgcggtc ctcacccagc agcttgagcc   9780
tggcctgggc tgttccccgg gcacccagtg gggctgtgct ggactacgag gtcaaatacc   9840
atgagaaggt aaggccatcc cccagccctg gggtgggtgg gcaatgggtt gtgctctcct   9900
ggctgggaca cctgggttgc aggcacctgg caggcatttg aattccagct ctgccatgga   9960
ttccctgggc agccttgggt aagccccttg gcctgtctga gcctcagact cttcatctat  10020
aaaatagtta ctgtaatagt taccagcagc tggacacagt ggctgaggtt gggtgcggtg  10080
gctcacgcct gtaataccaa gcactttggg aggctgaggc gggcagaatg cttgagccta  10140
ggagtttgag accagcctgg gcaacatggt gaaacttcat ctctataaaa aacttaaaat  10200
gggccgggcg cggtagctta cgcctgtaat cccagcactt tgggaggccg aggtgggcgg  10260
atcacaaggt caggagtatc gagaccatcc tggctaacac ggtgaaaccc catctctact  10320
aaaaatacaa aaaattagcc aggcgcggtg gcaggcgcct gtagtcccag ctactcggga  10380
ggctgaggca ggagaatggc gtgaacccag gaggcggagc ttgcagtgag ccgagatagc  10440
gccactgcag tccggcctgg gcgaaagaac aagactctgt ctccaaaaaa aaaaaaaaaa  10500
aaaaaaaacg caaaaaatac ttaaaatgaa aaaaattaga ctgggcacag tggctcatgc  10560
ctgtaatccc ggcactttgg gaggccgagg tgggtagaac acctggggtg aagagttcga  10620
gaccagcctg gccaacaagg tgaaatcccc gtctctacta caaatagcaa aatcagctga  10680
gtgtgttggc gggcccctgt aatcccagct actcaggagg ctgagacagg agaatcactg  10740
gaacccaagt gattctcgac ttgaggtcga ggctgcagtg agtcgtgttt gcaccattgc  10800
attccagcct gagaaagtga gaccttgtct taaaaaaaag gaatgatatt atgaatacag  10860
```

-continued

```
cacatggctt gcatgcgtaa gttctcccaa aggcctcacc agttgcaagg caggctagtg  10920
atgggagtgg agggcgaggg aaggaggcag gaagagcaac aggaacttgg gttcccgggt  10980
gacggccacc ccactacctc tcccggacag ggcgccgagg gtcccagcag cgtgcggttc  11040
ctgaagacgt cagaaaaccg ggcagagctg cgggggctga agcggggagc cagctacctg  11100
gtgcaggtac gggcgcgctc tgaggccggc tacgggccct tcggccagga acatcacagc  11160
cagacccaac tggatggtga gcctggggaa gggggtgagg gtgggggttg gaaagacccc  11220
caaagttcct gggaagaccc caggtctcca aagtcccatc atcttttttt tttttttttt  11280
tttttgagat ggagtcttgc tctgtccctc aggctggagt gcagtggcac catctccgct  11340
cactgcaacc tccgcctccc ggattcaagc cattctcctg cctcagcctc ccgagtagct  11400
gggattacag gcgcctgcca ccgcgcctgg ccgatttttt gtatttttag tagagacggg  11460
gcttcaccgc gttggccagg ctggtctcga actcctgacc ttgtgattcg cccgcctcgg  11520
cctcccgaag tgctgggatt acaggcatga gccactgcac ccggtcaaag tcctatcttc  11580
atgtccttct tcctgtggat cacatggcat gccctagaga ggagagaacg taagatgtcg  11640
aaaccaaaac caacagctga gttttgtgaa gtctggcctg cttcactctg tacccccagg  11700
ctggagcgca gttgctcgat caaagctcac tgcacagcca ggcacagtgg ctcaccctgt  11760
aaccccagca ctttgggagg ctgaagcagg aggatcactt gaggtcagga gttcgagacc  11820
agtctgacca gcatggtgaa accgcgtctc tactaaaaat atagaagtta gctgagcgtg  11880
gtggtgcaca cctgtaatcc cagctactcg ggaggctgag gcaggagaat cgcttgaacc  11940
tgggaggtgg aggttgcagt gagctgagat tgtgccagtg cactccagcc tgggcaacag  12000
agcaagactc tgtctcaaaa aaaaaaaagc tcaccgcagg cttgactttt agcaacaacc  12060
tgacccctga gctccccatt ccccatccaa caaaatggga atatcatgaa gcttcctgca  12120
gggctttgag gattggaggt aacaggttat ttttaatatg ctaggccagt ggctttcttt  12180
tttctttcac attttttttt ttgagacgga gtctcactct gttgcccagg ctggagtgcg  12240
gtggcgcgat ctcagctcac cgcaagctcc acctcctggt ctcgatctgc tgacctcctg  12300
atccacccgc ctcggcttcc cgaaatgctg ggactgctgg cgtgagccac cacgcccggc  12360
ctaacttttt cttttttttta agagacacgg tcttttttat cacccaggct ggagtgcggt  12420
ggcaccatca tagctcattg cagcctacaa ctcccgagct caaccaatcc ttccacctta  12480
gcctcccaag tagctggggc tataggcatg tgctaccgtg ctcaactaaa ttttttttta  12540
tgttttgttg agacagtttc cctatgttgc ccaggctggt ctcaaattcc tgacctcgag  12600
caatcctccc gcatcggcct cccaaagtgc tgggattaca ggcatgagcc gccacaccca  12660
gcattggacc agtggctttc taaaccttgt aatttttctgt aatagcttta ctgaaataca  12720
gttcccctgc catacaattt gcctgttcaa agtgtacaat cgatgacttt tgatacattc  12780
acagaattgt gcagtcacca ccacaagtaa ttttgggaca ttttcagcac cctcaaaaga  12840
gaccctatag cccttagcca tcacccccca cccagatctt tctgttgcct tagtccctgg  12900
caagcactaa cccactttct gtcttgaaat cttccagtgt ggtcttttgt gactgttcac  12960
cgagcagaat gttttcaagg tttatgtatg ttgtagtata tatccgtggg tttttttggt  13020
tgtggtttgt tttttgtttg ttttggaaac agggtctcgc tctgtcaccc aggctggagt  13080
gcagtggttc aattacagct cactgcagcc tcaacctccc aggctcaagt gatcctccca  13140
cctcagcctc ccaagcagct gggactgtag gcatgagcca ccatgcccag ctaatttttt  13200
ttggtatttt ttgtaaagac agggtttcac catgtttccc aggctggtct cgaactcctg  13260
```

-continued

```
agctcaggca atccacccac ctcagcctcc caaagtgctg tgattacagg catgagccac  13320
tggacctggc ctgtttttttg tttttgtttt gaacacacga ttttgctttg tcacccaggc  13380
tggaatgtaa tggtctgatc atagtgcatt gcagcctcaa actcctgggc tcaagcgatc  13440
ctcctacctc agcctcctga gtatctggga ccacacgtgc tcaccaccat gcttggctaa  13500
ttattattat tttttgatag agacggggtc ttgctatgtt tcccaggctg gtcttgaaca  13560
cctggcctca cacaatcctc ccacctcagt atctcagagt gctgggatta caggcatgag  13620
ccactgctcc tggccaatat ttcatttctt tttatggaga cgtaataatc agttgtatgg  13680
aaatagctga ttttgttttt tattgtatct tttggtgaac atttcaattg tatcgacttt  13740
ttggataaaa acctgaaaat gtttcacctt tagaacgttt cattgaatgg agattttttt  13800
gtggactctg gtatttatac tagaaccaaa tcaaaaccac tctggcggct gggcatgcct  13860
aggctggttt gagactagcc tgtccaacct ggtgaaagcc catctctact aaaaatacac  13920
aaattagccg agcatggtgg tacacacctg taatcccagc tactcaggag gctgaggcag  13980
gagaatcgca gaacccggga ggcggagatt gcagtgagct gagattgcgc cactgcactc  14040
cagcctgggc gacagagtga gactgcgtct caaaaaaaca aacaaaaaat tactctggca  14100
gtaagaaaag atttcgaaac ttcctccctt gccctgaggt acttcagagg agcctgctgg  14160
cccctggggg agagtttgaa acccactgtt tgttccctga ccttgcctgc ttgtgtcctc  14220
tccctccacc tgtcccctgt actggggacc tgttctcagg agatcacagt tcattgctca  14280
aagccggggc tggggcctcc tacaggacca tcagtttctc ctgatcagca gcctttcctt  14340
ccgcagagag cgagggctgg cgggagcagc tggccctgat tgcgggcacg gcagtcgtgg  14400
gtgtggtcct ggtcctggtg gtcattgtgg tcgcagttct ctgcctcagg taagggctct  14460
gacacccaga ggcccctgga agccctcagt tgatggccac ctgcctgggt gctacaggac  14520
aagcctttct ggctgtcccc agcctctttt tacttgaaat cttctccaat ccctgctcct  14580
tcctttggtg tgtgtgcctc ataaagatgt gtgactcagt ttacctttttg ttcctttccc  14640
atcggctaca ggaagcagag caatgggaga gaagcagaat attcggacaa acacggacag  14700
tatctcatcg gacatggtgg gttgccctaa tttgatggga atagggggctt ggggccgggt  14760
gtggtggctc ctatctataa tcccagcact ttgggaggca gaggtgggca gatcacttga  14820
ggtcaggagt tcgagaccag cctggccaac atgttgaaac tccatctcta taaaaaaatac  14880
atcagtcagc caggcatggt ggtgggcacc tgtaatccca gctactcagg aggctgaggc  14940
agaagaatca ttttaacccg ggaggcggag attgcagtga gccaagatcg cgccactgcg  15000
ctccaggcct gggtgacaga gcgagactcc atctcaggaa aaaaaaaaaa aaaaaaaaaa  15060
accacggaga caggggtttg gggctaaaag ctatgagccg agcctccgag tccagtggga  15120
gttaattccc agctgacggg gccctgcctg atttctcagg tactaaggtc tacatcgacc  15180
ccttcactta tgaagaccct aatgaggctg tgagggaatt tgcaaaagag atcgatgtct  15240
cctacgtcaa gattgaagag gtgattggtg caggtgagag ccgaaggctg cccgggcacc  15300
tgggaacgaa gcgggggtgg gcagggccac actggagcgg gagagctgat gacctctgcg  15360
tccttgtttg aaggtgagtt tggcgaggtg tgccggggggc ggctcaaggc cccagggaag  15420
aaggagagct gtgtggcaat caagaccctg aagggtggct acacggagcg gcagcggcgt  15480
gagtttctga gcgaggcctc catcatgggc cagttcgagc accccaatat catccgcctg  15540
gagggcgtgg tcaccaacag catgcccgtc atgattctca cagagttcat ggagaacggc  15600
gccctggact ccttcctgcg ggtgagcacc ctccctggct tctgcggcca cccggagttc  15660
```

-continued

```
ccacttacac ccagaggcca cttgggttaa gaagccagga cagacagtgg gtcccaggtc  15720
acctcctcca gccttttcct cttgggctaa gccctggtcc tctgcctttt ctttttttta  15780
agacagagcc tcgctctgtc gcccaggctg gagtgcagtg gcgcgatctc ggctcattgc  15840
tgtctccacc tccagggttc aagcgattct cctgcctcag tctcccaagt agctggtact  15900
ataggcatgc accaccatgc tgactaattt ttgtattttt agtagacaca gggtttcacc  15960
atgtaggcca ggctggtatc aaactcctga cctcaagtga tctccccacc tcagcctccc  16020
aaagtgctgg tattacaggt gtgaggcacc acgcctggcc agccctctgc ctttaatttt  16080
ccctctggga aaggctgggc tcctgggacc ttcctttccc actgccccat acagctgaag  16140
gttgtcattc cttctttttt tttttaattt tgttttaatt gaattttttt tttttgagat  16200
ggagtttcac tcttgttgcc caggccggag tgcaatggca agatcttggc tcaccgcaac  16260
ctccgcctcc caggttcaag cgattctcct gccttagcct ccccagtagc tgggattata  16320
ggcatgtgcc accacgcttg actaattttg tatttttagt agagacgggg gtttctctgt  16380
gttggtcagg ctggtctcga actcccgacc tcaggtgatc cgcctgcctc ggcctcccaa  16440
agtgctggga ttacagacgt gagccaccgc gcccggccaa tttttttttt ttttttttaa  16500
gacagagtct cactctgtcc tctaggctgg agtgcagtgg tgcattcata gctcactgta  16560
gccttgacct cctgggctca agtgatcctc ccgcctcagc ctcctgagta gctggaacta  16620
cactcatgta ccaccatgct cagcaaattt ttaaaatttt ttgtagagac aggatctcga  16680
taggttgccc aggctggtct gaactcctgg cctcaagcga gcctccctcc tcagcctccc  16740
acagcactgg gattgcaggc atgagccact gtgcctggcc tgtcattcct tcttttgaca  16800
aatatttact gagtgctttc tacgcaccgg tcatcctccc agtccccagg aataaagcta  16860
tacacacggc aaactggatt tctcctcttg gggagcagag ggtctaatgg ggcaggggga  16920
ctgaaaatta gcaagtaaat agacaggctt tttaaaaaag taaacaaatc atttcaaatg  16980
tgaaaaaaag caaacggggt ccttcatgca gatgtggcta gagaggaaag agaactgctt  17040
aatttatttg gtcactttac cagattttac tgactttttt tttttttta actttattaa  17100
gcttttcttt tttcttgaga tggagtttcc atctgtcacc caggctggag tgcagtggtg  17160
cgttcttggc tcaccgcaac gtccacctcc tgggttcaag tgattctcct gcctcagcct  17220
cctgagtagc ttggaattgc atggcatgca ccaccatacc cagctgatgt ttgtattttt  17280
agtagagaca gggtttcatc atgttgccca ggctggtctt gaactcctgg gctcaagtga  17340
tccacccatc tcggcccctc aaagtgctgg gattacaggc atgagccacc atgcctggcc  17400
taggcatctt tttaaaaaaa tcaaaacatt tttctatgta gcaaaataac attgcattga  17460
acagagttat agcgattccc tagcgtcatt gaatacccag ttgattttca cgtttctcta  17520
gttgttctaa agatgtcctt cactgctgct ttattccaac caggatccag ttcaagaccg  17580
ggctttgtac ctggttatta tatatatttt atttatttat tttagaaaca aggtcttgcc  17640
ctttcgccca gtttagagtg cagtggtgca atcatagctc actgcagcct ccaaactcct  17700
tggctcaggt gatcctcctg cctcagcctc ctgggtagct ggaactacag gtgcacacca  17760
ccacacctgg ctaattttta aattttttac ggagatgggg gtctcgctat gttgcccagg  17820
ctggtctcaa actcctggac tcaagcgatc ctccctcctt aacctctcaa agtgctggga  17880
ttacaggcgt gagccaccac gcctgctgat tattatattt tcgagcctct ctaaatcttg  17940
agcagttcct catgatgaca ctgacacact gaagggttag gtcccttgtc cgcctgaatg  18000
tcttgatttc tggatttatg aaattcttct tatgggatca tttagcttgt ctctctgtat  18060
```

-continued

```
ttcctgtaag agaagctcta tctgatgtgg ggttttttttg gttttgtttg tttgtttttt  18120
gagatggagt cctgctgtcg cccaggctgg agtgcagtgg cacaatctcg gctcactgca  18180
acctccgcct cctgggttca agagattctt ctgcctcagc ctcctgagta gctgggacta  18240
caggcgagtg ccaccatgcc cagctaattt ttgtattttt agtagagaca gggtttcacc  18300
atattggcca ggatggtctc gaacttctga cctcgtgatc tgcccaccac ctcagcctcc  18360
cacagtgctg ggattacagg catgagccac tatgcccggc taatttttgt atttttagta  18420
gagacagggc ttcgccatgt tggccaggct gatctgaaac ccctggcctc aagccatcca  18480
ccctccttgg cctcccaaag tgctgggatt aaacgcgtga gccaccgtgc ctggtcgaag  18540
agacagaaag ggtcttaaag gttcagtgac acacacctgt aatcccagca ctttgggaag  18600
ctgaggctgg tggatcactc gaggccagga gttagagatc accctgggca acatggtgaa  18660
accccgtctc tacacaaaat acaaaaatgg gcagagcatg atggtgcata tctgtagtcc  18720
cagctactcg ggaggctgag gcgggaggat cacttaagcc tgggagatcg aggctgtagt  18780
gagccatcat tgcactactg cattccagcc tgggcgatcc catctcttaa aaagagagag  18840
agatgggaag accagcacag gtgaaactgg tgaacagagg agagatggta gatgctgcat  18900
tgggcagtgt gacgggaacc cgctggaggg ctttggcagg agagtagttt aagaggatcc  18960
cagctgggca cagtggctca cacttgtgat cccagcactt ggggaggccg gggcaggtgg  19020
atcacttgag gtcaggagtt cgagaccagc ctggccaaca tggtgaaacc ctgtctgtac  19080
taaaaataca aaaaccagcc aggcatggtg gtgcacccct gtaatcccag ctactcagga  19140
gactaagaca ggagaatcgc ttgaactcag gaggcagagg ttgcagtgag ccaagatcac  19200
gccactttac tccagcctgg gcagtagagc gagactccat ctcaaaaaaa taaataaata  19260
aaaagacctc tttgctgggt gctagggagc aagagcagga gctgggagag gcctgcagca  19320
gaagcctgtt gccagcatcc aggccgtggg gtgaagggaa gggtttggat ttgggacatg  19380
tcttggaagc atcaccagca gaacttgctg atggattgga agtggctggt gagggagaaa  19440
agggggtcaa aggaaactct gaggtctata ccctgaccat ctggcaagtg gtggtgttgc  19500
cacaaactga gcggggagta gggcaggtgc aggtctggag gatggattca aaattcagtt  19560
tttggagtct atgtccctgg ttctgtaggg ctgcagatgg tctgccaaat cttagcggaa  19620
cccagaatac gggatttgtt tactgtctgt gacttgttgg tttccctggt gagagcaaac  19680
tctttaaagg tcaaggttgg gcttcagacc ttggtttttg caccgatcat tggtcatact  19740
gcagttcctc actcttctct tgcaaatcca tacacagcta gtccaagaga gctgaacagc  19800
tttgtggttg gatcagcacc aatgtatctc cacctgtaga cgggttgctc aggtgactca  19860
tgcctgtaat cccagcacct tgggaggcca aggtgggaag attgcttgag gccaggagtt  19920
ggagacaagc ctgggaaaca cagtgagacc ccatatctac caaaaaaacc cctttgtttt  19980
aattagccag gtgcagtggt gtgcacctat agtcccagct actaaggagg ctgaggcaga  20040
aggatcattt gagcccagga gtttaaggct gcggtgaacc atgatcgtgc cactgcactc  20100
caacctgggg gaaagaaaga gaccttgtct ctaaaaaaac taaaaaacag aaaagcattt  20160
gttgagtatt tcctgggtat aaagcagtgt accaggttaa atggaaggaa aagttgaaat  20220
aatttttcaa ctcataatcc gattgggaga gactgaatgc ttaccattga agcaggaacc  20280
attgtaagca atgtgttgtg atactgtagc aagagctgag aaaacttggg aaaagagaaa  20340
ggaggaaggc tcacctgagg gagttggggg gcttgcccta caggtgagtt gtgaggtggg  20400
tctggaagtg acagatgcag tttaggaagt ggacgggagg ctgggtacgg tgactcaaca  20460
```

-continued

```
tctgtaatcc cagtgctttg ggagacccag gcggaaggat cgcttcaggc caggagttaa  20520
agaccagcct gggcaacata gtgggaacct atctctacta aaaattaaaa aattatccag  20580
gcataatggc acatgcctat tgttccagct actcaggagg cttgcctgag cccaggaggt  20640
tgaggctgca gtgagctatg atggcaccac tgcactccag cctgggcgac agaacaagac  20700
cctgtctcta aaaaaaaaag atgtggatgg gagggggaac ggtgggtggg ctgtcctcac  20760
caagcccccca ccctatctgc tctccagcta aacgacggac agttcacagt catccagctc  20820
gtgggcatgc tgcggggcat cgcctcgggc atgcggtacc ttgccgagat gagctacgtc  20880
caccgagacc tggctgctcg caacatccta gtcaacagca acctcgtctg caaagtgtct  20940
gactttggcc tttcccgatt cctggaggag aactcttccg atcccaccta cacgagctcc  21000
ctggtaatgc tgggggtaat actgggtgtg agcttcttag ggccaggtgg gcagggcagg  21060
ttggaaaggt gggaggctga gggtttggca gccctgctcc agggagagga tacaggagca  21120
ggctgtgggt ggggggacag tcagctccag gaagccgact tccagatgtc taggaaaata  21180
acagttggat aacctgggca acatagcaag accccatctc tacaaaaaaa ttaaaagatt  21240
agccaggcgc agtggcatgc acctgtagtc ccagctactt gggaggttga ggcaggagga  21300
ttgcttaagc ccaggagttg gaggctgcag tgagctatga atgtgccact gtactgcaga  21360
ctgggcgaca gagcaagacc ctgtctcaaa agaacagtgg ccaggtgtgg tggctcacgc  21420
ctgtaaatcc agcactttgg gaggctgagg caggaggatc gcctgaggtc aggagttcga  21480
gaccagcctg gccaacatgg gaaaaccctg tcgctactaa aaatacaaaa ttagctgagg  21540
gtggtggtac acgcctgtaa tccgagctac tcaggaggct gaggtaggag aaccagttga  21600
acccgggagg cggagtttca gtgagccaag atcgcaccac tgcactccaa cctgggcaaa  21660
cagagttgga gagtaggagg cttggggcct gagctagggg gaaaaagcag aggcaggtgg  21720
gggactgggg ggcagtgtgc tgggtctggt gagtccctca gtgagtcccc cagctcacct  21780
tttctccttt ttctgcaggg aggaaagatt cccatccgat ggactgcccc ggaggccatt  21840
gccttccgga agttcacttc cgccagtgat gcctggagtt acgggattgt gatgtgggag  21900
gtgatgtcat ttggggagag gccgtactgg gacatgagca atcaggacgt aagtgtcccg  21960
tggtcctacc aagctttcct cgagtgttct ctcacctggg atttggggtg aagggtgggt  22020
tcccagagag tcatcactgc tgggttcttg agaccatgga gatgacaaaa aggagaattg  22080
atctttgtat caaagagttg agatacaggg ccaggcctag tggctcaagc ctgtaatccc  22140
agcactttgg gaggccaagg tgggcagatc acctaaggtt aggagttcaa gaccagcctg  22200
gccaacatgg tgaaaccccg tctctaaaaa aatacaaaaa attagcccag catgatgggc  22260
gggtgcctgt aatcccagct actcaggagg ctgagacagg ataatcgctt gaacccagga  22320
acagaggttg cagtgagctg agatcacgcc attgctttcc agcctgggca actgagcgag  22380
actctgtctt aataaataaa taaaagagtt gggtacagca tatttgggtc gcagaaggat  22440
gcagagatgg agggcagggt tgagaggtaa catgtctgta tcatagccca agagctgctg  22500
gggccttcag ccacagagag cttcaactcc ggctaggagg attcctggat ctgttatttt  22560
ttggggggct gtggctccta tcctaccatc ttccaagtca ccatttcctg ggcctgttag  22620
catctttgct tttcctggac agcctcaccc agagcttctt cccctctttc caggtgatca  22680
atgccattga acaggactac cggctgcccc cgccccccaga ctgtcccacc tccctccacc  22740
agctcatgct ggactgttgg cagaaagacc ggaatgcccg gccccgcttc cccccaggtgg  22800
tcagcgccct ggacaagatg atccggaacc ccgccagcct caaaatcgtg gcccgggaga  22860
```

-continued

```
atggcgggtg aggactgcag agaatgggcc ctccttcccg ctctctgccc ccactccttg  22920
cccagaagtg tccgttcatt ggtgttgggt gggagggcct ctgtccgcct ctgcaaggct  22980
gggttccacc tcctccccg gacctgggcc tggtactcag cattcctccc catccttgcc  23040
ccctagggcc tcacaccctc tcctggacca gcggcagcct cactactcag cttttggctc  23100
tgtgggcgag tggcttcggg ccatcaaaat gggaagatac gaagaaagtt tcgcagccgc  23160
tggctttggc tccttcgagc tggtcagcca gatctctgct gagtaagcag tggcaggagc  23220
tggagtgggg ctgggagagc ggggcagctg gagtcaggcc cacggggtct ccaggggctt  23280
ttggggtcag cttcgggtgc caatgctgtc ttcttgcact gcgctcatgc catgcctaga  23340
agggccccag aggagcagtc acagccccat ggagctgagg acccaaggac tctttggggc  23400
cagcctgccc gcctcacctc ctcctgccat cacagccctg ggccatcgcg cttccgcctc  23460
tcacttctag ctatctttgt gcatctatct gcattccagg cccggctctc acggtaacaa  23520
tgtgtcaact cgggttctct ttttccaacc ataaaaggag aagattgggc taggttttgg  23580
agatcctctt cagcttttat gtgaaatggt tttatgattc cttgcctccc aaaggctgcg  23640
tatccccact tggcctttgt ctgctactcc ccctttctgc cttcccgttc ctctcccaag  23700
atctcctctc accccaggtt gaataacaga aatagaagga atagaaatct gaaggccggg  23760
catggtggct catgcctgta atgccagcac tttgggaggc cgaggtgggc agatcacttg  23820
aggttaggag ttcgagacca ttgtggacaa cttggtgaaa ccttatgtct actaaaaata  23880
caaaaattag ctgggcatgg tggtgcgtgc ctgtaatacc agctactgag gaggctgagg  23940
caggagaatc gcttgaaccc gggaggtgga ggttgcagtg agccgagatc gcaccactgc  24000
actccagcct ggatgacaga gtgaaattcc atctcaaaaa aaaaaaaaaa aaaaaaaaag  24060
aaatgtgaag gccaggtggt ggctcacgcc tgtaatctca gcactttggg aggctcaggt  24120
ggaccgattg cttgagccca ggagtttgag agcagcctgg ccaaaatagc aaaaccccat  24180
ctctacaaaa caaaaacaaa aaaattagct gggcatggtg gtgcgtgcct gtggtcccag  24240
ctactcagga ggctagagcc agagggtctc aggccagtct gcccctgccc cacggggcct  24300
gggcacatcc ctccctaatt cttcccagcc tctctctgac ccagggggcc tcctctccct  24360
tttttcccct tatctcagcc tccagccatc agcaacctcc tcttcctctc cacccagctc  24420
ttcctctccc acttcggcct tttctttctc acactccatt tccctctacg gcaatctgtg  24480
cagcctcttc ccccagtctc attttgcggg cttttctctc ttttctttcc ttccctggca  24540
cccaagccaa aggccctgcc tctggcctcc agccctaccc ccttctgcgg ttgcacagaa  24600
ggatggctgc ccagctctta aaaaaactgc ccgggaactg ttgacatctg ttctccctcc  24660
cccgctggct tttctgattg gcttacaatc ctgaggctag gaccgtctca ggagccaaga  24720
gaggagagcg gccacaggga acctagggtc tcaccaagct ctcctttcct tctgcaggga  24780
cctgctccga atcggagtca ctctggcggg acaccagaag aaaatcttgg ccagtgtcca  24840
gcacatgaag tcccaggcca agccgggaac cccgggtggg acaggaggac cggccccgca  24900
gtactgacct gcaggaactc cccaccccag ggacaccgcc tccccatttt ccggggcaga  24960
gtggggactc acagaggccc ccagccctgt gccccgctgg attgcacttt gagcccgtgg  25020
ggtgaggagt tggcaatttg gagagacagg atttgggggt tctgccataa taggagggga  25080
aaatcacccc ccagccacct cggggaactc cagaccaagg gtgagggcgc ctttccctca  25140
ggactgggtg tgaccagagg aaaaggaagt gcccaacatc tcccagcctc cccaggtgcc  25200
cccctcacct tgatgggtgc gttcccgcag accaaagaga gtgtgactcc cttgccagct  25260
```

-continued

```
ccagagtggg ggggctgtcc cagggggcaa gaaggggtgt cagggcccag tgacaaaatc  25320

attggggttt gtagtcccaa cttgctgctg tcaccaccaa actcaatcat tttttccct  25380

tgtaaatgcc cctcccccag ctgctgcctt catattgaag gtttttgagt tttgtttttg  25440

gtcttaattt ttctccccgt tcccttttg tttcttcgtt ttgtttttct accgtccttg  25500

tcataacttt gtgttggagg gaacctgttt cactatggcc tcctttgccc aagttgaaac  25560

aggggcccat catcatgtct gtttccagaa cagtgccttg gtcatcccac atccccggac  25620

cccgcctggg acccccaagc tgtgtcctat gaaggggtgt ggggtgaggt agtgaaaagg  25680

gcggtagttg gtggtggaac ccagaaacgg acgccggtgc ttggaggggt tcttaaatta  25740

tatttaaaaa agtaactttt tgtataaata aaagaaaatg ggacgtgtcc cagctccagg  25800

ggtgatgggg gtgatggact agatttctaa ggagagtggg gctgggtagg gagggctttg  25860

tggctgaccg agaggtgtca gaggtctgga ggctgcaggg ctgtaggggc tggaacttgg  25920

ttatcagccc cagggtatgt ttgaggtggt ggggtggggg ccgagcgaga tgaatcattc  25980

gcagctgctt ctaacgtctc                                          26000
```

<210> SEQ ID NO 392
<211> LENGTH: 4235
<212> TYPE: DNA
<213> ORGANISM: Homo sapiens

<400> SEQUENCE: 392

```
ctcggcccgg cggcgcgagc agagccactc cagggagggg gggagaccgc gagcggccgg     60

ctcagccccc gccacccggg gcgggacccc gaggccccgg agggacccca actccagcca    120

cgtcttgctg cgcgcccgcc cggcgcggcc actgccagca cgctccgggc ccgccgcccg    180

cgcgcgcggc acagacgcgg ggccacactt ggcgccgccg cccggtgccc cgcacgctcg    240

catgggcccg cgctgagggc cccgacgagg agtcccgcgc ggagtatcgg cgtccacccg    300

cccagggaga gtcagacctg ggggggcgag ggccccccaa actcagttcg gatcctaccc    360

gagtgaggcg gcgccatgga gctccgggtg ctgctctgct gggcttcgtt ggccgcagct    420

ttggaagaga ccctgctgaa cacaaaattg gaaactgctg atctgaagtg ggtgacattc    480

cctcaggtgg acgggcagtg ggaggaactg agcggcctgg atgaggaaca gcacagcgtg    540

cgcacctacg aagtgtgtga cgtgcagcgt gccccgggcc aggcccactg gcttcgcaca    600

ggttgggtcc cacggcgggg cgccgtccac gtgtacgcca cgctgcgctt caccatgctc    660

gagtgcctgt ccctgcctcg ggctgggcgc tcctgcaagg agaccttcac cgtcttctac    720

tatgagagcg atgcggacac ggccacggcc ctcacgccag cctggatgga gaacccctac    780

atcaaggtgg acacggtggc cgcggagcat ctcacccgga agcgccctgg ggccgaggcc    840

accgggaagg tgaatgtcaa gacgctgcgt ctgggaccgc tcagcaaggc tggcttctac    900

ctggccttcc aggaccaggg tgcctgcatg gccctgctat ccctgcacct cttctacaaa    960

aagtgcgccc agctgactgt gaacctgact cgattcccgg agactgtgcc tcgggagctg   1020

gttgtgcccg tggccggtag ctgcgtggtg gatgccgtcc ccgcccctgg ccccagcccc   1080

agcctctact gccgtgagga tggccagtgg gccgaacagc cggtcacggg ctgcagctgt   1140

gctccggggt tcgaggcagc tgaggggaac accaagtgcc gagcctgtgc ccagggcacc   1200

ttcaagcccc tgtcaggaga agggtcctgc cagccatgcc cagccaatag ccactctaac   1260

accattggat cagccgtctg ccagtgccgc gtcgggtact tccgggcacg cacagacccc   1320

cggggtgcac cctgcaccac ccctccttcg gctccgcgga gcgtggtttc ccgcctgaac   1380
```

-continued

```
ggctcctccc tgcacctgga atggagtgcc cccctggagt ctggtggccg agaggacctc   1440
acctacgccc tccgctgccg ggagtgccga cccggaggct cctgtgcgcc ctgcgggggga   1500
gacctgactt ttgaccccgg cccccgggac ctggtggagc cctgggtggt ggttcgaggg   1560
ctacgtcctg acttcaccta tacctttgag gtcactgcat tgaacggggt atcctcctta   1620
gccacggggc ccgtcccatt tgagcctgtc aatgtcacca ctgaccgaga ggtacctcct   1680
gcagtgtctg acatccgggt gacgcggtcc tcacccagca gcttgagcct ggcctgggct   1740
gttccccggg cacccagtgg ggctgtgctg gactacgagg tcaaatacca tgagaagggc   1800
gccgagggtc ccagcagcgt gcggttcctg aagacgtcag aaaaccgggc agagctgcgg   1860
gggctgaagc ggggagccag ctacctggtg caggtacggg cgcgctctga ggccggctac   1920
gggcccttcg gccaggaaca tcacagccag acccaactgg atgagagcga gggctggcgg   1980
gagcagctgg ccctgattgc gggcacggca gtcgtgggtg tggtcctggt cctggtggtc   2040
attgtggtcg cagttctctg cctcaggaag cagagcaatg ggagagaagc agaatattcg   2100
gacaaacacg gacagtatct catcggacat ggtactaagg tctacatcga ccccttcact   2160
tatgaagacc ctaatgaggc tgtgagggaa tttgcaaaag agatcgatgt ctcctacgtc   2220
aagattgaag aggtgattgg tgcaggtgag tttggcgagg tgtgccgggg gcggctcaag   2280
gccccaggga agaaggagag ctgtgtggca atcaagaccc tgaagggtgg ctacacggag   2340
cggcagcggc gtgagtttct gagcgaggcc tccatcatgg gccagttcga gcaccccaat   2400
atcatccgcc tggagggcgt ggtcaccaac agcatgcccg tcatgattct cacagagttc   2460
atggagaacg gcgccctgga ctccttcctg cggctaaacg acggacagtt cacagtcatc   2520
cagctcgtgg gcatgctgcg gggcatcgcc tcgggcatgc ggtaccttgc cgagatgagc   2580
tacgtccacc gagacctggc tgctcgcaac atcctagtca acagcaacct cgtctgcaaa   2640
gtgtctgact ttggcctttc ccgattcctg gaggagaact cttccgatcc cacctacacg   2700
agctccctgg gaggaaagat tcccatccga tggactgccc cggaggccat tgccttccgg   2760
aagttcactt ccgccagtga tgcctggagt tacgggattg tgatgtggga ggtgatgtca   2820
tttggggaga ggccgtactg ggacatgagc aatcaggacg tgatcaatgc cattgaacag   2880
gactaccggc tgcccccgcc cccagactgt cccacctccc tccaccagct catgctggac   2940
tgttggcaga aagaccggaa tgcccggccc cgcttccccc aggtggtcag cgccctggac   3000
aagatgatcc ggaaccccgc cagcctcaaa atcgtggccc gggagaatgg cggggcctca   3060
caccctctcc tggaccagcg gcagcctcac tactcagctt ttggctctgt gggcgagtgg   3120
cttcgggcca tcaaaatggg aagatacgaa gaaagtttcg cagccgctgg ctttggctcc   3180
ttcgagctgg tcagccagat ctctgctgag gacctgctcc gaatcggagt cactctggcg   3240
ggacaccaga agaaaatctt ggccagtgtc cagcacatga agtcccaggc caagccggga   3300
accccgggtg ggacaggagg accggccccg cagtactgac ctgcaggaac tccccacccc   3360
agggacaccg cctccccatt ttccggggca gagtggggac tcacagaggc ccccagccct   3420
gtgccccgct ggattgcact ttgagcccgt ggggtgagga gttggcaatt tggagagaca   3480
ggatttgggg gttctgccat aataggaggg gaaaatcacc ccccagccac ctcggggaac   3540
tccagaccaa gggtgagggc gcctttccct caggactggg tgtgaccaga ggaaaaggaa   3600
gtgcccaaca tctcccagcc tccccaggtg cccccctcac cttgatgggt gcgttcccgc   3660
agaccaaaga gagtgtgact cccttgccag ctccagagtg ggggggctgt cccagggggc   3720
aagaaggggt gtcagggccc agtgacaaaa tcattggggt ttgtagtccc aacttgctgc   3780
```

-continued

```
tgtcaccacc aaactcaatc attttttttcc cttgtaaatg cccctccccc agctgctgcc   3840

ttcatattga aggtttttga gttttgtttt tggtcttaat ttttctcccc gttccctttt   3900

tgtttcttcg ttttgttttt ctaccgtcct tgtcataact ttgtgttgga gggaacctgt   3960

ttcactatgg cctcctttgc ccaagttgaa acaggggccc atcatcatgt ctgtttccag   4020

aacagtgcct tggtcatccc acatccccgg accccgcctg ggaccccccaa gctgtgtcct   4080

atgaaggggt gtggggtgag gtagtgaaaa gggcggtagt tggtggtgga acccagaaac   4140

ggacgccggt gcttggaggg gttcttaaat tatatttaaa aaagtaactt tttgtataaa   4200

taaaagaaaa tgggacgtgt cccagctcca ggggt                              4235
```

<210> SEQ ID NO 393
<211> LENGTH: 43948
<212> TYPE: DNA
<213> ORGANISM: Homo sapiens

<400> SEQUENCE: 393

```
gcgcctcgga gctgcctgcg ggcgcacgcc gtcttccccg ccagtctgcc ccggaggatt     60

gggggtccca gcctgcgtcc cgtcagtccc ttcttggccc ggagtgcgcg gagctgggag    120

tggcttcgcc atggctgtga gaagggactc cgtgtggaag tactgctggg gtgttttgat    180

ggttttatgc agaactgcga tttccaaatc gatagtttta gagcctatct attggaattc    240

ctcgaactcc aagtaagtgg cgtccgcgat cccccctatgt ccccgccccg gggtccgccg    300

cgccgtccgg gcgggaggag gggtcagtcc gcggggcctc ggagcctgtt tctggaacct    360

cggttccccg tcccccaccc ccaaccccccg ccccatttca ctaggtggag actcctcgct    420

cggctttcca acccgagccc cgctggaacg gacggtctct ccgcctttcc tcccccgaac    480

gctcccaggc gctaaaagct actatcggct cgggtgtcaa gtccgggaag gtgtccgatg    540

gcgatacctg accctctcct gttttcgagg acgaaggaca tggccacaat ctaggctggc    600

cggcacgcgg ggactggtgg gctctggaga gaggcggaga tgctgcattc gcggggagcg    660

cgggcggcgt ggtccggggc ccgcgggcgg gcgaccgggg tggcaggacg ctggcagcga    720

agcgcgttct ggagagggga gcctggagtc gctacgctgc ccgcagagcc ctggagccgg    780

ggcgccttgg caccgcgccg ccagcccgag ggtgcgcggg gagctcgcct gcttcgcagg    840

agaactcggg cgtcgagccc tttcctccgc gccggggaga cgggccttag gcttctccct    900

gagggcccgc cgcacctcgg cctcccgctt cgttcataag ccggtagccc cggagtatgc    960

ggtctcgatg gccgacctga ttgtaatgca cttcctataa aagcttaggg ccctgcccag   1020

tcgacactgc tcctgaagcc ttctccctcg ggaccctggt aggaatggga tccttaggat   1080

cagatttgct cttaccggac tctacagccg ggagcgagcc aggccttgtg gagagtaact   1140

ttcagtttgg gccaccagag tgcattcaga atttagaaaa tcccatccat ccctaaatct   1200

gtgtggtcat aactcgtagt catctgggta ttcagtactg tgtatcccct tatttcgaat   1260

cacagccaaa acatatttta cagaatcttg gaattgtagt ctcgggaaac ttggagaaga   1320

agtatgcaga cattagctgg tttctggaga aaacgtttga gatcagaagc aaaatcaatg   1380

gcctaattga agttgagcaa gttgggcctg gttttaggag aaaagaaatg ggggattgat   1440

ttagaaatca cgtcttaaag gagtgtgtcc attctcttaa aagtgtcaaa tttcaaattc   1500

actaacatgt taaccaagaa tcccttcatg aaaagggcga aaacgtcggt tacaaatcgg   1560

tttaaacaaa tgtttgtatg atgctagaag gcactttcaa caccgctcat acggagaagt   1620

tacttagctc tgcctccttc catgtagtct gctcttgcat ggattatatt tttaatgtaa   1680
```

-continued

```
attgttgtat ttgctgatga agtactggcg gcggcatctt tgcatcgatg ccggctcggg   1740
aggcgccagg tggtgccgga aggagccggg ctaggacctc gcgcagcagc gggtcccgga   1800
gtccgggaga ggcgggcggg cgggcgaggc ggtcgcgggg agcccgcggc gccgctgccc   1860
gcccggtgcc tccagaggtc actcttccat gcggaatcgc gcagcgccag gcctcgcccc   1920
tcccccaggc cgcctgctcc agccactctg cactttcact gaccggttct ctttgaggct   1980
gttttttttt ttcttatgag gatttaatat ttctgtttaa atctagttga aagcaattcc   2040
gttagcctct tcagcgttta gttcggtgtg tgtatcttta tctttgcgct atattaacta   2100
ttagtttgtg tgtatccggt aggagaatta gaaataccta gttgggagaa aaagaaaagt   2160
agaacaatag ttatttcaac ctaaggttta gacgttaata acttcttttt gtaatgtgtc   2220
gagatggggg gtcctggggg gaggtgacag gtactcacca ctcccccccc ccattctgat   2280
gatgaagatg agtctgtctt tccagctatg tccagacctg cgagggccct gcgtttctgg   2340
aagcctgccg tttgcgcggt tgaggttgct gctgctgtct tgtcctccac agcagcattt   2400
cttttaaaat tctcctgata acggcctgcc tggatgactg gataatgtgt gcctggaaaa   2460
ggtctccctt gcagctgaat gctagctcca gagatcagaa agatttcttc ctgtaggagc   2520
cataggaaag agtcctctct aagtttttga gaatgcatac aaccccctga tgacaggggg   2580
tcgctttcct tggggaagtt ttatatttat ttccagagga aagtttgaat cggtaaatat   2640
gatgtggcag gaaggtaatc aaatgcattg aagtttcaca tcagttccta tgaactgtgg   2700
aacaattcat ttgtaatgaa gccgccatca gtaattagat ttgtttcatt cagaggtcag   2760
ctttttttagc aggtggtcga cacagggagc atgcagcagc tgtttggata cagggtccag   2820
aaaacccttt gtaaattcag cgtctccgta actactttaa tcacattgtc ggctctcccg   2880
tccctgactg tatgtaataa tggaaagatg tcctgcgtgc tgaaacagta gctgccctgt   2940
taggttattc acattgcttt gatacgttct ggtagagttg ggtccgttgt agccattttg   3000
gttgtttaaa gttttggttt ttttttgtt tttttttaa ttcagcagag aacagtaatg   3060
cctagcttcc gtttttaact taacacttca gtagaacatt ttcttccaag agggagattt   3120
tggcctaagt aaagtagtgg gctctttttt aaaaaaaaat taattttact ttaatgtgag   3180
caaatctgta ttggtatggt gttctgcaat gcattacact gactttgaaa atttcgagta   3240
ctaatgcctt atgtctgggg ttaccattcc ctgtgcatca catactagtt agttaacata   3300
gcattttgct tttcccatgt aatttttttcc ctatataata ctggattcct gatactaatt   3360
gacttgatac aaaagaatgg ctggatgata tccagataac gtataataca tgggcttcac   3420
cacaatcagg ctctgaataa atacagacct gtcagagatt gataaaataa actacaatgg   3480
atagtgctgt ttaaacagtc cattcaataa catatataag ccagcctgcc ttccattgtg   3540
tctgaaattc ttatttttgt aggtaaacaa atgcacattc agcactgatt gaatagcccc   3600
ttgaactatg ctccacagtt tgcgtttggg ttaatcttgt cggttttaat atagagagaa   3660
aaaagctcaa agcaccaggg gtggaattgt tagtgctttc acatccacat tcctcacatt   3720
ttgtcaggat gataaactgt aggtaatgga ctgtcgttgt tctgcaggac aactgagcca   3780
ggcagagcac aaagactaag ctaaagcgat acctcacaac atgcttggta gccttctttt   3840
cagatgagaa tttatttgag aatcatgtgt ctagggactg cacatcttaa cctcaacagt   3900
tacagcttca agccccagaa acaggagctg gaggttaaga tgatttgcta agcacctggt   3960
tctaaatctt ttacaaagca taagctgttg acgctggttc tgccgacgca aagacatgca   4020
gatgactcca acatttccag aggcttctga cttaagctaa agtgtgtgga caggtgaatt   4080
```

-continued

```
cgccatgggc ctggagacca gcttgctaaa aactatgtgt ttgaatggtt cctccagaca   4140
gagtcagctg aagaacaatt ggtggattta tattaaaacc tcttgtctgt aaacttactg   4200
aggtgcatcc ttcggttggt ggatcagtga gataattgcc ttcagatgga cattgcaact   4260
ggagcaacta aatccttgct gtctttcctt cctctgaaat cttccaggta gctcccgaga   4320
gcttcagtat gacaccaaac ttcgggcgac gttttagagt gcgttcacct aatgggaaac   4380
tattcgagat cccagcgtga ctgcagtaat gcgtcatagg aatgggagtg gcaggggaaa   4440
aggaaataca gattgtagac cctaataaaa aaatttttag gaaagatatt tctttaacgt   4500
tttatgagaa cttcattctt aaaatactta attgcaaatt agacaaatag aagtgctctt   4560
ctaaggaagg tgattaaact ggtcctccta tcagcctaat ctctgcctgc ctttgctgct   4620
gacataaaga acctgttttt caggtcactt aatatacatc tacatagatt tgcttatgag   4680
ctcacccttt gtgtagcgga gtagagcctt aaagaggagt gctcaactgt ttaaaatatt   4740
ttgattaaaa tatgcagaac ccatagaact ataagcttct agtcaggaat tagctctttc   4800
agggaacagc tccccccttc tttttaaggg gggaattaga aggaggctgg gggaggaata   4860
taagaacagc aaagaaggaa ggatagcaaa tgggacatgt tccgaacagc ttggaaaaac   4920
tcctgtggct tcattgtctc tataaagcca aagaatacaa agacataagc aattcagccc   4980
ttctcccatg atggaagatg taaaccgttg acatgcctcc cctgtttaac ttgtttaatt   5040
ctcattttaa attcagcacg atactagccg tgtgaactct gaagatttct ttagtaatcc   5100
attttgtagt tccgaatcaa aaacaaagtg aaagggtctg acacaatttg cttttatttt   5160
taggcaaatc aaccctggtc atagttaata aggggattac aactcagact aggtctttac   5220
agatgtgatg taaatcaagg gcagagtata aagaaactga tccctttttga ttgaagtata   5280
gtaaaaaggc atagagaaac tagcagcagt aatctgattg tatggcaata aaaccaccat   5340
tttctgtctt tcagataaaa ataatgtggt aaatccatgc agttcataag atgtaaaggc   5400
agataaaggg tgaagccatg gcaacatata gattagcttg atgttagaaa tgacacgtct   5460
ctgaaaaggg cgcgggacga aggcccttgc ctccaggctg ttgggcatta tgtgagaacc   5520
acacagactt ggaaactggg attaggaagt atgaaagctc tacttgtggt ctgggatggc   5580
tgaggcagta aagaaaagct gctcagttct tgctcattgg tggtggataa tatggcaaag   5640
gtagatttca ttgactgcct tttttataga ttgagattgg ggctgattaa aacttcagat   5700
cactgcagtt gttagggcct gggagatttt cctttttaac tcctggccta acagcagcag   5760
ccgttctgta ggattaactg cacttcgcgg tcgttgcctt aatctatttg ggcttcaggc   5820
agggacatgc tgggaaggaa cagagaccag aggggatagg tagggctggg gttatctgaa   5880
aagaaaacag agaccttttg atttcagcca tcttttcaga cccagctccc tctcccgctg   5940
catgggagaa gcaaaggtaa acaggacaca ttgtccctct ccctcagcca cagagctctt   6000
ctgtgagttt tgtctttccc accctggaaa aaaagataaa atacaatttt taaaagggga   6060
gggaggaatt tagttttaat tcaaatgagt agtaatccaa tatgccaaaa gcagtgggct   6120
ctacctagat gtaattttac tcgtaaatgt gagtcttaaa ctttgagttg aatggggcag   6180
gctgttagag gtggtgtaaa ttacaggatt ataaaaatgt tagtgctgcc cagccttaaa   6240
gtcaaaaaca gaaaaatctc tgtgctgttg agtcttcccg ccctctctcc tgaacaacct   6300
tgtaagtaag ctagactttt gtttttgcct tccatacttt ccatttcagc cattaaacaa   6360
aataagccat tgaaaccacg attgggttcc atgcagagtg acatccgcaa tcgggtcaag   6420
ccagaaggaa atacttgctc gattgccccc tatttggcat tacaggaaag tctccacact   6480
```

-continued

```
ttggaagagt ctgaactctc aagacattga aaatgccaaa ggctgcaaac accctgtgtc   6540
tttcttgatg gagtgcatct tggtgtgttt tacaaagggg aattcagtgc tgttttttttg   6600
ttgttgttgt tgtttttttt ttttaaagag cagcataggg cccttctaga ctcttggatt   6660
ctgtgtctga caaaaatggt cattaaatga gcaatattat aatttagacc catttcactg   6720
atttgttcc aaattctcaa ctgacttgag catctgtttg gggctgtaga tacattgccc   6780
ttgttgactg tttttctcgt ttctatggga attactgtag ccattactat gtagctttca   6840
tagactcaaa acatttttaa agtattgcat ataggctggc catatccagt gcctgttact   6900
ttaccttctt tttctaactt aatgcagcag tctgtattaa cagatccatt tcatttgtct   6960
agcttcatca gagagaggct accccctgat ttacaggctg ctcacatcca agcaccttgc   7020
attctacact tgacagtgat tgctaatggc ccattcaact aaagtatttg cttgttaaca   7080
gggaacagaa catgataaat gtccagcaag cttgctgcct ccttcagctt ttcaaacgca   7140
gactggtgca tatttatggc aggcaaatga caaaagaaaa agctgaattg ccctggcctc   7200
cagctttcta tcagaaacag ggttaaagtg attaaagcaa tcattcaaga aagccctgcc   7260
gtttgtttac taaccttcat ccaacattta gctttgtagt ctacctgtga gaagatattt   7320
cagaagtatt agagataagg aaggaggatc tagcaaacca gtgaaaagag taggtgacca   7380
gttataaaat gctttccatg cacattgaat gccaggcgaa cctatttctg ttattccagc   7440
agacaatcag cagtggctct agattattaa catatttcc tttcatgtat aaattcaaat   7500
atgtaattct agtccaaagc attctgtggc tggtaagcac atacttgctg atttcaaata   7560
agaaaacata gcaagggaaa gctccattaa acaagttgtt tctgccctta gtaattctct   7620
aaacaagata ggaagaaaaa gtggacagta gtggagtatt aatagtgtgc tcttttcatt   7680
ctctaaagca cgagtaagta agcgttcaaa ctactctgtg gtgggcatac atttagagcg   7740
ctgtgaatga accactgctg ttctgccata cttaatttat ttatattatt atttttattt   7800
tattgttgtt tttatgtatt attataatta tttatttata ttactaattt attttctcaa   7860
tttaaatcct gttgcatcca attttaatta cagtttttgt atctgccttc ccatacttgc   7920
tacccacgtc cccattgcca ctgcggcctt atccatgttt tctgtgtaca ccactctcgt   7980
atcaccccag aataattatg agtgctaccc agactttga aaccactaga gtcaacatgt   8040
ttgtctttga ggaaagccaa tgatgcttta gcatttttgg caggggtgga tgtgtgttta   8100
agtggggtgg gtgcagctcc ttattgtctg cctattctac tgttgttccc aatccacatt   8160
ccctgcgggg cacctaacct gtgtgcatag caaagaattt ccgaccttca gagccagaag   8220
tgtttctcaa ttgatctctt ccagcctagg gttatagctg atgaattata atccttgctc   8280
tttccacacc tttacctggg cttaccatgg ccctaaaaca tttgcccaga atcagaattg   8340
tctcatgagt gagtggggca aggcaaatcc tgttccagac cagctgagaa tgtacctagc   8400
tgcagaagaa gttagaaagt gtcatctttt acttatctac cagaactata ttcgaggtac   8460
attttagatt taaaaaaaaa gcaagttctc gtaggccttg aatccccccc ttgctatggg   8520
aaaatggatc attattataa tggactgtcc agtaaagttc atgatttctc ctagacatgt   8580
tctctctctt tatgacctag atcaagagtg atctctttaa gtcttttctt cataatccca   8640
cagcactttg tacttagatg tacttagaaa gaaccatata cacggtacgt catgattgat   8700
atgcaagcct tcaccactct acctgtccta aaagtcaggg acacaccttc ttcatttcat   8760
cagtccctac ttctatccag cattggcatc cagtaagtat tagtggaatg gacagacaac   8820
ccgaatttgt gctgatggca gtttaccctg ttttaactgt catccttctg ctactagaca   8880
```

-continued

```
tggatgagac ctgagacgat gggactgctc agaggtccct ggctcttgaa ctttagggca   8940
ccagaatccc ctgcagggct tgagaaaaca ggggtttctg ggccccaccc ccagagttcc   9000
tgattcctga ggtctggggt ggggcttgaa gatggacatg tttaacaagc tcccaggtga   9060
cgctggcaac tgctgcctca gggccatgct gagaaccctc gccctacaca aacctttctg   9120
ggaaaacaac tcaacattaa agctgtttgg ggatctctga agaaatctgt agtccttgcc   9180
ttgttggggg agcatcaggg atctaaccat tgatggtgga gtatttgttg ttaattcagc   9240
aagcaactat taagtgttag gcctgttact cggctctaac aatacaaggc agagtgacct   9300
gtaccctcga gatttaaagt ctaagtcctg tagagagaag cccaggtggg agcaagcaca   9360
tttagagtta ggtgcttggt gcaaggtggg gacacagaag aagggaatgg catttgcctc   9420
tggaggggtc cggaaacagc ctagggagga ggagcttgag tcttgaaata ctgtgggcat   9480
ctctaagcaa agtcacagta gacagctgaa ataaagaaaa tagtaagcaa gccaaagaaa   9540
cagtatttca gccaagggca gcgtgtgtct atcacgtcca cctgtgaaca cgtcccagga   9600
ttctctgcat ccggccattg ctcaagacag atccctcaca ggaacagcta agccactgat   9660
ttcagctacc tgttcacgtg agaattatca gtacctactg cttttcaaaa tgagtatgat   9720
catggatagg tgaggcaatt cagtttcgca gagacagtag ggcaagtgcc actgtagttt   9780
agttaagggc acatgcttta gagtttggct atgtgagtcc aatcccagtt tagccattta   9840
ttagctgggt agctttagga gcagtagcct tagtgtctct cagttgtccc atctctataa   9900
tagggacaat aacataatag tgctgaataa aagagtaaca aaattttggt caacatttaa   9960
tgtatttaaa gagctaagct ccgtgattgg cacaatgaac caatcaatca aacaccagtt  10020
gttattaata aaagtcagtt gaatatgtac tgtgtgcctg gccgtggttc aatttgcctt  10080
tgcatacaag gaaaaaatta aaatactctg ttaataaaga ctatagcata atactttcac  10140
cttaaacttc ttgatgttaa tttattttgt ttacctgcca aacttctact cattccttat  10200
gactttctgc tacatgaaac accctttgta attcttttgt cctattaaat taagttctct  10260
ctcctctgct ttcctgcttt tggtgctttc taataacact tttaaccctg gactttctca  10320
ttcagctgtg caactgtgga ctgagaggag gctctttgaa ttcattttgt atattctagt  10380
agagagtact gtgagcagtt gggttgttga atgaatacat taattcaacc tggagggatg  10440
ggcagtattg catttttttac attgatatta catgatattt agaaaactgc ttaactggtg  10500
gacgttgttt tattaacagc attttgtgta tagcactcac tatgtgccag ctgctattct  10560
aactgcctga caaatactcc tgaaaccttc atggtaacca tatgagggaa gcacttttaa  10620
tatatccata ataccaacgg ggagactgtg gccaaattgg ttaattaact tagccaaagt  10680
catattgaac taataagtgg atttaaaccc agctagtctg gggccagggt ccctctttta  10740
atcttctgcc tcctgcttat gctgttgcat ggagtagtct ttatcatata actaaattaa  10800
gcatgcattt gcttaaagca gtgcatacat gatggatcaa aaagtttgtg gtataattgg  10860
tttaattctg tcattatcca ttttgattta tagtcacttt cttatgatgg tcgtgtagtt  10920
ttaaatggaa cctttgaatc tttgatataa taaggttatg tcaaatcttg ggtataataa  10980
ggttataccc aatggaaaca gaataatgat cagcccattt aaaggatgac tggagagtta  11040
ttacaataca taatagtcat gcatatattg agtagtattc ctttggtaac attttccttt  11100
taaaaattgt aacatttgat tgttccttgt tgggagaaaa ggaggtcaga tttttgaggg  11160
gagatccatt tggtgagatg ctgagtgtgt gtcaagctaa ggagatagta tgacatcttt  11220
tttagagtct agtcacaatt aaatgccatt ttattttgga ttttgggatc cgtgccagct  11280
```

-continued

```
tccagcttgt cagagctgag aagactcaaa tcaagtccag gcttatttct acagcaaact  11340
gggattctgg cttcttgccg gtggattcat tcagtacagc ccatctggct tttgatgttc  11400
tgcaagtttg gagccatttg ttgaaggaag ccaggcggtg aatattggtg gtcctggggt  11460
tctcttgact ccaagtggtg ccccttggtt tgcattttca ccatgcttag catctgctta  11520
cctggagacc atgcagccgc cggccagagg tctccaacaa ccaaatcttc atgcctttta  11580
gaactcagag tccccagcac atcctccttc ctcctccttg tccaattact ttcatgcagt  11640
tctcagtagc tgcttgtttg aatcacttat agtatttaac ttctagggtg tttttgggtt  11700
ttggtcaagg taattccagg ctgaatgtgg tgactaagca ggaaataaat gggtcgtcct  11760
caaagttaca gtggagcgct gtttctattt tcctaaggta cacagttgtg ggggcgatcc  11820
gtatggaagt caggaaccca gtctgatttt gcttcctttt gatggtagca gtacagacct  11880
ggctgttttg tagcctgctt tgtttttctt ccttttcttc cctaacttca cgggctgtgg  11940
caaagccctg agacgtgcag gaaaatgtct cctgtcatac gcccacagca gacctagccc  12000
tgaccctcct ctgaagccca ggaaggaggt atctgtgaag cagcctgctt gtaaagcaat  12060
tgcacacagc cttgtaaact gtgttactgg gctgattata cttgattggc aaggtgaatc  12120
tcttatagca aaagagaact tggagagttt tatctcatct tatgccttat taatttgttc  12180
attctttaat tacacagcca cctattgagc accctattta tgcaaggtac ctggtcgggg  12240
gtcagaggga gggtcccatg gtaaacgaga cagactcaat cctggaggag caggaatggc  12300
agcccctcgc tgggctgttg gccccaccaa aagggaaagg tttcatttta ataatacatg  12360
ggtgaatcat ttttgtcaat aggcaaaatt ctttgtagtt aaaaaaaaat atgatggtag  12420
gaaggaaagg gatgggcaga gggttaaaac aaaagatatg ctctccctaa ctctagattg  12480
tagtattgtt atgcttgtca ctgtagctga attccatttc tttgagtttt ttcaatgcca  12540
aggcattccc tgtatgactt acgtgagcct ttcatctccg cgatttttcc cattcaggta  12600
aatgagcaaa tggatttgaa cactcatatc taaaacaaga gagaaccagc tggaaatgcc  12660
ctttgaattt ctttctctat gtaaaccatt tttctttctg gtgcctcacc tataaataac  12720
aggagttcca ccttccttta tagactcttg ctgaaagcat ggtttggaac aagaccgtac  12780
aggtgcacac aaattacagt tgggaaagaa gcctgcagtg catcttgtct ctgaaggtta  12840
tgaaatcctc cttttagtaa tggagctggc gtgatcaagc cagcaggatg aaatttggca  12900
tttgtgagat caccccccctt ctcacttgcc cactgtacat agcatcccag ccttactctt  12960
caaatctcca cattttttct tatctagcta caaaattcat aggctgattt ttttggggtg  13020
cgtgtgtggt tttttttttg ttttttttggt aaataaagac ctgcattttt attttgatat  13080
aggtggttga gttttgtctt taatttcatg acagagattt aactagtctc aacttttgaa  13140
aagacaacaa tgatatttgg ggatcacaca cttaaagtta gatttctaga tgattaatac  13200
caaagtagat gattttttag cctcagccat ttataggtat gcccttctgt gaatttttta  13260
tgacagtgaa aatcatggca cagataaaaa ttaaataaat acttctgtta ttttcctgaa  13320
gaaaaaaaaa aaaagcttaa actatgagaa tactgtcttt gagcacttta aaataaaatt  13380
gacttcagcc agcaggattt tgagcattac atcacaaata aaaaacaaga ttaacatcaa  13440
aaggagtcag ttttcattca attgtgcagc actgtgggct gtgaaattta atattatttt  13500
gactcatatg ctaattgtag actgacagag gaaaatggat tgtgtttaaa taaaaggata  13560
cacagcatca cacgcagctg tatcaaatac aagttgaggt ctttgggcca ggaactgggg  13620
gccctctagc tctgttattg cagattcaag tttgacaaat aaaactttcc tttagactgt  13680
```

-continued

```
agtttaatta cttttttca aaggtatgcg tgatgaagag gcacaaatac acctcacctt  13740
gaagagttgc taaactggtt tgtgtgccga tcagttcacc gtgtgtttga atttctgtgc  13800
ttctcatctt tccttttctt gaaaagattt tgcttgtcat tggtgtgaat tgtacccccc  13860
acccccaccc atctagtctt tgctctcaga tttataacac tttaatggtt ccaaattgta  13920
tagcctgctc ttagacccct tttcttttcc ttgaataaat caggttcatg ttgcagacga  13980
tatttgtttt aggaaagtgt gaaagaaggg gcacctgtga aaacacgcaa ttgttccaac  14040
acacatatac atccaaatta aagcagaaaa tgtcaaagcc tccaatcact accttatttc  14100
ttggaggttt aaagccgctg agaagatagt ggtgccctcg ctggaagttt taaggtaatt  14160
actttttact ctaagcagta gtatctggta acctaattcc gtataaacct gacaccctat  14220
cgctacaccc cagtatttct ctgatttcag aataagtctg cgtagaaact tgttctgatg  14280
ttaaagtgca aaagggggca gtaaagtgct atccacaaaa aaggaaaaac attttccaag  14340
tatttcttat tactgcctgt gtctttcgta ggccctgcct ttatttattc attttataac  14400
aaaactctta tgtttggggc attcagagaa taccttatta agctgttgca gcaatctagc  14460
attaaatgga agacatgcaa gactgaagat cctgcctgtt tatgaagtgt gccatcaaat  14520
tcacatgctc atgatgcaga gtccttcttt gggagtattc gtattcccaa gtgcacagag  14580
cacttcggaa aggagccttg gtctttggtg ttaatgctct cctagctccg tatagatgtg  14640
gcaggcccaa agtacatggt ggggtgaagg gtcaagggtt tgggcttatc cagagcagcg  14700
tgcatccttt gtcaggaggt gactggaaac accagccaat tacagcagaa ctgcagactg  14760
ctcatctgca ttcggaattg cagatgaacc agtttgtact cgacttctct tcttcactgt  14820
aggctttgac atttaattaa aaattaaagc cttttatgga aaaagtacat gttttccaaa  14880
atggggtaaa ttcgaagtat acttgataca gaacactggc ttgggaataa acctgtgata  14940
ttacatgact tttggtttgc aactgctagg ctgagcctct ttgtaaagct gggatttaga  15000
atctttgaaa tgtttgtaca gttcaatgat taagcataaa ttgtatatat tcccttttt  15060
tcacttattt gagtaaacaa gtttgttact acagcttctg tggactcaga gatttatgta  15120
ttaaataggc cacaacttca actaggataa ttttatttat ctgcttgtta gggaattgca  15180
tcaaaagttt aagtctgtag gcattaaata ttttaaatgc ttatttttaa agtcaattat  15240
gaaagatagc acaaagtttt tctgaaacta cattaaaaaa ataatgtttt aatcttatca  15300
caaaagcatt gactatttat tgcaaagaaa acacagaaag ctaaaaatca ttctaagtcc  15360
accattcagt agcccaaagt ggtctcaggt aaaggcggtg tgtgtgacca tttgtttatg  15420
gttgtctccg tgcagtcagc aaaataaaca gaacaacatg ccatatatta ttgatgtgta  15480
tattttcaac tgaaattagc catctgctta caatgatcat atacactaat ggtataattt  15540
tgaaatgaaa agaaaaataa aataattctt tgtggagagt aatgcgaatt gacttatgaa  15600
tctcgccctg cttggcagtt tgctctagag gtagaagagc tttatgtgtg ggcctcctcc  15660
ccccccacac atttattctg ctcacacttg caccagcatc catgtcagga ctcaccttgt  15720
cctgttacat gagtaacatg gccctgattc tcaagtgcat gataactgcc ataattacac  15780
ataaatatta aatatttaaa tagatcttta cgtgtgtaat attaggtaga agtggctctg  15840
gatcgaatct gatgcttttt aaatagaagc tttcccacaa catttccaag cactgtcatc  15900
gtgtctgtct cgatttgggg tttacctggc ctagttatct gtctgggtgt agaaactggt  15960
agttcctgtt tgtatctttt ttgttctgat ctctttattc tgtgtcagct aaatattctt  16020
gcagtcagtt actaacatat taactcatcc ttgtttggaa actttggcat atccttccat  16080
```

-continued

```
ggtttccttc cgtggacctg tcgcgtctct caggagagcc accaggtata ttgtcacaca  16140
tttcgcatgt attttcagag actacagcag catcaagtgg ccccccagcg atttgggttt  16200
tcttctcggt taatctacac tctttggcca accgtgagaa aacttgtaag aaggcatcag  16260
atgtttgtgc taaggtgcgt gtagtatggt cagaggaaga aagaagcagg gaaaatggag  16320
tggccgtggg tgggagggga agcagggagt gcaatttcgg gttcactaca cagctctcca  16380
taaacttctc cactgctggc ttcccacgga tcctcctatt acactgggca aagtgcagaa  16440
atagatcagg cgaccactgc ctccgtccat ttcccaggca ccctgtgaga cccgataatg  16500
caatacaggt cagcagaaaa gtccagactt gacatcccaa cgtgccatgg tctggtctgt  16560
gaatgaaaat cacatgaggt gacctctgaa ctctaagtgg ctggtttatg ttttcagtgt  16620
attaggcccg tgttttaaac aagcatgtgc tcgtagtgta ggttaaaact ttctgttgtc  16680
ttcattaatt atgctgtgtt ctagtctatt aatattaaag aatattgtgt tgcataatga  16740
ctaatttttt tattttttgg agacggagtc ttgctctgtc acccaggctg gagtgcagta  16800
gtgcgatctc ggctcactgc aacctccgcc tctcggattc aagcaattct ctgtctcagc  16860
ctccgagtaa ctaggactac aggcgcccgc caccatgccc agctaagtgt tgtattttta  16920
atagagacgg ggttttacca tcttggccag gctggtcttg aactcctgac ctcgtgatcc  16980
acccgcctca gcctcccaaa gtgctgggat tataggcgtg agccaccacg cctggcaaca  17040
taaggactat tttttaaagt ttttacaatt atgactgtga agttgaaatg tctaaattat  17100
tagagatcca gtttagatta ctaaatattt atgtctaatt gagatgatta gacttagcca  17160
aagtatccat gtagaagtat tagagtctag attggtgaaa aacttgaaaa agcttggctt  17220
aagttcaata ggtaatccaa gagtaaaaac agattccaat atcagatctt ttcaccatag  17280
tcatgttaag tttggaagcc ctacttgagt gtttccagtt ttttccacat tatattgtgt  17340
ctatatttga ttcaaaggca gggcatctat tgtcttgctt aggactgatt cactgggaaa  17400
agccactgga gttgcctatt tccactcagt atgcctcact cttagagtag cttcccatgg  17460
ttcccaggca ggccctccag tgagaatgca ccaagccaca cgccatggcc tgggaagcag  17520
tcctgaacct ggagattgtc ttgatggaaa ggaagaggca gccttcccct cccaggaaga  17580
tagtagagag cctgctctga cttcgctcag ggatggaact ggtctggctc agttctctct  17640
cctgtgtggg acatgaatca ctcttggtgg tctttgcttt ttatttgggc ttaaaatcag  17700
cagactttat taaatgacac ctctctctaa ccactctctg tctgggcgaa gtttaacaag  17760
aacagcctcc ccccatgtgg tatgggttgt aactgtggcg gtttccctct gctgtttttg  17820
gttacaagat gaacattatc tgaacacaca gaaagaaatc tgtatttggc atccataatg  17880
gaaagtcagt ttagtaattt aaacttagcc agttatcatc atcataattc tttttaacac  17940
tttcaaagtc agcataggag aagtgtattg ttgaatatta caaaatattt agggcataga  18000
tagatgtgct gtgtagtttg atttgttaat gtgtctaagc aatcaaagca acagaattca  18060
aatataaacc ccatcacttc caaaatagga actctgttta ctgacttgat tataacatat  18120
ggaactcaat tgttttccat taaaaaatga tactattagg aaactcaccc catttctttt  18180
tcatatatat tctgctattt gcataattgt ctggagtcca tatgtaatat taaatgtaaa  18240
acacaaatgc catgtagctg gtctgtttct tcctcacctt ttggttcctg gcctcctggg  18300
gaagggttgc acatctgagc cgtggtctca gatgactgcc tcggaagaag cctcttccct  18360
tcaggcacca ctgatgtgtg cttggtgtgg agctagactt tccctggctc tccatgtgac  18420
gctcacatgt gcgtgtcttg atttccctta acttcatggc ttatctatga acagcttgat  18480
```

-continued

```
ttgggggaaa aaaatgtgtt tcccaatgct ggagttataa ttgaatgtgc tgcagtcaaa  18540
actgaaatgt gtgcagagaa agggggcttt tcctgtcatg ctcattgggc accagtgtgt  18600
cttcacctgt tttgtgtgtt aggtccatgc gtcatgctga aatgaagaac atgggatgta  18660
tggggctttg gacagtgctg agccaaaagc aagtgctcaa aagcagctgt gtttgtatta  18720
ttagtggttc tggaggtggc tgattgcctt gcattttaag tagagaggga ttgtagaaga  18780
ctgccaatac ttagaacttt ttccagagag gaagggtcag aaactgcatc tgcagggctc  18840
cttgctctcc agaaatgcca gtgtgcctgg gagggcatct tcagaaatcc agtctctcct  18900
cctcagtgtg tcctgtaccg actcagtggt tctgtcttca gaattcctat catgtctgtg  18960
atctgcaaat agtggtattt aatttgactt caatttgtat aaatgttagc ttctatttgt  19020
tcattcctat tttttgttca attaatacat tatttattga gcatctactc tgtgtcagcc  19080
ccttgggtgt ttaatactga attagtcaca tgtgggactt gcctgccctc agggagctag  19140
actataaatt cctaatgatc agtggtctcc acttttctgt cactcataat gtctggcaca  19200
acataggtta cttgagttgt tacactcaca gtactgttgt ttgctgccat ggtgctttag  19260
gaagtgtgag agttcccggg aggcagagtc aataatgcag actacacgta gtgaaaacat  19320
ggccaggaga gctgtagttc aggctctcag ctcaactgca ctctgtccac tgagaagcca  19380
taatttcttc acttaaagtg actgtgcgct atggctgttt atatatacgc ttaaaaagta  19440
aaagctgcta aaccactcaa ggattggggc cttttgtatt gatttaatta aaggaacaat  19500
cattgtttta atgagctcta gaaacaatta cttttgaaga gccgaggatc aaattcttgc  19560
ctcacgtttt gccacagtgt gttctgaaag gtgaattaat gcttttggaa tcatcaggaa  19620
tagtgagctt tgtcacgatt tactttttac aagcgtatct aatatgcata ttgaaatgtg  19680
agcctcccca ccacacttcc gctttgataa gcatcccccg gattgccgtc actgaccatt  19740
atagattttt aacaaagttg gacagtacac actgaatgaa aactttacat caaggaaggc  19800
ctggcgtgtt tgtaaaatga attaaaaggc tcattaaatg atttatatga cttacgcctt  19860
ctgaaaatat ggcctcaaac acagagatcc ccaaagccac accgacccct gcgtcccatg  19920
ttctcgacct caccgcatca gcaccagcaa gacctgtcgc tgagacggtg agtgatgaga  19980
gtcaagagga gtgacttgca tggcctggga ggaaacctcc tgtgaatctt tagttaagca  20040
ggaaaaaaaa aatcctcatg aaggaaacag gatcttggga gcattttgaa tgaagaagga  20100
gcttagtgag ccaaacttga gacatagggt gtaatgtggg agagttttaa gatttgcaga  20160
gatgtacagc ttgggagggg gtgtaatgca ttttcttaaa agagctgaat gaatggttga  20220
ggaaatgggt acatctggtt tggttaagga tcctaatctc tgaagcctgg gatgcccccca  20280
gggcttgtaa tttaggaata cttcccctaa tagtagctaa cccttatata gtgctgtctg  20340
tgcaggctac aaaaggagca gattaaggat agaaaaggtt tggagtgtat gagaaaccct  20400
aggcaggaat tgactcctgg tgtttgtaaa ccttaaagat gtcctaaaaa ggtcaaggaa  20460
taagacagga gaaaaaggaa atgtcaggaa gatgatcaat ttaatgttta tggaatttag  20520
tttgtactta ctgcccggca tcttgcctga ggtttttaac ctcagcagca catcagaatt  20580
actgtgtgtg tgttggaggg gctgggggag ataaagaaat tagcctcatc ccaaacattc  20640
tgattcagtc tgttacttga gaaactgaat tgtgttttgt ccataaagaa gatgaaattg  20700
tctacagaga acacattgcc attcacaagg ttgaggggat accacagaga ggctcccact  20760
gtgatttgca tttgtcaaaa gttctagaga attcttcaac agtacacaca tggttgtttt  20820
aaatatatca ttgttataaa aattcgtttt gagttctgtt tcacagaaag tttttttgaa  20880
```

-continued

```
tgaatgaatg tcatatatcc ttgctaaagg agctcagtta aaaaaaaagg gaccatcctt  20940
ctcttttggg ggttgtacag taacacattc ccaagaaaga ggtaacagcc acatacattt  21000
ttcttcccaa taaagagtgt gggtttttaa tatgaatcca tagtatgatt tctgttatgt  21060
tttgtgctgc ttcataacca cactcatgca cttttcagaa aattaatacc attcattagc  21120
ataaatcata aactattccc ttggtatggg tttgaaattg ggggtgccct atcatccttg  21180
ctttatctct tagtgaatta tgaccctgta gtcatcatgg ctggtgggcg tctctggtta  21240
aagaaagggt tggattggaa ggattcagag gcgattcttt gttcttaggc tttaatattt  21300
taatgagcct gcaggcttgg ctgcttacga acgagctgag atttctaagt gtgttgttag  21360
tgttagcact tgtagaagga tgttcattag gaagttcttg tttcagtttt tcagagaaac  21420
tccccattaa gaaagatcat tcaggaacat ggctaccaag aaagaggaaa gggaggaggg  21480
aggctttcag ctataagcat taaggggata ttgtatcagt agtcttagtt ctaaagattt  21540
gcttctgaga attaattgga gcaaatacat ctcaagggaa gaaaaaaaaa gatttatagg  21600
gcagggacag tagttgtcct tgcaagtaga ggacacttca ttttgcagct gaatcaatac  21660
cacaactaat tatttctggt tatcttttac gcatttgtaa gacattgctt ttgttcagtg  21720
taataaaaaa cccattgttt gatcagtgac tgactaatta tgataagtaa tttgaaacat  21780
tcttgatgaa acttgtctgt taattaacat caacagcaca gggaaactaa caggacaaca  21840
aagtattagt ggatccactg ttccctccaa ttgacgagct ttctctgtgg catgcccaat  21900
aaactaaagc tgccaatggt taaaaaataa caaacatgtg ggagatctga ctcaccacgg  21960
aggaagagtt atggtaaagt tacacaaagg agtactgaaa tattacaagc gaggggggtgg  22020
taaagaaatg tcagcaggta gcctgatcct acagcttaga gtaaggaaag tggtttcttt  22080
ctgtctttcc tttttctttt aaagcttaat tccaaaatac attcatccca tattgatctg  22140
aagtaagaga cttttgataa attaaagtgt gaatctgaaa atgtgtagtt tgggattatg  22200
ggcattgcct ggctatcttg taactgtcat taatactgtt aatttttatc aactcaatgg  22260
cttttttttc ttatgctttt agatttctac ctggacaagg actggtacta tacccacaga  22320
taggagacaa attggatatt atttgcccca aagtggactc taaaactgtt ggccagtatg  22380
aatattataa agtttatatg gttgataaag accaagcaga cagatgcact attaagaagg  22440
aaaatacccc tctcctcaac tgtgccaaac cagaccaaga tatcaaattc accatcaagt  22500
ttcaagaatt cagccctaac ctctggggtc tagaatttca gaagaacaaa gattattaca  22560
ttatatgtaa gtataatttt attcatttat tttatagaaa ttaagataag ctatataggt  22620
ttgtatcaat tttttgtttc cttaaaatta ttgtgacaaa taatttgatg aaaatctatg  22680
tggaaaaatt gtcccccccc cctttttttt tttcaaagaa aacttcattg aatttgggac  22740
cctgtgctac cagtattcat taagtataca tacccaaaga gaaaaaaaaa cactagaatt  22800
cttaatagta ttgaaataaa tgtattatat gaatatattc agcatctcta ctgacaaaac  22860
catttttaag gaccattggt ggattttgat aggtaaatct tgtgcattgc cttttctctt  22920
cacccatcca tccattcatt cactcattca tttcgtattt attctgtgcc agagactgtg  22980
cttaagggct agggattcag cagtgaaagg tggtaaaata gcatgttttc ctcaagaagt  23040
taacagtcta gagaagatgg agctcataaa ttcgaaagat ggggatgaca ggtcacatta  23100
aaaccagatt cagaagaaaa agacgaaact tggtttgctt agtacattac tctttttttgc  23160
atacatatat ataatttgac acgctgtttc aagaagagat ggtacgtatc ccttgggtca  23220
tatctgaggc tgacttgtga ggatgtgaag tcagctgatg agcacatttg gagcccacgc  23280
```

-continued

```
ctactatgtg cagatctctc gtcagcgtca ttcccagggc cccaggtggt gttaaagtct  23340
aggtgactca gacagctgtt cgcgtcattc aagcaatgaa gtcttttttc ttaatttctt  23400
tggtttaaaa ttatactcat aattaattgg gttgaatttt ccagtggctt ggttaccata  23460
gacttcagtt tattagggaa ctgctatctg ccactggttt attatttgcc ccaaggtgga  23520
ctctaaaact ttaggtagga gactcttggt gatcaaactg aaactcttgc atctcaacct  23580
atgagccgca ctttattgtt attttatttt tttagagaca gggtctagct ttgttgccga  23640
ggctggcgtg cagtggcatg atcacagctc actgtagcct tgaactccag ggctcaagtg  23700
atcctcccac ctcagcctcc aagtagctcg gactacaggc atgtgccact gcacccagct  23760
caagagctac acttcaaagc acagaatgaa aacctatttt taaagccaac ttgatacata  23820
gagtagctta ccaagaatta gtaacaacaa caacaagaaa aaaaagagag aatgtggtag  23880
agtatatact tagtaaggag taattattat aaaataaaag cattctgaaa tgaaacaggt  23940
agatggggtg gccaagtatg cagcatagta gggaaatctt tgaaaatgta aaatagttac  24000
caggtaaaat aaatggaaac tttaagcttt tggaagccta acaatgtatt tatattagta  24060
aagactttat tttttattt tattttattt tatttttgag acggagtctc tctctttcgt  24120
caggctggag tgcagtggcg tgatctcggc tcactgcaac ctccacctcc tgggttcaag  24180
tgattctcct gcctcagcct cccaagtagc tgggactaca ggtgtgcgct aatttttgta  24240
tttttagtca agacggggtt tcaccatgtt ggccaggatc atctggatct cttgaccttg  24300
tgatccttcc gccttggcct cccaaagtac tgggattcca ggcgtgagcc accgcgcctg  24360
gccttagtaa agacttttaa agtaagactt tttcagtgaa agctactgtt aggcatgaca  24420
tttacaggca actgaaactg atcagatgca tttattaaga aggttaatgc ccctaggtgg  24480
ggtgggagaa agaaggtcgt ggtacgggaa gaggggacac actagagatg agatgcccta  24540
gggcagtgaa cgcatgtccc taatgcgtgg atgcagccca cgtccaccga taatgccgac  24600
acacccagag tctctcttct tactttagct tatgacttca cgaagaatgc tttgcaaatt  24660
ctaagttcgc actgggcgca agtggaattt tagtaaacat taagagttta acctttagtg  24720
tgaaataata tgcaagatat gcaaataatt gtttaccaac atctctttgc ttaatgtggt  24780
gagcatttaa taattgcttt ttattaatac atgagagatt tgtatttaga agcagtttaa  24840
tttataatta taatattaat ctacacaata acgacatcta ttattttctt tttttggaaa  24900
ctcttcatac cacactaaca ggttcattgc agttactgaa ctactctggc catcagagct  24960
ctccttagag ttacgattta ccatgcaaaa gcatatggta gcctgggata aatgaatctt  25020
tcttaataca gaattgaggg tctcaagttt gaaactacga gaggctattt gaatgttgct  25080
ttgggggact gtcataaggg ctgggtggag gactcagggc taagaagttt gccaggaagt  25140
ccagttgaga ctttcagcag agttgaaaga cttccacgat ggcgtaggca gaggaaggcg  25200
tttcagatac ttgggaaaat atagaagcca atttctcacc caccctacag caaagctcat  25260
tgatctacaa gtttccctag aaaggaaatg ggaaatgcag agaacaaatg ttaaaatagt  25320
tttagaaatt aatattgact ttgtattgct tctgcataag ttccaagaca ccaaaacaat  25380
gaatggattt taaaaagtca ctactttgca tatcagacaa atgcacacac acacacacac  25440
acacacacac acacacacac acacacagtc aagctctgta ctggcttttt tgagaaggaa  25500
agtgtttgaa gttagtaatt tttatatcag tacatttata aatagtgcta ggtagcatga  25560
cggaaagtat taaaatttac atgtatattt ttaacacttc aaatcgttgg ttcactttga  25620
gacagtaaat aatattagca tttgagttca gctttaataa attctacatg ggtttaaccc  25680
```

-continued

```
caaatctgag tgtctagttg gtaagcgcct tcagaacgag cagtgttata ataaatatgt  25740
tattgtgtgc tggtttcttt ccatggagag gaaaaagaga cctgatgctt tggaggagtg  25800
cttgactttt ccccagtgag gagtagtcca gagggactga cttgcattgg ggagtaccct  25860
acatgaacag catttcagaa gaattaaacc aggaacctag agtcctactt gctagtcctg  25920
cttcctaagc ttaatgagaa agtcaatttt atttctttga actttaattt atttccctaa  25980
aaaacgcttt tagtattgtc attgttctgg ctaatgatgg cggtctcctc cagtttcaag  26040
ccaccttagg gctgggcata caaatgcaat ataggatcac ttgttagtgt ggtttcaaat  26100
ggacatgatc ctctgtaaat tctttaaaaa catttaattt gatttgtggt gttacctgct  26160
ttaaaatata gtcatcacac ttgtgagttt cagacgtgaa tatgaatttt taatttgaac  26220
tgtattttta aacacactaa gtattaacta agtcccctta ggagatatgt ggcaaactga  26280
tatgcatcct cattcattct tctcatagat ggttatttgt tttttaactt gtggcaaaat  26340
tatatatgaa tggtcaccga cttaaaatag ttccacttaa atttttcaac tttctgatgg  26400
gtttattgga gtattaaatg tattttcaat ttaatgatat tttcagctta ccttgtgctt  26460
atcaagtatc aagacatagc cccacctaag tcatggagca tctgtatatg ggtttttatt  26520
cttgtttaga attgactttt tcaagtgacc tatttcagta attagccctg ggcctgattt  26580
gcataatgag atctcctaat cttcaagtaa tgcaaagatg gagatattat ggccatgtgg  26640
tctgaagaga ccttttcttt attatgttca gatctttaat tgccttaaaa atagagtagc  26700
taatttacct aacctctagt tattttatta ttgtctttaa agtttttttt aatgttcatg  26760
aaataactgt tctgaaattg cctattttca agggaagctg tgtcttagac ttactaaatg  26820
ctccagttga tactgggaaa gccttcttgt gttcgtagcc tttatccgta gagttttctt  26880
tgcagcattt tctgtgcctg gtttagtttc ttttcagagg cgacacccag agctgaatga  26940
gtcagcaggt ttggtgtgtc gaccctttgc aacagctgtc cttacgaagg ttctgtgggc  27000
tggttattct accttcgcat aaaaccttgc aaaataaccc acaaagaggt tttcgtcaca  27060
ctaccaaaat catgtgagtc agagatggat gaaaaatgaa tgccattgtg ttcatacttt  27120
tccagtgaac agtagctaca gcagagctgt tagacaaaga aaaccgtatt aatgaagcgc  27180
ctcccaattt agcttcatat ggcttttgca ttattttgct gcaaatccat agctaagaca  27240
catcttgtgg catagtccgt aagtcatctt tccgaaggac tgtttgatta aaggttgttc  27300
tgtgagatcc accctgtgtt gttcatggca tcctcttgga ggcctccctc actctccatg  27360
ccttggcaaa gtcttcctta aggaacactg aacaagtctg gagaagctgc catttcttag  27420
ggccctcatt ggttcagttg tctatagctt tttatttttt attttttttt taataaagag  27480
tatgtaaaat tggaaagctt cacaaacagc tttgctattt tttagacatg tactccactt  27540
ctaagcaaaa tcacaaaata aagtaaaatg cttccacaaa tataatgaaa caatattctt  27600
aaagaatcaa agcagaagaa cttcagagtc tgttgcttat gttaagcata tatttgtttt  27660
cttctctgct tttgatttac ttatttctgg ggtgtaggtt tggcaagtag tactgaaacg  27720
tactgaatgc actgttcttt agcaagatag ttacaggagc tttcaaatgt cctcttaaca  27780
tatagatttc ttttagaata tagaataatg tgtgggctgt ataaagcgat tatgtgcttt  27840
atttgatgaa ttatttatgt acgataaatg tagcaaaagc cacatttcca tcattaaatg  27900
taatcccatt tggtgataca gcaacatcag cctgtcattt gggtcctctg attgaggggt  27960
gaggatttct gtttgatacc ttgtgcataa tggctgcgtt caagcattta aactcatttt  28020
tatttctaac ctacagctgt catctttgta ataggatatt catcagaatc ttgccagaga  28080
```

-continued

```
ctgtgcattt gggatcttgg gggatacagc accaccacca ccctccccct gtccaagaga  28140
aacagatcaa catcttaggt tgagagtctg gggtctggaa gacccgagtt cctgagtgcc  28200
ctttgacaag taacttaacc cctgtctgcc tcagtctctt catctgtaaa gtggggataa  28260
tgacagcacc tgcttcacag ggttgatggg aatccagatg tggtgggata tagaaaatgc  28320
ttattacttc cacctttgac accaaataca tataactaag agttaacttt ggagcagggg  28380
aggaagtgtg aggctccagg ctggaggcag acctgtgttc ggctgcaagc tggagaggat  28440
ggaccccaaa agcttggctg atttgaagtc catccataaa atggaactcc agagagttta  28500
cacgtttcag taatgctgca taacttaatt ataagatctt ctctctttgt cttctttcag  28560
tgttataaaa gctcttttgt ccttgagctt cctttaccaa gaaacatgca tttatgtatc  28620
tttttgttca tggaattgcc caagcttgtt agcagatcct ttgtaagacc caaaagagac  28680
agacagggga ggagtcttca gatacatata atcatttttc ccaatttcca tgttaccagc  28740
cttgccagga ctttttctca gttccctgtt acacaatgaa aatagtgtct ctttattgat  28800
aattttagta gcatcctaat gtggtataaa tcgtcttcca gagaagaaaa tgtgtcaggg  28860
ttgcgttatc actgaggcta gctgggaaag tagatcagcc cattagtctg ataattcgaa  28920
gcgttgtttc tgttatttct gaacatcatg tgaactcctt ttctgggtgt attaaaggtt  28980
ttcccagtgt gtgtcagtga gactcctgat tgaatttaat atgaataaag ataaattctt  29040
tacatttaag gattaaagtc tcagcttctg cttaacttga gattgcactg agaaactcct  29100
ggctctcggg tatagcggag tcacgacctg gggatgtctg tcccatatgg ctctgtgtgt  29160
aagaagaaaa agctgctgtg gacggagact ctgttcacat taaatgacat cacctaagcc  29220
atcatgacag caagaattat ttaggaattg ctcagaataa aactgccttc attatttcat  29280
aaaatgtatc ttggtatctt tagcacctta tttatggctt tttaaaggtt cactgggatt  29340
tataaataat tggacaatgc tagagaccta gtacaagaat gaaagaggac aggcttcttt  29400
cttaataacc tttaaacatt catcaggaag ataaaacttt aaagcaaaat aaaacacatg  29460
aaaatagcca agatgcacag accagacaag caaatactac tttaacttat ttgtatagtt  29520
cttaagagtc acatttgttc ctgaagtttc aaaatctcgg gctgagtgtt tgatcactta  29580
gggaagtgtt gtggccttca catactcttg tctcactttg aagtctagaa acacaggtct  29640
tagagcaatt tttatcactg tgagaaagct gaaacttagt gtgagtagct tagtacaatt  29700
cagttggcca tcaaatgtca gaaacaaaac tcagtccagg gccgctggac ccttaggccg  29760
gcgttgttag tttacaacag tgcctcctgg gtccaaacat ctaagtgcac atgtagcaat  29820
agtaaagata gtatgtatgc atacataaca catatgtaga gacagcagag tatacgtaca  29880
cacatgttgc atacatagca acagcagaga agctcatgaa ctataaagga tggactgtat  29940
gcttgtatca gacattttgg tactgacgct ttgtcatata ttgtgtaaca tataaccagc  30000
ttgcaatcat ctgcccccaa agttgaacta agaaaatcct acagggtact aggaaaggaa  30060
ggccattggg aaaaggtggt tatagtggca atttgttagc tcttatgaat tttctttttc  30120
tttttagaca tactcttaat tccatttttt caataaatct atactatttt gtgtttttat  30180
gttagcaagt actttaagcc cctcaataga aagttgctac atcatatagt gattaaaaat  30240
aaaaatctct caaacataca agtagaggtg gtatgagact tcaaattccc ttagccaagt  30300
acaagtgcag cagttttgtt ggctggctgg ctgcatagaa ggactgatgg attggcagac  30360
cctcaagctg gagtgtaatt gatctcatta cagaggagcc aggctgggtg acagttgtgc  30420
tttgcaagtg gtttttttgca ttggtgaagt agcccatttt gttgttcctg atgttaaaca  30480
```

-continued

```
ggggatgaag gtattctttt attggcacaa acgcgggaaa ttgctctgga ttcttagagg  30540
atagaacatg tcccctggac ggaataaggt tcatgtgtag ggcaaattta gataggggca  30600
ccttattggg gttactactg gtctctagat ggtcaaagca aacaacatgt ccatctaagc  30660
tgtgatgtcc atctaagctg tgtgtgtcca tgagagtgac gcattttctc ctctgcagtg  30720
ttgttatatt ctaaactgtc agcagacatt aattcggtcg ctggtgaagt cccaccgcct  30780
agagatgaac tctgcctccg atggatgttt tccacttcag tgccactcgt ctcgcaatta  30840
ctgggtcatt aatatcattg catgcaatta gtgacagtag aaagagctag agggttgtgg  30900
gatgtgcacc ctccccacca tgaacttttt actctgaccc tttcccagct agaccttttc  30960
gtatcttggc aaggatattt taatgattga gactgtcaga atcttcagag caggcactgg  31020
attatgtgct ggaaataatt cactcaaaca cctgcttctc catggttcag aatattttca  31080
ttagatatta tcactatccc ttccctggga agtttcattt ttaaaaatct gatgcttaag  31140
tacagctaat atagacaata gggaattatg ttttatcttt agaactctta cattattctt  31200
ttctttaaaa atgtgagctg agtcattgct attgcagtgg tcatctggcc gcctattttt  31260
aaaacacaat tcctctatct tagtagattt tggcccatat taagcatatc aagaatgact  31320
tttttttttt caagacatgg ggttttattg ggggcttata tacaaggaaa gagagagtcc  31380
agtggcagtg ggctggacaa gatatccaca tggccctgtg gcagtgagct gggcaggaaa  31440
actgcaactg cttgcaaaca gcatgtagtt catctatagc attttcactt aacaccaccc  31500
agctaatgac ttccacctgg caaccttcat ttaatccaga acttaggacc tcgagtccct  31560
gtacggccca tgttccacag gatgggccga gggctcagct gttcctcata gacaaggaat  31620
gactctccac attggccact cccggattcc ctagctcagg acacatattc aggtgtgtct  31680
aaggctggct cttctatgtg aagttactta ttcttttacc attgactctc atgttcccac  31740
tatattaagt ttttctgaat tactgtggca ataagaaacg gtcccttaaa ttatactaga  31800
agaaaagctt tttttttgtt ttgtttttta ttttgaaatt atgttaaatt tttttttctta  31860
actgagagat tccacctgca taaatcgtca taacttttaa cagtaagatc ttagacttag  31920
aaagtgatgt ttttcctcaa cagaatttat taaaaatcaa gacaccaagc tgttccaaac  31980
aatagtttga ggggaaataa aataaacaac tccataaata atcttatgtt gttaaacatg  32040
tctctagcaa aacaaacaaa caaaaaagtc gggggttggg ggaggtgcag tttattgcca  32100
gtactgtctg gtctttctca gaaaagcgtc agtgtacatc actgagcctg gacggtatgt  32160
tttcttgatc tatacccccct atgtgtacat gtgcttgcac gcacacacat gtagacacgc  32220
acacatgtgc acctgccatc actttctgct cttccgtctt ttcactcttg agtgtctgta  32280
gccagtagct ttccaggtct gtatagtcaa agatacctat ggccctgaat gtcttcactg  32340
attgctattt gacattcata cggtttttaa tggttaaaag gctttatgcg aaagctgtga  32400
tagaatttct cctgttctag atgtggtgtt tattgcttta ttttgtgact tttctctcag  32460
tagattgacc ttctccctca gtgtccaagc ctcgcatagc atgatggcac ctgtaaactc  32520
agttctgtat cctggtatcc tttctcttcc caagtagaag caattaagta atatatgtca  32580
tcaaaacctt ttaagtgcac atacaaacaa aatcaactta ccaaactgct tcaaagttgt  32640
tccatgttta acactcttct ttctgagctc tgggtagaat gtcctattat tgttcatcat  32700
gaatatttga aattaaagaa ataaaactgt accattttct ttaagagcat ccatttgtac  32760
ttgataacat cttcagtcat atttcaatgc tggcaaagag gaggggagtt ctaaactgtg  32820
actcaatttt agaatctact ttttccaaat tattctgttt agtgcagaaa actaattaat  32880
```

-continued

```
agtgttgcat agaaaagtca ctgaagctaa gccagttatt acttcttaat gcatgattta  32940
ctgctttaag ttttcaaaac acaaccatag caatgtggta ttaattcaag tgattcttcc  33000
tatcatattg aacgatattt tcacgggtga aaaactcaca catcctacat cactgatagt  33060
ttatacagtg ttttagctgt ggctccctgc atgcaaaata agagttaatc aaatgtcagt  33120
gagaaccatc tcatcaagta gagggcttgt tttgtttaaa ttaactttgc taagtataaa  33180
tttcttcttg aaaataaatt ctgggccggg cgcggtggct cacgcctgta atcctagcac  33240
tttgggaggc cgaggcgggc ggatcacgag gtcaggagat cgagaccaaa ctggctaaca  33300
ctgtgaaacc ccgtctctac taaaaataca aaaaatgagc cgggtgtggt ggcgggctcc  33360
tgtagtccca gctactcggg aggctgaggc aggagaatgg cgtgaacctg ggaggcagag  33420
cttgtggtga gccaagatca caccactgca ctccagcctg ggtgacagag cgagactccg  33480
tctcaaaaaa aaaaaaaagg aaaataaatt cttctgtatt tttctttctt caagtgaggc  33540
catttagggg aaagtatacc ataaaacttg ctctaagata aggcaaattt ggtattatag  33600
gatgaagtgc tatgtgattt gaagtaatgc tgaatttttt aaatatatta aactaaacaa  33660
gaataatgag gccctcggaa agtcatgatt atatttctca tttttctcat tttaaagcca  33720
cagtgaaaaa cacataaaag gaagaagtta gaaaaaaaaa tgaatgaaat tctttttttc  33780
cttttggcaa attaaataga tgtttctgtt tcagaagatt ttattaatta actttaaaga  33840
aacagtcatt tatttttggc attcagtgaa cactatcatt tccatgttta gaacttttct  33900
tctaagttag catcttaaaa gataactgtg aaactcaagg cattcaacta cattaatttg  33960
agtttcagaa attgaattct tgtttctaga gtacatagtt tgaattgatg tcagggtgtt  34020
aaatagataa atcttagctt cctaggttgt atattcacac taattatttt tttatcagcc  34080
ttcttatttt tcaacttacc ttattctttt tgtttttttg acactcagat ttgatagccc  34140
tgtggtagaa gaaaacagta atacagtttg gtttgttgtt gtgtttgtgt ttattttaaa  34200
gtcacggctt tgctttccat gttgttactg gattatgctt tttttaattc ttcagtttgc  34260
caagataaca gtcttccgat cttcagaagt ctgtatcaag cttaaggaaa ctgatgtgta  34320
ggaagactcg cctaagaagt ccaaattagc aaggctagca tgtgaggaca tgctggaaaa  34380
gaatagttcc catagatatt gacagagaat gttcataaaa tgctacttgt tttgtggtta  34440
catgagagta acttgtgtcc agtgcagctg tatgtaaggg caacgttttt attctgacga  34500
ctctgtggtt ttcatgaccc tggatgctta tcatgtctct ctgttggact tcttcaacgg  34560
agttgataca aatacttgct tccaagtgtc catctgccct ctcctccatc ctggccccat  34620
acaaatacgc tacattttta aataatttga aataccctca atagtattta tatttcctgg  34680
tgcttcattc tttccataag aactgtgata ccattattct gtaggatttt tttgtgcttc  34740
cccgtttcac atctctgtgc cagtgagacc catatatcgg tgcaaatcca gaagtttgat  34800
tgtccatctg attagcacac tgttagcaat gtggtggact aaacacagcc aagatgtggg  34860
gctggagctt agcctcctgg gagcagagcg gtgaacatca gatgaagaca tgtgaaaatg  34920
gagtactact tcctcttcct ggggatgggc taaaaagcac agccagaaat attcttgccc  34980
ttccagtctg ctttacagtt actcactggt tctctttttt ttcctactca gataaccagt  35040
atactcttcc cagtgactaa gaactgcaga taagtatagg tgcaaataga tggcaaaccg  35100
cagatggcag ctgtgtggtt tcagatgtgc tgcagaactt ttagacgatg tgaacgcaag  35160
gaactttttt gctgagcagt aatctctacc cactggaaat taggccctgg ggggaacaat  35220
gtagtgactt ctatatactt actacatgca gttagacccc tgaagcaaaa gcttttaaaa  35280
```

-continued

```
acaggctgta aaatgcccat gtatctttat taagcctatt ttccaactgg atagagaaat  35340
tttctggtaa tttttaaatt tgtaaagtct attttttttcc tgagccaagg gaaaaaaaat  35400
atctgggccc taaaagctta gttataacaa tgttattttt tctatctctg aatgattaaa  35460
tgtgatttca tttatgtagc aatactatga ttgtggctgc attagatcac gctgatagaa  35520
agatacaaag aaaaactaag tataatgaac taacaattta ttttcactct ttctctaagt  35580
taaaaattcc cagtacattc aaatgaacaa tgaaaataat tgcagaattg tctcctgaaa  35640
tggaaataga ttttttttcc caagcattag caatttcttg ttatttttca aaatcagcca  35700
ctaagccttt cagagcttct tggtgactat tgcaggagaa atcagaatat taatcttgtg  35760
gttttatttc agagttcgct gccaggaagg aggtataatt gggataggag actttttttt  35820
tttagctgtg tcactgttca aggagggggg tttggaacct cagcataaga attacactct  35880
gtgatgagga tgtagcaggg gagaagaaag gtgattttca ctatgggaag ctatacttac  35940
atcaagtata aaatagactg aagtcatttt gaattacgtt atacttgtaa agtttacctc  36000
ctggagtttc agttagtacc agtgtactaa ctgggttaaa acagttcatg gcaccttaga  36060
tcatttctaa ctcatggcaa aaatctttcc tggtggaacg tgtaactgta ttttaaatgc  36120
ccctttataa gcaaccaagt atttgggatg ttattttgat attagtagtg aatttttcag  36180
tatcttccag taccctttgc aagtcacagg ttgacttaaa aggaaaagaa gcaaaatgct  36240
gaatatagca gaaaaactgt ctgcattcag actgttcagc ccacttttgc tccccacgtg  36300
gcaagcacac tcccccaaac aagcaatagc ctgtggcttc agaggaacct acaaaggcag  36360
catctgtaga tttttccttc ttcaactcta agacttgaat gtttccctct tccccacaca  36420
cttttttttt aaaccaagaa ataaaaaagt tttcactctt aaaggtgcaa agcagtttca  36480
ttcttatgca acacagcctt cctcctactg tcttatagtc tgtggatgtt aaattataga  36540
ttccaattga attttaatac tctagagatt ttacatttgt ggttgtcaag accccgtttt  36600
ggtaaaccta gggagctccg cacaaaagca ttgatattca gaaaaggcac tgacctacaa  36660
attaaaagaa aaaaaaatca aataatgtgc acctcttgtg cttccagttt gacaaagcag  36720
aagtcatcag cagtttctcc ctctgcagac gcagttctca attctattta caagtaactg  36780
ctctactgtg cctgttttc tcttgctgat actcatttaa ttgtttttct tttggatctg  36840
aatctttgac tgtcttttcc ccctcaagat taaaataaat acatctgtat tcctcccctt  36900
tctttctgtg cactgccctt cagatctcat tttgtcattt ttcagcttag tgttgaaact  36960
tttagcaaca aaaagtcagt tacttacttt gagtaagtaa ctcaaagtaa gttaactttg  37020
agtttgagtg cacttttgcg tgtaggttca tttatgtgct tgtgaattta aaaacattgg  37080
gattccacct gaatgaagta aaccaaacat tttaaactat cagccagata gagacatcag  37140
cctttcactt ctttctatat gcagacatat cctaattttt tagaaaaatc aaataggaaa  37200
attctcaaca attaattgaa gattatagct ctgctctgaa atggtccaga aataggatct  37260
gctcatagaa actcatagtt tgaagcctct gggaggaaag gatactttaa aatttagtca  37320
catatttgga ggagggaaaa gggaaagagc agaatgaaga actgaaaaaa atcacacacc  37380
ggggcctgtc gtgaggtggg ggactggggg agggatagca ttaggagata tacctaatgt  37440
aaatgacgag ttaacaggcg cagcccacca acatggcaca cgtatacata tgtaacaaac  37500
ctgcacgttg tgcacatgta ccctagaact taaagtataa taaaaaaaaa ttttaatagc  37560
cccattaaat aattaaaaag atttttttta gattcacaga agtgtacaaa atttttaggt  37620
tttttttttt ttaagctgtc tgctgaatag tttcttaatg gtctacaatg tttgtatcta  37680
```

-continued

```
caaacagata ctgtctgctt cttactaccc ttccaagaca agtattatta tggcaattat  37740
tgcccagttt cccgggaaaa atttatccac agttacagaa gaatgagatg caattgtgag  37800
actgtaaagt ttaagcaagc actcagagaa gcacagtgat atgtatgcac agaagaggca  37860
gtctttgttt tgaggaaaac agtgaaagta aagttaattc aagaccacaa agacaagtaa  37920
ataagtgcct tatttttgta gttaatataa tttcagtgga atgcatattt ctaccataaa  37980
tgcatataga acttgtttgc tgacctactg tttggaaaac aaacaatccc attagaagaa  38040
tgtctttggg atttattttt accagaaaat caatcctttt ttcagtccct tgcaaagtac  38100
agtgttacaa gccaagactt tgataatcag gtagaaaatg gatttaaatt gcagaaatgt  38160
atatgaaaca cttttgttcc ttgccccttg aactttaggg gaatgaaaat gtctagcact  38220
ctccaccttc ttttctctcc tggaacttga actgtaattc aaagcctgtt tctcattaaa  38280
gtacctggca gcctatctct ttacagcttg agttacaaag ctattcagag acctcgctgg  38340
tctaaagaga cagaacaagg atgtgtttaa atagagcata ggctgttgaa aaaaaaaatg  38400
ctgaaaatgg taaaatgatt ctgtccttcc ttccactcct cactgctgag gtggagaggg  38460
aattcagttg gtgaacacca gcaagtggct ggtaaaagtc cccactttct ctccagggct  38520
gccacaggac ccagaatgag tggtgggcat gtgtgtgaac cctctattca gccagagttt  38580
tcccgcaaca ggtagtttgg ttgaagaggt tgactaaggt tgacattggc agtaataaca  38640
cgtatgttct tctgatttac aaaacgatgg aggaaaaagg ggagattttg aagacctgat  38700
ttctggtata cttcttaagc atgcataagg ctgaaaaaag aagacaaggg ttgtgggagg  38760
ctcctggtct agtgtttaca gaacttggat gcttgacaaa cagagcgtca agctaattgt  38820
tcttgaagca ggaaatctgc agtggaggaa gcaggtgtgg ggggatgatt accacgtttg  38880
gaaatggctg cattaactat tttgctcttc tgagtttggc cccaaaagag tccatagact  38940
ttttgaagga tgccatccct tttatttata gactaacatt aaatcagtca tttgtgaagg  39000
aaggagaaag tgcctaaata aatttggagt cagatagcat acgtgcggca gtgtttccga  39060
tatccatttc tctttatttc tttttctttt tctttttggc tttcagcatc cccatacttt  39120
cagaaaactt gtgactaaga gtgaattctt atttttcaaa ttgttttcag acatttcatg  39180
ttcatgtaaa cttggcttat tgatttcctg atttttcttt atttttttgt tttgtccatt  39240
ttatttttaa tcagctacat caaatgggtc tttggagggc ctggataacc aggagggagg  39300
ggtgtgccag acaagagcca tgaagatcct catgaaagtt ggacaaggta aagaccatct  39360
gctgcttcat gacgccactg tgacctggtg tagcccccag ctagtatggt gctaatgttg  39420
ccgatgccca ccttcattcg ctcttctttt tagttttcaa agcaaaccct tctgcacttt  39480
gagccactga cagatttcct caagtcaatg tactaagctt ttattggaga tctaagagtt  39540
aagatcagca aggtagaatg tctattgcca tagatagata gatagataga tagataatag  39600
atagatagat agatagatag atatttcttt ttaaaaagca aaacactttg gttcaaaatc  39660
aaaatatcca gaatgaaaac taaaagcttg tgcagttttg ctcatttctg aatcttgact  39720
acagaagagt tttgttcatt gtgacttttc caatatagat aacctattgt gcagaaagaa  39780
ataattattc ttctaattaa aaattggtat agtagtcaat caacttgctc agttaaattg  39840
aaatgtcatc tgcaatgctt tgcctgccaa atgcaagaat ccctatagtt tccacagatg  39900
gcctcacgtt ctaaacctct gaaataacta gtataaccat tttgttttaa aagaaaaatt  39960
atattcttgt atttcacagt actttgcata aagactctta tgttcattgc tattcatgcc  40020
tgttgaaata tatatgcagc tcctaaagct agatattgtc agatgtctgt gccgtaatta  40080
```

-continued

```
atcatttgtt tttcatatag atgcaagttc tgctggatca accaggaata aagatccaac  40140
aagacgtcca gaactagaag ctggtacaaa tggaagaagt tcgacaacaa gtccctttgt  40200
aaaaccaaat ccaggtataa cagcatgatc tgtgtgtatg gaggtctgtg ggtaccacat  40260
tcttagtagt atcttaaaag gtagggcaga gtctaaagac ttctaaccag ttaggattag  40320
ctggaagtta cagtgatcag gaatctttgc tgtcagtgag tcattattaa ttacactcaa  40380
taagaacaaa ataactcatt ccaatgaaag tcatatattc aaaggagtag agttcatgag  40440
ctgtaagtgc cagttattag aactactctg tcaggccaaa ggtttcattg gctgacattt  40500
tatcaagctg gttgtcaact ccagcttaaa gctgatgtta atgtatatgt aattaatgtg  40560
ctaatccctc atctaattat atctaagcca cagagggttt aattgatcct cttctaaatt  40620
ttaaatggta acatttttaa atattgcata atagtatttt ttcaggtggt tatcgttatt  40680
ttgtttcaca ttttccatgt aaaagaaaat attaaacagg tccctgacaa aagtgtagaa  40740
taccagataa aattgtccgt cgttgacctt cgttttctta acagtcttgg aacaaatagt  40800
tctgtatttg ttaccatgct aatgaaggtt ttatagagta gctgttgagc agacatcagc  40860
agttttgtat taggattgtt gtgtgcttgc ttggtcgttg tgcaaattta tcgtctgcag  40920
caatattcca tccctttcca agagtcaagg agggaagttg ttatttctaa ctttcaatga  40980
caagatgtgt caaattcttg tgacaaactg ataaatggat aatataatga tgccaggcag  41040
ttttttagtg cttaacattt gggctggcag tctgttcggt gtgagagttt ctgctgcctt  41100
ccaaatatat tttaagtgta aatcaaataa tacagacgag ttacgagctg aacattttcc  41160
caggccccct cactccttcc gcgttcccga gctgttctgt tctgccagga ggcagggctc  41220
ttctttagaa ggcaggccct ttgaaggttt gcatgaaact ccctttctca aaggaggcgg  41280
aagagcaata ccacataaac gctcaccgct gacctggaga attggccact tcccttttc   41340
ttccctgccg ctgccccagg ctggctgaca cgggttagaa gatgaagcaa gatcaagggc  41400
tggctgtcac cgacagtctg tgctcttgct ggataatgat acaaaggaaa ccctgtggct  41460
tgggagggta gggaagtccc tcctagagat acctctcatt tcctttgcg ttgagctctt   41520
agacgaggta ttggcgaggc aaagtccagc ttctagttag taataagcct ggcttatttt  41580
tcacattttt aagggtcata aaagcagtcc gtctgcactg ggacagcagt aactatctct  41640
gacctttct gtctccgcgt ctgcaggttc tagcacagac ggcaacagcg ccggacattc   41700
ggggaacaac atcctcggtt ccgaagtggc cttatttgca gggattgctt caggatgcat  41760
catcttcatc gtcatcatca tcacgctggt ggtcctcttg ctgaagtacc ggaggagaca  41820
caggaagcac tcgccgcagc acacgaccac gctgtcgctc agcacactgg ccacacccaa  41880
gcgcagcggc aacaacaacg gctcagagcc cagtgacatt atcatcccgc taaggactgc  41940
ggacagcgtc ttctgccctc actacgagaa ggtcagcggc gactacgggc acccggtgta  42000
catcgtccag gagatgcccc cgcagagccc ggcgaacatt tactacaagg tctgagaggg  42060
accctggtgg tacctgtgct ttcccagagg acacctaatg tcccgatgcc tcccttgagg  42120
gtttgagagc ccgcgtgctg gagaattgac tgaagcacag caccggggga gagggacact  42180
cctcctcgga agagcccgtc gcgctggaca gcttacctag tcttgtagca ttcggccttg  42240
gtgaacacac acgctccctg gaagctggaa gactgtgcag aagacgccca ttcggactgc  42300
tgtgccgcgt cccacgtctc ctcctcgaag ccatgtgctg cggtcactca ggcctctgca  42360
gaagccaagg gaagacagtg gtttgtggac gagagggctg tgagcatcct ggcaggtgcc  42420
ccaggatgcc acgcctggaa gggccggctt ctgcctgggg tgcatttccc ccgcagtgca  42480
```

-continued

```
taccggactt gtcacacgga cctcgggcta gttaaggtgt gcaaagatct ctagagttta  42540

gtccttactg tctcactcgt tctgttaccc agggctctgc agcacctcac ctgagacctc  42600

cactccacat ctgcatcact catggaacac tcatgtctgg agtcccctcc tccagccgct  42660

ggcaacaaca gcttcagtcc atgggtaatc cgttcataga aattgtgttt gctaacaagg  42720

tgccctttag ccagatgcta ggctgtctgc gaagaaggct aggagttcat agaagggagt  42780

ggggctgggg aaagggctgg ctgcaattgc agctcactgc tgctgcctct gaaacagaaa  42840

gttggaaagg aaaaaagaaa aaagcaatta ggtagcacag cactttggtt ttgctgagat  42900

cgaagaggcc agtaggagac acgacagcac acacagtgga ttccagtgca tggggaggca  42960

ctcgctgtta tcaaatagcg atgtgcagga agaaaagccc ctcttcattc cggggaacaa  43020

agacgggtat tgttgggaaa ggaacaggct tggagggaag ggagaaagta ggccgctgat  43080

gatatattcg ggcaggactg ttgtggtact ggcaataaga tacacagctc cgagctgtag  43140

gagagtcggt ctgctttgga tgattttta agcagactca gctgctatac ttatcacatt  43200

ttattaaaca cagggaaagc atttaggaga atagcagaga gccaaatctg acctaaaagt  43260

tgaaaagcca aaggtcaaac aggctgtaat tccatcatca tcgttgttat taaagaatcc  43320

ttatctataa aaggtaggtc agatccccct cccccaggt tcctccttcc cctcccgatt  43380

gagccttacg acactttggt ttatgcggtg ctgtccgggt gccagggctg cagggtcggt  43440

actgatggag gctgcagcgc ccggtgctct gtgtcaaggt gaagcacata cggcagacct  43500

cttagagtcc ttaagacgga agtaaattat gatgtccagg gggagaagga agataggacg  43560

tatttataat aggtatatag aacacaaggg atataaaatg aaagattttt actaatatat  43620

attttaaggt tgcacacagt acacaccaga agatgtgaaa ttcatttgtg gcaattaagt  43680

ggtcccaatg ctcagcgctt aaaaaaacaa attggacagc tacttctggg aaaaacaaca  43740

tcattccaaa aagaacaata atgagagcaa atgcaaaaat aaccaagtcc tccgaaggca  43800

tctcacggaa ccgtagacta ggaagtacga gccccacaga gcaggaagcc gatgtgactg  43860

catcatatat ttaacaatga caagatgttc cggcgtttat ttctgcgttg ggttttccct  43920

tgccttatgg gctgaagtgt tctctaga                                    43948
```

<210> SEQ ID NO 394
<211> LENGTH: 4335
<212> TYPE: DNA
<213> ORGANISM: Homo sapiens

<400> SEQUENCE: 394

```
gcgcggagct gggagtggct tcgccatggc tgtgagaagg gactccgtgt ggaagtactg     60

ctggggtgtt ttgatggttt tatgcagaac tgcgatttcc aaatcgatag ttttagagcc    120

tatctattgg aattcctcga actccaaatt tctacctgga caaggactgg tactataccc    180

acagatagga gacaaattgg atattatttg ccccaaagtg gactctaaaa ctgttggcca    240

gtatgaatat tataaagttt atatggttga taaagaccaa gcagacagat gcactattaa    300

gaaggaaaat acccctctcc tcaactgtgc caaaccagac caagatatca aattcaccat    360

caagtttcaa gaattcagcc ctaacctctg gggtctagaa tttcagaaga acaaagatta    420

ttacattata tctacatcaa atgggtcttt ggagggcctg gataaccagg agggaggggt    480

gtgccagaca agagccatga agatcctcat gaaagttgga caagatgcaa gttctgctgg    540

atcaaccagg aataaagatc caacaagacg tccagaacta gaagctggta caaatggaag    600

aagttcgaca acaagtccct ttgtaaaacc aaatccaggt tctagcacag acggcaacag    660
```

-continued

```
cgccggacat tcggggaaca acatcctcgg ttccgaagtg gccttatttg cagggattgc    720
ttcaggatgc atcatcttca tcgtcatcat catcacgctg gtggtcctct tgctgaagta    780
ccggaggaga cacaggaagc actcgccgca gcacacgacc acgctgtcgc tcagcacact    840
ggccacaccc aagcgcagcg gcaacaacaa cggctcagag cccagtgaca ttatcatccc    900
gctaaggact gcggacagcg tcttctgccc tcactacgag aaggtcagcg gggactacgg    960
gcacccggtg tacatcgtcc aggagatgcc cccgcagagc ccggcgaaca tttactacaa   1020
ggtctgagag ggaccctggt ggtacctgtg ctttcccaga ggacacctaa tgtcccgatg   1080
cctcccttga gggtttgaga gcccgcgtgc tggagaattg actgaagcac agcaccgggg   1140
gagagggaca ctcctcctcg gaagagcccg tcgcgctgga cagcttacct agtcttgtag   1200
cattcggcct tggtgaacac acacgctccc tggaagctgg aagactgtgc agaagacgcc   1260
cattcggact gctgtgccgc gtcccacgtc tcctcctcga agccatgtgc tgcggtcact   1320
caggcctctg cagaagccaa gggaagacag tggtttgtgg acgagagggc tgtgagcatc   1380
ctggcaggtg ccccaggatg ccacgcctgg aagggccggc ttctgcctgg ggtgcatttc   1440
ccccgcagtg cataccggac ttgtcacacg gacctcgggc tagttaaggt gtgcaaagat   1500
ctctagagtt tagtccttac tgtctcactc gttctgttac ccagggctct gcagcacctc   1560
acctgagacc tccactccac atctgcatca ctcatggaac actcatgtct ggagtcccct   1620
cctccagccg ctggcaacaa cagcttcagt ccatgggtaa tccgttcata gaaattgtgt   1680
ttgctaacaa ggtgcccttt agccagatgc taggctgtct gcgaagaagg ctaggagttc   1740
atagaaggga gtggggctgg ggaaagggct ggctgcaatt gcagctcact gctgctgcct   1800
ctgaaacaga aagttggaaa ggaaaaaaga aaaaagcaat taggtagcac agcactttgg   1860
ttttgctgag atcgaagagg ccagtaggag acacgacagc acacacagtg gattccagtg   1920
catggggagg cactcgctgt tatcaaatag cgatgtgcag gaagaaaagc ccctcttcat   1980
tccggggaac aaagacgggt attgttggga aaggaacagg cttggaggga agggagaaag   2040
taggccgctg atgatatatt cgggcaggac tgttgtggta ctggcaataa gatacacagc   2100
tccgagctgt aggagagtcg gtctgctttg gatgattttt taagcagact cagctgctat   2160
acttatcaca ttttattaaa cacagggaaa gcatttagga gaatagcaga gagccaaatc   2220
tgacctaaaa gttgaaaagc caaaggtcaa acaggctgta attccatcat catcgttgtt   2280
attaaagaat ccttatctat aaaaggtagg tcagatcccc ctccccccag gttcctcctt   2340
cccctcccga ttgagcctta cgacactttg gtttatgcgg tgctgtccgg gtgccagggc   2400
tgcagggtcg gtactgatgg aggctgcagc gcccggtgct ctgtgtcaag gtgaagcaca   2460
tacggcagac ctcttagagt ccttaagacg gaagtaaatt atgatgtcca gggggagaag   2520
gaagatagga cgtatttata ataggtatat agaacacaag ggatataaaa tgaaagattt   2580
ttactaatat atattttaag gttgcacaca gtacacacca gaagatgtga aattcatttg   2640
tggcaattaa gtggtcccaa tgctcagcgc ttaaaaaaac aaattggaca gctacttctg   2700
ggaaaaacaa catcattcca aaaagaacaa taatgagagc aaatgcaaaa ataaccaagt   2760
cctccgaagg catctcacgg aaccgtagac taggaagtac gagccccaca gagcaggaag   2820
ccgatgtgac tgcatcatat atttaacaat gacaagatgt tccggcgttt atttctgcgt   2880
tgggttttcc cttgccttat gggctgaagt gttctctaga atccagcagg tcacactggg   2940
ggcttcaggt gacgatttag ctgtggctcc ctcctcctgt cctccccgc accccctccc   3000
ttctgggaaa caagaagagt aaacaggaaa cctacttttt atgtgctatg caaaatagac   3060
```

-continued

```
atctttaaca tagtcctgtt actatggtaa cactttgctt tctgaattgg aagggaaaaa   3120

aaatgtagcg acagcatttt aaggttctca gacctccagt gagtacctgc aaaaatgagt   3180

tgtcacagaa attatgatcc tctatttcct gaacctggaa atgatgttgg tccaaagtgc   3240

gtgtgtgtat gtgtgagtgg gtgcgtggta tacatgtgta catatatgta taatatatat   3300

ctacaatata tattatatat atctatatca tatttctgtg gagggttgcc atggtaacca   3360

gccacagtac atatgtaatt ctttccatca ccccaacctc tcctttctgt gcattcatgc   3420

aagagtttct tgtaagccat cagaagttac ttttaggatg gggggagaggg gcgagaaggg   3480

gaaaaatggg aaatagtctg attttaatga aatcaaatgt atgtatcatc agttggctac   3540

gttttggttc tatgctaaac tgtgaaaaat cagatgaatt gataaaagag ttccctgcaa   3600

ccaattgaaa agtgttctgt gcgtctgttt tgtgtctggt gcagaatatg acaatctacc   3660

aactgtccct ttgtttgaag ttggtttagc tttggaaagt tactgtaaat gccttgcttg   3720

tatgatcgtc cctggtcacc cgactttgga atttgcacca tcatgtttca gtgaagatgc   3780

tgtaaatagg ttcagatttt actgtctatg gatttggggt gttacagtag ccttattcac   3840

ctttttaata aaaatacaca tgaaaacaag aaagaaatgg cttttcttac ccagattgtg   3900

tacatagagc aatgttggtt ttttataaag tctaagcaag atgttttgta taaaatctga   3960

attttgcaat gtatttagct acagcttgtt taacggcagt gtcattcccc tttgcactgt   4020

aatgaggaaa aaatggtata aaaggttgcc aaattgctgc atatttgtgc cgtaattatg   4080

taccatgaat atttatttaa aatttcgttg tccaatttgt aagtaacaca gtattatgcc   4140

tgagttataa atattttttt ctttctttgt tttattttaa tagcctgtca taggttttaa   4200

atctgcttta gtttcacatt gcagttagcc ccagaaaatg aaatccgtga agtcacattc   4260

cacatctgtt tcaaactgaa tttgttctta aaaaaataaa atattttttt cctatggaaa   4320

aaaaaaaaaa aaaaa                                                    4335
```

<210> SEQ ID NO 395
<211> LENGTH: 987
<212> TYPE: PRT
<213> ORGANISM: Homo sapiens

<400> SEQUENCE: 395

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Asp Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140
```

-continued

```
His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Val
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Leu Ala Leu Ile Ala Gly Thr
    530                 535                 540

Ala Val Val Gly Val Val Leu Val Leu Val Val Ile Val Val Ala Val
545                 550                 555                 560
```

-continued

```
Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
        595                 600                 605

Glu Ile Asp Val Ser Tyr Val Lys Ile Glu Glu Val Ile Gly Ala Gly
    610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
            660                 665                 670

His Pro Asn Ile Ile Arg Leu Glu Gly Val Val Thr Asn Ser Met Pro
        675                 680                 685

Val Met Ile Leu Thr Glu Phe Met Glu Asn Gly Ala Leu Asp Ser Phe
    690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
        755                 760                 765

Ser Ser Asp Pro Thr Tyr Thr Ser Ser Leu Gly Gly Lys Ile Pro Ile
    770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Pro Asp Cys Pro Thr Ser
        835                 840                 845

Leu His Gln Leu Met Leu Asp Cys Trp Gln Lys Asp Arg Asn Ala Arg
    850                 855                 860

Pro Arg Phe Pro Gln Val Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
            900                 905                 910

Gly Glu Trp Leu Arg Ala Ile Lys Met Gly Arg Tyr Glu Glu Ser Phe
        915                 920                 925

Ala Ala Ala Gly Phe Gly Ser Phe Glu Leu Val Ser Gln Ile Ser Ala
    930                 935                 940

Glu Asp Leu Leu Arg Ile Gly Val Thr Leu Ala Gly His Gln Lys Lys
945                 950                 955                 960
```

-continued

```
Ile Leu Ala Ser Val Gln His Met Lys Ser Gln Ala Lys Pro Gly Thr
                965                 970                 975

Pro Gly Gly Thr Gly Gly Pro Ala Pro Gln Tyr
            980                 985


<210> SEQ ID NO 396
<211> LENGTH: 333
<212> TYPE: PRT
<213> ORGANISM: Homo sapiens

<400> SEQUENCE: 396

Met Ala Val Arg Arg Asp Ser Val Trp Lys Tyr Cys Trp Gly Val Leu
 1               5                  10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
        35                  40                  45

Val Leu Tyr Pro Gln Ile Gly Asp Lys Leu Asp Ile Ile Cys Pro Lys
    50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Ala Leu Phe Ala Gly Ile Ala Ser Gly Cys Ile Ile Phe Ile Val
225                 230                 235                 240

Ile Ile Ile Thr Leu Val Val Leu Leu Leu Lys Tyr Arg Arg Arg His
                245                 250                 255

Arg Lys His Ser Pro Gln His Thr Thr Thr Leu Ser Leu Ser Thr Leu
            260                 265                 270

Ala Thr Pro Lys Arg Ser Gly Asn Asn Asn Gly Ser Glu Pro Ser Asp
        275                 280                 285

Ile Ile Ile Pro Leu Arg Thr Ala Asp Ser Val Phe Cys Pro His Tyr
    290                 295                 300

Glu Lys Val Ser Gly Asp Tyr Gly His Pro Val Tyr Ile Val Gln Glu
305                 310                 315                 320

Met Pro Pro Gln Ser Pro Ala Asn Ile Tyr Tyr Lys Val
                325                 330
```